US007795391B2

(12) United States Patent
Jakobovits et al.

(10) Patent No.: US 7,795,391 B2
(45) Date of Patent: Sep. 14, 2010

(54) PROTEIN SHOWING ENHANCED EXPRESSION IN CANCER CELLS

(75) Inventors: Aya Jakobovits, Beverly Hills, CA (US); Arthur B. Raitano, Los Angeles, CA (US); Daniel E. H. Afar, Brisbane, CA (US); Douglas Saffran, Encinitas, CA (US); Rene S. Hubert, Los Angeles, CA (US); Mary Faris, Los Angeles, CA (US); Pia M. Challita-Eid, Encino, CA (US)

(73) Assignee: Agensys, Inc., Santa Monica, CA (US)

( * ) Notice: Subject to any disclaimer, the term of this patent is extended or adjusted under 35 U.S.C. 154(b) by 269 days.

(21) Appl. No.: 11/751,621

(22) Filed: May 21, 2007

(65) Prior Publication Data

US 2007/0270575 A1 Nov. 22, 2007

Related U.S. Application Data

(60) Division of application No. 10/147,368, filed on May 15, 2002, now Pat. No. 7,361,338, which is a continuation-in-part of application No. 10/001,469, filed on Oct. 31, 2001, now Pat. No. 7,208,280, which is a continuation-in-part of application No. 09/680,728, filed on Oct. 5, 2000, now Pat. No. 6,790,631.

(60) Provisional application No. 60/157,902, filed on Oct. 5, 1999, provisional application No. 60/291,118, filed on May 15, 2001.

(51) Int. Cl.
*C07K 14/00* (2006.01)

(52) U.S. Cl. .................... 530/350; 435/320.1; 536/23.1

(58) Field of Classification Search ................. 530/350; 435/320.1; 536/23.1
See application file for complete search history.

(56) References Cited

U.S. PATENT DOCUMENTS

| | | | |
|---|---|---|---|
| 5,530,101 | A | 6/1996 | Queen et al. |
| 5,756,309 | A | 5/1998 | Soppet et al. |
| 5,795,572 | A | 8/1998 | Diegel et al. |
| 5,844,093 | A | 12/1998 | Kettleborough et al. |
| 5,948,890 | A | 9/1999 | Soppet et al. |
| 6,800,746 | B2 | 10/2004 | Xu et al. |
| 2002/0022248 | A1 | 2/2002 | Xu et al. |
| 2002/0192763 | A1 | 12/2002 | Xu et al. |
| 2003/0022237 | A1 | 1/2003 | Feder et al. |
| 2003/0088059 | A1 | 5/2003 | Zozulya |
| 2003/0113798 | A1 | 6/2003 | Burmer et al. |
| 2003/0213004 | A1 | 11/2003 | Jakobovits et al. |

FOREIGN PATENT DOCUMENTS

| | | |
|---|---|---|
| EP | 1074617 | 2/2001 |
| EP | 1270724 | 1/2003 |
| GB | 2211504 | 7/1989 |
| WO | WO-93/17715 | 9/1993 |
| WO | WO-96/39435 | 12/1996 |
| WO | WO 97/25426 | 7/1997 |
| WO | WO-99/06550 | 2/1999 |
| WO | WO-00/04149 | 1/2000 |
| WO | WO-00/20590 | 4/2000 |
| WO | WO-01/22920 | 4/2001 |
| WO | WO-01/25272 | 4/2001 |
| WO | WO-01/25434 | 4/2001 |
| WO | WO-01/27158 | 4/2001 |
| WO | WO-02/28899 | 4/2001 |
| WO | WO-02/30268 | 4/2001 |
| WO | WO-01/31014 | 5/2001 |
| WO | WO-01/34802 | 5/2001 |
| WO | WO-01/39798 | 6/2001 |
| WO | WO-01/51633 | 7/2001 |
| WO | WO-01/57188 | 8/2001 |
| WO | WO-01/60860 | 8/2001 |
| WO | WO-01/68805 | 9/2001 |
| WO | WO-01/73032 | 10/2001 |
| WO | WO-01/74904 | 10/2001 |
| WO | WO-01/98526 | 12/2001 |
| WO | WO-02/16548 | 2/2002 |
| WO | WO-02/24726 | 3/2002 |
| WO | WO-02/061087 | 8/2002 |
| WO | WO-02/089747 | 11/2002 |
| WO | WO-02/092842 | 11/2002 |
| WO | WO-03/009814 | 2/2003 |

(Continued)

OTHER PUBLICATIONS

Schmid S et al, 2001 (J comparative Neurology, 430(2): 160-71).*
Conner et al, 1996 (Mol Brain Res, 42: 1-17).*
Straub P et al, 1993, J Biol Chem 268(29): 21997-20003.*
Kouklis PD et al, 1993, J Cell Science, 106(pt 3): 919-28.*
Guate et al, 1999 (BJU Internatl, 84: 495-502).*
Lopez-Ilasaca, Biochemical Pharmacology (1998) 56:269-277.
Chen et al., Oncogene (1996) 12:741-751.
Diatchenko et al., PNAS USA (1996) 93(12):6025-6030.
Ji et al., BMC Genomics (2002) 3:12.
Liang et al., Cancer Research (1992) 52:6966-6968.
Madsen et al., Endocrinology (1983) 113(6):2135-2144.

(Continued)

*Primary Examiner*—Larry R. Helms
*Assistant Examiner*—Minh Tam Davis
(74) *Attorney, Agent, or Firm*—Morrison & Foerster LLP

(57) ABSTRACT

A novel gene (designated 101P3A11 or PHOR-1) and its encoded protein, and variants thereof, are described wherein 101P3A11 exhibits tissue specific expression in normal adult tissue, and is aberrantly expressed in the cancers listed in Table I. Consequently, 101P3A11 provides a diagnostic, prognostic, prophylactic and/or therapeutic target for cancer. The 101P3A11 gene or fragment thereof, or its encoded protein, or variants thereof, or a fragment thereof, can be used to elicit a humoral or cellular immune response; antibodies or T cells reactive with 101P3A11 can be used in active or passive immunization.

6 Claims, 85 Drawing Sheets

OTHER PUBLICATIONS

Watson and Flemming, Cancer Research (1994) 54:4598-4602.
Alberts et al., Molecular Biology of the Cell, 3rd Edition (1994) p. 465.
Bepler et al., Genomics (1999) 55(2):164-175.
Birnbaumer, Cell (1992) 71:1069.
Boon, Adv. Can. Res. (1992) 58:177-210.
Bowie et al., Science (1990) 257:1306-1310.
Burgess et al., Journal of Cell Biology (1990) 11:2129-2138.
Burmer, Environmental Health Perspectives (1991) 93:27-31.
Busken et al., Digestive Disease Week Abstracts and Itinerary Planner (2003) abstract No. 850.
Chang et al., Leukemia (2003) 17:1263-1293.
Craft et al., Cancer Res. (1999) 59:5030-036.
Crystal, Science (1995) 270:404-410.
Curti, Crit. Rev. in Oncology/Hematology (1993) 14:29-39.
Deonarain, Expert Opin. Ther. Pat. (1998) 8:53-69.
EMBL Sequence Accession No. A06681.Gcg_Geneseq_D, Jun. 13, 2000 (first entry).
EMBL Sequence Accession No. AF101565, Jan. 29, 1999, Nov. 8, 2000.
Evans et al., Am. J. Obstet. Gynecol. (1994) 171(4):1055-1057.
Ezzell, J. NIH Res. (1995) 7:46-49.
Fu et al., EMBO Journal (1996) 15:4392-4401.
Gillies et al., Human Antibodies and Hybridomas (1990) 1(1):47-54.
Greenspan et al., Nature Biotechnology (1999) 7:936-937.
Greulich and Erikson, J. Biol. Chem. (1998) 273:13280.
Gura, Science (1997) 278:1041-1042.
Hartwell et al., Science (1997) 278:1064-1068.
Herbert et al., The Dictionary of Immunology, Academic Press, 4th edition, 1995, p. 58.
Holmes, Exp. Opin. Invest. Drugs (2001) 10:511-519.
Hubert et al., Proc. Natl. Acad. Sci. USA (1999) 96(25):14523-14528.
Hummler et al., PNAS USA (1994) 91:5647-5661.
International Search Report for PCT/US02/15520, mailed on Oct. 20, 2004, 4 pages.
Jain, Sci. Am. (1994) 271:58-65.
Jansen, Pediatric Res. (1995) 37(6):681-686.
Klein et al., Nat. Med. (1997) 3:402.
Lai et al., Clin. Cancer Res. (2000) 6(8):3172-3176.
Lazar et al., Molecular and Cell Biology (1988) 8:1247-1252.
Liebmann and Bohmer, Curr. Med. Chem. (2000) 7:911.
Malnic et al., Cell (1999) 96:713.
Maniatis et al. (Eds.), Mol. Cloning (1989) Cold Spring Harbor Laboratory, Cold Spring Harbor, p. 17.31.
Maudsley et al., J. Biol. Chem. (2000) 275:9572.
McLean and Hill, Eur. J. Of Cancer (1993) 29A:2243-2248.
Miller, FASEB J. (1995) 9:190-199.
Montesano et al., Int'l J. Cancer (1996) 69:225-235.
Muller et al., MCB (1991) 11:1785.
Nageneseq, EMBL Sequence Accession No. X40518, Jun. 18, 1999 (first entry).
Oya and Schulz, Br. J. Cancer (2000) 83(5):626-631.
Pinto et al., Clin. Cancer Res. (1996) 2(9):1445-1451.
Raming et al., Nature (1993) 361:353.
Raming et al., Receptor Channels (1998) 6:141.
Rampsrch Granli Reports, pp. 2-5, earli, 2002.
Reiter et al., Proc. Natl. Acad. Sci. USA (1998) 95:1735.
Rogers et al. Bioscience Reports (1988) 8:359-368.
Roitt et al., Immunology (1998) 4th ed., Mosby, London, pp. 7.7-7.8.
Shantz and Pegg, Int. J. of Biochem. and Cell Biol. (1999) 31:107-122.
Sjogren, Immunotechnology (1997) 3(3):161-172.
Spitler, Cancer Biotherapy (1995) 10:1-3.
Su et al., Proc. Natl. Acad. Sci. USA (1996) 93:7252.
Svaren et al., J. Biol. Chem. (2000) 275(49):38524-38531.
Tao et al., The Journal of Immunology (1989) 143(8):2595-2601.
Verma, Nature (1997) 389:239-242.
Walter et al., Nat. Genetics (1994) 7:22.
Welch et al., Int. J. Cancer (1989) 43:449-457.
White et al., Ann. Rev. Med. (2001) 52:125-145.
Xu Xin et al., FASEB J. (2001) 15:A313.
Supplementary Partial European Search Report for EP 02 73 6898, mailed on Oct. 4, 2005, 4 pages.
Banki et al., JBC (1994) 269(4):2847-2851.
Bendayan et al., J. Histochem. Cytochem. (1995) 43(9):881-886.

* cited by examiner

Figure 1. 101P3A11 SSH sequence of 427 nucleotides (SEQ ID NO: 26)

1 GATCAAACTT CTTTTCCATT CAGAGTCCTC TGATTCAGAT TTTAATGTTA ACATTTTGGA
61 AGACAGTATT CAGAAAAAAA ATTTCCTTAA TAAAAATACA ACTCAGATCC TTCAAATATG
121 AAACTGGTTG GGGAATCTCC ATTTTTTCAA TATTATTTTC TTCTTTGTTT TCTTGCTACG
181 TATAATTATT AATATCCTGA CTAGGTTGTG GTTGGAGGGT TATTACTTTT CATTTTACCA
241 TGCAGTCCAA ATCTAAACTG CTTCTACTGA TGGTTTACAG CATTCTGAGA TAAGAATGGT
301 ACATCTAGAG AACATTTGCC AAAGGCCTAA GCACAGCAAA GGAAAATAAA CACAGAATAT
361 AATAAAATGA GATAATCTAG CTTAAAACTA TAACTTCCTC TTTAGAACTC CCAACCACAT
421 TTGGATC

Figure 2A-1

The cDNA (SEQ ID. NO. : 27) and amino acid sequence (SEQ ID. NO. : 19) of 101P3A11 v.1.

The 3136 nucleotide sequence of 101P3A11 v.1 is shown. The start methionine is underlined. The open reading frame extends from nucleic acid 130-1086 including the stop codon.

```
   1 cagagaggctgtatttcagtgcagcctgccagacctcttctggaggaagactggacaaag
  61 ggggtcacacattccttccatacggttgagcctctacctgcctggtgctggtcacagttc
   1          M  M  V  D  P  N  G  N  E  S  S  A  T  Y  F  I  L
 121 agcttcttcATGATGGTGGATCCCAATGGCAATGAATCCAGTGCTACATACTTCATCCTA
  18 I  G  L  P  G  L  E  E  A  Q  F  W  L  A  F  P  L  C  S  L
 181 ATAGGCCTCCCTGGTTTAGAAGAGGCTCAGTTCTGGTTGGCCTTCCCATTGTGCTCCCTC
  38 Y  L  I  A  V  L  G  N  L  T  I  I  Y  I  V  R  T  E  H  S
 241 TACCTTATTGCTGTGCTAGGTAACTTGACAATCATCTACATTGTGCGGACTGAGCACAGC
  58 L  H  E  P  M  Y  I  F  L  C  M  L  S  G  I  D  I  L  I  S
 301 CTGCATGAGCCCATGTATATATTTCTTTGCATGCTTTCAGGCATTGACATCCTCATCTCC
  78 T  S  S  M  P  K  M  L  A  I  F  W  F  N  S  T  T  I  Q  F
 361 ACCTCATCCATGCCCAAAATGCTGGCCATCTTCTGGTTCAATTCCACTACCATCCAGTTT
  98 D  A  C  L  L  Q  I  F  A  I  H  S  L  S  G  M  E  S  T  V
 421 GATGCTTGTCTGCTACAGATTTTTGCCATCCACTCCTTATCTGGCATGGAATCCACAGTG
 118 L  L  A  M  A  F  D  R  Y  V  A  I  C  H  P  L  R  H  A  T
 481 CTGCTGGCCATGGCTTTTGACCGCTATGTGGCCATCTGTCACCCACTGCGCCATGCCACA
 138 V  L  T  L  P  R  V  T  K  I  G  V  A  A  V  V  R  G  A  A
 541 GTACTTACGTTGCCTCGTGTCACCAAAATTGGTGTGGCTGCTGTGGTGCGGGGGGCTGCA
 158 L  M  A  P  L  P  V  F  I  K  Q  L  P  F  C  R  S  N  I  L
 601 CTGATGGCACCCCTTCCTGTCTTCATCAAGCAGCTGCCCTTCTGCCGCTCCAATATCCTT
 178 S  H  S  Y  C  L  H  Q  D  V  M  K  L  A  C  D  D  I  R  V
 661 TCCCATTCCTACTGCCTACACCAAGATGTCATGAAGCTGGCCTGTGATGATATCCGGGTC
 198 N  V  V  Y  G  L  I  V  I  I  S  A  I  G  L  D  S  L  L  I
 721 AATGTCGTCTATGGCCTTATCGTCATCATCTCCGCCATTGGCCTGGACTCACTTCTCATC
 218 S  F  S  Y  L  L  I  L  K  T  V  L  G  L  T  R  E  A  Q  A
 781 TCCTTCTCATATCTGCTTATTCTTAAGACTGTGTTGGGCTTGACACGTGAAGCCCAGGCC
 238 K  A  F  G  T  C  V  S  H  V  C  A  V  F  I  F  Y  V  P  F
 841 AAGGCATTTGGCACTTGCGTCTCTCATGTGTGTGCTGTGTTCATATTCTATGTACCTTTC
 258 I  G  L  S  M  V  H  R  F  S  K  R  R  D  S  P  L  P  V  I
 901 ATTGGATTGTCCATGGTGCATCGCTTTAGCAAGCGGCGTGACTCTCCGCTGCCCGTCATC
 278 L  A  N  I  Y  L  L  V  P  P  V  L  N  P  I  V  Y  G  V  K
 961 TTGGCCAATATCTATCTGCTGGTTCCTCCTGTGCTCAACCCAATTGTCTATGGAGTGAAG
 298 T  K  E  I  R  Q  R  I  L  R  L  F  H  V  A  T  H  A  S  E
1021 ACAAAGGAGATTCGACAGCGCATCCTTCGACTTTTCCATGTGGCCACACACGCTTCAGAG
 318 P  *
1081 CCCTAGgtgtcagtgatcaaacttcttttccattcagagtcctctgattcagattttaat
1141 gttaacattttggaagacagtattcagaaaaaaaatttccttaataaaaaatacaactca
1201 gatccttcaaatatgaaactggttggggaatctccatttttcaatattattttcttctt
1261 tgttttcttgctacatataattattaataccctgactaggttgtggttggagggttatta
```

Figure 2A-2

1321 cttttcattttaccatgcagtccaaatctaaactgcttctactgatggtttacagcattc
1381 tgagataagaatggtacatctagagaacatttgccaaaggcctaagcacggcaaaggaaa
1441 ataaacacagaatataataaaatgagataatctagcttaaaactataacttcctcttcag
1501 aactcccaaccacattggatctcagaaaaatgctgtcttcaaaatgacttctacagagaa
1561 gaaataatttttcctctggacactagcacttaaggggaagattggaagtaaagccttgaa
1621 aagagtacatttacctacgttaatgaaagttgacacactgttctgagagttttcacagca
1681 tatggaccctgtttttcctatttaattttcttatcaaccctttaattaggcaaagatatt
1741 attagtaccctcattgtagccatgggaaaattgatgttcagtggggatcagtgaattaaa
1801 tggggtcatacaagtataaaaattaaaaaaaaaaaagacttcatgcccaatctcatatga
1861 tgtggaagaactgttagagagaccaacagggtagtgggttagagatttccagagtcttac
1921 attttctagaggaggtatttaatttcttctcactcatccagtgttgtatttaggaatttc
1981 ctggcaacagaactcatggctttaatcccactagctattgcttattgtcctggtccaatt
2041 gccaattacctgtgtcttggaagaagtgatttctaggttcaccattatggaagattctta
2101 ttcagaaagtctgcatagggcttatagcaagttatttatttttaaaagttccataggtga
2161 ttctgataggcagtgaggttagggagccaccagttatgatgggaagtatggaatggcagg
2221 tcttgaagataacattggccttttgagtgtgactcgtagctggaaagtgagggaatcttc
2281 aggaccatgctttatttggggctttgtgcagtatggaacagggactttgagaccaggaaa
2341 gcaatctgacttaggcatgggaatcaggcatttttgcttctgaggggctattaccaaggg
2401 ttaataggtttcatcttcaacaggatatgacaacagtgttaaccaagaaactcaaattac
2461 aaatactaaaacatgtgatcatatatgtggtaagtttcatttcttttttcaatcctcagg
2521 ttccctgatatggattcctataacatgctttcatccccttttgtaatggatatcatattt
2581 ggaaatgcctatttaatacttgtatttgctgctggactgtaagcccatgagggcactgtt
2641 tattattgaatgtcatctctgttcatcattgactgctctttgctcatcattgaatccccc
2701 agcaaagtgcctagaacataatagtgcttatgcttgacaccggttatttttcatcaaacc
2761 tgattccttctgtcctgaacacatagccaggcaattttccagccttctttgagttgggta
2821 ttattaaattctggccattacttccaatgtgagtggaagtgacatgtgcaatttctatac
2881 ctggctcataaaaccctcccatgtgcagcctttcatgttgacattaaatgtgacttggga
2941 agctatgtgttacacagagtaaatcaccagaagcctggatttctgaaaaaactgtgcaga
3001 gccaaacctctgtcatttgcaactcccacttgtatttgtacgaggcagttggataagtga
3061 aaaataaagtactattgtgtcaagaaaaaaaaaaaaaaaaaaaaaaaaaaaaaaaaaaaa
3121 aaaaaaaaaaaaaaaa

Figure 2B-1

The cDNA (SEQ ID. NO. :29) and amino acid sequence (SEQ ID. NO. :30) of 101P3A11 v.2. The 2466 nucleotide sequence of 101P3A11 v.2 is shown. The start methionine is underlined. The open reading frame extends from nucleic acid 130-348 including the stop codon.

```
   1 cagagaggctgtatttcagtgcagcctgccagacctcttctggaggaagactggacaaag
  61 ggggtcacacattccttccatacggttgagcctctacctgcctggtgctggtcacagttc
   1          M  M  V  D  P  N  G  N  E  S  S  A  T  Y  F  I  L
 121 agcttcttcATGATGGTGGATCCCAATGGCAATGAATCCAGTGCTACATACTTCATCCTA
  18 I  G  L  P  G  L  E  E  A  Q  F  W  L  A  F  P  L  C  S  L
 181 ATAGGCCTCCCTGGTTTAGAAGAGGCTCAGTTCTGGTTGGCCTTCCCATTGTGCTCCCTC
  38 Y  L  I  A  V  L  A  S  G  V  T  L  R  C  P  S  S  W  P  I
 241 TACCTTATTGCTGTGCTAGCAAGCGGCGTGACTCTCCGCTGCCCGTCATCTTGGCCAATA
  58 S  I  C  W  F  L  L  C  S  T  Q  L  S  M  E  *
 301 TCTATCTGCTGGTTCCTCCTGTGCTCAACCCAATTGTCTATGGAGTGAagacaaaggaga
 361 ttcgacagcgcatccttcgacttttccatgtggccacacacgcttcagagccctaggtgt
 421 cagtgatcaaacttcttttccattcagagtcctctgattcagattttaatgttaacattt
 481 tggaagacagtattcagaaaaaaatttccttaataaaaaatacaactcagatccttcaa
 541 atatgaaactggttggggaatctccatttttcaatattattttcttctttgttttcttg
 601 ctacatataattattaataccctgactaggttgtggttggagggttattacttttcattt
 661 taccatgcagtccaaatctaaactgcttctactgatggtttacagcattctgagataaga
 721 atggtacatctagagaacatttgccaaaggcctaagcacggcaaaggaaaataaacacag
 781 aatataataaaatgagataatctagcttaaaactataacttcctcttcagaactcccaac
 841 cacattggatctcagaaaaatgctgtcttcaaaatgacttctacagagaagaaataattt
 901 ttcctctggacactagcacttaaggggaagattggaagtaaagccttgaaaagagtacat
 961 ttacctacgttaatgaaagttgacacactgttctgagagttttcacagcatatggaccct
1021 gtttttcctatttaatttcttatcaaccctttaattaggcaaagatattattagtaccc
1081 tcattgtagccatgggaaaattgatgttcagtggggatcagtgaattaaatggggtcata
1141 caagtataaaaattaaaaaaaaaaagacttcatgcccaatctcatatgatgtggaagaa
1201 ctgttagagagaccaacagggtagtgggttagagatttccagagtcttacattttctaga
1261 ggaggtatttaatttcttctcactcatccagtgttgtatttaggaatttcctggcaacag
1321 aactcatggctttaatcccactagctattgcttattgtcctggtccaattgccaattacc
1381 tgtgtcttggaagaagtgatttctaggttcaccattatggaagattcttattcagaaagt
1441 ctgcatagggcttatagcaagttatttatttttaaaagttccataggtgattctgatagg
1501 cagtgaggttagggagccaccagttatgatgggaagtatggaatggcaggtcttgaagat
1561 aacattggccttttgagtgtgactcgtagctggaaagtgagggaatcttcaggaccatgc
1621 tttatttggggctttgtgcagtatggaacagggactttgagaccaggaaagcaatctgac
1681 ttaggcatgggaatcaggcattttgcttctgaggggctattaccaagggttaataggtt
1741 tcatcttcaacaggatatgacaacagtgttaaccaagaaactcaaattacaaatactaaa
1801 acatgtgatcatatatgtggtaagtttcatttcttttcaatcctcaggttccctgata
1861 tggattcctataacatgctttcatccccttttgtaatggatatcatatttggaaatgcct
1921 atttaatacttgtatttgctgctggactgtaagcccatgagggcactgtttattattgaa
1981 tgtcatctctgttcatcattgactgctctttgctcatcattgaatcccccagcaaagtgc
2041 ctagaacataatagtgcttatgcttgacaccggttatttttcatcaaacctgattccttc
```

Figure 2B-2

```
2101 tgtcctgaacacatagccaggcaatttccagccttctttgagttgggtattattaaatt
2161 ctggccattacttccaatgtgagtggaagtgacatgtgcaatttctatacctggctcata
2221 aaaccctcccatgtgcagcctttcatgttgacattaaatgtgacttgggaagctatgtgt
2281 tacacagagtaaatcaccagaagcctggatttctgaaaaaactgtgcagagccaaacctc
2341 tgtcatttgcaactcccacttgtatttgtacgaggcagttggataagtgaaaaataaagt
2401 actattgtgtcaagaaaaaaaaaaaaaaaaaaaaaaaaaaaaaaaaaaaaaaaaaaaaaa
2461 aaaaaa
```

Figure 2C-1

The cDNA (SEQ ID. NO. :31) and amino acid sequence (SEQ ID. NO. :32) of 101P3A11 v.3.

The 3136 nucleotide sequence of 101P3A11 v.3 is shown. The start methionine is underlined. The open reading frame extends from nucleic acid 130-1086 including the stop codon.

```
   1 cagagaggctgtatttcagtgcagcctgccagacctcttctggaggaagactggacaaag
  61 ggggtcacacattccttccatacggttgagcctctacctgcctggtgctggtcacagttc
   1          M  M  V  D  P  N  G  N  E  S  S  A  T  Y  F  I  L
 121 agcttcttcATGATGGTGGATCCCAATGGCAATGAATCCAGTGCTACATACTTCATCCTA
  18 I  G  L  P  G  L  E  E  A  Q  F  W  L  A  F  P  L  C  S  L
 181 ATAGGCCTCCCTGGTTTAGAAGAGGCTCAGTTCTGGTTGGCCTTCCCATTGTGCTCCCTC
  38 Y  L  I  A  V  L  G  N  L  T  I  I  Y  I  V  R  T  E  H  S
 241 TACCTTATTGCTGTGCTAGGTAACTTGACAATCATCTACATTGTGCGGACTGAGCACAGC
  58 L  H  E  P  M  Y  I  F  L  C  M  L  S  G  I  D  I  L  I  S
 301 CTGCATGAGCCCATGTATATATTTCTTTGCATGCTTTCAGGCATTGACATCCTCATCTCC
  78 T  S  S  M  P  K  M  L  A  I  F  W  F  N  S  T  T  I  Q  F
 361 ACCTCATCCATGCCCAAAATGCTGGCCATCTTCTGGTTCAATTCCACTACCATCCAGTTT
  98 D  A  C  L  L  Q  M  F  A  I  H  S  L  S  G  M  E  S  T  V
 421 GATGCTTGTCTGCTACAGATGTTTGCCATCCACTCCTTATCTGGCATGGAATCCACAGTG
 118 L  L  A  M  A  F  D  R  Y  V  A  I  C  H  P  L  R  H  A  T
 481 CTGCTGGCCATGGCTTTTGACCGCTATGTGGCCATCTGTCACCCACTGCGCCATGCCACA
 138 V  L  T  L  P  R  V  T  K  I  G  V  A  A  V  V  R  G  A  A
 541 GTACTTACGTTGCCTCGTGTCACCAAAATTGGTGTGGCTGCTGTGGTGCGGGGGGCTGCA
 158 L  M  A  P  L  P  V  F  I  K  Q  L  P  F  C  R  S  N  I  L
 601 CTGATGGCACCCCTTCCTGTCTTCATCAAGCAGCTGCCCTTCTGCCGCTCCAATATCCTT
 178 S  H  S  Y  C  L  H  Q  D  V  M  K  L  A  C  D  D  I  R  V
 661 TCCCATTCCTACTGCCTACACCAAGATGTCATGAAGCTGGCCTGTGATGATATCCGGGTC
 198 N  V  V  Y  G  L  I  V  I  I  S  A  I  G  L  D  S  L  L  I
 721 AATGTCGTCTATGGCCTTATCGTCATCATCTCCGCCATTGGCCTGGACTCACTTCTCATC
 218 S  F  S  Y  L  L  I  L  K  T  V  L  G  L  T  R  E  A  Q  A
 781 TCCTTCTCATATCTGCTTATTCTTAAGACTGTGTTGGGCTTGACACGTGAAGCCCAGGCC
 238 K  A  F  G  T  C  V  S  H  V  C  A  V  F  I  F  Y  V  P  F
 841 AAGGCATTTGGCACTTGCGTCTCTCATGTGTGTGCTGTGTTCATATTCTATGTACCTTTC
 258 I  G  L  S  M  V  H  R  F  S  K  R  R  D  S  P  L  P  V  I
 901 ATTGGATTGTCCATGGTGCATCGCTTTAGCAAGCGGCGTGACTCTCCGCTGCCCGTCATC
 278 L  A  N  I  Y  L  L  V  P  P  V  L  N  P  I  V  Y  G  V  K
 961 TTGGCCAATATCTATCTGCTGGTTCCTCCTGTGCTCAACCCAATTGTCTATGGAGTGAAG
 298 T  K  E  I  R  Q  R  I  L  R  L  F  H  V  A  T  H  A  S  E
1021 ACAAAGGAGATTCGACAGCGCATCCTTCGACTTTTCCATGTGGCCACACACGCTTCAGAG
 318 P  *
1081 CCCTAGgtgtcagtgatcaaacttcttttccattcagagtcctctgattcagattttaat
1141 gttaacattttggaagacagtattcagaaaaaaaatttccttaataaaaaatacaactca
1201 gatccttcaaatatgaaactggttggggaatctccatttttcaatattattttcttctt
```

Figure 2C-2

```
1261 tgttttcttgctacatataattattaataccctgactaggttgtggttggagggttatta
1321 cttttcattttaccatgcagtccaaatctaaactgcttctactgatggtttacagcattc
1381 tgagataagaatggtacatctagagaacatctgccaaaggcctaagcacggcaaaggaaa
1441 ataaacacagaatataataaaatgagataatctagcttaaaactataacttcctcttcag
1501 aactcccaaccacattggatctcagaaaaatgctgtcttcaaaatgacttctacagagaa
1561 gaaataatttttcctctggacactagcacttaaggggaagattggaagtaaagccttgaa
1621 aagagtacatttacctacgttaatgaaagttgacacactgttctgagagttttcacagca
1681 tatggacccctgtttttcctatttaattttcttatcaacccttaattaggcaaagatatt
1741 attagtaccctcattgtagccatgggaaaattgatgttcagtggggatcagtgaattaaa
1801 tggggtcatacaagtataaaattaaaaaaaaaaaagacttcatgcccaatctcatatga
1861 tgtggaagaactgttagagagaccaacagggtagtgggttagagatttccagagtcttac
1921 attttctagaggaggtatttaatttcttctcactcatccagtgttgtatttaggaatttc
1981 ctggcaacagaactcatggctttaatcccactagctattgcttattgtcctggtccaatt
2041 gccaattacctgtgtcttggaagaagtgatttctaggttcaccattatggaagattctta
2101 ttcagaaagtctgcatagggcttatagcaagttatttatttttaaaagttccataggtga
2161 ttctgataggcagtgaggttagggagccaccagttatgatgggaagtatggaatggcagg
2221 tcttgaagataacattggccttttgagtgtgactcgtagctggaaagtgagggaatcttc
2281 aggaccatgctttatttggggctttgtgcagtatggaacagggactttgagaccaggaaa
2341 gcaatctgacttaggcatgggaatcaggcatttttgcttctgaggggctattaccaaggg
2401 ttaataggtttcatcttcaacaggatatgacaacagtgttaaccaagaaactcaaattac
2461 aaatactaaaacatgtgatcatatatgtggtaagtttcattttctttttcaatcctcagg
2521 ttccctgatatggattcctataacatgctttcatccccttttgtaatggatatcatattt
2581 ggaaatgcctatttaatacttgtatttgctgctggactgtaagcccatgagggcactgtt
2641 tattattgaatgtcatctctgttcatcattgactgctctttgctcatcattgaatccccc
2701 agcaaagtgcctagaacataatagtgcttatgcttgacaccggttatttttcatcaaacc
2761 tgattccttctgtcctgaacacatagccaggcaattttccagccttctttgagttgggta
2821 ttattaaattctggccattacttccaatgtgagtggaagtgacatgtgcaatttctatac
2881 ctggctcataaaaccctcccatgtgcagcctttcatgttgacattaaatgtgacttggga
2941 agctatgtgttacacagagtaaatcaccagaagcctggatttctgaaaaaactgtgcaga
3001 gccaaacctctgtcatttgcaactcccacttgtatttgtacgaggcagttggataagtga
3061 aaaataaagtactattgtgtcaagaaaaaaaaaaaaaaaaaaaaaaaaaaaaaaaaaaaa
3121 aaaaaaaaaaaaaaaa
```

Figure 3A. Amino acid sequence of 101P3A11 v.1 (SEQ ID. NO. :19). The 101P3A11 v.1 protein has 318 amino acids.

```
  1 MMVDPNGNES SATYFILIGL PGLEEAQFWL AFPLCSLYLI AVLGNLTIIY IVRTEHSLHE
 61 PMYIFLCMLS GIDILISTSS MPKMLAIFWF NSTTIQFDAC LLQIFAIHSL SGMESTVLLA
121 MAFDRYVAIC HPLRHATVLT LPRVTKIGVA AVVRGAALMA PLPVFIKQLP FCRSNILSHS
181 YCLHQDVMKL ACDDIRVNVV YGLIVIISAI GLDSLLISFS YLLILKTVLG LTREAQAKAF
241 GTCVSHVCAV FIFYVPFIGL SMVHRFSKRR DSPLPVILAN IYLLVPPVLN PIVYGVKTKE
301 IRQRILRLFH VATHASEP
```

Figure 3B. Amino acid sequence of 101P3A11 v.2 (SEQ ID. NO. :30). The 101P3A11 v.2 protein has 72 amino acids.

```
  1 MMVDPNGNES SATYFILIGL PGLEEAQFWL AFPLCSLYLI AVLASGVTLR CPSSWPISIC
 61 WFLLCSTQLS ME
```

Figure 3C. Amino acid sequence of 101P3A11 v.3 (SEQ ID. NO. :32). The 101P3A11 v.3 protein has 318 amino acids.

```
  1 MMVDPNGNES SATYFILIGL PGLEEAQFWL AFPLCSLYLI AVLGNLTIIY IVRTEHSLHE
 61 PMYIFLCMLS GIDILISTSS MPKMLAIFWF NSTTIQFDAC LLQMFAIHSL SGMESTVLLA
121 MAFDRYVAIC HPLRHATVLT LPRVTKIGVA AVVRGAALMA PLPVFIKQLP FCRSNILSHS
181 YCLHQDVMKL ACDDIRVNVV YGLIVIISAI GLDSLLISFS YLLILKTVLG LTREAQAKAF
241 GTCVSHVCAV FIFYVPFIGL SMVHRFSKRR DSPLPVILAN IYLLVPPVLN PIVYGVKTKE
301 IRQRILRLFH VATHASEP
```

Figure 4

Alignment of 101P3A11 (Sbjct) with mouse olfactory receptor S25 (Query)

```
Query: 34  GNYTVVTEFILLGLTDDITVSVILFVMFLIVYSVTLMGNLNIIVLIRTSPQLHTPMYLFL 93
           GN +  T FIL+GL         L      +Y + ++GNL II ++RT   LH PMY+FL
Sbjct: 6   GNESSATYFILIGLPGLEEAQFWLAFPLCSLYLIAVLGNLTIIYIVRTEHSLHEPMYIFL 65

Query: 94  SHLAFLDIGYSSSVTPIMLRGFLRKGTFIPVAGCVAQLCIVVAFGTSESFLLASMAYDRY 153
             L+ +DI  S+S  P ML  F    T I    C+ Q+  + +    ES +L +MA+DRY
Sbjct: 66  CMLSGIDILISTSSMPKMLAIFWFNSTTIQFDACLLQIFAIHSLSGMESTVLLAMAFDRY 125

Query: 154 VAICSPLLYSTQMSSTVCILLVGTSYLGGWVNAWIFTGCSLNLSFCGPNKINHFFCDYSP 213
           VAIC PL ++T ++      +   + + G             L FC  N ++H +C +
Sbjct: 126 VAICHPLRHATVLTLPRVTKIGVAAVVRGAALMAPLPVFIKQLPFCRSNILSHSYCLHQD 185

Query: 214 LLKLSCSHDFSFEVIPAISSGSIIVVTVFIIALSYVYILVSILKMRSTEGRQKAFSTCTS 273
           ++KL+C       V   I   S I +   +I+ SY+ IL ++L + + E + KAF TC S
Sbjct: 186 VMKLACDDIRVNVVYGLIVIISAIGLDSLLISFSYLLILKTVLGL-TREAQAKAFGTCVS 244

Query: 274 HLTAVTLFFGTITFIYVMPQSSYSTDQNK----VVSVFYTVVIPMLNPLIYSFRNKEVKE 329
           H+ AV +F+  + FI +     +S  ++     +++  Y +V P+LNP++Y  + KE+++
Sbjct: 245 HVCAVFIFY--VPFIGLSMVHRFSKRRDSPLPVILANIYLLVPPVLNPIVYGVKTKEIRQ 302

Query: 330 AMKKL 334
            + +L
Sbjct: 303 RILRL 307
```

101P3A11 Hydrophilicity profile
(Hopp T.P., Woods K.R., 1981.
Proc. Natl. Acad. Sci. U.S.A. 78:3824-3828)

101P3A11 Hydropathicity Profile
(Kyte J., Doolittle R.F., 1982. J. Mol. Biol. 157:105-132)

101P3A11 % Accessible Residues Profile
(Janin J., 1979. Nature 277:491-492)

101P3A11 Average Flexibility Profile
(Bhaskaran R., Ponnuswamy P.K., 1988. Int. J. Pept. Protein Res. 32:242-255)

101P3A11 Beta-turn Profile
(Deleage, G., Roux B. 1987. Protein Engineering 1:289-294)

1. VP1 (Kidney, Lung, Liver)
2. VP2 (Pancreas, Colon, Stomach)
3. Prostate xenograft Pool
4. Prostate Cancer Pool
5. Kidney Cancer Pool
6. Colon Cancer Pool
7. Breast Cancer Pool
8. Metastasis Pool
9. H2O

*Prostate Cancer Pool = gleason 6, 8, 9*
*Kidney Cancer Pool = grade 2, 2, 3*
*Colon Cancer Pool = stage II, III, IV*
*Breast Cancer Pool = grade 1, 2, 3*
*Metastasis Pool = colon to lung, colon to liver, ovary to fall. tube*

*NP = Normal Prostate*
*NB = Normal Bladder*
*NK = Normal Kidney*
*NC = Normal Colon*

Figure 12B
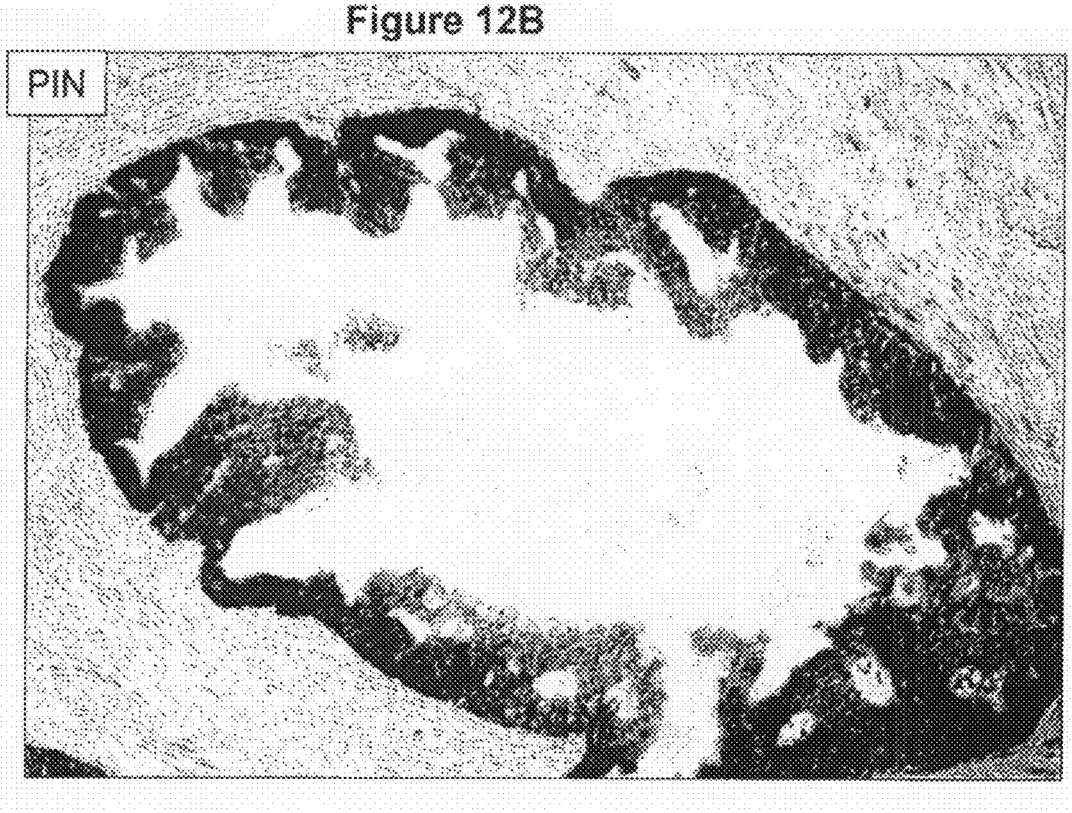
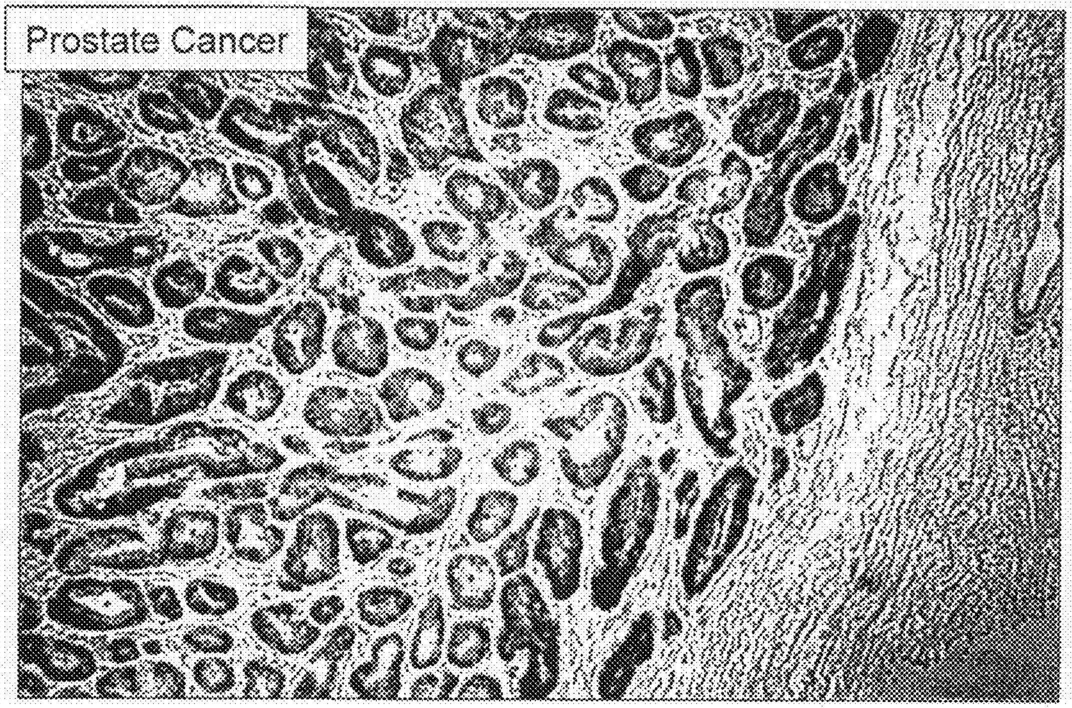
Figure 12C

Figure 12D
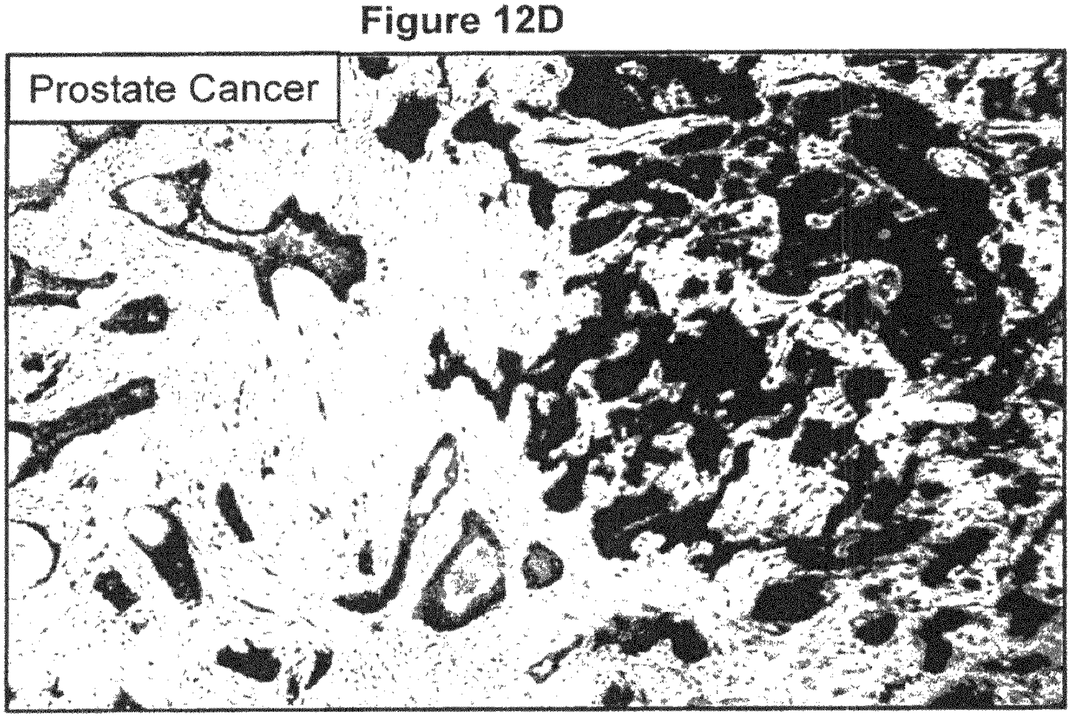
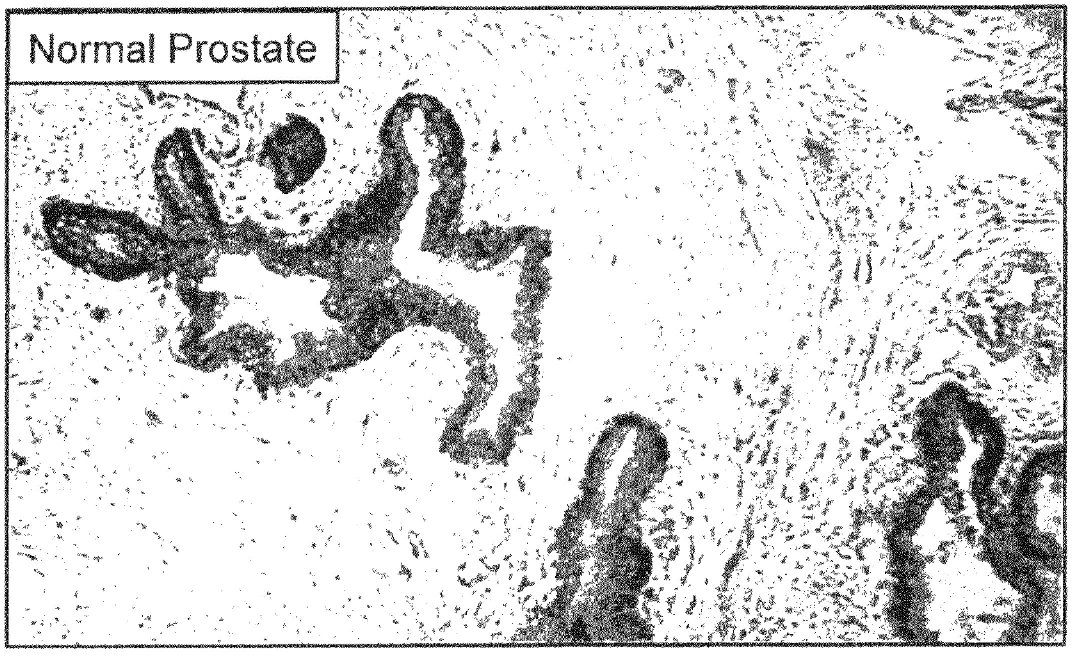
Figure 12E

P1, Stage I
P2, Stage IV

*CL* = *Colon cancer cell line T84*
*N* = *Normal colon*
*Nat* = *Normal Adjacent Tissue*
*T* = *Tumor*

Pt.1, Papillary carcinoma, stage I
Pt.2, Invasive papillary carcinoma
Pt.3, Clear cell type grade 1/3, focally 2/3
Pt.4, Clear cell type, stage III
Pt.5, Clear cell type, stage III
Pt.6, Clear cell type, stage III

*N = Normal kidney*
*$N_{AT}$ = Normal adjacent tumor*
*T = Tumor*

1. LAPC-9 cell line charcoal-stripped FBS, 14 hrs
2. LAPC-9 cell line charcoal-stripped FBS, 14 hrs + mibolerone
3. LAPC-9 cell line charcoal-stripped FBS, 24 hrs
4. LAPC-9 cell line charcoal-stripped FBS, 24 hrs + mibolerone 1. 300.19
2. 300.19/neo-pSRα
3. 300.19/101P3A11-pSRα
4. LAPC-4AD
5. LAPC-9AD

Figure 19A

```
         10        20        30        40        50        60        70
          |         |         |         |         |         |         |
MVDPNGNESSATYFILIGLPGLEEAQFWLAFPLCSLYLIAVLGNLTIIYIVRTEHSLHEPMYIFLCMLSG
cccccccccceeeeeeeccccchhhhhhhhhcchhhhhhhhhccccceeeeeeeeecccchhhhhhhhhhcc
IDILISTSSMPKMLAIFWFNSTTIQFDACLLQIFAIHSLSGMESTVLLAMAFDRYVAICHPLRHATVLTL
ceeeeeccchhhheeeecccccceehhhhhhhhhhhcccccchhhhhhhhhhhhhhhhhcccccceeeeeec
PRVTKIGVAAVVRGAALMAPLPVFIKQLPFCRSNILSHSYCLHQDVMKLACDDIRVNVVYGLIVIISAIG
cccheehhhhhhhhhhhhcccchhhheccccccchhcchhhhhhhhhhhhhhhhceeeeeeeeeeeeehhc
LDSLLISFSYLLILKTVLGLTREAQAKAFGTCVSHVCAVFIFYVPFIGLSMVHRFSKRRDSPLPVILANI
hhhhhhhhhhhhhhhhhhhhhhhhhhhhhcccceeeeeeeeeeeehchcchhhhhhhccccccccccheeeeeh
YLLVPPVLNPIVYGVKTKEIRQRILRLFHVATHASEP
hhhccccccccheeeecchhhhhhhhhhhheeecccccc
```

c: random coil (30.60%)
e: extended strand (21.45%)
h: alpha helix (47.95%)

Figure 23: Alignment of 101P3A11-PHOR-1 with the rat GPCR RA1C (gi|3420759).

Identities = 179/299 (59%), Positives = 231/299 (76%), Gaps = 1/299 (0%)

```
PHOR: 14  FILIGLPGLEEAQFWLAFPLCSLYLIAVLGNLTIIYIVRTEHSLHEPMYIFLCMLSGIDI 73
          F+LIG+PGLEEA FW  FPL S+Y +A+ GN  +++IVRTE SLH PMY+FLCML+ ID+
RA1C: 11  FMLIGIPGLEEAHFWFGFPLLSMYAVALFGNCIVVFIVRTERSLHAPMYLFLCMLAAIDL 70

PHOR: 74  LISTSSMPKMLAIFWFNSTTIQFDACLLQIFAIHSLSGMESTVLLAMAFDRYVAICHPLR 133
           +STS+MPK+LA+FWF+S  I FDACL Q+F IH+LS +EST+LLAMAFDRYVAICHPLR
RA1C: 71  ALSTSTMPKILALFWFDSREITFDACLAQMFFIHALSAIESTILLAMAFDRYVAICHPLR 130

PHOR: 134 HATVLTLPRVTKIGVAAVVRGAALMAPLPVFIKQLPFCRSNILSHSYCLHQDVMKLACDD 193
          HA VL      +IG+ A+VRG+    PLP+ IK+L FC SN+LSHSYC+HQDVMKLA  D
RA1C: 131 HAAVLNNTVTVQIGMVALVRGSLFFFPLPLLIKRLAFCHSNVLSHSYCVHQDVMKLAYTD 190

PHOR: 194 IRVNVVYGLIVIISAIGLDSLLISFSYLLILKTVLGL-TREAQAKAFGTCVSHVCAVFIF 252
             NVVYGL  I+  +G+D + IS SY LI++ VL L ++  +AKAFGTCVSH+  V  F
RA1C: 191 TLPNVVYGLTAILLVMGVDVMFISLSYFLIIRAVLQLPSKSERAKAFGTCVSHIGVVLAF 250

PHOR: 253 YVPFIGLSMVHRFSKRRDSPLPVILANIYLLVPPVLNPIVYGVKTKEIRQRILRLFHVA 311
          YVP IGLS+VHRF    D  + V++ ++YLL+PPV+NPI+YG KTK+IR R+L +F ++
RA1C: 251 YVPLIGLSVVHRFGNSLDPIVHVLMGDVYLLLPPVINPIIYGAKTKQIRTRVLAMFKIS 309
```

Figure 24: Alignment of 101P3A11-PHOR-1 with the human prostate specific GPCR.(gi|13540539)

Identities = 179/299 (59%), Positives = 233/299 (77%), Gaps = 1/299 (0%)

```
PHOR: 14  FILIGLPGLEEAQFWLAFPLCSLYLIAVLGNLTIIYIVRTEHSLHEPMYIFLCMLSGIDI 73
          F+LIG+PGLE+A FW+ FPL S+Y++A+ GN  +++IVRTE SLH PMY+FLCML+ ID+
GPCR: 11  FVLIGIPGLEKAHFWVGFPLLSMYVVAMFGNCIVVFIVRTERSLHAPMYLFLCMLAAIDL 70

PHOR: 74  LISTSSMPKMLAIFWFNSTTIQFDACLLQIFAIHSLSGMESTVLLAMAFDRYVAICHPLR 133
           +STS+MPK+LA+FWF+S  I F+ACL Q+F IH+LS +EST+LLAMAFDRYVAICHPLR
GPCR: 71  ALSTSTMPKILALFWFDSREISFEACLTQMFFIHALSAIESTILLAMAFDRYVAICHPLR 130

PHOR: 134 HATVLTLPRVTKIGVAAVVRGAALMAPLPVFIKQLPFCRSNILSHSYCLHQDVMKLACDD 193
          HA VL      +IG+ AVVRG+    PLP+ IK+L FC SN+LSHSYC+HQDVMKLA  D
GPCR: 131 HAAVLNNTVTAQIGIVAVVRGSLFFFPLPLLIKRLAFCHSNVLSHSYCVHQDVMKLAYAD 190

PHOR: 194 IRVNVVYGLIVIISAIGLDSLLISFSYLLILKTVLGL-TREAQAKAFGTCVSHVCAVFIF 252
             NVVYGL  I+  +G+D + IS SY LI++TVL L ++  +AKAFGTCVSH+  V  F
GPCR: 191 TLPNVVYGLTAILLVMGVDVMFISLSYFLIIRTVLQLPSKSERAKAFGTCVSHIGVVLAF 250

PHOR: 253 YVPFIGLSMVHRFSKRRDSPLPVILANIYLLVPPVLNPIVYGVKTKEIRQRILRLFHVA 311
          YVP IGLS+VHRF        + V++ +IYLL+PPV+NPI+YG KTK+IR R+L +F ++
GPCR: 251 YVPLIGLSVVHRFGNSLHPIVRVVMGDIYLLLPPVINPIIYGAKTKQIRTRVLAMFKIS 309
```

Figure 25: Alignment with human olfactory receptor 5II12 (gi|14423836)

```
Identities = 163/304 (53%), Positives = 214/304 (69%), Gaps = 1/304 (0%)

PHOR: 7   NESSATYFILIGLPGLEEAQFWLAFPLCSLYLIAVLGNLTIIYIVRTEHSLHEPMYIFLC 66
          N +   +F+L G+PGLE +  WL+ PLC +Y +A+ GN  I+  VR E SLHEPMY FL
HOR5: 5   NVTHPAFFLLTGIPGLESSHSWLSGPLCVMYAVALGGNTVILQAVRVEPSLHEPMYYFLS 64

PHOR: 67  MLSGIDILISTSSMPKMLAIFWFNSTTIQFDACLLQIFAIHSLSGMESTVLLAMAFDRYV 126
          MLS  D+ IS +++P +L  F  N+  I FDACL+Q+F IH  S MES +LLAM+FDRYV
HOR5: 65  MLSFSDVAISMATLPTVLRTFCLNARNITFDACLIQMFLIHFFSMMESGILLAMSFDRYV 124

PHOR: 127 AICHPLRHATVLTLPRVTKIGVAAVVRGAALMAPLPVFIKQLPFCRSNILSHSYCLHQDV 186
          AIC PLR+ATVLT   +  +G+ A  R    + PLP  IK+LP CRSN+LSHSYCLH D+
HOR5: 125 AICDPLRYATVLTTEVIAAMGLGAAARSFITLFPLPFLIKRLPICRSNVLSHSYCLHPDM 184

PHOR: 187 MKLACDDIRVNVVYGLIVIISAIGLDSLLISFSYLLILKTVLGL-TREAQAKAFGTCVSH 245
          M+LAC DI +N +YGL V++S  G+D   I  SY+LIL++V+   +RE + KA  TCVSH
HOR5: 185 MRLACADISINSIYGLFVLVSTFGMDLFFIFLSYVLILRSVMATASREERLKALNTCVSH 244

PHOR: 246 VCAVFIFYVPFIGLSMVHRFSKRRDSPLPVILANIYLLVPPVLNPIVYGVKTKEIRQRIL 305
          + AV  FYVP IG+S VHRF K     + V+++N+YL VPPVLNP++Y  KTKEIR+ I
HOR5: 245 ILAVLAFYVPMIGVSTVHRFGKHVPCYIHVLMSNVYLFVPPVLNPLIYSAKTKEIRRAIF 304

PHOR: 306 RLFH 309
          R+FH
HOR5: 305 RMFH 308
```

Figure 31A-31B
Fig. 31A
Fig. 31B
1% FBS
10% FBS
Neo
101P3A11
Neo
101P3A11
Anti Phospho-p38
Anti-p38

Figure 32

| | | Fold change in [cAMP] | |
|---|---|---|---|
| | | PC3-Neo | PC3-PHOR |
| 0.1%FBS | -PTX | 1 | 4.302 |
| | +PTX | 1.403 | 2.577 |
| 10%FBS | -PTX | 2.738 | 6.978 |
| | +PTX | 2.163 | 2.752 |

Fold Change in cAMP accumulation was calculated relative to PC3-neo cells grown in 0.1%FBS

| Treatment | Fold Increase in cAMP PC3 | PC3-PHOR |
|---|---|---|
| 0.1% FBS | 1± 0.42 | 5.73 ± 0.47 |
| PTX 1ug/ml | 0.74± 0.28 | 2.12 ± 0.09 |
| anti-PHOR | 0.97± 0.35 | 4.01± 0.64 |

| Cell Line | Colony number Average |
|---|---|
| 3T3-neo | 0.5 |
| 3T3-101P3A11 | 686 |
| 3T3-Ras | 249 |

Figure 47
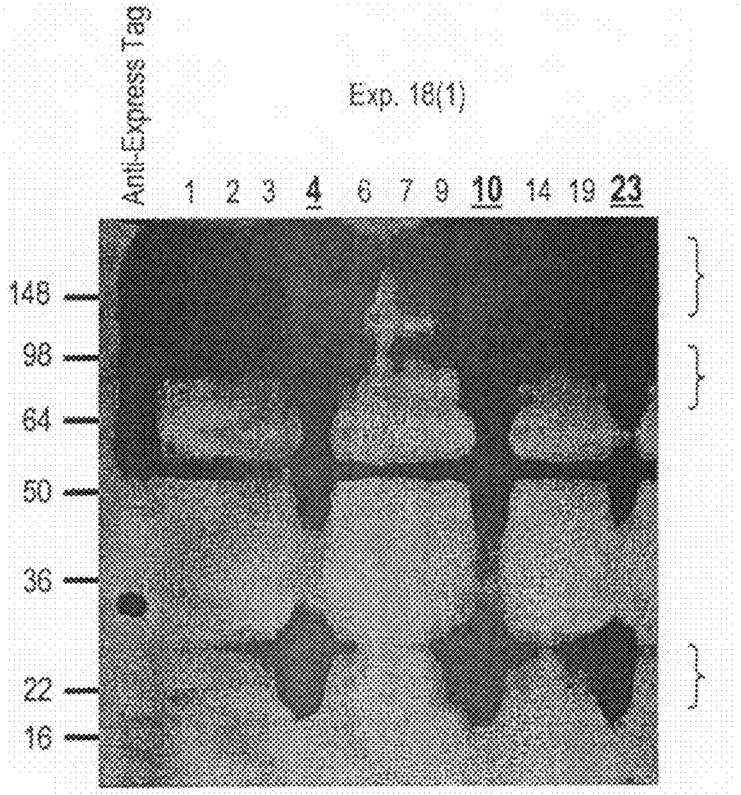
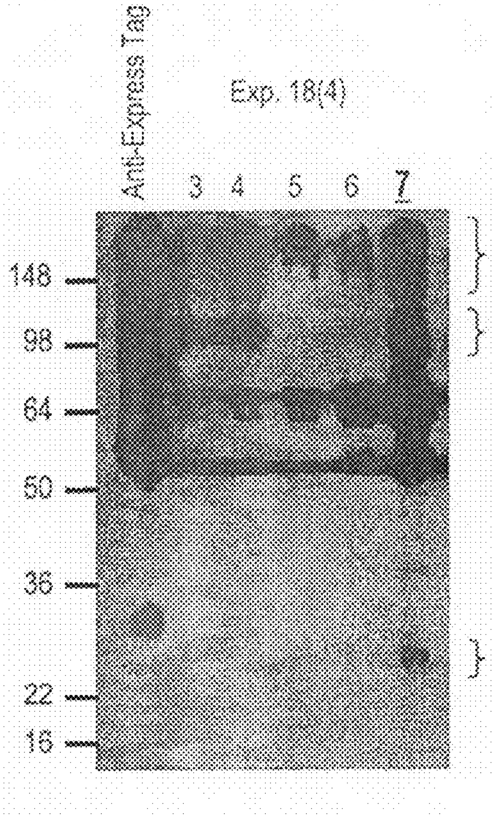

| | 9 | 13 | 16 | 20 | 23 | 27 |
|---|---|---|---|---|---|---|
| 3T3-Neo | 0 | 0 | 0 | 0 | 0 | 0 |
| 3T3-AGS-3 | 156 | 229 | 457 | 958 | 2028 | 4011.2 |
| 3T3-12V-Ras | 140 | 284 | 706 | 3034 | Dead | |

Figure 63
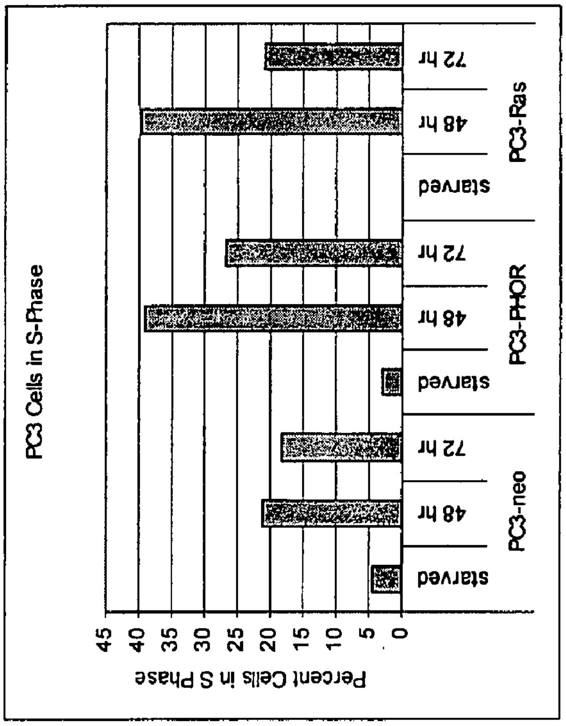
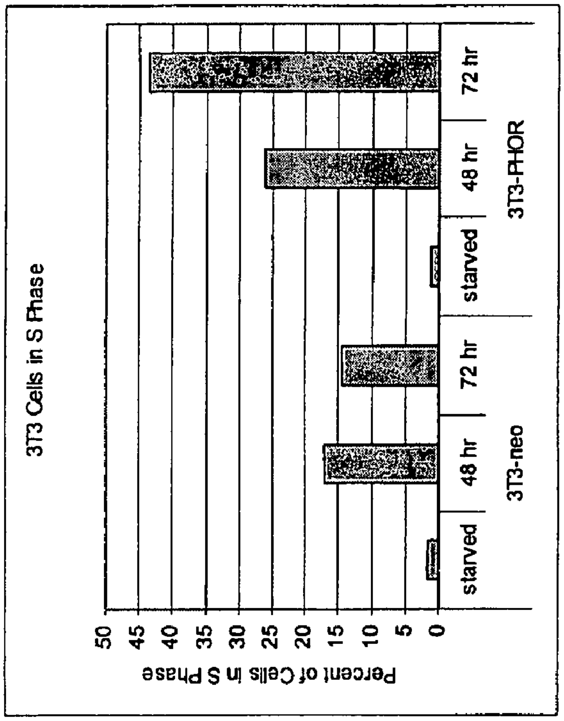

Figure 65A

A) Alignment of 101P3A11 (SEQ ID NO: 33) with MOR 18-1. gi|18479284 (SEQ ID NO: 34)

Score = 522 bits (1345), Expect = e-147
Identities = 295/316 (93%), Positives = 305/316 (96%)

```
Query: 2   MVDPNGNESSATYFILIGLPGLEEAQFWLAFPLCSLYLIAVLGNLTIIYIVRTEHSLHEP 61
           MV  N NESSATYFILIGLPGLEE QFWLAFPLCSLYLIAVLGNLTIIYIVRTEHSLHEP
Sbjct: 1   MVGFNSNESSATYFILIGLPGLEEVQFWLAFPLCSLYLIAVLGNLTIIYIVRTEHSLHEP 60

Query: 62  MYIFLCMLSGIDILISTSSMPKMLAIFWFNSTTIQFDACLLQIFAIHSLSGMESTVLLAM 121
           MYIFLCMLSG+DILISTSSMPKM+AIFWFNSTTIQFDACL+Q+FAIHSLSGMESTVLLAM
Sbjct: 61  MYIFLCMLSGLDILISTSSMPKMMAIFWFNSTTIQFDACLVQMFAIHSLSGMESTVLLAM 120

Query: 122 AFDRYVAICHPLRHATVLTLPRVTKIGVAAVVRGAALMAPLPVFIKQLPFCRSNILSHSY 181
           AFDRYVAICHPLRHATVLTLPRV KIG+AAVVRGA LMAPLPVFIK+LPFCRSNILSHSY
Sbjct: 121 AFDRYVAICHPLRHATVLTLPRVAKIGMAAVVRGAVLMAPLPVFIKRLPFCRSNILSHSY 180

Query: 182 CLHQDVMKLACDDIRVNVVYGLIVIISAIGLDSLLISFSYLLILKTVLGLTREAQAKAFG 241
           CLHQDVMKLAC DIRVN++YGLIVIISAIGLDSLLISFSYLLILKTVLGLTREAQAKAFG
Sbjct: 181 CLHQDVMKLACADIRVNIIYGLIVIISAIGLDSLLISFSYLLILKTVLGLTREAQAKAFG 240

Query: 242 TCVSHVCAVFIFYVPFIGLSMVHRFSKRRDSPLPVILANIYLLVPPVLNPIVYGVKTKEI 301
           TCVSHVCAVFIFYVPFIGLSMVHRFSKRRDS LPVI+ANIYLLVPPVLNPIVYGVKTKEI
Sbjct: 241 TCVSHVCAVFIFYVPFIGLSMVHRFSKRRDSLLPVIMANIYLLVPPVLNPIVYGVKTKEI 300

Query: 302 RQRILRLFHVATHASE 317
           RQRILRLF V TH S+
Sbjct: 301 RQRILRLFLVTTHTSD 316
```

B) Alignment of 101P3A11 (SEQ ID NO: 35) with Rat Olfactory Receptor Ralc (gi|18202242) (SEQ ID NO: 36)

Score = 339 bits (869), Expect = 2e-92
Identities = 179/299 (59%), Positives = 231/299 (76%), Gaps = 1/299 (0%)

```
Query: 15  FILIGLPGLEEAQFWLAFPLCSLYLIAVLGNLTIIYIVRTEHSLHEPMYIFLCMLSGIDI 74
           F+LIG+PGLEEA FW  FPL S+Y +A+ GN  +++IVRTE SLH PMY+FLCML+ ID+
Sbjct: 11  FMLIGIPGLEEAHFWFGFPLLSMYAVALFGNCIVVFIVRTERSLHAPMYLFLCMLAAIDL 70

Query: 75  LISTSSMPKMLAIFWFNSTTIQFDACLLQIFAIHSLSGMESTVLLAMAFDRYVAICHPLR 134
            +STS+MPK+LA+FWF+S  I FDACL Q+F IH+LS +EST+LLAMAFDRYVAICHPLR
Sbjct: 71  ALSTSTMPKILALFWFDSREITFDACLAQMFFIHALSAIESTILLAMAFDRYVAICHPLR 130

Query: 135 HATVLTLPRVTKIGVAAVVRGAALMAPLPVFIKQLPFCRSNILSHSYCLHQDVMKLACDD 194
           HA VL      +IG+ A+VRG+     PLP+ IK+L FC SN+LSHSYC+HQDVMKLA  D
Sbjct: 131 HAAVLNNTVTVQIGMVALVRGSLFFFPLPLLIKRLAFCHSNVLSHSYCVHQDVMKLAYTD 190

Query: 195 IRVNVVYGLIVIISAIGLDSLLISFSYLLILKTVLGL-TREAQAKAFGTCVSHVCAVFIF 253
              NVVYGL  I+  +G+D + IS SY LI++ VL L ++  +AKAFGTCVSH+  V  F
Sbjct: 191 TLPNVVYGLTAILLVMGVDVMFISLSYFLIIRAVLQLPSKSERAKAFGTCVSHIGVVLAF 250

Query: 254 YVPFIGLSMVHRFSKRRDSPLPVILANIYLLVPPVLNPIVYGVKTKEIRQRILRLFHVA 312
           YVP IGLS+VHRF    D  + V++ ++YLL+PPV+NPI+YG KTK+IR R+L +F ++
Sbjct: 251 YVPLIGLSVVHRFGNSLDPIVHVLMGDVYLLLPPVINPIIYGAKTKQIRTRVLAMFKIS 309
```

C) Alignment of 101P3A11 (SEQ ID NO: 37) with Human Prostate Specific GPCR (gi|13540539), aka_HUMAN Olfactory receptor 51E2 (SEQ ID NO: 38)

Score = 338 bits (867), Expect = 4e-92
Identities = 179/299 (59%), Positives = 233/299 (77%), Gaps = 1/299 (0%)

```
Query: 15  FILIGLPGLEEAQFWLAFPLCSLYLIAVLGNLTIIYIVRTEHSLHEPMYIFLCMLSGIDI 74
           F+LIG+PGLE+A FW+ FPL S+Y++A+ GN  +++IVRTE SLH PMY+FLCML+ ID+
Sbjct: 11  FVLIGIPGLEKAHFWVGFPLLSMYVVAMFGNCIVVFIVRTERSLHAPMYLFLCMLAAIDL 70
```

Figure 65B

```
Query: 75  LISTSSMPKMLAIFWFNSTTIQFDACLLQIFAIHSLSGMESTVLLAMAFDRYVAICHPLR 134
            +STS+MPK+LA+FWF+S  I F+ACL Q+F IH+LS +EST+LLAMAFDRYVAICHPLR
Sbjct: 71  ALSTSTMPKILALFWFDSREISFEACLTQMFFIHALSAIESTILLAMAFDRYVAICHPLR 130

Query: 135 HATVLTLPRVTKIGVAAVVRGAALMAPLPVFIKQLPFCRSNILSHSYCLHQDVMKLACDD 194
           HA VL      +IG+ AVVRG+    PLP+ IK+L FC SN+LSHSYC+HQDVMKLA  D
Sbjct: 131 HAAVLNNTVTAQIGIVAVVRGSLFFFPLPLLIKRLAFCHSNVLSHSYCVHQDVMKLAYAD 190

Query: 195 IRVNVVYGLIVIISAIGLDSLLISFSYLLILKTVLGL-TREAQAKAFGTCVSHVCAVFIF 253
              NVVYGL  I+  +G+D + IS SY LI++TVL L ++  +AKAFGTCVSH+  V   F
Sbjct: 191 TLPNVVYGLTAILLVMGVDVMFISLSYFLIIRTVLQLPSKSERAKAFGTCVSHIGVVLAF 250

Query: 254 YVPFIGLSMVHRFSKRRDSPLPVILANIYLLVPPVLNPIVYGVKTKEIRQRILRLFHVA 312
           YVP IGLS+VHRF       + V++ +IYLL+PPV+NPI+YG KTK+IR R+L +F ++
Sbjct: 251 YVPLIGLSVVHRFGNSLHPIVRVVMGDIYLLLPPVINPIIYGAKTKQIRTRVLAMFKIS 309
```

Figure 67A. The cDNA and amino acid sequence of the open reading frames of codon optimized s101P3A11 v.1

```
  1 M  M  V  D  P  N  G  N  E  S  S  A  T  Y  F  I  L  I  G  L
  1 atgatggtggaccccaacggcaacgagtcctccgccacctacttcatcctgatcggcctg
 21 P  G  L  E  E  A  Q  F  W  L  A  F  P  L  C  S  L  Y  L  I
 61 cccggcctggaggaggcccagttctggctggccttccccctgtgctccctgtacctgatc
 41 A  V  L  G  N  L  T  I  I  Y  I  V  R  T  E  H  S  L  H  E
121 gccgtgctgggcaacctgaccatcatctacatcgtgcgcaccgagcactccctgcacgag
 61 P  M  Y  I  F  L  C  M  L  S  G  I  D  I  L  I  S  T  S  S
181 cccatgtacatcttcctgtgcatgctgtccggcatcgacatcctgatctccacctcctcc
 81 M  P  K  M  L  A  I  F  W  F  N  S  T  T  I  Q  F  D  A  C
241 atgcccaagatgctggccatcttctggttcaactccaccaccatccagttcgacgcctgc
101 L  L  Q  I  F  A  I  H  S  L  S  G  M  E  S  T  V  L  L  A
301 ctgctgcagatcttcgccatccactccctgtccggcatggagtccaccgtgctgctggcc
121 M  A  F  D  R  Y  V  A  I  C  H  P  L  R  H  A  T  V  L  T
361 atggccttcgaccgctacgtggccatctgccacccctgcgccacgccaccgtgctgacc
141 L  P  R  V  T  K  I  G  V  A  A  V  V  R  G  A  A  L  M  A
421 ctgccccgcgtgaccaagatcggcgtggccgccgtggtgcgcggcgccgccctgatggcc
161 P  L  P  V  F  I  K  Q  L  P  F  C  R  S  N  I  L  S  H  S
481 cccctgcccgtgttcatcaagcagctgcccttctgccgctccaacatcctgtcccactcc
181 Y  C  L  H  Q  D  V  M  K  L  A  C  D  D  I  R  V  N  V  V
541 tactgcctgcaccaggacgtgatgaagctggcctgcgacgacatccgcgtgaacgtggtg
201 Y  G  L  I  V  I  I  S  A  I  G  L  D  S  L  L  I  S  F  S
601 tacggcctgatcgtgatcatctccgccatcggcctggactccctgctgatctccttctcc
221 Y  L  L  I  L  K  T  V  L  G  L  T  R  E  A  Q  A  K  A  F
661 tacctgctgatcctgaagaccgtgctgggcctgacccgcgaggcccaggccaaggccttc
241 G  T  C  V  S  H  V  C  A  V  F  I  F  Y  V  P  F  I  G  L
721 ggcacctgcgtgtcccacgtgtgcgccgtgttcatcttctacgtgcccttcatcggcctg
261 S  M  V  H  R  F  S  K  R  R  D  S  P  L  P  V  I  L  A  N
781 tccatggtgcaccgcttctccaagcgccgcgactcccccctgcccgtgatcctggccaac
281 I  Y  L  L  V  P  P  V  L  N  P  I  V  Y  G  V  K  T  K  E
841 atctacctgctggtgccccccgtgctgaaccccatcgtgtacggcgtgaagaccaaggag
301 I  R  Q  R  I  L  R  L  F  H  V  A  T  H  A  S  E  P  *
901 atccgccagcgcatcctgcgcctgttccacgtggccacccacgcctccgagccctag
```

Figure 67B. The cDNA and amino acid sequence of the open reading frames of codon optimized s101P3A11 v.3.

```
  1 M  M  V  D  P  N  G  N  E  S  S  A  T  Y  F  I  L  I  G  L
  1 atgatggtggaccccaacggcaacgagtcctccgccacctacttcatcctgatcggcctg
 21 P  G  L  E  E  A  Q  F  W  L  A  F  P  L  C  S  L  Y  L  I
 61 cccggcctggaggaggcccagttctggctggccttcccctgtgctccctgtacctgatc
 41 A  V  L  G  N  L  T  I  I  Y  I  V  R  T  E  H  S  L  H  E
121 gccgtgctgggcaacctgaccatcatctacatcgtgcgcaccgagcactccctgcacgag
 61 P  M  Y  I  F  L  C  M  L  S  G  I  D  I  L  I  S  T  S  S
181 cccatgtacatcttcctgtgcatgctgtccggcatcgacatcctgatctccacctcctcc
 81 M  P  K  M  L  A  I  F  W  F  N  S  T  T  I  Q  F  D  A  C
241 atgcccaagatgctggccatcttctggttcaactccaccaccatccagttcgacgcctgc
101 L  L  Q  I  F  A  I  H  S  L  S  G  M  E  S  T  V  L  L  A
301 ctgctgcagatcttcgccatccactccctgtccggcatggagtccaccgtgctgctggcc
121 M  A  F  D  R  Y  V  A  I  C  H  P  L  R  H  A  T  V  L  T
361 atggccttcgaccgctacgtggccatctgccacccctgcgccacgccaccgtgctgacc
141 L  P  R  V  T  K  I  G  V  A  A  V  V  R  G  A  A  L  M  A
421 ctgccccgcgtgaccaagatcggcgtggccgccgtggtgcgcggcgccgccctgatggcc
161 P  L  P  V  F  I  K  Q  L  P  F  C  R  S  N  I  L  S  H  S
481 cccctgcccgtgttcatcaagcagctgcccttctgccgctccaacatcctgtcccactcc
181 Y  C  L  H  Q  D  V  M  K  L  A  C  D  D  I  R  V  N  V  V
541 tactgcctgcaccaggacgtgatgaagctggcctgcgacgacatccgcgtgaacgtggtg
201 Y  G  L  I  V  I  I  S  A  I  G  L  D  S  L  L  I  S  F  S
601 tacggcctgatcgtgatcatctccgccatcggcctggactccctgctgatctccttctcc
221 Y  L  L  I  L  K  T  V  L  G  L  T  R  E  A  Q  A  K  A  F
661 tacctgctgatcctgaagaccgtgctgggcctgacccgcgaggcccaggccaaggccttc
241 G  T  C  V  S  H  V  C  A  V  F  I  F  Y  V  P  F  I  G  L
721 ggcacctgcgtgtcccacgtgtgcgccgtgttcatcttctacgtgcccttcatcggcctg
261 S  M  V  H  R  F  S  K  R  R  D  S  P  L  P  V  I  L  A  N
781 tccatggtgcaccgcttctccaagcgccgcgactcccccctgcccgtgatcctggccaac
281 I  Y  L  L  V  P  P  V  L  N  P  I  V  Y  G  V  K  T  K  E
841 atctacctgctggtgccccccgtgctgaaccccatcgtgtacggcgtgaagaccaaggag
301 I  R  Q  R  I  L  R  L  F  H  V  A  T  H  A  S  E  P  *
901 atccgccagcgcatcctgcgcctgttccacgtggccacccacgcctccgagccctag
```

Figure 69A

Nucleotide sequence alignment of 101P3A11 v.1 (SEQ ID NO: 27) and 101P3A11 v.2 (SEQ ID NO: 29)

```
101P3A11v.1      CAGAGAGGCTGTATTTCAGTGCAGCCTGCCAGACCTCTTCTGGAGGAAGACTGGACAAAG 60
101P3A11v.2      CAGAGAGGCTGTATTTCAGTGCAGCCTGCCAGACCTCTTCTGGAGGAAGACTGGACAAAG 60
                 ************************************************************

101P3A11v.1      GGGGTCACACATTCCTTCCATACGGTTGAGCCTCTACCTGCCTGGTGCTGGTCACAGTTC 120
101P3A11v.2      GGGGTCACACATTCCTTCCATACGGTTGAGCCTCTACCTGCCTGGTGCTGGTCACAGTTC 120
                 ************************************************************

101P3A11v.1      AGCTTCTTCATGATGGTGGATCCCAATGGCAATGAATCCAGTGCTACATACTTCATCCTA 180
101P3A11v.2      AGCTTCTTCATGATGGTGGATCCCAATGGCAATGAATCCAGTGCTACATACTTCATCCTA 180
                 ************************************************************

101P3A11v.1      ATAGGCCTCCCTGGTTTAGAAGAGGCTCAGTTCTGGTTGGCCTTCCCATTGTGCTCCCTC 240
101P3A11v.2      ATAGGCCTCCCTGGTTTAGAAGAGGCTCAGTTCTGGTTGGCCTTCCCATTGTGCTCCCTC 240
                 ************************************************************

101P3A11v.1      TACCTTATTGCTGTGCTAGGTAACTTGACAATCATCTACATTGTGCGGACTGAGCACAGC 300
101P3A11v.2      TACCTTATTGCTGTGCTAG----------------------------------------- 259
                 *******************

101P3A11v.1      CTGCATGAGCCCATGTATATATTTCTTTGCATGCTTTCAGGCATTGACATCCTCATCTCC 360
101P3A11v.2      ------------------------------------------------------------

101P3A11v.1      ACCTCATCCATGCCCAAAATGCTGGCCATCTTCTGGTTCAATTCCACTACCATCCAGTTT 420
101P3A11v.2      ------------------------------------------------------------

101P3A11v.1      GATGCTTGTCTGCTACAGATTTTTGCCATCCACTCCTTATCTGGCATGGAATCCACAGTG 480
101P3A11v.2      ------------------------------------------------------------

101P3A11v.1      CTGCTGGCCATGGCTTTTGACCGCTATGTGGCCATCTGTCACCCACTGCGCCATGCCACA 540
101P3A11v.2      ------------------------------------------------------------

101P3A11v.1      GTACTTACGTTGCCTCGTGTCACCAAAATTGGTGTGGCTGCTGTGGTGCGGGGGGCTGCA 600
101P3A11v.2      ------------------------------------------------------------

101P3A11v.1      CTGATGGCACCCCTTCCTGTCTTCATCAAGCAGCTGCCCTTCTGCCGCTCCAATATCCTT 660
101P3A11v.2      ------------------------------------------------------------

101P3A11v.1      TCCCATTCCTACTGCCTACACCAAGATGTCATGAAGCTGGCCTGTGATGATATCCGGGTC 720
101P3A11v.2      ------------------------------------------------------------

101P3A11v.1      AATGTCGTCTATGGCCTTATCGTCATCATCTCCGCCATTGGCCTGGACTCACTTCTCATC 780
101P3A11v.2      ------------------------------------------------------------

101P3A11v.1      TCCTTCTCATATCTGCTTATTCTTAAGACTGTGTTGGGCTTGACACGTGAAGCCCAGGCC 840
101P3A11v.2      ------------------------------------------------------------

101P3A11v.1      AAGGCATTTGGCACTTGCGTCTCTCATGTGTGTGCTGTGTTCATATTCTATGTACCTTTC 900
101P3A11v.2      ------------------------------------------------------------

101P3A11v.1      ATTGGATTGTCCATGGTGCATCGCTTTAGCAAGCGGCGTGACTCTCCGCTGCCCGTCATC 960
101P3A11v.2      -----------------------------CAAGCGGCGTGACTCTCCGCTGCCCGTCATC 290
```

Figure 69B

```
                                                  ********************************
101P3A11v.1       TTGGCCAATATCTATCTGCTGGTTCCTCCTGTGCTCAACCCAATTGTCTATGGAGTGAAG
1020
101P3A11v.2       TTGGCCAATATCTATCTGCTGGTTCCTCCTGTGCTCAACCCAATTGTCTATGGAGTGAAG 350
                  ************************************************************

101P3A11v.1       ACAAAGGAGATTCGACAGCGCATCCTTCGACTTTTCCATGTGGCCACACACGCTTCAGAG
1080
101P3A11v.2       ACAAAGGAGATTCGACAGCGCATCCTTCGACTTTTCCATGTGGCCACACACGCTTCAGAG 410
                  ************************************************************

101P3A11v.1       CCCTAGGTGTCAGTGATCAAACTTCTTTTCCATTCAGAGTCCTCTGATTCAGATTTTAAT
1140
101P3A11v.2       CCCTAGGTGTCAGTGATCAAACTTCTTTTCCATTCAGAGTCCTCTGATTCAGATTTTAAT 470
                  ************************************************************

101P3A11v.1       GTTAACATTTTGGAAGACAGTATTCAGAAAAAAAATTTCCTTAATAAAAAATACAACTCA
1200
101P3A11v.2       GTTAACATTTTGGAAGACAGTATTCAGAAAAAAAATTTCCTTAATAAAAAATACAACTCA 530
                  ************************************************************

101P3A11v.1       GATCCTTCAAATATGAAACTGGTTGGGGAATCTCCATTTTTTCAATATTATTTTCTTCTT
1260
101P3A11v.2       GATCCTTCAAATATGAAACTGGTTGGGGAATCTCCATTTTTTCAATATTATTTTCTTCTT 590
                  ************************************************************

101P3A11v.1       TGTTTTCTTGCTACATATAATTATTAATACCCTGACTAGGTTGTGGTTGGAGGGTTATTA
1320
101P3A11v.2       TGTTTTCTTGCTACATATAATTATTAATACCCTGACTAGGTTGTGGTTGGAGGGTTATTA 650
                  ************************************************************

101P3A11v.1       CTTTTCATTTTACCATGCAGTCCAAATCTAAACTGCTTCTACTGATGGTTTACAGCATTC
1380
101P3A11v.2       CTTTTCATTTTACCATGCAGTCCAAATCTAAACTGCTTCTACTGATGGTTTACAGCATTC 710
                  ************************************************************

101P3A11v.1       TGAGATAAGAATGGTACATCTAGAGAACATTTGCCAAAGGCCTAAGCACGGCAAAGGAAA
1440
101P3A11v.2       TGAGATAAGAATGGTACATCTAGAGAACATTTGCCAAAGGCCTAAGCACGGCAAAGGAAA 770
                  ************************************************************

101P3A11v.1       ATAAACACAGAATATAATAAAATGAGATAATCTAGCTTAAAACTATAACTTCCTCTTCAG
1500
101P3A11v.2       ATAAACACAGAATATAATAAAATGAGATAATCTAGCTTAAAACTATAACTTCCTCTTCAG 830
                  ************************************************************

101P3A11v.1       AACTCCCAACCACATTGGATCTCAGAAAAATGCTGTCTTCAAAATGACTTCTACAGAGAA
1560
101P3A11v.2       AACTCCCAACCACATTGGATCTCAGAAAAATGCTGTCTTCAAAATGACTTCTACAGAGAA 890
                  ************************************************************

101P3A11v.1       GAAATAATTTTTCCTCTGGACACTAGCACTTAAGGGGAAGATTGGAAGTAAAGCCTTGAA
1620
101P3A11v.2       GAAATAATTTTTCCTCTGGACACTAGCACTTAAGGGGAAGATTGGAAGTAAAGCCTTGAA 950
                  ************************************************************

101P3A11v.1       AAGAGTACATTTACCTACGTTAATGAAAGTTGACACACTGTTCTGAGAGTTTTCACAGCA
1680
101P3A11v.2       AAGAGTACATTTACCTACGTTAATGAAAGTTGACACACTGTTCTGAGAGTTTTCACAGCA
1010
                  ************************************************************
```

Figure 69C

```
101P3A11v.1     TATGGACCCTGTTTTTCCTATTTAATTTTCTTATCAACCCTTTAATTAGGCAAAGATATT
1740
101P3A11v.2     TATGGACCCTGTTTTTCCTATTTAATTTTCTTATCAACCCTTTAATTAGGCAAAGATATT
1070
                ************************************************************

101P3A11v.1     ATTAGTACCCTCATTGTAGCCATGGGAAAATTGATGTTCAGTGGGGATCAGTGAATTAAA
1800
101P3A11v.2     ATTAGTACCCTCATTGTAGCCATGGGAAAATTGATGTTCAGTGGGGATCAGTGAATTAAA
1130
                ************************************************************

101P3A11v.1     TGGGGTCATACAAGTATAAAAATTAAAAAAAAAAAAGACTTCATGCCCAATCTCATATGA
1860
101P3A11v.2     TGGGGTCATACAAGTATAAAAATTAAAAAAAAAAAAGACTTCATGCCCAATCTCATATGA
1190
                ************************************************************

101P3A11v.1     TGTGGAAGAACTGTTAGAGAGACCAACAGGGTAGTGGGTTAGAGATTTCCAGAGTCTTAC
1920
101P3A11v.2     TGTGGAAGAACTGTTAGAGAGACCAACAGGGTAGTGGGTTAGAGATTTCCAGAGTCTTAC
1250
                ************************************************************

101P3A11v.1     ATTTTCTAGAGGAGGTATTTAATTTCTTCTCACTCATCCAGTGTTGTATTTAGGAATTTC
1980
101P3A11v.2     ATTTTCTAGAGGAGGTATTTAATTTCTTCTCACTCATCCAGTGTTGTATTTAGGAATTTC
1310
                ************************************************************

101P3A11v.1     CTGGCAACAGAACTCATGGCTTTAATCCCACTAGCTATTGCTTATTGTCCTGGTCCAATT
2040
101P3A11v.2     CTGGCAACAGAACTCATGGCTTTAATCCCACTAGCTATTGCTTATTGTCCTGGTCCAATT
1370
                ************************************************************

101P3A11v.1     GCCAATTACCTGTGTCTTGGAAGAAGTGATTTCTAGGTTCACCATTATGGAAGATTCTTA
2100
101P3A11v.2     GCCAATTACCTGTGTCTTGGAAGAAGTGATTTCTAGGTTCACCATTATGGAAGATTCTTA
1430
                ************************************************************

101P3A11v.1     TTCAGAAAGTCTGCATAGGGCTTATAGCAAGTTATTTATTTTTAAAAGTTCCATAGGTGA
2160
101P3A11v.2     TTCAGAAAGTCTGCATAGGGCTTATAGCAAGTTATTTATTTTTAAAAGTTCCATAGGTGA
1490
                ************************************************************

101P3A11v.1     TTCTGATAGGCAGTGAGGTTAGGGAGCCACCAGTTATGATGGGAAGTATGGAATGGCAGG
2220
101P3A11v.2     TTCTGATAGGCAGTGAGGTTAGGGAGCCACCAGTTATGATGGGAAGTATGGAATGGCAGG
1550
                ************************************************************

101P3A11v.1     TCTTGAAGATAACATTGGCCTTTTGAGTGTGACTCGTAGCTGGAAAGTGAGGGAATCTTC
2280
101P3A11v.2     TCTTGAAGATAACATTGGCCTTTTGAGTGTGACTCGTAGCTGGAAAGTGAGGGAATCTTC
1610
                ************************************************************

101P3A11v.1     AGGACCATGCTTTATTTGGGGCTTTGTGCAGTATGGAACAGGGACTTTGAGACCAGGAAA
2340
101P3A11v.2     AGGACCATGCTTTATTTGGGGCTTTGTGCAGTATGGAACAGGGACTTTGAGACCAGGAAA
1670
```

Figure 69D

```
                    ************************************************************
101P3A11v.1         GCAATCTGACTTAGGCATGGGAATCAGGCATTTTTGCTTCTGAGGGGCTATTACCAAGGG
2400
101P3A11v.2         GCAATCTGACTTAGGCATGGGAATCAGGCATTTTTGCTTCTGAGGGGCTATTACCAAGGG
1730
                    ************************************************************

101P3A11v.1         TTAATAGGTTTCATCTTCAACAGGATATGACAACAGTGTTAACCAAGAAACTCAAATTAC
2460
101P3A11v.2         TTAATAGGTTTCATCTTCAACAGGATATGACAACAGTGTTAACCAAGAAACTCAAATTAC
1790
                    ************************************************************

101P3A11v.1         AAATACTAAAACATGTGATCATATATGTGGTAAGTTTCATTTTCTTTTTCAATCCTCAGG
2520
101P3A11v.2         AAATACTAAAACATGTGATCATATATGTGGTAAGTTTCATTTTCTTTTTCAATCCTCAGG
1850
                    ************************************************************

101P3A11v.1         TTCCCTGATATGGATTCCTATAACATGCTTTCATCCCCTTTTGTAATGGATATCATATTT
2580
101P3A11v.2         TTCCCTGATATGGATTCCTATAACATGCTTTCATCCCCTTTTGTAATGGATATCATATTT
1910
                    ************************************************************

101P3A11v.1         GGAAATGCCTATTTAATACTTGTATTTGCTGCTGGACTGTAAGCCCATGAGGGCACTGTT
2640
101P3A11v.2         GGAAATGCCTATTTAATACTTGTATTTGCTGCTGGACTGTAAGCCCATGAGGGCACTGTT
1970
                    ************************************************************

101P3A11v.1         TATTATTGAATGTCATCTCTGTTCATCATTGACTGCTCTTTGCTCATCATTGAATCCCCC
2700
101P3A11v.2         TATTATTGAATGTCATCTCTGTTCATCATTGACTGCTCTTTGCTCATCATTGAATCCCCC
2030
                    ************************************************************

101P3A11v.1         AGCAAAGTGCCTAGAACATAATAGTGCTTATGCTTGACACCGGTTATTTTTCATCAAACC
2760
101P3A11v.2         AGCAAAGTGCCTAGAACATAATAGTGCTTATGCTTGACACCGGTTATTTTTCATCAAACC
2090
                    ************************************************************

101P3A11v.1         TGATTCCTTCTGTCCTGAACACATAGCCAGGCAATTTTCCAGCCTTCTTTGAGTTGGGTA
2820
101P3A11v.2         TGATTCCTTCTGTCCTGAACACATAGCCAGGCAATTTTCCAGCCTTCTTTGAGTTGGGTA
2150
                    ************************************************************

101P3A11v.1         TTATTAAATTCTGGCCATTACTTCCAATGTGAGTGGAAGTGACATGTGCAATTTCTATAC
2880
101P3A11v.2         TTATTAAATTCTGGCCATTACTTCCAATGTGAGTGGAAGTGACATGTGCAATTTCTATAC
2210
                    ************************************************************

101P3A11v.1         CTGGCTCATAAAACCCTCCCATGTGCAGCCTTTCATGTTGACATTAAATGTGACTTGGGA
2940
101P3A11v.2         CTGGCTCATAAAACCCTCCCATGTGCAGCCTTTCATGTTGACATTAAATGTGACTTGGGA
2270
                    ************************************************************
```

Figure 69E

```
101P3A11v.1        AGCTATGTGTTACACAGAGTAAATCACCAGAAGCCTGGATTTCTGAAAAAACTGTGCAGA
3000
101P3A11v.2        AGCTATGTGTTACACAGAGTAAATCACCAGAAGCCTGGATTTCTGAAAAAACTGTGCAGA
2330
                   ************************************************************

101P3A11v.1        GCCAAACCTCTGTCATTTGCAACTCCCACTTGTATTTGTACGAGGCAGTTGGATAAGTGA
3060
101P3A11v.2        GCCAAACCTCTGTCATTTGCAACTCCCACTTGTATTTGTACGAGGCAGTTGGATAAGTGA
2390
                   ************************************************************

101P3A11v.1        AAAATAAAGTACTATTGTGTCAAGAAAAAAAAAAAAAAAAAAAAAAAAAAAAAAAAAAAA
3120
101P3A11v.2        AAAATAAAGTACTATTGTGTCAAGAAAAAAAAAAAAAAAAAAAAAAAAAAAAAAAAAAAA
2450
                   ************************************************************

101P3A11v.1        AAAAAAAAAAAAAAAA 3136
101P3A11v.2        AAAAAAAAAAAAAAAA 2466
                   ****************
```

Figure 70. Peptide sequences of protein coded by 101P3A11 v.2 (SEQ ID NO:30)

```
MMVDPNGNES SATYFILIGL PGLEEAQFWL AFPLCSLYLI AVLASGVTLR CPSSWPISIC      60
WFLLCSTQLS ME                                                         72
```

Figure 71. Amino acid sequence alignment of 101P3A11 v.1 (SEQ ID NO:19) and 101P3A11 v.2 (SEQ ID NO: 30)

```
101P3A11v.1       MMVDPNGNESSATYFILIGLPGLEEAQFWLAFPLCSLYLIAVLGNLTIIYIVRTEHSLHE 60
101P3A11v.2_      MMVDPNGNESSATYFILIGLPGLEEAQFWLAFPLCSLYLIAVLA---------------- 44
                  ********************************************.. :      :. :  .

101P3A11v.1       PMYIFLCMLSGIDILISTSSMPKMLAIFWFNSTTIQFDACLLQIFAIHSLSGMESTVLLA
120
101P3A11v.2_      ---------SGVTLRCP-SSWP--ISICWF-------------LLCSTQLS-ME------ 72
                  .     .  **: :  .:** *. ::* **.::: . .:.  .::.  .**.**::   :

101P3A11v.1       MAFDRYVAICHPLRHATVLTLPRVTKIGVAAVVRGAALMAPLPVFIKQLPFCRSNILSHS
180
101P3A11v.2_      ------------------------------------------------------------
                   : .   : . .   :: : .  :. . ::   .:: :. .    . . . . :.  : :

101P3A11v.1       YCLHQDVMKLACDDIRVNVVYGLIVIISAIGLDSLLISFSYLLILKTVLGLTREAQAKAF
240
101P3A11v.2_      ------------------------------------------------------------
                   .  .. . :...   .   .      :: . .:   : :     .:  . : .:.:.:

101P3A11v.1       GTCVSHVCAVFIFYVPFIGLSMVHRFSKRRDSPLPVILANIYLLVPPVLNPIVYGVKTKE
300
101P3A11v.2_      ------------------------------------------------------------
                  .:. :  .:       .  . :     :.  .:. .    :.      ..  ..   . .:..

101P3A11v.1       IRQRILRLFHVATHASEP 318
101P3A11v.2_      ------------------
                    .        :: ::..
```

PROTEIN SHOWING ENHANCED EXPRESSION IN CANCER CELLS

CROSS-REFERENCE TO RELATED APPLICATIONS

This application is a divisional application of U.S. Ser. No. 10/147,368 filed May 15, 2002 and now allowed which is a continuation-in-part of U.S. application Ser. No. 10/001,469, filed Oct. 31, 2001, and now allowed, which is a continuation-in-part of U.S. application Ser. No. 09/680,728, filed Oct. 5, 2000, now U.S. Pat. No. 6,799,631, which claims benefit of priority from U.S. Provisional Application Ser. No. 60/157,902, filed Oct. 5, 1999. application Ser. No. 10/001,469 also claims priority under 35 U.S.C. §119(e) to Provisional Application 60/291,118, filed May 15, 2001. Each of the applications referenced in this paragraph are hereby incorporated in their entireties as if fully set forth herein.

REFERENCE TO SEQUENCE LISTING SUBMITTED VIA EFS-WEB

This application was filed electronically via the USPTO EFS-WEB server, as authorized and set forth in MPEP §1730 II.B.2.(a)(A), and this electronic filing includes an electronically submitted sequence (SEQ ID) listing; the entire content of this sequence listing is herein incorporated by reference for all purposes. The sequence listing is identified on the electronically filed .txt file as follows:

| File Name | Date of Creation | Size (bytes) |
|---|---|---|
| 511582002413.txt | May 17, 2007 | 77,824 |

FIELD OF THE INVENTION

The invention described herein relates to a gene and its encoded protein, termed 101P3A11 or PHOR-1, expressed in certain cancers, and to diagnostic and therapeutic methods and compositions useful in the management of cancers that express 101P3A11. The PHOR-1 cDNA was deposited under the terms of the Budapest Treaty on Jul. 2, 1999, with the American Type Culture Collection (ATCC; 10801 University Blvd., Manassas, Va. 20110-2209 USA) as plasmid p101P3A11, and has been assigned Accession No. PTA-312.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep. 2 (9): 1445-51), STEAP (Hubert, et al., Proc Natl Acad Sci USA. 1999 Dec. 7; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and 8 per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992-1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 1% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996. In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992-1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992-1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequalae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992-1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

G protein-coupled receptors (GPCR) share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as the carboxy terminus, interact with the G protein. There is evidence that in certain GPCRs the first intracellular loop is also important for G-protein interactions. Currently, Gq, Gs, Gi, and Go are G proteins that have been identified.

Under physiological conditions, GPCRs exist in the cell membrane in equilibrium between two different states or conformations: an "inactive" state and an "active" state. A receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries, including but not exclusively limited to, modifications to the amino acid sequence of the receptor, provide alternative mechanisms other than ligands to stabilize the active state conformation. These approaches effectively stabilize the receptor in an active state by simulating the effect of a ligand binding to the receptor. Stabilization by such ligand-independent approaches is termed "constitutive receptor activation." A receptor for which the endogenous ligand is unknown or not identified is referred to as an "orphan receptor."

Concerning traditional compound screening, in general, the use of an orphan receptor for screening purposes to identify compounds that modulate a biological response associated with such receptor has not been possible. This is because the traditional "dogma" regarding screening of compounds mandates that the ligand for the receptor be known, whereby compounds that competitively bind with the receptor, i.e., by interfering or blocking the binding of the natural ligand with the receptor, are selected. By definition, then, this approach has no applicability with respect to orphan receptors. Thus, by adhering to this dogmatic approach to the discovery of therapeutics, the art, in essence, has taught and has been taught to forsake the use of orphan receptors unless and until the natural ligand for the receptor is discovered. The pursuit of an endogenous ligand for an orphan receptor can take several years and cost millions of dollars.

Furthermore, and given that there are an estimated 2,000 GPCRs in the human genome, the majority of which being orphan receptors, the traditional dogma castigates a creative approach to the discovery of therapeutics to these receptors. Numerous orphan G protein-coupled receptors are constitutively active in their endogenous state. Mouse olfactory receptor MOR 18-1 (>gi|18479284, FIG. 65). The endogenous ligand for 101P3A11 is unknown.

SUMMARY OF THE INVENTION

The present invention relates to a gene, designated 101P3A11, that has now been found to be over-expressed in the cancer(s) listed in Table I. Northern blot expression analysis of 101P3A11 gene expression in normal tissues shows a restricted expression pattern in adult tissues. The nucleotide (FIG. 2) and amino acid (FIG. 2, and FIG. 3) sequences of 101P3A11 are provided. The tissue-related profile of 101P3A11 in normal adult tissues, combined with the over-expression observed in the tissues listed in Table I, shows that 101P3A11 is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 101P3A11 genes, mRNAs, and/or coding sequences, preferably in isolated form, including polynucleotides encoding 101P3A11-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 317 or 318; or more than 317 or 318 contiguous amino acids of a 101P3A11-related protein, as well as the peptides/proteins themselves; DNA, RNA, DNA/RNA hybrids, and related molecules, polynucleotides or oligonucleotides complementary or having at least a 90% homology to the 101P3A11 genes or mRNA sequences or parts thereof, and polynucleotides or oligonucleotides that hybridize to the 101P3A11 genes, mRNAs, or to 101P3A11-encoding polynucleotides. Also provided are means for isolating cDNAs and the genes encoding 101P3A11. Recombinant DNA molecules containing 101P3A11 polynucleotides, cells transformed or transduced with such molecules, and host-vector systems for the expression of 101P3A11 gene products are also provided. The invention further provides antibodies that bind to 101P3A11 proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments there is a proviso that the entire nucleic acid sequence of FIG. 2 is not encoded and/or the entire amino acid sequence of FIG. 2 is not prepared, either of which can be in respective human unit dose forms. In certain embodiments, the entire nucleic acid sequence of FIG. 2 is encoded and/or the entire amino acid sequence of FIG. 2 is prepared, either of which can be in respective human unit dose forms.

The invention further provides methods for detecting the presence and status of 101P3A11 polynucleotides and proteins in various biological samples, as well as methods for identifying cells that express 101P3A11. A typical embodiment of this invention provides methods for monitoring 101P3A11 gene products in a tissue or hematology sample having or suspected of having some form of growth dysregulation such as cancer.

The invention further provides various immunogenic or therapeutic compositions and strategies for treating cancers that express 101P3A11 such as cancers of tissues listed in Table I, including therapies aimed at inhibiting the transcription, translation, processing or function of 101P3A11 as well as cancer vaccines. In one aspect, the invention provides compositions, and methods comprising them, for treating a cancer that expresses 101P3A11 in a human subject wherein the composition comprises a carrier suitable for human use and a human unit dose of one or more than one agent that inhibits the production or function of 101P3A11. Preferably, the carrier is a uniquely human carrier. In another aspect of the invention, the agent is a moiety that is immunoreactive with 101P3A11 protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 101P3A11 and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 101P3A11 as described above. The one or more than one nucleic acid molecule may also be, or encodes, a molecule that inhibits production of 101P3A11. Non-limiting examples of such molecules include, but are not limited to, those complementary to a nucleotide sequence essential for production of 101P3A11 (e.g. antisense sequences or molecules that form a triple helix with a nucleotide double helix essential for 101P3A11 production) or a ribozyme effective to lyse 101P3A11 mRNA.

Note: To determine the starting position of any peptide set forth in Tables V-XVIII and XXII to IL (collectively HLA Peptide Tables) respective to its parental protein, e.g., variant 1, variant 2, etc., reference is made to three factors: the particular variant, the length of the peptide in an HLA Peptide Table, and the Search Peptides in Table LII. Generally, a unique Search Peptide is used to obtain HLA peptides of a particular for a particular variant. The position of each Search Peptide relative to its respective parent molecule is listed in Table LII. Accordingly if a Search Peptide begins at position “X”, one must add the value “X−1” to each position in Tables V-XVIII and XXII to IL to obtain the actual position of the HLA peptides in their parental molecule. For example if a particular Search Peptide begins at position 150 of is parental molecule, one must add 150−1, i.e., 149 to each HLA peptide amino acid position to calculate the position of that amino acid in the parent molecule.

BRIEF DESCRIPTION OF THE FIGURES

FIG. 1. The 101P3A11 SSH sequence (SEQ ID NO:26).

FIGS. 2A-2C. The cDNA and amino acid sequence of 101P3A11 variants 1-3 (SEQ ID NOS:27 and 19, SEQ ID NOS: 29 and 30, and SEQ ID NOS: 31 and 32). The start methionine is underlined. The open reading frame for variants 1 and 3 extends from nucleic acid 133 to 1086 including the stop codon. The codon for the initial M in each variant can be omitted as the shorter peptide can have a more favorable Kozak sequence).

FIGS. 3A-C. Amino acid sequences of 101P3A11 variants 1-3 (SEQ ID NOS:19, 30, 32).

FIG. 4. Alignment of 101P3A11 (Sbjct) (SEQ ID NO:143) with mouse olfactory receptor S25 (Query) (SEQ ID NO:144). The transmembrane regions of 101P3A11 and mouse olfactory receptor S25 (ORS25) predicted using the TMHMM algorithm are highlighted in gray. The amino acids of ORS25 predicted (Floriano, W. B., et al, 2000, Proc. Natl. Acad. Sci., USA, 97:10712-10716) to be involved in binding of the ligand hexanol and/or involved in the formation of the ligand binding pocket are italicized and bolded in the Figure, and are: Leu 131, Val 134, Val 135, Gly 138, Thr 139, Ser 193, Ser 197, Phe 225, Ala 230, Ile 231, Gly 234, Thr 284, Phe 287, Gln 300, Lys 302.

FIG. 12B. Photomicrograph showing 101P3A11 expression in prostatic intraepithelial neoplasia (PIN) by in situ hybridization with an anti-sense 101P3A11 riboprobe.

FIG. 12C. Photomicrograph showing 101P3A11 expression in prostate cancer tissue by in situ hybridization with an anti-sense 101P3A11 riboprobe.

FIG. 12D. Photomicrograph showing 101P3A11 expression in prostate cancer by in situ hybridization with an anti-sense 101P3A11 riboprobe. Note up-regulation of expression relative to normal prostate, FIG. 12E.

FIG. 12E. Photomicrograph showing 101P3A11 expression in normal prostate by in situ hybridization with an anti-sense 101P3A11 riboprobe.

FIGS. 19A-19C. Secondary structure and transmembrane prediction for 101P3A11. FIG. 19A: The secondary structure of 101P3A11 protein (SEQ ID NO: 28) was predicted using the HNN—Hierarchical Neural Network method, accessed from the ExPasy molecular biology server. This method predicts the presence and location of alpha helices, extended strands, and random coils from the primary protein sequence. The percent of the protein in a given secondary structure is also given. FIG. 19B is a schematic representation of the probability of existence of transmembrane regions and orientation of 101P3A11 based on the TMpred algorithm of Hofmann and Stoffel which utilizes TMBASE (K. Hofmann, W. Stoffel. TMBASE—A database of membrane spanning protein segments Biol. Chem. Hoppe-Seyler 374:166, 1993). FIG. 19C is a schematic representation of the probability of the existence of transmembrane regions and the extracellular and intracellular orientation of 101P3A11 based on the TMHMM algorithm of Sonnhammer, von Heijne, and Krogh (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998). The TMpred and TMHMM algorithms are accessed from the ExPasy molecular biology server. The results of the transmembrane prediction programs presented in FIGS. 19B and 19C depict 101P3A11 as containing 7 transmembrane domains consistent with that of a G-protein coupled receptor.

FIG. 23. Alignment of 101P3A11-PHOR-1 (Phor) (SEQ ID NO:35) with the rat GPCR RA1C (gi|3420759) (SEQ ID NO:36). Identities=179/299 (59%), Positives=231/299 (76%), Gaps=1/299 (0%).

FIG. 24. Alignment of 101P3A11-PHOR-1 (Phor) (SEQ ID NO:37) with the human prostate specific GPCR. (gi|13540539) (SEQ ID NO:38). Identities=179/299 (59%), Positives=233/299 (77%), Gaps=1/299 (0%).

FIG. 25. Alignment of 101P3A11-PHOR-1 (Phor) (SEQ ID NO:145) with human olfactory receptor 51I12, HOR5, (gi|14423836) (SEQ ID NO:146). Identities=163/304 (53%), Positives=214/304 (69%), Gaps=1/304 (0%).

FIG. 32. 101P3A11 Induced Accumulation of cAMP in PC3 Cells. Expression of 101P3A11 increased the accumulation of cAMP in cells treated with 0.1% and 10% FBS. FBS-induced cAMP accumulation in 101P3A11 cells was inhibited by pertussis toxin.

FIG. 36A: blotting with anti-phospho ERK antibodies; FIG. 36B: blotting with anti-ERK antibodies. Supernatants from PC3, PC3-101P3A11, PrEC and LAPC42 cells induce ERK phosphorylation in PC3 101P3A11 but not PC3 cells. Supernatants from 3T3 and 293T cells had little specific effect on ERK phosphorylation.

FIG. 47: Recognition of PHOR-1 protein by PHOR-1 mAbs

FIG. 63: AGS-3 Enhances Cell Cycle Entry of 3T3 and PC3 Cells FIG. 65A-65B: Nucleic Acid Alignments (SEQ ID NOS: 33-34; 35-36; 37-38)

FIGS. 67A-67B. The cDNA and amino acid sequence of the open reading frames of codon optimized s101P3A11 v.1 (A) (SEQ ID NOS:27 and 19) and s101P3A11 v.3 (B) (SEQ ID NOS:31-32).

FIG. 69A-69E. The nucleotide sequence alignment of 101P3A11 v1 (SEQ ID NO:27) and 101P3A11 v2 (SEQ ID NO:29).

FIG. 70. The peptide sequences of protein coded by 101P3A11 v2 (SEQ ID NO:30)

FIG. 71. The amino acid sequence alignment of 101P3A11 v1 (SEQ ID NO:28) (SEQ ID NO:19) and 101P3A11 v2 (SEQ ID NO:30).

DETAILED DESCRIPTION OF THE INVENTION

Outline of Sections

Figure 5:
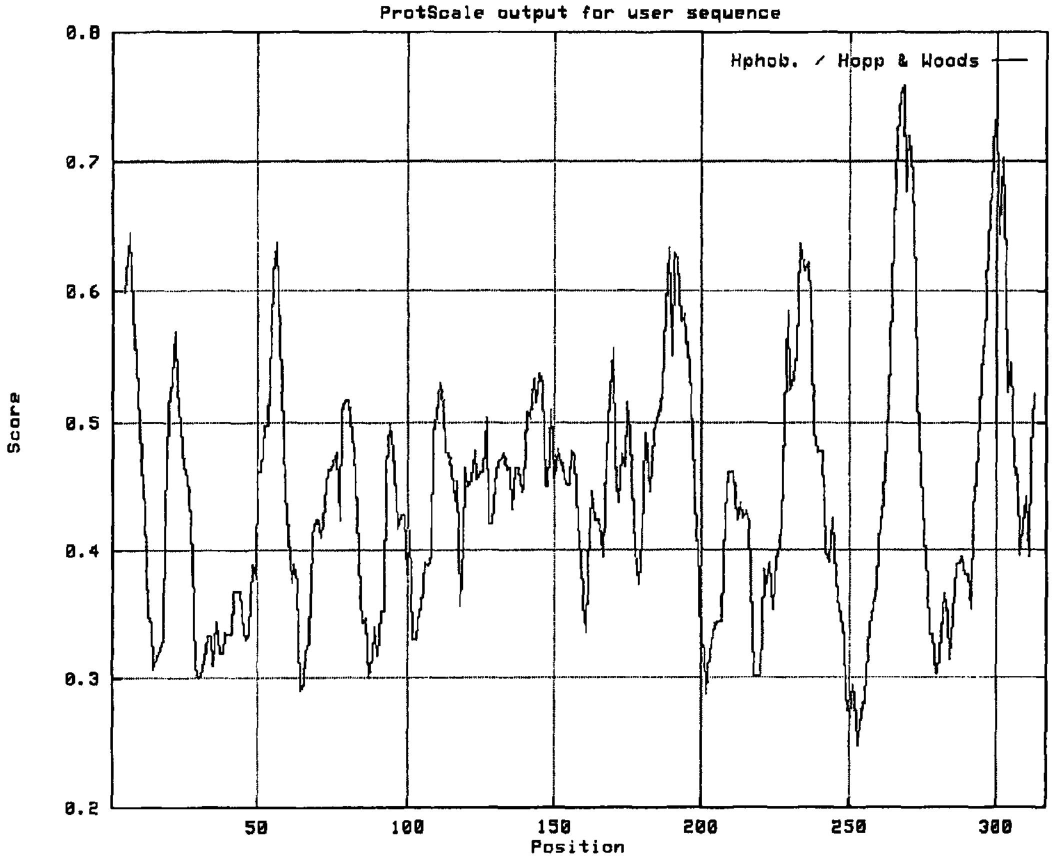
FIG. 5. Hydrophilicity amino acid profile of 101P3A11 determined by computer algorithm sequence analysis using the method of Hopp and Woods (Hopp T.P., Woods K.R., 1981. Proc. Natl. Acad. Sci. U.S.A. 78:3824-3828) accessed on the Protscale website through the ExPasy molecular biology server.

I.) Definitions
II.) 101P3A11 Polynucleotides
II.A.) Uses of 101P3A11 Polynucleotides
II.A.1.) Monitoring of Genetic Abnormalities
II.A.2.) Antisense Embodiments
II.A.3.) Primers and Primer Pairs
II.A.4.) Isolation of 101P3A11-Encoding Nucleic Acid Molecules
II.A.5.) Recombinant Nucleic Acid Molecules and Host-Vector Systems
III.) 101P3A11-related Proteins
III.A.) Motif-bearing Protein Embodiments
III.B.) Expression of 101P3A11-related Proteins
III.C.) Modifications of 101P3A11-related Proteins
III.D.) Uses of 101P3A11-related Proteins
IV.) 101P3A11 Antibodies
V.) 101P3A11 Cellular Immune Responses
VI.) 101P3A11 Transgenic Animals
VII.) Methods for the Detection of 101P3A11
VIII.) Methods for Monitoring the Status of 101P3A11-related Genes and Their Products
IX.) Identification of Molecules That Interact With 101P3A11
X.) Therapeutic Methods and Compositions
X.A.) Anti-Cancer Vaccines
X.B.) 101P3A11 as a Target for Antibody-Based Therapy
X.C.) 101P3A11 as a Target for Cellular Immune Responses
X.C.1. Minigene Vaccines
X.C.2. Combinations of CTL Peptides with Helper Peptides X.C.3. Combinations of CTL Peptides with T Cell Priming Agents
X.C.4. Vaccine Compositions Comprising DC Pulsed with CTL and/or HTL Peptides
X.D.) Adoptive Immunotherapy
X.E.) Administration of Vaccines for Therapeutic or Prophylactic Purposes
XI.) Diagnostic and Prognostic Embodiments of 101P3A11.
XII.) Inhibition of 101P3A11 Protein Function
XII.A.) Inhibition of 101P3A11 With Intracellular Antibodies
XII.B.) Inhibition of 101P3A11 with Recombinant Proteins
XII.C.) Inhibition of 101P3A11 Transcription or Translation
XII.D.) General Considerations for Therapeutic Strategies
XIII.) KITS/Articles of Manufacture
XIV.) Evaluation of GPCRs and Modulators Thereof
XV.) Screening of Candidate Compounds
XVI.) GPCR Fusion Proteins

I.) Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 101P3A11 (either by removing the underlying glycosylation site or by deleting the glycosylation by chemical and/or enzymatic means), and/or adding one or more glycosylation sites that are not present in the native sequence 101P3A11. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 101P3A11-related protein). For example an analog of a 101P3A11 protein can be specifically bound by an antibody or T cell that specifically binds to 101P3A11.

The term "antibody" is used in the broadest sense. Therefore an "antibody" can be naturally occurring or man-made such as monoclonal antibodies produced by conventional hybridoma technology. Anti-101P3A11 antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-101P3A11 antibodies and clones thereof (including agonist, antagonist and neutralizing antibodies) and anti-101P3A11 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, *Pseudomonas exotoxin* (PE) A, PE40, abrin, abrin A chain, modeccin A chain, alpha-sarcin, gelonin, mitogellin, restrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/

100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 101P3A11 genes or that encode polypeptides other than 101P3A11 gene product or fragments thereof. A skilled artisan can readily employ nucleic acid isolation procedures to obtain an isolated 101P3A11 polynucleotide. A protein is said to be "isolated," for example, when physical, mechanical or chemical methods are employed to remove the 101P3A11 proteins from cellular constituents that are normally associated with the protein. A skilled artisan can readily employ standard purification methods to obtain an isolated 101P3A11 protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage T×N×M+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a 101P3A11-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. In another embodiment, for example, the primary anchor residues of a peptide that will bind an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

A "recombinant" DNA or RNA molecule is a DNA or RNA molecule that has been subjected to molecular manipulation in vitro.

Non-limiting examples of small molecules include compounds that bind or interact with 101P3A11, ligands including hormones, neuropeptides, chemokines, odorants, phospholipids, and functional equivalents thereof that bind and preferably inhibit 101P3A11 protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 101P3A11 protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1-150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 101P3A11 protein shown in FIG. 2 or FIG. 3. An analog is an example of a variant protein. Splice isoforms and single nucleotides polymorphisms (SNPs) are further examples of variants.

The "101P3A11-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 101P3A11 proteins or fragments thereof, as well as fusion proteins of a 101P3A11 protein and a heterologous polypeptide are also included. Such 101P3A11 proteins are collectively referred to as the 101P3A11-related proteins, the proteins of the invention, or 101P3A11. The term "101P3A11-related protein" refers to a polypeptide fragment or a 101P3A11 protein sequence of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 317 or 318 or more amino acids.

"Active ingredient" in the context of a "Pharmaceutical Composition" shall mean a component of a Pharmaceutical Composition that provides the primary pharmaceutical benefit, as opposed to an "inactive ingredient" which would generally be recognized as providing no pharmaceutical benefit.

"Agonists" shall mean moieties that activate the intracellular response when they bind to the receptor, or enhance GTP binding to membranes. In the context of the disclosed invention, a Pharmaceutical Candidate comprising a 101P3A11 Agonist can be utilized for affecting metabolism. "Partial agonists" shall mean moieties that activate the intracellular response when they bind to the receptor to a lesser degree/extent than do agonists, or enhance GTP binding to membranes to a lesser degree/extent than do agonists.

"Antagonist" shall mean moieties that competitively bind to the receptor at the same site as the agonists but which do not activate the intracellular response initiated by the active form of the receptor, and can thereby inhibit the intracellular responses by agonists or partial agonists. Antagonists do not diminish the baseline intracellular response in the absence of an agonist or partial agonist.

"Candidate compound," in the context of the disclosed invention, shall mean a small molecule that is amenable to a screening technique.

"Composition" shall having a meaning in accordance with standard use. For example, a composition can mean a material comprising at least two compounds, components or substituents; for example, and not limitation, a Pharmaceutical Composition comprising at least one Active Ingredient and at least one other component.

"Compound efficacy" shall mean a measurement of the ability of a compound to inhibit or stimulate receptor functionality, as opposed to receptor binding affinity.

"Constitutive receptor activation" shall mean stabilization of a receptor in the active state by means other than binding of the receptor with its endogenous ligand or a chemical equivalent thereof.

"Contact" or "contacting" shall mean bringing at least two moieties together, whether in an in vitro system or an in vivo system.

"Endogenous" shall mean a material that a mammal naturally produces. Endogenous in reference to, for example and not limitation, the term "receptor" shall mean that which is naturally produced by a mammal (for example, and not limitation, a human), yeast, bacterium or a virus. In contrast, the term "non-endogenous" in this context shall mean that which is not naturally produced by a mammal (for example, and not limitation, a human) yeast, bacterium or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

"G protein coupled receptor fusion protein" and "GPCR fusion protein," in the context of the invention disclosed herein, each mean a non-endogenous protein comprising an endogenous, constitutively activated orphan GPCR fused to at least one G protein, most preferably, the alpha (a) subunit of such G protein (this being the subunit that binds GTP), with the G protein preferably being of the same type as the G protein that naturally couples with endogenous orphan GPCR. For example, and not limitation, in an endogenous state, the G protein "Gsa" is the predominate G protein that couples with 101P3A11 such that a GPCR Fusion Protein based upon 101P3A11 would be a non-endogenous protein comprising 101P3A 11 fused to Gscc. The G protein can be fused directly to the c-terminus of the endogenous, constitutively active orphan GPCR or there may be spacers between the two.

"Inhibit" or "inhibiting", in relationship to the term "response" shall mean that a response is decreased or prevented in the presence of a compound as opposed to in the absence of the compound.

"Inverse agonists" shall mean moieties that bind the endogenous form of the receptor, and which inhibit the baseline intracellular response initiated by the active endogenous form of the receptor below the normal base level of activity that is observed in the absence of the endogenous ligand, agonists or partial agonists, or decrease GTP binding to membranes. Preferably, the baseline intracellular response is decreased in the presence of the inverse agonist by at least 30%, more preferably by at least 50%, and most preferably by at least 75%, as compared with the baseline response in the absence of the inverse agonist. Biologically, "101P3A11 inverse agonist" shall mean moieties that can be assessed in vivo by factors other than just determination that the moiety has interacted with 101P3A11.

"Ligand" shall mean an endogenous, naturally occurring molecule specific for an endogenous, naturally occurring receptor.

"Pharmaceutical composition" shall mean a composition comprising at one Active Ingredient and at least one ingredient that is not an Active Ingredient (for example and not limitation, a filler, dye, or a mechanism for slow release), whereby the composition is amenable to investigation for a specified, efficacious outcome in a mammal or in cells thereof such as in vitro (e.g., without limitation, the mammal is a human). Those of ordinary skill in the art will understand and appreciate the techniques appropriate for determining whether an active ingredient has a desired efficacious outcome based upon the needs of the artisan.

"Small molecule", in the context of the invention disclosed herein, is a non-protein based moiety; for example, and not limitation, NF449 is a small molecule within the context of this invention. In a preferred embodiment, the endogenous ligand for a receptor is not a "small molecule."

II.) 101P3A11 Polynucleotides

One aspect of the invention provides polynucleotides corresponding or complementary to all or part of a 101P3A11 gene, mRNA, and/or coding sequence, preferably in isolated form, including polynucleotides encoding a 101P3A11-related protein and fragments thereof, DNA, RNA, DNA/RNA hybrid, and related molecules, polynucleotides or oligonucleotides complementary to a 101P3A11 gene or mRNA sequence or a part thereof, and polynucleotides or oligonucleotides that hybridize to a 101P3A11 gene, mRNA, or to a 101P3A11 encoding polynucleotide (collectively, "101P3A11 polynucleotides"). In all instances when referred to in this section, T can also be U in FIG. 2.

Figure 6:
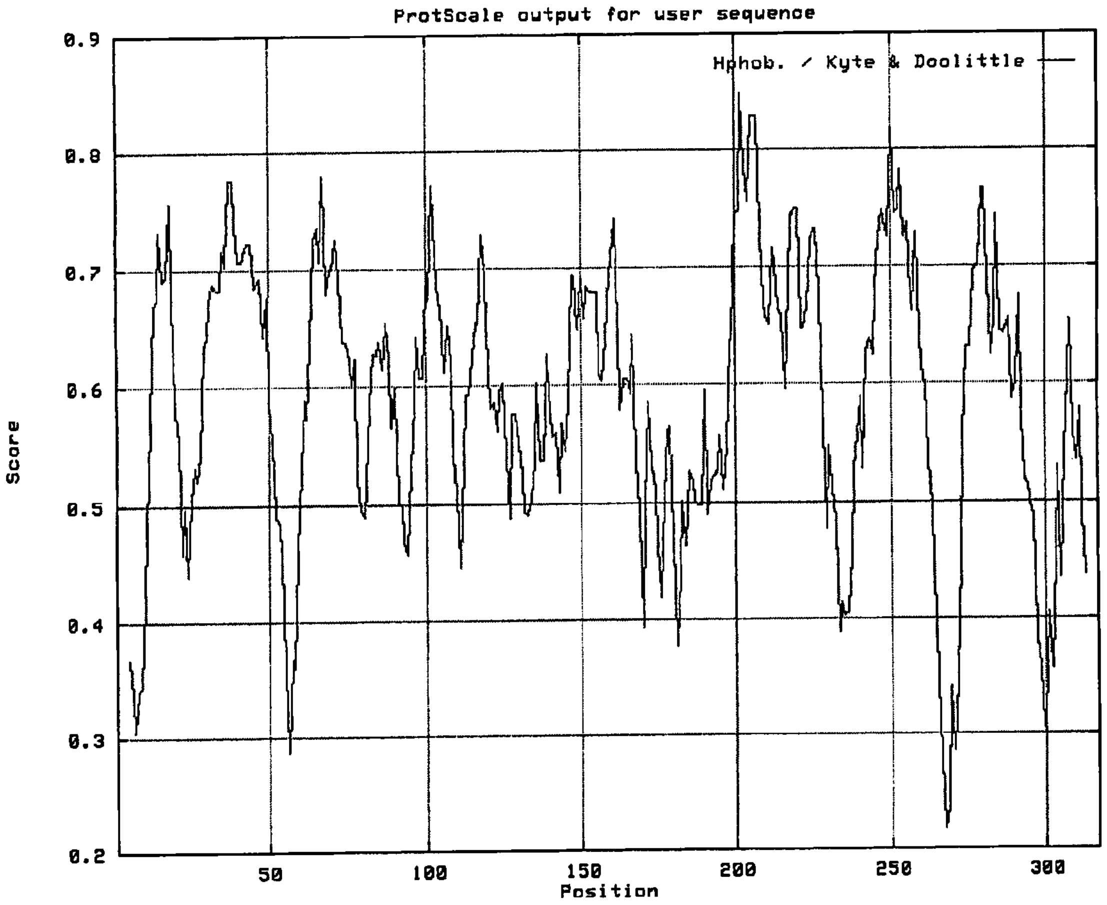
FIG. 6. Hydropathicity amino acid profile of 101P3A11 determined by computer algorithm sequence analysis using the method of Kyte and Doolittle (Kyte J., Doolittle R.F., 1982. J. Mol. Biol. 157:105-132) accessed on the ProtScale website through the ExPasy molecular biology server.
Figure 7:
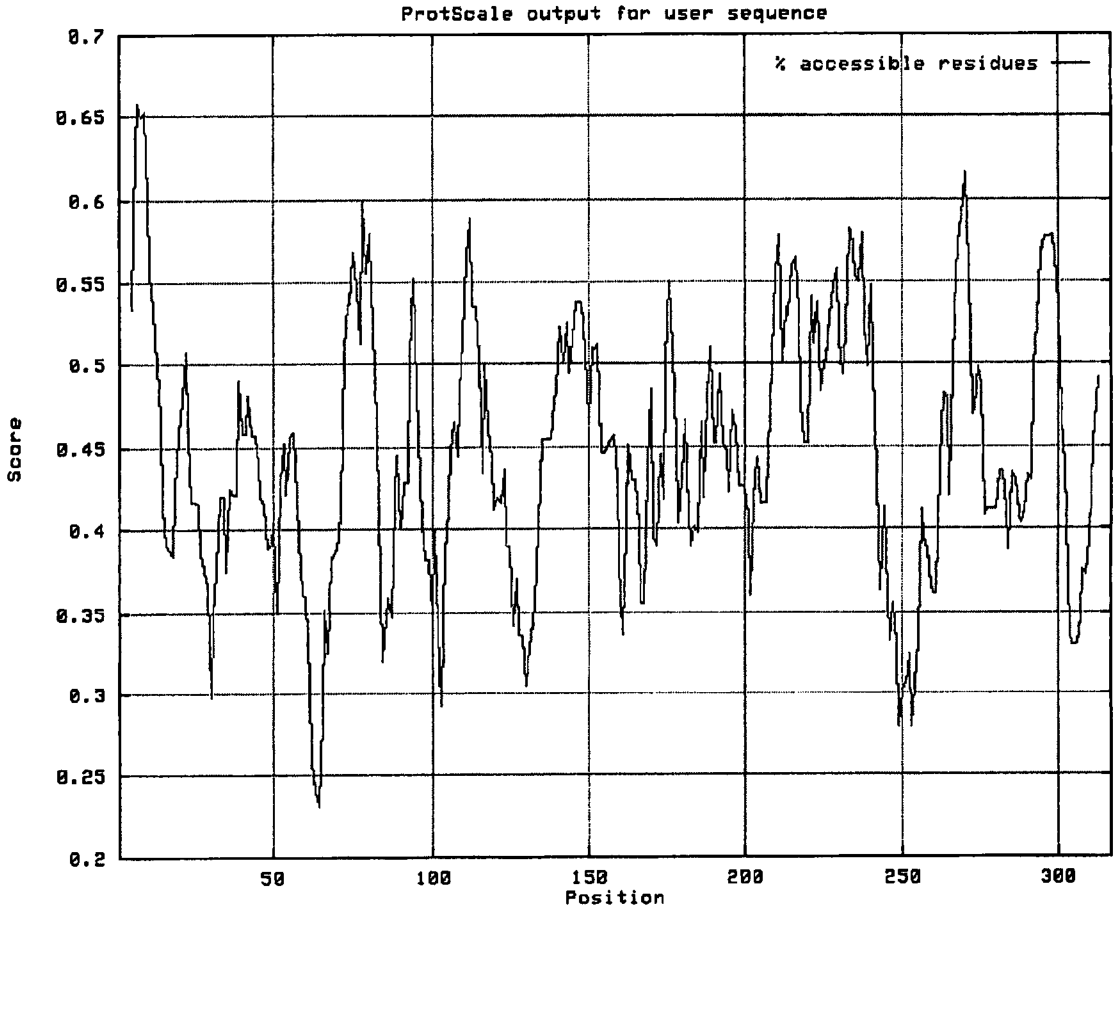
FIG. 7. Percent accessible residues amino acid profile of 101P3A11 determined by computer algorithm sequence analysis using the method of Janin (Janin J., 1979 Nature 277:491-492) accessed on the ProtScale website through the ExPasy molecular biology server.
Figure 8:
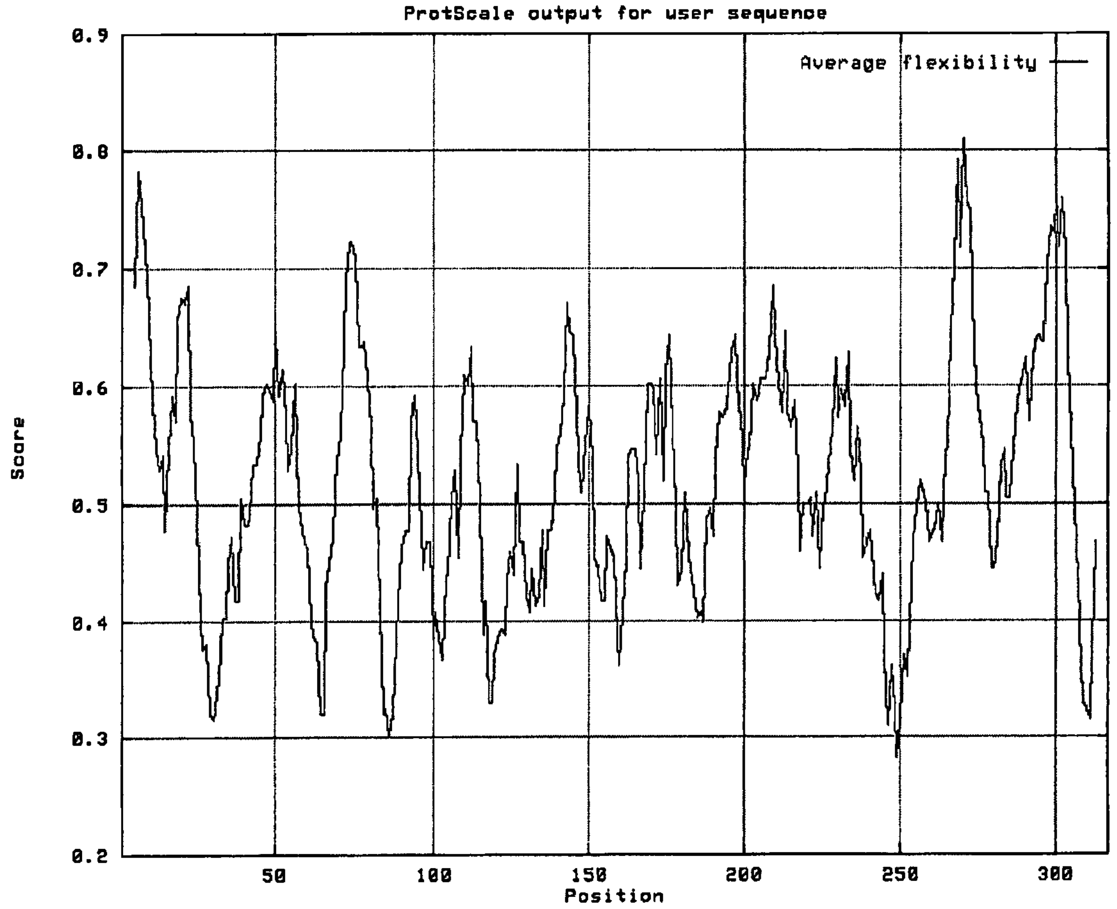
FIG. 8. Average flexibility amino acid profile of 101P3A11 determined by computer algorithm sequence analysis using the method of Bhaskaran and Ponnuswamy (Bhaskaran R., and Ponnuswamy P.K., 1988. Int. J. Pept. Protein Res. 32:242-255) accessed on the ProtScale website through the ExPasy molecular biology server.
Figure 9:
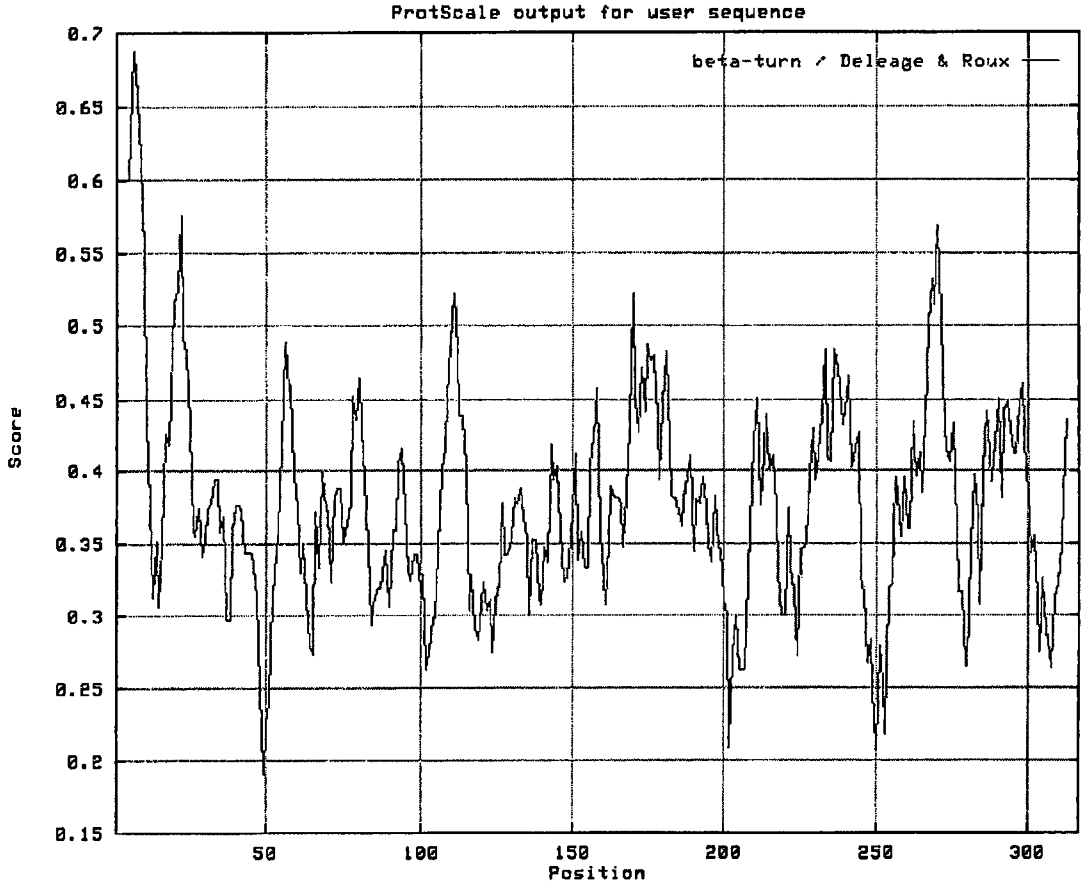
FIG. 9. Beta-turn amino acid profile of 101P3A11 determined by computer algorithm sequence analysis using the method of Deleage and Roux (Deleage, G., Roux B. 1987 Protein Engineering 1:289-294) accessed on the ProtScale website through the ExPasy molecular biology server.

Embodiments of a 101P3A11 polynucleotide include: a 101P3A11 polynucleotide having the sequence shown in FIG. 2, the nucleotide sequence of 101P3A11 as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 101P3A11 nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 130 through nucleotide residue number 1086, optionally including the last, stop codon, wherein T can also be U;

(III) a polynucleotide comprising, consisting essentially of, or consisting of the sequence as shown in FIG. 2A, from nucleotide residue number 133 through nucleotide residue number 1086, optionally including the last, stop codon, wherein T can also be U;

(N) a polynucleotide comprising, consisting essentially of, or consisting of the sequence as shown in FIG. 2B, from nucleotide residue number 130 through nucleotide residue number 348, optionally including the last, stop codon, wherein T can also be U;

(V) a polynucleotide comprising, consisting essentially of, or consisting of the sequence as shown in FIG. 2B, from nucleotide residue number 133 through nucleotide residue number 348, optionally including the stop codon, wherein T can also be U;

(VI) a polynucleotide comprising, consisting essentially of, or consisting of the sequence as shown in FIG. 2C, from nucleotide residue number 130 through nucleotide residue number 1086, optionally including the last, stop codon, wherein T can also be U;

(VII) a polynucleotide comprising, consisting essentially of, or consisting of the sequence as shown in FIG. 2C, from nucleotide residue number 133 through nucleotide residue number 1086, optionally including the last, stop codon, wherein T can also be U;

(VIII) a polynucleotide that encodes a 101P3A11-related protein that is at least 90% homologous to an entire amino acid sequence shown in FIGS. 2A-C;

(IX) a polynucleotide that encodes a 101P3A11-related protein that is at least 90% identical to an entire amino acid sequence shown in FIGS. 2A-C;

(X) a polynucleotide that encodes at least one peptide set forth in Tables V-XVIII and XXII to IL, optionally with a proviso that the polynucleotide is not a contiguous sequence from a nucleic acid sequence of FIG. 2;

(XI) a polynucleotide that encodes at least two peptides selected from the peptides set forth in Tables V-XVIII and XXII to IL, optionally with a proviso that the polynucleotide is not a contiguous sequence from a nucleic acid sequence of FIG. 2;

(XII) a polynucleotide that encodes at least two peptides selected from the peptides set forth in Tables V-XVIII and XXII to IL, optionally with a proviso that the polynucleotide is not a contiguous sequence from a nucleic acid sequence of FIG. 2;

(XIII) a polynucleotide that encodes a peptide region of at least 5 amino acids of a peptide of FIG. 3A or 3C in any whole number increment up to 317 or 318 that includes an amino acid position having a value greater than 0.5 in the Hydrophilicity profile of FIG. 5;

(XIV) a polynucleotide that encodes a peptide region of at least 5 amino acids of a peptide of FIG. 3A or 3C in any whole number increment up to 317 or 318 that includes an amino acid position having a value less than 0.5 in the Hydropathicity profile of FIG. 6;

(XV) a polynucleotide that encodes a peptide region of at least 5 amino acids of a peptide of FIG. 3A or 3C in any whole number increment up to 317 or 318 that includes an amino acid position having a value greater than 0.5 in the Percent Accessible Residues profile of FIG. 7;

(XVI) a polynucleotide that encodes a peptide region of at least 5 amino-acids of a peptide of FIG. 3A or 3C in any whole number increment up to 317 or 318 that includes an amino acid position having a value greater than 0.5 in the Average Flexibility profile of FIG. 8;

(XVII) a polynucleotide that encodes a peptide region of at least 5 amino acids of a peptide of FIG. 3A or 3C in any whole number increment up to 317 or 318 that includes an amino acid position having a value greater than 0.5 in the Beta-turn profile of FIG. 9;

(XVIII) a polynucleotide that encodes a peptide region of at least 5 amino acids of a peptide of FIG. 3B in any whole number increment up to 317 or 318 that includes an amino acid position having a value greater than 0.5 in the Hydrophilicity profile of FIG. 5;

(XIX) a polynucleotide that encodes a peptide region of at least 5 amino acids of a peptide of FIG. 3B in any whole number increment up to 317 or 318 that includes an amino acid position having a value less than 0.5 in the Hydropathicity profile of FIG. 6;

(XX) a polynucleotide that encodes a peptide region of at least 5 amino acids of a peptide of FIG. 3B in any whole number increment up to 317 or 318 that includes an amino acid position having a value greater than 0.5 in the Percent Accessible Residues profile of FIG. 7;

(XXI) a polynucleotide that encodes a peptide region of at least 5 amino acids of a peptide of FIG. 3B in any whole number increment up to 317 or 318 that includes an amino acid position having a value greater than 0.5 in the Average Flexibility profile of FIG. 8;

(XXII) a polynucleotide that encodes a peptide region of at least 5 amino acids of a peptide of FIG. 3B in any whole number increment up to 317 or 318 that includes an amino acid position having a value greater than 0.5 in the Beta-turn profile of FIG. 9;

(XXIII) a polynucleotide that encodes monoclonal antibody or binding region thereof secreted by a hybridoma entitled X18(1)4 deposited with American Type Culture Collection (ATCC; 10801 University Blvd., Manassas, Va. 20110-2209 USA) as Accession No. PTA-4351 on 15 May 2002;

(XXIV) a polynucleotide that encodes monoclonal antibody or binding region thereof secreted by a hybridoma entitled X18(1)10 deposited with American Type Culture Collection (ATCC; 10801 University Blvd., Manassas, Va. 20110-2209 USA) as Accession No. PTA-4352 on 15 May 2002;

(XXV) a polynucleotide that encodes monoclonal antibody or binding region thereof secreted by a hybridoma entitled X18(1)23 deposited with American Type Culture Collection (ATCC; 10801 University Blvd., Manassas, Va. 20110-2209 USA) as Accession No. PTA-4353 on 15 May 2002;

(XXVI) a polynucleotide that encodes monoclonal antibody or binding region thereof secreted by a hybridoma entitled X18(4)7 deposited with American Type Culture Collection (ATCC; 10801 University Blvd., Manassas, Va. 20110-2209 USA) as Accession No. PTA-4354 on 15 May 2002;

(XXVII) a polynucleotide that is fully complementary to a polynucleotide of any one of (I)-(XXVI); and, (XXVIII) a peptide that is encoded by any of (I)-(XXVI);

(XXIX) a peptide that occurs at least twice in Tables V-XVIII and XXII to IL collectively, or an oligonucleotide that encodes such HLA peptide;

(XXX) a peptide that occurs at least once in Tables V-XVIII and at least once in tables XXII to IL, or an oligonucleotide that encodes such HLA peptide;

(XXXI) a peptide which comprises peptide regions, or an oligonucleotide encoding the peptide, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, orhaving a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8;

v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXXII) a polynucleotide of any of (I)-(XXVII) or peptide of (XXVIII)-(XXXI) together with a pharmaceutical excipient and/or in a human unit dose form.

As used herein, a range is understood to specifically disclose all whole unit positions thereof.

Typical embodiments of the invention disclosed herein include 101P3A11 polynucleotides that encode specific portions of 101P3A11 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 80, 85, 90, 95, 100, 125, 150, 175, 200, 225, 250, 375, 300 or 317 or 318 contiguous amino acids of 101P3A11.

For example, representative embodiments of the invention disclosed herein include: polynucleotides and their encoded peptides themselves encoding about amino acid 1 to about amino acid 10 of the 101P3A11 protein shown in FIG. 2 or FIG. 3, polynucleotides encoding about amino acid 10 to about amino acid 20 of the 101P3A11 protein shown in FIG. 2 or FIG. 3, polynucleotides encoding about amino acid 20 to about amino acid 30 of the 101P3A11 protein shown in FIG. 2 or FIG. 3, polynucleotides encoding about amino acid 30 to about amino acid 40 of the 101P3A11 protein shown in FIG. 2 or FIG. 3, polynucleotides encoding about amino acid 40 to about amino acid 50 of the 101P3A11 protein shown in FIG. 2 or FIG. 3, polynucleotides encoding about amino acid 50 to about amino acid 60 of the 101P3A11 protein shown in FIG. 2 or FIG. 3, or polynucleotides encoding about amino acid 60 to about amino acid 70 or amino acid 317 or 318 of the 101P3A11 protein shown in FIG. 2 or FIG. 3. Accordingly polynucleotides encoding portions of the amino acid sequence (of about 10 amino acids), of amino acids 1 through the carboxyl terminal amino acid of the 101P3A11 protein are embodiments of the invention. Wherein it is understood that each particular amino acid position discloses that position plus or minus five amino acid residues.

Polynucleotides encoding relatively long portions of a 101P3A11 protein are also within the scope of the invention. For example, polynucleotides encoding from about amino acid 1 (or 20 or 30 or 40 etc.) to about amino acid 20, (or 30, or 40 or 50 etc.) of the 101P3A11 protein "or variant" shown in FIG. 2 or FIG. 3 can be generated by a variety of techniques well known in the art. These polynucleotide fragments can include any portion of the 101P3A11 sequence as shown in FIG. 2.

Additional illustrative embodiments of the invention disclosed herein include 101P3A11 polynucleotide fragments encoding one or more of the biological motifs contained within a 101P3A11 protein "or variant" sequence, including one or more of the motif-bearing subsequences of a 101P3A11 protein "or variant" set forth in Tables V-XVIII and XXII to IL. In another embodiment, typical polynucleotide fragments of the invention encode one or more of the regions of 101P3A11 protein or variant that exhibit homology to a known molecule. In another embodiment of the invention, typical polynucleotide fragments can encode one or more of the 101P3A11 protein or variant N-glycosylation sites, cAMP and cGMP-dependent protein kinase phosphorylation sites, casein kinase II phosphorylation sites or N-myristoylation site and amidation sites.

Note that to determine the starting position of any peptide set forth in Tables V-XVIII and Tables XXII to IL (collectively HLA Peptide Tables) respective to its parental protein, e.g., variant 1, variant 2, etc., reference is made to three factors: the particular variant, the length of the peptide in an HLA Peptide Table, and the Search Peptides listed in Table LVII. Generally, a unique Search Peptide is used to obtain HLA peptides for a particular variant. The position of each Search Peptide relative to its respective parent molecule is listed in Table LLII. Accordingly if a Search Peptide begins at position "X", one must add the value "X minus 1" to each position in Tables V-XVIII and Tables XXII-IL to obtain the actual position of the HLA peptides in their parental molecule. For example if a particular Search Peptide begins at position 150 of its parental molecule, one must add 150−1, i.e., 149 to each HLA peptide amino acid position to calculate the position of that amino acid in the parent molecule.

II.A.) Uses of 101P3A11 Polynucleotides

II.A.1.) Monitoring of Genetic Abnormalities

The polynucleotides of the preceding paragraphs have a number of different specific uses. The human 101P3A11 gene maps to the chromosomal location set forth in the Example entitled "Chromosomal Mapping of 101P3A11." For example, because the 101P3A11 gene maps to this chromosome, polynucleotides that encode different regions of the 101P3A11 proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 101P3A11 proteins provide new tools that can be used to delineate, with greater precision than previously possible, cytogenetic abnormalities in the chromosomal region that encodes 101P3A11 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 101P3A11 was shown to be highly expressed in bladder and other cancers, 101P3A11 polynucleotides are used in methods assessing the status of 101P3A11 gene products in normal versus cancerous tissues. Typically, polynucleotides that encode specific regions of the 101P3A11 proteins are used to assess the presence of perturbations (such as deletions, insertions, point mutations, or alterations resulting in a loss of an antigen etc.) in specific regions of the 101P3A11 gene, such as regions containing one or more motifs. Exemplary assays include both RT-PCR assays as well as single-strand conformation polymorphism (SSCP) analysis (see, e.g., Marrogi et al, J. Cutan. Pathol. 26(8): 369-378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 101P3A11. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 101P3A11 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 101P3A11. See for example, Jack Cohen, Oligodeoxynucleotides, Antisense Inhibitors of Gene Expression, CRC Press, 1989; and Synthesis 1:1-5 (1988). The 101P3A11 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693-4698 (1990); and Iyer, R. P. et al., J. Am. Chem. Soc. 112: 1253-1254 (1990). Additional 101P3A11 antisense oligonucleotides of the present invention include morpholino antisense oligonucleotides known in the art (see, e.g., Partridge et al., 1996, Antisense & Nucleic Acid Drug Development 6: 169-175).

The 101P3A11 antisense oligonucleotides of the present invention typically can be RNA or DNA that is complementary to and stably hybridizes with the first 100 5' codons or last 100 3' codons of a 101P3A11 genomic sequence or the corresponding mRNA. Absolute complementarity is not required, although high degrees of complementarity are preferred. Use of an oligonucleotide complementary to this region allows for the selective hybridization to 101P3A11 mRNA and not to mRNA specifying other regulatory subunits of protein kinase. In one embodiment, 101P3A11 antisense oligonucleotides of the present invention are 15 to 30-mer fragments of the antisense DNA molecule that have a sequence that hybridizes to 101P3A11 mRNA. Optionally, 101P3A11 antisense oligonucleotide is a 30-mer oligonucleotide that is complementary to a region in the first 10 5' codons or last 10 3' codons of 101P3A11. Alternatively, the antisense molecules are modified to employ ribozymes in the inhibition of 101P3A11 expression, see, e.g., L. A. Couture & D. T. Stinchcomb; *Trends Genet.* 12: 510-515 (1996).

II.A.3.) Primers and Primer Pairs

Further specific embodiments of this nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 101P3A11 polynucleotide in a sample and as a means for detecting a cell expressing a 101P3A11 protein.

Examples of such probes include polypeptides comprising all or part of the human 101P3A11 cDNA sequence shown in FIG. 2. Examples of primer pairs capable of specifically amplifying 101P3A11 mRNAs are also described in the Examples. As will be understood by the skilled artisan, a great many different primers and probes can be prepared based on the sequences provided herein and used effectively to amplify and/or detect a 101P3A11 mRNA.

The 101P3A11 polynucleotides of the invention are useful for a variety of purposes, including but not limited to their use as probes and primers for the amplification and/or detection of the 101P3A11 gene(s), mRNA(s), or fragments thereof; as reagents for the diagnosis and/or prognosis of prostate cancer and other cancers; as coding sequences capable of directing the expression of 101P3A11 polypeptides; as tools for modulating or inhibiting the expression of the 101P3A11 gene(s) and/or translation of the 101P3A11 transcript(s); and as therapeutic agents.

The present invention includes the use of any probe as described herein to identify and isolate a 101P3A11 or 101P3A11 related nucleic acid sequence from a naturally occurring source, such as humans or other mammals, as well as the isolated nucleic acid sequence per se, which would comprise all or most of the sequences found in the probe used.

II.A.4.) Isolation of 101P3A11-Encoding Nucleic Acid Molecules

The 101P3A11 cDNA sequences described herein enable the isolation of other polynucleotides encoding 101P3A11 gene product(s), as well as the isolation of polynucleotides encoding 101P3A11 gene product homologs, alternatively spliced isoforms, allelic variants, and mutant forms of a 101P3A11 gene product as well as polynucleotides that encode analogs of 101P3A11-related proteins. Various molecular cloning methods that can be employed to isolate full length cDNAs encoding a 101P3A11 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 101P3A11 gene cDNAs can be identified by probing with a labeled 101P3A11 cDNA or a fragment thereof. For example, in one embodiment, a 101P3A11 cDNA (e.g., FIG. 2) or a portion thereof can be synthesized and used as a probe to retrieve overlapping and full-length cDNAs corresponding to a 101P3A11 gene. A 101P3A11 gene itself can be isolated by screening genomic DNA libraries, bacterial artificial chromosome libraries (BACs), yeast artificial chromosome libraries (YACs), and the like, with 101P3A11 DNA probes or primers.

II.A.5.) Recombinant Nucleic Acid Molecules and Host-Vector Systems

The invention also provides recombinant DNA or RNA molecules containing a 101P3A11 polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 101P3A11 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 101P3A11 or a fragment, analog or homolog thereof can be used to generate 101P3A11 proteins or fragments thereof using any number of host-vector systems routinely used and widely known in the art.

A wide range of host-vector systems suitable for the expression of 101P3A11 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11: 1785). Using these expression vectors, 101P3A11 can be expressed in several prostate cancer and non-prostate cell lines, including for example 293, 293T, rat-1, NIH 3T3 and TsuPr1. The host-vector systems of the invention are useful for the production of a 101P3A11 protein or fragment thereof. Such host-vector systems can be employed to study the functional properties of 101P3A11 and 101P3A11 mutations or analogs.

Recombinant human 101P3A11 protein or an analog or homolog or fragment thereof can be produced by mammalian cells transfected with a construct encoding a 101P3A11-related nucleotide. For example, 293T cells can be transfected with an expression plasmid encoding 101P3A11 or fragment, analog or homolog thereof, a 101P3A11-related protein is expressed in the 293T cells, and the recombinant 101P3A11 protein is isolated using standard purification methods (e.g., affinity purification using anti-101P3A11 antibodies). In another embodiment, a 101P3A11 coding sequence is subcloned into the retroviral vector pSRαMSVtkneo and used to infect various mammalian cell lines, such as NIH 3T3, TsuPr1, 293 and rat-1 in order to establish 101P3A11 expressing cell lines. Various other expression systems well known in the art can also be employed. Expression constructs encoding a leader peptide joined in frame to a 101P3A11 coding sequence can be used for the generation of a secreted form of recombinant 101P3A11 protein.

As discussed herein, redundancy in the genetic code permits variation in 101P3A11 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell. Biol.,* 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

III.) 101P3A11-Related Proteins

Another aspect of the present invention provides 101P3A11-related proteins. Specific embodiments of 101P3A11 proteins comprise a polypeptide having all or part of the amino acid sequence of human 101P3A11 as shown in FIG. 2 or FIG. 3. Alternatively, embodiments of 101P3A11 proteins comprise variant, homolog or analog polypeptides that have alterations in the amino acid sequence of 101P3A11 shown in FIG. 2 or FIG. 3.

Embodiments of a 101P3A11 polynucleotide include: a 101P3A11 polynucleotide having the sequence shown in FIG. 2, the nucleotide sequence of 101P3A11 as shown in FIG. 2 wherein T is U; at least 10 contiguous nucleotides of a polynucleotide having the sequence as shown in FIG. 2; or, at leatst 10 contiguous nucleotides of a polynucleotide having the sequence as shown in FIG. 2 where T is U. For example, embodiments of 101P3A11 nucleotides comprise, without limitation:

(I) a protein comprising, consisting essentially of, or consisting of a sequence as shown in FIG. 2;

(II) a 101P3A11-related protein that is at least 90% homologous to an entire amino acid sequence shown in FIGS. 2A-C;

(III) a 101P3A11-related protein that is at least 90% identical to an entire amino acid sequence shown in FIGS. 2A-C;

(IV) a protein that comprises at least one peptide set forth in Tables V-XVIII or Tables XXII to IL, optionally with a proviso that it is not an entire protein of FIG. 2;

(V) a protein that comprises at least one peptide set forth in Tables V-XVIII, collectively, which peptide is also set forth in Tables XXII to IL, collectively, optionally with a proviso that it is not an entire protein of FIG. 2;

(VI) a protein that comprises at least two peptides selected from the peptides set forth in Tables V-XVIII and XXII to IL, optionally with a proviso that it is not an entire protein of FIG. 2;

(VII) a protein that comprises at least two peptides selected from the peptides set forth in Tables V-XVIII and XXII to IL, with a proviso that the protein is not a contiguous sequence from an amino acid sequence of FIG. 2;

(VIII) a protein that comprises at least one peptide selected from the peptides set forth in Tables V-XVIII; and at least one peptide set forth in Tables XXII to IL, with a proviso that the protein is not a contiguous sequence from an amino acid sequence of FIG. 2;

(IX) a polypeptide comprising at least 5 amino acids of a protein of FIG. 3A or 3C in any whole number increment up to 317 or 318 that includes an amino acid position having a value greater than 0.5 in the Hydrophilicity profile of FIG. 5;

(X) a polypeptide comprising at least 5 amino acids of a protein of FIG. 3A or 3C in any whole number increment up to 317 or 318 that includes an amino acid position having a value less than 0.5 in the Hydropathicity profile of FIG. 6;

(XI) a polypeptide comprising at least 5 amino acids of a protein of FIG. 3A or 3C in any whole number increment up to 317 or 318 that includes an amino acid position having a value greater than 0.5 in the Percent Accessible Residues profile of FIG. 7;

(XII) a polypeptide comprising at least 5 amino acids of a protein of FIG. 3A or 3C in any whole number increment up to 317 or 318 that includes an amino acid position having a value greater than 0.5 in the Average Flexibility profile of FIG. 8;

(XIII) a polypeptide comprising at least 5 amino acids of a protein of FIG. 3A or. 3C in any whole number increment up to 317 or 318 that includes an amino acid position having a value greater than 0.5 in the Beta-turn profile of FIG. 9;

(XIV) a polypeptide comprising at least 5 amino acids of a protein of FIG. 3B in any whole number increment up to 72 that includes an amino acid position having a value greater than 0.5 in the Hydrophilicity profile of FIG. 5;

(XV) a polypeptide comprising at least 5 amino acids of a protein of FIG. 3 in any whole number increment up to 72 that includes an amino acid position having a value less than 0.5 in the Hydropathicity profile of FIG. 6;

(XVI) a polypeptide compiising at least 5 amino acids of a protein of FIG. 3 in any whole number increment up to 72 that includes an amino acid position having a value greater than 0.5 in the Percent Accessible Residues profile of FIG. 7;

(XVII) a polypeptide comprising at least 5 amino acids of a protein of FIG. 3 in any whole number increment up to 72 that includes an amino acid position having a value greater than 0.5 in the Average Flexibility profile of FIG. 8;

(XVIII) a polypeptide comprising at least 5 amino acids of a protein of FIG. 3 in any whole number increment up to 72 that includes an amino acid position having a value greater than 0.5 in the Beta-turn profile of FIG. 9;

(XIX) a monoclonal antibody or binding region thereof secreted by a hybridoma entitled X18(1)4 deposited with American Type Culture Collection (ATCC; 10801 University Blvd., Manassas, Va. 20110-2209 USA) as Accession No. PTA-4351 on 15 May 2002;

(XX) a monoclonal antibody or binding region thereof secreted by a hybridoma entitled X18(1)10 deposited with American Type Culture Collection (ATCC; 10801 University Blvd., Manassas, Va. 20110-2209 USA) as Accession No. PTA-4352 on 15 May 2002;

(XXI) a monoclonal antibody or binding region thereof secreted by a hybridoma entitled X18(1)23 deposited with American Type Culture Collection (ATCC; 10801 University Blvd., Manassas, Va. 20110-2209 USA) as Accession No. PTA-4353 on 15 May 2002;

(XXII) a monoclonal antibody or binding region thereof secreted by a hybridoma entitled X18(4)7deposited with American Type Culture Collection (ATCC; 10801 University Blvd., Manassas, Va. 20110-2209 USA) as Accession No. PTA-4354 on 15 May 2002;

(XXIII) a peptide that occurs at least twice in Tables V-XVIII and XXII to IL, collectively;

(XXIV) a peptide that occurs at least once in Tables V-XVIII, and at least once in tables XXII to IL;

(XXV) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9;

(XXVI) a peptide of (I)-(XXV) together with a pharmaceutical excipient and/or in a human unit dose form.

As used herein, a range is understood to specifically disclose all whole unit positions thereof.

Typical embodiments of the invention disclosed herein include 101P3A11 polynucleotides that encode specific portions of 101P3A11 mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, or 317 or 318 contiguous amino acids of 101P3A11.

In general, naturally occurring allelic variants of human 101P3A11 protein share a high degree of structural identity and homology (e.g., 90% or more homology). Typically, allelic variants of a 101P3A11 protein contain conservative amino acid substitutions within the 101P3A11 sequences described herein or contain a substitution of an amino acid from a corresponding position in a homologue of 101P3A11. One class of 101P3A11 allelic variants are proteins that share a high degree of homology with at least a small region of a particular 101P3A11 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, or 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS 1992 Vol 89 10915-10919; Lei et al., J Biol Chem 1995 May 19; 270(20):11882-6).

Embodiments of the invention disclosed herein include a wide variety of art-accepted variants or analogs of 101P3A11 proteins such as polypeptides having amino acid insertions, deletions and substitutions. 101P3A11 variants can be made using methods known in the art such as site-directed mutagenesis, alanine scanning, and PCR mutagenesis. Site-directed mutagenesis (Carter et al., *Nucl. Acids Res.,* 13:4331 (1986); Zoller et al., *Nucl. Acids Res.,* 10:6487 (1987)), cassette mutagenesis (Wells et al., Gene, 34:315 (1985)), restriction selection mutagenesis (Wells et al., *Philos. Trans. R. Soc. London SerA,* 317:415 (1986)) or other known techniques can be performed on the cloned DNA to produce the 101P3A11 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 101P3A11 variants, analogs or homologs, have the distinguishing attribute of having at least one epitope that is "cross reactive" with a 101P3A11 protein having an amino acid sequence of FIG. 3. As used in this sentence, "cross reactive" means that an antibody or T cell that specifically binds to a 101P3A11 variant also specifically binds to a 101P3A11 protein having an amino acid sequence set forth in FIG. 3. A polypeptide ceases to be a variant of a protein shown in FIG. 3, when it no longer contains any epitope capable of being recognized by an antibody or T cell that specifically binds to the starting 101P3A11 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol. 2000 165(12): 6949-6955; Hebbes et al., Mol Immunol (1989) 26(9):865-73; Schwartz et al., J Immunol (1985) 135(4): 2598-608.

Other classes of 101P3A11-related protein variants share 70%, 75%, 80%, 85% or 90% or more similarity with an amino acid sequence of FIG. 3, or a fragment thereof. Another specific class of 101P3A11 protein variants or analogs comprise one or more of the 101P3A11 biological motifs described herein or presently known in the art. Thus, encompassed by the present invention are analogs of 101P3A11 fragments (nucleic or amino acid) that have altered functional (e.g., immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 101P3A11 protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 101P3A11 protein shown in FIG. 2 or FIG. 3.

Moreover, representative embodiments of the invention disclosed herein include polypeptides consisting of about amino acid 1 to about amino acid 10 of a 101P3A11 protein shown in FIG. 2 or FIG. 3, polypeptides consisting of about amino acid 10 to about amino acid 20 of a 101P3A11 protein shown in FIG. 2 or FIG. 3, polypeptides consisting of about amino acid 20 to about amino acid 30 of a 101P3A11 protein shown in FIG. 2 or FIG. 3, polypeptides consisting of about amino acid 30 to about amino acid 40 of a 101P3A11 protein shown in FIG. 2 or FIG. 3, polypeptides consisting of about amino acid 40 to about amino acid 50 of a 101P3A11 protein shown in FIG. 2 or FIG. 3, polypeptides consisting of about amino acid 50 to about amino acid 60 of a 101P3A11 protein shown in FIG. 2 or FIG. 3, polypeptides consisting of about amino acid 60 to about amino acid 70 of a 101P3A11 protein shown in FIG. 2 or FIG. 3, polypeptides consisting of about amino acid 70 to about amino acid 80 of a 101P3A11 protein shown in FIG. 2 or FIG. 3, polypeptides consisting of about amino acid 80 to about amino acid 90 of a 101P3A11 protein shown in FIG. 2 or FIG. 3, polypeptides consisting of about amino acid 90 to about amino acid 100 of a 101P3A11 protein shown in FIG. 2 or FIG. 3, etc. throughout the entirety of a 101P3A11 amino acid sequence. Moreover, polypeptides consisting of about amino acid 1 (or 20 or 30 or 40 etc.) to about amino acid 20, (or 130, or 140 or 150 etc.) of a 101P3A11 protein shown in FIG. 2 or FIG. 3 are embodiments of the invention. It is to be appreciated that the starting and stopping positions in this paragraph refer to the specified position as well as that position plus or minus 5 residues.

101P3A11-related proteins are generated using standard peptide synthesis technology or using chemical cleavage methods well known in the art. Alternatively, recombinant methods can be used to generate nucleic acid molecules that encode a 101P3A11-related protein. In one embodiment, nucleic acid molecules provide a means to generate defined fragments of a 101P3A11 protein (or variants, homologs or analogs thereof).

III.A.) Motif-Bearing Protein Embodiments

Additional illustrative embodiments of the invention disclosed herein include 101P3A11 polypeptides comprising the amino acid residues of one or more of the biological motifs contained within a 101P3A11 polypeptide sequence set forth in FIG. 2 or FIG. 3. Various motifs are known in the art, and a protein can be evaluated for the presence of such motifs by a number of publicly available Internet sites (see, e.g., Epimatrix™ and Epimer™.

Motif bearing subsequences of all 101P3A11 variant proteins are set forth and identified in Tables V-XVIII and XXII TO ILI.

Table XIX sets forth several frequently occurring motifs based on pfam searches (see URL address pfam.wustl.edu/). The columns of Table XIX list (1) motif name abbreviation, (2) percent identity found amongst the different member of the motif family, (3) motif name or description and (4) most common function; location information is included if the motif is relevant for location.

Polypeptides comprising one or more of the 101P3A11 motifs discussed above are useful in elucidating the specific characteristics of a malignant phenotype in view of the observation that the 101P3A11 motifs discussed above are associated with growth dysregulation and because 101P3A11 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables V-XVIII and XXII TO IL. CTL epitopes can be determined using specific algorithms to identify peptides within a 101P3A11 protein that are capable of optimally binding to specified HLA alleles (e.g., Table IV; Epimatrix™ and Epimer™. Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, one can substitute out a deleterious residue in favor of any other residue, such as a preferred residue as defined in Table IV; substitute a less-preferred residue with a preferred residue as defined in Table IV; or substitute an originally-occurring preferred residue with another preferred residue as defined in Table IV. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the invention include polypeptides comprising combinations of the different motifs set forth in Table XX, and/or, one or more of the predicted CTL epitopes of Tables V-XVII and XXII-XLVII, and/or, one or more of the predicted HTL epitopes of Tables XLVIII-LI, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

101P3A11-related proteins are embodied in many forms, preferably in isolated form. A purified 101P3A11 protein molecule will be substantially free of other proteins or molecules that impair the binding of 101P3A11 to antibody, T cell or other ligand. The nature and degree of isolation and purification will depend on the intended use. Embodiments of a 101P3A11-related proteins include purified 101P3A11-related proteins and functional, soluble 101P3A11-related proteins. In one embodiment, a functional, soluble 101P3A11 protein or fragment thereof retains the ability to be bound by antibody, T cell or other ligand.

The invention also provides 101P3A11 proteins comprising biologically active fragments of a 101P3A11 amino acid sequence shown in FIG. 2 or FIG. 3. Such proteins exhibit properties of the starting 101P3A11 protein, such as the ability to elicit the generation of antibodies that specifically bind an epitope associated with the starting 101P3A11 protein; to be bound by such antibodies; to elicit the activation of HTL or CTL; and/or, to be recognized by HTL or CTL that also specifically bind to the starting protein.

101P3A11-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-101P3A11 antibodies, or T cells or in identifying cellular factors that bind to 101P3A11. For example, hydrophilicity profiles can be generated, and immunogenic peptide fragments identified, using the method of Hopp, T. P. and Woods, K. R., 1981, Proc. Natl. Acad. Sci. U.S.A. 78:3824-3828. Hydropathicity profiles can be generated, and immunogenic peptide fragments identified, using the method of Kyte, J. and Doolittle, R. F., 1982, J. Mol. Biol. 157:105-132. Percent (%) Accessible Residues profiles can be generated, and immunogenic peptide fragments identified, using the method of Janin J., 1979, Nature 277:491-492. Average Flexibility profiles can be generated, and immunogenic peptide fragments identified, using the method of Bhaskaran R., Ponnuswamy P. K., 1988, Int. J. Pept. Protein Res. 32:242-255. Beta-turn profiles can be generated, and immunogenic peptide fragments identified, using the method of Deleage, G., Roux B., 1987, Protein Engineering 1:289-294.

CTL epitopes can be determined using specific algorithms to identify peptides within a 101P3A11 protein that are capable of optimally binding to specified HLA alleles (e.g., by using the SYFPEITHI site; the listings in Table IV(A)-(E); Epimatrix™ and Epimer™; and BIMAS. Illustrating this, peptide epitopes from 101P3A11 that are presented in the context of human MHC Class I molecules, e.g., HLA-A1, A2, A3, A11, A24 B7 and B35 were predicted (see, e.g., Tables V-XVIII, XXII TO IL). Specifically, the complete amino acid sequence of the 101P3A11 protein and relevant portions of other variants, i.e., for HLA Class I predictions 9 flanking redisues on either side of a point mutation, and for HLA Class II predictions 14 flanking residues on either side of a point mutation, were entered into the HLA Peptide Motif Search algorithm found in the Bioinformatics and Molecular Analysis Section (BIMAS) web site; and the site SYFPEITHI was used.

The HLA peptide motif search algorithm was developed by Dr. Ken Parker based on binding of specific peptide sequences in the groove of HLA Class I molecules, in particular HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149: 3580-7 (1992)). Selected results of 101P3A11 predicted binding peptides are shown in Tables V-XVIII and XXII TO IL herein. In Tables V-XVIII and XXII TO IL, selected candidates, 9-mers, 10-mers, and 15-mers for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class II motifs available in the art or which become part of the art such as set forth in Table IV (or determined using World Wide Web site URL syfpeithi.bmi-heidelberg.com/, or BIMAS, bimas.dcrt.nih.gov/) are to be "applied" to a 101P3A11 protein in accordance with the invention. As used in this context "applied" means that a 101P3A11 protein is evaluated, e.g., visually or by computer-based patterns finding methods, as appreciated by those of skill in the relevant art. Every subsequence of a 101P3A11 protein of 8, 9, 10, or 11 amino acid residues that bears an HLA Class I motif, or a subsequence of 9 or more amino acid residues that bear an HLA Class II motif are within the scope of the invention.

III.B.) Expression of 101P3A11-Related Proteins

In an embodiment described in the examples that follow, 101P3A11 can be conveniently expressed in cells (such as 293T cells) transfected with a commercially available expression vector such as a CMV-driven expression vector encoding 101P3A11 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 101P3A11 protein in transfected cells. The secreted HIS-tagged 101P3A11 in the culture media can be purified, e.g., using a nickel column using standard techniques.

III.C.) Modifications of 101P3A11-Related Proteins

Modifications of 101P3A11-related proteins such as covalent modifications are included within the scope of this invention. One type of covalent modification includes reacting targeted amino acid residues of a 101P3A11 polypeptide with an organic derivatizing agent that is capable of reacting with selected side chains or the N- or C-terminal residues of a 101P3A11 protein. Another type of covalent modification of a 101P3A11 polypeptide included within the scope of this invention comprises altering the native glycosylation pattern of a protein of the invention. Another type of covalent modification of 101P3A11 comprises linking a 101P3A11 polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337.

The 101P3A11-related proteins of the present invention can also be modified to form a chimeric molecule comprising 101P3A11 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 101P3A11 sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 101P3A11. A chimeric molecule can comprise a fusion of a 101P3A11- related protein with a polyhistidine epitope tag, which provides an epitope to which immobilized nickel can selectively bind, with cytokines or with growth factors. The epitope tag is generally placed at the amino- or carboxyl-terminus of a 101P3A11 protein. In an alternative embodiment, the chimeric molecule can comprise a fusion of a 101P3A11-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 101P3A11 polypeptide in place of at least one variable region within an Ig molecule. In a preferred embodiment, the immunoglobulin fusion includes the hinge, CH2 and CH3, or the hinge, CHI, CH2 and CH3 regions of an IgGI molecule. For the production of immunoglobulin fusions see, e.g., U.S. Pat. No. 5,428, 130 issued Jun. 27, 1995.

III.D.) Uses of 101P3A11-Related Proteins

The proteins of the invention have a number of different specific uses. As 101P3A11 is highly expressed in prostate and other cancers, 101P3A11-related proteins are used in methods that assess the status of 101P3A11 gene products in normal versus cancerous tissues, thereby elucidating the malignant phenotype. Typically, polypeptides from specific regions of a 101P3A11 protein are used to assess the presence of perturbations (such as deletions, insertions, point mutations etc.) in those regions (such as regions containing one or more motifs). Exemplary assays utilize antibodies or T cells targeting 101P3A11-related proteins comprising the amino acid residues of one or more of the biological motifs contained within a 101P3A11 polypeptide sequence in order to evaluate the characteristics of this region in normal versus cancerous tissues or to elicit an immune response to the epitope. Alternatively, 101P3A11-related proteins that contain the amino acid residues of one or more of the biological motifs in a 101P3A11 protein are used to screen for factors that interact with that region of 101P3A11.

101P3A11 protein fragments/subsequences are particularly useful in generating and characterizing domain-specific antibodies (e.g., antibodies recognizing an extracellular or intracellular epitope of a 101P3A11 protein), for identifying agents or cellular factors that bind to 101P3A11 or a particular structural domain thereof, and in various therapeutic and diagnostic contexts, including but not limited to diagnostic assays, cancer vaccines and methods of preparing such vaccines.

Proteins encoded by the 101P3A11 genes, or by analogs, homologs or fragments thereof, have a variety of uses, including but not limited to generating antibodies and in methods for identifying ligands and other agents and cellular constituents that bind to a 101P3A11 gene product. Antibodies raised against a 101P3A11 protein or fragment thereof are useful in diagnostic and prognostic assays, and imaging methodologies in the management of human cancers characterized by expression of 101P3A11 protein, such as those listed in Table I. Such antibodies can be expressed intracellularly and used in methods of treating patients with such cancers. 101P3A11-related nucleic acids or proteins are also used in generating HTL or CTL responses.

Various immunological assays useful for the detection of 101P3A11 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 101P3A11-expressing cells (e.g., in radioscintigraphic imaging methods). 101P3A11 proteins are also particularly useful in generating cancer vaccines, as further described herein.

IV.) 101P3A11 Antibodies

Another aspect of the invention provides antibodies that bind to 101P3A11-related proteins. Preferred antibodies specifically bind to a 101P3A11-related protein and do not bind (or bind weakly) to peptides or proteins that are not 101P3A11-related proteins. For example, antibodies that bind 101P3A11 can bind 101P3A11-related proteins such as the homologs or analogs thereof.

101P3A11 antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 101P3A11 is also expressed or overexpressed in these other cancers. Moreover, intracellularly expressed antibodies (e.g., single chain antibodies) are therapeutically useful in treating cancers in which the expression of 101P3A11 is involved, such as advanced or metastatic prostate cancers.

The invention also provides various immunological assays useful for the detection and quantification of 101P3A11 and mutant 101P3A11-related proteins. Such assays can comprise one or more 101P3A11 antibodies capable of recognizing and binding a 101P3A11-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 101P3A11 are also provided by the invention, including but not limited to radioscintigraphic imaging methods using labeled 101P3A11 antibodies. Such assays are clinically useful in the detection, monitoring, and prognosis of 101P3A11 expressing cancers such as prostate cancer.

101P3A11 antibodies are also used in methods for purifying a 101P3A11-related protein and for isolating 101P3A11 homologues and related molecules. For example, a method of purifying a 101P3A11-related protein comprises incubating a 101P3A11 antibody, which has been coupled to a solid matrix, with a lysate or other solution containing a 101P3A11-related protein under conditions that permit the 101P3A11 antibody to bind to the 101P3A11-related protein; washing the solid matrix to eliminate impurities; and eluting the 101P3A11-related protein from the coupled antibody. Other uses of 101P3A11 antibodies in accordance with the invention include generating anti-idiotypic antibodies that mimic a 101P3A11 protein.

Various methods for the preparation of antibodies are well known in the art. For example, antibodies can be prepared by immunizing a suitable mammalian host using a 101P3A11-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 101P3A11 can also be used, such as a 101P3A11

GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 101P3A11-related protein is synthesized and used as an immunogen.

In addition, naked DNA immunization techniques known in the art are used (with or without purified 101P3A11-related protein or 101P3A11 expressing cells) to generate an immune response to the encoded immunogen (for review, see Donnelly et al., 1997, Ann. Rev. Immunol. 15: 617-648).

The amino acid sequence of a 101P3A11 protein as shown in FIG. 2 or FIG. 3 can be analyzed to select specific regions of the 101P3A11 protein for generating antibodies. For example, hydrophobicity and hydrophilicity analyses of a 101P3A11 amino acid sequence are used to identify hydrophilic regions in the 101P3A11 structure. Regions of a 101P3A11 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824-3828. Hydropathicity profiles can be generated using the method of Kyte, J. and Doolittle, R. F., 1982, J. Mol. Biol. 157:105-132. Percent (%) Accessible Residues profiles can be generated using the method of Janin J., 1979, Nature 277:491-492. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each region identified by any of these programs or methods is within the scope of the present invention. Methods for the generation of 101P3A11 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodimide reagents are used; in other instances linking reagents such as those supplied by Pierce Chemical Co., Rockford, Ill., are effective. Administration of a 101P3A11 immunogen is often conducted by injection over a suitable time period and with use of a suitable adjuvant, as is understood in the art. During the immunization schedule, titers of antibodies can be taken to determine adequacy of antibody formation.

101P3A11 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 101P3A11-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 101P3A11 protein can also be produced in the context of chimeric or complementarity determining region (CDR) grafted antibodies of multiple species origin. Humanized or human 101P3A11 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 101P3A11 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 101P3A11 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. Nos. 6,162,963 issued 19 Dec. 2000; 6,150,584 issued 12 Nov. 2000; and, 6,114,598 issued 5 Sep. 2000). This method avoids the in vitro manipulation required with phage display technology and efficiently produces high affinity authentic human antibodies.

Reactivity of 101P3A11 antibodies with a 101P3A11-related protein can be established by a number of well known means, including Western blot, immunoprecipitation, ELISA, and FACS analyses using, as appropriate, 101P3A11-related proteins, 101P3A11-expressing cells or extracts thereof. A 101P3A11 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 101P3A11 epitopes are generated using methods generally known in the art. Homodimeric antibodies can also be generated by cross-linking techniques known in the art (e.g., Wolff et al., Cancer Res. 53: 2560-2565).

Thus, the present invention relates to polyclonal and monoclonal antibodies raised in response to either 101P3A11, or biologically active fragments thereof. The polyclonal and/or monoclonal antibodies of the present invention, especially 101P3A11 neutralizing antibodies (antibodies that block 101P3A11 function and/or block its binding with ligands), will also be useful as therapeutics to modulate 101P3A11 expression and/or activity. In addition, the polyclonal and/or monoclonal antibodies of the present invention are useful as (1) diagnostics for qualitative and/or quantitative detection of 101P3A11 expression in a variety of immunoassays, e.g., Western blotting; immunohistochemistry and immunoprecipitation (of samples/biopsies of material such as tissue, serum, blood, urine or semen); and, (ii) as noted above, inhibition of 101P3A11 function using 101P3A11 neutralizing antibodies for the treatment of diseases associated with 101P3A11 overexpression such as cancers of tissues listed in Table I. Antibodies that antagonize the effect of 101P3A11 (for example, inhibition of 101P3A11's ability to protect certain cells from apoptosis, cell death or inhibition of 101P3A11's ability to bind to its ligand) can be administered directly by methods known in the art (see, e.g., Antibodies in Human Diagnosis and Therapy by Raven Press, New York (1977)). Monoclonal antibodies are especially preferred for the treatment of tumors associated with an abnormal 101P3A11 expression. For example, a 101P3A11 monoclonal antibody which slows the progression of a cancer associated with an increase in 101P3A11 expression within cancer cells, and in turn can cause tumor shrinkage over time, will be especially useful.

A useful paradigm is the early success of Herceptin™, a recombinant DNA-derived humanized monoclonal antibody that selectively binds to the extracellular domain of the human epidermal growth factor 2 (HER2). The antibody is produced in CHO cells and the final product is available as a lyophilized powder. HER2 has been shown to be overexpressed in 25-30% of primary breast cancers. In turn, administration of Herceptin™ has been shown to inhibit the proliferation of tumor cells which overexpress HER2. A prospective 101P3A11 monoclonal antibody can be "humanized" by methods well known in the art, such as Xenomouse™ technology (Abgenix), or antibody phage display, in order to reduce any unwanted immunological effects of human administration of the antibody. Alternatively, the 101P3A11-based antibody can be a chimera, most likely a mouse/human or rat/human chimera. In addition, any such therapeutic 101P3A11-based antibody can be administered alone or within a regime that includes other cancer therapies, such as known chemotherapeutic agents, which can act in concert to reduce tumor growth associated with increased 101P3A11 expression. Another example of the use of monoclonal antibodies to treat various cancers is Rituxan™, a recombinant DNA-based mouse/human chimeric monoclonal antibody which has been shown to be effective in treating patients with low grade B-cell non-Hodgkin's lymphoma (NHL), a cancer of the immune system. Rituxan targets and destroys white blood cells (B cells) involved in the disease, resulting insignificant tumor shrinkage with less severe side-effects than most cancer treatments. Additional monoclonal antibodies currently under development include (i) an anti-CD-20 monoclonal antibody to treat patients with low-grade lymphomas, (ii) a combination anti-EGFr antibody with doxorubicin in patients with hormone refractory prostate cancer as well as a combination anti-EGFr antibody with cisplatin in patients with head and neck and lung cancer. A 101P3A11 anti-idiotype antibody can also be administered so as to stimulate a host immune response to tumors overexpressing 101P3A11. Therefore, it is evident that 101P3A11 antibodies, especially 101P3A11 monoclonal antibodies, are potentially useful tools, along or in combination with other cancer therapies, for direct therapeutic intervention of cancers characterized by an increase in 101P3A11 expression.

Skilled artisans understand that equivalent molecules known in the art which mimic the inhibitory activity of an antibody capable of inhibiting 101P3A11 function are aspects of the presently disclosed methods which employ an antibody capable of inhibiting 101P3A11 function. Examples of such molecules include anti-101P3A11 peptide mimetics which inhibit the growth of at least a comparable or like manner to an antibody capable of inhibiting 101P3A11 function.

Polyclonal Antibodies

The antibodies of the invention also comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent can include a 101P3A11 polypeptide or a fusion protein thereof. It can be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which can be employed include Freund's complete adjuvant and MPL-TDM adjuvant (monophosphoryl Lipid A, synthetic trehalose dicorynomycolate). The immunization protocol can be selected by one skilled in the art without undue experimentation. The mammal can then be bled, and the serum assayed for antibody titer. If desired, the mammal can be boosted until the antibody titer increases or plateaus.

Monoclonal Antibodies

The antibodies of the invention can, alternatively, be monoclonal antibodies. Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include a 101P3A11 polypeptide or a fusion protein thereof.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Alternatively, SLAM technology can be employed for screening as appreciated by one of skill in the art.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Vir. An example of such a murine myeloma cell line is P3X63AgU.1. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the 101P3A11. Preferably, the binding specificity of monoclonal antibodies produced by the hybridoma cells is determined by immunoprecipitation or by an in in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones can be subcloned by limiting dilution procedures and grown by standard methods (Goding, Monoclonal Antibodies: Principles and Practice, Academic Press, (1986)). Suitable culture media for this purpose include, for example, Dulbecco's Modified Eagle's Medium or RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see, e.g., U.S. Pat. No. 4,816,567; Morrison et al., *Proc. Natl. Acad. Sci. USA,* 81:6851-6855 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody. Optionally, chimeric antibodies can be constructed which include at least one variable or hypervariable domain of an anti-101P3A11 antibody selected from the antibodies disclosed herein.

Optionally, the antibody capable of inhibiting 101P3A11 function of the present invention will bind to the same epitope(s) as any of the antibodies disclosed herein. This can be determined by conducting various assays, such as described herein. For instance, to determine whether a monoclonal antibody has the same specificity as the antibodies referred to herein, one can compare its activity in blocking assays or inhibition assays or functional assays.

The antibodies of the invention include "cross-linked" antibodies. The term "cross-linked" as used herein refers to binding of at least two IgG molecules together to form one (or single) molecule. The 101P3A11 antibodies can be cross-linked using various linker molecules and optionally the antibodies are cross-linked using an anti-IgG molecule, complement, chemical modification or molecular engineering. It is appreciated by those skilled in the art that complement has a relatively high affinity to antibody molecules once the antibodies bind to cell surface membrane. Accordingly, complement can be used as a cross-linking molecule to link two or more antibodies bound to cell surface membrane. Among the various murine Ig isotypes, IgM, IgG2a and IgG2b are known to fix complement.

The antibodies of the invention can optionally comprise dimeric antibodies, as well as multivalent forms of antibodies. Those skilled in the art can construct such dimers or multivalent forms by techniques known in the art and using the anti-101P3A11 antibodies herein.

The antibodies of the invention can also comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')2 fragment that has two antigen combining sites and is still capable of cross-linking antigen.

The Fab fragments produced in the antibody digestion also contain the constant domains of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

Single chain Fv fragments can also be produced, such as described in Iliades et al, FEBS Letters, 409:437-441 (1997). Coupling of such single chain fragments using various linkers is described in Kortt et al., Protein Engineering, 10:423-433 (1997).

In addition to the antibodies described herein, it is contemplated that chimeric or hybrid antibodies are prepared using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

The 101P3A11 antibodies of the invention further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988); and Presta, Curr. Op. Struct. Biol., 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Sources of such import residues or import variable domains (or CDRs) include antibodies that specifically bind 101P3A11.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296-2308 (1993); Chothia and Lesk, J. Mol. Biol., 196:901-917 (1987)). Another method uses a particular framework derived from the consensus sequence of all human antibodies of a particular subgroup of light or heavy chains. The same framework can be used for several different humanized antibodies (Carter et al., Proc. Natl. Acad. Sci. USA, 89:4285-4289 (1992); Presta et al., J. Immunol., 151:2623-2632 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679 published 3 Mar. 1994).

Human monoclonal antibodies can be made via an adaptation of the hybridoma method first described by Kohler and Milstein by using human B lymphocytes as the fusion partner. Human B lymphocytes producing an antibody of interest can, for example, be isolated from a human individual, after obtaining informed consent. For instance, the individual can be producing antibodies against an autoantigen as occurs with certain disorders such as systemic lupus erythematosus (Shoenfeld et al. J. Clin. Invest., 70:205 (1982)), immune-mediated thrombocytopenic purpura (ITP) (Nugent et al. Blood, 70(1):16-22 (1987)), or cancer. Alternatively, or additionally, lymphocytes can be immunized in vitro. For instance, one can expose isolated human peripheral blood lymphocytes in vitro to a lysomotrophic agent (e.g., L-leucine-O-methyl ester, L-glutamic acid dimethly ester or L-leucyl-L-leucine-O-methyl ester) (U.S. Pat. No. 5,567,610, Borrebaeck et al.); and/or T-cell depleted human peripheral blood lymphocytes can be treated in vitro with adjuvants such as 8-mercaptoguanosine and cytokines (U.S. Pat. No. 5,229,275, Goroff et al.).

The B lymphocytes recovered from the subject or immunized in vitro, are then generally immortalized in order to generate a human monoclonal antibody. Techniques for immortalizing the B lymphocyte include, but ate not limited to: (a) fusion of the human B lymphocyte with human, murine myelomas or mouse-human heteromyeloma cells; (b) viral transformation (e.g. with an Epstein-Barr virus; see Nugent et al., supra, for example); (c) fusion with a lymphoblastoid cell line; or (d) fusion with lymphoma cells.

Lymphocytes can be fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared ate seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Suitable human myeloma and mouse-human heteromyeloma cell lines have been described (Kozbor, J. Immunol., 133:3001 (1984); Brodeur et al., Monoclonal Antibody Production Techniques and Applications, pp. 51-63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A chromatography, gel electrophoresis, dialysis, or affinity chromatography.

Human antibodies can also be generated using a non-human host, such as a mouse, which is capable of producing human antibodies. As noted above, transgenic mice are now available that are capable, upon immunization, of producing a full repertoire of human antibodies in the absence of endogenous immunoglobulin production. For example, it has been described that the homozygous deletion of the antibody heavy-chain joining region JH) gene in chimeric and germ-line mutant mice results in complete inhibition of endogenous antibody production. Transfer of the human germ-line immunoglobulin gene array in such germ-line mutant mice resulted in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); U.S. Pat. No. 5,591,669; U.S. Pat. No. 5,589,369; and U.S. Pat. No. 5,545,807. Human antibodies can also be prepared using SCID-hu mice (Duchosal et al Nature 355:258-262 (1992)).

In another embodiment, the human antibody can be selected from a human antibody phage display library. The preparation of libraries of antibodies or fragments thereof is well known in the art and any of the known methods can be used to construct a family of transformation vectors which can be introduced into host cells. Libraries of antibody light and heavy chains in phage (Huse et al., Science, 246:1275 (1989)) or of fusion proteins in phage or phagemid can be prepared according to known procedures. See, for example, Vaughan et al, Nature Biotechnology 14:309-314 (1996); Barbas et al., Proc. Natl. Acad. Sci., USA, 88:7978-7982 (1991); Marks et al., J. Mol. Biol., 222:581-597 (1991); Hoogenboom and Winter, J. Mol. Biol., 227:381-388 (1992); Barbas et al., Proc. Natl. Acad. Sci., USA, 89: 4457-4461 (1992); Griffiths et al., EMBO Journal, 13:3245-3260 (1994); de Kruif et al., J. Mol. Biol., 248:97-105 (1995); WO 98/05344; WO 98/15833; WO 97/47314; WO 97/44491; WO 97/35196; WO 95/34648; U.S. Pat. No. 5,712,089; U.S. Pat. No. 5,702,892; U.S. Pat. No. 5,427,908; U.S. Pat. No. 5,403,484; U.S. Pat. No. 5,432,018; U.S. Pat. No. 5,270,170; WO 92/06176; WO 99/06587; U.S. Pat. No. 5,514,548; WO 97/08320; and U.S. Pat. No. 5,702,892. The antigen of interest is panned against the phage library using procedures known in the field for selecting phage-antibodies which bind to the target antigen.

The 101P3A11 antibodies, as described herein, will optionally possess one or more desired biological activities or properties. Such antibodies can include but are not limited to chimeric, humanized, human, and affinity matured antibodies. As described above, the antibodies can be constructed or engineered using various techniques to achieve these desired activities or properties. In one embodiment, the 101P3A11 antibody will have a 101P3A11 binding affinity of at least $10^{-5}$ M, preferably at least in the range of $10^{-6}$ M to $10^{-7}$ M, mote preferably, at least in the range of $10^{-8}$ M to $10^{-12}$ M and even more preferably, at least in the range of $10^{-9}$ M to $10^{-12}$ M. The binding affinity of the antibody can be determined without undue experimentation by testing the antibody in accordance with techniques known in the art, including Scatchard analysis (Munson and Pollard, Anal. Biochem., 107: 220 (1980)). For example, a 101P3A11 antibody can be assayed for binding affinity to 101P3A11, including constructs or fragments thereof.

In another embodiment, the antibody interacts in such a way to create a steric conformation which prevents binding of an antibody capable of inhibiting or enhancing 101P3A11 function. The epitope binding property of the antibody of the present invention can be determined using techniques known in the art.

Other Modifications

Other modifications of the 101P3A11 antibodies are contemplated herein. The antibodies of the present invention can be modified by conjugating the antibody to a cytotoxic agent (like a toxin molecule) or a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. This technology is also referred to as "Antibody Dependent Enzyme Mediated Prodrug Therapy" (ADEPT).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; caspases such as caspase-3; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population.

The enzymes can be covalently bound to the antibodies by techniques well known in the art such as the use of heterobifunctional crosslinking reagents. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Further modifications to the polypeptides of the invention are contemplated. For example, the antibodies can be linked to one of a variety of nonproteinaceous polymers, e.g., polyethylene glycol, polypropylene glycol, polyoxyalkylenes, or copolymers of polyethylene glycol and polypropylene glycol. The antibody also can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). To increase the serum half life of the antibody, one can incorporate a salvage receptor binding epitope into the antibody (especially an antibody fragment) as described, e.g., in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Formulations

The antibody capable of inhibiting 101P3A11 function are preferably administered in a carrier. The molecules can be administered in a single carrier, or alternatively, can be included in separate carriers. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the carrier to render the formulation isotonic. Examples of the carrier include saline, Ringer's solution and dextrose solution. The pH of the solution is preferably from about 5 to about 8, and more preferably from about 7.4 to about 7.8. It will be apparent to those persons skilled in the art that certain carriers are preferred depending upon, for instance, the route of administration and concentration of agent being administered. The carrier can be in the form of a lyophilized formulation or aqueous solution.

Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN®, PLURONICS® or polyethylene glycol (PEG).

The formulation can also contain more than one active compound as necessary for the particular indication being treated, preferably those with complementary activities, and preferably that do not adversely affect each other. Alternatively, or in addition, the composition can comprise a cytotoxic agent, cytokine or growth inhibitory agent. Such molecules are suitably present in combination in amounts that are effective for the purpose intended.

The antibody capable of inhibiting 101P3A11 function can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drag delivery systems (for example, liposomes, albumin microspheres, microemulsions, nano-particles and nanocapsules) or in macroemulsions. Such techniques are disclosed in Remington's Pharmaceutical Sciences 16th edition, Oslo, A. Ed. (1980).

The formulations to be used for in vivo administration should be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and (ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Modes of Administration

An antibody(s) capable of inhibiting 101P3A11 function can be administered in accord with known methods, such as intravenous administration as a bolus or by continuous infusion over a period of time, by intramuscular, intraperitoneal, intrathecal, subcutaneous, intra-articular, intrasynovial, intrathecal, oral, topical, or inhalation routes. Optionally, administration can be performed through mini-pump infusion using various commercially available devices.

Effective dosages and schedules for administering an antibody capable of inhibiting 101P3A11 function can be determined empirically, and making such determinations is within the skill in the art. Effective dosage or amount of an antibody capable of inhibiting 101P3A11 function used alone may range from about 1 μg/kg to about 100 mg/kg of body weight or more per day. Interspecies scaling of dosages can be performed in a manner known in the art, e.g., as disclosed in Mordenti et al., Pharmaceut. Res., 8:1351 (1991). Those skilled in the art will understand that the dosage of an antibody capable of inhibiting 101P3A11 function that must be administered will vary depending on, for example, the mammal which will receive the an antibody capable of inhibiting 101P3A11 function, the route of administration, and other drugs or therapies being administered to the mammal.

Depending on the type of cells and/or severity of the disease, about 1 μg/kg to 15 mg/kg (e.g. 0.1-20 mg/kg) of antibody is an initial candidate dosage for administration, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens can be useful.

It is contemplated that yet additional therapies can be employed in the methods. The one or more other therapies can include but are not limited to, other chemotherapies (or chemotherapeutic agents) and/or radiation therapy, immunoadjuvants, growth inhibitory agents, cytokines, and other non-Her-2 antibody-based therapies. Examples include interleukins (e.g., IL-1, IL-2, IL-3, IL-6), leukemia inhibitory factor, interferons, erythropoietin, thrombopoietin, and anti-VEGF antibody. Other agents known to inhibit the growth of mammalian cells-can also be employed, and such agents include TNF-α, CD30 ligand, 4-1BB ligand, and Apo-1 ligand.

Additional chemotherapies contemplated by the invention include chemical substances or drugs which are known in the art and are commercially available, such as Adriamycin, Doxorubicin, 5-Fluorouracil, Cytosine arabinoside ("Ara-C"), Cyclophosphamide, Leucovorin, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carrainomycin, Amimopterin, Dactinomycin, Mitomycins, Esperamicins (see U.S. Pat. No. 4,675,187), Melphalan and other related nitrogen mustards. Also included are agents that act to regulate or inhibit hormone action on tumors such as tamoxifen and onaptistone.

Preparation and dosing schedules for such chemotherapy can be used according to manufacturers' instructions or as determined empirically by the skilled practitioner. Preparation and dosing schedules for such chemotherapy are also described in Chemotherapy Service Ed., M. C. Perry, Williams & Wins, Baltimore, Md. (1992). The chemotherapeutic agent can precede, or follow administration with the antibody capable of inhibiting 101P3A11 function, or can be given simultaneously therewith.

The chemotherapy is preferably administered in a carrier, such as those described above. The mode of administration of the chemotherapy can be the same as employed for an antibody capable of modulating, such as inhibiting or enhancing, 101P3A11 function, or it can be administered via a different mode.

Radiation therapy can be administered according to protocols commonly employed in the art and known to the skilled artisan. Such therapy can include cesium, iridium, iodine, or cobalt radiation. The radiation therapy can be whole body irradiation, or can be directed locally to a specific site or tissue in or on the body. Typically, radiation therapy is administered in pulses over a period of time from about 1 to about 2 weeks. The radiation therapy can, however, be administered over longer periods of time. Optionally, the radiation therapy can be administered as a single dose or as multiple, sequential doses.

An antibody capable of inhibiting 101P3A11 function (and one or more other therapies) can be administered concurrently or sequentially. Following administration of an antibody capable of inhibiting 101P3A11 function, treated cells in vitro can be analyzed. Where there has been in vivo treatment, a treated mammal can be monitored in various ways well known to the skilled practitioner. For instance, tumor mass can be observed physically, by biopsy or by standard x-ray imaging techniques.

V.) 101P3A11 Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317: 359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., *J. Immunol.* 160: 3363, 1998; Rammensee, et al., *Immunogenetics* 41:178, 1995; Rammensee et al., SYFPEITHI, access via World Wide Web at URL syfpeithi.bmi-heidelberg.com/; Sette, A. and Sidney, J. *Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al., *Cell* 74:929-937, 1993; Kondo et al., *J. Immunol.* 155:4307-4312, 1995; Sidney et al., *J. Immunol.* 157:3480-3490, 1996; Sidney et al., *Human Immunol.* 45:79-93, 1996; Sette, A. and Sidney, *J. Immunogenetics* 1999 November; 50(3-4):201-12, Review).

Furthermore, x-ray crystallographic analyses of HLA-peptide complexes have revealed pockets within the peptide binding cleft/groove of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D.C., *J. Mol. Biol.* 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1-2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 101P3A11 Transgenic Animals

Nucleic acids that encode a 101P3A11-related protein can also be used to generate either transgenic animals or "knock out" animals that, in turn, are useful in the development and screening of therapeutically useful reagents. In accordance with established techniques, cDNA encoding 101P3A11 can be used to clone genomic DNA that encodes 101P3A11. The cloned genomic sequences can then be used to generate transgenic animals containing cells that express DNA that encode 101P3A11. Methods for generating transgenic animals, particularly animals such as mice or rats, have become conventional in the art and are described, for example, in U.S. Pat. Nos. 4,736,866 issued 12 Apr. 1988, and 4,870,009 issued 26 Sep. 1989. Typically, particular cells would be targeted for 101P3A11 transgene incorporation with tissue-specific enhancers.

Transgenic animals that include a copy of a transgene encoding 101P3A11 can be used to examine the effect of increased expression of DNA that encodes 101P3A11. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 101P3A11 can be used to construct a 101P3A11 "knock out" animal that has a defective or altered gene encoding 101P3A11 as a result of homologous recombination between the endogenous gene encoding 101P3A11 and altered genomic DNA encoding 101P3A11 introduced into an embryonic cell of the animal. For example, cDNA that encodes 101P3A11 can be used to clone genomic DNA encoding 101P3A11 in accordance with established techniques. A portion of the genomic DNA encoding 101P3A11 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell,* 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 101P3A11 polypeptide.

VII.) Methods for the Detection of 101P3A11

Another aspect of the present invention relates to methods for detecting 101P3A11 polynucleotides and 101P3A11-related proteins, as well as methods for identifying a cell that expresses 101P3A11. The expression profile of 101P3A11 makes it a diagnostic marker for metastasized disease. Accordingly, the status of 101P3A11 gene products provides information useful for predicting a variety of factors including susceptibility to advanced stage disease, rate of progression, and/or tumor aggressiveness. As discussed in detail herein, the status of 101P3A11 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 101P3A11 polynucleotides in a biological sample, such as serum, bone, prostate, and other tissues, urine, semen, cell preparations, and the like. Detectable 101P3A11 polynucleotides include, for example, a 101P3A11 gene or fragment thereof, 101P3A11 mRNA, alternative splice variant 101P3A11 mRNAs, and recombinant DNA or RNA molecules that contain a 101P3A11 polynucleotide. A number of methods for amplifying and/or detecting the presence of 101P3A11 polynucleotides are well known in the art and can be employed in the practice of this aspect of the invention.

In one embodiment, a method for detecting a 101P3A11 mRNA in a biological sample comprises producing cDNA from the sample by reverse transcription using at least one primer; amplifying the cDNA so produced using a 101P3A11 polynucleotides as sense and antisense primers to amplify 101P3A11 cDNAs therein; and detecting the presence of the amplified 101P3A11 cDNA. Optionally, the sequence of the amplified 101P3A11 cDNA can be determined.

In another embodiment, a method of detecting a 101P3A11 gene in a biological sample comprises first isolating genomic DNA from the sample; amplifying the isolated genomic DNA using 101P3A11 polynucleotides as sense and antisense primers; and detecting the presence of the amplified 101P3A11 gene. Any number of appropriate sense and antisense probe combinations can be designed from a 101P3A11 nucleotide sequence (see, e.g., FIG. 2) and used for this purpose.

The invention also provides assays for detecting the presence of a 101P3A11 protein in a tissue or other biological sample such as serum, semen, bone, prostate, urine, cell preparations, and the like. Methods for detecting a 101P3A11-related protein are also well known and include, for example, immunoprecipitation, immunohistochemical analysis, Western blot analysis, molecular binding assays, ELISA, ELIFA and the like. For example, a method of detecting the presence of a 101P3A11-related protein in a biological sample comprises first contacting the sample with a 101P3A11 antibody, a 101P3A11-reactive fragment thereof, or a recombinant protein containing an antigen binding region of a 101P3A11 antibody; and then detecting the binding of 101P3A11-related protein in the sample.

Methods for identifying a cell that expresses 101P3A11 are also within the scope of the invention. In one embodiment, an assay for identifying a cell that expresses a 101P3A11 gene comprises detecting the presence of 101P3A11 mRNA in the cell. Methods for the detection of particular mRNAs in cells are well known and include, for example, hybridization assays using complementary DNA probes (such as in situ hybridization using labeled 101P3A11 riboprobes, Northern blot and related techniques) and various nucleic acid amplification assays (such as RT-PCR using complementary primers specific for 101P3A11, and other amplification type detection methods, such as, for example, branched DNA, SISBA, TMA and the like). Alternatively, an assay for identifying a cell that expresses a 101P3A11 gene comprises detecting the presence of 101P3A11-related protein in the cell or secreted by the cell. Various methods for the detection of proteins are well known in the art and are employed for the detection of 101P3A11-related proteins and cells that express 101P3A11-related proteins.

101P3A11 expression analysis is also useful as a tool for identifying and evaluating agents that modulate 101P3A11 gene expression. For example, 101P3A11 expression is significantly upregulated in prostate cancer, and is expressed in cancers of the tissues listed in Table I. Identification of a molecule or biological agent that inhibits 101P3A11 expression or over-expression in cancer cells is of therapeutic value. For example, such an agent can be identified by using a screen that quantifies 101P3A11 expression by RT-PCR, nucleic acid hybridization or antibody binding.

VIII.) Methods for Monitoring the Status of 101P3A11-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 101P3A11 expression in cancers) allows for early detection of such aberrant physiology, before a pathologic state such as cancer has progressed to a stage that therapeutic options are more limited and or the prognosis is worse. In such examinations, the status of 101P3A11 in a biological sample of interest can be compared, for example, to the status of 101P3A11 in a corresponding normal sample (e.g. a sample from that individual or alternatively another individual that is not affected by a pathology). An alteration in the status of 101P3A11 in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306-14 and U.S. Pat. No. 5,837,501) to compare 101P3A11 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 101P3A11 expressing cells) as well as the level, and biological activity of expressed gene products (such as 101P3A11 mRNA, polynucleotides and polypeptides). Typically, an alteration in the status of 101P3A11 comprises a change in the location of 101P3A11 and/or 101P3A11 expressing cells and/or an increase in 101P3A11 mRNA and/or protein expression.

101P3A11 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of a 101P3A11 gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 101P3A11 in a biological sample is evaluated by various methods utilized by skilled artisans including, but not limited to genomic Southern analysis (to examine, for example perturbations in a 101P3A11 gene), Northern analysis and/or PCR analysis of 101P3A11 mRNA (to examine, for example alterations in the polynucleotide sequences or expression levels of 101P3A11 mRNAs), and, Western and/or immunohistochemical analysis (to examine, for example alterations in polypeptide sequences, alterations in polypeptide localization within a sample, alterations in expression levels of 101P3A11 proteins and/or associations of 101P3A11 proteins with polypeptide binding partners). Detectable 101P3A11 polynucleotides include, for example, a 101P3A11 gene or fragment thereof, 101P3A11 mRNA, alternative splice variants, 101P3A11 mRNAs, and recombinant DNA or RNA molecules containing a 101P3A11 polynucleotide.

The expression profile of 101P3A11 makes it a diagnostic marker for local and/or metastasized disease, and provides information on the growth or oncogenic potential of a biological sample. In particular, the status of 101P3A11 provides information useful for predicting susceptibility to particular disease stages, progression, and/or tumor aggressiveness. The invention provides methods and assays for determining 101P3A11 status and diagnosing cancers that express 101P3A11, such as cancers of the tissues listed in Table I. For example, because 101P3A11 mRNA is so highly expressed in prostate and other cancers relative to normal prostate tissue, assays that evaluate the levels of 101P3A11 mRNA transcripts or proteins in a biological sample can be used to diagnose a disease associated with 101P3A11 dysregulation, and can provide prognostic information useful in defining appropriate therapeutic options.

The expression status of 101P3A11 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 101P3A11 in biological samples such as those from individuals suffering from, or suspected of suffering from a pathology characterized by dysregulated cellular growth, such as cancer.

As described above, the status of 101P3A11 in a biological sample can be examined by a number of well-known procedures in the art. For example, the status of 101P3A11 in a biological sample taken from a specific location in the body can be examined by evaluating the sample for the presence or absence of 101P3A11 expressing cells (e.g. those that express 101P3A11 mRNAs or proteins). This examination can provide evidence of dysregulated cellular growth, for example, when 101P3A11-expressing cells are found in a biological sample that does not normally contain such cells (such as a lymph node), because such alterations in the status of 101P3A11 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Semin. Surg. Oncol. 18(1): 17-28 (2000) and Freeman et al., J Urol 1995 August 154(2 Pt 1):474-8).

In one aspect, the invention provides methods for monitoring 101P3A11 gene products by determining the status of 101P3A11 gene products expressed by cells from an individual suspected of having a disease associated with dysregulated cell growth (such as hyperplasia or cancer) and then comparing the status so determined to the status of 101P3A11 gene products in a corresponding normal sample. The presence of aberrant 101P3A11 gene products in the test sample relative to the normal sample provides an indication of the presence of dysregulated cell growth within the cells of the individual.

In another aspect, the invention provides assays useful in determining the presence of cancer in an individual, comprising detecting a significant increase in 101P3A11 mRNA or protein expression in a test cell or tissue sample relative to expression levels in the corresponding normal cell or tissue. The presence of 101P3A11 mRNA can, for example, be evaluated in tissues including but not limited to those listed in Table I. The presence of significant 101P3A11 expression in any of these tissues is useful to indicate the emergence, presence and/or severity of a cancer, since the corresponding normal tissues do not express 101P3A11 mRNA or express it at lower levels.

In a related embodiment, 101P3A11 status is determined at the protein level rather than at the nucleic acid level. For example, such a method comprises determining the level of 101P3A11 protein expressed by cells in a test tissue sample and comparing the level so determined to the level of 101P3A11 expressed in a corresponding normal sample. In one embodiment, the presence of 101P3A11 protein is evaluated, for example, using immunohistochemical methods. 101P3A11 antibodies or binding partners capable of detecting 101P3A11 protein expression are used in a variety of assay formats well known in the art for this purpose.

In a further embodiment, one can evaluate the status of 101P3A11 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 101P3A11 may be indicative of the presence or promotion of a tumor. Such assays therefore have diagnostic and predictive value where a mutation in 101P3A11 indicates a potential loss of function or increase in tumor growth.

A wide variety of assays for observing perturbations in nucleotide and amino acid sequences are well known in the art. For example, the size and structure of nucleic acid or amino acid sequences of 101P3A11 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 7 Sep. 1999, and 5,952,170 issued 17 Jan. 1995).

Additionally, one can examine the methylation status of a 101P3A11 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al., Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes that cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 101P3A11. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 101P3A11 expression. The presence of RT-PCR amplifiable 101P3A11 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 101P3A11 mRNA or 101P3A11 protein in a tissue sample, its presence indicating susceptibility to cancer, wherein the degree of 101P3A11 mRNA expression correlates to the degree of susceptibility. In a specific embodiment, the presence of 101P3A11 in prostate or other tissue is examined, with the presence of 101P3A11 in the sample providing an indication of prostate cancer susceptibility (or the emergence or existence of a prostate tumor). Similarly, one can evaluate the integrity 101P3A11 nucleotide and amino acid sequences in a biological sample, in order to identify perturbations in the structure of these molecules such as insertions, deletions, substitutions and the like. The presence of one or more perturbations in 101P3A11 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 101P3A11 mRNA or 101P3A11 protein expressed by tumor cells, comparing the level so determined to the level of 101P3A11 mRNA or 101P3A11 protein expressed in a corresponding normal tissue taken from the same individual or a normal tissue reference sample, wherein the degree of 101P3A11 mRNA or 101P3A11 protein expression in the tumor sample relative to the normal sample indicates the degree of aggressiveness. In a specific embodiment, aggressiveness of a tumor is evaluated by determining the extent to which 101P3A11 is expressed in the tumor cells, with higher expression levels indicating more aggressive tumors. Another embodiment is the evaluation of the integrity of 101P3A11 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 101P3A11 mRNA or 101P3A11 protein expressed by cells in a sample of the tumor, comparing the level so determined to the level of 101P3A11 mRNA or 101P3A11 protein expressed in an equivalent tissue sample taken from the same individual at a different time, wherein the degree of 101P3A11 mRNA or 101P3A11 protein expression in the tumor sample over time provides information on the progression of the cancer. In a specific embodiment, the progression of a cancer is evaluated by determining 101P3A11 expression in the tumor cells over time, where increased expression over time indicates a progression of the cancer. Also, one can evaluate the integrity 101P3A11 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 101P3A11 gene and 101P3A11 gene products (or perturbations in 101P3A11 gene and 101P3A11 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 101P3A11 gene and 101P3A11 gene products (or perturbations in 101P3A11 gene and 101P3A11 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 101P3A11 gene and 101P3A11 gene products (or perturbations in 101P3A11 gene and 101P3A11 gene products) and another factor associated with malignancy entails detecting the overexpression of 101P3A11 mRNA or protein in a tissue sample, detecting the overexpression of PSA mRNA or protein in a tissue sample (or PSCA or PSM expression), and observing a coincidence of 101P3A11 mRNA or protein and PSA mRNA or protein overexpression (or PSCA or PSM expression). In a specific embodiment, the expression of 101P3A11 and PSA mRNA in prostate tissue is examined, where the coincidence of 101P3A11 and PSA mRNA overexpression in the sample indicates the existence of prostate cancer, prostate cancer susceptibility or the emergence or status of a prostate tumor.

Methods for detecting and quantifying the expression of 101P3A11 mRNA or protein are described herein, and standard nucleic acid and protein detection and quantification technologies are well known in the art. Standard methods for the detection and quantification of 101P3A11 mRNA include in situ hybridization using labeled 101P3A11 riboprobes, Northern blot and related techniques using 101P3A11 polynucleotide probes, RT-PCR analysis using primers specific for 101P3A11, and other amplification type detection methods, such as, for example, branched DNA, SISBA, TMA and the like. In a specific embodiment, semi-quantitative RT-PCR is used to detect and quantify 101P3A11 mRNA expression. Any number of primers capable of amplifying 101P3A11 can be used for this purpose, including but not limited to the various primer sets specifically described herein. In a specific embodiment, polyclonal or monoclonal antibodies specifically reactive with the wild-type 101P3A11 protein can be used in an immunohistochemical assay of biopsied tissue.

IX.) Identification of Molecules that Interact with 101P3A11

The 101P3A11 protein and nucleic acid sequences disclosed herein allow a skilled artisan to identify proteins, small molecules and other agents that interact with 101P3A11, as well as pathways activated by 101P3A11 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. Nos. 5,955,280 issued 21 Sep. 1999, 5,925,523 issued 20 Jul. 1999, 5,846,722 issued 8 Dec. 1998 and 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 101P3A11 protein sequences. In such methods, peptides that bind to 101P3A11 are identified by screening libraries that encode a random or controlled collection of amino acids. Peptides encoded by the libraries are expressed as fusion proteins of bacteriophage coat proteins, the bacteriophage particles are then screened against the 101P3A11 protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 101P3A11 protein sequences are disclosed for example in U.S. Pat. Nos. 5,723,286 issued 3 Mar. 1998 and 5,733,731 issued 31 Mar. 1998.

Alternatively, cell lines that express 101P3A11 are used to identify protein-protein interactions mediated by 101P3A11. Such interactions can be examined using immunoprecipitation techniques (see, e.g., Hamilton B. J., et al. Biochem. Biophys. Res. Commun. 1999, 261:646-51). 101P3A11 protein can be immunoprecipitated from 101P3A11-expressing cell lines using anti-101P3A11 antibodies. Alternatively, antibodies against His-tag can be used in a cell line engineered to express fusions of 101P3A11 and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 101P3A11 can be identified through related embodiments of such screening assays. For example, small molecules can be identified that interfere with protein function, including molecules that interfere with 101P3A11's ability to mediate phosphorylation and de-phosphorylation, interaction with DNA or RNA molecules as an indication of regulation of cell cycles, second messenger signaling or tumorigenesis. Similarly, small molecules that modulate 101P3A11-related ion channel, protein pump, or cell communication functions are identified and used to treat patients that have a cancer that expresses 101P3A11 (see, e.g., Hille, B., Ionic Channels of Excitable Membranes 2$^{nd}$ Ed., Sinauer Assoc., Sunderland, Mass., 1992). Moreover, ligands that regulate 101P3A11 function can be identified based on their ability to bind 101P3A11 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 101P3A11 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators which activate or inhibit 101P3A11.

An embodiment of this invention comprises a method of screening for a molecule that interacts with a 101P3A11 amino acid sequence shown in FIG. 2 or FIG. 3, comprising the steps of contacting a population of molecules with a 101P3A11 amino acid sequence, allowing the population of molecules and the 101P3A11 amino acid sequence to interact under conditions that facilitate an interaction, determining the presence of a molecule that interacts with the 101P3A11 amino acid sequence, and then separating molecules that do not interact with the 101P3A11 amino acid sequence from molecules that do. In a specific embodiment, the method further comprises purifying, characterizing and identifying a molecule that interacts with the 101P3A11 amino acid sequence. The identified molecule can be used to modulate a function performed by 101P3A11. In a preferred embodiment, the 101P3A11 amino acid sequence is contacted with a library of peptides.

X.) Therapeutic Methods and Compositions

The identification of 101P3A11 as a protein that is normally expressed in a restricted set of tissues, but which is also expressed in prostate and other cancers, opens a number of therapeutic approaches to the treatment of such cancers. As contemplated herein, 101P3A11 functions as a transcription factor involved in activating tumor-promoting genes or repressing genes that block tumorigenesis.

Accordingly, therapeutic approaches that inhibit the activity of a 101P3A11 protein are useful for patients suffering from a cancer that expresses 101P3A11. These therapeutic approaches generally fall into two classes. One class comprises various methods for inhibiting the binding or association of a 101P3A11 protein with its binding partner or with other proteins. Another class comprises a variety of methods for inhibiting the transcription of a 101P3A11 gene or translation of 101P3A11 mRNA.

X.A.) Anti-Cancer Vaccines

The invention provides cancer vaccines comprising a 101P3A11-related protein or 101P3A11-related nucleic acid. In view of the expression of 101P3A11, cancer vaccines prevent and/or treat 101P3A11-expressing cancers with minimal or no effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Such methods can be readily practiced by employing a 101P3A11-related protein, or a 101P3A11-encoding nucleic acid molecule and recombinant vectors capable of expressing and presenting the 101P3A11 immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1):66-78; Maruyama et al., Cancer Immunol Immunother 2000 June 49(3):123-32) Briefly, such methods of generating an immune response (e.g. humoral and/or cell-mediated) in a mammal, comprise the steps of: exposing the mammal's immune system to an immunoreactive epitope (e.g. an epitope present in a 101P3A11 protein shown in FIG. 3 or analog or homolog thereof) so that the mammal generates an immune response that is specific for that epitope (e.g. generates antibodies that specifically recognize that epitope). In a preferred method, a 101P3A11 immunogen contains a biological motif, see e.g., Tables V-XVIII and XXII TO IL, or a peptide of a size range from 101P3A11 indicated in FIG. 5, FIG. 6, FIG. 7, FIG. 8, and FIG. 9.

The entire 101P3A11 protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148: 1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 101P3A11-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 101P3A11 protein that bind corresponding HLA alleles (see e.g., Table IV; Epimer™ and Epimatrix™, Brown University (URL www.brown.edu/Research/TB-HIV_Lab/epimatrix/epimatrix.html); and, BIMAS, (URL bimas.dcrt.nih.gov/; SYFPEITHI at URL syfpeithi.bmi-heidelberg.com/). In a preferred embodiment, a 101P3A11 immunogen contains one or more amino acid sequences identified using techniques well known in the art, such as the sequences shown in Tables V-XVIII and XXII TO IL or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motif/supermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 101P3A11 protein) so that an immune response is generated. A typical embodiment consists of a method for generating an immune response to 101P3A11 in a host, by contacting the host with a sufficient amount of at least one 101P3A11 B cell or cytotoxic T-cell epitope or analog thereof; and at least one periodic interval thereafter re-contacting the host with the 101P3A11 B cell or cytotoxic T-cell epitope or analog thereof. A specific embodiment consists of a method of generating an immune response against a 101P3A11-related protein or a man-made multiepitopic peptide comprising: administering 101P3A11 immunogen (e.g. a 101P3A11 protein or a peptide fragment thereof, a 101P3A11 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 101P3A11 immunogen by: administering in vivo to muscle or skin of the individual's body a DNA molecule that comprises a DNA sequence that encodes a 101P3A11 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 101P3A11, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 101P3A11. Constructs comprising DNA encoding a 101P3A11-related protein/immunogen and appropriate regulatory sequences can be injected directly into muscle or skin of an individual, such that the cells of the muscle or skin take-up the construct and express the encoded 101P3A11 protein/immunogen.. Alternatively, a vaccine comprises a 101P3A11-related protein. Expression of the 101P3A11-related protein immunogen results in the generation of prophylactic or therapeutic humoral and cellular immunity against cells that bear a 101P3A11 protein. Various prophylactic and therapeutic genetic immunization techniques known in the art can be used. Nucleic acid-based delivery is described, for instance, in Wolff et. al., Science 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922, 687).

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 101P3A11. Constructs comprising DNA encoding a 101P3A11-related protein/immunogen and appropriate regulatory sequences can be injected directly into muscle or skin of an individual, such that the cells of the muscle or skin take-up the construct and express the encoded 101P3A11 protein/immunogen. Alternatively, a vaccine comprises a 101P3A11-related protein. Expression of the 101P3A11-related protein immunogen results in the generation of prophylactic or therapeutic humoral and cellular immunity against cells that bear a 101P3A11 protein. Various prophylactic and therapeutic genetic immunization techniques known in the art can be used (for review, see information and references published at Internet address www.genweb.com). Nucleic acid-based delivery is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658-663; Tsang et al. *J. Natl. Cancer Inst.* 87:982-990 (1995)). Non-viral delivery systems can also be employed by introducing naked DNA encoding a 101P3A11-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 101P3A11-related nucleic acid molecule. In one embodiment, the full-length human 101P3A11 cDNA is employed. In another embodiment, 101P3A11 nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 101P3A11 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 101P3A11 peptides to T cells in the context of MHC class I or II molecules. In one embodiment, autologous dendritic cells are pulsed with 101P3A11 peptides capable of binding to MHC class I and/or class II molecules. In another embodiment, dendritic cells are pulsed with the complete 101P3A11 protein. Yet another embodiment involves engineering the overexpression of a 101P3A11 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186: 1177-1182). Cells that express 101P3A11 can also be engineered to express immune modulators, such as GM-CSF, and used as immunizing agents.

X.B.) 101P3A11 as a Target for Antibody-Based Therapy

101P3A11 is an attractive target for antibody-based therapeutic strategies. A number of antibody strategies are known in the art for targeting both extracellular and intracellular molecules (see, e.g., complement and ADCC mediated killing as well as the use of intrabodies). Because 101P3A11 is expressed by cancer cells of various lineages relative to corresponding normal cells, systemic administration of 101P3A11-immunoreactive compositions are prepared that exhibit excellent sensitivity without toxic, non-specific and/ or non-target effects caused by binding of the immunoreactive composition to non-target organs and tissues. Antibodies specifically reactive with domains of 101P3A11 are useful to treat 101P3A11-expressing cancers systemically, either as conjugates with a toxin or therapeutic agent, or as naked antibodies capable of inhibiting cell proliferation or function.

101P3A11 antibodies can be introduced into a patient such that the antibody binds to 101P3A11 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 101P3A11, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 101P3A11 sequence shown in FIG. 2 or FIG. 3. In addition, skilled artisans understand that it is routine to conjugate antibodies to cytotoxic agents (see, e.g., Slevers et al. *Blood* 93:11 3678-3684 (Jun. 1, 1999)). When cytotoxic and/or therapeutic agents are delivered directly to cells, such as by conjugating them to antibodies specific for a molecule expressed by that cell (e.g. 101P3A11), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-101P3A11 antibody) that binds to a marker (e.g. 101P3A11) expressed, accessible to binding or localized on the cell surfaces. A typical embodiment is a method of delivering a cytotoxic and/or therapeutic agent to a cell expressing 101P3A11, comprising conjugating the cytotoxic agent to an antibody that immunospecifically binds to a 101P3A11 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-101P3A11 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 101P3A11 antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized $IgG_4$ kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 101P3A11 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637-4642, 1993), Prewett et al. (International J. of Onco. 9:217-224, 1996), and Hancock et al. (Cancer Res. 51:4575-4580, 1991) describe the use of various antibodies together with chemotherapeutic agents.

Although 101P3A11 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 101P3A11 expression, preferably using immunohistochemical assessments of tumor tissue, quantitative 101P3A11 imaging, or other techniques that reliably indicate the presence and degree of 101P3A11 expression. Immunohistochemical analysis of tumor biopsies or surgical specimens is preferred for this purpose. Methods for immunohistochemical analysis of tumor tissues are well known in the art.

Anti-101P3A11 monoclonal antibodies that treat prostate and other cancers include those that initiate a potent immune response against the tumor or those that are directly cytotoxic. In this regard, anti-101P3A11 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-101P3A11 mAbs that exert a direct biological effect on tumor growth are useful to treat cancers that express 101P3A11. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-101P3A11 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 101P3A11 antigen with high affinity but exhibit low or no antigenicity in the patient.

Therapeutic methods of the invention contemplate the administration of single anti-101P3A11 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-101P3A11 mAbs can be administered concomitantly with other therapeutic modalities, including but not limited to various chemotherapeutic agents, androgen-blockers, immune modulators (e.g., IL-2, GM-CSF), surgery or radiation. The anti-101P3A11 mAbs are administered in their "naked" or unconjugated form, or can have a therapeutic agent(s) conjugated to them.

Anti-101P3A11 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-101P3A11 antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10-1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-101P3A11 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 101P3A11 expression in the patient, the extent of circulating shed 101P3A11 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 101P3A11 in a given sample (e.g. the levels of circulating 101P3A11 antigen and/or 101P3A11 expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-101P3A11 antibodies can also be used in anti-cancer therapy as a vaccine for inducing an immune response to cells expressing a 101P3A11-related protein. In particular, the generation of anti-idiotypic antibodies is well known in the art; this methodology can readily be adapted to generate anti-idiotypic anti-101P3A11 antibodies that mimic an epitope on a 101P3A11-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

X.C.) 101P3A11 as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$). Moreover, an adjuvant such as a synthetic cytosine-phosphorothiolated-guanine-containing (CpG) oligonucleotides has been found to increase CTL responses 10- to 100-fold. (see, e.g. Davila and Celis, J. Immunol. 165:539-547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 101P3A11 antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3-4 epitopes that come from at least one tumor associated antigen (TAA). For HLA Class II a similar rationale is employed; again 3-4 epitopes are selected from at least one TAA (see, e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 101P3A11, the PADRE® universal helper T cell epitope or multiple HTL epitopes from 101P3A11, (see e.g., Tables V-XVIII and XXII to IL), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830-843 QYIKANSKFIGITE (SEQ ID NO: 39), *Plasmodium falciparum* circumsporozoite (CS) protein at positions 378-398 DIEKKIAKMEKASSVFNVVNS (SEQ ID NO: 40), and *Streptococcus* 18 kD protein at positions 116-131 GAVDSILGGVATYGAA (SEQ ID NO: 41). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 42), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime an immune response to the target antigen. Moreover, because the induction of neutralizing antibodies can also be primed with $P_3CSS$-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 101P3A11. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 101P3A11.

X.D. Adoptive Immunotherapy

Antigenic 101P3A11-related peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 101P3A11. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 101P3A11. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 101P3A11-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 101P3A11, a vaccine comprising 101P3A11-specific CTL may be more efficacious in killing tumor cells in patient with advanced disease than alternative embodiments.

It is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, $17^{th}$ Edition, A. Gennaro, Editor, Mack Publishing Co., Easton, Pa., 1985). For example a peptide dose for initial immunization can be from about 1 to about 50,000 μg, generally 100-5,000 μg, for a 70 kg patient. For example, for nucleic acids an initial immunization may be performed using an expression vector in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5\text{-}10^7$ to $5\times10^9$ pfu.

For antibodies, a treatment generally involves repeated administration of the anti-101P3A11 antibody preparation, via an acceptable route of administration such as intravenous injection (IV), typically at a dose in the range of about 0.1 to about 10 mg/kg body weight. In general, doses in the range of 10-500 mg mAb per week are effective and well tolerated. Moreover, an initial loading dose of approximately 4 mg/kg patient body weight IV, followed by weekly doses of about 2 mg/kg IV of the anti-101P3A11 mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 101P3A11 expression in the patient, the extent of circulating shed 101P3A11 antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 μg-1 mg, 1 mg-50 mg, 50 mg-100 mg, 100 mg-200 mg, 200 mg-300 mg, 400 mg-500 mg, 500 mg-600 mg, 600 mg-700 mg, 700 mg-800 mg, 800 mg-900 mg, 900 mg-1 g, or 1 mg-700 mg. In certain embodiments, the dose is in a range of 2-5 mg/kg body weight, e.g., with follow on weekly doses of 1-3 mg/kg; 0.5 mg, 1, 2, 3, 4, 5, 6, 7, 8, 9, 10 mg/kg body weight followed, e.g., in two, three or four weeks by weekly doses; 0.5-10 mg/kg body weight, e.g., followed in two, three or four weeks by weekly doses; 225, 250, 275, 300, 325, 350, 375, 400 mg $m^2$ of body area weekly; 1-600 mg $m^2$ of body area weekly; 225-400 mg $m^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5, 10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5\times10^{10}$ cells. A dose may also about $10^6$ cells/$m^2$ to about $10^{10}$ cells/$m^2$, or about $10^6$ cells/$m^2$ to about $10^8$ cells/$m^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, immunogenic peptides are preferably supplied in finely divided form along with a surfactant and propellant. Typical percentages of peptides are about 0.01%-20% by weight, preferably about 1%-10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%-20% by weight of the composition, preferably about 0.25-5%. The balance of the composition is ordinarily propellant. A carrier can also be included, as desired, as with, e.g., lecithin for intranasal delivery.

XI.) Diagnostic and Prognostic Embodiments of 101P3A11

As disclosed herein, 101P3A11 polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 101P3A11 in normal tissues, and patient specimens").

101P3A11 can be analogized to a prostate associated antigen PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August; 162(2):293-306 (1999) and Fortier et al., J. Nat. Cancer Inst. 91(19): 1635-1640(1999)). A variety of other diagnostic markers are also used in similar contexts including p53 and K-ras (see, e.g., Tulchinsky et al., Int J Mol Med 1999 July 4(1):99-102 and Minimoto et al., Cancer Detect Prev 2000; 24(1):1-12). Therefore, this disclosure of 101P3A11 polynucleotides and polypeptides (as well as 101P3A11 polynucleotide probes and anti-101P3A11 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 101P3A11 polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 101P3A11 polynucleotides described herein can be utilized in the same way to detect 101P3A11 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 101P3A11 polypeptides described herein can be utilized to generate antibodies for use in detecting 101P3A11 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 101P3A11 polynucleotides and/or polypeptides can be used to provide evidence of metastasis. For example, when a biological sample from tissue that does not normally contain 101P3A11-expressing cells (lymph node) is found to contain 101P3A11-expressing cells such as the 101P3A11 expression seen in LAPC4 and LAPC9, xenografts isolated from lymph node and bone metastasis, respectively, this finding is indicative of metastasis.

Alternatively 101P3A11 polynucleotides and/or polypeptides can be used to provide evidence of cancer, for example, when cells in a biological sample that do not normally express 101P3A11 or express 101P3A11 at a different level are found to express 101P3A11 or have an increased expression of 101P3A11 (see, e.g., the 101P3A11 expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 101P3A11) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 101P3A11 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in the Example entitled "Expression analysis of 101P3A11 in normal tissues, and patient specimens," where a 101P3A11 polynucleotide fragment is used as a probe to show the expression of 101P3A11 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December 11(6):407-13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 101P3A11 polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 101P3A11 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 101P3A11 biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 101P3A11 polypeptide shown in FIG. 3).

As shown herein, the 101P3A11 polynucleotides and polypeptides (as well as the 101P3A11 polynucleotide probes and anti-101P3A11 antibodies or T cells used to identify the presence of these molecules) exhibit specific properties that make them useful in diagnosing cancers such as those listed in Table I. Diagnostic assays that measure the presence of 101P3A11 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 101P3A11 polynucleotides and polypeptides (as well as the 101P3A11 polynucleotide probes and anti-101P3A11 antibodies used to identify the presence of these molecules) need to be employed to confirm a metastases of prostatic origin.

Finally, in addition to their use in diagnostic assays, the 101P3A11 polynucleotides disclosed herein have a number of other utilities such as their use in the identification of oncogenetic associated chromosomal abnormalities in the chromosomal region to which the 101P3A11 gene maps (see the Example entitled "Chromosomal Mapping of 101P3A11" below). Moreover, in addition to their use in diagnostic assays, the 101P3A11-related proteins and polynucleotides disclosed herein have other utilities such as their use in the forensic analysis of tissues of unknown origin (see, e.g., Takahama K Forensic Sci Int 1996 Jun. 28; 80(1-2): 63-9).

Additionally, 101P3A11-related proteins or polynucleotides of the invention can be used to treat a pathologic condition characterized by the over-expression of 101P3A11. For example, the amino acid or nucleic acid sequence of FIG. 2 or FIG. 3, or fragments of either, can be used to generate an immune response to a 101P3A11 antigen. Antibodies or other molecules that react with 101P3A11 can be used to modulate the function of this molecule, and thereby provide a therapeutic benefit.

XII.) Inhibition of 101P3A11 Protein Function

The invention includes various methods and compositions for inhibiting the binding of 101P3A11 to its binding partner or its association with other protein(s) as well as methods for inhibiting 101P3A11 function.

XII.A.) Inhibition of 101P3A11 with Intracellular Antibodies

In one approach, a recombinant vector that encodes single chain antibodies that specifically bind to 101P3A11 are introduced into 101P3A11 expressing cells via gene transfer technologies. Accordingly, the encoded single chain anti-101P3A11 antibody is expressed intracellularly, binds to 101P3A11 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL (SEQ ID NO: 43) amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 101P3A11 in the nucleus, thereby preventing its activity within the nucleus. Nuclear targeting signals are engineered into such 101P3A11 intrabodies in order to achieve the desired targeting. Such 101P3A11 intrabodies are designed to bind specifically to a particular 101P3A11 domain. In another embodiment, cytosolic intrabodies that specifically bind to a 101P3A11 protein are used to prevent 101P3A11 from gaining access to the nucleus, thereby preventing it from exerting any biological activity within the nucleus (e.g., preventing 101P3A11 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 101P3A11 with Recombinant Proteins

In another approach, recombinant molecules bind to 101P3A11 and thereby inhibit 101P3A11 function. For example, these recombinant molecules prevent or inhibit 101P3A11 from accessing/binding to its binding partner(s) or associating with other protein(s). Such recombinant molecules can, for example, contain the reactive part(s) of a 101P3A11 specific antibody molecule. In a particular embodiment, the 101P3A11 binding domain of a 101P3A11 binding partner is engineered into a dimeric fusion protein, whereby the fusion protein comprises two 101P3A11 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 101P3A11, whereby the dimeric fusion protein specifically binds to 101P3A11 and blocks 101P3A11 interaction with a binding partner. Such dimeric fusion proteins are further combined into multimeric proteins using known antibody linking technologies.

XII.C.) Inhibition of 101P3A11 Transcription or Translation

The present invention also comprises various methods and compositions for inhibiting the transcription of the 101P3A11 gene. Similarly, the invention also provides methods and compositions for inhibiting the translation of 101P3A11 mRNA into protein.

In one approach, a method of inhibiting the transcription of the 101P3A11 gene comprises contacting the 101P3A11 gene with a 101P3A11 antisense polynucleotide. In another approach, a method of inhibiting 101P3A11 mRNA translation comprises contacting a 101P3A11 mRNA with an antisense polynucleotide. In another approach, a 101P3A11 specific ribozyme is used to cleave a 101P3A11 message, thereby inhibiting translation. Such antisense and ribozyme based methods can also be directed to the regulatory regions of the 101P3A11 gene, such as 101P3A11 promoter and/or enhancer elements. Similarly, proteins capable of inhibiting a 101P3A11 gene transcription factor are used to inhibit 101P3A11 mRNA transcription. The various polynucleotides and compositions useful in the aforementioned methods have been described above. The use of antisense and ribozyme molecules to inhibit transcription and translation is well known in the art.

Other factors that inhibit the transcription of 101P3A11 by interfering with 101P3A11 transcriptional activation are also useful to treat cancers expressing 101P3A11. Similarly, factors that interfere with 101P3A11 processing are useful to treat cancers that express 101P3A11. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 101P3A11 (i.e., antisense, ribozyme, polynucleotides encoding intrabodies and other 101P3A11 inhibitory molecules). A number of gene therapy approaches are known in the art. Recombinant vectors encoding 101P3A11 antisense polynucleotides, ribozymes, factors capable of interfering with 101P3A11 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 101P3A11 to a binding partner, etc.

In vivo, the effect of a 101P3A11 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Kits/Articles of Manufacture

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a FIG. 2-*related* protein or a FIG. 2 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequences in FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy or non-therapeutic application, such as a diagnostic or laboratory application, and can also indicate directions for either in vivo or in vitro use, such as those described herein. Directions and or other information can also be included on an insert(s) or label(s) which is included with or on the kit.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass or plastic. The container can hold amino acid sequence(s), small molecule(s), nucleic acid sequence(s), and/or antibody(s), in one embodiment the container holds a polynucleotide for use in examining the mRNA expression profile of a cell, together with reagents used for this purpose.

The container can alternatively hold a composition which is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 101P3A11 and modulating the function of 101P3A11.

The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I. The article of manufacture can further comprise a second container comprising a pharmaceutically-acceptable buffer, such as phosphate-buffered saline, Ringer's solution and/ordextrose solution. It can further include other materials desirable from a commercial and user standpoint, including other buffers, diluents, filters, stirrers, needles, syringes, and/or package inserts with indications and/or instructions for use.

XIV.) Evaluation of GPCRs and Modulators Thereof

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been recognized is that it is the active state of the receptor that is most useful for discovering agonists, partial agonists, and inverse agonists of the receptor. For those diseases that result from an overly active receptor, what is desired in a therapeutic, drug is a compound which acts to diminish the active state of a receptor, not necessarily a drug which is an antagonist to the endogenous ligand. This is because a compound (e.g., therapeutic, prophylactic, diagnostic, prognostic, or laboratory reactant) that reduces the activity of the active receptor state need not bind at the same site as the endogenous ligand. In accordance with the present disclosure, any search for relevant compounds should start by screening compounds against the ligand-independent active state. The search, then, is for an inverse agonist to the active state receptor.

Screening candidate compounds against orphan receptors, for example, including and not limited to, 101P3A11 and 101P3A11 Fusion Protein, allows for the direct identification of candidate compounds which act at the orphan cell surface receptor, without requiring any prior knowledge or use of the receptor's endogenous ligand. By determining areas within the body where such receptors are expressed and/or over-expressed, it is possible to determine related disease/disorder states which are associated with the expression and/or over expression of these receptors; such an approach is disclosed herein.

Disease/Disorder Identification and/or Selection.

Inverse agonists and agonists to 101P3A11 can be identified by the methodologies disclosed herein. Such inverse agonists and agonists are ideal candidates as lead compounds in drug discovery programs for treating diseases related to this receptor. Indeed, an antagonist to such a receptor (even if the ligand were known) may be ineffective given that the receptor is activated even in the absence of ligand-receptor binding. Because of the ability to directly identify inverse agonists and agonists to these receptors, thereby allowing for the development of pharmaceutical compositions, a search for diseases and disorders associated with these receptors is possible. For example, 101P3A11 is expressed in cancers of the tissues set forth in Table I.

XV.) Screening of Candidate Compounds

General GPCR Screening Assay techniques

When a G protein receptor becomes constitutively active, it binds to a G protein (for example Gq, Gs, Gi, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [35S]GTP7S, can be used to monitor enhanced binding to membranes which express constitutively activated receptors. It is reported that [35 S]GTP7S can be used to monitor G protein coupling to membranes in the absence and presence of ligand. An example of this monitoring, among other examples well-known and available to those in the art, was reported by Traynor and Nahorski in 1995 (Mol. Pharmacol. 1995 April; 47(4):848-54). Generally, this preferred use of this assay system is for initial screening of candidate compounds because the system is generically applicable to all G protein-coupled receptors regardless of the particular G protein that interacts with the intracellular domain of the receptor.

Specific GPCR Screening Assay Techniques

Once candidate compounds are identified using the "generic" G protein-coupled receptor assay (i.e. an assay to select compounds that are agonists, partial agonists, or inverse agonists), farther screening to confirm that the compounds have interacted at the receptor site is preferred. For example, a compound identified by the "generic" assay may not bind to the receptor, but may instead merely "uncouple" the G protein from the intracellular domain.

Thus, by screening those candidate compounds, which have been identified using a "generic" assay in an agonist and/or antagonist competitive binding assay, farther refinement in the selection process is provided.

In the case of 101P3A11 it has been determined that this receptor couples the G protein Gs.

Gs stimulates the enzyme adenylyl cyclase (Gi, on the other hand, inhibits this enzyme).

Adenylyl cyclase catalyzes the conversion of ATP to cANT; thus, assays that detect cANT can be utilized, for example and not limitation, cell-based cANT assay, to determine if a candidate compound is an inverse agonist to the receptor (i.e., such a compound which contacts the receptor would decrease the levels of cAMP relative to the uncontacted receptor). As a result, "cyclase-based assays" can be used to further screen those compounds selected from an agonist and/or antagonist competitive binding assay.

XVI.) GPCR Fusion Proteins

The use of an endogenous, constitutively activated orphan GPCRs, such as 101P3A11, for use in screening of candidate compounds for the direct identification of inverse agonists, agonists and partial agonists, provides a unique challenge in that, by definition, the endogenous receptor is active even in the absence of an endogenous ligand bound thereto.

Thus, in order to differentiate between, e.g., the endogenous receptor in the presence of a candidate compound and the endogenous receptor in the absence of that compound, with an aim of such a differentiation to allow for an understanding as to whether such compound may be an inverse agonist, agonist, partial agonist or have no affect on such a receptor, it is preferred that an approach be utilized that can enhance such differentiation. A preferred approach is the use of a GPCR Fusion Protein.

Generally, once it is determined that an endogenous orphan GPCR is constitutively activate, using the assay techniques set forth herein (as well as others known in the art), it is possible to determine the predominant G protein that couples with the endogenous GPCR. Coupling of the G protein to the GPCR provides a signaling pathway that can be assessed. Because it is most preferred that screening take place by use of a mammalian expression system, such a system will be expected to have endogenous G protein therein. Thus, by definition, in such a system, the endogenous, constitutively active orphan GPCR will continuously signal. In this regard, it is preferred that this signal be enhanced such that in the presence of, e.g., an inverse agonist to the receptor, it is more likely that one will be able to more readily differentiate, particularly in the context of screening, between the receptor when it is contacted with the inverse agonist.

A GPCR Fusion Protein is intended to enhance the efficacy of G protein coupling with the endogenous GPCR. The GPCR Fusion Protein appears to be important for screening with an endogenous, constitutively activated GPCR because such an approach increases the signal that is most preferably utilized in such screening techniques. This is important in facilitating a significant "signal to noise" ratio. A significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. The criteria of importance for such a GPCR Fusion Protein construct is that the endogenous GPCR sequence and the G protein sequence both be in-frame (preferably, the sequence for the endogenous GPCR is upstream of the G protein sequence) and that the "stop" codon of the GPCR must be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Both approaches have been evaluated, and in terms of measurement of the activity of the GPCR, the results are substantially the same; however, there is a preference (based upon convenience) for use of a spacer in that some restriction sites that are not used will, upon expression, effectively, become a spacer. Most preferably, the G protein that couples to the endogenous GPCR will have been identified prior to the creation of the GPCR Fusion Protein construct. Because there are only a few G proteins that have been identified, it is preferred that a construct comprising the sequence of the G protein (i.e., a universal G protein construct) be available for insertion of an endogenous GPCR sequence therein; this provides for efficiency in the context of large-scale screening of a variety of different endogenous GPCRs having different sequences.

Pharmaceutical Compositions Candidate compounds selected for further development as active ingredients can be formulated into pharmaceutical compositions using techniques well known to those in the art. Suitable pharmaceutically-acceptable carriers are available to those in the art; for example, see Remington's Pharmaceutical Sciences, 16t" Edition, 1980, Mack Publishing Co., (Oslo et al., eds.).

EXAMPLES

Various aspects of the invention are further described and illustrated by way of the several examples that follow, none of which are intended to limit the scope of the invention.

Example 1

Expression Analysis of 101P3A11 in Normal Tissues and Patient Specimens

Figure 10A:
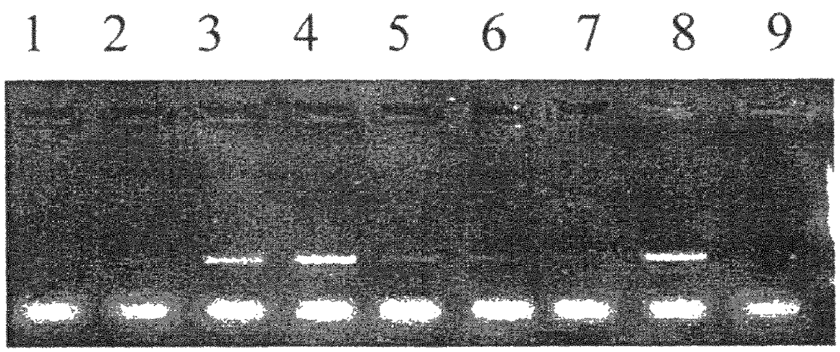
FIG. 10A. Expression of 101P3A11 by RT-PCR. First strand cDNA was prepared from vital pool 1 (VP1: liver, lung and kidney), vital pool 2 (VP2, pancreas, colon and stomach), prostate xenograft pool, prostate cancer pool, kidney cancer pool, colon cancer pool, breast cancer pool, and cancer metastasis pool. Normalization was performed by PCR using primers to actin and GAPDH. Semi-quantitative PCR, using primers to 101P3A11, was performed at 30 cycles of amplification. Expression of 101P3A11 was observed in prostate xenograft pool, prostate cancer pool, kidney cancer pool, colon cancer pool, breast cancer pool, and cancer metastasis pool, but not in VP1 and VP2.
Figure 10B:
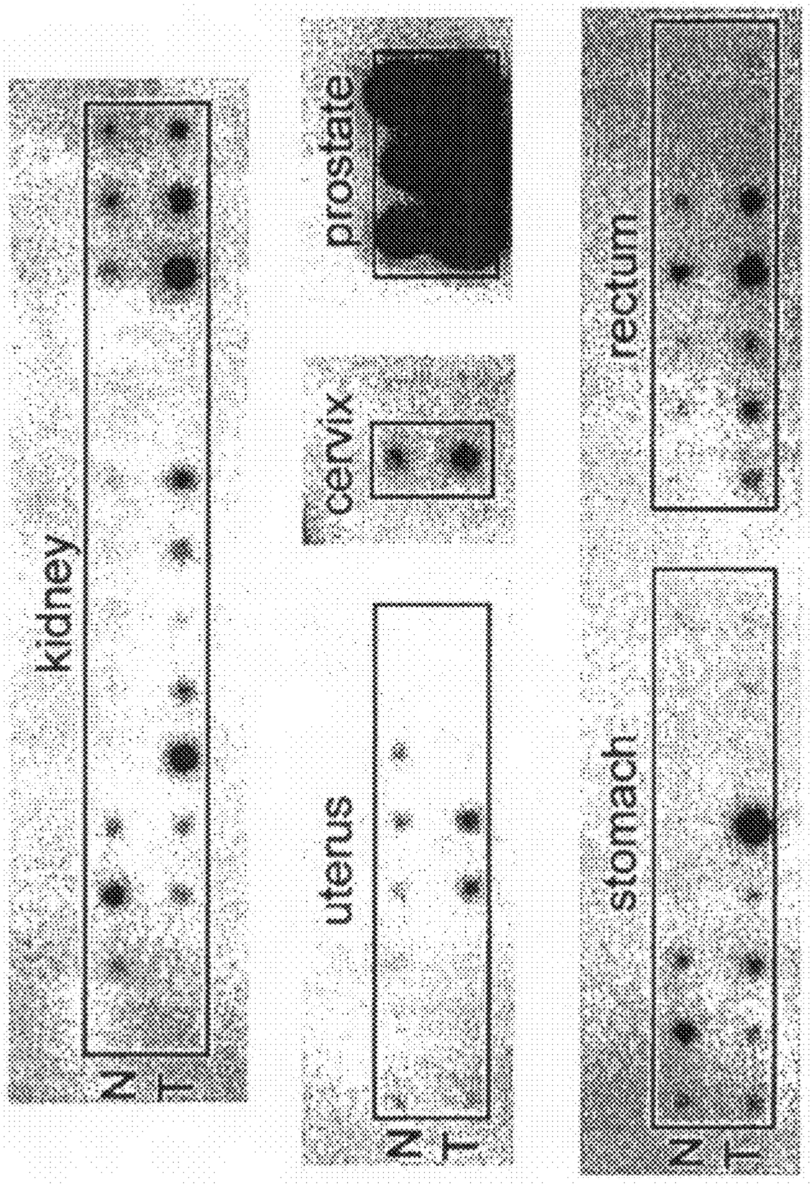
FIG. 10B. Expression of 101P3A11 in human cancers demonstrated by dot blot analysis of tumor RNA (T) and normal RNA (N) matched samples using patient-derived amplified cDNAs. Up-regulation of PHOR-1 expression was found in 3 of 3 prostate cancer patients, 6 of 14 kidney cancer patients, 2 of 8 uterine cancer patients, 3 of 8 stomach cancer patients and 7 of 7 rectal cancer patients.

Analysis of 101P3A11 by RT-PCR is shown in FIG. 10A. First strand cDNA was prepared from vital pool 1 (VP1: liver, lung and kidney), vital pool 2 (VP2, pancreas, colon and stomach), prostate xenograft pool, prostate cancer pool, kidney cancer pool, colon cancer pool, breast cancer pool, and cancer metastasis pool. Normalization was performed by PCR using primers to actin and GAPDH. Semi-quantitative PCR, using primers to 101P3A11, was performed at 30 cycles of amplification. Expression of 101P3A11 was observed in prostate xenograft pool, prostate cancer pool, kidney cancer pool, colon cancer pool, breast cancer pool, and cancer metastasis pool, but not in VP1 and VP2. Dot blots using patient-derived amplified cDNAs (Clontech, CA) show upregulation of PHOR-1 in 3/3 prostate cancer patients, 6/14 kidney cancer patients, 2/8 uterine cancer, 1/1 cervical cancer, 3/8 stomach cancer, and in 7/7 rectal cancer patients (FIG. 10B).

Figure 11:
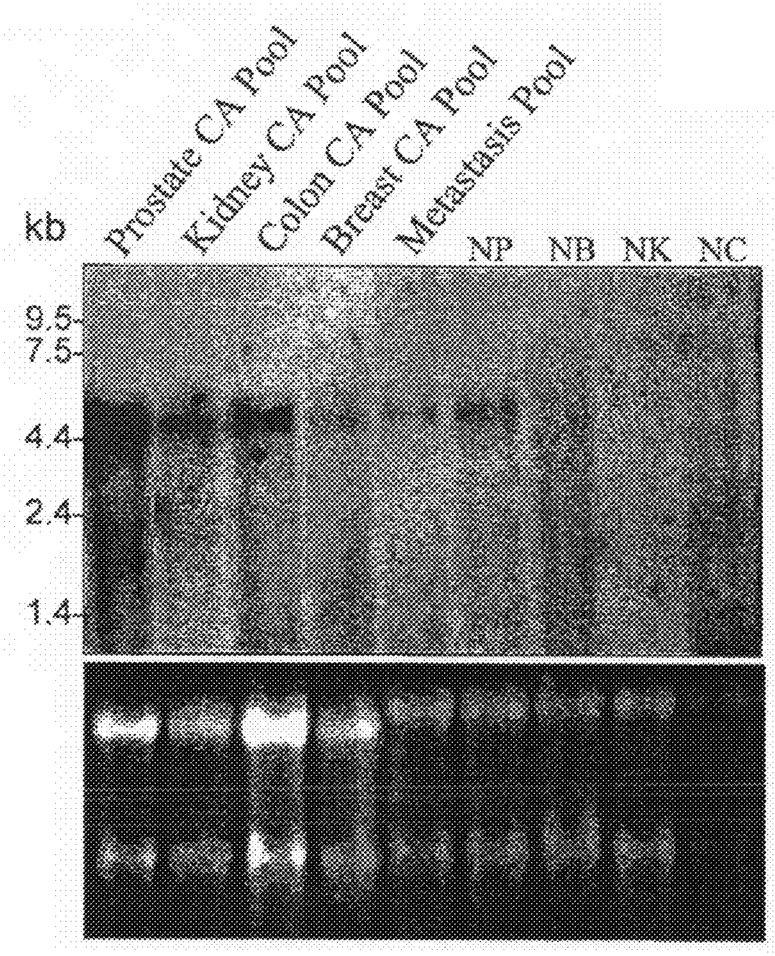
FIG. 11. Expression of 101P3A11 in human patient cancer specimens. RNA was extracted from a pool of three prostate cancer tumors, kidney cancer tumors, colon cancer tumors, breast cancer tumors, and a cancer metastasis pool derived from cancer patients, as well as from normal prostate (NP), normal bladder (NB), normal kidney (NK) and normal colon (NC). Northern blots with 10 μg of total RNA/lane were probed with a 101P3A11 fragment. Size standards in kilobases (kb) are indicated on the side. The results showed expression of 101P3A11 in prostate cancer tumors, kidney cancer tumors, colon cancer tumors, breast cancer tumors, cancer metastasis pool, bladder cancer pool, and in the normal prostate but not in the other normal tissues. A picture of the ethidium-bromide staining of the RNA gel is also presented.

Expression of 101P3A11 was assayed in a panel of human patient cancer specimens (FIG. 11). RNA was extracted from a pool of three prostate cancer tumors, kidney cancer tumors, colon cancer tumors, breast cancer tumors, and cancer metastasis pool derived from cancer patients, as well as from normal prostate (NP), normal bladder (NB), normal kidney (NK) and normal colon (NC). Northern blots with 10 μg of total RNA/lane were probed with a 101P3A11 sequence fragment. Size standards in kilobases (kb) are indicated on the side. The results show expression of 101P3A11 in prostate cancer tumors, kidney cancer tumors, colon cancer tumors, breast cancer tumors, cancer metastasis pool, bladder cancer pool, and in the normal prostate but not in the other normal tissues.

Figure 12A:
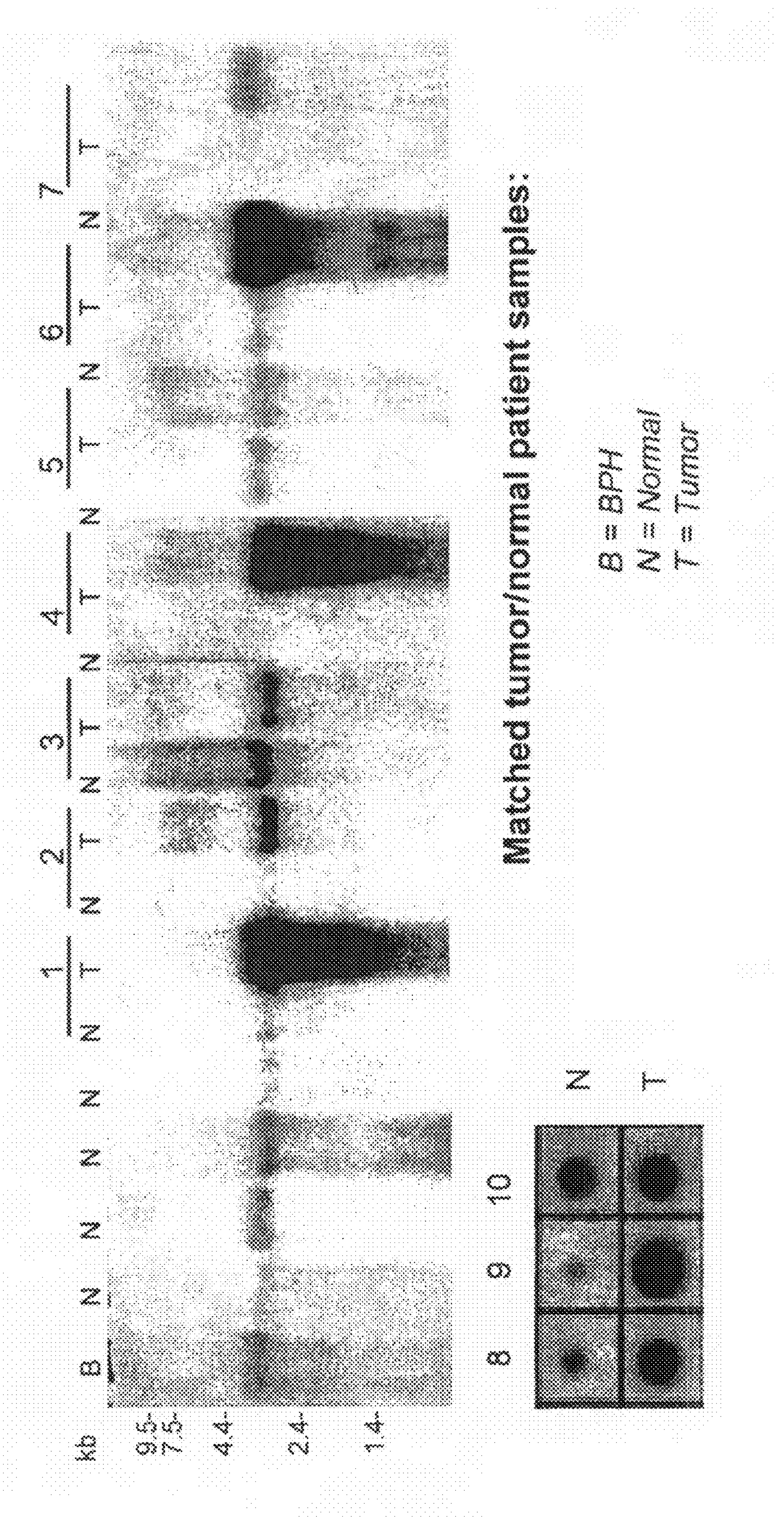
FIG. 12A. Expression of 101P3A11 in prostate cancer patient specimens. RNA was extracted from prostate tumors (T) and their normal adjacent tissues (Nat) derived from prostate cancer patients. Northern blots with 10 μg of total RNA/lane were probed with 101P3A11 sequences. Results show upregulated expression of 101P3A11 in 8 of 10 tumor specimens.

Northern blot analysis on individual prostate patient tumor specimens is shown in FIG. 12A. RNA was extracted from prostate tumors (T) and their normal adjacent tissues (Nat) derived from prostate cancer patients. Northern blots with 10 μg of total RNA/lane were probed with 101P3A11 sequence. Results showed expression of 101P3A11 in all three patient specimens, and expression is especially upregulated in one of the three prostate tumor tissues.

RNA in situ analysis using anti-sense 101P3A11 riboprobe showed significant glandular epithelial and basal cell expression in normal prostate (4/4), PIN (1/1), and prostate cancer (6/6) patients. 101P3A11 sense riboprobe had little to no staining. The RNA in situ staining in PIN and prostate cancer is shown in FIG. 12B and FIG. 12C. The staining intensity in the cancer cells was generally higher than that observed in normal glands (FIGS. 12D and 12E). The RNA in situ results also demonstrate that the expression observed in the prostate tissues is in the glandular epithelia, basal cells, and cancer cells.

Figures 40A, 40B, 40C, 40D, 40E, 40F:
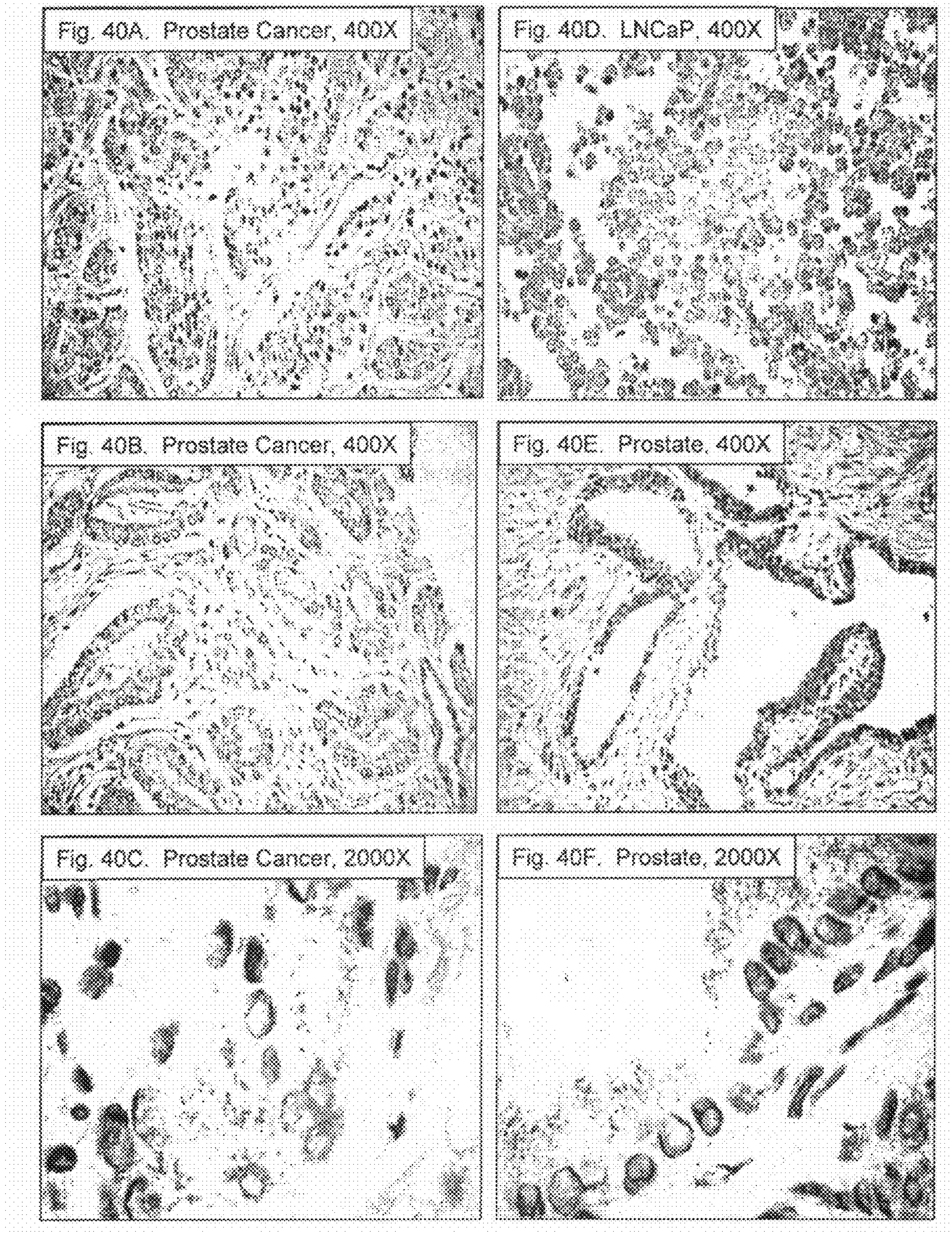
FIGS. 40A-40F. Photomicrographs showing immunohistochemical analysis using anti-101P3A11 (peptide 1; amino acids 1-14) rabbit polyclonal antibody on formalin fixed and paraffin embedded prostate cancer tissues (FIG. 40A); anti-101P3A11 (peptide 1; amino acids 1-14) rabbit polyclonal antibody on formalin fixed and paraffin embedded prostate cancer cell line, LNCaP (FIG. 40B); anti-101P3A11 (peptide 1; amino acids 1-14) rabbit polyclonal antibody on formalin fixed and paraffin embedded prostate cancer tissues (FIG. 40C); anti-101P3A11 (peptide 1; amino acids 1-14) rabbit polyclonal antibody on formalin fixed and paraffin embedded normal prostate (FIG. 40D); anti-101P3A11 (peptide 1; amino acids 1-14) rabbit polyclonal antibody on formalin fixed and paraffin embedded prostate cancer tissues (FIG. 40E); and anti-101P3A11 (peptide 1; amino acids 1-14) rabbit polyclonal antibody on formalin fixed and paraffin embedded normal prostate (FIG. 40F).

Endogenous expression of the 101P3A11 protein is demonstrated in the immunohistochemistry analysis of the anti-101P3A11 (PEPTIDE 1: amino acids 1-14) rabbit polyclonal antibody (FIG. 40A-40F). Staining in prostate cancer is greater than the staining observed in normal prostate. The staining is localized apically within the luminal epithelia of the normal prostate (FIGS. 40E and 40F). The staining observed in prostate cancer is also localized apically in low to intermediate grade cancer (FIGS. 40B and 40C) and throughout all cells of more advanced prostate cancer (FIG. 40A). Staining was observed in 19/20 normal prostate patients and in all of the nineteen prostate cancer patients analyzed. The prostate cancer cell line, LNCaP also shows similar staining (FIGS. 40D and 40F) in almost all cells.

Figures 41A, 41B, 41C, 41D, 41E, 41F:
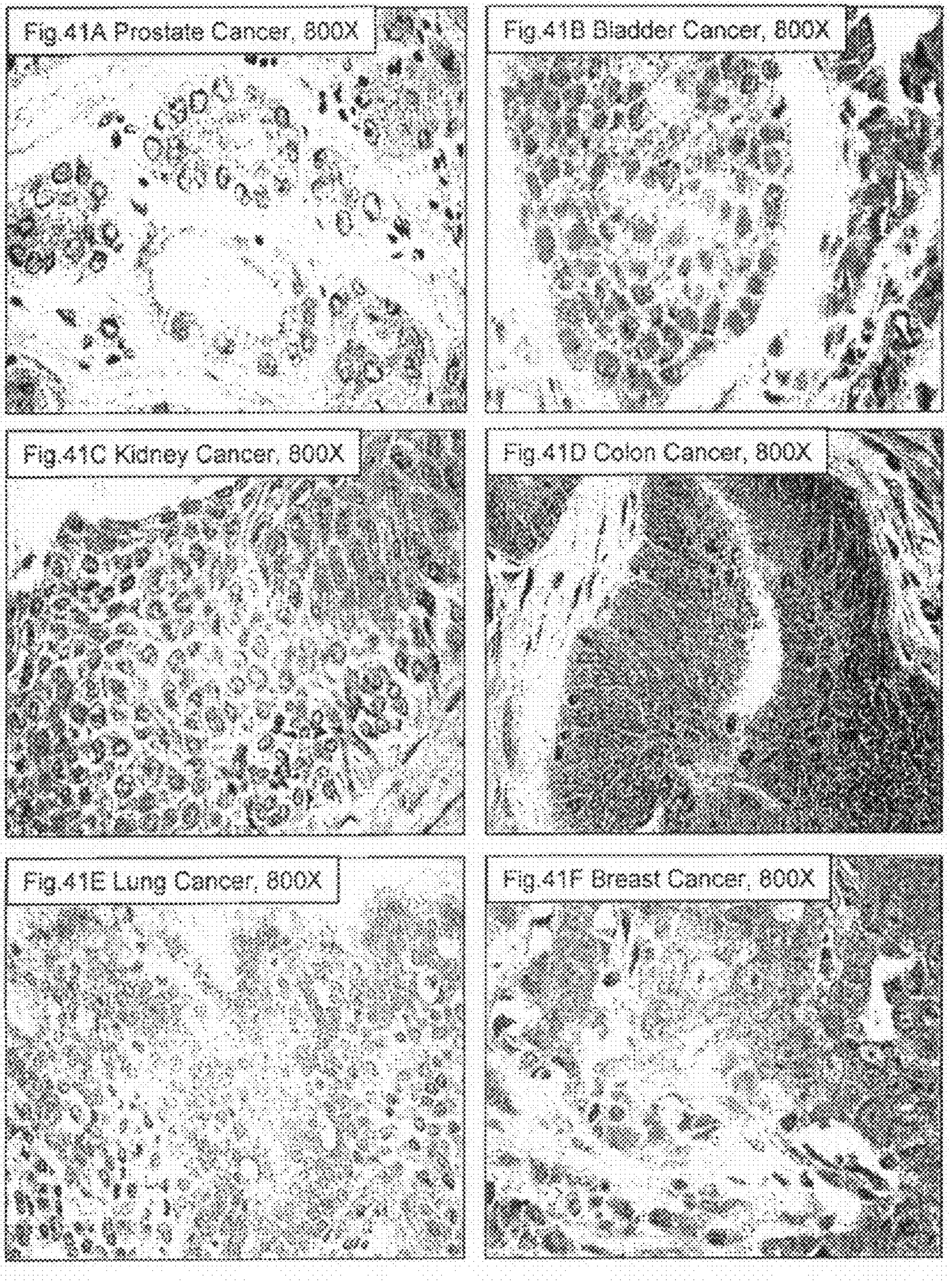
FIGS. 41A-41F. Photomicrographs showing immunohistochemical analysis using anti-101P3A11 (peptide 1; amino acids 1-14) rabbit polyclonal antibody on formalin fixed and paraffin embedded prostate cancer tissues (FIG. 41A); anti-101P3A11 (peptide 1; amino acids 1-14) rabbit polyclonal antibody on formalin fixed and paraffin embedded bladder cancer tissues (FIG. 41B); anti-101P3A11 (peptide 1; amino acids 1-14) rabbit polyclonal antibody on formalin fixed and paraffin embedded kidney cancer tissues (FIG. 41C); anti-101P3A11 (peptide 1; amino acids 1-14) rabbit polyclonal antibody on formalin fixed and paraffin embedded colon cancer tissues (FIG. 41D); anti-101P3A11 (peptide 1; amino acids 1-14) rabbit polyclonal antibody on formalin fixed and paraffin embedded lung cancer tissues (FIG. 41E); and anti-101P3A11 (peptide 1; amino acids 1-14) rabbit polyclonal antibody on formalin fixed and paraffin embedded breast cancer tissues (FIG. 41F).

In addition, the present protocol was used to identify endogenous expression of the 101P3A11 protein in prostate cancer, bladder cancer, kidney cancer, colon cancer, lung cancer, and breast cancer. Immunohistochemical analysis was performed with the anti-101P3A11 (PEPTIDE 1: amino acids 1-14) rabbit polyclonal antibody (prostate cancer, FIG. 41A; bladder cancer, FIG. 41B; kidney cancer, FIG. 41C; colon cancer, FIG. 41D; lung cancer, FIG. 41E; and breast cancer, FIG. 41F). Specific staining is observed in tumor cells of the six cancers analyzed.

Figure 13:
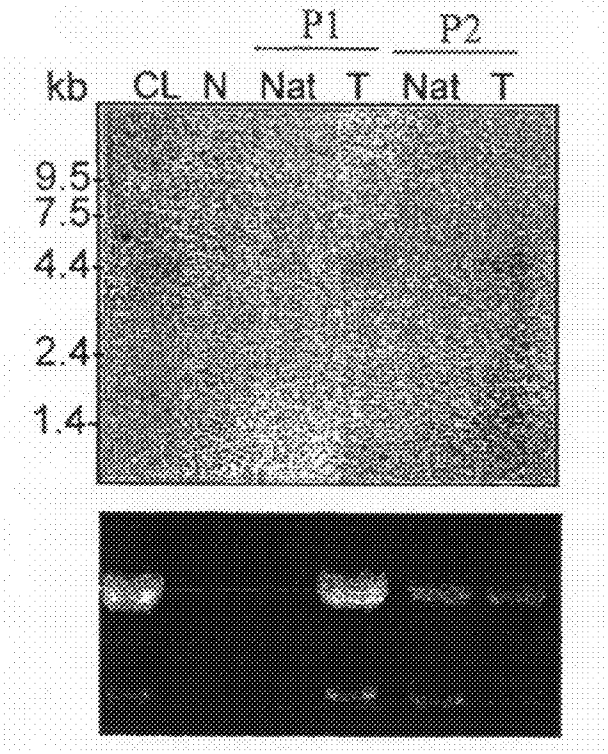
FIG. 13. Expression of 101P3A11 in colon cancer patient specimens. RNA was extracted from colon tumors (T) and their normal adjacent tissues (Nat) derived from colon cancer patients. Northern blots with 10 μg of total RNA/lane were probed with 101P3A11 sequences. Size standards in kilobases (kb) are indicated on the side. Results showed expression of 101P3A11 in colon tumors but not in normal tissues. Expression was also seen in the colon cancer cell line T84. A picture of the ethidium-bromide staining of the RNA gel is also presented.
Figure 14:
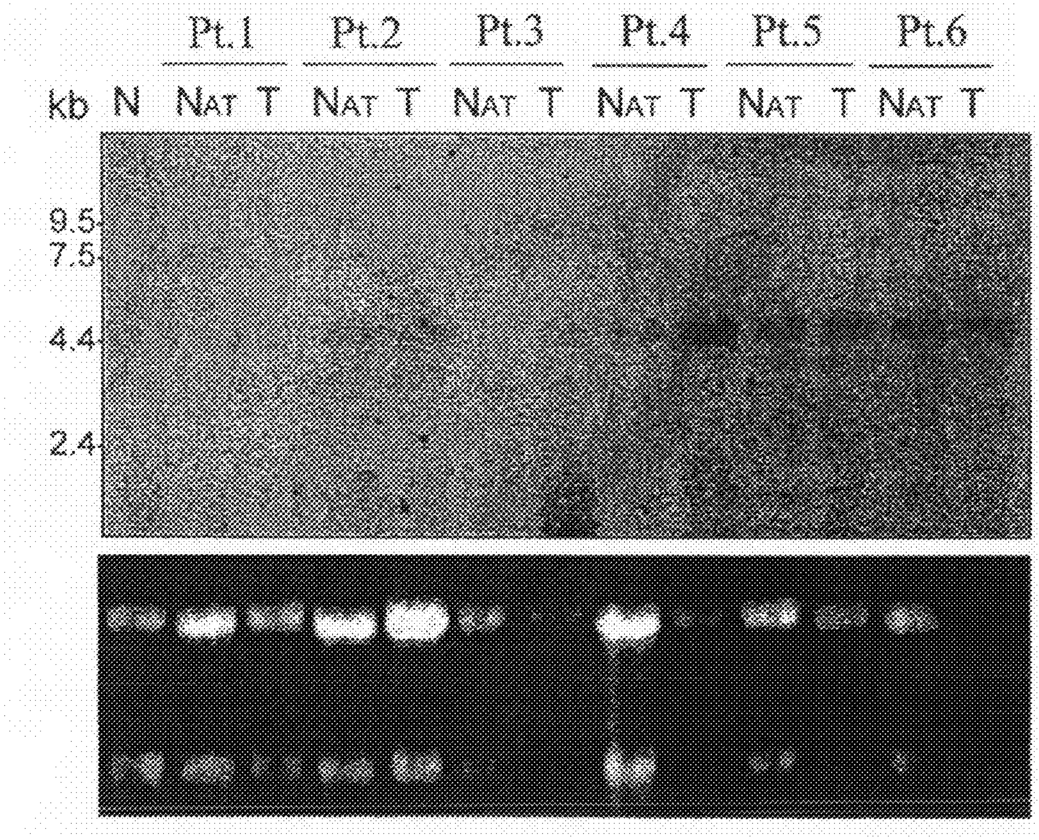
FIG. 14. Expression of 101P3A11 in kidney cancer patient specimens. RNA was extracted from kidney tumors (T) and their normal adjacent tissues (Nat) derived from kidney cancer patients. Northern blots with 10 μg of total RNA/lane were probed with 101P3A11 sequences. Size standards in kilobases (kb) are indicated on the side. The results showed expression of 101P3A11 in five of six kidney tumor specimens. The expression detected in normal adjacent tissues (isolated from diseased tissues) but not in normal tissues (isolated from healthy donors) indicates that these tissues are not fully normal and that 101P3A11 is expressed in early stage tumors. A picture of the ethidium-bromide staining of the RNA gel is also presented.

Expression of 101P3A11 was also detected in the tumors of two colon cancer patients but not in normal colon tissues (FIG. 13), and in five out of six kidney tumors isolated from kidney cancer patients (FIG. 14). The expression detected in normal adjacent tissues (isolated from diseased tissues) but not in normal tissues of the kidney (isolated from healthy donors) indicates that these tissues are not fully normal and that 101P3A11 is expressed in early stage tumors.

Figures 15A, 15B, 15C:
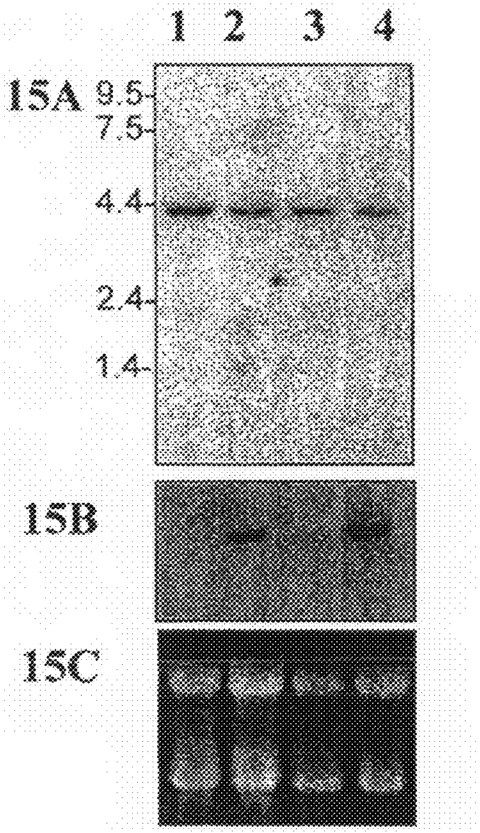
FIGS. 15A-15C. Androgen regulation of 101P3A11 in tissue culture cells. LAPC-9 cells were grown in charcoal-stripped medium and stimulated with the synthetic androgen mibolerone, for either 14 or 24 hours. Northern blots with 10 μg of total RNA/lane were probed with 101P3A11 sequences (FIG. 15A). A picture of the ethidium-bromide staining of the RNA gel is also presented (FIG. 15C). Results showed expression of 101P3A11 was not regulated by androgen. The experimental samples were confirmed by testing for the expression of the androgen-regulated prostate cancer gene PSA (FIG. 15B). This experiment showed that, as expected, PSA levels go down in presence of charcoal-stripped serum, and expression is induced at 14 and 24 hours in presence of mibolerone.

In order to assay for androgen regulation of 101P3A11 expression, LAPC-9 cells were grown in charcoal-stripped medium and stimulated with the synthetic androgen mibolerone, for either 14 or 24 hours (FIG. 15A, FIG. 15B, and FIG. 15C). Northern blots with 10 μg of total RNA/lane were probed with the 101P3A11 sequences (FIG. 15A). A picture of the ethidium-bromide staining of the RNA gel is also presented (FIG. 15C). Results showed expression of 101P3A11 is not regulated by androgen. The experimental samples were confirmed by testing for the expression of the androgen-regulated prostate cancer gene PSA (FIG. 15B). This experiment showed that, as expected, PSA levels go down in presence of charcoal-stripped serum, and expression is induced at 14 and 24 hours in presence of mibolerone.

Figure 16:
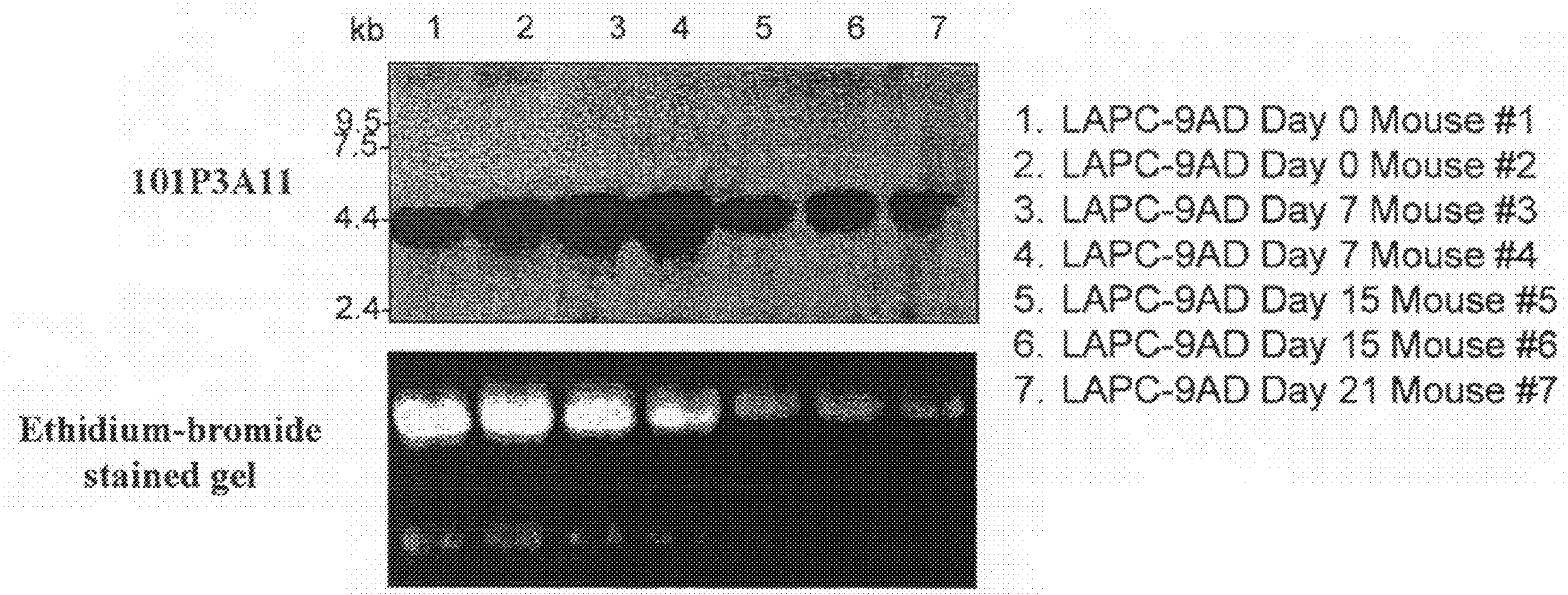
FIG. 16. Androgen regulation of 101P3A11 in vivo. Male mice were injected with LAPC-9AD tumor cells. When tumors reached a palpable size (0.3-0.5 cm in diameter), mice were castrated and tumors harvested at different time points following the castration. RNA was isolated from the xenograft tissues. Northern blots with 10 μg of total RNA/lane were probed with 101P3A11 sequences. Size standards in kilobases (kb) are indicated on the side. A picture of the ethidium-bromide staining of the RNA gel is also presented. The results showed that expression of 101P3A11 is not androgen regulated.

Analysis of androgen regulation of 101P3A11 in vivo is shown in FIG. 16. Male mice were injected with LAPC-9AD tumor cells. When tumors reached a palpable size, mice were castrated and tumors harvested at different time points following castration. RNA was isolated from the xenograft tissues. Northern blots with 10 μg of total RNA/lane were probed with 101P3A11 sequences. Size standards in kilobases (kb) are indicated on the side. A picture of the ethidium-bromide staining of the RNA gel is also presented in FIG. 16. The results showed that expression of 101P3A11 was not affected by androgen deprivation, and therefore, is not androgen regulated.

Example 2

Splice Variants/Transcript Variants of 101P3A11

Transcript variants are variants of mature mRNA from the same gene which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516-22); Grail (URL compbio.ornl.gov/Grail-bin/EmptyGrailForm) and GenScan (URL genes.mit.edu/GENSCAN.html). For a general discussion of splice variant identification protocols see, e.g., Southan, C., A genomic perspective on human proteases, FEBS Lett. 2001 Jun. 8; 498(2-3):214-8; de Souza, S. J., et al., Identification of human chromosome 22 transcribed sequences with ORF expressed sequence tags, Proc. Natl. Acad Sci USA. 2000 Nov. 7; 97(23):12690-3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et al., Albumin banks peninsula: a new termination variant characterized by electrospray mass spectrometry, Biochem Biophys Acta. 1999 Aug. 17; 1433(1-2): 321-6; Ferranti P, et al., Differential splicing of pre-messenger RNA produces multiple forms of mature caprine alpha(s1)-casein, Eur J Biochem. 1997 Oct. 1; 249(1):1-7. For PCR-based Validation: Wellmann S, et al., Specific reverse transcription-PCR quantification of vascular endothelial growth factor (VEGF) splice variants by LightCycler technology, Clin Chem. 2001 April; 47(4):654-60; Jia, H. P., et al., Discovery of new human beta-defensins using a genomics-based approach, Gene. 2001 Jan. 24; 263(1-2): 211-8. For PCR-based and 5' RACE Validation: Brigle, K. E., et al., Organization of the murine reduced folate carrier gene and identification of variant splice forms, Biochem Biophys Acta. 1997 Aug. 7; 1353(2): 191-8).

It is known in the art that genomic regions are modulated in cancers. When the genomic region to which a gene maps is modulated in a particular cancer, the alternative transcripts or splice variants of the gene are modulated as well. Disclosed herein is that 101P3A11 has a particular expression profile related to cancer. Alternative transcripts and splice variants of 101P3A11 may also be involved in cancers in the same or different tissues, thus serving as tumor-associated markers/antigens.

The exon composition of the original transcript, designated as 101P3A11 v.1, are:

| Exon number | Start | End |
|---|---|---|
| 1 | 1 | 90 |
| 2 | 91 | 3136 |

Figure 46:
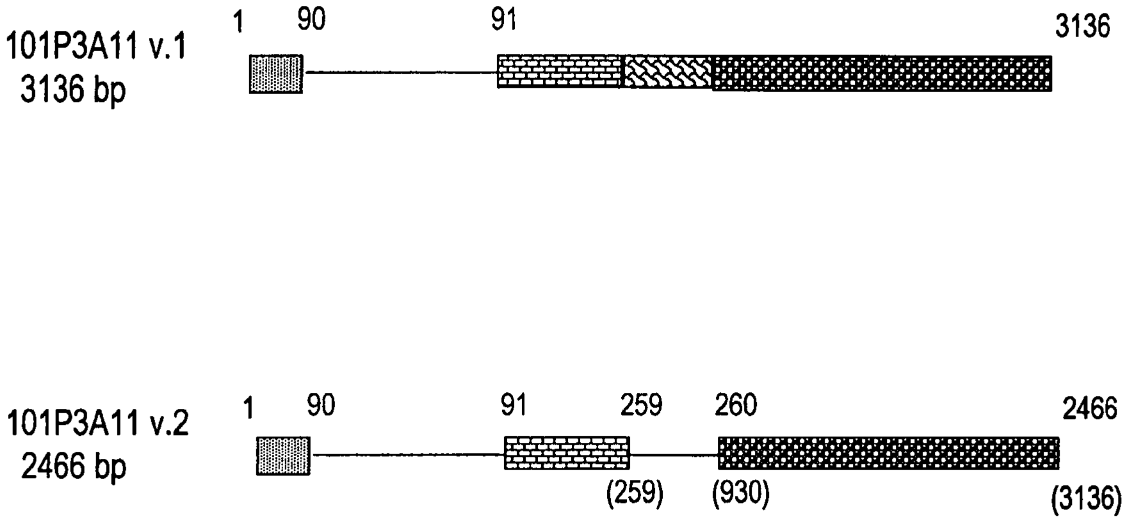
FIG. 46: Exon Map

Using the full-length gene and EST sequences, one transcript variant was identified, designated as 101P3A11 v.2. Compared with 101P3A11 v.1, transcript variant 101P3A11 v.2 has spliced out a fragment from the second exon of variant 1, as shown in FIG. 46. All other exons are the same corresponding exons of 101P3A11 v.1. Theoretically, each different combination of exons in spatial order, e.g. exons 2 and 3, is a potential splice variant. FIG. 46 shows the schematic alignment of exons of the two transcript variants.

FIG. 2 shows nucleotide sequence of the transcript variant (101P3A11 v.2). FIG. 69 shows the alignment of the transcript variant with nucleic acid sequence of 101P3A11 v.1. FIG. 70 lays out amino acid translation of the transcript variant for the identified reading frame orientation. FIG. 71 displays alignments of the amino acid sequence encoded by the splice variant with that of 101P3A11 v.1.

Example 3

Single Nucleotide Polymorphisms (SNPs) of 101P3A11

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, "SNP analysis to dissect human traits," Curr. Opin. Neurobiol. 2001 October; 11(5):637-641; M. Pirmohamed and B. K. Park, "Genetic susceptibility to adverse drug reactions," Trends Pharmacol. Sci. 2001 June; 22(6):298-305; J. H. Riley, C. J. Allan, E. Lai and A. Roses, "The use of single nucleotide polymorphisms in the isolation of common disease genes," Pharmacogenomics. 2000 February; 1(1):39-47; R. Judson, J. C. Stephens and A. Windemuth, "The predictive power of haplotypes in clinical response," Pharmacogenomics. 2000 February; 1(1):15-26).

SNPs are identified by a variety of art-accepted methods (P. Bean, "The promising voyage of SNP target discovery," Am. Clin. Lab. 2001 October-November; 20(9):18-20; K. M. Weiss, "In search of human variation," Genome Res. 1998 July; 8(7):691-697; M. M. She, "Enabling large-scale pharmacogenetic studies by high-throughput mutation detection and genotyping technologies," Clin. Chem. 2001 February; 47(2): 164-172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221-225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235-258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329-340).

Figure 44:
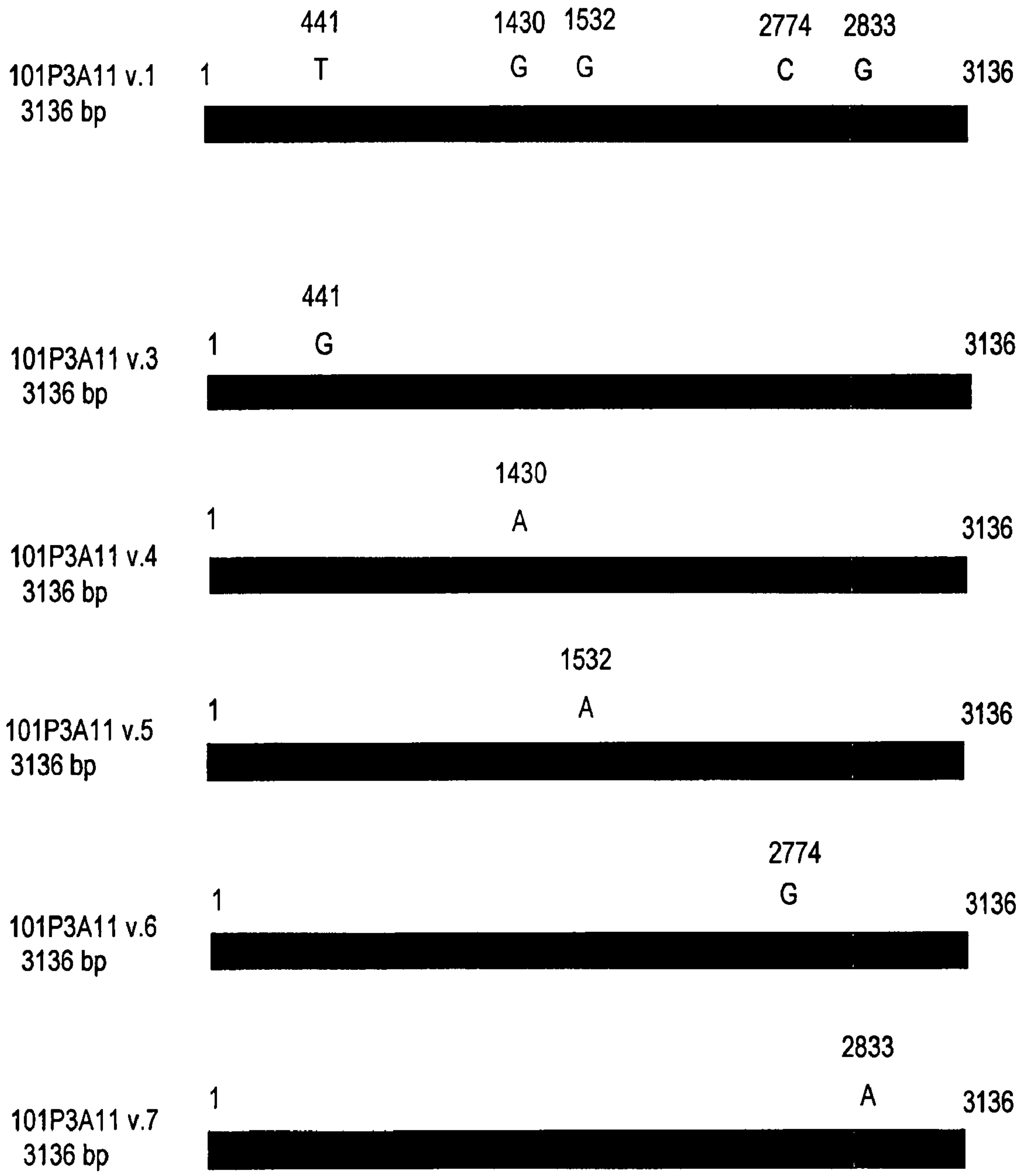
FIG. 44: Schematic of 101P3A11 Gene Variants
Figure 45:
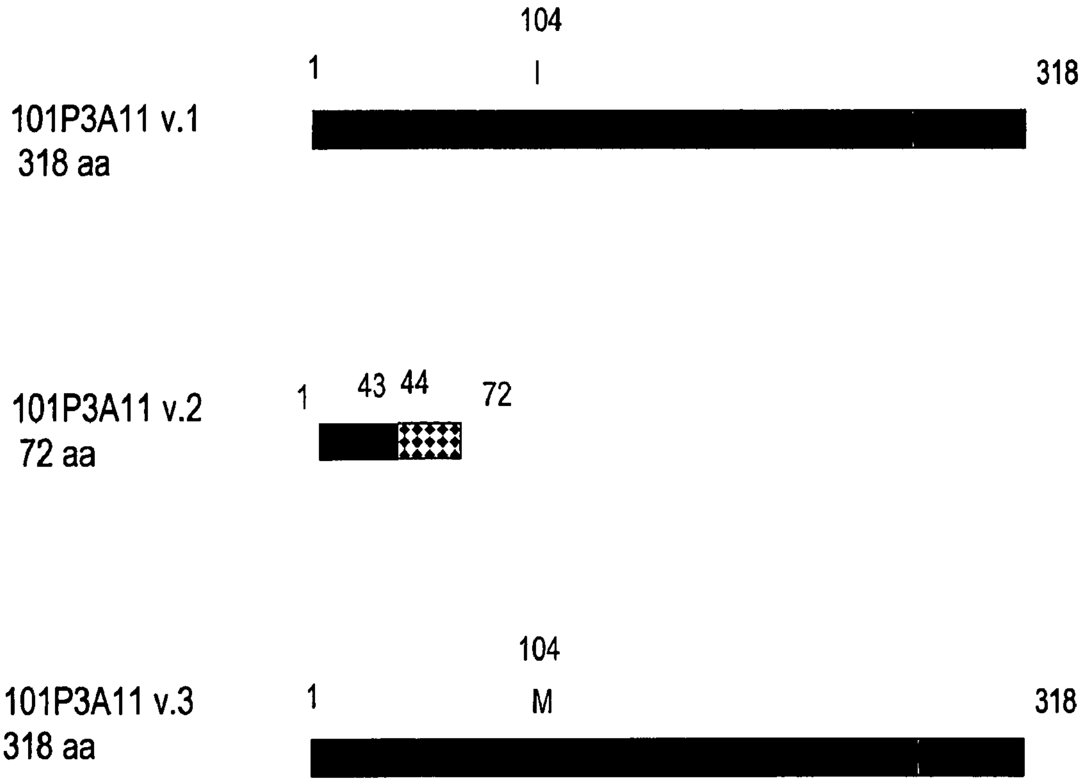
FIG. 45: Schematic of 101P3A11 Proteins Variants

Using the methods described above, five SNPs were identified in the original transcript, 101P3A11 v.1, at positions 441 (T/G), 1430 (G/A), 1532 (G/A), 2774 (C/G), and 2833 (G/A). The transcripts or proteins with alternative alleles were designated as variants 101P3A11 v.3, v.4, v.5, v.6 and v.7, respectively. FIG. 44 shows the schematic alignment of the SNP variants. FIG. 45 shows the schematic alignment of protein variants, corresponding to nucleotide variants. Nucleotide variants that code for the same amino acid sequence as variant 1 are not shown in FIG. 11. These alleles of the SNPs, though shown separately here, can occur in different combinations (haplotypes) and in any one of the transcript variants (such as 101P3A11 v.2) that contains the sequence context of the SNPs.

Example 4

Production of Recombinant 101P3A11 in Prokaryotic and Yeast Systems

To express recombinant 101P3A11 in prokaryotic cells, the full or partial length 101P3A11 cDNA sequences can be cloned into any one of a variety of expression vectors known in the art. One or more of the following regions of 101P3A11 are expressed in these constructs, amino acids 1 to 317; or any 8, 9, 10, 11, 12, 13, 14, 15, 16, 17, 18, 19, 20, 21, 22, 23, 24, 25, 26, 27, 28, 29, 30 or more contiguous amino acids from 101P3A11, variants, or analogs thereof.

A. In Vitro Transcription and Translation Constructs:

pCRII: To generate 101P3A11 sense and anti-sense RNA probes for RNA in situ investigations, pCRII constructs (Invitrogen, Carlsbad, Calif.) are generated encoding either all or fragments of the 101P3A11 cDNA. The pCRII vector has Sp6 and T7 promoters flanking the insert to drive the transcription of 101P3A11 RNA for use as probes in RNA in situ hybridization experiments. These probes are used to analyze the cell and tissue expression of 101P3A11 at the RNA level. Transcribed 101P3A11 RNA representing the cDNA amino acid coding region of the 101P3A11 gene is used in in vitro translation systems such as the TnT™ Coupled Reticulolysate System (Promega, Corp., Madison, Wis.) to synthesize 101P3A11 protein.

B. Bacterial Constructs:

pGEX Constructs: To generate recombinant 101P3A11 proteins in bacteria that are fused to the Glutathione S-transferase (GST) protein, all or parts of the 101P3A11 cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 101P3A11 protein sequences with GST fused at the amino-terminus and a six histidine epitope (6×His) at the carboxyl-terminus. The GST and 6×His tags permit purification of the recombinant fusion protein from induced bacteria with the appropriate affinity matrix and allow recognition of the fusion protein with anti-GST and anti-His antibodies. The 6×His tag is generated by adding 6 histidine codons to the cloning primer at the 3' end, e.g., of the open reading frame (ORF). A proteolytic cleavage site, such as the PreScission™ recognition site in pGEX-6P-1, can be employed that permits cleavage of the GST tag from 101P3A11-related protein. The ampicillin resistance gene and pBR322 origin permit selection and maintenance of the pGEX plasmids in *E. coli*. In one embodiment, amino acids 86-317 are cloned into the pGEX-2T expression vector, the protein is expressed and purified.

pMAL Constructs: To generate, in bacteria, recombinant 101P3A11 proteins that are fused to maltose-binding protein (MBP), all or parts of the 101P3A11 cDNA protein coding sequence are fused to the MBP gene by cloning into the pMAL-c2X and pMAL-p2X vectors (New England Biolabs, Beverly, Mass.). These constructs allow controlled expression of recombinant 101P3A11 protein sequences with MBP fused at the amino-terminus and a 6×His epitope tag at the carboxyl-terminus. The MBP and 6×His tags permit purification of the recombinant protein from induced bacteria with the appropriate affinity matrix and allow recognition of the fusion protein with anti-MBP and anti-His antibodies. The 6×His epitope tag is generated by adding 6 histidine codons to the 3' cloning primer. A Factor Xa recognition site permits cleavage of the pMAL tag from 101P3A11. The pMAL-c2X and pMAL-p2X vectors are optimized to express the recombinant protein in the cytoplasm or periplasm respectively. Periplasm expression enhances folding of proteins with disulfide bonds. In one embodiment, amino acids 86-310 is cloned into the pMAL-c2X expression vector, the protein is expressed and purified.

pET Constructs: To express 101P3A11 in bacterial cells, all or parts of the 101P3A11 cDNA protein coding sequence are cloned into the pET family of vectors (Novagen, Madison, Wis.). These vectors allow tightly controlled expression of recombinant 101P3A11 protein in bacteria with and without fusion to proteins that enhance solubility, such as NusA and thioredoxin (Trx), and epitope tags, such as 6×His and S-Tag™ that aid purification and detection of the recombinant protein. For example, constructs are made utilizing pET NusA fusion system 43.1 such that regions of the 101P3A11 protein are expressed as amino-terminal fusions to NusA.

C. Yeast Constructs:

pESC Constructs: To express 101P3A11 in the yeast species *Saccharomyces cerevisiae* for generation of recombinant protein and functional studies, all or parts of the 101P3A11 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is used to confirm protein-protein interactions of 101P3A11. In addition, expression in yeast yields similar post-translational modifications, such as glycosylations and phosphorylations, that are found when expressed in eukaryotic cells.

pESP Constructs: To express 101P3A11 in the yeast species *Saccharomyces pombe*, all or parts of the 101P3A11 cDNA protein coding sequence are cloned into the pESP family of vectors. These vectors allow controlled high level expression of a 101P3A11 protein sequence that is fused at either the amino terminus or at the carboxyl terminus to GST which aids purification of the recombinant protein. A Flag™ epitope tag allows detection of the recombinant protein with anti-Flag™ antibody.

Example 5

Production of Recombinant 101P3A11 in Higher Eukaryotic Systems

A. Mammalian Constructs:

To express recombinant 101P3A11 in eukaryotic cells, full or partial length 101P3A11 cDNA sequences can be cloned into any one of a variety of expression vectors known in the art. One or more of the following regions of 101P3A11 are expressed in these constructs, amino acids 1 to 318 of v.1 and v.3, amino acids to 72 of v.2; or any 5, 6, 7, 8, 9, 10, 11, 12, 13, 14, 15, 16, 17, 18, 19, 20, 21, 22, 23, 24, 25, 26, 27, 28, 29, 30 or more contiguous amino acids from 101P3A11, variants, or analogs thereof.

Figure 66:
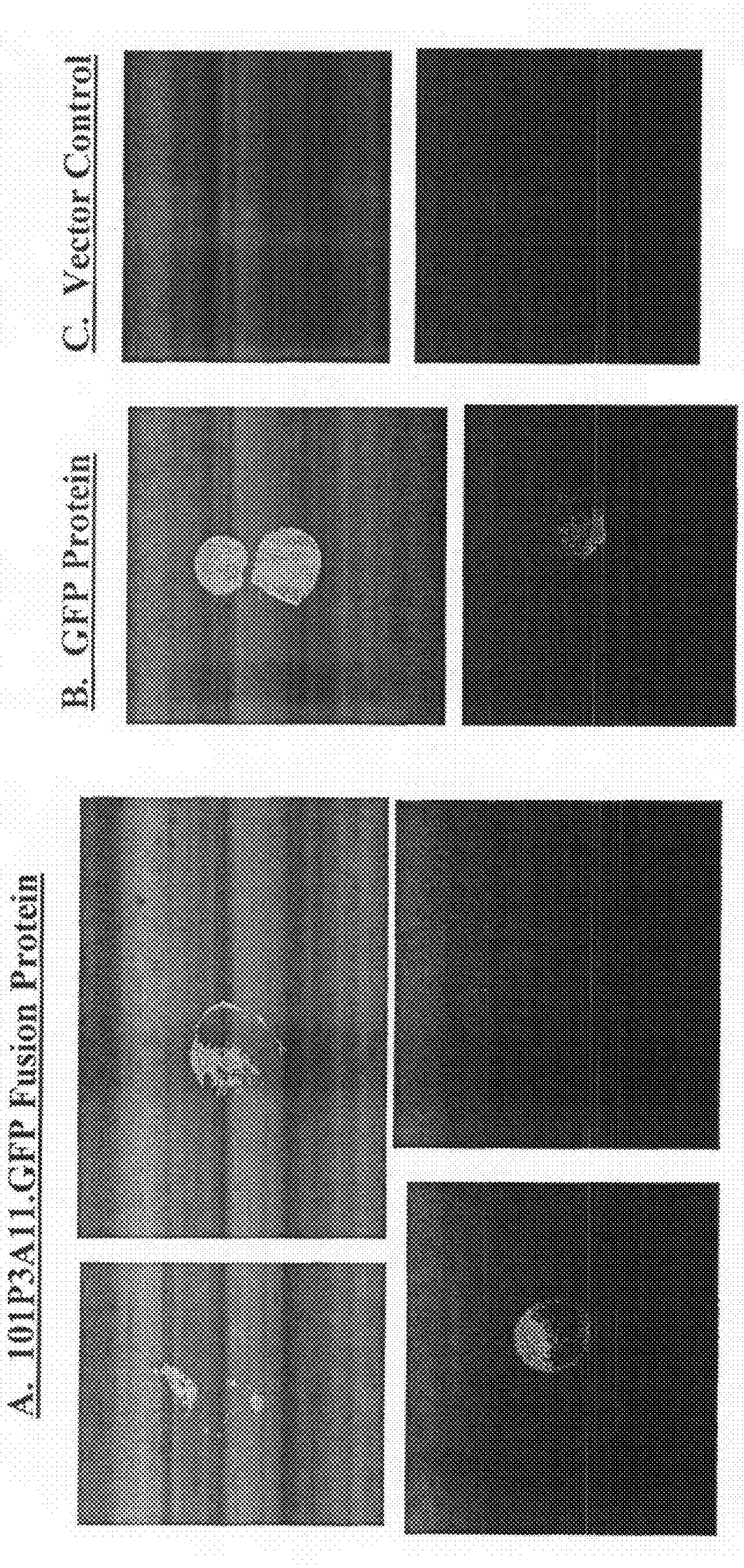
FIG. 66. Expression and detection of 101P3A11.GFP fusion protein. The pcDNA3.1/101P3A11.GFP vector was constructed. 293T cells were transfected with either the pcDNA3.1/101P3A11.GFP recombinant expression vector (A), pcDNA3.1/GFP vector (B) or control pcDNA3.1 vector (C). Cells were harvested 24 hours later and analyzed by microscopy for detection of green fluorescence. Results show expression of the 101P3A11.GFP fusion protein is localized mostly at the cell membrane, whereas expression of the free GFP is throughout the cells. The control vector did not show any fluorescence. We conclude that the 101P3A11.GFP fusion protein is expressed from the pcDNA3.1/101P3A11.GFP construct, and that the fusion protein is localized at the cell membrane.

The constructs can be transfected into any one of a wide variety of mammalian cells such as 293T cells. Transfected 293T cell lysates can be probed with the anti-101P3A11 polyclonal serum, described herein.

pcDNA4/HisMax Constructs: To express 101P3A11 in mammalian cells, the 101P3A11 ORF was cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli.* pcDNA3.1/MycHis Constructs: To express 101P3A11 in mammalian cells, the 101P3A11 ORF, with a consensus Kozak translation initiation site, was cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli.* pcDNA3.1/GFP Construct: To express 101P3A11 in mammalian cells and to allow detection of the recombinant proteins using fluorescence, the 101P3A11 ORF, with a consensus Kozak translation initiation site, was cloned into pcDNA3.1/GFP. Protein expression was driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1/GFP vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli.* FIG. 66 shows expression and detection of 101P3A11.GFP fusion protein. 293T cells were transfected with either pcDNA3.1/101P3A11.GFP recombinant expression vector (A), pcDNA3.1/GFP vector (B) or control pcDNA3.1 vector (C). Cells were harvested 24 hours later and analyzed by microscopy for detection of green fluorescence. Results show expression of the 101P3A11.GFP fusion protein is localized mostly at the cell membrane, whereas expression of the free GFP is throughout the cells. The control vector did not show any fluorescence. We conclude that the 101P3A11.GFP fusion protein is expressed from the pcDNA3.1/101P3A11.GFP construct, and that the fusion protein is localized at the cell membrane.

Additional constructs with an amino-terminal GFP fusion are made in pcDNA3.1/NT-GFP-TOPO spanning the entire length of the 101P3A11 proteins.

Figure 68:
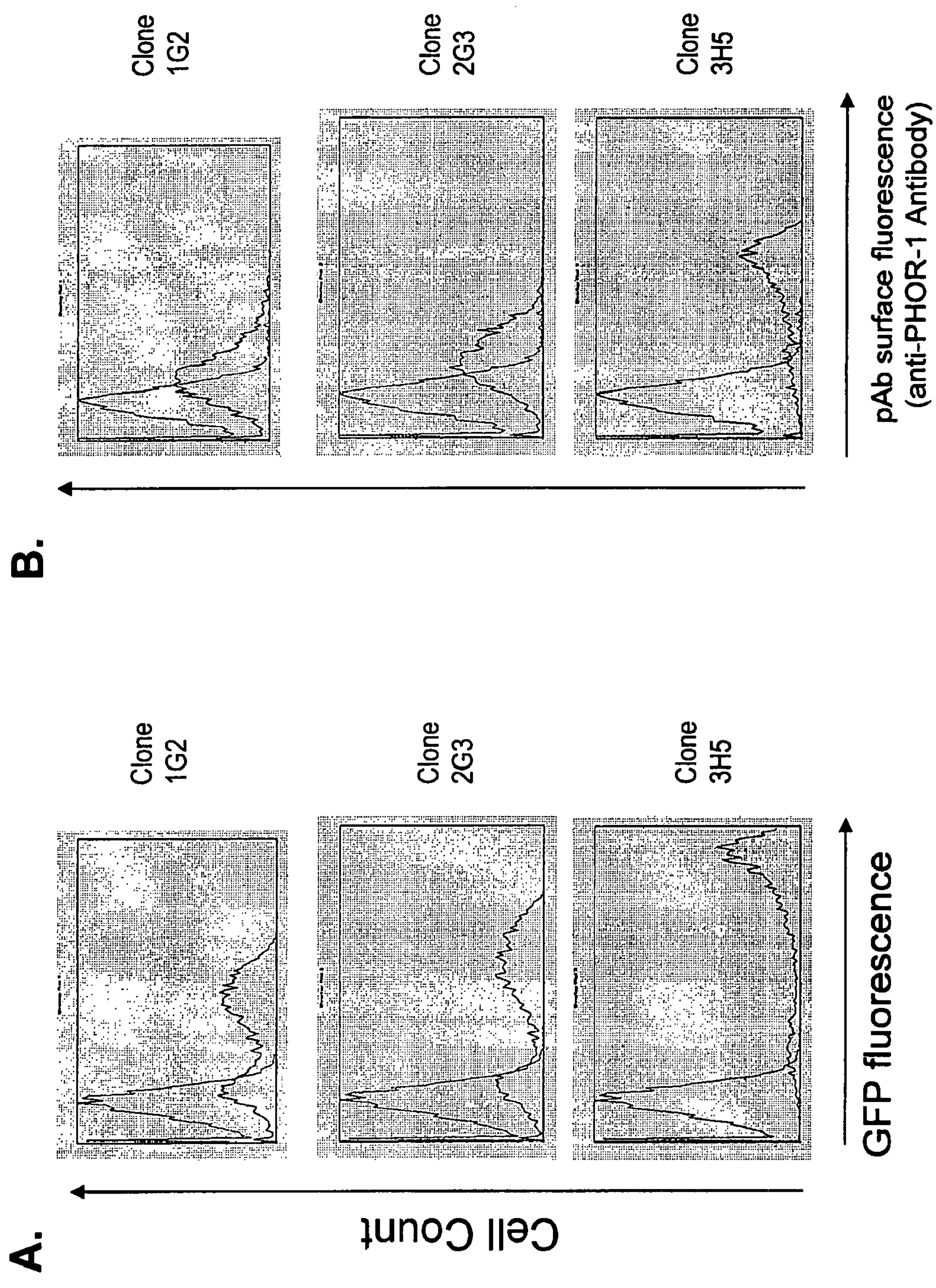
FIG. 68. Expression and detection of codon optimized s101P3A11.GFP fusion protein. The pcDNA3.1/s101P3A11.GFP vector for codon optimized 101P3A11 was constructed. 293T cells were transfected with either pcDNA3.1 vector control (light line), or one of the three different pcDNA3.1/s101P3A11.GFP vector clones, 1G2, 2G3, or 3H5 (dark line). Cells were harvested 24 hours later and either analyzed directly for green fluorescence (A), or stained viably using polyclonal anti-101P3A11 antibody (B) and analyzed by flow cytometry. Results show strong expression of the codon optimized PHOR-1.GFP fusion protein at the cell surface.

Codon optimized 101P3A11: To enhance protein translation of 101P3A11, the nucleic acid sequence of 101P3A11 was codon optimized (s101P3A11). The sequence of codon optimized s101P3A11 is listed in FIG. 67. The s101P3A11 was cloned into the pcDNA3.1/GFP construct and into the pSRa retroviral vector, to generate the s101P3A11.GFP fusion protein. The recombinant protein has the Green Fluorescent Protein (GFP) fused to the carboxyl-terminus facilitating non-invasive, in vivo detection and cell biology studies. FIG. 68 shows expression and detection of the codon optimized s101P3A1.GFP fusion protein. 293T cells were transfected with either pcDNA3.1 vector control (light line), or one of the three different pcDNA3.1/s101P3A11.GFP vector clones, 1G2, 2G3, or 3H5 (dark line). Cells were harvested 24 hours later and either analyzed directly for green fluorescence (A), or stained viably using polyclonal anti-101P3A11 antibody (B) and analyzed by flow cytometry. Results show strong expression of the codon optimized s101P3A11.GFP fusion protein at the cell surface of transfected cells.

PAPtag: The 101P3A11 ORF, or portions thereof, of 101P3A11 are cloned into pAPtag-5 (GenHunter Corp. Nashville, Tenn.). This construct generates an alkaline phosphatase fusion at the carboxyl-terminus of the 101P3A11 proteins while fusing the IgGκ signal sequence to the amino-terminus. Constructs are also generated in which alkaline phosphatase with an amino-terminal IgGκ signal sequence is fused to the amino-terminus of 101P3A11 proteins. The resulting recombinant 101P3A11 proteins are optimized for secretion into the media of transfected mammalian cells and can be used to identify proteins such as ligands or receptors that interact with the 101P3A11 proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli.* ptag5: The 101P3A11 ORF, or portions thereof, of 101P3A11 are cloned into pTag-5. This vector is similar to pAPtag but without the alkaline phosphatase fusion. This construct generated 101P3A11 protein with an amino-terminal IgGκ signal sequence and myc and 6×His epitope tags at the carboxyl-terminus that facilitate detection and affinity purification. The resulting recombinant 101P3A11 protein was optimized for secretion into the media of transfected mammalian cells, and was used as immunogen or ligand to identify proteins such as ligands or receptors that interact with the 101P3A11 proteins. Protein expression is driven from the CMV promoter. The Zeocin resistance gene present in the vector allows for selection of mammalian cells expressing the protein, and the ampicillin resistance gene permits selection of the plasmid in *E. coli.*

PsecFc: The 101P3A11 ORF, or portions thereof, of 101P3A11 are also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 101P3A11 proteins, while fusing the IgGκ signal sequence to N-terminus. 101P3A11 fusions utilizing the murine IgG1 Fc region are also used. The resulting recombinant 101P3A11 proteins are optimized for secretion into the media of transfected mammalian cells, and can be used as immunogens or to identify proteins such as ligands or receptors that interact with the 101P3A11 protein. Protein expression is driven from the CMV promoter. The hygromycin resistance gene present in the vector allows for selection of mammalian cells that express the recombinant protein, and the ampicillin resistance gene permits selection of the plasmid in *E. coli.*

Figure 17:
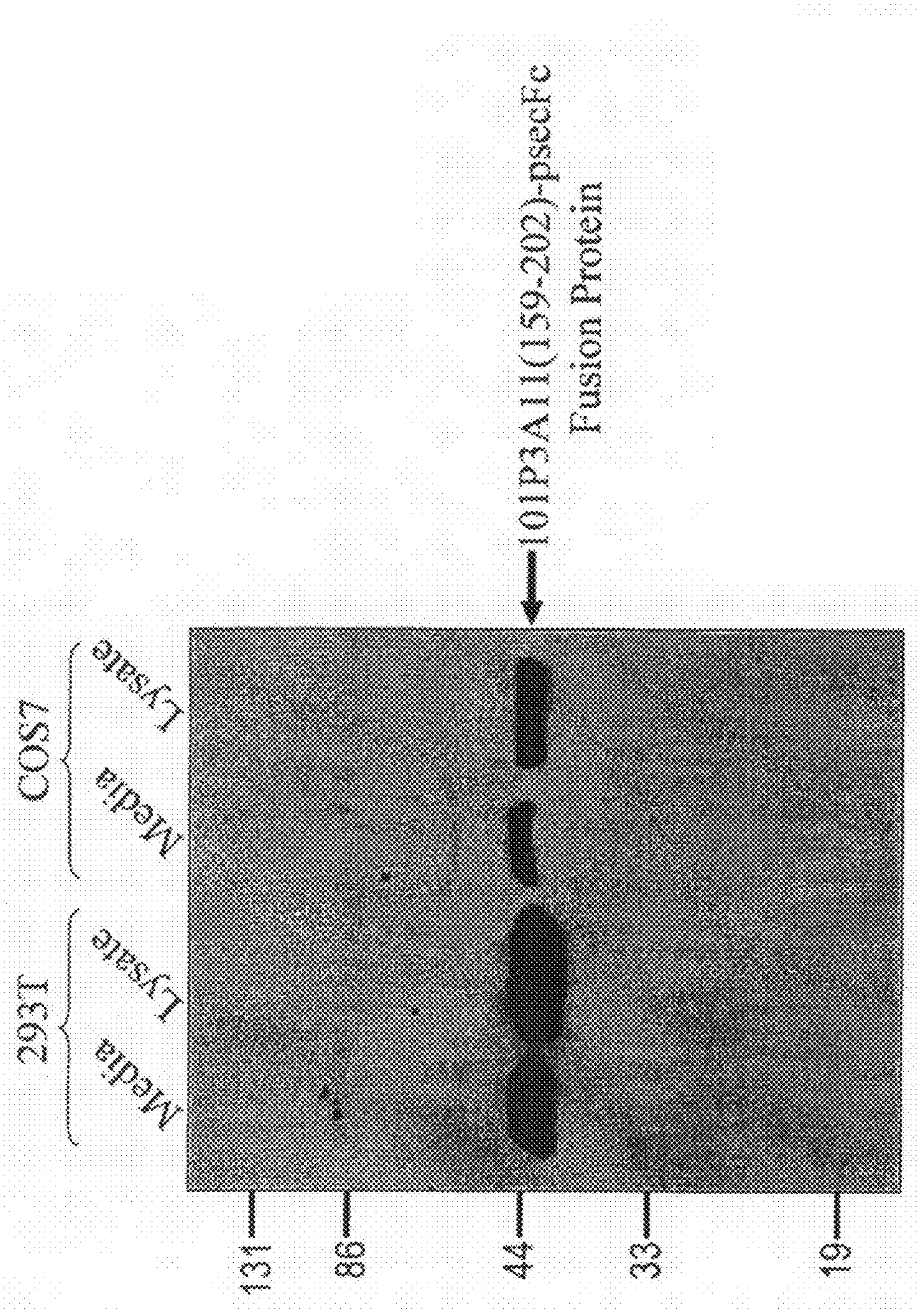
FIG. 17. Expression and detection of 101P3A11(159-202)-psecFc fusion protein. The 101P3A11(159-202)-psecFc vector was constructed. The recombinant expression vector DNA was transfected into either 293T cells or Cos-7 cells. Cells as well as culture supernatants (media) were harvested 24 hours later. The cells were lysed, and run on SDS-PAGE gel along with the media samples. The gel was transferred to nitrocellulose, stained with HRP-labeled anti-human IgG and developed using the ECL chemiluminescence detection kit. Results showed expression of the 101P3A11(159-202)-psecFc fusion protein in the lysates of both 293T and Cos-7 cells. The 101P3A11(159-202)-psecFc fusion protein was also secreted and detected in the culture supernatants of both cell types.
Figure 18:
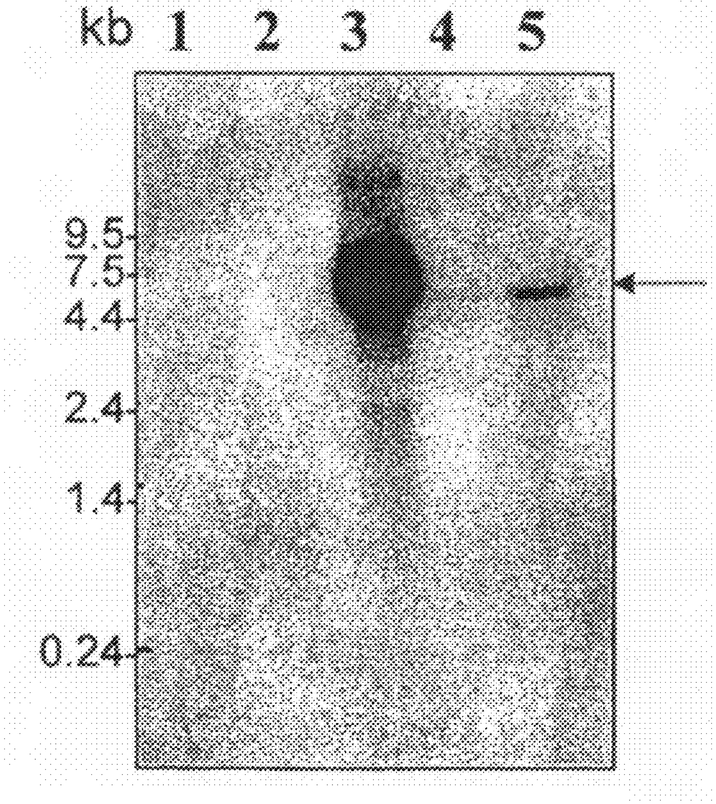
FIG. 18. Expression of 101P3A11 in 300.19 cells following retroviral-mediated gene delivery. 300.19 cells were transduced with the pSRα retroviral vector encoding the 101P3A11 gene. Following selection with neomycin, the cells were expanded and RNA was extracted. A Northern blot with 10 μg of total RNA/lane was probed with the 101P3A11 sequence. Size standards in kilobases (kb) are indicated on the side. Results showed expression of the 101P3A11 transcript driven from the retroviral LTR. LAPC-4AD and LAPC-9AD showed expression of the endogenous 101P3A11 transcript. The Figure shows results of a short exposure of the autoradiogram.

The amino acid region 159-202 of the 101P3A11 ORF was cloned into psecFc. The resulting recombinant 101P3A11 (159-202)-psecFc construct was transfected into 293T and Cos-7 cells, and the expression of recombinant 101P3A11 (159-202)-psecFc protein assayed by Western blotting (FIG. 17). Results show that 101P3A11(159-202)-psecFc fusion protein was expressed in the lysates of both 293T and Cos-7 cells. The 101P3A11(159-202)-psecFc fusion protein was also secreted and detected in the culture supernatants of both cell types.

pSRα Constructs: To generate mammalian cell lines that express 101P3A11, constitutively, the ORF of 101P3A11 was cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus was used to infect a variety of mammalian cell lines, resulting in the integration of the cloned gene, 101P3A11, into the host cell lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. FIG. 18 shows that 101P3A11 was expressed using the pSRα retroviral vector in the cell line 300.19. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 101P3A11 sequences to allow detection using anti-Flag antibodies. For example, the FLAG™ sequence 5' gat tac aag gat gac gac gat aag 3' (SEQ ID NO: 44) is added to cloning primer at the 3' end of the ORF. Additional pSRα constructs are made to produce both amino-terminal and carboxyl-terminal GFP and myc/6×His fusion proteins of the full-length 101P3A11 proteins.

Additional Viral Vectors: Additional constructs are made for viral-mediated delivery and expression of 101P3A11. High virus titer leading to high level expression of 101P3A11 is achieved in viral delivery systems such as adenoviral vectors and herpes amplicon vectors. The 101P3A11 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 101P3A11 coding sequences or fragments thereof are cloned into the HSV-1 vector (Imgenex) to generate herpes viral vectors. The viral vectors are thereafter used for infection of various cell lines such as SCaBER, NIH 3T3, 293 or rat-1 cells.

Regulated Expression Systems: To control expression of 101P3A11 in mammalian cells, coding sequences of 101P3A11, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 101P3A11. These vectors are thereafter used to control expression of 101P3A11 in various cell lines such as SCaBER, NIH 3T3, 293 or rat-1 cells.

B. Baculovirus Expression Systems

To generate recombinant 101P3A11 proteins in a baculovirus expression system, 101P3A11 ORF, or portions thereof, are cloned into the baculovirus transfer vector pBlueBac 4.5 (Invitrogen), which provides a His-tag at the N-terminus. Specifically, pBlueBac-101P3A11 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 101P3A11 protein is then generated by infection of HighFive insect cells (Invitrogen) with purified baculovirus. Recombinant 101P3A11 protein can be detected using anti-101P3A11 or anti-His-tag antibody. 101P3A11 protein can be purified and used in various cell-based assays or as immunogen to generate polyclonal and monoclonal antibodies specific for 101P3A11.

Example 5

Production of Recombinant 101P3A11 in Higher Eukaryotic Systems

A. Mammalian Constructs:

To express recombinant 101P3A11 in eukaryotic cells, full or partial length 101P3A11 cDNA sequences can be cloned into any one of a variety of expression vectors known in the art. One or more of the following regions of 101P3A11 are expressed in these constructs, amino acids 1 to 317 or 318; or any 5, 6, 7, 8, 9, 10, 11, 12, 13, 14, 15, 16, 17, 18, 19, 20, 21, 22, 23, 24, 25, 26, 27, 28, 29, 30 or more contiguous amino acids from 101P3A11, variants, or analogs thereof.

The constructs can be transfected into any one of a wide variety of mammalian cells such as 293T cells. Transfected 293T cell lysates can be probed with the anti-101P3A11 polyclonal serum, described herein.

pcDNA4/HisMax Constructs: To express 101P3A11 in mammalian cells, the 101P3A11 ORF was cloned into pcDNA4/HisMax Version A (Invitrogen, Carlsbad, Calif.). Protein expression is driven from the cytomegalovirus (CMV) promoter and the SP16 translational enhancer. The recombinant protein has Xpress™ and six histidine (6×His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli.* pcDNA3.1/MycHis Constructs: To express 101P3A11 in mammalian cells, the 101P3A11 ORF, with a consensus Kozak translation initiation site, was cloned into pcDNA3.1/MycHis Version A (Invitrogen, Carlsbad, Calif.). Protein expression is driven from the cytomegalovirus (CMV) promoter. The recombinant proteins have the myc epitope and 6×His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli.* pcDNA3.1/CT-GFP-TOPO Construct: To express 101P3A11 in mammalian cells and to allow detection of the recombinant proteins using fluorescence, the 101P3A11 ORF, with a consensus Kozak translation initiation site, was cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. Additional constructs with an amino-terminal GFP fusion are made in pcDNA3.1/NT-GFP-TOPO spanning the entire length of the 101P3A11 proteins.

PAPtag: The 101P3A11 ORF, or portions thereof, of 101P3A11 are cloned into pAPtag-5 (GenHunter Corp. Nashville, Tenn.). This construct generates an alkaline phosphatase fusion at the carboxyl-terminus of the 101P3A11 proteins while fusing the IgGκ signal sequence to the amino-terminus. Constructs are also generated in which alkaline phosphatase with an amino-terminal IgGκ signal sequence is fused to the amino-terminus of 101P3A11 proteins. The resulting recombinant 101P3A11 proteins are optimized for secretion into the media of transfected mammalian cells and can be used to identify proteins such as ligands or receptors that interact with the 101P3A11 proteins. Protein expression is driven from the CMV promoter and the recombinant proteins also contain myc and 6×His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli.* ptag5: The 101P3A11 ORF, or portions thereof, of 101P3A11 are cloned into pTag-5. This vector is similar to pAPtag but without the alkaline phosphatase fusion. This construct generated 101P3A11 protein with an amino-terminal IgGκ signal sequence and myc and 6×His epitope tags at the carboxyl-terminus that facilitate detection and affinity purification. The resulting recombinant 101P3A11 protein was optimized for secretion into the media of transfected mammalian cells, and was used as immunogen or ligand to identify proteins such as ligands or receptors that interact with the 101P3A11 proteins. Protein expression is driven from the CMV promoter. The Zeocin resistance gene present in the vector allows for selection of mammalian cells expressing the protein, and the ampicillin resistance gene permits selection of the plasmid in *E. coli.*

PsecFc: The 101P3A11 ORF, or portions thereof, of 101P3A11 are also cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the carboxyl-terminus of the 101P3A11 proteins, while fusing the IgGκ signal sequence to N-terminus. 101P3A11 fusions utilizing the murine IgG1 Fc region are also used. The resulting recombinant 101P3A11 proteins are optimized for secretion into the media of transfected mammalian cells, and can be used as immunogens or to identify proteins such as ligands or receptors that interact with the 101P3A11 protein. Protein expression is driven from the CMV promoter. The hygromycin resistance gene present in the vector allows for selection of mammalian cells that express the recombinant protein, and the ampicillin resistance gene permits selection of the plasmid in *E. coli.*

The amino acid region 159-202 of the 101P3A11 ORF was cloned into psecFc. The resulting recombinant 101P3A11 (159-202)-psecFc construct was transfected into 293T and Cos-7 cells, and the expression of recombinant 101P3A11 (159-202)-psecFc protein assayed by Western blotting (FIG. 17). Results show that 101P3A11(159-202)-psecFc fusion protein was expressed in the lysates of both 293T and Cos-7 cells. The 101P3A11(159-202)-psecFc fusion protein was also secreted and detected in the culture supernatants of both cell types.

pSRα Constructs: To generate mammalian cell lines that express 101P3A11, constitutively, the ORF of 101P3A11 was cloned into pSRα constructs. Amphotropic and ecotropic retroviruses were generated by transfection of pSRα constructs into the 293T-10A1 packaging line or co-transfection of pSRα and a helper plasmid (containing deleted packaging sequences) into the 293 cells, respectively. The retrovirus was used to infect a variety of mammalian cell lines, resulting in the integration of the cloned gene, 101P3A11, into the host cell lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. FIG. 18 shows that 101P3A11 was expressed using the pSRα retroviral vector in the cell line 300.19. The retroviral vectors can thereafter be used for infection and generation of various cell lines using, for example, PC3, NIH 3T3, TsuPr1, 293 or rat-1 cells.

Additional pSRα constructs are made that fuse an epitope tag such as the FLAG™ tag to the carboxyl-terminus of 101P3A11 sequences to allow detection using anti-Flag antibodies. For example, the FLAG™ sequence 5' gat tac aag gat gac gac gat aag 3' (SEQ ID NO: 45) is added to cloning primer at the 3' end of the ORF. Additional pSRα constructs are made to produce both amino-terminal and carboxyl-terminal GFP and myc/6×His fusion proteins of the full-length 101P3A11 proteins.

Additional Viral Vectors: Additional constructs are made for viral-mediated delivery and expression of 101P3A11. High virus titer leading to high level expression of 101P3A11 is achieved in viral delivery systems such as adenoviral vectors and herpes amplicon vectors. The 101P3A11 coding sequences or fragments thereof are amplified by PCR and subcloned into the AdEasy shuttle vector (Stratagene). Recombination and virus packaging are performed according to the manufacturer's instructions to generate adenoviral vectors. Alternatively, 101P3A11 coding sequences or fragments thereof are cloned into the HSV-1 vector (Imgenex) to generate herpes viral vectors. The viral vectors are thereafter used for infection of various cell lines such as SCaBER, NIH 3T3, 293 or rat-1 cells.

Regulated Expression Systems: To control expression of 101P3A11 in mammalian cells, coding sequences of 101P3A11, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 101P3A11. These vectors are thereafter used to control expression of 101P3A11 in various cell lines such as SCaBER, NIH 3T3, 293 or rat-1 cells.

B. Baculovirus Expression Systems

To generate recombinant 101P3A11 proteins in a baculovirus expression system, 101P3A11 ORF, or portions thereof, are cloned into the baculovirus transfer vector pBlueBac 4.5 (Invitrogen), which provides a His-tag at the N-terminus. Specifically, pBlueBac-101P3A11 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 101P3A11 protein is then generated by infection of HighFive insect cells (Invitrogen) with purified baculovirus. Recombinant 101P3A11 protein can be detected using anti-101P3A11 or anti-His-tag antibody. 101P3A11 protein can be purified and used in various cell-based assays or as immunogen to generate polyclonal and monoclonal antibodies specific for 101P3A11.

Example 6

Antigenicity Profiles and Secondary Structure

FIG. 5, FIG. 6, FIG. 7, FIG. 8, and FIG. 9 depict graphically five amino acid profiles of the 101P3A11 amino acid sequence, each assessment available by accessing the ProtScale website located on the World Wide Web at (expasy.ch/cgi-bin/protscale.pl) on the ExPasy molecular biology server.

These profiles: FIG. 5, Hydrophilicity, (Hopp T. P., Woods K. R., 1981. Proc. Natl. Acad. Sci. U.S.A. 78:3824-3828); FIG. 6, Hydropathicity, (Kyte J., Doolittle R. F., 1982. J. Mol. Biol. 157:105-132); FIG. 7, Percentage Accessible Residues (Janin J., 1979 Nature 277:491-492); FIG. 8, Average Flexibility, (Bhaskaran R., and Ponnuswamy P. K., 1988. Int. J. Pept. Protein Res. 32:242-255); FIG. 9, Beta-turn (Deleage, G., Roux B. 1987 Protein Engineering 1:289-294); and optionally others available in the art, such as on the ProtScale website, were used to identify antigenic regions of the 101P3A11 protein. Each of the above amino acid profiles of 101P3A11 were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus are available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed portions of the protein and thus are accessible to immune recognition, such as by antibodies.

Antigenic sequences of the 101P3A11 protein indicated, e.g., by the profiles set forth in FIG. 5, FIG. 6, FIG. 7, FIG. 8, and/or FIG. 9 are used to prepare immunogens, either peptides or nucleic acids that encode them, to generate anti-101P3A11 antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 101P3A11 protein. In particular, peptide immunogens of the invention can comprise, a peptide region of at least 5 amino acids of FIG. 2 in any whole number increment up to 317 or 318 that includes an amino acid position having a value greater than 0.5 in the Hydrophilicity profile of FIG. 5; a peptide region of at least 5 amino acids of FIG. 2 in any whole number increment up to 317 or 318 that includes an amino acid position having a value less than 0.5 in the Hydropathicity profile of FIG. 6; a peptide region of at least 5 amino acids of FIG. 2 in any whole number increment up to 317 or 318 that includes an amino acid position having a value greater than 0.5 in the Percent Accessible Residues profile of FIG. 7; a peptide region of at least 5 amino acids of FIG. 2 in any whole number increment up to 317 or 318 that includes an amino acid position having a value greater than 0.5 in the Average Flexibility profile on FIG. 8; and, a peptide region of at least 5 amino acids of FIG. 2 in any whole number increment up to 317 or 318 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 101P3A11, namely the predicted presence and location of alpha helices, extended strands, and random coils, is predicted from the primary amino acid sequence using the HNN—Hierarchical Neural Network method (Guermeur, 1997, accessed from the ExPasy molecular biology server. The analysis indicates that 101P3A11 is composed 47.95% alpha helix, 21.45% extended strand, and 30.60% random coil (FIG. 19A).

Figures 19B, 19C:
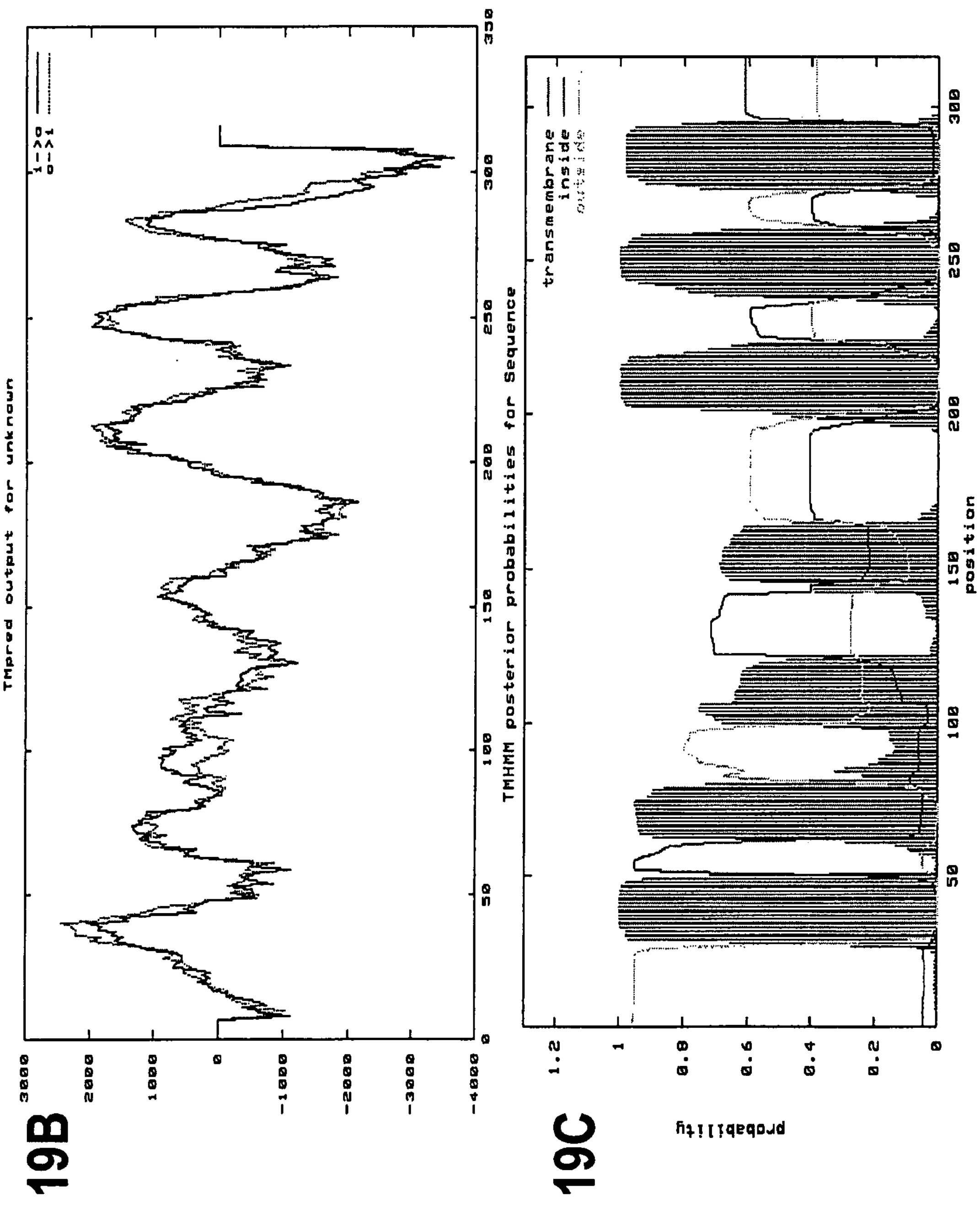
Figure 20:
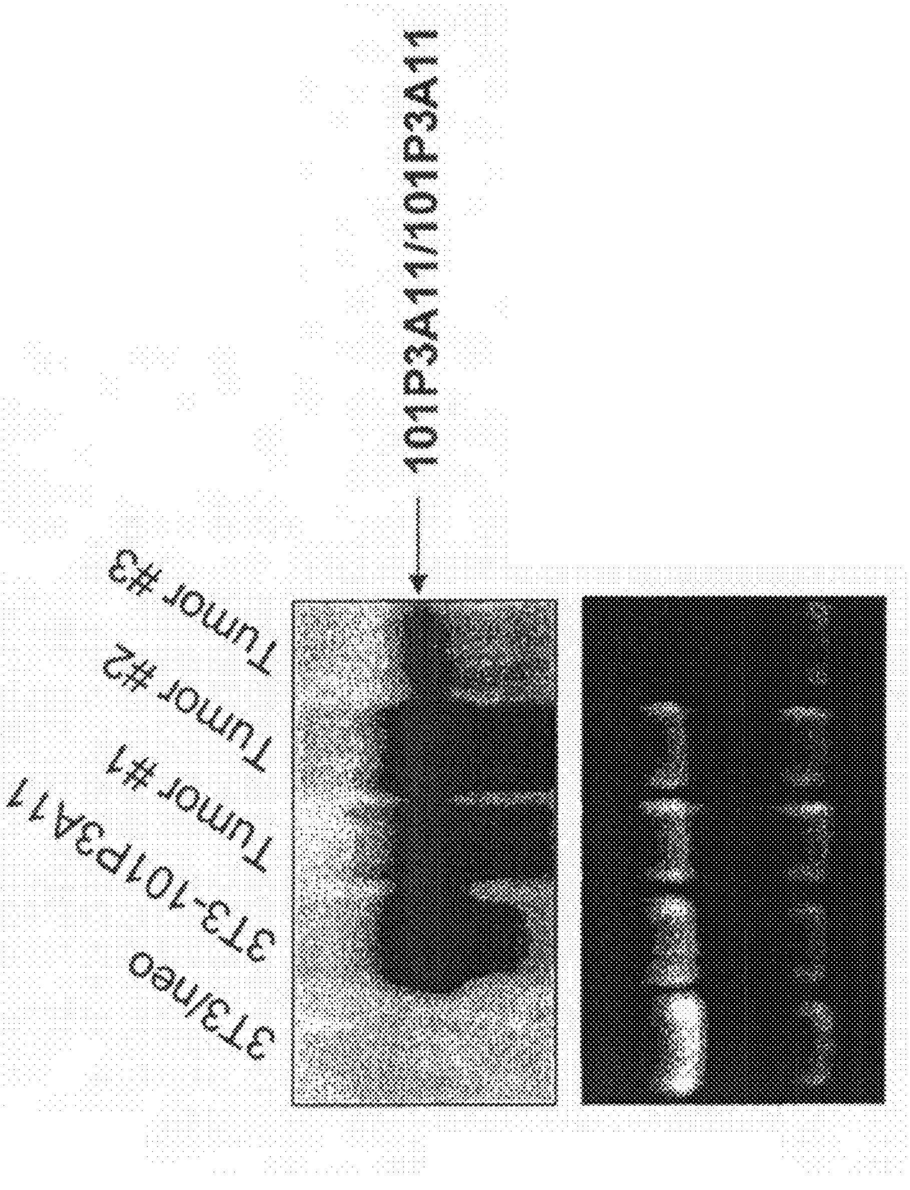
FIG. 20. Expression of 101P3A11 in NIH-3T3 Tumors. Mice were injected subcutaneously with control 3T3-neo or NIH3T3 cells expressing 101P3A11. Tumors were allowed to grow, the mice were then sacrificed and tumors harvested. RNA was isolated from LAPC-4AD and LAPC-4AI xenografts, 3T3-neo and 3T3-101P3A11 cells grown in culture were used as controls. RNA isolated from six different tumors derived from 3T3-101P3A11 cells (Tumor #1-3) were compared by Northern blotting. Northern blots with 10 μg of total RNA/lane were probed with 101P3A11 sequence. A picture of the ethidium-bromide staining of the RNA gel is also presented. Results showed expression of 101P3A11 in all 3T3-101P3A11 tumors as well as in 3T3/101P3A11 cells used to derive the tumors, but not in the negative control cells 3T3/neo cells.

Analysis for the potential presence of transmembrane domains in 101P3A11 was carried out using a variety of transmembrane prediction algorithms accessed from the ExPasy molecular biology server. The programs predict the presence of 7 transmembrane domains in 101P3A11, consistent with the structure of a G-protein coupled receptor. Shown graphically in FIG. 19A are the results of analysis using the TMpred (FIG. 19B) and TMHMM (FIG. 19C) prediction programs depicting the location of the 7 transmembrane domains. The results of each program, namely the amino acids encoding the transmembrane domains are summarized in Table XXI.

Example 7

Generation of 101P3A11 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 101P3A11 protein, computer algorithms are employed in design of immunogens that, based on amino acid sequence analysis are antigenic and available for recognition by the immune system of the immunized host (see the Example entitled "Antigenicity Profiles and Secondary Structure"). Such regions would generally be hydrophilic, flexible, in beta-turn conformations, and/or exposed on the surface of the protein (see, e.g., FIG. 5, FIG. 6, FIG. 7, FIG. 8, or FIG. 9 for amino acid profiles that indicate such regions of 101P3A11).

For example, 101P3A11 recombinant bacterial fusion proteins or peptides containing hydrophilic, flexible, beta-turn regions of the 101P3A11 amino acid sequence, such as amino acids 1-23, plus or minus 1-10 amino acids at available termini, and amino acids 159-202, plus or minus 1-10 amino acids at available termini, are used as antigens to generate polyclonal antibodies in New Zealand White rabbits. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 1-23 of 101P3A11 is conjugated to KLH and used to immunize the rabbit. Alternatively the immunizing agent may include all or portions of the 101P3A11 protein, analogs or fusion proteins thereof. For example, the 101P3A11 amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding amino acids 86-317, plus or minus 1-10 amino acids at available termini, is produced and purified and used as immunogen. Other recombinant bacterial fusion proteins that may be employed include maltose binding protein, LacZ, thioredoxin, NusA, or an immunoglobulin constant region (see the section entitled "Production of 101P3A11 in Prokaryotic Systems" and Current Protocols In Molecular Biology, Volume 2, Unit 16, Frederick M. Ausubul et al. eds., 1995; Linsley, P.S., Brady, W., Urnes, M., Grosmaire, L., Damle, N., and Ledbetter, L.(1991) J. Exp. Med. 174, 561-566).

In addition to bacterial derived fusion proteins, mammalian expressed protein antigens are also used. These antigens are expressed from mammalian expression vectors such as the Tag5 and Fc-fusion vectors (see the section entitled "Production of Recombinant 101P3A11 in Eukaryotic Systems"), and retain post-translational modifications such as glycosylations found in native protein. In one embodiment, amino acids 159-202 is cloned into the Tag5 mammalian secretion vector. The recombinant protein is purified by metal chelate chromatography from tissue culture supernatants of 293T cells stably expressing the recombinant vector. The purified Tag5 101P3A11 protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 μg, typically 100-200 μg, of fusion protein or peptide conjugated to KLH mixed in complete Freund's adjuvant (CFA). Rabbits are then injected subcutaneously every two weeks with up to 200 μg, typically 100-200 μg, of the immunogen in incomplete Freund's adjuvant (IFA). Test bleeds are taken approximately 7-10 days following each immunization and used to monitor the titer of the antiserum by ELISA.

To test reactivity and specificity of immune serum, such as the rabbit serum derived from immunization with Tag5 101P3A11 encoding amino acids 159-202, the full-length 101P3A11 cDNA is cloned into pcDNA 3.1 myc-his expression vector (Invitrogen, see the Example entitled "Production of Recombinant 101P3A11 in Eukaryotic Systems"). After transfection of the constructs into 293T cells, cell lysates are probed with the anti-101P3A11 serum and with anti-His antibody (Santa Cruz Biotechnologies, Santa Cruz, Calif.) to determine specific reactivity to denatured 101P3A11 protein using the Western blot technique. Immunoprecipitation and flow cytometric analyses of 293T and other recombinant 101P3A11-expressing cells determine recognition of native protein by the antiserum. In addition, Western blot, immunoprecipitation, fluorescent microscopy, and flow cytometric techniques using cells that endogenously express 101P3A11 are carried out to test specificity.

The anti-serum from the Tag5 101P3A11 immunized rabbit is affinity purified by passage over a column composed of the Tag5 antigen covalently coupled to Affigel matrix (Bio-Rad, Hercules, Calif.). The serum is then further purified by protein G affinity chromatography to isolate the IgG fraction. Serum from rabbits immunized with fusion proteins, such as GST and MBP fusion proteins, are purified by depletion of antibodies reactive to the fusion partner sequence by passage over an affinity column containing the fusion partner either alone or in the context of an irrelevant fusion protein. Sera from other His-tagged antigens and peptide immunized rabbits as well as fusion partner depleted sera are affinity purified by passage over a column matrix composed of the original protein immunogen or free peptide.

Example 8

Generation of 101P3A11 Monoclonal Antibodies (mAbs)

In one embodiment, therapeutic mAbs to 101P3A11 comprise those that react with epitopes of the protein that would disrupt or modulate the biological function of 101P3A11, for example those that would disrupt its interaction with ligands or proteins that mediate or are involved in its biological activity. Therapeutic mAbs also comprise those that specifically bind epitopes of 101P3A11 exposed on the cell surface and thus are useful in targeting mAb-toxin conjugates. Monoclonal antibodies may also be raised to other antigenic epitopes of 101P3A11 including amino acid sequences predicted to be in intracellular regions. These monoclonal antibodies are useful as intrabodies if they disrupt the signaling mechanisms of 101P3A11, such as the interaction with heterotrimeric G proteins. Such antibodies are also useful as diagnostic agents for techniques such as immunohistochemistry. Immunogens for generation of such mAbs include those designed to encode or contain the entire 101P3A11 protein or regions of the 101P3A11 protein predicted to be exposed to the extracellular environment or hydrophilic cytoplasmic environment, and/antigenic from computer analysis of the amino acid sequence (see, e.g., FIG. 5, FIG. 6, FIG. 7, FIG. 8, or FIG. 9, and the Example entitled "Antigenicity Profiles and Secondary Structure"). Immunogens include peptides, recombinant bacterial proteins, and mammalian expressed Tag 5 proteins and human and murine IgG FC fusion proteins. In addition, cells expressing high levels of 101P3A11, such as 293T-101P3A11 or 300.19-101P3A11 murine Pre-B cells, are used to immunize mice.

To generate mAbs to 101P3A11, mice are first immunized intraperitoneally (IP) with, typically, 10-50 μg of protein immunogen or $10^7$ 101P3A11-expressing cells mixed in complete Freund's adjuvant. Alternatively, mice are immunized intradermally. Mice are then subsequently immunized IP every 2-4 weeks with, typically, 10-50 μg of protein immunogen or $10^7$ cells mixed in incomplete Freund's adjuvant. Alternatively, MPL-TDM adjuvant is used in immunizations. In addition to the above protein and cell-based immunization strategies, a DNA-based immunization protocol is employed in which a mammalian expression vector encoding 101P3A11 sequence is used to immunize mice by direct injection of the plasmid DNA. For example, the predicted first extracellular loop, amino acids 82-104, or second extracellular loop of 101P3A11, amino acids 159-202, or the third extracellular loop, amino acids 258-275 (in each instance plus or minus 10 amino acids) is cloned into the Tag5 mammalian secretion vector and the recombinant vector is used as immunogen. In another example the same amino acids are cloned into an Fc-fusion secretion vector in which the 101P3A11 sequence is fused at the amino-terminus to an IgK leader sequence and at the carboxyl-terminus to the coding sequence of the human IgG Fc region. This recombinant vector is then used as immunogen. Amino acid sequences from intracellular regions may also be used as antigens using similar strategies. These regions include amino acids 50-63, amino acids 121-146, amino acids 261-275, and amino acids 295-318 (in each instance plus or minus 10 amino acids, except for the C-terminus residue). The plasmid immunization protocols are used in combination with purified proteins expressed from the same vector and with cells expressing 101P3A11.

During the immunization protocol, test bleeds are taken 7-10 days following an injection to monitor titer and specificity of the immune response. Once appropriate reactivity and specificity is obtained as determined by ELISA, Western blotting, immunoprecipitation, fluorescence microscopy, and flow cytometric analyses, fusion and hybridoma generation is then carried out with established procedures well known in the art (see, e.g., Harlow and Lane, 1988).

In one embodiment for generating 101P3A11 monoclonal antibodies, a Tag5-101P3A11 antigen encoding amino acids 159-202 is expressed and purified from stably transfected 293T cells. Balb C mice are initially immunized intraperitoneally with 25 μg of the Tag5-101P3A11 protein mixed in complete Freund's adjuvant. Mice are subsequently immunized every two weeks with 25 μg of the antigen mixed in incomplete Freund's adjuvant for a total of three immunizations. ELISA using the Tag5 antigen determines the titer of serum from immunized mice. Reactivity and specificity of serum to full length 101P3A11 protein is monitored by Western blotting, immunoprecipitation and flow cytometry using 293T cells transfected with an expression vector encoding the 101P3A11 cDNA (see e.g., the Example entitled "Production of Recombinant 101P3A11 in Eukaryotic Systems"). Other recombinant 101P3A11-expressing cells or cells endogenously expressing 101P3A11 are also used. Mice showing the strongest reactivity are rested and given a final injection of Tag5 antigen in PBS and then sacrificed four days later. The spleens of the sacrificed mice are harvested and fused to SPO/2 myeloma cells using standard procedures (Harlow and Lane, 1988). Supernatants from HAT selected growth wells are screened by ELISA, Western blot, immunoprecipitation, fluorescent microscopy, and flow cytometry to identify 101P3A11 specific antibody-producing clones.

The binding affinity of a 101P3A11 monoclonal antibody is determined using standard technologies. Affinity measurements quantify the strength of antibody to epitope binding and are used to help define which 101P3A11 monoclonal antibodies preferred, e.g., for diagnostic or therapeutic use, as appreciated by one of skill in the art. The BIAcore system (Uppsala, Sweden) is a preferred method for determining binding affinity. The BIAcore system uses surface plasmon resonance (SPR, Welford K. 1991, Opt. Quant. Elect. 23: 1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 9

HLA Class I and Class II Binding Assays

HLA class I and class II binding assays using purified HLA molecules are performed in accordance with disclosed protocols (e.g., PCT publications WO 94/20127 and WO 94/03205; Sidney et al., *Current Protocols in Immunology* 18.3.1 (1998); Sidney, et al., *J. Immunol.* 154:247 (1995); Sette, et al., *Mol. Immunol.* 31:813 (1994)). Briefly, purified MHC molecules (5 to 500 nM) are incubated with various unlabeled peptide inhibitors and 1-10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10-20% of the total radioactivity. All subsequent inhibition and direct binding assays are performed using these HLA concentrations.

Since under these conditions [label]<[HLA] and $IC_{50} \geqq$ [HLA], the measured $IC_{50}$ values are reasonable approximations of the true $K_D$ values. Peptide inhibitors are typically tested at concentrations ranging from 120 μg/ml to 1.2 ng/ml, and are tested in two to four completely independent experiments. To allow comparison of the data obtained in different experiments, a relative binding Figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 10

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables V-XVIII and XXII TO IL employ the protein sequence data from the gene product of 101P3A11 set forth in FIGS. 2 and 3; the specific peptides used to generate the tables are listed in Table LII.

Computer searches for epitopes bearing HLA Class I or Class II supermotifs or motifs are performed as follows. All translated 101P3A11 protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or ΔG) of peptide-HLA molecule interactions can be approximated as a linear polynomial function of the type:

$$``\Delta G" = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol.* 267:1258-126, 1997; (see also Sidney et al., *Human Immunol.* 45:79-93, 1996; and Southwood et al., *J. Immunol.* 160:3363-3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-Reactive Peptides

Protein sequences from 101P3A11 are scanned utilizing motif identification software, to identify 8-, 9- 10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-Bearing Epitopes

The 101P3A11 protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of ≦500 nM, often ≦200 nM, are then tested for binding cross-reactivity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 101P3A11 protein(s) scanned above is also analyzed for the presence of 8-, 9-10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of ≦500 nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 101P3A11 protein can also be performed to identify HLA-A1- and A24-motif-containing sequences.

High affinity and/or cross-reactive binding epitopes that bear other motif and/or supermotifs are identified using analogous methodology.

Example 11

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 0.221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 μg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10\times10^6$ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dynal immunomagnetic beads (Dynabeads® M-450) and the Detacha-Bead® reagent. Typically about $200\text{-}250\times10^6$ PBMC are processed to obtain $24\times10^6$ CD8+ T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of $20\times10^6$ cells/ml. The magnetic beads are washed 3 times with PBS/AB serum, added to the cells (140 μl beads/$20\times10^6$ cells) and incubated for 1 hour at 4° C. with continuous mixing. The beads and cells are washed 4× with PBS/AB serum to remove the nonadherent cells and resuspended at $100\times10^6$ cells/ml (based on the original cell number) in PBS/AB serum containing 100 μl/ml Detacha-Bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5-7 minutes, washed once with PBS with 1% BSA, counted and pulsed with 40 μg/ml of peptide at a cell concentration of $1\text{-}2\times10^6$/ml in the presence of 3 μg/ml $\beta_2$-microglobulin for 4 hours at 20° C. The DC are then irradiated (4,200 rads), washed 1 time with medium and counted again.

Setting up induction cultures: 0.25 ml cytokine-generated DC (at $1\times10^5$ cells/ml) are co-cultured with 0.25 ml of CD8+ T-cells (at $2\times10^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at $5\times10^6$ cells/ml and irradiated at ~4200 rads. The PBMCs are plated at $2\times10^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml $\beta_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2-3 days later at 50 IU/ml (Tsai et al., *Critical Reviews in Immunology* 18(1-2):65-75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont, Wilmington, Del.) for 1 hour at 37° C. Labeled target cells are resuspended at $10^6$ per ml and diluted 1:10 with K562 cells at a concentration of $3.3\times10^6$/ml (an NK-sensitive erythroblastoma cell line used to reduce non-specific lysis). Target cells (100 μl) and effectors (100 μl) are plated in 96 well round-bottom plates and incubated for 5 hours at 37° C. At that time, 100 μl of supernatant are collected from each well and percent lysis is determined according to the formula:

[(cpm of the test sample−cpm of the spontaneous $^{51}$Cr release sample)/(cpm of the maximal $^{51}$Cr release sample−cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 μg/ml 0.1M $NaHCO_3$, pH8.2) overnight at 4° C. The plates are washed with $Ca^{2+}$, $Mg^{2+}$-free PBS/0.05% Tween 20 and blocked with PBS/10% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of $1\times10^6$ cells/ml. The plates are incubated for 48 hours at 37° C. with 5% $CO_2$.

Recombinant human IFN-gamma is added to the standard wells starting at 400 pg or 1200 pg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5-15 minutes. The reaction is stopped with 50 microliter/well 1M $H_3PO_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, $5\times10^4$ CD8+ cells are added to a T25 flask containing the following: $1\times10^6$ irradiated (4,200 rad) PBMC (autologous or allogeneic) per ml, $2\times10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercapto-ethanol, L-glutamine and penicillin/streptomycin. Recombinant human IL2 is added 24 hours later at a final concentration of 2001 U/ml and every three days thereafter with fresh media at 50 IU/ml. The cells are split if the cell concentration exceeds $1\times10^6$/ml and the cultures are assayed between days 13 and 15 at E:T ratios of 30, 10, 3 and 1:1 in the $^{51}$Cr release assay or at $1\times10^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and $5\times10^4$ CD8$^+$ cells are added to a T25 flask containing the following: $1\times10^6$ autologous PBMC per ml which have been peptide-pulsed with 10 μg/ml peptide for two hours at 37° C. and irradiated (4,200 rad); $2\times10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 101P3A11. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 12

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-Supermotif-Bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (*J. Immunol.* 157:3480-3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 101P3A11-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of single amino acid substitutions, the binding properties and/or cross-reactivity of peptide ligands for HLA supertype molecules can be modulated.

Example 13

Identification and Confirmation of 101P3A11-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 101P3A11-derived, HLA class II HTL epitopes, a 101P3A11 antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160:3363-3373, 1998). These protocols, specific for individual DR molecules, allow the scoring, and ranking, of 9-mer core regions. Each protocol not only scores peptide sequences for the presence of DR-supermotif primary anchors (i.e., at position I and position 6) within a 9-mer core, but additionally evaluates sequences for the presence of secondary anchors. Using allele-specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 101P3A11-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 β1, DR2w2 β2, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 101P3A11-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 101P3A11 antigens are analyzed for sequences carrying one of the two DR3-specific binding motifs reported by Geluk et al. (*J. Immunol.* 152:5742-5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 14

Immunogenicity of 101P3A11-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 101P3A11-expressing tumors.

Example 15

Calculation of Phenotypic Frequencies of HLA-Supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1−(SQRT(1−af)) (see, e.g., Sidney et al., *Human Immunol.* 45:79-93, 1996). To obtain overall phenotypic frequencies, cumulative gene frequencies are calculated, and the cumulative antigen frequencies derived by the use of the inverse formula [af=1−$(1-Cgf)^2$].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1−A)). Confirmed members of the A3-like supertype are A3, A1, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501-03, B51, B*5301, B*5401, B*5501-2, B*5601, B*6701, and B*7801 (potentially also B*1401, B*3504-06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analogous approach can be used to estimate population coverage achieved with combinations of class II motif-bearing epitopes.

Immunogenicity studies in humans (e.g., Bertoni et al., *J. Clin. Invest* 100:503, 1997; Doolan et al., *Immunity* 7:97, 1997; and Threlkeld et al., *J. Immunol.* 159: 1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 16

CTL Recognition of Endogenously Processed Antigens after Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with 101P3A11 expression vectors.

The results demonstrate that CTL lines obtained from animals primed with peptide epitope recognize endogenously synthesized 101P3A11 antigen. The choice of transgenic mouse model to be used for such an analysis depends upon the epitope(s) that are being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 17

Activity of CTL-HTL Conjugated Epitopes in Transgenic Mice

This example illustrates the induction of CTLs and HTLs in transgenic mice, by use of a 101P3A11-derived CTL and HTL peptide vaccine compositions. The vaccine composition used herein comprise peptides to be administered to a patient with a 101P3A11-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753-4761, 1997). For example, A2/K$^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., *J. Exp. Med.* 173:1007, 1991)

In vitro CTL activation: One week after priming, spleen cells ($30\times10^6$ cells/flask) are co-cultured at 37° C. with syngeneic, irradiated (3000 rads), peptide coated lymphoblasts ($10\times10^6$ cells/flask) in 10 ml of culture medium/T25 flask. After six days, effector cells are harvested and assayed for cytotoxic activity.

Assay for cytotoxic activity: Target cells (1.0 to $1.5\times10^6$) are incubated at 37° C. in the presence of 200 μl of $^{51}$Cr. After 60 minutes, cells are washed three times and resuspended in R10 medium. Peptide is added where required at a concentration of 1 μg/ml. For the assay, $10^4$ $^{51}$Cr-labeled target cells are added to different concentrations of effector cells (final volume of 200 μl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the effector (E):target (T) ratio of 50:1 (i.e., $5\times10^5$ effector cells for 10,000 targets) in the absence of peptide and 5:1 (i.e., $5\times10^4$ effector cells for 10,000 targets) in the presence of peptide, the specific lytic units would be: $[(1/50{,}000)-(1/500{,}000)]\times10^6=18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 18

Selection of CTL and HTL Epitopes for Inclusion in a 101P3A11-Specific Vaccine This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 101P3A11 clearance. The number of epitopes used depends on observations of patients who spontaneously clear 101P3A11. For example, if it has been observed that patients who spontaneously clear 101P3A11-expressing cells generate an immune response to at least three (3) epitopes from 101P3A11 antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site, at URL bimas.dcrt.nih.gov/.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 101P3A11 thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 101P3A11.

Example 19

Construction of "Minigene" Multi-Epitope DNA Plasmids

This example discusses the construction of a minigene expression plasmid. Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 101P3A11, are selected such that multiple supermotifs/motifs are represented to ensure broad population coverage. Similarly, HLA class II epitopes are selected from 101P3A11 to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 μg of each of two oligonucleotides are annealed and extended: In an example using eight oligonucleotides, i.e., four pairs of primers, oligonucleotides 1+2, 3+4, 5+6, and 7+8 are combined in 100 μl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 μg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 20

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683-692, 1996; Demotz et al., *Nature* 342:682-684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567-576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751-761, 1994.

For example, to confirm the capacity of a DNA minigene construct containing at least one HLA-A2 supermotif peptide to induce CTLs in vivo, HLA-A2.1/$K^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}Cr$ release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-$A^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3H$-thymidine incorporation proliferation assay, (see, e.g., Alexander et al. Immunity 1:751-761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., Barnett et al., *Aids Res. and Human Retroviruses* 14, Supplement 3:S299-S309, 1998) or recombinant vaccinia, for example, expressing a minigene or DNA encoding the complete protein of interest (see, e.g., Hanke et al., *Vaccine* 16:439-445, 1998; Sedegah et al., *Proc. Natl. Acad. Sci. USA* 95:7648-53, 1998; Hanke and McMichael, *Immunol. Letters* 66: 177-181, 1999; and Robinson et al., *Nature Med.* 5:526-34, 1999).

For example, the efficacy of the DNA minigene used in a prime boost protocol is initially evaluated in transgenic mice. In this example, A2.1/$K^b$ transgenic mice are immunized IM with 100 μg of a DNA minigene encoding the immunogenic peptides including at least one HLA-A2 supermotif-bearing peptide. After an incubation period (ranging from 3-9 weeks), the mice are boosted IP with $10^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 21

Peptide Compositions for Prophylactic Uses

Vaccine compositions of the present invention can be used to prevent 101P3A11 expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 101P3A11-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100-5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 101P3A11-associated disease.

Alternatively, a composition typically comprising transfecting agents is used for the administration of a nucleic acid-based vaccine in accordance with methodologies known in the art and disclosed herein.

Example 22

Polyepitopic Vaccine Compositions Derived from Native 101P3A11 Sequences

A native 101P3A11 polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 101P3A11 antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 101P3A11, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 23

Polyepitopic Vaccine Compositions from Multiple Antigens

The 101P3A11 peptide epitopes of the present invention are used in conjunction with epitopes from other target tumor-associated antigens, to create a vaccine composition that is useful for the prevention or treatment of cancer that expresses 101P3A11 and such other antigens. For example, a vaccine composition can be provided as a single polypeptide that incorporates multiple epitopes from 101P3A11 as well as tumor-associated antigens that are often expressed with a target cancer associated with 101P3A11 expression, or can be administered as a composition comprising a cocktail of one or more discrete epitopes. Alternatively, the vaccine can be administered as a minigene construct or as dendritic cells which have been loaded with the peptide epitopes in vitro.

Example 24

Use of Peptides to Evaluate an Immune Response

Peptides of the invention may be used to analyze an immune response for the presence of specific antibodies, CTL or HTL directed to 101P3A11. Such an analysis can be performed in a manner described by Ogg et al., *Science* 279: 2103-2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 101P3A11 HLA-A*0201-specific CTL frequencies from HLA A*0201-positive individuals at different stages of disease or following immunization comprising a 101P3A11 peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 μl of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 101P3A11 epitope, and thus the status of exposure to 101P3A11, or exposure to a vaccine that elicits a protective or therapeutic response.

Example 25

Use of Peptide Epitopes to Evaluate Recall Responses

The peptide epitopes of the invention are used as reagents to evaluate T cell responses, such as acute or recall responses, in patients. Such an analysis may be performed on patients who have recovered from 101P3A11-associated disease or who have been vaccinated with a 101P3A11 vaccine.

For example, the class I restricted CTL response of persons who have been vaccinated may be analyzed. The vaccine may be any 101P3A11 vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 μg/ml), and Hepes (10 mM) containing 10% heat-inactivated human AB serum (complete RPMI) and plated using microculture formats. A synthetic peptide comprising an epitope of the invention is added at 10 μg/ml to each well and HBV core 128-140 epitope is added at 1 μg/ml to each well as a source of T cell help during the first week of stimulation.

In the microculture format, $4\times10^5$ PBMC are stimulated with peptide in 8 replicate cultures in 96-well round bottom plate in 100 μl/well of complete RPMI. On days 3 and 10, 100 μl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}Cr$ release, based on comparison with non-diseased control subjects as previously described (Rehermann, et al., *Nature Med.* 2:1104, 1108, 1996; Rehermann et al., *J. Clin. Invest.* 97:1655-1665, 1996; and Rehermann et al. *J. Clin. Invest.* 98:1432-1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670-2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 μM, and labeled with 100 μCi of $^{51}Cr$ (Amersham Corp., Arlington Heights, Ill.) for 1 hour after which they are washed four times with HBSS.

Cytolytic activity is determined in a standard 4-h, split well $^{51}Cr$ release assay using U-bottomed 96 well plates containing 3,000 targets/well. Stimulated PBMC are tested at effector/target (E/T) ratios of 20-50:1 on day 14. Percent cytotoxicity is determined from the formula: 100×[(experimental release−spontaneous release)/maximum release−spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 101P3A11 or a 101P3A11 vaccine.

Similarly, Class II restricted HTL responses may also be analyzed. Purified PBMC are cultured in a 96-well flat bottom plate at a density of $1.5\times10^5$ cells/well and are stimulated with 10 μg/ml synthetic peptide of the invention, whole 101P3A11 antigen, or PHA. Cells are routinely plated in replicates of 4-6 wells for each condition. After seven days of culture, the medium is removed and replaced with fresh medium containing 10 U/ml IL-2. Two days later, 1 μCi $^3H$-thymidine is added to each well and incubation is continued for an additional 18 hours. Cellular DNA is then harvested on glass fiber mats and analyzed for $^3H$-thymidine incorporation. Antigen-specific T cell proliferation is calculated as the ratio of $^3H$-thymidine incorporation in the presence of antigen divided by the $^3H$-thymidine incorporation in the absence of antigen.

Example 26

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 μg of peptide composition;

Group II: 3 subjects are injected with placebo and 6 subjects are injected with 50 μg peptide composition;

Group III: 3 subjects are injected with placebo and 6 subjects are injected with 500 μg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 27

Phase II Trials in Patients Expressing 101P3A11

Phase II trials are performed to study the effect of administering the CTL-HTL peptide compositions to patients having cancer that expresses 101P3A11. The main objectives of the trial are to determine an effective dose and regimen for inducing CTLs in cancer patients that express 101P3A11, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21-65 and represent diverse ethnic backgrounds. All of them have a tumor that expresses 101P3A11.

Clinical manifestations or antigen-specific T-cell responses are monitored to assess the effects of administering the peptide compositions. The vaccine composition is found to be both safe and efficacious in the treatment of 101P3A11-associated disease.

Example 28

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5-5 mg at multiple sites. The nucleic acid (0.1 to 1000 μg) can also be administered using a gene gun. Following an incubation period of 3-4 weeks, a booster dose is then administered. The booster can be recombinant fowlpox virus administered at a dose of $5\text{-}10^7$ to $5\times10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 101P3A11 is generated.

Example 29

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 101P3A11 protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although 2-50×$10^6$ DC per patient are typically administered, larger number of DC, such as $10^7$ or $10^8$ can also be provided. Such cell populations typically contain between 50-90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive 5×$10^6$ DC, then the patient will be injected with a total of 2.5×$10^8$ peptide-loaded PBMC. The percent DC mobilized by an agent such as Progenipoietin™ is typically estimated to be between 2-10%, but can vary as appreciated by one of skill in the art.

Ex Vivo Activation of CTL/HTL Responses

Alternatively, ex vivo CTL or HTL responses to 101P3A11 antigens can be induced by incubating, in tissue culture, the patient's, or genetically compatible, CTL or HTL precursor cells together with a source of APC, such as DC, and immunogenic peptides. After an appropriate incubation time (typically about 7-28 days), in which the precursor cells are activated and expanded into effector cells, the cells are infused into the patient, where they will destroy (CTL) or facilitate destruction (HTL) of their specific target cells, i.e., tumor cells.

Example 30

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 101P3A11. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 101P3A11 to isolate peptides corresponding to 101P3A11 that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 31

Complementary Polynucleotides

Sequences complementary to the 101P3A11-encoding sequences, or any parts thereof, are used to detect, decrease, or inhibit expression of naturally occurring 101P3A11. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 101P3A11. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 101P3A11-encoding transcript.

Example 32

Purification of Naturally-Occurring or Recombinant 101P3A11 Using 101P3A11-Specific Antibodies Naturally occurring or recombinant 101P3A11 is substantially purified by immunoaffinity chromatography using antibodies specific for 101P3A11. An immunoaffinity column is constructed by covalently coupling anti-101P3A11 antibody to an activated chromatographic resin, such as CNBr-activated SEPHAROSE (Amersham Pharmacia Biotech). After the coupling, the resin is blocked and washed according to the manufacturer's instructions.

Media containing 101P3A11 are passed over the immunoaffinity column, and the column is washed under conditions that allow the preferential absorbance of 101P3A11 (e.g., high ionic strength buffers in the presence of detergent). The column is eluted under conditions that disrupt antibody/101P3A11 binding (e.g., a buffer of pH 2 to pH 3, or a high concentration of a chaotrope, such as urea or thiocyanate ion), and GCR.P is collected.

Example 33

Identification of Molecules which Interact with 101P3A11

101P3A11, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled 101P3A11, washed, and any wells with labeled 101P3A11 complex are assayed. Data obtained using different concentrations of 101P3A11 are used to calculate values for the number, affinity, and association of 101P3A11 with the candidate molecules.

Example 34

In Vivo Assay for 101P3A11 Tumor Growth Promotion

The effect of the 101P3A11 protein on tumor cell growth can be confirmed in vivo by gene overexpression in a variety of cancer cells, including prostate, kidney, colon and bladder. For example, SCID mice can be injected subcutaneously on one flank with $1\times10^6$ prostate, kidney, colon or bladder cancer cells (such as PC3, LNCaP, SCaBER, UM-UC-3, SK-CO, Caco, RT4, T24, Caki, A-498 and SW839 cells) containing tkNeo empty vector or 101P3A11.

At least two strategies can be used:

(1) Constitutive 101P3A11 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems.

Figure 21:
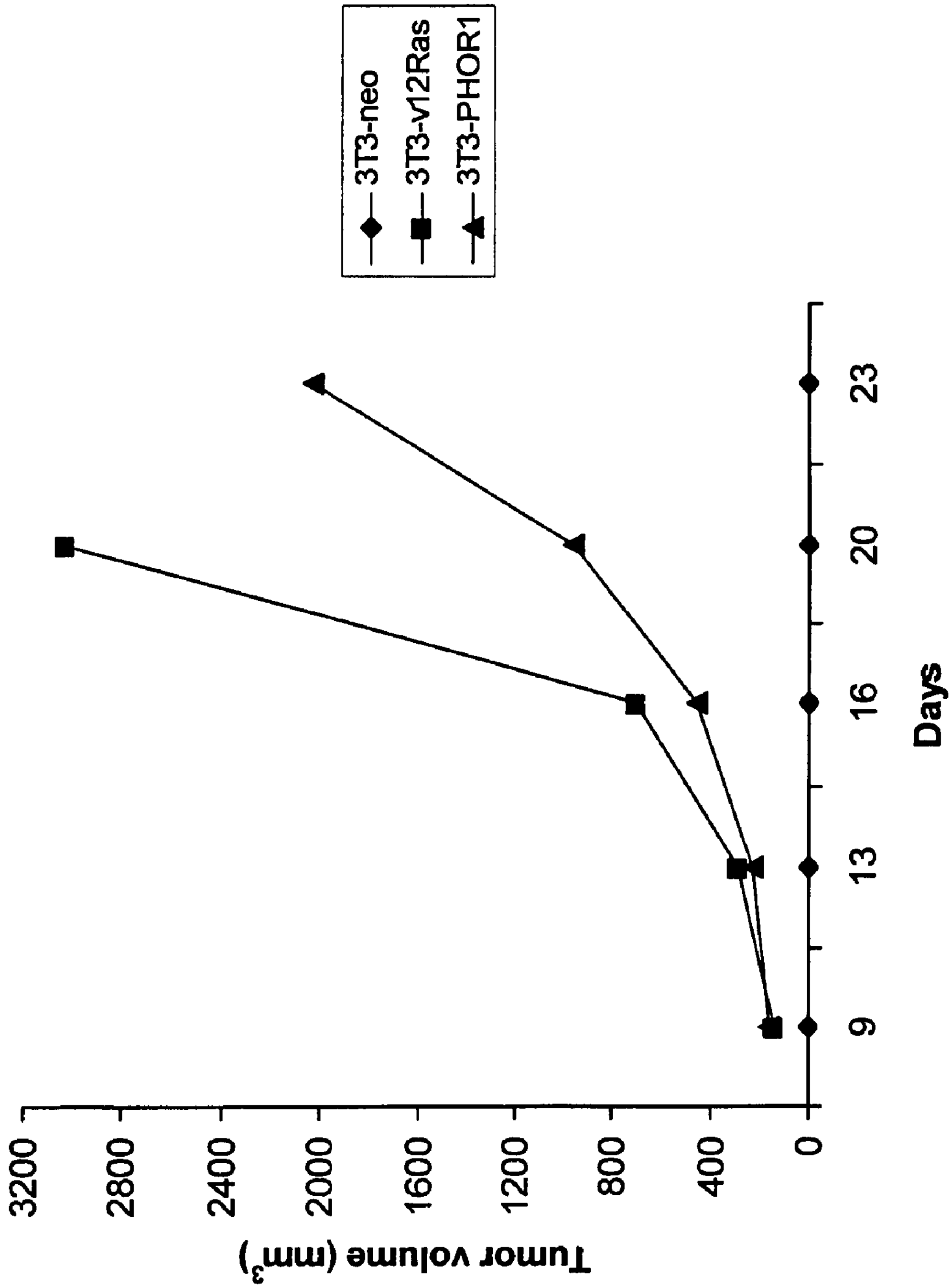
FIG. 21. 101P3A11 Induces Tumor Formation of 3T3 Cells. Injection of 106 3T3-neo, 3T3-Ras or 3T3-101P3A11 cells (106 of the indicated cells mixed with Matrigel) subcutaneously into 6 male SCID mice (right flank) revealed that 6/6 3T3-v12Ras-injected mice formed tumors, 6/6 3T3-101P3A11-injected mice formed tumors, and 0/6 3T3-neo-injected mice formed tumors. Each data point represents the mean tumor volume (n=6) in each group.
Figure 42:
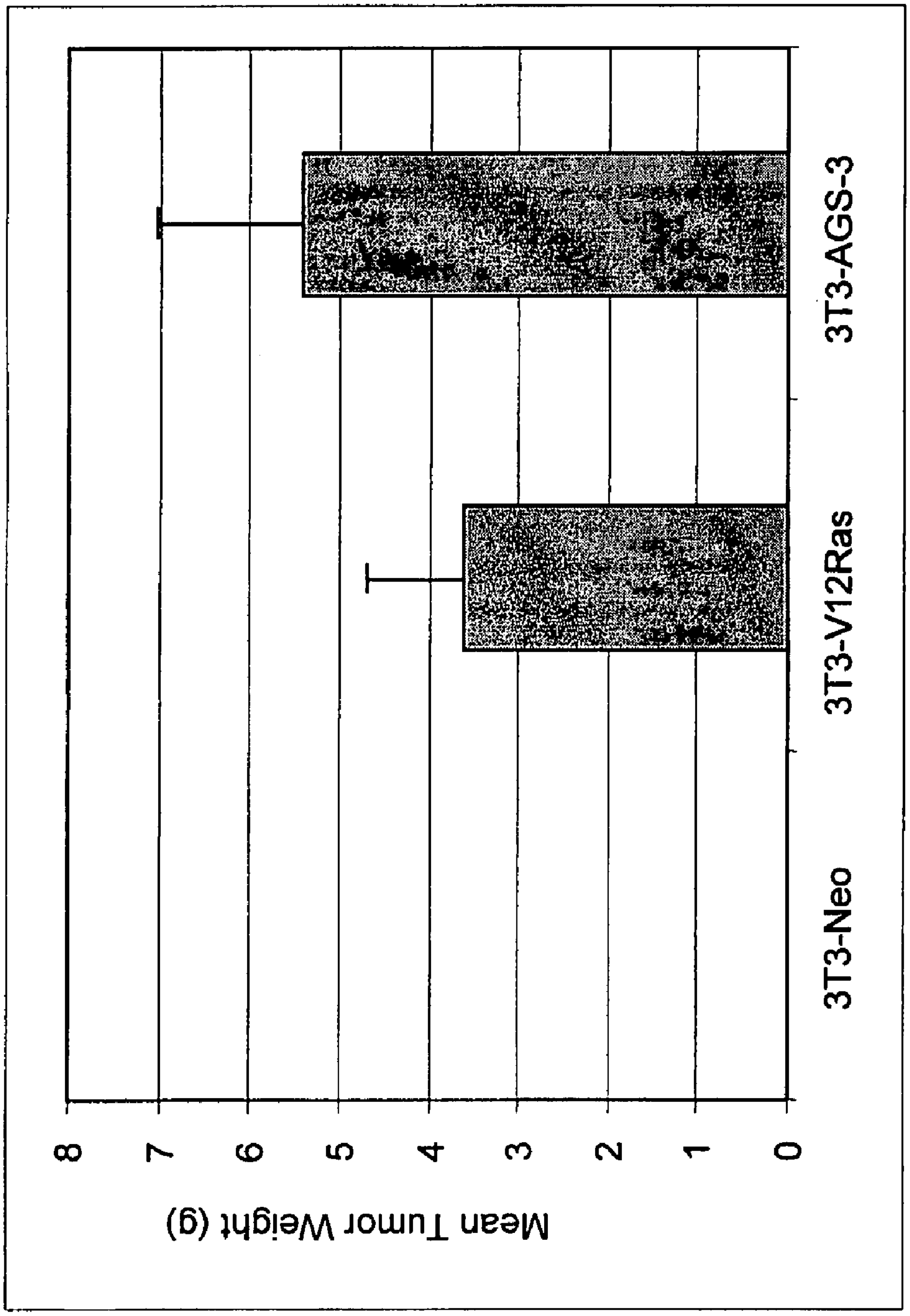
FIG. 42 shows that 101P3A11 induces orthotopic growth of tumors. $5\times10^5$ cells were injected orthotopically into SCID mice, 7 mice per group; tumor weight was evaluated 24-25 days post cell injection.

(2) Regulated expression under control of an inducible vector system, such as ecdysone, tet, etc., can be used provided such promoters are compatible with the host cell systems. Tumor volume is then monitored at the appearance of palpable tumors and is followed over time to validate that 101P3A11-expressing cells grow at a faster rate and that tumors produced by 101P3A11-expressing cells demonstrate characteristics of altered aggressiveness (e.g., enhanced metastasis, vascularization, reduced responsiveness to chemotherapeutic drugs). FIG. 21 compares subcutaneous growth of control 3T3-neo and 3T3-101P3A11 cells. One million cells stably expressing neo or 101P3A11 were injected subcutaneously in SCID mice along with matrigel. Tumor volume was evaluated by caliper measurements. This experiment demonstrates that expression of 101P3A11 in NIH 3T3 cells is induces tumor formation in 6/6 mice. In an experiment comparing the effect of a strong oncogene such as Ras to that of 101P3A11, we showed that 101P3A11 induced tumor growth of 3T3 cells in a more rapid and aggressive manner that $^{12}$V-Ras (FIG. M8). The results indicated that expression of 101P3A11 is sufficient to induce tumor formation in vivo. FIG. 42 shows demonstrates that 101P3A11 induces orthotopic growth of tumors. Additionally, SCID mice were implanted with the same 3T3-101P3A11 cells orthotopically in the prostate to determine if 101P3A11 has an effect on local growth in the prostate or on the ability of the cells to metastasize, specifically to lungs or lymph nodes. This experiment (Figure M10) shows that while control 3T3-neo cells fail to induce tumor formation in the prostate of SCID mice, significant tumor growth was seen in cells expressing 101P3A11. In an analogous manner, cells can be implanted orthotopically in the bladder, colon or kidney. (Saffran, D., et al., PNAS 10:1073-1078; Fu, X., et al., Int. J. Cancer, 1991. 49: p. 938-939; Chang, S., et al., Anticancer Res., 1997. 17: p. 3239-3242; Peralta, E. A., et al., J. Urol., 1999. 162: p. 1806-1811). The tumor enhancing effect of 101P3A11 was also observed when 101P3A11 is expressed in prostate cancer cells such as PC3 and introduced into the prostate of SCID mice (Figure M11). A 2.5 fold increase in tumor weight is observed in tumors expressing 101P3A11 relative to control cells.

Expression od 101P3A11 also enhances tumor growth and progression in the tibia os SCID mice. Clinical studies have repeatedly shown that prostate cancer may become metastatic to the bone. In order to investigate the contribution of 101P3A11 to bone tropism and tumor growth in the bone, control and 101P3A11-expressing cells were compared for their ability to induce tumor growth in the tibia of SCID mice. Experiments in Figures M14 and M15 show that injection of 101P3A11 expressing 3T3 or PC3 cells into the bone of SCID mice results in increase tumor growth and tumor formation relative to control cells.

Figure 22:
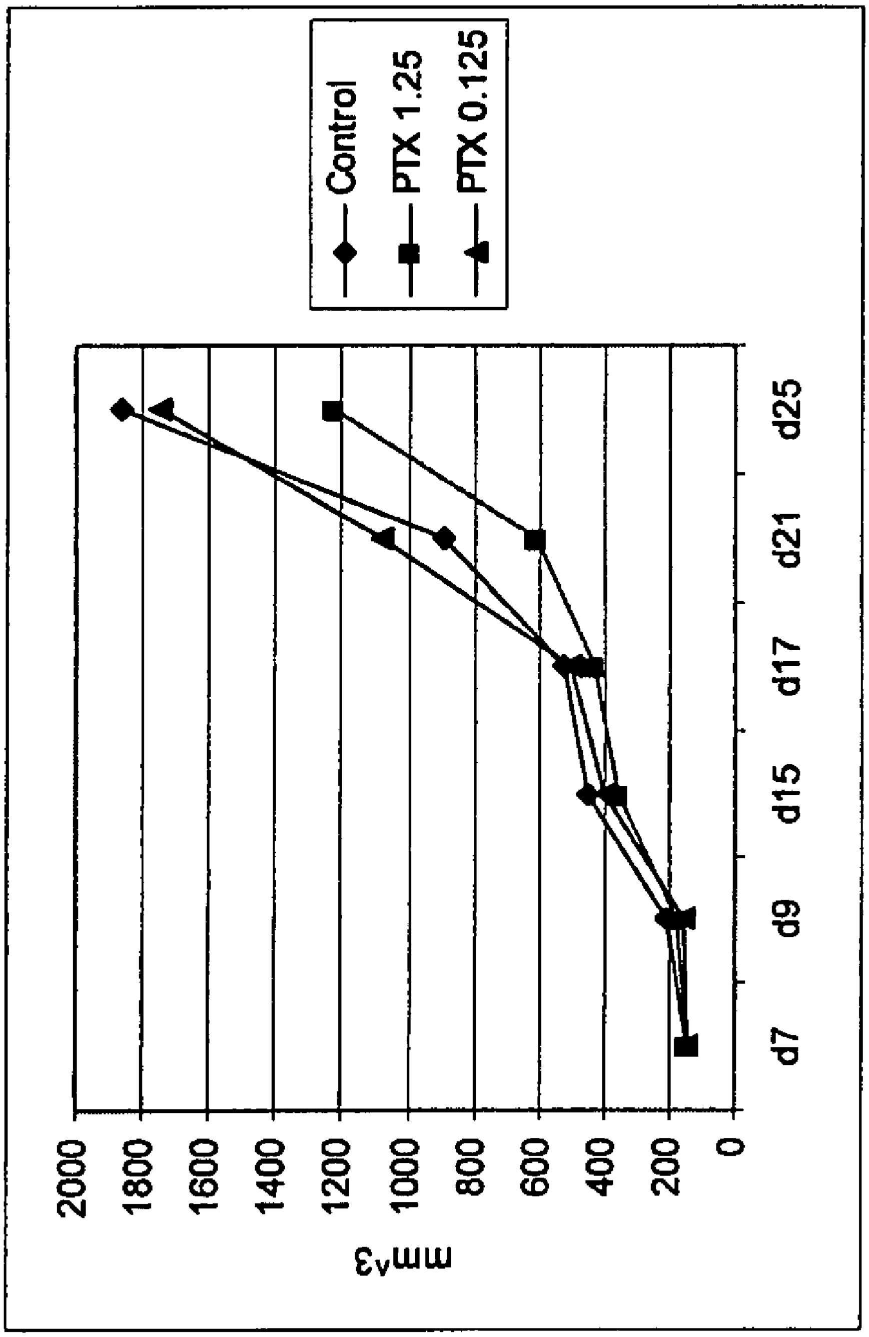
FIG. 22. PTX reduces the in vivo growth of 3T3-101P3A11 Tumors. Pertussis toxin was found to inhibit the sub-cutaneous growth of 3T3-101P3A11 tumors in SCID mice in a dose dependent manner.

Furthermore, these assays is useful to confirm the anti-101P3A11 inhibitory effects of candidate therapeutic compositions, such as for example, 101P3A11 antibodies or intrabodies, and 101P3A11 antisense molecules or ribozymes, or 101P3A11 directed small molecules. In FIG. 22, we depict the effect of a small molecule, pertussis toxin (PTX) on tumor formation by 3T3-101P3A11 cells. In this experiment, SCID mice were injected with 3T3-101P3A11 alone or in conjunction with PTX. Each mouse was given 5 doses of PTX at 3-4 days interval. Tumor volume was evaluated by caliper measurements. FIG. 22 shows that PTX inhibits tumor growth in a dose dependent manner. Delivery of PTX at shorter intervals, such as 5 time per week, resulted in a larger rate of inhibition of tumor growth, with 70% inhibition of tumor growth observed after 25 days (Figure M9). Similarly, treatment with the G-protein inhibitor suramin inhibits the growth of 3T3-101P3A11 tumors (Figure M13). In addition to demonstrating that 101A3P11 plays an important role in tumor growth, FIGS. 21 22 and M9 identify a signaling pathway associated with 101P3A11 and indicate that 101P3A11 produced its effect on tumor growth by activating an adenylate cyclase dependent pathway.

Example 35

101P3A11 Monoclonal Antibody-Mediated Inhibition of Tumors In Vivo

The significant expression of 101P3A11 in cancer tissues, together with its restricted expression in normal tissues, makes 101P3A11 an excellent target for antibody therapy. In cases where the monoclonal antibody target is a cell surface protein, as is 101P3A11, antibodies have been shown to be efficacious at inhibiting tumor growth (See, e.g., Saffran, D., et al., PNAS 10:1073-1078). In cases where the target is not on the cell surface, such as PSA and PAP in prostate cancer, antibodies have also been shown to recognize and inhibit growth of cells expressing those proteins (Saffran, D.C., et al., Cancer and Metastasis Reviews, 1999. 18: 437-449). As with any cellular protein with a restricted expression profile, 101P3A11 is a target for T cell-based immunotherapy.

Accordingly, the therapeutic efficacy of anti-101P3A11 mAbs in human colon, kidney, bladder and prostate cancer mouse models is modeled in 101P3A11-expressing kidney, colon, bladder or prostate cancer xenografts or cancer cell lines, such as those described in the Example entitled "In vivo Assay for 101P3A11 Tumor Growth Promotion", that have been engineered to express 101P3A11.

Antibody efficacy on tumor growth and metastasis formation is confirmed, e.g., in a mouse orthotopic prostate, colon, bladder or kidney cancer xenograft model. The antibodies can be unconjugated, or can be conjugated to a therapeutic modality, as appreciated in the art. It is confirmed that anti- 101P3A11 mAbs inhibit formation of 101P3A11-expressing kidney, colon, bladder and prostate tumors. Anti-101P3A11 mAbs also retard the growth of established orthotopic tumors and prolong survival of tumor-bearing mice. These results indicate the utility of anti-101P3A11 mAbs in the treatment of local and advanced stages of cancer. (See, e.g., Saffran, D., et al., PNAS 10:1073-1078).

Administration of anti-101P3A11 mAbs retard established orthotopic tumor growth and inhibit metastasis to distant sites, resulting in a significant prolongation in the survival of tumor-bearing mice. These studies indicate that 101P3A11 is an attractive target for immunotherapy and demonstrate the therapeutic potential of anti-101P3A11 mAbs for the treatment of local and metastatic kidney, colon, bladder and prostate cancer. Similar studies manifest that 101P3A11 is safe and effective when used in combination with other therapeutic modalities such as surgery, radiation therapy, hormone therapy or chemotherapy.

This example demonstrates that unconjugated 101P3A11 monoclonal antibodies effectively to inhibit the growth of human bladder tumors grown in SCID mice; accordingly a combination of such efficacious monoclonal antibodies is also effective.

Tumor Inhibition Using Multiple Unconjugated 101P3A11 mAbs

Materials and Methods

101P3A11 Monoclonal Antibodies:

Monoclonal antibodies are raised against 101P3A11 as described in the Example entitled "Generation of 101P3A11 Monoclonal Antibodies (mAbs)." The antibodies are characterized by ELISA, Western blot, FACS, and immunoprecipitation for their capacity to bind 101P3A11. Epitope mapping data for the anti-101P3A11 mAbs, as determined by ELISA and Western analysis, recognize epitopes on the 101P3A11 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of UM-UC3, J82, CaKi1, 769P, CaOv1 or PAM tumor xenografts.

Cell Lines

The bladder, kidney and ovary carcinoma cell lines, UM-UC3, J82, CaKi1, 769P, CaOv1 and PAM as well as the fibroblast line NIH 3T3 (American Type Culture Collection) are maintained in DMEM supplemented with L-glutamine and 10% FBS.

A UM-UC3-101P3A11, J82-101P3A11, CaKi1-101P3A11, 769P-101P3A11, CaOv1-101P3A11, PA1-101P3A and 3T3-101P3A11 cell populations are generated by retroviral gene transfer as described in Hubert, R. S., et al., Proc Natl Acad Sci USA, 1999. 96(25): 14523.

Xenograft Mouse Models.

Subcutaneous (s.c.) tumors are generated by injection of $1\times10^6$ cancer cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by caliper measurements, and the tumor volume is calculated as length×width×height. Mice with s.c. tumors greater than 1.5 cm in diameter are sacrificed.

Orthotopic injections are performed under anesthesia by using ketamine/xylazine. For bladder orthotopic studies, an incision is made through the abdomen to expose the bladder, and tumor cells ($5\times10^5$) mixed with Matrigel are injected into the bladder wall in a 10-μl volume. To monitor tumor growth, mice are palpated and blood is collected on a weekly basis to measure BTA levels. For kidney and ovary orthopotic models, an incision is made through the abdominal muscles to expose the kidney or the ovary. Tumor cells mixed with Matrigel are injected under the kidney capsule or into the ovary in a 10-μl volume (Yoshida Y et al, Anticancer Res. 1998, 18:327; Ahn et al, Tumour Biol. 2001, 22:146). To monitor tumor growth, blood is collected on a weekly basis measuring G250 and SM047 levels. The mice are segregated into groups for the appropriate treatments, with anti-101P3A11 or control mAbs being injected i.p.

Anti-101P3A11 mAbs Inhibit Growth of 101P3A11-Expressing Xenograft-Cancer Tumors The effect of anti-101P3A11 mAbs on tumor formation is tested on the growth and progression of bladder, kidney and ovarian cancer xenografts using UC3-101P3A11, J82-101P3A11, CaKi1-101P3A11, 769P-101P3A11, CaOv1-101P3A11 and PA1-101P3A11 orthotopic models. As compared with the s.c. tumor model, the orthotopic model, which requires injection of tumor cells directly in the mouse bladder, kidney and ovary, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allowed us to follow the therapeutic effect of mAbs on clinically relevant end points.

Accordingly, tumor cells are injected into the mouse bladder, kidney or ovary, and 2 days later, the mice are segregated into two groups and treated with either: a) 200-500 μg, of anti-101P3A11 Ab, or b) PBS three times per week for two to five weeks.

A major advantage of the orthotopic cancer models is the ability to study the development of metastases. Formation of metastasis in mice bearing established orthotopic tumors is studies by IHC analysis on lung sections using an antibody against a tumor-specific cell-surface protein such as anti-CK20 for bladder cancer, anti-G250 for kidney cancer and SM047 antibody for ovarian cancer models (Lin S et al, Cancer Detect Prev. 2001; 25:202; McCluggage W et al, Histopathol 2001, 38:542).

Mice bearing established orthotopic tumors are administered 1000 μg injections of either anti-101P3A11 mAb or PBS over a 4-week period. Mice in both groups are allowed to establish a high tumor burden, to ensure a high frequency of metastasis formation in mouse lungs. Mice then are killed and their bladders, livers, bone and lungs are analyzed for the presence of tumor cells by IHC analysis.

These studies demonstrate a broad anti-tumor efficacy of anti-101P3A11 antibodies on initiation and progression of prostate and kidney cancer in xenograft mouse models. Anti-101P3A11 antibodies inhibit tumor formation of tumors as well as retarding the growth of already established tumors and prolong the survival of treated mice. Moreover, anti-101P3A11 mAbs demonstrate a dramatic inhibitory effect on the spread of local bladder, kidney and ovarian tumor to distal sites, even in the presence of a large tumor burden. Thus, anti-101P3A11 mAbs are efficacious on major clinically relevant end points (tumor growth), prolongation of survival, and health.

Example 36

Therapeutic and Diagnostic Use of Anti-101P3A11 Antibodies in Humans

Anti-101P3A11 monoclonal antibodies are safely and effectively used for diagnostic, prophylactic, prognostic and/or therapeutic purposes in humans. Western blot and immunohistochemical analysis of cancer tissues and cancer xenografts with anti-101P3A11 mAb show strong extensive staining in carcinoma but significantly lower or undetectable levels in normal tissues. Detection of 101P3A11 in carcinoma and in metastatic disease demonstrates the usefulness of the mAb as a diagnostic and/or prognostic indicator. Anti-101P3A11 antibodies are therefore used in diagnostic applications such as immunohistochemistry of kidney biopsy specimens to detect cancer from suspect patients.

As determined by flow cytometry, anti-101P3A11 mAb specifically binds to carcinoma cells. Thus, anti-101P3A11 antibodies are used in diagnostic whole body imaging applications, such as radioimmunoscintigraphy and radioimmunotherapy, (see, e.g., Potamianos S., et. al. Anticancer Res 20(2A):925-948 (2000)) for the detection of localized and metastatic cancers that exhibit expression of 101P3A11. Shedding or release of an extracellular domain of 101P3A11 into the extracellular milieu, such as that seen for alkaline phosphodiesterase B10 (Meerson, N. R., Hepatology 27:563-568 (1998)), allows diagnostic detection of 101P3A11 by anti-101P3A11 antibodies in serum and/or urine samples from suspect patients.

Anti-101P3A11 antibodies that specifically bind 101P3A11 are used in therapeutic applications for the treatment of cancers that express 101P3A11. Anti-101P3A11 antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-101P3A11 antibodies are tested for efficacy of tumor prevention and growth inhibition in the SCID mouse cancer xenograft models, e.g., kidney cancer models AGS-K3 and AGS-K6, (see, e.g., the Example entitled "101P3A11 Monoclonal Antibody-mediated Inhibition of Bladder, Kidney and Ovarian Tumors In vivo"). Conjugated and unconjugated anti-101P3A11 antibodies are used as a therapeutic modality in human clinical trials either alone or in combination with other treatments as described in following Examples.

Example 37

Human Clinical Trials for the Treatment and Diagnosis of Human Carcinomas Through Use of Human Anti-101P3A11 Antibodies In Vivo Antibodies are used in accordance with the present invention which recognize an epitope on 101P3A11, and are used in the treatment of certain tumors such as those listed in Table I. Based upon a number of factors, including 101P3A11 expression levels, tumors such as those listed in Table I are presently preferred indications. In connection with each of these indications, three clinical approaches are successfully pursued.

I.) Adjunctive therapy: In adjunctive therapy, patients are treated with anti-101P3A11 antibodies in combination with a chemotherapeutic or antineoplastic agent and/or radiation therapy. Primary cancer targets, such as those listed in Table I, are treated under standard protocols by the addition anti-101P3A11 antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-101P3A11 antibodies are utilized in several adjunctive clinical trials in combination with the chemotherapeutic or antineoplastic agents adriamycin (advanced prostrate carcinoma), cisplatin (advanced head and neck and lung carcinomas), taxol (breast cancer), and doxorubicin (preclinical).

II.) Monotherapy: In connection with the use of the anti-101P3A11 antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-101P3A11 antibodies, the radiolabeled antibodies are utilized as a diagnostic and/or imaging agent. In such a role, the labeled antibodies localize to both solid tumors, as well as, metastatic lesions of cells expressing 101P3A11. In connection with the use of the anti-101P3A11 antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}In$)-101P3A11 antibody is used as an imaging agent in a Phase I human clinical trial in patients having a carcinoma that expresses 101P3A11 (by analogy see, e.g., Divgi et al. *J. Natl. Cancer Inst.* 83:97-104 (1991)). Patients are followed with standard anterior and posterior gamma camera. The results indicate that primary lesions and metastatic lesions are identified Dose and Route of Administration As appreciated by those of ordinary skill in the art, dosing considerations can be determined through comparison with the analogous products that are in the clinic. Thus, anti-101P3A11 antibodies can be administered with doses in the range of 5 to 400 mg/m$^2$, with the lower doses used, e.g., in connection with safety studies. The affinity of anti-101P3A11 antibodies relative to the affinity of a known antibody for its target is one parameter used by those of skill in the art for determining analogous dose regimens. Further, anti-101P3A11 antibodies that are fully human antibodies, as compared to the chimeric antibody, have slower clearance; accordingly, dosing in patients with such fully human anti-101P3A11 antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-101P3A11 antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-101P3A11 antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-101P3A11 antibodies. As will be appreciated, one criteria that can be utilized in connection with enrollment of patients is 101P3A11 expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 101P3A11. Standard tests and follow-up are utilized to monitor each of these safety concerns. Anti-101P3A11 antibodies are found to be safe upon human administration.

Example 38

Human Clinical Trial Adjunctive Therapy with Human Anti-101P3A11 Antibody and Chemotherapeutic Agent(s)

A phase I human clinical trial is initiated to assess the safety of six intravenous doses of a human anti-101P3A11 antibody in connection with the treatment of a solid tumor, e.g., a cancer of a tissue listed in Table I. In the study, the safety of single doses of anti-101P3A11 antibodies when utilized as an adjunctive therapy to an antineoplastic or chemotherapeutic agent, such as cisplatin, topotecan, doxorubicin, adriamycin, taxol, or the like, is assessed. The trial design includes delivery of six single doses of an anti-101P3A11 antibody with dosage of antibody escalating from approximately about 25 mg/m$^2$ to about 275 mg/m$^2$ over the course of the treatment in accordance with the following schedule:

| | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 101P3A11. Standard tests and follow-up are utilized to monitor each of these safety concerns. Patients are also assessed for clinical outcome, and particularly reduction in tumor mass as evidenced by MRI or other imaging.

The anti-101P3A11 antibodies are demonstrated to be safe and efficacious, Phase II trials confirm the efficacy and refine optimum dosing.

Example 39

Human Clinical Trial: Monotherapy with Human Anti-101P3A11 Antibody

Anti-101P3A11 antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-101P3A11 antibodies.

Example 40

Human Clinical Trial: Diagnostic Imaging with Anti-101P3A11 Antibody

Once again, as the adjunctive therapy discussed above is safe within the safety criteria discussed above, a human clinical trial is conducted concerning the use of anti-101P3A11 antibodies as a diagnostic imaging agent. The protocol is designed in a substantially similar manner to those described in the art, such as in Divgi et al. *J. Natl. Cancer Inst.* 83:97-104 (1991). The antibodies are found to be both safe and efficacious when used as a diagnostic modality.

Example 41

Identification of 101P3A11 Sequences Involved in Ligand Binding

As shown in FIG. 4, the transmembrane regions of 101P3A11 and mouse olfactory receptor S25 (ORS25) predicted using the TMHMM algorithm are highlighted in gray. The amino acids of ORS25 predicted by Floriano, et al. to be involved in binding of the ligand hexanol and/or involved in the formation of the ligand binding pocket are italicized and bolded in FIG. 4, and are listed below. (Floriano, W. B., et al, 2000, Proc. Natl. Acad. Sci., USA, 97:10712-10716)

| | |
|---|---|
| Leu 131 | Ala 230 |
| Val 134 | Ile 231 |
| Val 135 | Gly 234 |
| Gly 138 | Thr 284 |
| Thr 139 | Phe 287 |
| Ser 193 | Gln 300 |
| Ser 197, | Lys 302 |
| Phe 225 | |

Sequences of 101P3A11 involved in ligand binding are identified based on homology to mouse olfactory receptor S25. Shown is the amino acid alignment of 101P3A11 with mouse olfactory receptor S25 depicting the predicted transmembrane domains of each GPCR. The amino acids of S25 involved in the recognition and binding of its ligand hexanol or that lie in the proximity of the binding pocket (Floriano, W. B., et al, 2000, Proc. Natl. Acad. Sci., USA, 97:10712-10716), are also shown. These amino acids lie close to or within the transmembrane domains of ORS25. Accordingly, the structurally homologous regions of 101P3A11 are involved in the binding of its cognate ligand. These regions encode the amino acids of the first extracellular loop and of the amino terminal end of transmembrane domain 3 (amino acids 82-112), the amino acids at the carboxyl terminal end of transmembrane domain 4 and into the second extracellular loop (amino acids 160-185), the amino acids at the end of the second extracellular loop and into transmembrane domain 5 (amino acids 186-212), and the amino acids at the carboxyl terminal end of transmembrane domain 6, the third extracellular loop, and the amino terminal end of transmembrane domain 7 (amino acids 250-280). Thus, ligands of 101P3A11 are identified that interact with at least 3 of the following regions of 101P3A11: amino acids 82-112, amino acids 160-185, amino acids 186-212, and, amino acids 250-280.

Example 42

Homology Comparison of 101P3A11 to Known Sequences

The 101P3A11 protein of FIG. 3 has 318 amino acids with calculated molecular weight of 35.2 kDa, and pI of 8.7. 101P3A11 is predicted to be a cell surface protein. Cellular localization was demonstrated by FACS analysis and immunofluorescence in cells engineered to express 101P3A11, as shown in Figure M17 (panel B). Immunofluorescence staining of permeabilized cells revealed that 101P3A11 becomes internalized and localizes then to the cytosol (Figure M17).

101P3A11 shows best homology to rat olfactory receptor RA1c (gi 3420759) sharing 59% identity and 76% homology with that protein. 101P3A11 also shows homology to human prostate specific GPCR (gi 13540539) and human. olfactory receptor 51I12 (gi 14423836), sharing 59% identities/77% homology, and 53% identities/69% homology with each, respectively (FIGS. 23-25). More recent studies have identified a mouse homolog of 101P3A11, namely MOR 18-1, (gi 18479284, FIG. 65). MOR18-1 is a mouse olfactory receptor that shares 93% identity and 96% homology with the 101P3A11 protein.

In addition to 101P3A11 variant I used predominantly in the studies listed below, 101P3A11 has 2 additional variants. Variant 3 is a SNP of variant 1 and exhibits a mutation at position 104, with an exchange of isoleusine to methionine at that position. Variant 3 is expected to be localized to the cell surface, in a manner similar to variant 1, and exhibits the same motifs and transmembrane domains as variant 1 (table XXI). Variant 2 of 101P3A11 is 72 amino acids long, contains 2 transmembranes and localizes predominantly at the cell surface with some cytoplasmic localization.

Sequence and motif analysis indicate that 101P3A11 belongs to the family of olfactory receptors. Bioinformatic analysis revealed 101P3A11 to be a 7 transmembrane protein, with strong domain and structural homology to G-protein coupled receptors (GPCRs) (see Table XXI, TM Pred, Sosui, Pfam, Blocks, Print). Proteins that are members of the G-protein coupled receptor family exhibit an extracellular amino-terminus, three extracellular loops, three intracellular loops and an intracellular carboxyl terminus. G-protein coupled receptors are seven-transmembrane receptors that are stimulated by polypeptide hormones, neurotransmitters, chemokines and phospholipids (Civelli O et al, Trends Neurosci. 2001, 24:230; Vrecl M et al Mol. Endocrinol. 1998, 12:1818). Ligand binding traditionally occurs between the first and second extracellular loops of the GPCR. Upon ligand binding GPCRs transduce signals across the cell surface membrane by associating with trimeric G proteins. Their signals are transmitted via trimeric guanine-nucleotide binding proteins (G proteins) to effector enzymes or ion channels (Simon et al., 1991, Science 252: 802). Signal transduction and biological output mediated by GPCR can be modulated through various mechanisms including peptide mimics, small molecule inhibitors and GPCR kinases or GRK (Pitcher J A et al, J Biol Chem. 1999, 3; 274:34531; Fawzi A B, et al. 2001, Mol. Pharmacol., 59:30).

Recently, GPCRs have also been shown to link to mitogenic signaling pathways of tyrosine kinases (Luttrell et al., 1999, Science 283: 655; Luttrell et al., 1999 Curr Opin Cell Biol 11: 177). GPCRs are regulated by phosphorylation mediated by GPCR kinases (GRKs), which themselves are indirectly activated by the GPCRs (Pitcher et al., 1998, Ann. Rev. Biochem. 67: 653). Olfactory GPCRs transmit their signals by activating the cAMP pathway via adenylate cyclase resulting in downstream signaling to protein kinase A, and by activating the phospholipase C pathway by generating inositol 1,4,5-trisphosphate (IP3) and diacyl-glycerol (DAG) (Breer, 1993, Ciba Found Symp 179: 97; Bruch, 1996, Comp Biochem Physiol B Biochem Mol Biol 113:451). IP3 results in an increase in intracellular calcium, while DAG activates protein kinase C.

Recent studies have associated GPCRs with cellular transformation. In particular, KSHV G protein-coupled receptor was found to transform NIH 3T3 cells in vitro and induces multifocal KS-like lesions in KSHV-GPCR-transgenic mice (Schwarz M, Murphy P M. J Immunol 2001, 167:505). KSHV-GPCR was capable of producing its effect on endothelial cells and fibroblasts by activating defined signaling pathways, including the AKT survival pathway (Montaner S et al, Cancer Res 2001, 61:2641). In addition, KSHV-GPCR induced the activation of mitogenic pathways such as AP-1 and NFkB, resulting in the expression of pro-inflammatory genes (Schwarz M, Murphy P M. J Immunol 2001, 167:505). Other GPCR associated with tumor formation include G2A, and the PAR-1, which has been found to induce transformation of NIH 3T3 cells (Whitehead I et al, Oncogene 2001, 20:1547).

This information indicates that 101P3A11 plays a role in the transformation of mammalian cells, induces mitogenic responses including activation of various signaling pathways, and regulate gene transcription by transmitting cell surface signals to the nucleus, see also, the Example entitled, "In vivo Assay for 101P3A11 Tumor Growth Promotion".

Accordingly, when 101P3A11 functions as a regulator of cell transformation, tumor formation, or as a modulator of transcription involved in activating genes associated with inflammation, tumorigenesis or proliferation, 101P3A11 is used for therapeutic, diagnostic, prognostic and/or preventative purposes, in manners analogous to or that track other GPCRs as discussed herein and in the art.

Example 43

Identification and Confirmation of Potential Signal Transduction Pathways

Many mammalian proteins have been reported to interact with signaling molecules and to participate in regulating signaling pathways. (J Neurochem. 2001; 76:217-223). In particular, GPCRs have been reported to activate MAK cascades as well as G proteins, and been associated with the EGFR pathway in epithelial cells (Naor, Z., et al, Trends Endocrinol Metab. 2000, 11:91; Vacca F et al, Cancer Res. 2000, 60:5310; Della Rocca G. J., et al, J Biol Chem. 1999, 274: 13978). Using immunoprecipitation and Western blotting techniques, proteins are identified that associate with 101P3A11 and mediate signaling events. Several pathways known to play a role in cancer biology can be regulated by 101P3A11, including phospholipid pathways such as PI3K, AKT, etc, adhesion and migration pathways, including FAK, Rho, Rac-1, etc, as well as mitogenic/survival cascades such as ERK, p38, etc (Cell Growth Differ. 2000, 11:279; J Biol Chem. 1999, 274:801; Oncogene. 2000, 19:3003; J. Cell Biol. 1997, 138:913).

Using Western blotting and other techniques, the ability of 101P3A11 to regulate these pathways is confirmed. Cells expressing or lacking 101P3A11 are either left untreated or stimulated with cytokines, androgen and anti-integrin antibodies. Cell lysates were analyzed using anti-phospho-specific antibodies (Cell Signaling, Santa Cruz Biotechnology) in order to detect phosphorylation and regulation of ERK, p38, AKT, PI3K, PLC and other signaling molecules. Using such techniques, we showed that 101P3A11 alters the tyrosine phosphorylation pattern of NIH 3T3 cells (FIG. 26) indicating that 101P3A11 is regulating protein kinases and phosphatases. In the experiment, data shown in FIG. 26, control 3T3-neo and 3T3-101P3A11 cells were either treated with 0.5 or 10% FBS and whole cell lysates were analyzed by anti-phosphotyrosine Western blotting. Expression of 101P3A11 resulted in reduced phosphorylation of several proteins in NIH-3T3 cells, while inducing the phosphorylation of proteins at 79-81 and 28-32 kDa.

Using anti-Phospho-ERK antibodies, we demonstrated that expression of 101P3A11 induced ERK phosphorylation in the prostate cancer cell line PC3 (FIG. 27A and FIG. 27B), and that ERK phosphorylation in 101P3A11 expressing cells was regulated by GPCR ligands. In this experiment, control PC3-neo cells and PC3-101P3A11 cells were left untreated (0.1% FBS) or were stimulated with 10% FBS, lipophosphatidic acid (LPA), gastrin releasing peptide (GRP), leukotriene (LKB4) or platelet activating factor (PAF). The cells were lysed and analyzed by Western blotting using anti-Phospho-ERK (FIG. 27A) or anti-ERK (FIG. 27B) mAb. The results showed that expression of 101P3A11 mediated significant ERK phosphorylation by FBS, LPA, GRP and PAF, while LKB4 resulted in a more modest level of ERK phosphorylation in PC3-101P3A11 cells. In contrast, none of the GPCR ligands induced significant ERK phosphorylation in PC3-Neo cells, demonstrating the specificity of GPCR ligands-mediated responses in 101P3A11 expressing cells. The ERK overlay demonstrated equal loading, supporting the specificity of this data. In order to delineate the signaling pathway by which 101P3A11 mediates ERK phosphorylation in cancer cells, it was confirmed which of the two pathway inhibitors: MEK inhibitor PD98059 or the p38 inhibitor SB203580 regulate 101P3A11 mediated ERK phosphorylation (FIG. 28). To obtain this data, PC3-neo and PC3-101P3A11 cells were treated with media alone or in the presence of PD98059, SB203580, or genistein were stimulated with FBS or GRP. Cells were lysed and analyzed by Western blotting using anti-Phospho-ERK or anti-ERK mAb. Treatment with 10% FBS or with GRP induced the phosphorylation of ERK in PC3-101P3A11 but not in control PC3-neo cells. 101P3A11-mediated ERK phosphorylation was inhibited by the MEK-1 inhibitor PD98059 but not the p38 inhibitor SB203580 or genistein. The ERK overlay demonstrated equal loading, supporting the specificity of the results. These results were confirmed by those obtained in two additional sets of experiments. The inhibition of 101P3A11-mediated ERK phosphorylation by PD98059 demonstrates that 101P3A11 activated the classical MEK-ERK cascade, a pathway associated with mitogenesis, proliferation and tumorigenesis.

Figure 26:
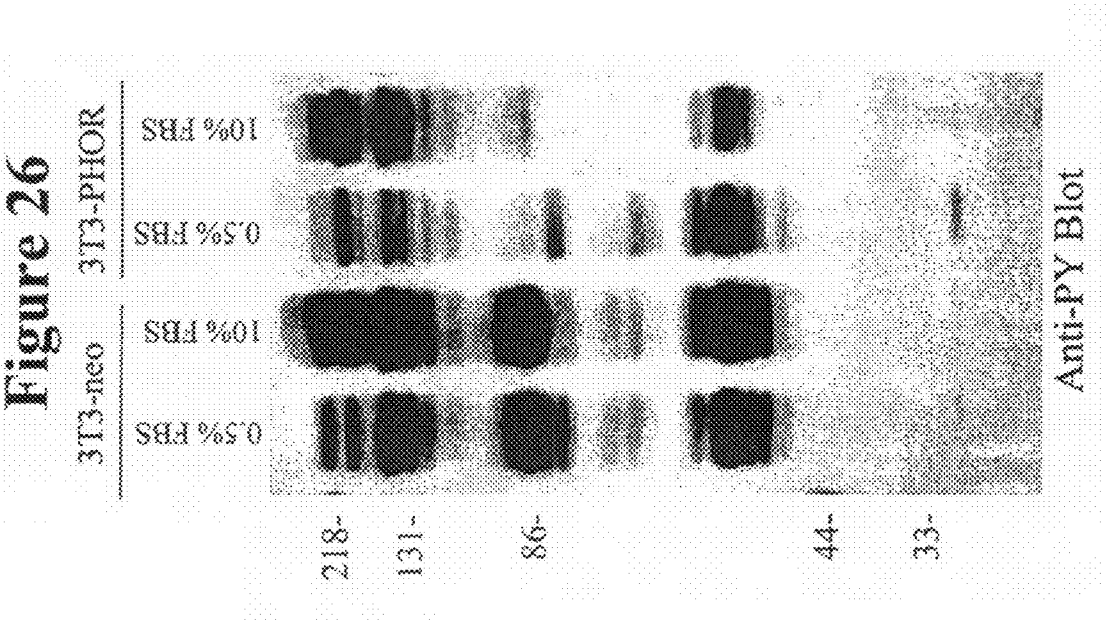
FIG. 26. 101P3A11 Modulated Tyrosine Phosphorylation in NIH-3T3 Cells. 101P3A11 mediated the de-phosphorylation of proteins at 200, 120-140, 85-90 and 55 kDa. 101P3A11 induced the phosphorylation of proteins at 80 and 29 kDa in NIH-3T3 cells.
Figure 27:
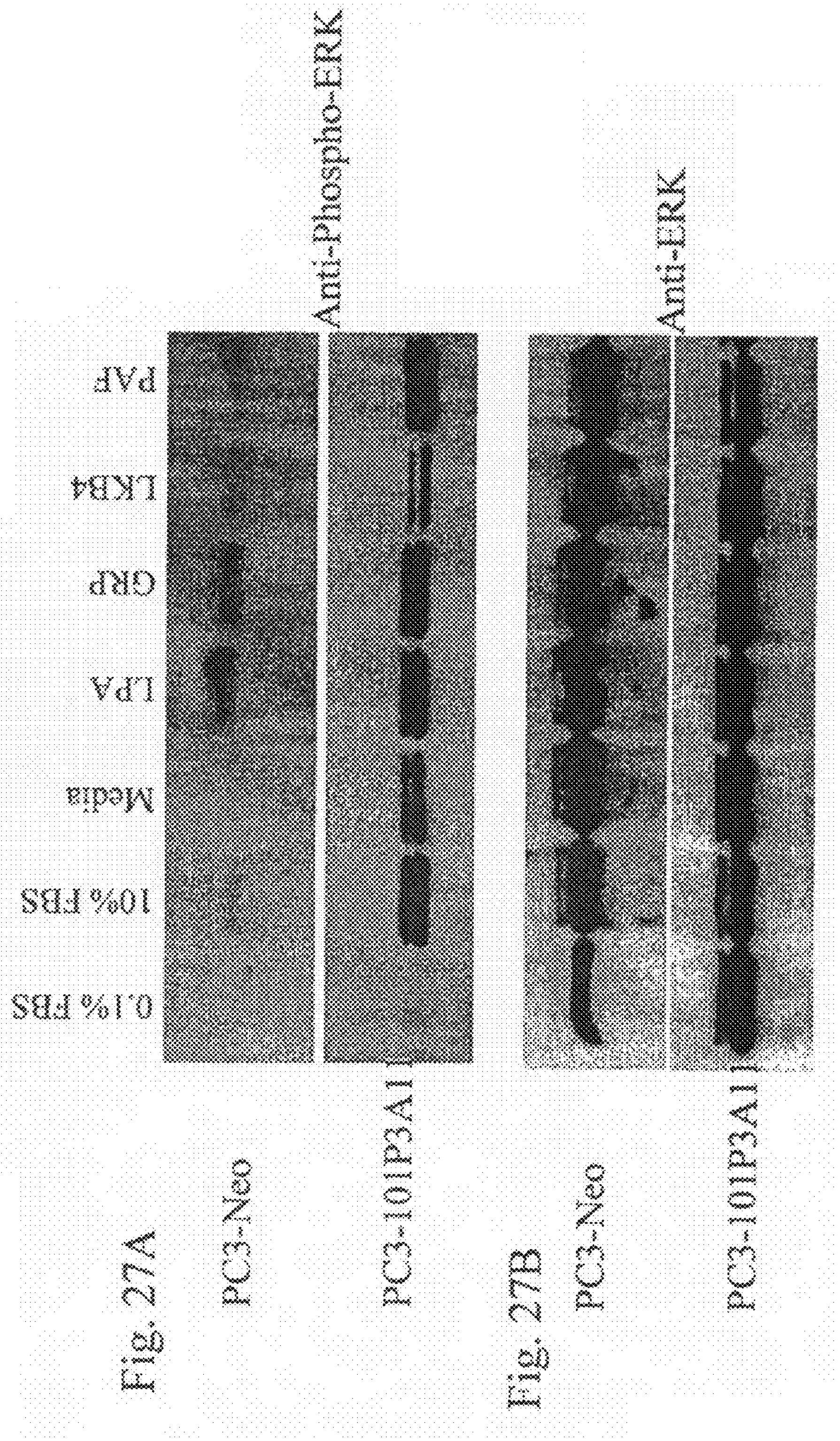
FIG. 27. ERK Phosphorylation by PCR ligands in 101P3A11 Expressing Cells. FBS, lipophosphatidic acid, gastrin releasing peptide, leukotriene and platelet activating factor induced the phosphorylation of ERK in 101P3A11 expressing cells.
Figure 28:
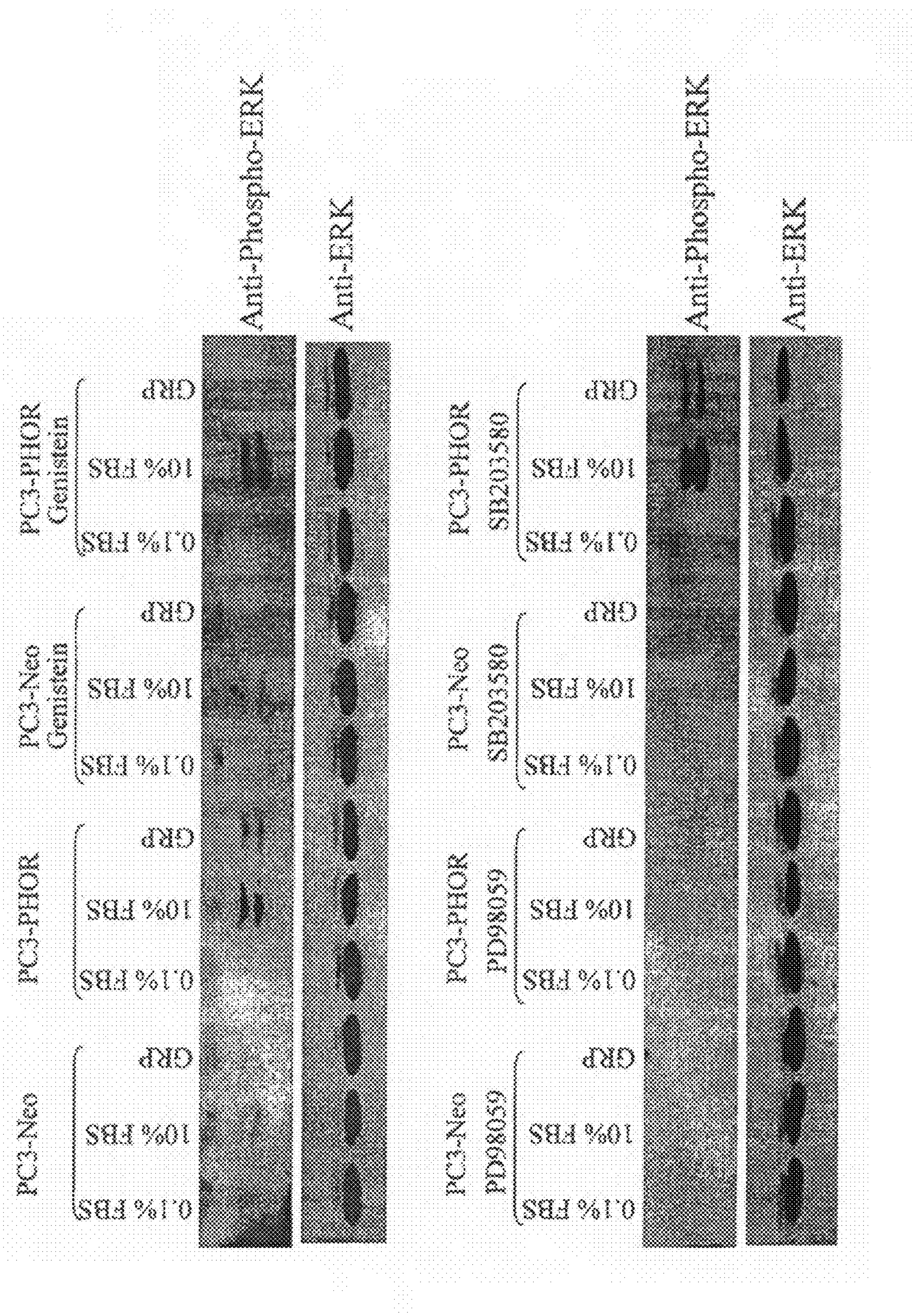
FIG. 28. Inhibition of 101P3A11-Mediated ERK Activation by PD98059. ERK phosphorylation was inhibited by a MEK specific (PD98059) but not a p38 specific (SB203580) inhibitor in PC3-101P3A11 cells.
Figure 29:
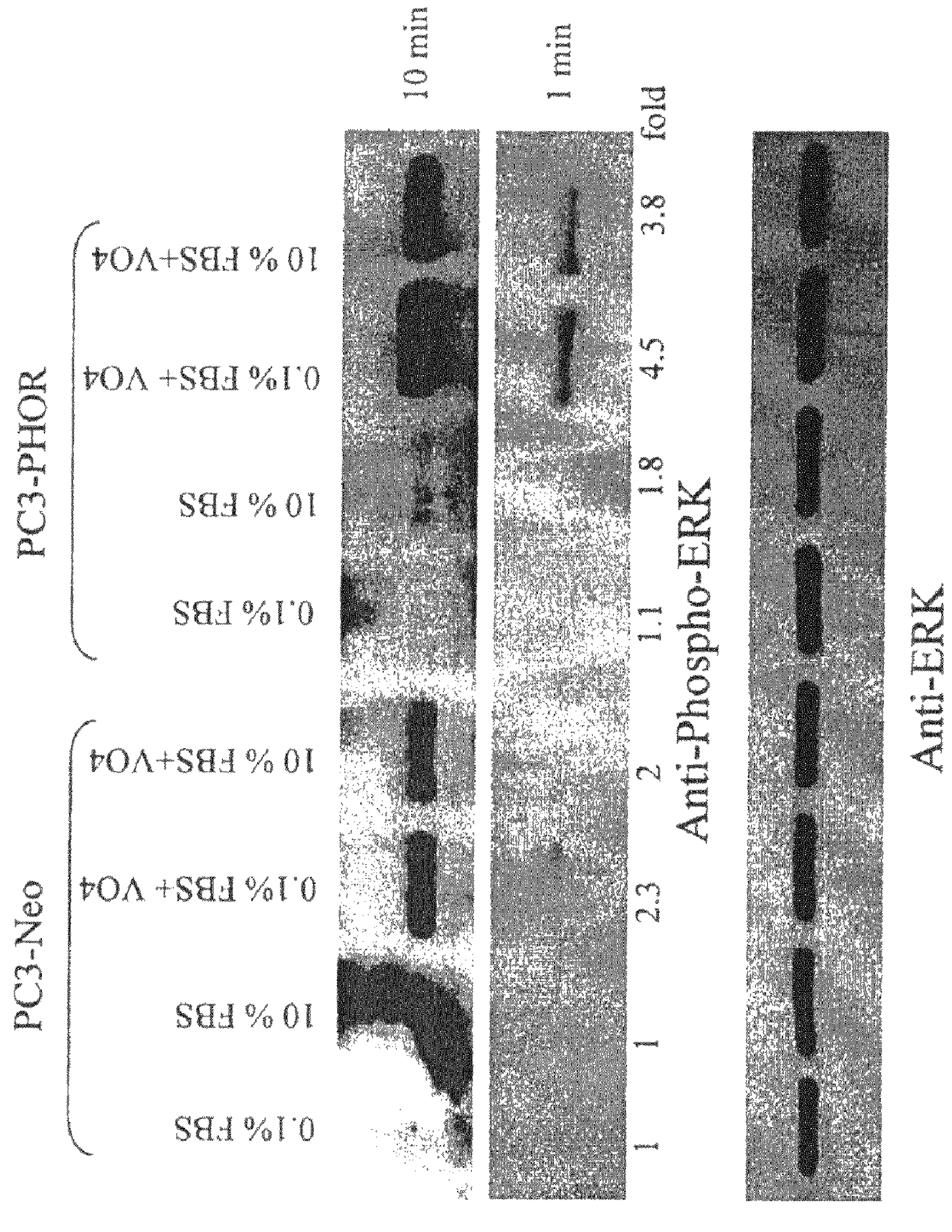
FIG. 29. Enhanced ERK Phosphorylation in Sodium Orthovanadate Treated PC3-101P3A11 Cells. Sodium orthovanadate induced increased ERK phosphorylation in PC3-101P3A11 cells relative to PC3-neo cells.

Results in FIGS. 26-28 indicate that 101P3A11 regulates the activity of kinases, including ERK, and phosphatases. In order to confirm the association of 101P3A11 with phosphatase activity, the effect of the protein phosphatase inhibitor sodium orthovanadate on 101P3A11 mediated ERK phosphorylation was determined (FIG. 29). PC3-neo and PC3-101P3A11 cells were grown in media alone or in the presence of sodium orthovanadate (Na3VO4), and were stimulated with 0.1% or 10% FBS. Cells were lysed and analyzed by Western blotting using anti-Phospho-ERK or anti-ERK mAb. Treatment with Na3VO4 resulted in a 4.5-fold increase in ERK phosphorylation in PC3-101P3A11 cells, compared to a two-fold increase in PC3-neo cells. Results in FIG. 29 confirm the contribution of protein phosphatases to 101P3A11 mediated signaling.

Figure 30:
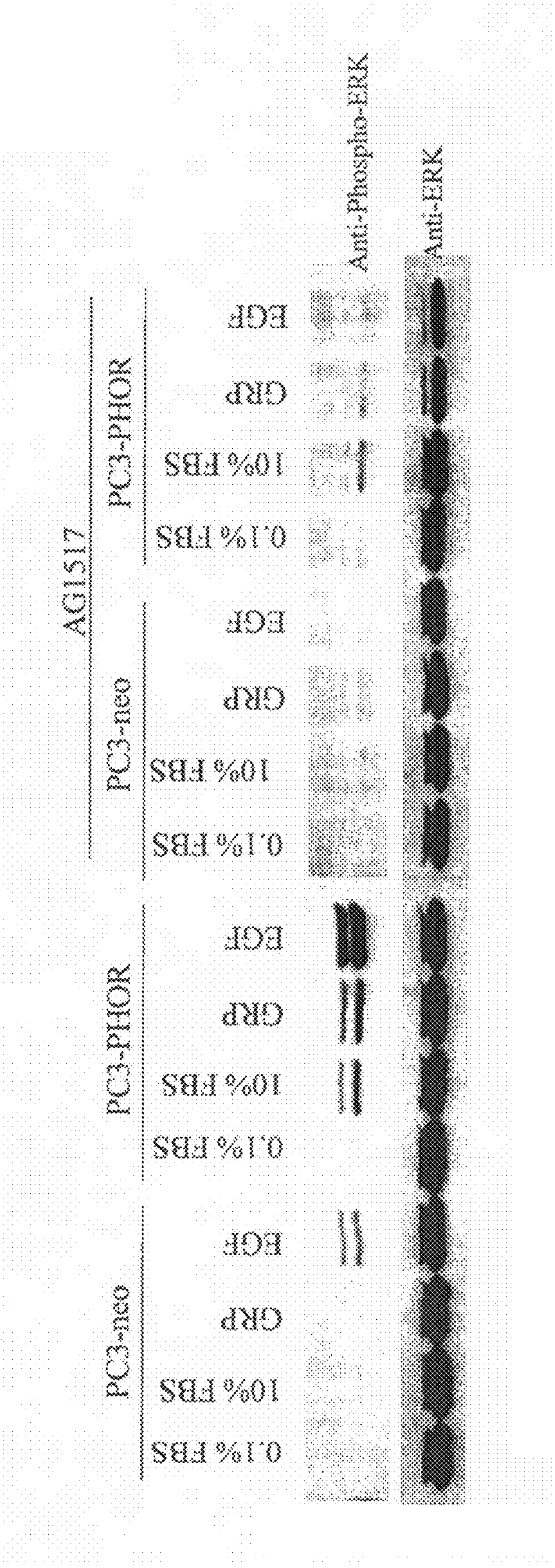
FIG. 30. Inhibition of 101P3A11-Mediated ERK Phosphorylation by AG1517. The EGFR inhibitor, AG1517, inhibits EGF-mediated ERK phosphorylation in control and 101P3A11-expressing PC3 cells. AG1517 partially inhibits 101P3A11 mediated ERK phosphorylation in PC3 cells.

Several GPCRs have been shown to transactivate receptor tyrosine kinases associated with the cell membrane, such as the EGF receptor (EGFR) (Pierce K. L., et al, J Biol Chem. 2001, 276:23155; Nath, D., et al, J Cell Sci. 2001, 114:1213). In order to determine whether 101P3A11 signaling results in the activation of EGFR, we compared the effect of the EGFR inhibitor, AG1517, on EGFR- and 101P3A11-mediated ERK phosphorylation (FIG. 30). In FIG. 30, PC3-neo and PC3-101P3A11 cells were grown in media alone (0.1% FBS) or in the presence of AG1517. The cells were stimulated with 0.1% or 10% FBS, GRP or EGF, lysed and analyzed by Western blotting using anti-Phospho-ERK or anti-ERK mAb. Treatment with 10% FBS, GRP and EGF induced ERK phosphorylation in PC3-101P3A11 cells. ERK phosphorylation by EGF was completely inhibited by AG1517. 101P3A11 mediated ERK phosphorylation in cells treated with 10% FBS was partially inhibited by AG1517. Data in FIG. 30 indicate that some cross talk occurred between 101P3A11 and EGFR signaling pathways.

Figures 31A, 31B:
FIGS. 31A-31B. Activation of p38 in PC3-101P3A11 Cells. Expression of 101P3A11 mediates p38 phosphorylation in cells treated with 10% FBS as shown by blotting with antibodies to phospho-p38 (FIG. 31A) compared to p38 (FIG. 31B).

In addition to activating the ERK cascade, 101P3A11 activated a parallel MAK pathway, namely p38. In FIG. 31A and FIG. 31B, PC3-neo and PC3-101P3A11 cells were grown in 1% or % FBS. Cells were lysed and analyzed by Western blotting using anti-Phospho-p38 (FIG. 31A) or anti-p38 (FIG. 31B) monoclonal antibody (mAb). Our results demonstrate that expression of 101P3A11 mediated p38 phosphorylation in cells treated with 10% FBS. Equal loading was demonstrated in the p38 overlay.

Results shown in FIGS. 26-30 and FIG. 31A-31B confirm that 101P3A11 activates several signaling pathways in cancer cells, including the ERK and p38 cascades. In addition to MAPK, 101P3A11 signaling was associated with protein phosphatase activity and EGFR transactivation. These signaling pathways have been associated with cell growth, survival and transcriptional activation, all of which play an important role in tumor initiation and progression. When 101P3A11 plays a role in the regulation of signaling pathways, whether individually or communally, it is used as a target for diagnostic, prognostic, preventative and/or therapeutic purposes.

To confirm that 101P3A11 directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress

2. SRE-luc, SRF/TCF/ELK1; MAPK/SAPK; growth/differentiation

3. AP-1-luc, FOS/JUN; MAPK/SAPK/PKC; growth/apoptosis/stress

4. ARE-luc, androgen receptor; steroids/MAPK; growth/differentiation/apoptosis 5. p53-luc, p53; SAPK; growth/differentiation/apoptosis 6. CRE-luc, CREB/ATF2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 101P3A11 are mapped and used for the identification and validation of therapeutic targets. When 101P3A11 is involved in cell signaling, it is used as target for diagnostic, prognostic, preventative and/or therapeutic purposes.

Example 44

101P3A11 Functions as a GPCR

Sequence and homology analysis of 101P3A11 indicated that 101P3A11 is a member of the olfactory receptor family of GPCR. Olfactory receptors are known to regulate biological responses by activating adenylate cyclase. In order to confirm that 101P3A11 functions as a GPCR and mediates the activation of adenylate cyclase, cAMP accumulation in PC3 and PC3-101P3A11 cells were compared (FIG. 32). Control PC3 and PC3-101P3A11 cells were grown in a low concentration of fetal bovine serum (FBS) for 14 hrs in the presence or absence of pertussis toxin (PTX). The cells were stimulated with 0.1% or 10% FBS, washed in PBS and lysed using a lysis buffer provided by Amersham Pharmacia. Intracellular concentration of cAMP was measured using a commercially available enzyme immunoassay (EIA) according to the manufacturer's recommendations (Amersham Pharmacia). Each assay was performed in duplicate. Calculations of cAMP concentrations were based on OD450 of the standard curve. Expression of 101P3A11 induced a four-fold increase in cAMP accumulation in the absence of stimulation. Treatment with 10% FBS further enhanced cAMP accumulation in PC3-101P3A11 cells to nearly seven-fold over control PC3-neo cells. 101P3A11 mediated cAMP accumulation was inhibited by PTX. These results were confirmed by two separate sets of experiments. Results shown in FIG. 32 demonstrate that 101P3A11 functions as a GPCR in prostate cancer cells and exhibits classical GPCR characteristics, such as cAMP accumulation that is inhibited by PTX.

Figure 33:
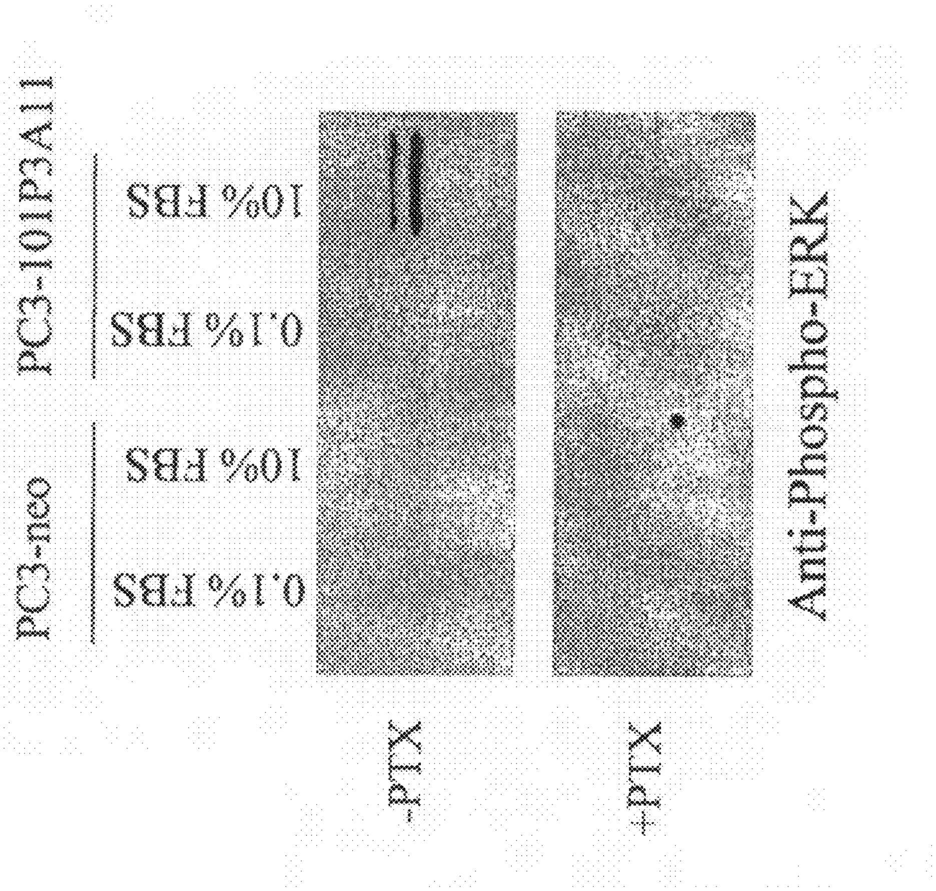
FIG. 33. Pertussis Toxin Inhibits 101P3A11 Mediated ERK Phosphorylation. Pertussis toxin inhibited FBS-mediated ERK phosphorylation in 101P3A11 expressing cells.
Figure 34:
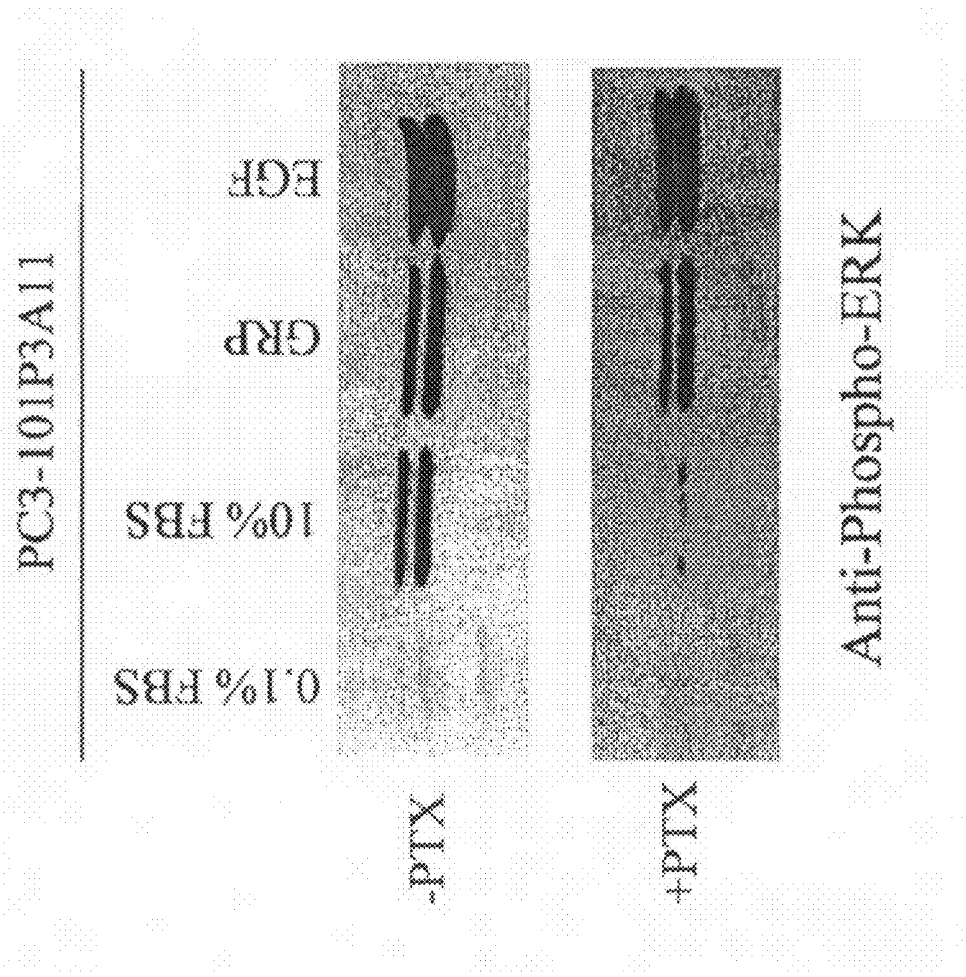
FIG. 34. Pertussis Toxin Inhibited ERK Phosphorylation in PC3-101P3A11 Cells. Pertussis toxin inhibited FBS-mediated ERK phosphorylation in 101P3A11 expressing cells. The inhibitory activity of pertussis toxin on ERK phosphorylation was more dramatic in FBS-treated than EGF or GRP-treated PC3-101P3A11 cells FIG. 35. Inhibition of 101P3A11-mediated signaling by Suranim, a G protein inhibitor. Control NIH 3T3 and 3T3-101P3A11 cells were grown in the presence of absence of G protein inhibitors Surinam and NF449. Proliferation was analyzed by Alamar blue after 72 hours. Suranim and NF449 inhibited the proliferation of 101P3A11 expressing but not control cells.

Since adenylate cyclase activity modulates intracellular levels of cAMP and induce downstream signaling events such as activation of protein kinase A, calcium and ERK MAPK signaling (Pierce K. L., et al, Oncogene. 2001, 20: 1532), we determined that PTX, an inhibitor of adenylate cyclase signaling, prevents 101P3A11-mediated ERK phosphorylation along with inhibiting cAMP accumulation (FIG. 33 and FIG. 34). PC3-neo and PC3-101P3A11 cells were grown overnight in 0.1% FBS in media alone or in the presence of pertussis toxin (PTX). Cells were stimulated with 0.1% or 10% FBS (FIG. 33) or 10% FBS, EGF or GRP (FIG. 34). Cells were lysed and analyzed by Western blotting using anti-Phospho-ERK mAb. Expression of 101P3A11 mediated ERK phosphorylation by 10% FBS in PC3 cells, which was inhibited by PTX (FIG. 33 and FIG. 34). In contrast, GRP and EGF-mediated ERK phosphorylation was relatively unaffected by PTX (FIG. 34), demonstrating the specificity of 101P3A11 mediated responses. These results were replicated in additional experiments. In addition to inhibiting ERK phosphorylation and 101P3A11-mediated signaling, PTX had a marked effect on the proliferation of PC3-101P3A11 but not control PC3-neo cells (Figure M6). Figure M6 shows that PTX inhibited the proliferation f 101P3A11 expressing cells in a dose dependent manner, and confirms that the GPCR function of 101P3A11 is important for tumor growth.

Figure 35:
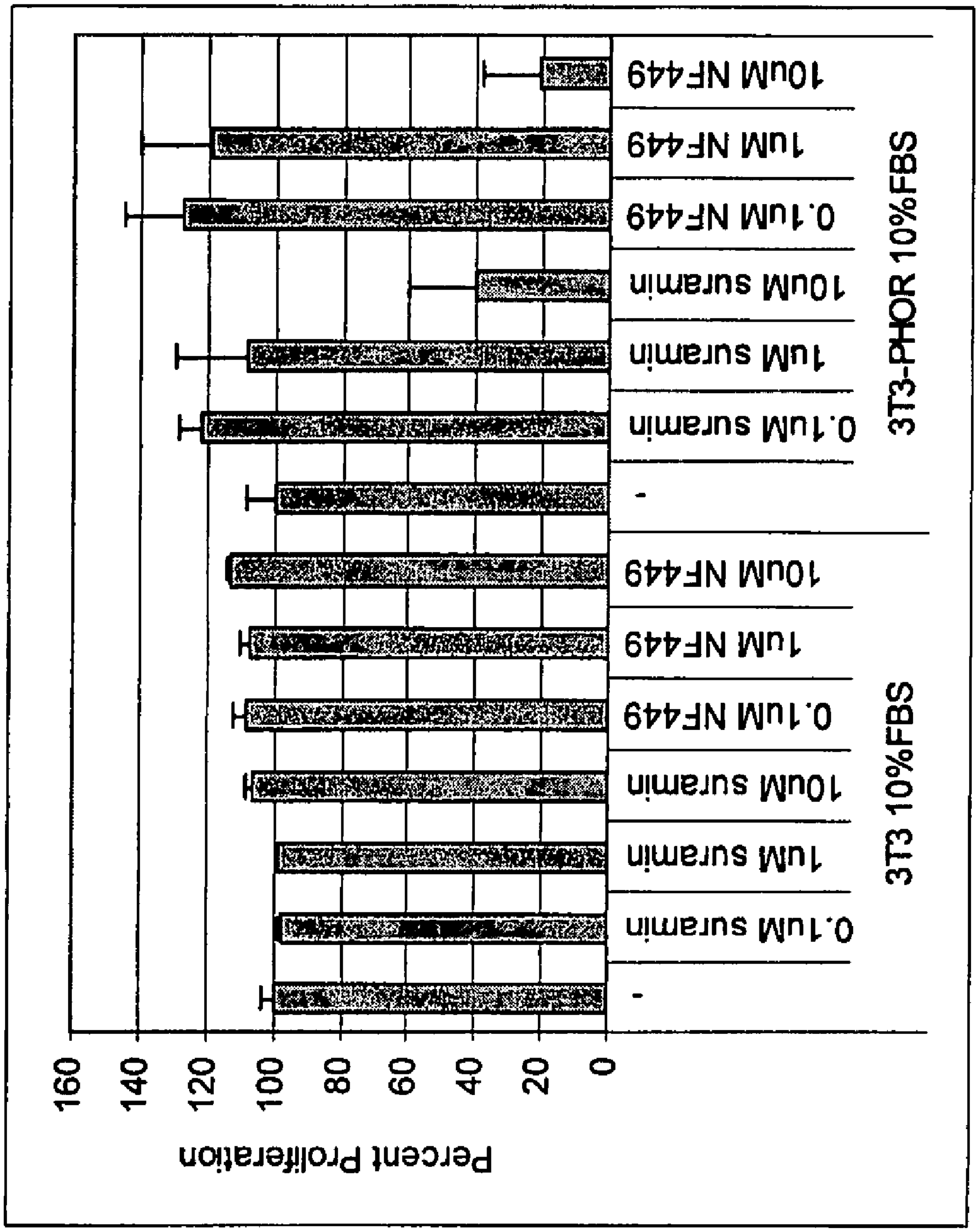

GPCR transmit their signal by activating trimeric G proteins. Once GPCRs are activated, the associated Ga subunit binds GTP, dissociates from the receptor and participates in downstream signaling events (Schild, D., and Restrepo, D. Physiol Rev. 1998, 78:429-66). In order to determine that inhibition of Ga subunits has an effect on 101P3A11 mediated cell growth, the effect of two Ga inhibitors on the proliferation of 3T3-101P3A11 cells was investigated. Control 3T3 and 3T3-101P3A11 cells were grown in the presence or absence of suramin or its derivative NF 449 (Sigma). Cells were analyzed for proliferation 72 hours later (FIG. 35). The experiment was performed in triplicate. The data showed that suramin and NF449 inhibited the proliferation of 3T3-101P3A11 cells by 60% and 80%, respectively. This response was 101P3A11 specific as suramin and NF449 had no effect on the proliferation of control 3T3 cells. Similarly, inhibition of G protein activation by suramin and NF449 in PC3 cells inhibits the proliferation of PC3-101P3A11 cells grown in 5% FBS (Figure M4). In parallel with the inhibitory effect of suramin and NF449 on PC3-101P3A11 proliferation, we demonstrate their inhibitory effect on 101P3A11-mediated signaling in prostate cancer cells (Figure M2). As shown in FIGS. 27 and 28, treatment with FBS induces ERK phosphorylation in 101P3A11-expressing cells. This ERK phosohorylation and activation was inhibited by suramin and NF449 in PC3-101P3A11 and 3T3-101P3A11 cells. ERK phosphorylation was inhibited in a dose dependent manner in PC3-101P3A11 cells treated with suramin. Thus, as 101P3A11 is involved in GPCR activity, it is used as target for diagnostic, prognostic, preventative and/or therapeutic purposes.

GPCRs can be activated by a variety of ligands, including hormones, neuropeptides, chemokines, odorants and phospholipids. In the case of olfactory receptors, individual olfactory receptors may recognize multiple odorants, and can are activated by a diverse array of molecules. These ligands and molecules recognized by a receptor (as described above) are small molecules as described herein.

Figures 36A, 36B:
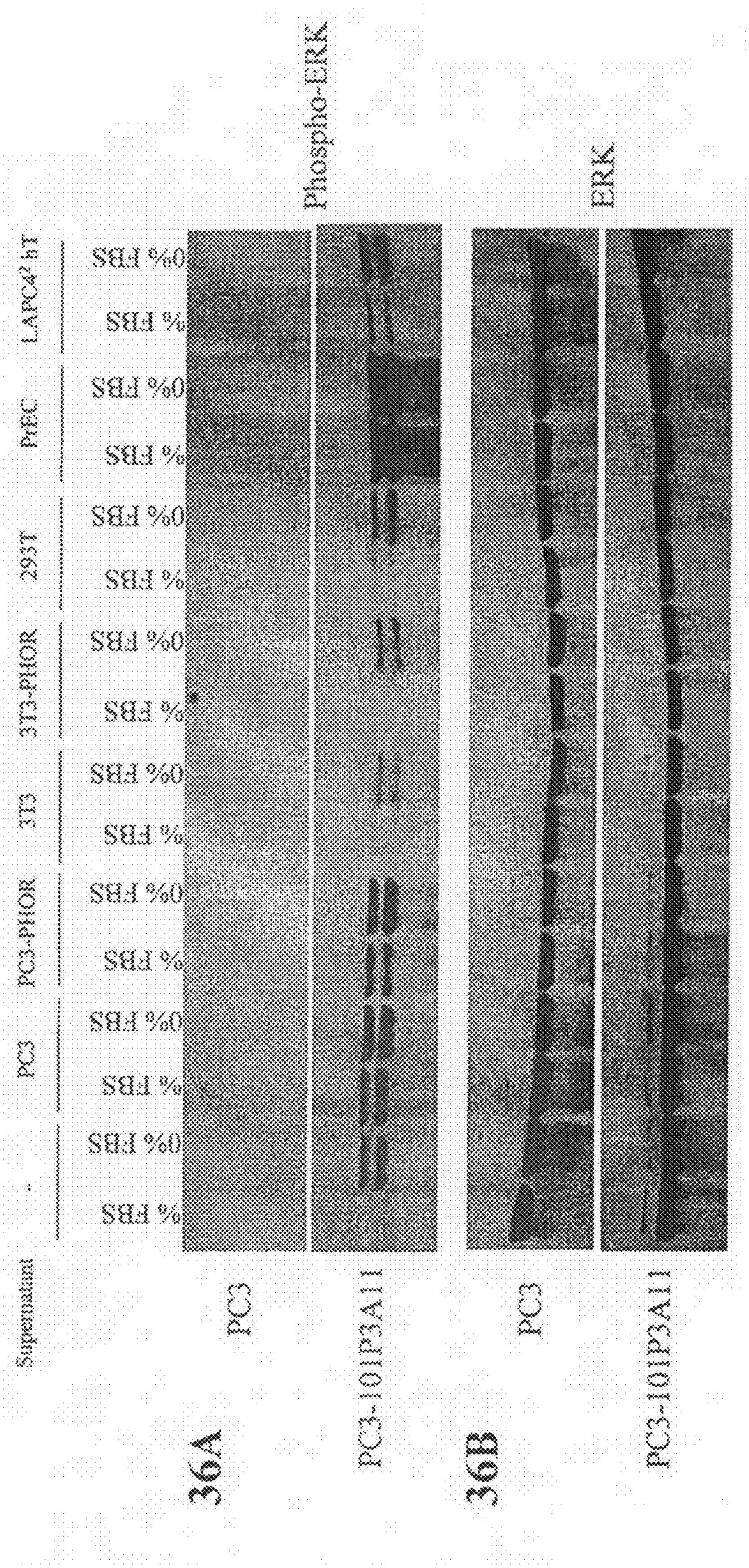
FIGS. 36A-36B. 101P3A11 Mediated ERK Phosphorylation By Conditioned Media.

In order to identify 101P3A11 (small molecule) ligand(s), the possibility that epithelial cells may be secreting 101P3A11 activators was investigated (FIG. 36A and FIG. 36B). Prostate cancer epithelial cells, (PC3, PC3-101P3A11, LAPC4$^2$hT), normal prostate cells (PrEC), fibroblasts (3T3, 3T3-101P3A11), and human kidney epithelial cells (293T) were grown in the presence or absence of FBS. Cell supernatants were collected and used to stimulate PC3 and PC3-101P3A11 cells. Cell lysates from resting and supernatant treated PC3 and PC3-101P3A11 cells were lysed and analyzed by Western blotting with anti-Phospho-ERK (FIG. 36A) and anti-ERK (FIG. 36B) mAb. As shown in FIG. 36A and FIG. 36B, supernatants form normal prostate cells, PrEC, and prostate cancer cells, PC3, PC3-101P3A11 and LAPC4$^2$hT, induced the phosphorylation of ERK in PC3-101P3A11 but not control PC3 cells. In contrast, no specific ERK phosphorylation was observed using supernatants from 3T3 or 293T cells. Our results show that prostate cells, grown in the absence of serum, produce one or more factors that contribute to the activation of 101P3A11 mediated signaling events. Thus, as 101P3A11 responds to stimuli and functions in signaling and GPCR activity, it is used as target for diagnostic, prognostic, preventative and/or therapeutic purposes.

Example 45

Inhibitors of 101P3A11 GPCR Function

As mentioned in the Example entitled "Homology Comparison of 101P3A11 to Known Sequences," GPCRs are activated by ligand binding to the extracellular loops, resulting in the activation of trimeric G proteins and the initiation of several signaling cascades. Using this information, several therapeutic and small molecule strategies are utilized to inhibit GPCR activation or downstream signaling events.

One strategy inhibits receptor and ligand binding. Recent studies using several types of GPCRs, have demonstrated the effectiveness of this strategy (Fawzi A B, et al. 2001, Mol. Pharmacol., 59:30). Using a compound named SCH-202676, they inhibited agonist and antagonist binding to GPCRs by allosterically hindering ligand-GPCR interaction. Using this and even more specific allosteric (small molecule) inhibitors, signal transduction through 101P3A11 is inhibited, thereby providing therapeutic, prognostic, diagnostic and/or prophylactic benefit.

A second approach is to inhibit G alpha subunit activation. Activation of GPCRs results in the exchange of GTP for GDP on the G alpha subunit of the trimeric G protein. Inhibition of Ga activation prevents the activation of downstream signaling cascades and therefore biological effects of GPCR. One molecule used to inhibit GDP exchange on Ga subunits is Suranim (Freissmuth M et al, 1996, Mol. Pharmacol, 49:602). Since suranim functions as a universal Ga inhibitor, it prevents the activation of most Ga subunits. Using techniques described, for example and without limitation, in the present Examples entitled "In vivo Assay for 101P3A11 Tumor Growth Promotion;" "Identification and Confirmation of Potential Signal Transduction Pathways," "101P3A11 Functions as a GPCR," and "Regulation of Transcription", small molecules are identified that selectively inhibit the Gα subunit that associates with 101P3A11, thereby providing therapeutic, prognostic, diagnostic and/or prophylactic benefit.

A third approach is to inhibit Gα subunit association with GPCR. In order for trimeric G proteins to be activated following GPCR/ligand interaction, it is necessary for them to associate with their corresponding GPCR. Mutational analysis has mapped the interaction of Gα to the first and third intracellular loops of GPCRs (Heller R at al. 1996, Biochem. Biophys. Res. Commun). Several studies have used synthetic (small molecule) peptides corresponding to the intracellular sequence of loops 1 and 3 as inhibitors (Mukherjee, S., et al. 1999, J. Biol. Chem.). Using such short peptides that serve as receptor mimics, they are used to compete for binding of Ga subunits to 101P3A11 and thereby provide therapeutic, prognostic, diagnostic and/or prophylactic benefit.

Thus, compounds and small molecules designed to inhibit 101P3A11 function and downstream signaling events are used for therapeutic diagnostic, prognostic and/or preventative purposes.

Example 46

Involvement in Tumor Progression

Figure 37:
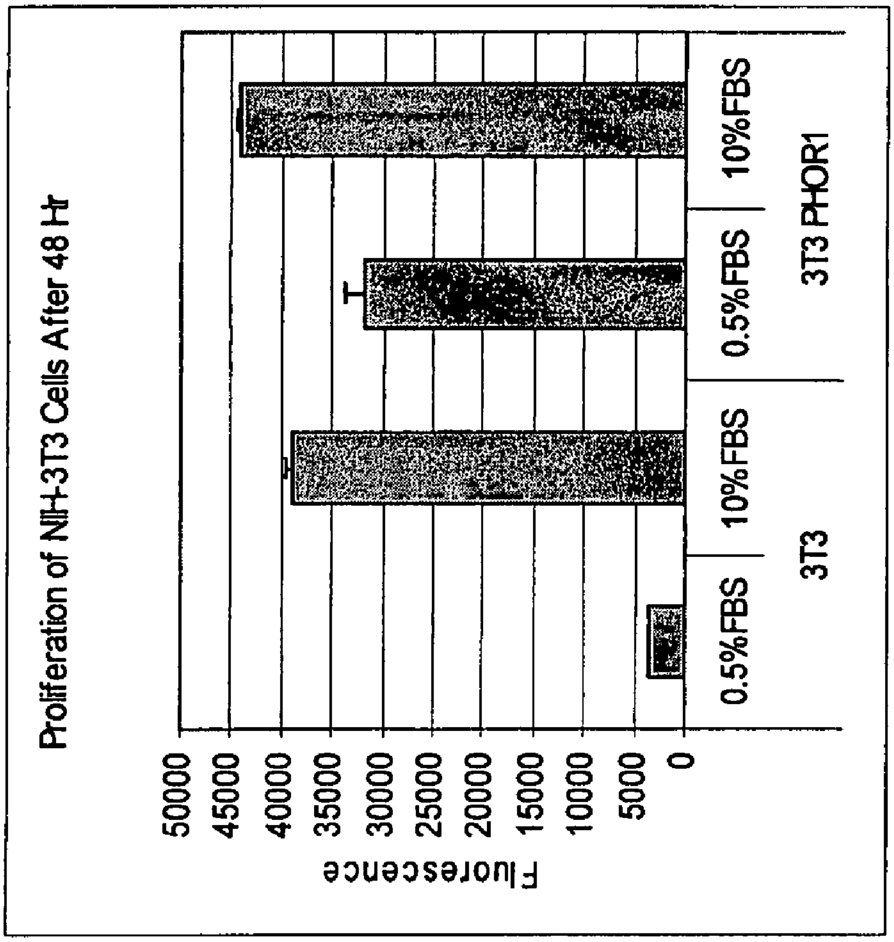
FIG. 37. 101P3A11 Enhances the Proliferation of 3T3 Cells. Control NIH 3T3 and 3T3-101P3A11 cells were grown in the presence of absence 0.5 or 10% FBS. Proliferation was analyzed by Alamar blue after 48 hours. Expression of 101P3A11 induced a 6 fold increase in the proliferation of 3T3 cells grown in 0.5% FBS.

The 101P3A11 gene can contribute to the growth of cancer cells. The role of 101P3A11 in tumor growth is confirmed in a variety of primary and transfected cell lines including prostate, colon, bladder and kidney cell lines, as well as NIH 3T3 cells engineered to stably express 101P3A11. Parental cells lacking 101P3A11 and cells expressing 101P3A11 are evaluated for cell growth using a well-documented proliferation assay (Fraser S P, et al., Prostate 2000; 44:61, Johnson D E, Ochieng J, Evans S L. Anticancer Drugs. 1996, 7:288). Using such a technique, we demonstrated (see FIG. 37) that 101P3A11 imparts a growth advantage on NIH 3T3 cells. 3T3-neo and 3T3-101P3A11 cells were grown in 0.5% or 10% FBS and analyzed 48 hours later. The assay was performed in triplicate. Expression of 101P3A11 resulted in 6-fold increase in proliferation relative to control 3T3 cells grown in 0.5% FBS. In addition, 101P3A11 imparts a growth advantage to PC3 cells as shown in Figures M7 and M16. PC3 cells grown in 0.5% and 10% FBS were compared to PC3-101P3A11. Figure M7 shows that expression of 101P3A11 enhances the proliferation of PC3 cells under both conditions. The effect of 101P3A11 was also observed on cell cycle progression. Control and 101P3A11-expressing cells were grown in low serum overnight, and treated with 10% FBS for 48 and 72 hrs. Cells were analyzed for BrdU and propidium iodide incorporation by FACS analysis. Figure M16 shows that expression of 101P3A11 enhances cell cycle entry in both 3T3 and PC3 cells.

Figure 43:
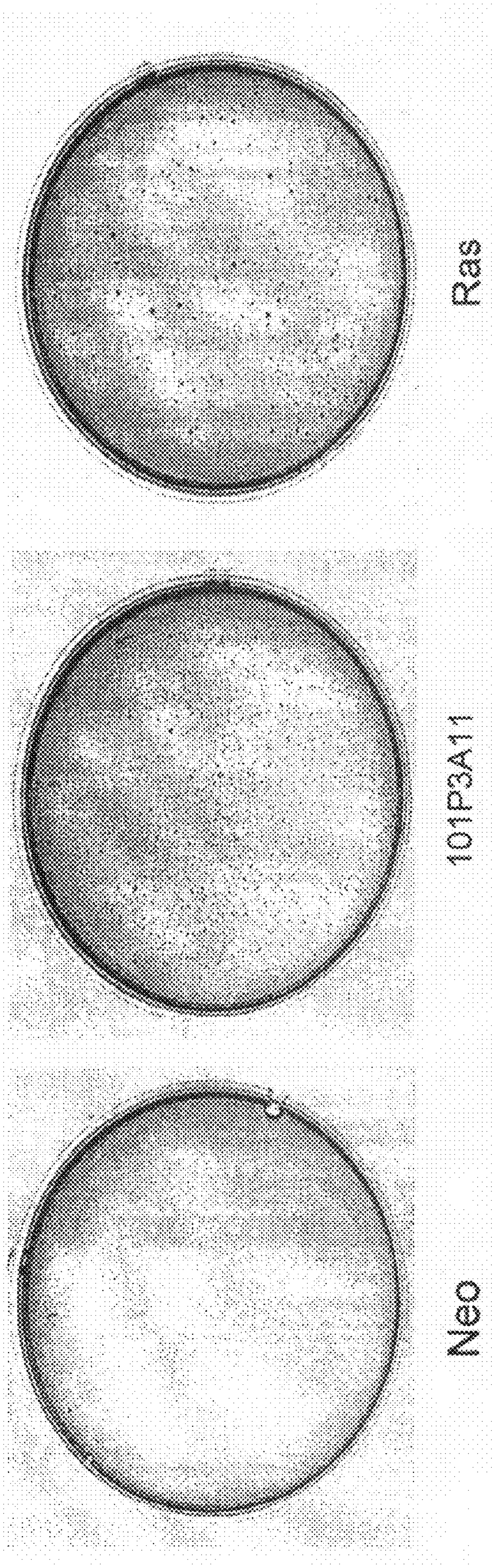
FIG. 43 shows that 101P3A11 induces colony formation in a soft agar assay.

To confirm the role of 101P3A11 in the transformation process, its effect in colony forming assays was investigated. Parental NIH-3T3 cells lacking 101P3A11 were compared to NIH-3T3 cells expressing 101P3A11, using a soft agar assay under stringent and more permissive conditions (Song Z. et al. Cancer Res. 2000; 60:6730). The results are shown in FIG. 43, where 101P3A11 induces colony formation of over 100 fold increase relative to neo resistant controls. We previously showed that expression of 101P3A11 in NIH 3T3 cells induces the growth of these cells in soft agar (129-24usu1), indicating that 101P3A11 participates in the process of transformation.

To confirm the role of 101P3A11 in invasion and metastasis of cancer cells, a well-established assay is used. A non-limiting example is the use of an assay which provides a basement membrane or an analog thereof used to detect whether cells are invasive (e.g., a Transwell Insert System assay (Becton Dickinson) (Cancer Res. 1999; 59:6010)). Control cells, including prostate, colon, bladder and kidney cell lines lacking 101P3A11 are compared to cells expressing 101P3A11. Cells are loaded with the fluorescent dye, calcein, and plated in the top well of a support structure coated with a basement membrane analog (e.g. the Transwell insert) and used in the assay. Invasion is determined by fluorescence of cells in the lower chamber relative to the fluorescence of the entire cell population.

101P3A11 can also play a role in cell cycle and apoptosis. Parental cells and cells expressing 101P3A11 are compared for differences in cell cycle regulation using a well-established BrdU assay (Abdel-Malek Z A. J Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle. Alternatively, the effect of stress on apoptosis is evaluated in control parental cells and cells expressing 101P3A11, including normal and tumor prostate, colon and lung cells. Engineered and parental cells are treated with various chemotherapeutic agents, such as etoposide, flutamide, etc, and protein synthesis inhibitors, such as cycloheximide. Cells are stained with annexin V-FITC and cell death is measured by FACS analysis. The modulation of cell death by 101P3A11 can play a critical role in regulating tumor progression and tumor load.

When 101P3A11 plays a role in cell growth, transformation, invasion or apoptosis, it is used as a target for diagnostic, prognostic, preventative and/or therapeutic purposes.

Example 47

Involvement in Angiogenesis

Angiogenesis or new capillary blood vessel formation is necessary for tumor growth (Hanahan, D.; Folkman, J.; Cell. 1996, 86:353; Folkman J. Endocrinology. 1998 139:441). Several assays have been developed to measure angiogenesis in vitro and in vivo, such as the tissue culture assays endothelial cell tube formation and endothelial cell proliferation. Using these assays as well as in vitro neo-vascularization, the role of 101P3A11 in angiogenesis, enhancement or inhibition, is confirmed.

For example, endothelial cells engineered to express 101P3A11 are evaluated using tube formation and proliferation assays. The effect of 101P3A11 is also confirmed in animal models in vivo. For example, cells either expressing or lacking 101P3A11 are implanted subcutaneously in immunocompromised mice. Endothelial cell migration and angiogenesis are evaluated 5-15 days later using immunohistochemistry techniques. 101P3A11 affects angiogenesis, and it is used as a target for diagnostic, prognostic, preventative and/or therapeutic purposes Example 48

Regulation of Transcription

The cell surface localization of 101P3A11 and its similarity to GPCRs indicate that 101P3A11 is effectively used as a modulator of the transcriptional regulation of eukaryotic genes. Regulation of gene expression is confirmed, e.g., by studying gene expression in cells expressing or lacking 101P3A11. For this purpose, two types of experiments are performed.

In the first set of experiments, RNA from parental and 101P3A11-expressing cells are extracted and hybridized to commercially available gene arrays (Clontech) (Smid-Koopman E et al. Br J Cancer. 2000. 83:246). Resting cells as well as cells treated with FBS or androgen are compared. Differentially expressed genes are identified in accordance with procedures known in the art. The differentially expressed genes are then mapped to biological pathways (Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Thus, 101P3A11 plays a role in gene regulation, and it is used as a target for diagnostic, prognostic, preventative and/or therapeutic purposes.

Example 49

Involvement in Cell Adhesion

Cell adhesion plays a critical role in tissue colonization and metastasis. 101P3A11 can participate in cellular organization, and as a consequence cell adhesion and motility. To confirm that 101P3A11 regulates cell adhesion, control cells lacking 101P3A11 are compared to cells expressing 101P3A11, using techniques previously described (see, e.g., Haier et al, Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. In another embodiment, cells lacking or expressing 101P3A11 are analyzed for their ability to mediate cell-cell adhesion using similar experimental techniques as described above. Both of these experimental systems are used to identify proteins, antibodies and/or small molecules that modulate cell adhesion to extracellular matrix and cell-cell interaction. Cell adhesion plays a critical role in tumor growth, progression, and, colonization, and 101P3A11 is involved in these processes. Thus, it serves as a diagnostic, prognostic, preventative and/or therapeutic modality.

Example 50

Protein-Protein Association

Several GPCRs have been shown to interact with other proteins, thereby regulating signal transduction, gene transcription, transformation and cell adhesion (Sexton P M et al, Cell Signal. 2001, 13:73; Turner C E, J Cell Sci. 2000, 23:4139). Using immunoprecipitation techniques as well as two yeast hybrid systems, proteins are identified that associate with 101P3A11. Immunoprecipitates from cells expressing 101P3A11 and cells lacking 101P3A11 are compared for specific protein-protein associations.

Studies are performed to confirm the extent of association of 101P3A11 with effector molecules, such as receptors, adaptor proteins and paxillin, kinases, phsophates and Ga proteins. Studies comparing 101P3A11 positive and 101P3A11 negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodology (Curr Opin Chem. Biol. 1999, 3:64). A vector carrying a library of proteins fused to the activation domain of a transcription factor is introduced into yeast expressing a 101P3A11-DNA-binding domain fusion protein and a reporter construct. Protein-protein interaction is detected by colorimetric reporter activity. Specific association with effector molecules and transcription factors directs one of skill to the mode of action of 101P3A11, and thus identifies therapeutic, prognostic, preventative and/or diagnostic targets for cancer. This and similar assays are also used to identify and screen for small molecules that interact with 101P3A11.

Thus it is found that 101P3A11 associates with proteins and small molecules. Accordingly, 101P3A11 and these proteins and small molecules are used for diagnostic, prognostic, preventative and/or therapeutic purposes.

Example 51

Biological Effect of Anti-101P3A11 Antibodies

Figure 38:
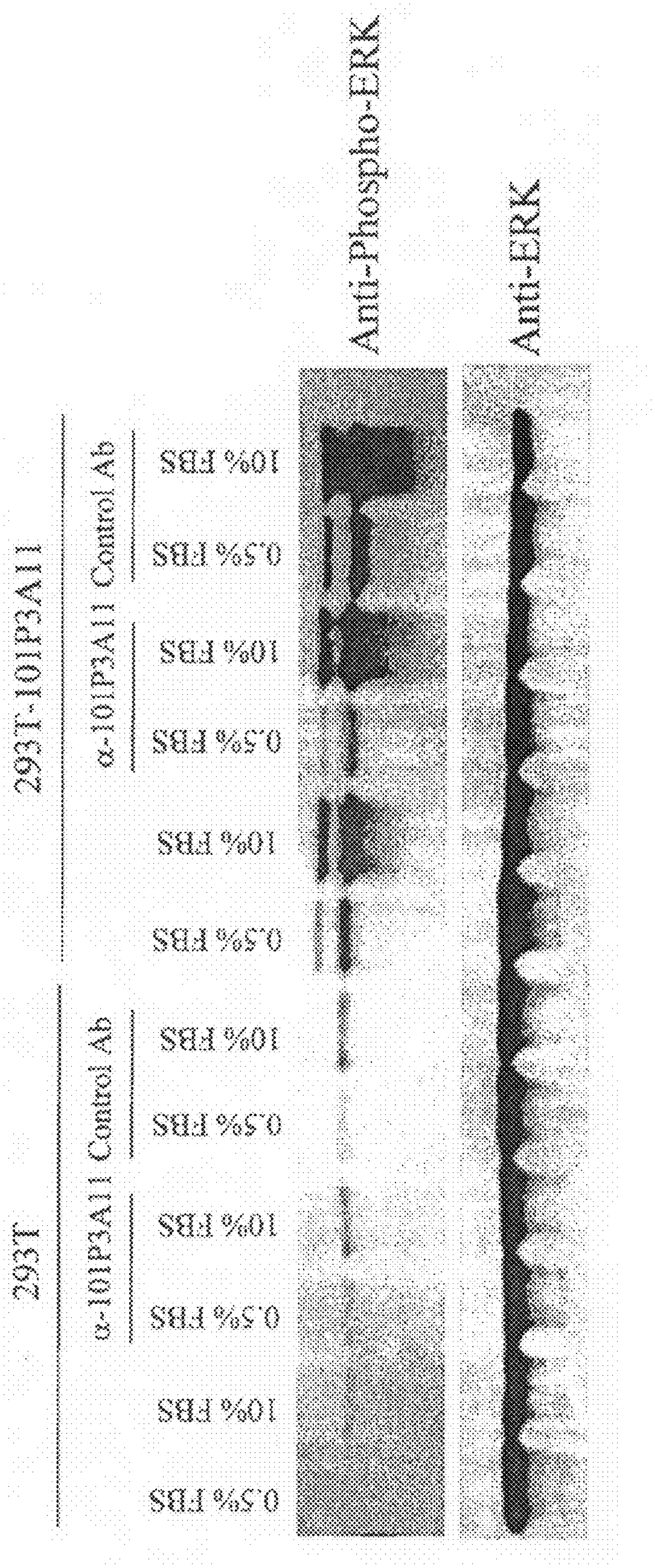
FIG. 38. Inhibition of 101P3A11 Mediated ERK Phosphorylation by 101P3A11 Specific Antibodies. Expression of 101P3A11 induced ERK phosphorylation in 293T cells. Anti-101P3A11 pAb inhibited ERK Phosphorylation in 293T-101P3A11 cells.
Figure 39:
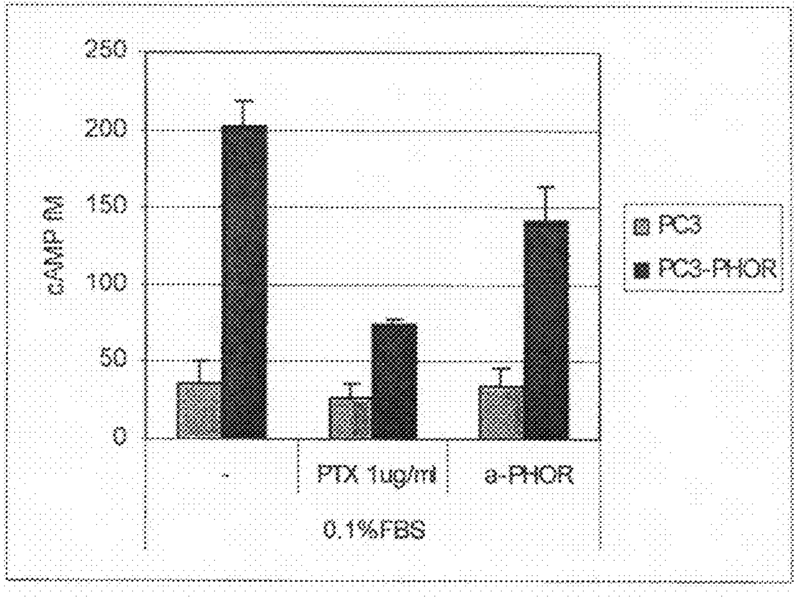
FIG. 39. Anti-101P3A11 Ab Mediated cAMP Accumulation in PC3-101P3A11 Cells. Control PC3 cells and cells expressing 101P3A11 were treated with anti-101P3A11 pAb for 2 min and evaluated for intracellular cAMP content. The assay was performed in duplicate.

The generation of anti-101P3A11 polyclonal Ab (pAb) using an amino-terminal peptide encoding amino acids 1-14 (MVDPNGNESSATYF; SEQ ID NO: 46) as antigen was reported in our Priority Application. The effect of this antibody on 101P3A11 mediated ERK phosphorylation (FIG. 38) and cAMP accumulation (FIG. 39) was determined. 293T cells were transfected with control or 101P3A11 cDNA. Cells were allowed to rest overnight, and treated with anti-101P3A11 or control Ab in the presence of 0.5% or 10% FBS. Cells were lysed and analyzed by Western blotting with anti-Phospho-ERK and anti-ERK mAb. FIG. 38 shows that expression of 101P3A11 induces ERK phosphorylation in cells treated with 0.5 or 10% FBS. Anti-101P3A11 pAb reduced the phosphorylation of ERK in 293T-101P3A11 cells treated with 0.5% FBS. The ERK overlay demonstrated equal loading, supporting the specificity of this data.

In order to confirm that anti-101P3A11 pAb has a detectable effect on cAMP accumulation, PC3 and PC3-101P3A11 cells were grown in 0.1% FBS and treated with anti-101P3A11 pAb. Cells were analyzed for cAMP content as described in FIG. 32. Expression of 101P3A11 induced a 5-fold increase in cAMP accumulation in PC3 cells, which was partially inhibited by PTX. Treatment of PC3-101P3A11 cells with anti-101P3A11 pAb resulted in a 4-fold increase in cAMP accumulation in PC3-101P3A11 but not control PC3 cells. Results shown in FIG. 38 and FIG. 39 indicate that anti-101P3A11 pAb produces a measurable biological effect in cells expressing 101P3A11. Accordingly, 101P3A11 is used as a target for diagnostic, prognostic, preventative and/or therapeutic purposes.

Example 52

101P3A11 Promoters

A eukaryotic cells promoter is a short DNA sequence located in the 5' region of a gene. It provides binding sites for RNA polymerase and associated transcriptional cofactors, which upon assembly promotes transcription of the gene. In humans, most genes are transcribed by RNA polymerase II. The promoter DNA sequence normally contains binding motifs for RNA polymerases and its associated cofactors and activators including a TATA-box, cap signal, CCAAT-box and the GC-box. A eukaryotic cell enhancer is DNA sequence where transcriptional factors and their associated coactivators or suppressors bind and interact with promoter-bound RNA polymerase to regulate the expression of the gene located next to the promoter. While a promoter(s) locates close to the transcription starting site(s) of a gene (usually 25-30 base pairs), enhancers can be found up to 50,000 base pairs in either direction to the transcription starting site(s) of the gene. There are many different gene regulatory proteins, namely transcription factors and their associated coactivators and cosuppressors that bind to specific enhancer sequences and regulate gene expression. These proteins, upon interaction with specific DNA regulatory sequences and with each other, allow each gene to be regulated up or down in different tissues and cell types. Chapter 9. "Control of gene expression" in Molecular Biology of the Cell. 3$^{rd}$ ed. Ed. by Alberts et al., (New York and London) Garland Publishing, 1994).

Tissue specific gene expression is associated with the presence of specific combinations of transcription factors and their associated coactivators and suppressors, the presence of specific binding sites present in the DNA regulatory region of the gene for these factors, and the activation or inactivation of signaling pathways that modulate their relative activity. For example, prostate specific expression of prostate specific antigen, (PSA, or human kallikrein 3), is dependent on the presence of androgen receptor binding elements in defined 5' upstream enhancer and promoter sequences of the gene and intact androgen receptor signaling pathway (Pang S, et al., Cancer Res 1997 Feb. 1; 57(3):495-9). It is also dependent on the presence of other cis-acting DNA regulatory elements in the promoter region (Zhang J, et al., Nucleic Acids Res. 1997, Aug. 1; 25(15):3143-50.) and on the expression of other transcription factors, such as the prostate specific ets-like transcription factor (Oettgen P, et al., J Biol Chem. 2000, Jan. 14; 275(2): 1216-25).

With the accumulation of data and knowledge on human gene expression, promoters and enhancers are identified using different algorithms and computer programs (Chapter 8 "Gene Prediction" in Bioinformatics—Sequence and Genome Analysis, ed. by David W. Mount. Cold Spring Harbor Laboratory Press, 2001). Accordingly, we identified (Table LV) promoters in a 5.04 kB 5' upstream genomic region of the 101P3A11 coding sequence using Neural Network Promoter Prediction computer program (Reese, M. G. and Eeckman, F.H. (1995) Novel Neural Network Algorithms for Improved Eukaryotic Promoter Site Recognition. Accepted talk for The Seventh International Genome Sequencing and Analysis Conference, Hyatt Regency, Hilton Head Island, South Carolina, September 16-20, 1995), indicated by the underlined sequences in Table LIV. Using a program called SIGNAL SCAN (Prestridge D. S. (1991) SIGNAL SCAN: A computer program that scans DNA sequences for eukaryotic transcriptional elements. CABIOS 7, 203-206.), which searches a comprehensive database of regulatory element binding sites, we found numerous transcriptional binding sites for various known transcription factors in the 5.04 kB sequence 5' to the 101P3A11 gene, suggesting the presence of specific enhancer regions that may mediate tissue specific 101P3A11 transcription. Such transcription factors include, but are not limited to, NFAT, NF-1, NF-E, CP2, AP1, AP-2, Spl, OCT-I, OCT-2, NFKB, CREB, CTF, TFIIA, TFIIB, TFIID, Pit-I, C/EBP, SRF, and various steroid receptors, such as glucocorticoid receptor (GR) and androgen receptors (AR) (Mitchell P J and Tijan R (1989) Science 245: 371). Comparison of the 5 kB upstream sequence of the 101P3A11 gene to the 5 kB upstream sequence of the PSA gene, 5 homologous regions were found that are important for prostate cell specific expression. Table LVI shows the alignment of the these sequences and also indicates predicted transcription factor binding sites common to both sequences identified using SIGNAL SCAN.

With the accumulation of data and knowledge on human gene expression, promoters and enhancers are identified using different algorithms and computer programs (Chapter 8 "Gene Prediction" in Bioinformatics—Sequence and Genome Analysis, ed. by David W. Mount. Cold Spring Harbor Laboratory Press, 2001). Accordingly, we identified (Table LV) promoters in a 5.04 kB 5' upstream genomic region of the 101P3A11 coding sequence using Neural Network Promoter Prediction computer program (http://www-.fruitfly.org/seq_tools/nnppAbst.html; Reese, M. G. and Eeckman, F. H. (1995) Novel Neural Network Algorithms for Improved Eukaryotic Promoter Site Recognition. Accepted talk for The Seventh International Genome Sequencing and Analysis Conference, Hyatt Regency, Hilton Head Island, S.C., Sep. 16-20, 1995), indicated by the underlined sequences in Table LIV. Using a program called SIGNAL SCAN (http://bimas.dcrt.nih.gov/molbio/signal/; Prestridge, D.S. (1991) SIGNAL SCAN: A computer program that scans DNA sequences for eukaryotic transcriptional elements. CABIOS 7, 203-206.), which searches a comprehensive database of regulatory element binding sites, we found numerous transcriptional binding sites for various known transcription factors in the 5.04 kB sequence 5' to the 101P3A11 gene, suggesting the presence of specific enhancer regions that may mediate tissue specific 101P3A11 transcription. Such transcription factors include, but are not limited to, NFAT, NF-1, NF-E, CP2, AP1, AP-2, Sp1, OCT-I, OCT-2, NFKB, CREB, CTF, TFIIA, TFIIB, TFIID, Pit-I, C/EBP, SRF, and various steroid receptors, such as glucocorticoid receptor (GR) and androgen receptors (AR) (Mitchell P J and Tijan R (1989) Science 245: 371). Comparison of the 5 kB upstream sequence of the 101P3A11 gene to the 5 kB upstream sequence of the PSA gene, 5 homologous regions were found that are important for prostate cell specific expression. Table LVI shows the alignment of the these sequences and also indicates predicted transcription factor binding sites common to both sequences identified using SIGNAL SCAN.

Experimentally, one defines the regions in the 5' genomic upstream regions of the 101P3A11 gene using various methods well known in the art, such as deletion and mutation analysis of the putative regulatory regions fused to a transcriptional reporter gene such as luciferase or chloramphenicol acetyl-transferase. These transcriptional reporter vectors are then introduced into cell lines, tissues, or transgenic animals to analyze the tissue and cell type specificity of transcription and expression of the reporter gene. To identify transcription factors and proteins that interact with specific 101P3A11 transcriptional regulatory sequences, one employs one or more of various techniques known in the art such as DNAse footprinting, gel mobility shift assays, and DNA/protein affinity chromatography. Various techniques concerning use of promoters are set forth, e.g., U.S. Pat. No. 5,919,652 which concerns embodiments of nucleic acid compositions that comprise prostate specific antigen (PSA) promoter alone or in combination with a cytomegalovirus (CMV) promoter and related uses; and, U.S. Pat. No. 6,110,702 which concerns PSA positive regulatory sequence (PSAR) and related uses.

Once regulatory sequences are identified that mediate 101P3A11 tissue-specific expression, these sequences are employed in various gene therapeutic strategies for cancer, such as driving tissue-specific expression of a toxic gene or a cell suicide gene. Such cell suicide strategies are currently employed using the PSA-promoter enhancer using the thymidine kinase/ganciclovir system (Suzuki S, Tadakuma T, Asano T, Hayakawa M. Cancer Res. 2001 Feb. 15; 61(4): 1276-90). Unlike PSA, which is an androgen regulated gene, 101P3A11 does not exhibit androgen regulated expression. Thus, identification and use of regulatory sequences of the 101P3A11 gene that mediate, e.g., prostate-specific, but androgen insensitive gene expression, is useful for the treatment of both early stage androgen sensitive and late stage androgen insensitive or hormone refractory prostate cancer.

Example 53

Generation of PHOR-1 Monoclonal Antibodies

The use of agents to identify the presence of PHOR-1 in biopsy specimens or to neutralize the effect of PHOR-1 has a beneficial effect in diagnosis, prognoosis, prophylaxis and/or therapy. One particularly useful class of anti PHOR-1 agents is antibodies, in particular monoclonal antibodies (mAbs) to PHOR-1. Anti PHOR-1 Abs, such as mAbs, are generated that react with the epitopes of the PHOR-1 protein such that they either indicate it's presence, disrupt or modulate it's biological function (for example those that would disrupt the interaction with ligands or proteins that mediate or are involved in it's biological activity) or are able to carry a toxin to the cell which is expressing PHOR-1.

The term anti PHOR-1 antibody as used herein is to be understood to cover antibodies to any epitope of the PHOR-1 gene product. Diagnostic mAbs, e.g. those used for imaging or immunocytochemistry, comprise those that specifically bind epitopes of PHOR-1 protein and thus demonstrate its presence. Therapeutic mAbs include those that are useful for diagnosis but also comprise those that specifically bind epitopes of PHOR-1 exposed on the cell surface and thus are useful to modulate growth and survival of cells expressing PHOR-1 by disrupting the function of a cell expressing PHOR-1 and/or disrupting the interaction of cells expressing PHOR-1 and the ligand for PHOR-1.

Preferred antibodies which form one aspect of the invention include but are not limited to antibodies named X18(1)4, X18(1)10, X18(1)23, X18(4)7 or prefixed by the number X20 and X47 and derivatives thereof, the production of which is described herein. Hybridomas, respectively, that produce these antibodies were deposited with the ATCC on 14 May 2002.

Pathological conditions which are characterized by the presence of PHOR-1 expression include, but are not restricted to, neoplasms of tissues such as those listed in Table I. One aspect of the invention provides a method of detecting the presence of PHOR-1. A further aspect of the invention provides a method of treatment of conditions characterized by the presence of PHOR-1, comprising administering an effective amount of an anti PHOR-1 antibody. The administration of anti-PHOR-1 antibody is particularly advantageous in the treatment of conditions characterized by the presence of PHOR-1.

The antibodies against PHOR-1 for use according to the invention can be from any species, and can belong to any immunoglobulin class. Thus, for example, the anti PHOR-1 antibody for use according to the invention can be an immunoglobulin G, Immunoglobulin M or immunoglobulin A, Immunoglobulin E.

The anti PHOR-1 antibody can be from an animal, for example mammalian or avian origin, and can be for example of murine, rat or human origin. The antibody can be a whole immunoglobulin, or a fragment thereof, for example a fragment derived by proteolytic cleavage of a whole antibody, such as $F(ab')_2$, Fab' or Fab fragments or fragments obtained by recombinant DNA techniques, for example Fv fragments.

Particularly useful antibodies for use according to the invention include humanized or fully human anti PHOR-1 antibodies and fragments thereof. These antibodies are produced by any suitable procedure including, but not restricted to, mammalian cell and bacterial cell fermentation systems.

The anti PHOR-1 mAbs are prepared by immunological techniques employing PHOR-1 antigens. Thus, for example, any suitable host can be injected (immunized) with a suitable reagent which makes PHOR-1 available as an immunogen. Immune cells from the host, for example splenocytes or lymphocytes, are recovered from the immunized host and immortalized, using for example the method of Kohler et al, Eur. J. Immunol. 6, 511 (1976), or their immunoglobulin genes can be isolated and transferred to an appropriate DNA vector for expression in an appropriate cell type. The resulting cells, generated by either technique, will be selected to obtain a single genetic line producing a single unique type of antibody more commonly known as a monoclonal antibody. Antibody fragments can be produced using techniques such as enzymatic digestion of whole antibodies e.g. with pepsin (Parham, J. Immunol. 131:2895 (1983)) or papain (Lamoyi and Nisonoff, J. Immunol. Meth. 56:235 (1983)), or by recombinant DNA techniques.

Suitable hosts for the production of Mab's to PHOR-1 include mice, rats, hamsters and rabbits. For example, mice are immunized with a number of different reagents which make PHOR-1 available as a source of antigenic material (immunogen). The route and timing if the immunizations will depend on the source and/or embodiment of the immunogen. Sources of immunogen for PHOR-1 include, but are not restricted to, peptide, protein, fusion protein, DNA, RNA, cells or cell membranes. These can be used separately as immunogens or in combination to produce a specific immune reaction to PHOR-1. The use and application of these various immunogens is described fully in the accompanying examples.

Example 54

Generation of Antibodies to PHOR1 Using Peptide Encoding the First 23 N' Terminal Amino Acids of PHOR-1 as the Immunogen In one embodiment eptides encoding the first 23 amino acids of PHOR-1 (MVDPNGNESSATYFILIGLPGLE) (SEQ ID: 47) were generated. These were, synthesized by SigmaGenosys using their custom peptide services. The peptide was synthesized with the addition of a Serine-Glycine-Serine-Glycine-Cysteine (SGSGC) C-terminal linker sequence and then coupled to KLH through the C-terminal cysteine residue. In this orientation the N-terminal PHOR-1 sequence remains free for antigenic recognition.

Balb/c mice were immunized intraperitoneally (i.p.) with 10 μg of peptide every 2 weeks over a 4 week period. The initial immunization was given i.p. in Complete Freunds Adjuvant (CFA) and the subsequent two immunizations were given i.p. in Incomplete Freunds Adjuvant (IFA).

To determine the specificity of the response following immunization, mice were bled 10 days after the final immunization. Reactivity was determined by Enzyme Linked Immunosorbent Assay (ELISA) using non-KLH conjugated (free) peptide as a target. All five mice had very high titers to the antigen.

Two mice with the highest titers were given a final boost of 10 μg peptide in PBS and sacrificed for fusion 3 days later. Spleen cells from the immunized mice were fused with mouse Sp2/0 myeloma cells using PEG 1500 according to standard protocols (Kohler et al, Eur. J. Immunol 6: 511 (1976)). Fused cells were plated in 10 96 well microtiter plates and hybridomas were selected using HAT media supplement. Supernatants from fusion wells were screened 10-17 days later by ELISA against PHOR-1 peptide. Twenty-one positive hybridomas were identified; these hybridomas are set forth in Table L

TABLE L

| Clone number | O.D. |
|---|---|
| X20(5)1 | 0.157 |
| X20(5)2 | 0.511 |
| X20(5)3 | 0.310 |
| X20(5)4 | 0.735 |
| X20(5)5 | 0.160 |
| X20(5)6 | 0.322 |
| X20(5)7 | 0.179 |
| X20(5)8 | 0.173 |
| X20(5)9 | 0.170 |
| X20(5)10 | 1.171 |
| X20(5)11 | 0.172 |
| X20(5)12 | 0.159 |
| X20(5)13 | 0.244 |
| X20(5)14 | 1.204 |
| X20(5)15 | 0.245 |
| X20(5)16 | 0.220 |
| X20(5)17 | 0.225 |
| X20(5)18 | 0.186 |
| X20(5)19 | 0.176 |
| X20(5)20 | 0.224 |
| X20(5)21 | 0.502 |

Example 55

Generation mAbs to PHOR1 Using DNA Immunization

Therapeutic mAbs to PHOR-1 comprise those that react with PHOR-1 epitopes that disrupt or modulate the biological function of PHOR-1, for example those that disrupt its interaction with ligands or proteins that mediate or are involved in its biological activity. Structural modeling and experimental binding data of the murine olfactory receptor S25 indicates that amino acid residues at the junction of extracellular loop 1 and transmembrane domain 3, the region of extracellular loop 2 between transmembrane domains 4 and 5, and the region of extracellular loop 3 between transmembrane domains 6 and 7 are involved in the binding of the ligand hexanol (Floriano, W. B., et al, 2000, Proc. Natl. Acad. Sci., USA, 97:10712-10716).

Thus, in one embodiment, a vector was constructed that encodes the amino acids of extracellular loop 2 (159-202) between transmembrane domains 4 and 5 of PHOR-1 fused at the C-terminus to the human immunoglobulin G1 (IgG) Fc (hinge, CH2, CH3 regions). This construct was used in a DNA based immunization strategy.

Five Balb/c mice were immunized intra-dermally (ID) at the base of their tail. Three immunizations were given to each mouse of 100 μg of DNA in PBS over a two week period. To increase the immune response, each mouse was given an i.p. boost of 2 μg of PHOR-1-Fc protein in tissue culture media 10 days after the final DNA immunization. Bleeds were collected 10 days after the final immunization and reactivity in the sera to the middle loop of PHOR-1 was tested by ELISA using PHOR-1-Fc fusion protein as a target (test 1). In parallel the sera were also tested on an unrelated human Fc fusion protein (test 2). Specific reactivity to the PHOR-1 portion of the fusion protein was indicated.

All mice were sacrificed and fusions and hybridoma selection was carried out as described in Example 54. Hybridoma supernatants were screened 10-17 days later by ELISA using PHOR1-Fc protein as target. PHOR-1-Fc positives were subsequently cross screened on irrelevant Fc proteins to identify PHOR specific clones. A total of 16 positives specific for PHOR1-Fc but not reactive to other Fc fusion proteins were identified, these hybridomas are set forth in Table LI.

TABLE LI

| Clone number | O.D. |
|---|---|
| X1(1)1 | 0.557 |
| X1(1)2 | 0.511 |
| X1(1)3 | 0.610 |
| X1(1)4 | 0.735 |
| X1(1)5 | 0.860 |
| X1(1)6 | 0.322 |
| X1(1)7 | 0.779 |
| X1(1)8 | 0.473 |
| X1(1)9 | 0.770 |
| X1(1)10 | 0.541 |
| X1(1)11 | 0.672 |
| X1(1)12 | 1.209 |
| X1(1)13 | 0.244 |
| X1a(2)1 | 1.109 |
| X1a(2)2 | .654 |
| X1a(2)3 | 0.220 |

Example 56

Generation of Monoclonal Antibodies Specific to Amino Acids 86-310 of PHOR-1

Figure 48:
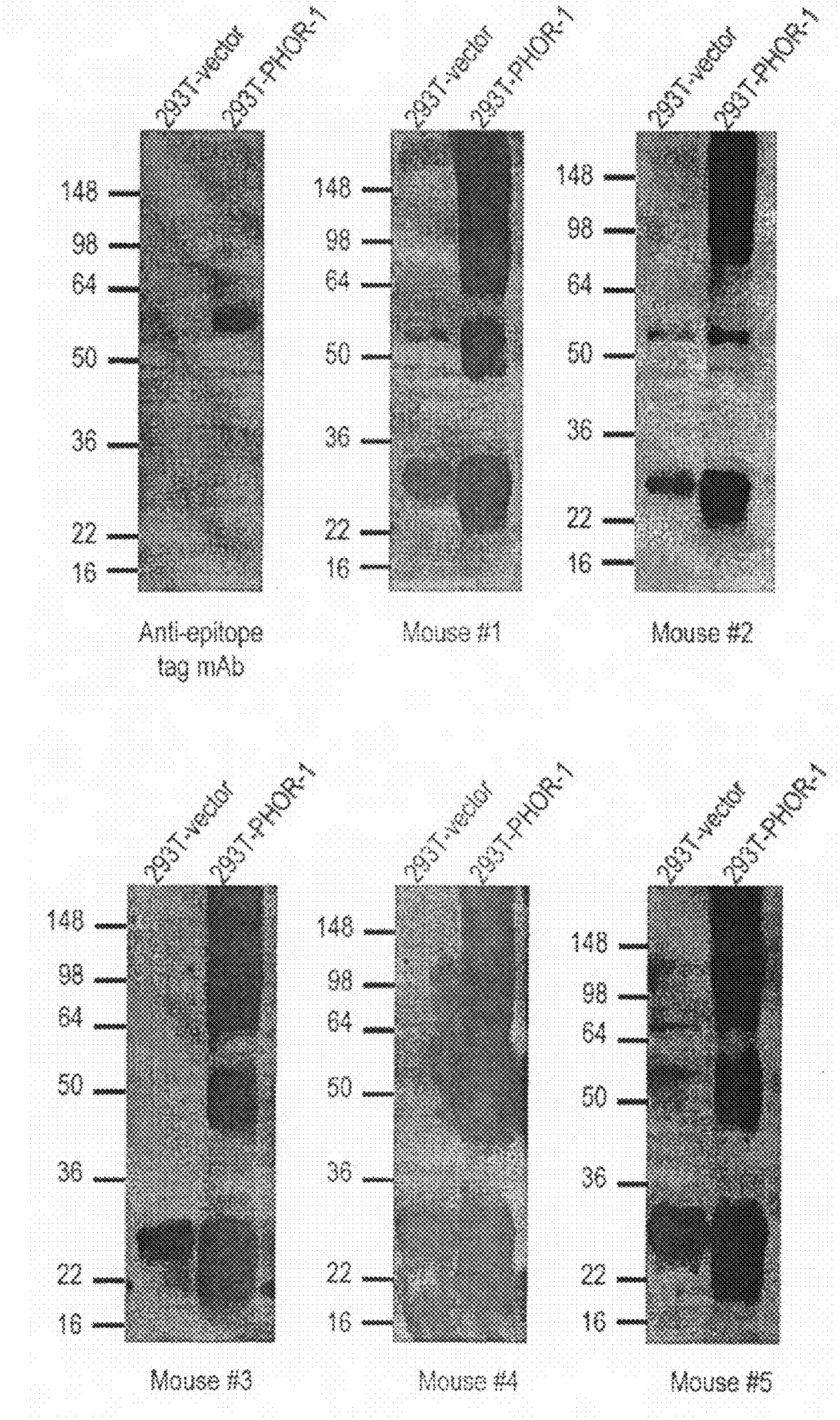
FIG. 48: Recognition of PHOR-1 protein in transfected 293T cells by sera from GST-PHOR-1 immunized mice.
Figure 49:
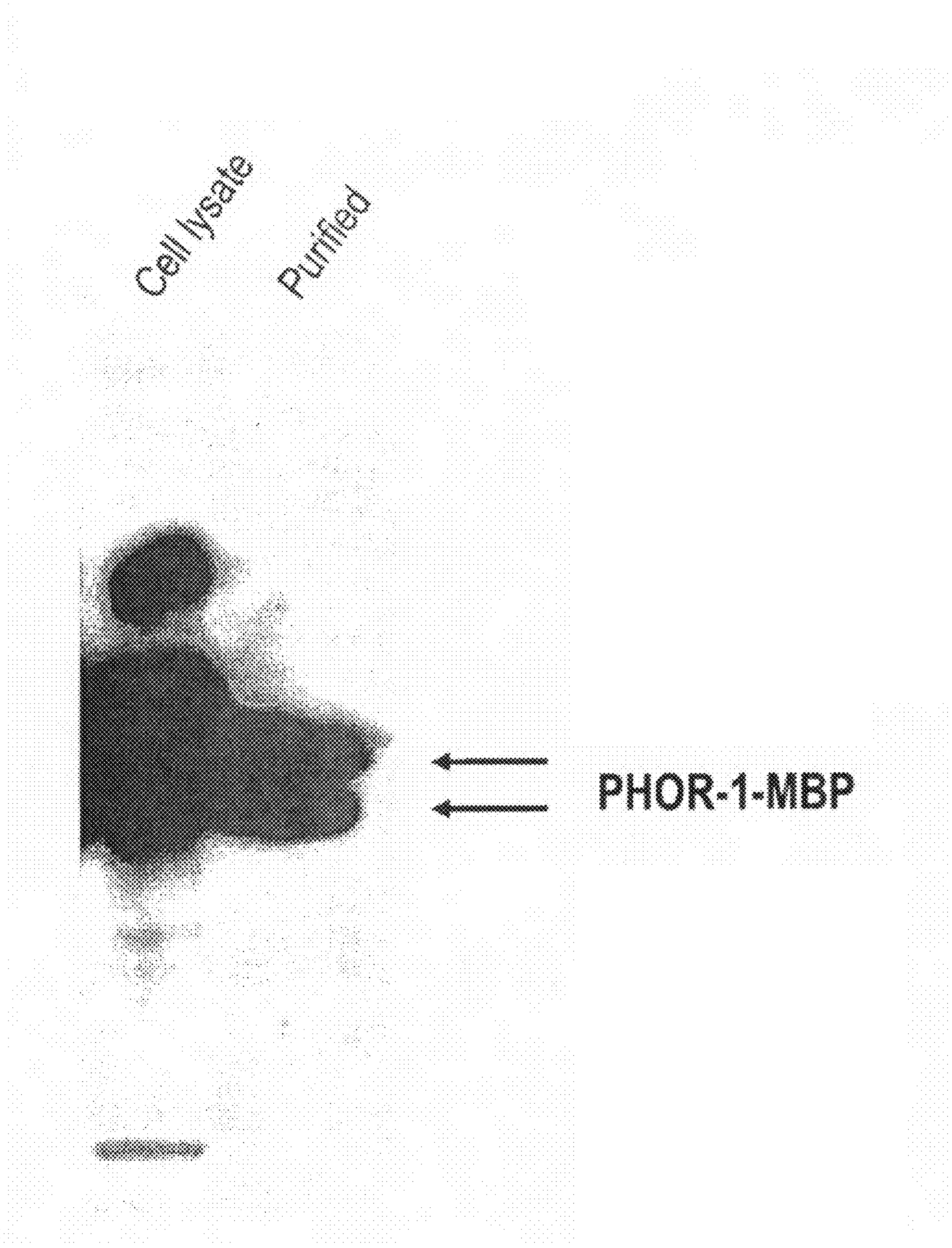
FIG. 49: Data showing that four hybridomas reactive to MBP-PHOR-1 exhibited strong specific reactivity to PHOR-1 protein expressed in cells. This was demonstrated by Western analysis of 293T cells transfected with the epitope tagged PHOR-1 cDNA
Figure 50:
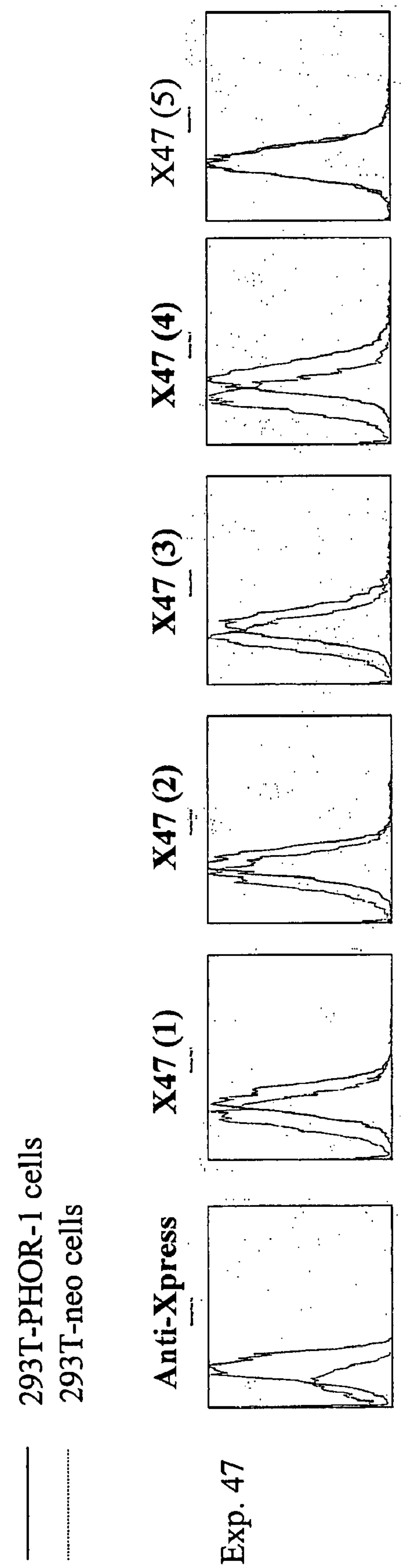
FIG. 50: Mouse polyclonal antibodies raised to amino acids 1-23 detect PHOR-1 expressed in 293T cells
Figure 51:
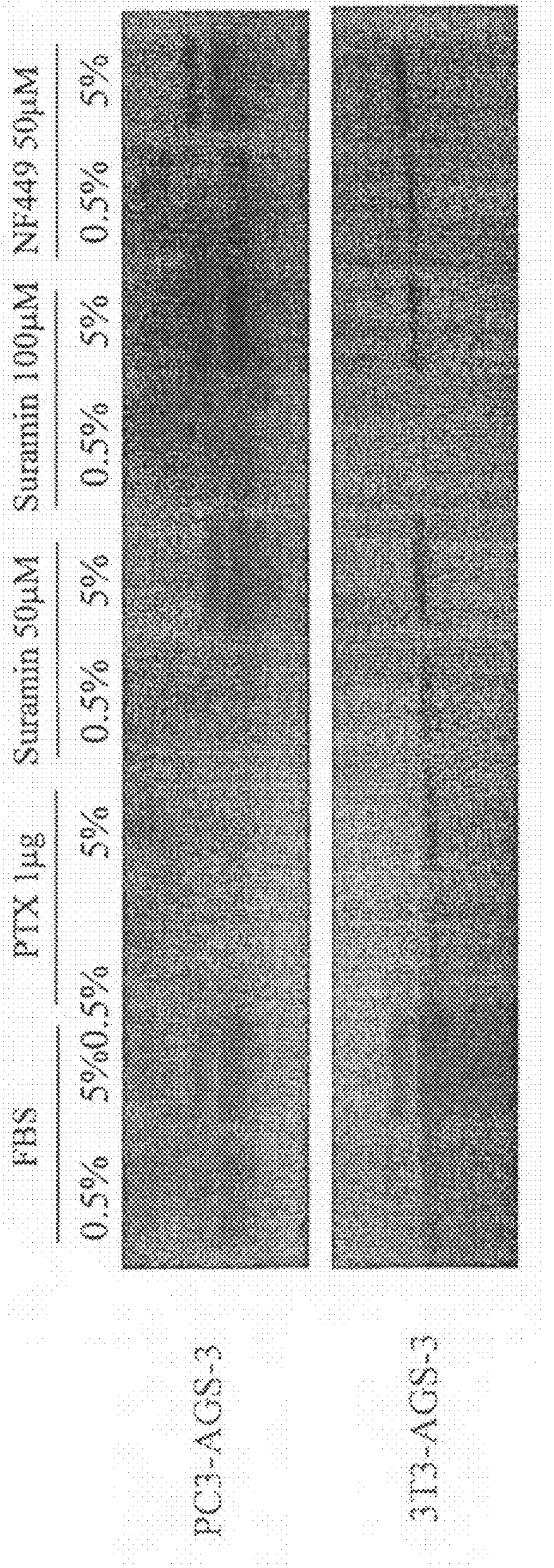
FIG. 51: Inhibition of ERK Phosphorylation by GPCR Inhibitors
Figure 52:
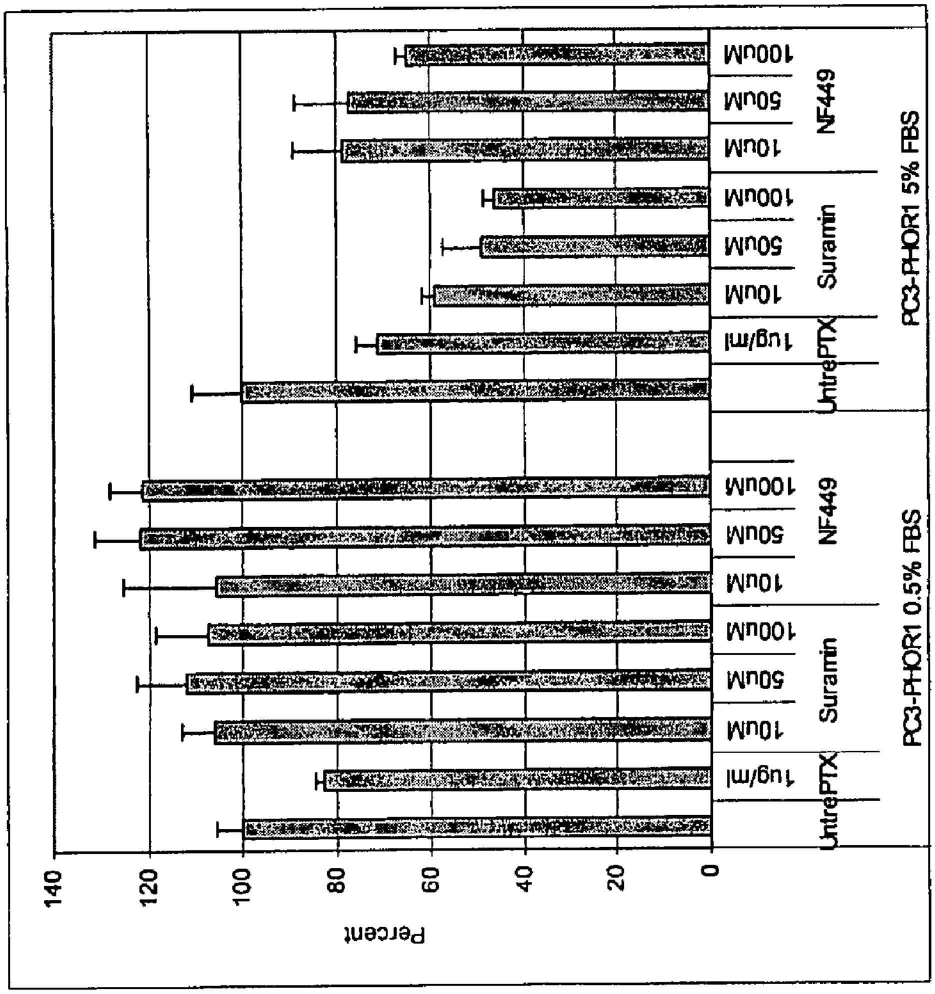
FIG. 52: Inhibition of PC3 Proliferation by GPCR Inhibitors
Figure 53:
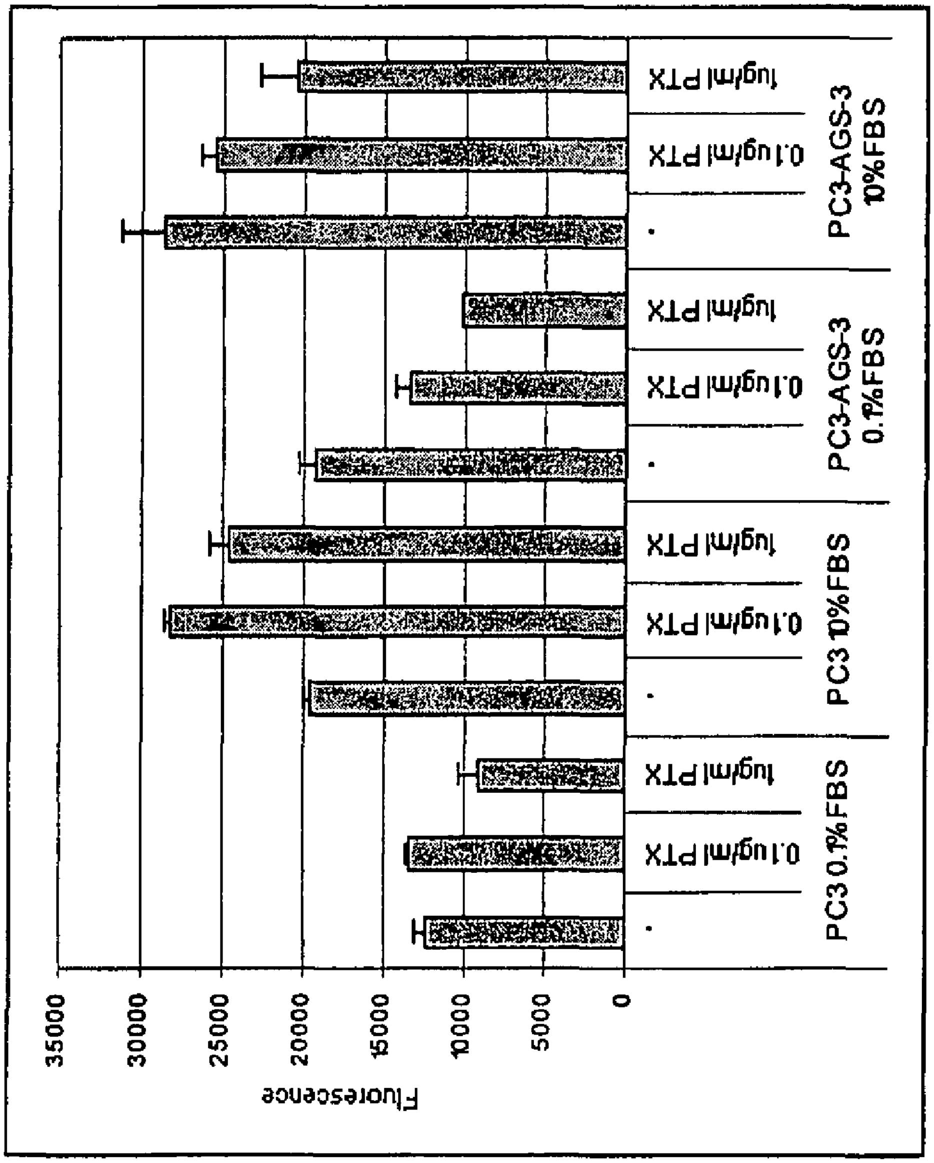
FIG. 53: Inhibition of PC3-AGS-3 Proliferation by PTX
Figure 54:
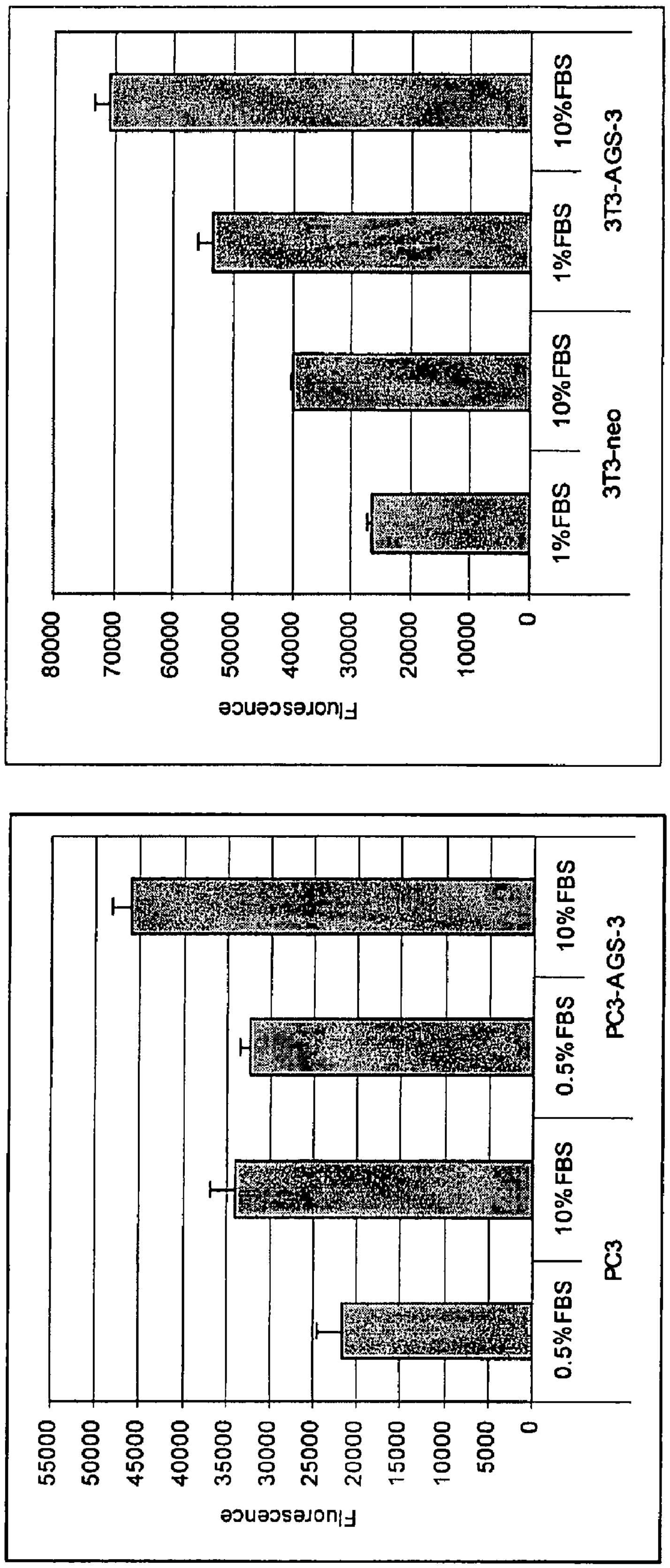
FIG. 54: AGS-3 Enhances Proliferation of 3T3 and PC3 Cells
Figure 55:
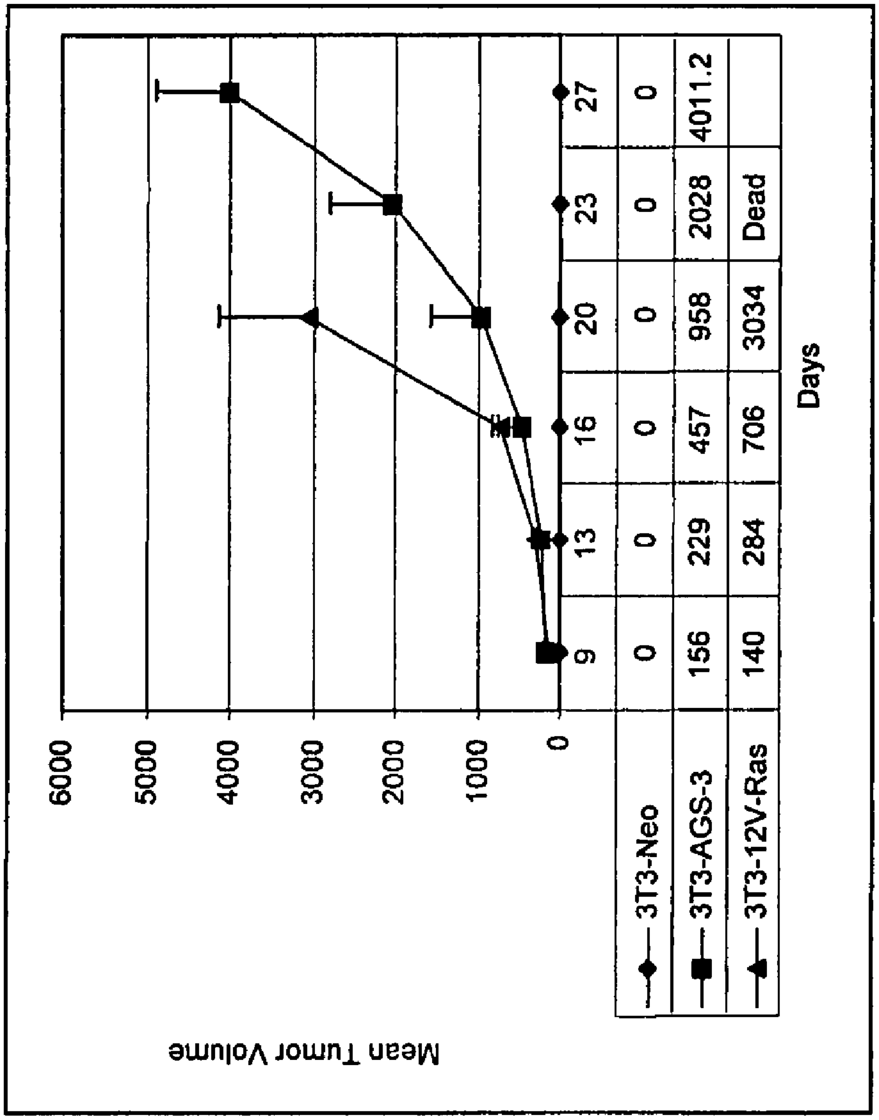
FIG. 55: AGS-3 Induces in vivo Tumor Formation of 3T3 Cells
Figure 56:
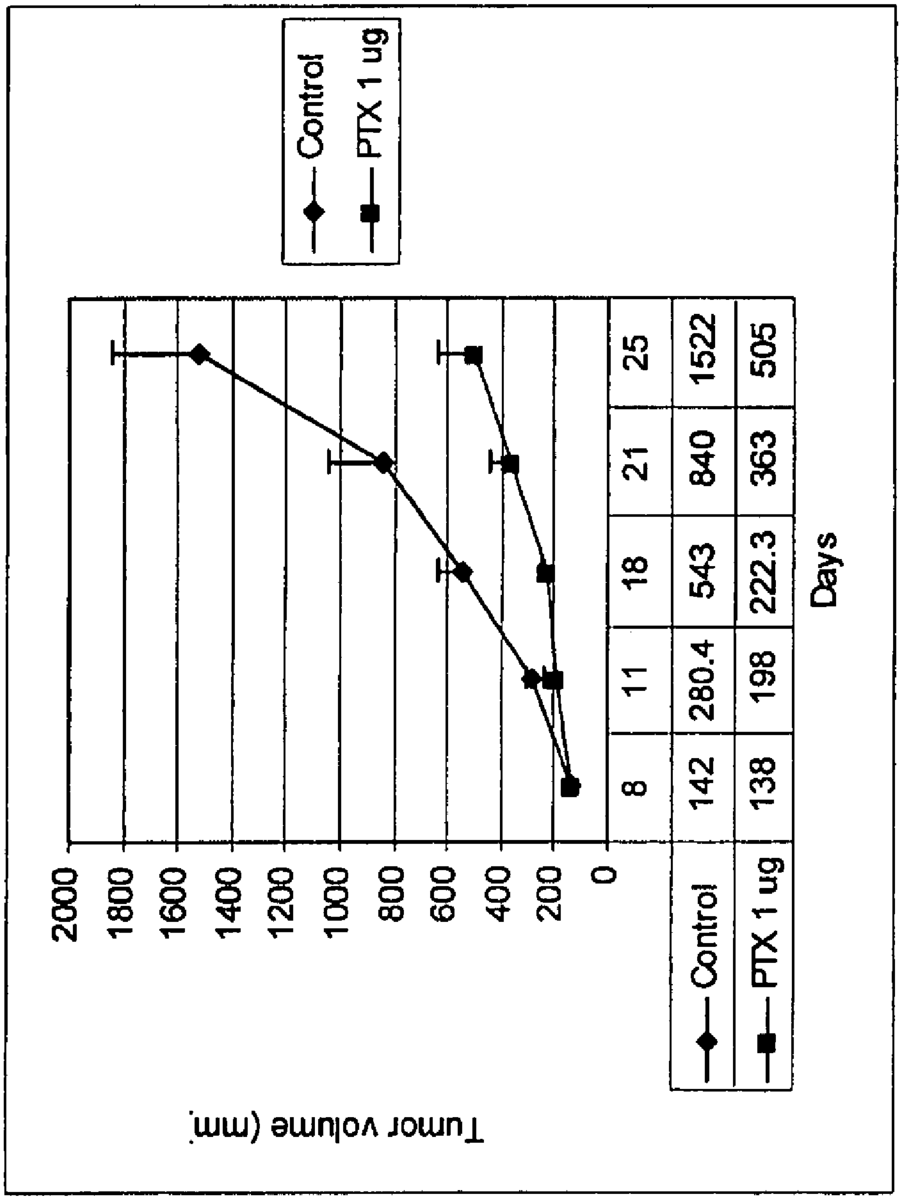
FIG. 56: Inhibition of 3T3-AGS-3 Tumor Formation by PTX
Figure 57:
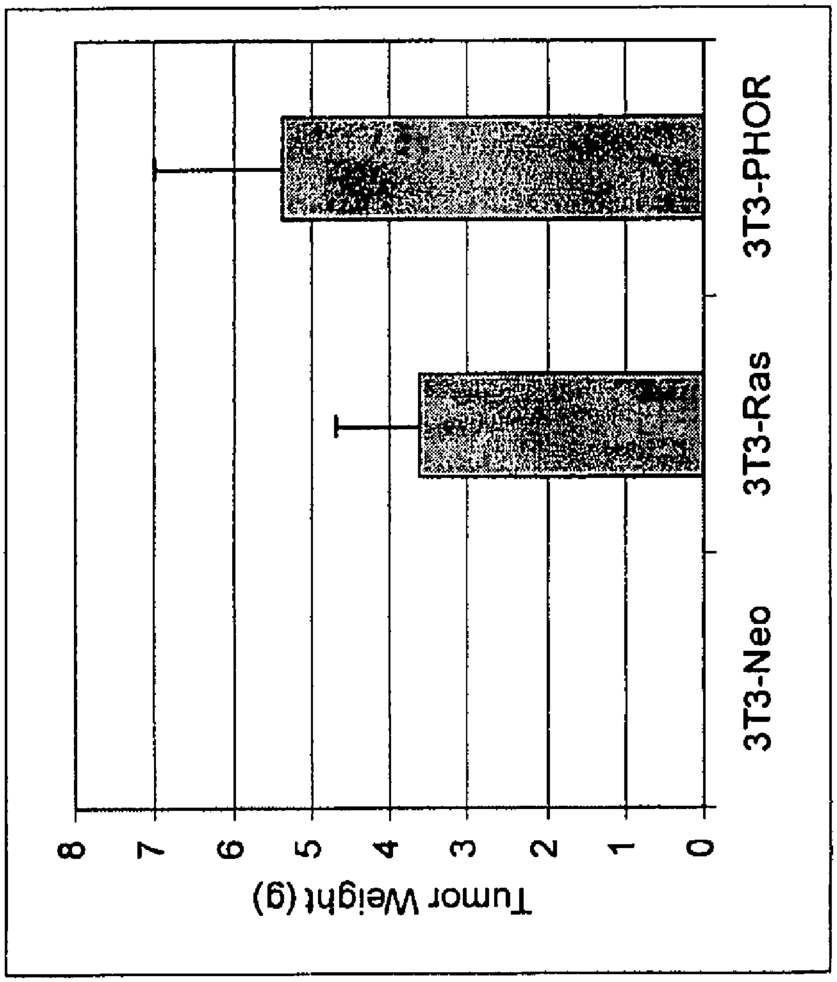
FIG. 57: AGS-3 Induces the Orthotopic Growth of 3T3 Tumors
Figure 58:
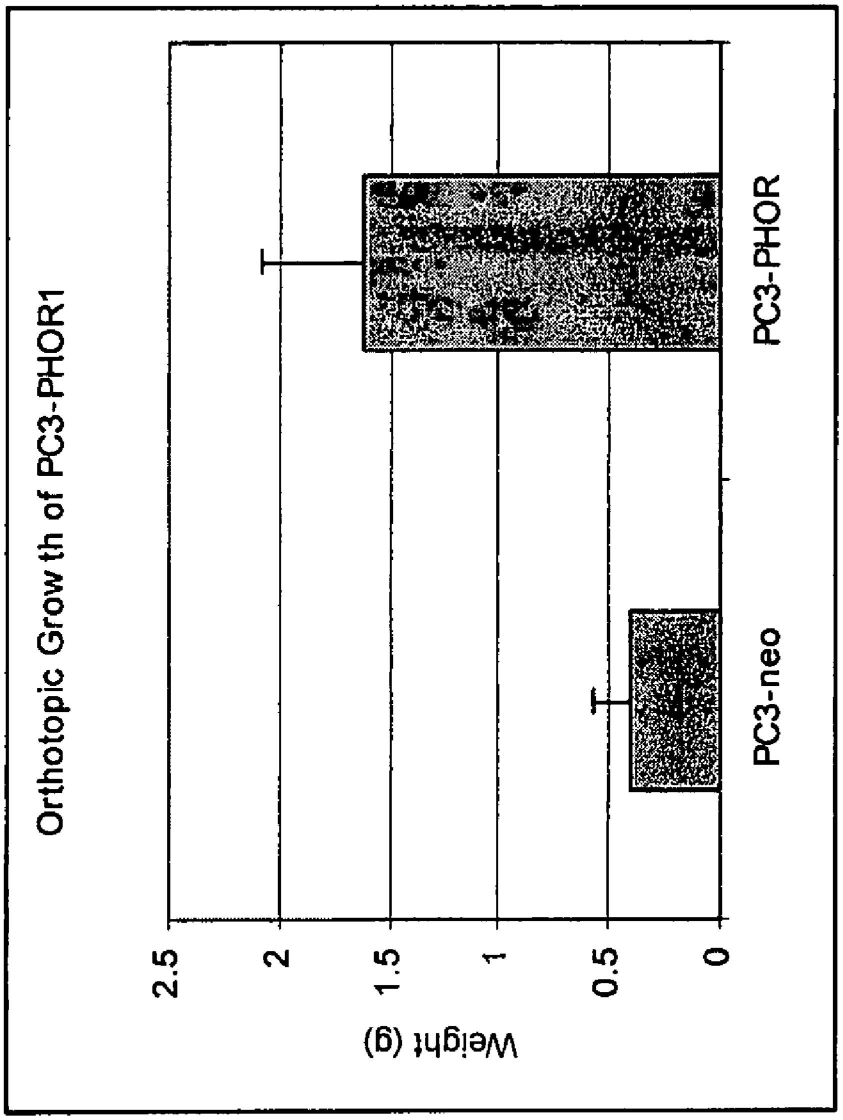
FIG. 58: AGS-3 Enhances Orthotopic Growth of PC3 Cells
Figure 59:
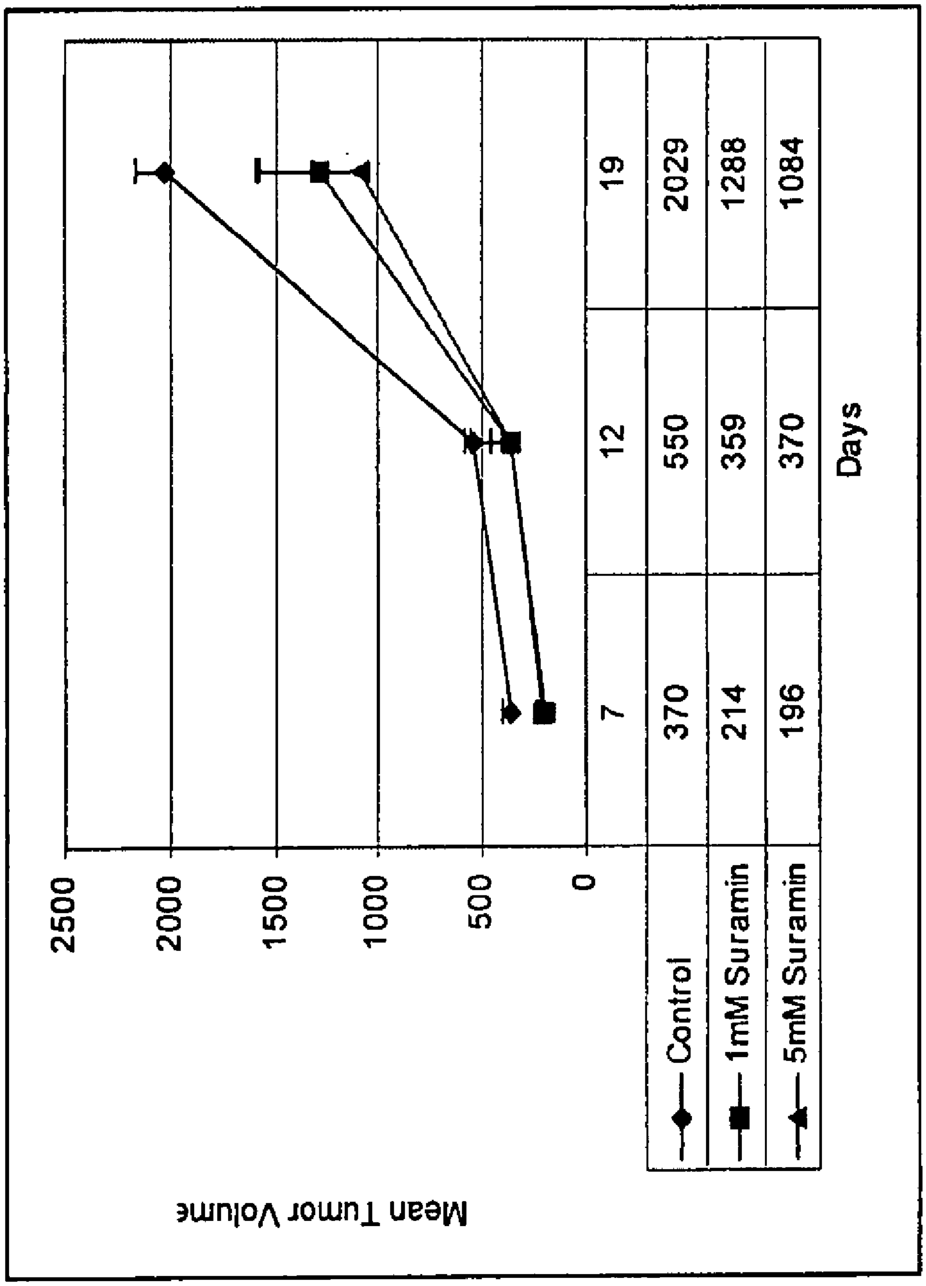
FIG. 59: Partial Inhibition of 3T3-AGS-3 Tumor Formation by Suramin
Figure 60:
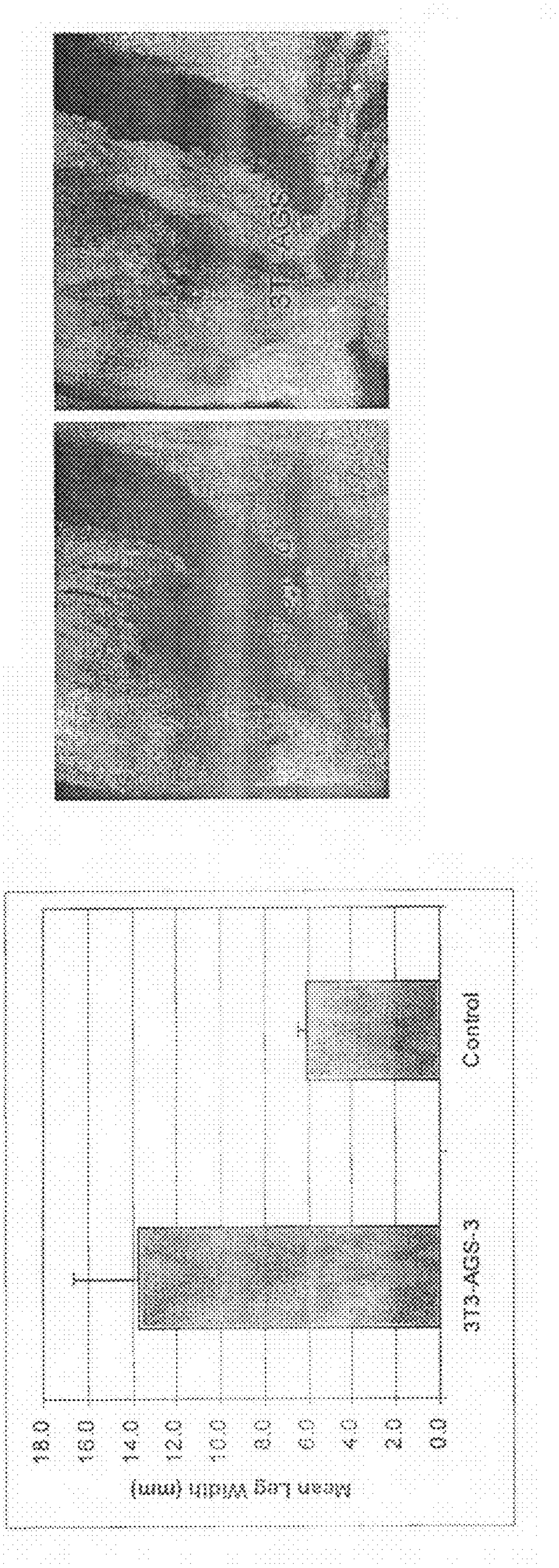
FIG. 60: AGS-3 Induces Intratibial Tumor Growth of 3T3Cells
Figure 61:
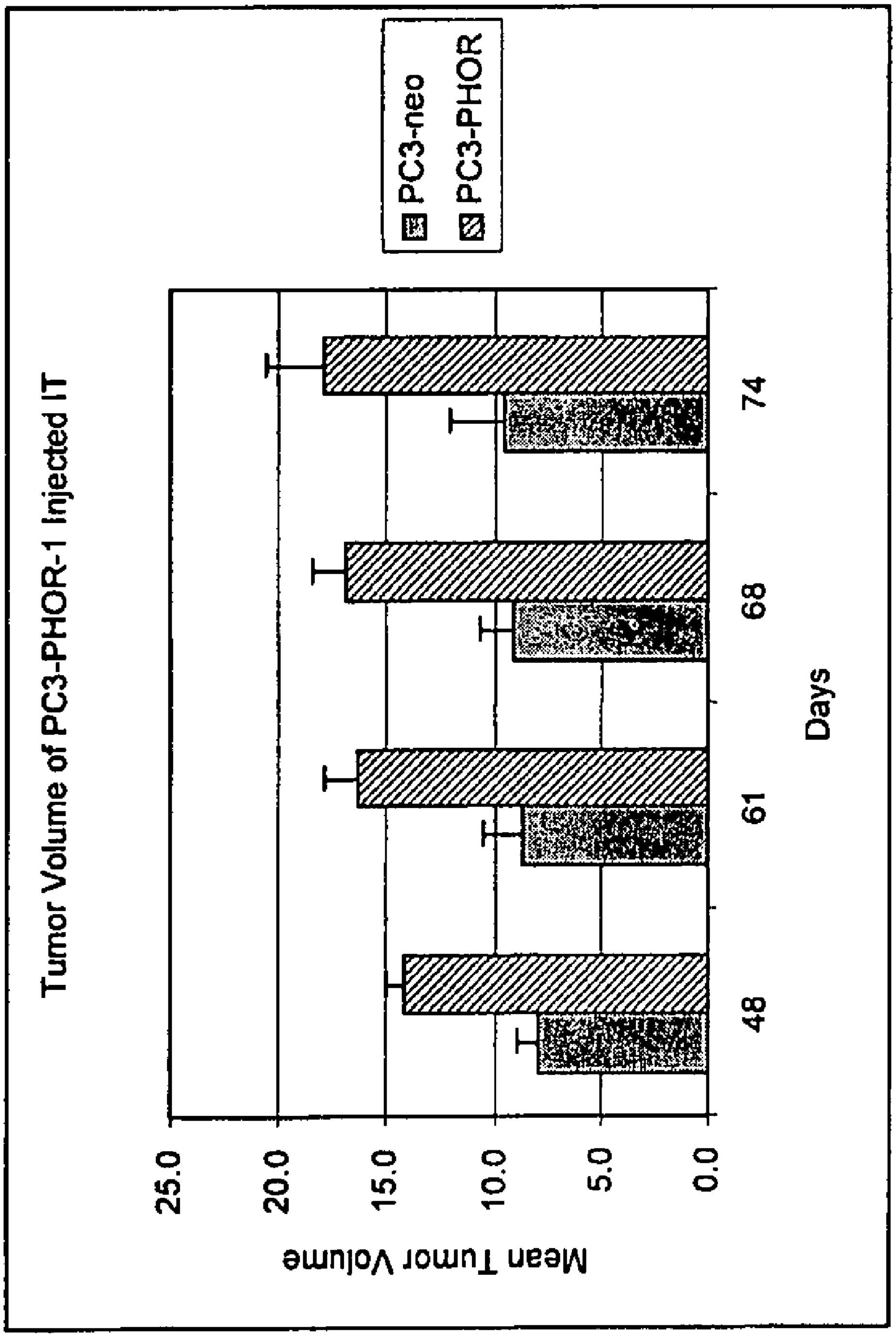
FIG. 61: AGS-3 Enhances Intratibial Tumor Growth of PC3 Cells
Figure 62:
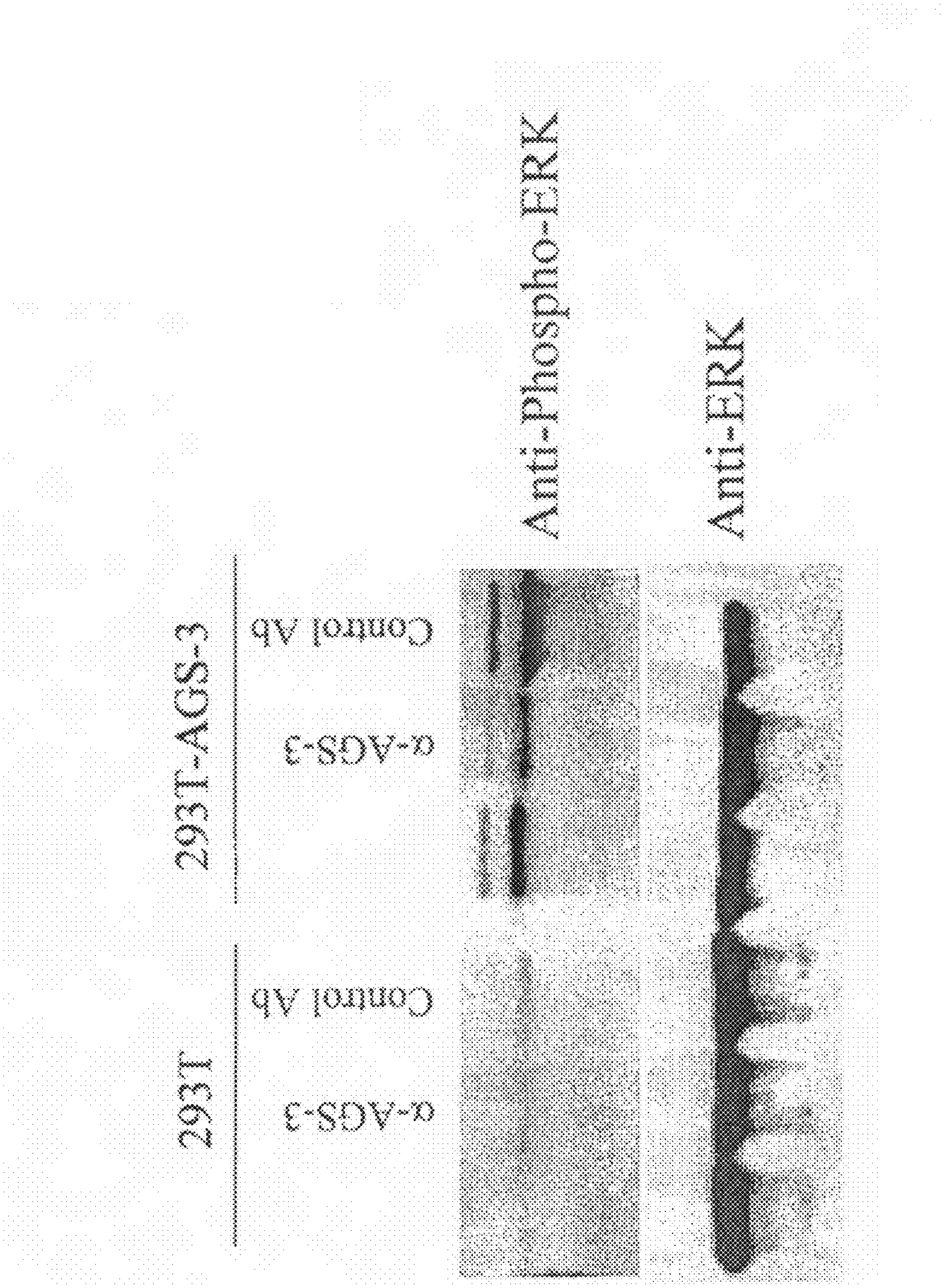
FIG. 62: Inhibition of AGS-3 Mediated ERK Phosphorylation by AGS-3 Specific Antibodies
Figure 64:
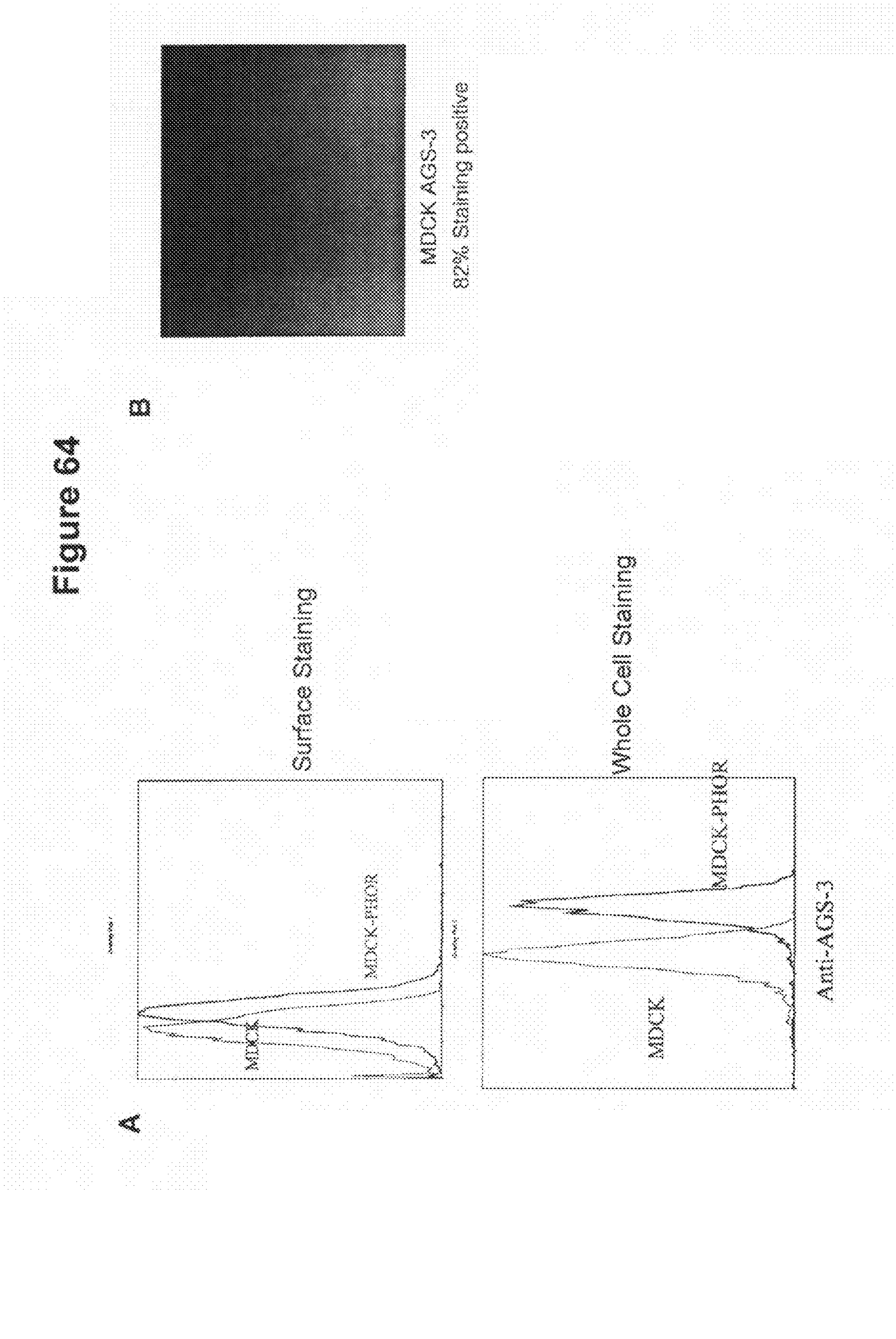
FIG. 64: Anti-AGS3 Staining of MDCK Cells

A fusion protein was constructed that encodes amino acids 86-310 of PHOR-1 fused at the amino terminus to glutathione-S-transferase (GST). This fusion protein, GST-PHOR-1, encompasses sequences that proceed transmembrane domain 3 through transmembrane domain 7 so that all of the extracellular loops of PHOR-1 are represented and the only extra-cellular domain that is not represented is the N' terminal. The fusion protein was purified from induced bacteria using standard glutathione affinity chromatography and used to immunize five mice following the protocol of Example 54. The PHOR-1 specific titer of the sera was determined following the fourth immunization (bleed 2) using a fusion protein composed of amino acids 86-310 of PHOR-1 fused to maltose binding protein (PHOR 1-MBP), see Table LII below and FIG. 49. The sera from each mouse specifically recognized PHOR-1 protein in 293T cells transfected with an epitope tagged PHOR-1 cDNA as assessed by Western analysis (FIG. 48). When screened on 293T-PHOR1 cells compared to 293T-neo cells by FACS several of the sera were positive indicating generation of antibodies specific to cell associated PHOR1, see FIG. 50.

TABLE LII

| Mouse | Titer, Bleed 2 |
|---|---|
| 1 | $1 \times 10^{-6}$ |
| 2 | $1 \times 10^{-6}$ |
| 3 | $2 \times 10^{-6}$ |
| 4 | $1 \times 10^{-6}$ |
| 5 | $5 \times 10^{-5}$ |

Two mice with high titers were given a final boost of MBP-PHOR-1 fusion protein in PBS and sacrificed for fusion 3 days later. Fusion and hybridoma growth selection was carried out as in Example 54. Hybridomas were screened by ELISA against GST-PHOR1 and cross-screened against MBP-PHOR-1 to identify PHOR-1 sequence reactive clones. 48 hybridomas were identified that exhibited specific reactivity to MBP-PHOR-1. These hybridomas are set forth in Table LIII.

TABLE LIII

| Number | Clone number | O.D. |
|---|---|---|
| 1 | X18(1)1 | 0.425 |
| 2 | X18(1)2 | 0.445 |
| 3 | X18(1)3 | 0.573 |
| 4 | **X18(1)4** | 0.228 |
| 5 | X18(1)5 | 0.218 |
| 6 | X18(1)6 | 0.333 |
| 7 | X18(1)7 | 1.459 |
| 8 | X18(1)8 | 0.260 |
| 9 | X18(1)9 | 0.253 |
| 10 | **X18(1)10** | 0.282 |
| 11 | X18(1)11 | 0.362 |
| 12 | X18(1)12 | 0.343 |
| 13 | X18(1)13 | 0.261 |
| 14 | X18(1)14 | 0.773 |
| 15 | X18(1)15 | 0.631 |
| 16 | X18(1)16 | 1.427 |
| 17 | X18(1)17 | 0.372 |
| 18 | X18(1)18 | 0.657 |
| 19 | X18(1)19 | 0.677 |
| 20 | X18(1)20 | 0.338 |
| 21 | X18(1)21 | 0.398 |
| 22 | X18(1)22 | 0.232 |
| 23 | **X18(1)23** | 0.560 |
| 24 | X18(1)24 | 0.554 |
| 25 | X18(1)25 | 0.442 |
| 26 | X18(4)1 | 0.848 |
| 27 | X18(4)2 | 0.420 |
| 28 | X18(4)3 | 0.230 |
| 29 | X18(4)4 | 0.333 |
| 30 | X18(4)5 | 0.389 |
| 31 | X18(4)6 | 0.264 |
| 32 | **X18(4)7** | 0.358 |
| 33 | X18(4)8 | 0.669 |
| 34 | X18(4)9 | 0.429 |
| 35 | X18(4)10 | 0.253 |
| 36 | X18(4)11 | 0.277 |
| 37 | X18(4)12 | 0.536 |
| 38 | X18(4)13 | 0.662 |
| 39 | X18(4)14 | 0.344 |
| 40 | X18(4)15 | 0.256 |
| 41 | X18(4)16 | 0.212 |
| 42 | X18(4)17 | 0.304 |
| 43 | X18(4)18 | 0.531 |
| 44 | X18(4)19 | 0.286 |
| 45 | X18(4)20 | 0.472 |
| 46 | X18(4)21 | 0.770 |
| 47 | X18(4)22 | 0.877 |
| 48 | X18(4)23 | 0.450 |

Four hybridomas reactive to MBP-PHOR-1 exhibited strong specific reactivity to PHOR-1 protein expressed in cells. This was demonstrated by Western analysis of 293T cells transfected with the epitope tagged PHOR-1 cDNA (FIG. 47). The positive clones are indicated in bold, namely 18(1)4; 18(1)10; 18(1)23; and, 18(4)7. Hybridomas expressing, respectively, 18(1)4; 18(1)10; 18(1)23; and, 18(4)7 were deposited with the ATCC on 14 May 2002.

Example 57

Activation of 101P3A11

It is possible to measure the constitutive and ligand-mediated activation of 101P3A11 using the cAMP accumulation assay mentioned in example 44 above or by measuring the binding of the GTP analog, namely [35S]GTPyS. [35S]GTPyS binding is generically applicable to all GPCRs; and occurs proximal to the membrane surface, where the GPCR is located. Preferably, a GPCR:Fusion-Protein is utilized for these assays. The assay utilizes the ability of G protein-coupled receptors to stimulate [35S] GTPyS binding to membranes expressing the relevant receptors. Therefore, the assay may be used to directly screen compounds and antibodies for their effect on the activation of 101P3A11.

A scintillation proximity assay can be utilized to monitor the binding of [35S] GTP7S to membranes expressing 101P3A11-Gs-Fusion Protein (expressed in 293 or 3T3 cells). In brief, membrane proteins are incubated with [35 S]GTPyS and GDP for 60 minutes. The assay plates are-counted in a scintillation counter.

Throughout this application, various website data content, publications, patent applications and patents are referenced. The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

| Tissues that Express 101P3A11 When Malignant |
|---|
| Normal Tissues: |
| Prostate |
| Ovary (by RT-PCR only) |
| Malignant Tissues: |
| Rectum |
| Prostate |
| Colon |

TABLE I-continued

| Tissues that Express 101P3A11 When Malignant |
|---|
| Kidney |
| Breast |
| Uterus |
| Cervix |
| Stomach |
| Metastases Pool |

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
| | 9 | −3 | −4 | −2 | −3 | −3 | −1 | −3 | −1 | −1 | −3 | −3 | −3 | −3 | −1 | −1 | −1 | −2 | −2 | C |
| | | 6 | 2 | −3 | −1 | −1 | −3 | −1 | −4 | −3 | 1 | −1 | 0 | −2 | 0 | −1 | −3 | −4 | −3 | D |
| | | | 5 | −3 | −2 | 0 | −3 | 1 | −3 | −2 | 0 | −1 | 2 | 0 | 0 | −1 | −2 | −3 | −2 | E |
| | | | | 6 | −3 | −1 | 0 | −3 | 0 | 0 | −3 | −4 | −3 | −3 | −2 | −2 | −1 | 1 | 3 | F |
| | | | | | 6 | −2 | −4 | −2 | −4 | −3 | 0 | −2 | −2 | −2 | 0 | −2 | −3 | −2 | −3 | G |
| | | | | | | 8 | −3 | −1 | −3 | −2 | 1 | −2 | 0 | 0 | −1 | −2 | −3 | −2 | 2 | H |
| | | | | | | | 4 | −3 | 2 | 1 | −3 | −3 | −3 | −3 | −2 | −1 | 3 | −3 | −1 | I |
| | | | | | | | | 5 | −2 | −1 | 0 | −1 | 1 | 2 | 0 | −1 | −2 | −3 | −2 | K |
| | | | | | | | | | 4 | 2 | −3 | −3 | −2 | −2 | −2 | −1 | 1 | −2 | −1 | L |
| | | | | | | | | | | 5 | −2 | −2 | 0 | −1 | −1 | −1 | 1 | −1 | −1 | M |
| | | | | | | | | | | | 6 | −2 | 0 | 0 | 1 | 0 | −3 | −4 | −2 | N |
| | | | | | | | | | | | | 7 | −1 | −2 | −1 | −1 | −2 | −4 | −3 | P |
| | | | | | | | | | | | | | 5 | 1 | 0 | −1 | −2 | −2 | −1 | Q |
| | | | | | | | | | | | | | | 5 | −1 | −1 | −3 | −3 | −2 | R |

TABLE III-continued

Adapted from the GCG Software 9.0 BLOSUM62 amino acid substitution matrix (block substitution matrix). The higher the value, the more likely a substitution is found in related, natural proteins.

| | | | | | |
|---|---|---|---|---|---|
| 4 | 1 | −2 | −3 | −2 | S |
| | 5 | 0 | −2 | −2 | T |
| | | 4 | −3 | −1 | V |
| | | | 11 | 2 | W |
| | | | | 7 | Y |

TABLE IV

HLA Class I/II Motifs/Supermotifs

TABLE IV (A): HLA Class I Supermotifs/Motifs

| | POSITION 2 (Primary Anchor) | POSITION 3 (Primary Anchor) | POSITION C Terminus (Primary Anchor) |
|---|---|---|---|
| SUPERMOTIFS | | | |
| A1 | **TI***LVMS* (SEQ ID NO: 48) | | **FWY** |
| A2 | **LIVM***ATQ* (SEQ ID NO: 49) | | **IV***MATL* (SEQ ID NO: 50) |
| A3 | **VSMA***TLI* (SEQ ID NO: 51) | | **RK** |
| A24 | **YF***WIVLMT* (SEQ ID NO: 52) | | **FI***YWLM* (SEQ ID NO: 53) |
| B7 | **P** | | **VILF***MWYA* (SEQ ID NO: 54) |
| B27 | **RHK** | | **FYL***WMIVA* (SEQ ID NO: 55) |
| B44 | **E***D* | | **FWYLIMVA** (SEQ ID NO: 56) |
| B58 | **ATS** | | **FWY***LIVMA* (SEQ ID NO: 57) |
| B62 | **QL***IVMP* (SEQ ID NO: 58) | | **FWYMIVLA** (SEQ ID NO: 59) |
| MOTIFS | | | |
| A1 | **TSM** | | **Y** |
| A1 | | **DE***AS* (SEQ ID NO:60) | **Y** |
| A2.1 | **LM***VQIAT* (SEQ ID NO: 61) | | **V***LIMAT* (SEQ ID NO: 62) |
| A3 | **LMVISATF***CGD* (SEQ ID NO: 63) | | **KYR***HFA* (SEQ ID NO: 64) |
| A11 | **VTMLISAGN***CDF* (SEQ ID NO: 65) | | **K***RYH* (SEQ ID NO: 66) |
| A24 | **YF***WM* (SEQ ID NO: 67) | | **FLIW** (SEQ ID NO: 68) |
| A*3101 | **MVT***ALIS* (SEQ ID NO: 69) | | **R***K* |
| A*3301 | **MVALF***IST* (SEQ ID NO: 70) | | **RK** |
| A*6801 | **AVT***MSLI* (SEQ ID NO: 71) | | **RK** |
| B*0702 | **P** | | **LMF***WYAIV* (SEQ ID NO: 72) |
| B*3501 | **P** | | **LMFWY***IVA* (SEQ ID NO: 73) |
| B51 | **P** | | **LIVF***WYAM* (SEQ ID NO: 74) |
| B*5301 | **P** | | **IMFWY***ALV* (SEQ ID NO: 75) |
| B*5401 | **P** | | **ATIV***LMFWY*(SEQ ID NO: 76) |

Bolded residues are preferred, italicized residues are less preferred: A peptide is considered motif-bearing if it has primary anchors at each primary anchor position for a motif or supermotif as specified in the above table.

TABLE IV (B)

HLA Class II Supermotif

| 1 | 6 | 9 |
|---|---|---|
| W, F, Y, V, .I, L | A, V, I, L, P, C, S, T | A, V, I, L, C, S, T, M, Y |

TABLE IV (C): HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VST*CPALIM* | MH | | MH |
| | deleterious | (SEQ ID NO: 77) | | | W | | (SEQ ID NO: 78) | R | | WDE |

TABLE IV-continued (C): HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR1 | preferred | MF*LIVWY* (SEQ ID NO: 79) | | | PAMQ (SEQ ID NO: 80) | | VMAT*SPLIC* (SEQ ID NO: 81) | M | | AVM |
| | deleterious | | C | CH | FD | CWD | | GDE | D | |
| DR7 | preferred | MF*LIVWY* (SEQ ID NO: 79) | M | W | A | | IVMS*ACTPL* (SEQ ID NO: 82) | M | | IV |
| | deleterious | | C | | G | | | GRD | N | G |
| DR3 | MOTIFS | 1° anchor 1 | 2 | 3 | 1° anchor 4 | 5 | 1° anchor 6 | | | |
| motif a preferred | | LIVMFY (SEQ ID NO: 83) | | | D | | | | | |
| motif b preferred | | LIVMEAY (SEQ ID NO: 84) | | | DNQEST (SEQ ID NO: 85) | | KRH | | | |
| DR Supermotif | | MF*LIVWY* (SEQ ID NO: 79) | | | | | VMSTA*CPLI* (SEQ ID NO: 86) | | | |

Italicized residues indicate less preferred or "tolerated" residues

TABLE IV (D): HLA Class I Supermotifs

| SUPER-MOTIFS | POSITION: | 1 | 2 | 3 | 4 | 5 | 6 | 7 | 8 | C-terminus |
|---|---|---|---|---|---|---|---|---|---|---|
| A1 | | | 1° Anchor TI*LVMS* (SEQ ID NO: 48) | | | | | | | 1° Anchor FWY |
| A2 | | | 1° Anchor LIVM*ATQ* (SEQ ID NO: 49) | | | | | | | 1° Anchor LIVMAT (SEQ ID NO: 87) |
| A3 | preferred | | 1° Anchor VSMA*TLI* (SEQ ID NO: 51) | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* (SEQ ID NO: 52) | | | | | | | 1° Anchor FIY*WLM* (SEQ ID NO: 88) |
| B7 | preferred | FWY (5/5) LIVM (3/5) (SEQ ID NO: 89) | 1° Anchor P | FWY (4/5) | | | | | FWY (3/5) | 1° Anchor VILF*MWYA* (SEQ ID NO: 54) |
| | deleterious | DE (3/5); P (5/5); G (4/5); A (3/5); QN (3/5) | | | | DE (3/5) | G (4/5) | QN (4/5) | DE (4/5) | |
| B27 | | | 1° Anchor RHK | | | | | | | 1° Anchor FYL*WMIVA* (SEQ ID NO: 55) |
| B44 | | | 1° Anchor E*D* | | | | | | | 1° Anchor FWYLIMVA (SEQ ID NO: 56) |
| B58 | | | 1° Anchor ATS | | | | | | | 1° Anchor FWY*LIVMA* (SEQ ID NO: 57) |
| B62 | | | 1° Anchor QL*IVMP* (SEQ ID NO: 58) | | | | | | | 1° Anchor FWY*MIVLA* (SEQ ID NO: 59) |

Italicized residues indicate less preferred or "tolerated" residues

TABLE IV (E): HLA Class I Motifs

| | POSITION: | 1 | 2 | 3 | 4 | 5 | 6 | 7 | 8 | 9 or C-terminus | C-terminus |
|---|---|---|---|---|---|---|---|---|---|---|---|
| A1 9-mer | preferred | GFYW (SEQ ID NO: 90) | 1° Anchor STM | DEA | YFW | | P | DEQN (SEQ ID NO: 91) | YFW | | 1° Anchor Y |
| | deleterious | DE | | RHKLIVMP (SEQ ID NO: 132) | A | G | A | | | | |
| A1 9-mer | preferred | GRHK (SEQ ID NO: 92) | ASTCLIVM (SEQ ID NO: 93) | 1° Anchor DEA*S* (SEQ ID NO: 60) | GSTC (SEQ ID NO: 94) | | ASTC (SEQ ID NO: 95) | LIVM (SEQ ID NO: 89) | DE | | 1° Anchor Y |
| | deleterious | A | RHKDEPYFW (SEQ ID NO: 102) | | DE | PQN | RHK | PG | GP | | |
| A1 10-mer | preferred | YFW | 1° Anchor STM | DEAQN (SEQ ID NO: 96) | A | YFWQN (SEQ ID NO: 97) | | PASTC (SEQ ID NO: 98) | GDE | P | 1° Anchor Y |
| | deleterious | GP | | RHKGLIVM (SEQ ID NO: 79) | DE | RHK | QNA | RHKYFW (SEQ ID NO: 100) | RHK | A | |
| A1 10-mer | preferred | YFW | STCLIVM (SEQ ID NO: 101) | 1° Anchor DEA*S* (SEQ ID NO: 60) | A | YFW | | PG | G | YFW | 1° Anchor Y |
| | deleterious | RHK | RHKDEPYFW (SEQ ID NO: 102) | | | P | G | | PRHK (SEQ ID NO: 103) | QN | |
| A2.1 9-mer | preferred | YFW | 1° Anchor LM*IVQAT* (SEQ ID NO: 104) | YFW | STC | YFW | | A | P | 1° Anchor V*LIMAT* (SEQ ID NO: 62) | |
| | deleterious | DEP | | DERKH (SEQ ID NO: 105) | | | RKH | DERKH (SEQ ID NO: 105) | | | |
| A2.1 10-mer | preferred | AYFW (SEQ ID NO: 114) | 1° Anchor LM*IVQAT* (SEQ ID NO: 104) | LVIM (SEQ ID NO: 91) | G | | G | | FYWLVIM (SEQ ID NO: 106) | | 1° Anchor V*LIMAT* (SEQ ID NO: 62) |
| | deleterious | DEP | | DE | RKHA (SEQ ID NO: 107) | P | | RKH | DERKH (SEQ ID NO: 105) | RKH | |
| A3 | preferred | RHK | 1° Anchor LMVISATFCGD (SEQ ID NO: 108) | YFW | PRHKYFW (SEQ ID NO: 109) | A | YFW | | P | 1° Anchor KYR*HFA* (SEQ ID NO: 64) | |
| | deleterious | DEP | | DE | | | | | | | |
| A11 | preferred | A | 1° Anchor VTLMISAGN*CDF* (SEQ ID NO: 110) | YFW | YFW | A | YFW | YFW | P | 1° Anchor K*RYH* (SEQ ID NO: 66) | |
| | deleterious | DEP | | | | | | A | G | | |
| A24 9-mer | preferred | YFWRHK (SEQ ID NO: 111) | 1° Anchor YFWM (SEQ ID NO: 67) | | STC | | | YFW | YFW | 1° Anchor FLIW (SEQ ID NO: 68) | |
| | deleterious | DEG | | DE | G | QNP | DERHK (SEQ ID NO: 112) | G | AQN | | |
| A24 10-mer | preferred | | 1° Anchor YFW*M* | | P | YFWP (SEQ ID | | P | | | 1° Anchor FLIW |

TABLE IV-continued (E): HLA Class I Motifs

| | POSITION: | 1 | 2 | 3 | 4 | 5 | 6 | 7 | 8 | 9 or C-terminus | C-terminus |
|---|---|---|---|---|---|---|---|---|---|---|---|
| | | | (SEQ ID NO: 67) | | | NO: 113) | | | | | (SEQ ID NO: 68) |
| | deleterious | | | GDE | QN | RHK | DE | A | QN | DEA | |
| A3101 | preferred | RHK | 1° Anchor MVT*ALIS* (SEQ ID NO: 69) | YFW | P | | YFW | YFW | AP | 1° Anchor R*K* | |
| | deleterious | DEP | | DE | | ADE | DE | DE | DE | | |
| A3301 | preferred | | 1° Anchor MVALF*IST* (SEQ ID NO: 70) | YFW | | | | AYFW (SEQ ID NO: 114) | | 1° Anchor RK | |
| | deleterious | GP | | DE | | | | | | | |
| A6801 | preferred | YFWSTC (SEQ ID NO: 115) | 1° Anchor AVT*MSLI* (SEQ ID NO: 71) | | | YFWLIVM (SEQ ID NO: 116) | | YFW | P | 1° Anchor RK | |
| | deleterious | GP | | DEG | | RHK | | | A | | |
| B0702 | preferred | RHKFWY (SEQ ID NO: 117) | 1° Anchor P | RHK | | RHK | RHK | RHK | PA | 1° Anchor LMF*WYAIV* (SEQ ID NO: 72) | |
| | deleterious | DEQNP (SEQ ID NO: 118) | | DEP | DE | DE | GDE | QN | DE | | |
| B3501 | preferred | FWYLIVM (SEQ ID NO: 119) | 1° Anchor P | FWY | | | | FWY | | 1° Anchor LMFWY*IVA* (SEQ ID NO: 73) | |
| | deleterious | AGP | | | | G | G | | | | |
| B51 | preferred | LIVMFWY (SEQ ID NO: 121) | 1° Anchor P | FWY | *STC* | FWY | | G | FWY | 1° Anchor LIVF*WYAM* (SEQ ID NO: 74) | |
| | deleterious | AGPDERHKSTC (SEQ ID NO: 122) | | | | DE | G | DEQN (SEQ ID NO: 91) | GDE | | |
| B5301 | preferred | LIVMFWY (SEQ ID NO: 121) | 1° Anchor P | FWY | STC | FWY | | LIVMFWY (SEQ ID NO: 121) | FWY IMFWY*ALV* (SEQ ID NO: 123) | 1° Anchor | |
| | deleterious | AGPQN (SEQ ID NO: 124) | | | | | G | RHKQN (SEQ ID NO: 125) | DE | | |
| B5401 | preferred | FWY | 1° Anchor P | FWYLIVM (SEQ ID NO: 119) | | LIVM | | ALIVM (SEQ ID NO: 126) | FWYAP (SEQ ID NO: 127) | 1° Anchor ATIV*LMFWY* (SEQ ID NO: 76) | |
| | deleterious | GPQNDE (SEQ ID NO: 128) | | GDESTC (SEQ ID NO: 129) | | RHKDE (SEQ ID NO: 130) | DE | QNDGE (SEQ ID NO: 131) | DE | | |

Italicized residues indicate less preferred or "tolerated" residues. The information in this Table is specific for 9-mers unless otherwise specified.

TABLE V

101P3A11-V1-A1-9 mers

| Start | Subsequence | Score | |
|---|---|---|---|
| 211 | GLDSLLISF | 25.000 | Portion of SEQ ID NO: 28; each start position is specified - the length of each peptide is 9 amino acids, the end position for each peptide is the start position plus eight |
| 30 | LAFPLCSLY | 5.000 | |
| 2 | MVDPNGNES | 5.000 | |
| 22 | GLEEAQFWL | 4.500 | |
| 213 | DSLLISFSY | 3.750 | |
| 42 | VLGNLTIIY | 2.500 | |
| 246 | HVCAVFIFY | 2.500 | |
| 112 | GMESTVLLA | 2.250 | |
| 58 | LHEPMYIFL | 2.250 | |
| 7 | GNESSATYF | 2.250 | |
| 260 | LSMVHRFSK | 1.500 | |
| 115 | STVLLAMAF | 1.250 | |
| 191 | ACDDIRVNV | 1.000 | |
| 159 | MAPLPVFIK | 1.000 | |
| 75 | LISTSSMPK | 1.000 | |
| 173 | RSNILSHSY | 0.750 | |
| 79 | SSMPKMLAI | 0.750 | |
| 71 | GIDILISTS | 0.500 | |
| 135 | HATVLTLPR | 0.500 | |
| 118 | LLAMAFDRY | 0.500 | |
| 117 | VLLAMAFDR | 0.500 | |
| 45 | NLTIIYIVR | 0.500 | |
| 232 | TREAQAKAF | 0.450 | |
| 181 | YCLHQDVMK | 0.400 | |
| 138 | VLTLPRVTK | 0.400 | |
| 184 | HQDVMKLAC | 0.375 | |
| 139 | LTLPRVTKI | 0.250 | |
| 6 | NGNESSATY | 0.250 | |
| 53 | RTEHSLHEP | 0.225 | |
| 257 | FIGLSMVHR | 0.200 | |
| 57 | SLHEPMYIF | 0.200 | |
| 243 | CVSHVCAVF | 0.200 | |
| 146 | KIGVAAVVR | 0.200 | |
| 126 | YVAICHPLR | 0.200 | |
| 157 | ALMAPLPVF | 0.200 | |
| 249 | AVFIFYVPF | 0.200 | |
| 288 | VLNPIVYGV | 0.200 | |
| 160 | APLPVFIKQ | 0.125 | |
| 274 | LPVILANIY | 0.125 | |
| 96 | QFDACLLQI | 0.125 | |
| 12 | ATYFILIGL | 0.125 | |
| 272 | SPLPVILAN | 0.125 | |
| 284 | LVPPVLNPI | 0.100 | |
| 158 | LMAPLPVFI | 0.100 | |
| 129 | ICHPLRHAT | 0.100 | |
| 9 | ESSATYFIL | 0.075 | |
| 177 | LSHSYCLHQ | 0.075 | |
| 91 | NSTTIQFDA | 0.075 | |
| 217 | ISFSYLLIL | 0.075 | |
| 56 | HSLHEPMYI | 0.075 | |
| 219 | FSYLLILKT | 0.075 | |
| 271 | DSPLPVILA | 0.075 | |
| 10 | SSATYFILI | 0.075 | |
| 78 | TSSMPKMLA | 0.075 | |
| 69 | LSGIDILIS | 0.075 | |
| 286 | PPVLNPIVY | 0.062 | |
| 163 | PVFIKQLPF | 0.050 | |
| 63 | YIFLCMLSG | 0.050 | |
| 254 | YVPFIGLSM | 0.050 | |
| 46 | LTIIYIVRT | 0.050 | |
| 182 | CLHQDVMKL | 0.050 | |
| 165 | FIKQLPFCR | 0.050 | |
| 289 | LNPIVYGVK | 0.050 | |
| 269 | RRDSPLPVI | 0.050 | |
| 216 | LISFSYLLI | 0.050 | |
| 234 | EAQAKAFGT | 0.050 | |
| 127 | VAICHPLRH | 0.050 | |
| 66 | LCMLSGIDI | 0.050 | |
| 84 | MLAIFWFNS | 0.050 | |
| 98 | DACLLQIFA | 0.050 | |
| 55 | EHSLHEPMY | 0.050 | |
| 277 | ILANIYLLV | 0.050 | |
| 241 | GTCVSHVCA | 0.050 | |
| 20 | LPGLEEAQF | 0.050 | |
| 101 | LLQIFAIHS | 0.050 | |

TABLE V-continued

101P3A11-V1-A1-9 mers

| Start | Subsequence | Score |
|---|---|---|
| 136 | ATVLTLPRV | 0.050 |
| 283 | LLVPPVLNP | 0.050 |
| 156 | AALMAPLPV | 0.050 |
| 251 | FIFYVPFIG | 0.050 |
| 261 | SMVHRFSKR | 0.050 |
| 99 | ACLLQIFAI | 0.050 |
| 11 | SATYFILIG | 0.050 |
| 198 | NVVYGLIVI | 0.050 |
| 34 | LCSLYLIAV | 0.050 |
| 68 | MLSGIDILI | 0.050 |
| 40 | IAVLGNLTI | 0.050 |
| 206 | IISAIGLDS | 0.050 |
| 204 | IVIISAIGL | 0.050 |
| 218 | SFSYLLILK | 0.050 |
| 189 | KLACDDIRV | 0.050 |
| 209 | AIGLDSLLI | 0.050 |
| 247 | VCAVFIFYV | 0.050 |
| 93 | TTIQFDACL | 0.050 |
| 23 | LEEAQFWLA | 0.045 |
| 298 | TKEIRQRIL | 0.045 |
| 35 | CSLYLIAVL | 0.030 |
| 76 | ISTSSMPKM | 0.030 |
| 114 | ESTVLLAMA | 0.030 |
| 244 | VSHVCAVFI | 0.030 |
| 92 | STTIQFDAC | 0.025 |

TABLE V

101P3A11-V1-A1-9 mers

| Start | Subsequence | Score | |
|---|---|---|---|
| 7 | VLASGVTLR | 0.100 | Portion of SEQ ID NO: 30; each start position is specified - the length of each peptide is 9 amino acids, the end position for each peptide is the start position plus eight |
| 18 | SSWPISICW | 0.075 | |
| 22 | ISICWFLLC | 0.075 | |
| 23 | SICWFLLCS | 0.050 | |
| 28 | LLCSTQLSM | 0.050 | |
| 8 | LASGVTLRC | 0.050 | |
| 15 | RCPSSWPIS | 0.020 | |
| 6 | AVLASGVTL | 0.020 | |
| 3 | YLIAVLASG | 0.020 | |
| 11 | GVTLRCPSS | 0.020 | |
| 1 | SLYLIAVLA | 0.020 | |
| 16 | CPSSWPISI | 0.013 | |
| 27 | FLLCSTQLS | 0.010 | |
| 5 | IAVLASGVT | 0.010 | |
| 4 | LIAVLASGV | 0.010 | |
| 14 | LRCPSSWPI | 0.005 | |
| 21 | PISICWFLL | 0.005 | |
| 19 | SWPISICWF | 0.005 | |
| 20 | WPISICWFL | 0.003 | |
| 2 | LYLIAVLAS | 0.003 | |
| 12 | VTLRCPSSW | 0.003 | |
| 10 | SGVTLRCPS | 0.003 | |
| 9 | ASGVTLRCP | 0.002 | |
| 17 | PSSWPISIC | 0.002 | |
| 24 | ICWFLLCST | 0.001 | |
| 29 | LCSTQLSME | 0.001 | |
| 25 | CWFLLCSTQ | 0.001 | |
| 26 | WFLLCSTQL | 0.001 | |
| 13 | TLRCPSSWP | 0.000 | |

TABLE V

101P3A11-V3-A1-9 mers

| Start | Subsequence | Score | |
|---|---|---|---|
| 1 | QFDACLLQM | 0.125 | Portion of SEQ ID NO: 32; each start position is |
| 3 | DACLLQMFA | 0.050 | |

TABLE V-continued

101P3A11-V3-A1-9 mers

| Start | Subsequence | Score | |
|---|---|---|---|
| 4 | ACLLQMFAI | 0.050 | specified - the length of each peptide is 9 amino acids, the end position for each peptide is the start position plus eight |
| 6 | LLQMFAIHS | 0.050 | |
| 5 | CLLQMFAIH | 0.020 | |
| 8 | QMFAIHSLS | 0.005 | |
| 2 | FDACLLQMF | 0.005 | |
| 9 | MFAIHSLSG | 0.003 | |
| 7 | LQMFAIHSL | 0.002 | |

TABLE VI

101P3A11-V1-A1-10 mers

| Start | Subsequence | Score | |
|---|---|---|---|
| 158 | LMAPLPVFIK | 5.000 | Portion of SEQ ID NO: 28; each start position is specified - the length of each peptide is 10 amino acids, the end position for each peptides is the start positon plus nine |
| 2 | MVDPNGNESS | 5.000 | |
| 79 | SSMPKMLAIF | 3.000 | |
| 192 | CDDIRVNVVY | 2.500 | |
| 41 | AVLGNLTIIY | 2.500 | |
| 23 | LEEAQFWLAF | 2.250 | |
| 298 | TKEIRQRILR | 2.250 | |
| 53 | RTEHSLHEPM | 2.250 | |
| 58 | LHEPMYIFLC | 2.250 | |
| 112 | GMESTVLLAM | 2.250 | |
| 288 | VLNPIVYGVK | 2.000 | |
| 217 | ISFSYLLILK | 1.500 | |
| 259 | GLSMVHRFSK | 1.000 | |
| 74 | ILISTSSMPK | 1.000 | |
| 22 | GLEEAQFWLA | 0.900 | |
| 114 | ESTVLLAMAF | 0.750 | |
| 244 | VSHVCAVFIF | 0.750 | |
| 285 | VPPVLNPIVY | 0.625 | |
| 191 | ACDDIRVNVV | 0.500 | |
| 117 | VLLAMAFDRY | 0.500 | |
| 211 | GLDSLLISFS | 0.500 | |
| 116 | TVLLAMAFDR | 0.500 | |
| 71 | GIDILISTSS | 0.500 | |
| 19 | WLAFPLCSLY | 0.500 | |
| 30 | LAFPLCSLYL | 0.500 | |
| 7 | GNESSATYFI | 0.450 | |
| 137 | TVLTLPRVTK | 0.400 | |
| 56 | HSLHEPMYIF | 0.300 | |
| 139 | LTLPRVTKIG | 0.250 | |
| 96 | QFDACLLQIF | 0.250 | |
| 129 | ICHPLRHATV | 0.200 | |
| 284 | LVPPVLNPIV | 0.200 | |
| 242 | TCVSHVCAVF | 0.200 | |
| 156 | AALMAPLPVF | 0.200 | |
| 248 | CAVFIFYVPF | 0.200 | |
| 19 | GLPGLEEAQF | 0.200 | |
| 260 | LSMVHRFSKR | 0.150 | |
| 210 | IGLDSLLISF | 0.125 | |
| 162 | LPVFIKQLFP | 0.125 | |
| 44 | GNLTIIYIVR | 0.125 | |
| 77 | STSSMPKMLA | 0.125 | |
| 245 | SHVCAVFIFY | 0.125 | |
| 212 | LDSLLISFSY | 0.125 | |
| 283 | LLVPPVLNPI | 0.100 | |
| 257 | FIGLSMVHRF | 0.100 | |
| 232 | TREAQAKAFG | 0.090 | |
| 9 | ESSATYFILI | 0.075 | |
| 10 | SSATYFILIG | 0.075 | |
| 69 | LSGIDILIST | 0.075 | |
| 271 | DSPLPVILAN | 0.075 | |
| 78 | TSSMPKMLAI | 0.075 | |
| 272 | SPLPVILANI | 0.050 | |
| 216 | LISFSYLLIL | 0.050 | |
| 273 | PLPVILANIY | 0.050 | |
| 224 | ILKTVLGLTR | 0.050 | |
| 126 | YVAICHPLRH | 0.050 | |
| 106 | AIHSLSGMES | 0.050 | |
| 199 | VVYGLIVIIS | 0.050 | |

TABLE VI-continued

101P3A11-V1-A1-10 mers

| Start | Subsequence | Score |
|---|---|---|
| 269 | RRDSPLPVIL | 0.050 |
| 94 | TIQFDACLLQ | 0.050 |
| 25 | EAQFWLAFPL | 0.050 |
| 92 | STTIQFDACL | 0.050 |
| 215 | LLISFSYLLI | 0.050 |
| 54 | TEHSLHEPMY | 0.050 |
| 42 | VLGNLTIIYI | 0.050 |
| 39 | LIAVLGNLTI | 0.050 |
| 205 | VIISAIGLDS | 0.050 |
| 159 | MAPLPVFIKQ | 0.050 |
| 68 | MLSGIDILIS | 0.050 |
| 36 | SLYLIAVLGN | 0.050 |
| 100 | CLLQIFAIHS | 0.050 |
| 57 | SLHEPMYIFL | 0.050 |
| 65 | FLCMLSGIDI | 0.050 |
| 203 | LIVIISAIGL | 0.050 |
| 276 | VILANIYLLV | 0.050 |
| 261 | SMVHRFSKRR | 0.050 |
| 208 | SAIGLDSLLI | 0.050 |
| 246 | HVCAVFIFYV | 0.050 |
| 176 | ILSHSYCLHQ | 0.050 |
| 290 | NPIVYGVKTK | 0.050 |
| 196 | RVNVVYGLIV | 0.050 |
| 11 | SATYFILIGL | 0.050 |
| 251 | FIFYVPFIGL | 0.050 |
| 98 | DACLLQIFAI | 0.050 |
| 222 | LLILKTVLGL | 0.050 |
| 181 | YCLHQDVMKL | 0.050 |
| 229 | LGLTREAQAK | 0.050 |
| 155 | GAALMAPLPV | 0.050 |
| 103 | QIFAIHSLSG | 0.050 |
| 209 | AIGLDSLLIS | 0.050 |
| 35 | CSLYLIAVLG | 0.030 |
| 110 | LSGMESTVLL | 0.030 |
| 83 | KMLAIFWFNS | 0.025 |
| 241 | GTCVSHVCAV | 0.025 |
| 172 | CRSNILSHSY | 0.025 |
| 270 | RDSPLPVILA | 0.025 |
| 6 | NGNESSATYF | 0.025 |
| 226 | KTVLGLTREA | 0.025 |
| 134 | RHATVLTLPR | 0.025 |
| 136 | ATVLTLPRVT | 0.025 |

TABLE VI

101P3A11-V2-1A-10 mers

| Start | Subsequence | Score | |
|---|---|---|---|
| 19 | SSWPISICWF | 0.150 | Portion of SEQ ID NO: 30; each start position is specified - the length of each peptide is 10 amino acids, the end position for each peptide is the start position plus nine |
| 7 | AVLASGVTLR | 0.100 | |
| 23 | ISICWFLLCS | 0.075 | |
| 28 | FLLCSTQLSM | 0.050 | |
| 2 | SLYLIAVLAS | 0.050 | |
| 8 | VLASGVTLRC | 0.050 | |
| 16 | RCPSSWPISI | 0.050 | |
| 1 | CSLYLIAVLA | 0.030 | |
| 6 | IAVLASGVTL | 0.020 | |
| 10 | ASGVTLRCPS | 0.015 | |
| 21 | WPISICWFLL | 0.013 | |
| 12 | GVTLRCPSSW | 0.010 | |
| 24 | SICWFLLCST | 0.010 | |
| 4 | YLIAVLASGV | 0.010 | |
| 15 | LRCPSSWPIS | 0.010 | |
| 5 | LIAVLASGVT | 0.010 | |
| 18 | PSSWPISICW | 0.008 | |
| 22 | PISICWFLLC | 0.005 | |
| 11 | SGVTLRCPSS | 0.005 | |
| 17 | CPSSWPISIC | 0.003 | |
| 29 | LLCSTQLSME | 0.001 | |
| 14 | TLRCPSSWPI | 0.001 | |
| 25 | ICWFLLCSTQ | 0.001 | |

TABLE VI-continued

101P3A11-V2-1A-10 mers

| Start | Subsequence | Score |
|---|---|---|
| 9 | LASGVTLRCP | 0.001 |
| 3 | LYLIAVLASG | 0.001 |
| 27 | WFLLCSTQLS | 0.001 |
| 26 | CWFLLCSTQL | 0.001 |
| 20 | SWPISICWFL | 0.001 |
| 13 | VTLRCPSSWP | 0.000 |

TABLE VI

101P3A11-V3-A1-10 mers

| Start | Subsequence | Score | |
|---|---|---|---|
| 2 | QFDACLLQMF | 0.250 | Portion of SEQ ID NO: 32; each start position is specified - the length of each peptide is 10 amino acids, the end position for each peptide is the start postion plus nine |
| 4 | DACLLQMFAI | 0.050 | |
| 6 | CLLQMFAIHS | 0.050 | |
| 9 | QMFAIHSLSG | 0.025 | |
| 5 | ACLLQMFAIH | 0.020 | |
| 7 | LLQMFAIHSL | 0.010 | |
| 1 | IQFDACLLQM | 0.007 | |
| 3 | FDACLLQMFA | 0.003 | |
| 8 | LQMFAIHSLS | 0.002 | |
| 10 | MFAIHSLSGM | 0.001 | |

TABLE VII

101P3A11-V1-A2-9 mers

| Start | Subsequence | Score | |
|---|---|---|---|
| 214 | SLLISFSYL | 825.977 | Portion of SEQ ID NO: 28; each start position is specified - the length of each peptide is 9 amino acids, the end position for each peptide is the start position plus eight |
| 288 | VLNPIVYGV | 271.948 | |
| 189 | KLACDDIRV | 243.432 | |
| 29 | WLAFPLCSL | 226.014 | |
| 247 | VCAVFIFYV | 215.192 | |
| 22 | GLEEAQFWL | 178.815 | |
| 277 | ILANIYLLV | 177.358 | |
| 221 | YLLILKTVL | 149.071 | |
| 215 | LLISFSYLL | 138.001 | |
| 15 | FILIGLPGL | 114.985 | |
| 158 | LMAPLPVFI | 70.450 | |
| 280 | NIYLLVPPV | 70.387 | |
| 109 | SLSGMESTV | 69.552 | |
| 83 | KMLAIFWFN | 54.625 | |
| 182 | CLHQDVMKL | 49.134 | |
| 26 | AQFWLAFPL | 46.480 | |
| 223 | LILKTVLGL | 42.494 | |
| 276 | VILANIYLL | 42.494 | |
| 38 | YLIAVLGNL | 29.382 | |
| 67 | CMLSGIDIL | 26.377 | |
| 119 | LAMAFDRYV | 25.398 | |
| 202 | GLIVIISAI | 23.995 | |
| 307 | RLFHVATHA | 18.382 | |
| 68 | MLSGIDILI | 17.736 | |
| 86 | AIFWFNSTT | 14.407 | |
| 50 | YIVRTEHSL | 13.512 | |
| 175 | NILSHSYCL | 10.868 | |
| 168 | QLPFCRSNI | 10.433 | |
| 61 | PMYIFLCML | 9.493 | |
| 102 | LQIFAIHSL | 8.469 | |
| 255 | VPFIGLSMV | 6.568 | |
| 121 | MAFDRYVAI | 5.605 | |
| 84 | MLAIFWFNS | 4.747 | |
| 199 | VVYGLIVII | 4.683 | |
| 161 | PLPVFIKQL | 4.108 | |
| 305 | ILRLFHVAT | 3.659 | |
| 216 | LISFSYLLI | 3.658 | |
| 156 | AALMAPLPV | 3.574 | |
| 284 | LVPPVLNPI | 3.569 | |
| 99 | ACLLQIFAI | 3.361 | |
| 41 | AVLGNLTII | 3.185 | |

TABLE VII-continued

101P3A11-V1-A2-9 mers

| Start | Subsequence | Score |
|---|---|---|
| 204 | IVIISAIGL | 3.178 |
| 94 | TIQFDACLL | 2.937 |
| 32 | FPLCSLYLI | 2.666 |
| 136 | ATVLTLPRV | 2.222 |
| 12 | ATYFILIGL | 2.184 |
| 111 | SGMESTVLL | 2.115 |
| 139 | LTLPRVTKI | 2.096 |
| 254 | YVPFIGLSM | 2.000 |
| 304 | RILRLFHVA | 1.969 |
| 34 | LCSLYLIAV | 1.775 |
| 39 | LIAVLGNLT | 1.742 |
| 219 | FSYLLILKT | 1.647 |
| 44 | GNLTIIYIV | 1.584 |
| 120 | AMAFDRYVA | 1.471 |
| 43 | LGNLTIIYI | 1.465 |
| 209 | AIGLDSLLI | 1.435 |
| 201 | YGLIVIISA | 1.270 |
| 282 | YLLVPPVLN | 1.268 |
| 93 | TTIQFDACL | 1.127 |
| 8 | NESSATYFI | 1.116 |
| 242 | TCVSHVCAV | 1.044 |
| 198 | NVVYGLIVI | 0.861 |
| 217 | ISFSYLLIL | 0.827 |
| 191 | ACDDIRVNV | 0.745 |
| 105 | FAIHSLSGM | 0.730 |
| 244 | VSHVCAVFI | 0.637 |
| 79 | SSMPKMLAI | 0.580 |
| 117 | VLLAMAFDR | 0.544 |
| 112 | GMESTVLLA | 0.528 |
| 273 | PLPVILANI | 0.528 |
| 35 | CSLYLIAVL | 0.487 |
| 101 | LLQIFAIHS | 0.481 |
| 70 | SGIDILIST | 0.459 |
| 143 | RVTKIGVAA | 0.435 |
| 151 | AVVRGAALM | 0.435 |
| 66 | LDMLSGIDI | 0.428 |
| 251 | FIFYVPFIG | 0.415 |
| 46 | LTIIYIVRT | 0.405 |
| 63 | YIFLCMLSG | 0.401 |
| 113 | MESTVLLAM | 0.378 |
| 169 | LPFCRSNIL | 0.360 |
| 85 | LAIFWFNST | 0.334 |
| 227 | TVLGLTREA | 0.322 |
| 154 | RGAALMAPL | 0.321 |
| 197 | VNVVYGLIV | 0.316 |
| 285 | VPPVLNPIV | 0.316 |
| 128 | AICHPLRHA | 0.314 |
| 150 | AAVVRGAAL | 0.297 |
| 208 | SAIGLDSLL | 0.297 |
| 77 | STSSMPKML | 0.297 |
| 57 | SLHEPMYIF | 0.288 |
| 207 | ISAIGLDSL | 0.267 |
| 159 | ALMAPLPVF | 0.260 |
| 40 | IAVLGNLTI | 0.246 |
| 36 | SLYLIAVLG | 0.238 |
| 18 | IGLPGLEEA | 0.230 |
| 275 | PVILANIYL | 0.226 |
| 187 | VKMLACDDI | 0.220 |
| 100 | CLLQIFAIH | 0.215 |

TABLE VII

101P3A11-V2-A2-9mers

Portion of SEQ ID NO: 30; each start position is specified - the length of each peptide is 9 amino acids, the end portion for each peptide is the start position plus eight.

| Start | Subsequence | Score |
|---|---|---|
| 20 | WPISICWFL | 26.460 |
| 4 | LIAVLASGV | 16.258 |

TABLE VII-continued

101P3A11-V2-A2-9mers
Portion of SEQ ID NO: 30; each start position is specified - the length of each peptide is 9 amino acids, the end portion for each peptide is the start position plus eight.

| Start | Subsequence | Score |
|---|---|---|
| 1 | SLYLIAVLA | 15.898 |
| 28 | LLCSTQLSM | 8.446 |
| 6 | AVLASGVTL | 6.916 |
| 24 | ICWFLLCST | 1.579 |
| 27 | FLLCSTQLS | 1.268 |
| 3 | YLIAVLASG | 0.788 |
| 21 | PISICWFLL | 0.637 |
| 26 | WFLLCSTQL | 0.252 |
| 8 | LASGVTLRC | 0.117 |
| 22 | ISICWFLLC | 0.105 |
| 23 | SICWFLLCS | 0.090 |
| 16 | CPSSWPISI | 0.068 |
| 7 | VLASGVTLR | 0.058 |
| 14 | LRCPSSWPI | 0.018 |
| 5 | IAVLASGVT | 0.009 |
| 11 | GVTLRCPSS | 0.007 |
| 12 | VTLRCPSSW | 0.007 |
| 13 | TLRCPSSWP | 0.006 |
| 18 | SSWPISICW | 0.004 |
| 17 | PSSWPISIC | 0.001 |
| 10 | SGVTLRCPS | 0.000 |
| 29 | LCSTQLSME | 0.000 |
| 15 | RCPSSWPIS | 0.000 |
| 2 | LYLIAVLAS | 0.000 |
| 19 | SWPISICWF | 0.000 |
| 9 | ASGVTLRCP | 0.000 |
| 25 | CWFLLCSTQ | 0.000 |

TABLE VII

101P3A11-V3-A1-9 mers

| Start | Subsequence | Score | |
|---|---|---|---|
| 7 | LQMFAIHSL | 31.334 | Portion of SEQ ID NO: 32; |
| 4 | ACLLQMFAI | 3.361 | each start position is |
| 6 | LLQMAAIHS | 0.481 | specified - the length of |
| 5 | CLLQMFAIH | 0.215 | each peptide is 9 amino |
| 8 | QMFAIHSLS | 0.199 | acids, the end position |
| 3 | DACLLQMFA | 0.028 | for each peptide is the |
| 1 | QFDACLLQM | 0.003 | start position plus eight |

TABLE VII-continued

101P3A11-V3-A1-9 mers

| Start | Subsequence | Score |
|---|---|---|
| 2 | FDACLLQMF | 0.001 |
| 9 | MFAIHSLSG | 0.000 |

TABLE VIII

101P3A11-V1-A2-10 mers

| Start | Subsequence | Score | |
|---|---|---|---|
| 57 | SLHEPMYIFL | 722.583 | Portion of SEQ ID NO: 28; |
| 118 | LLAMAFDRYV | 494.237 | each start position is |
| 214 | SLLISFSYLL | 300.355 | specified - the length |
| 42 | VLGNLTIIYI | 224.357 | of each peptide is 10 |
| 157 | ALMAPLPVFI | 212.307 | amino acids, the end |
| 251 | FIFYVPFIGL | 94.987 | position for each pep- |
| 276 | VILANIYLLV | 90.231 | tide is the start |
| 222 | LLILKTVLGL | 83.527 | position plus nine |
| 101 | LLQIFAIHSL | 83.527 | |
| 140 | TLPRVTKIGV | 69.552 | |
| 254 | YVPFIGLSMV | 64.388 | |
| 95 | IQFDACLLQI | 62.741 | |
| 246 | HVCAVFIFYV | 57.690 | |
| 63 | YIFLCMLSGI | 56.155 | |
| 65 | FLCMLSGIDI | 47.991 | |
| 249 | AVFIFYVPFI | 42.727 | |
| 283 | LLVPPVLNPI | 40.792 | |
| 138 | VLTLPRVTKI | 40.792 | |
| 38 | YLIAVLGNLT | 34.279 | |
| 238 | KAFGICVSHV | 28.772 | |
| 67 | CMLSGIDILI | 27.879 | |
| 235 | AQAKAFGTCV | 26.797 | |
| 215 | LLISFSYLLI | 26.604 | |
| 83 | KMLAIFWFNS | 26.114 | |
| 84 | MLAIFWFNST | 24.070 | |
| 22 | GLEEAQFWLA | 18.576 | |
| 45 | NLTIIYIVRT | 17.140 | |
| 219 | FSYLLILKTV | 15.371 | |
| 304 | RILRLFHVAT | 14.407 | |
| 143 | RVIKIGVAAV | 13.997 | |
| 167 | KQLPFCRSNI | 13.698 | |
| 182 | CLHQDVMKLA | 11.426 | |
| 120 | AMAFDRYVAI | 11.302 | |
| 30 | LAFPLCSLYL | 10.264 | |
| 109 | SLSGMESTVL | 8.759 | |
| 168 | QLPFCRSNIL | 8.759 | |
| 228 | VLGLTREAQA | 8.446 | |
| 302 | RQRILRLFHV | 7.149 | |
| 190 | LACDDIRVNV | 6.733 | |
| 206 | IISAIGLDSL | 5.628 | |
| 181 | YCLHQDVMKL | 5.459 | |
| 86 | AIFWFNSTTI | 5.308 | |
| 243 | CVSHVCAVFI | 5.021 | |
| 203 | LIVIISAIGL | 4.993 | |
| 230 | GLTREAQAKA | 4.968 | |
| 292 | IVYGVKTKEI | 4.966 | |
| 216 | LISFSYLLIL | 4.709 | |
| 160 | APLPVFIKQL | 4.510 | |
| 284 | LVPPVLNPIV | 4.242 | |
| 280 | NIYLLVPPVL | 3.854 | |
| 26 | AQFWLAFPLC | 3.541 | |
| 33 | PLCSLYLIAV | 3.519 | |
| 299 | KEIRQRILRL | 3.344 | |
| 75 | LISTSSMPKM | 2.671 | |
| 201 | YGLIVIISAI | 2.666 | |
| 196 | RVNVVYGLIV | 2.495 | |
| 39 | LIAVLGNLTI | 2.439 | |
| 241 | GTCVSHVCAV | 2.222 | |
| 223 | LILKTVLGLT | 1.927 | |
| 121 | MAFDRYVAIC | 1.678 | |
| 21 | PGLEEAQFWL | 1.485 | |
| 8 | NESSATYFIL | 1.482 | |
| 17 | LIGLPGLEEA | 1.309 | |

TABLE VIII-continued

101P3A11-V1-A2-10 mers

| Start | Subsequence | Score |
|---|---|---|
| 274 | LPVILANIYL | 1.304 |
| 221 | YLLILKTVLG | 1.268 |
| 287 | PVLNPIVYGV | 1.139 |
| 111 | SGMESTVLLA | 1.132 |
| 92 | STTIQFDACL | 1.127 |
| 100 | CLLQIFAIHS | 1.048 |
| 279 | ANIYLLVPPV | 1.044 |
| 128 | AICHPLRHAT | 1.025 |
| 155 | GAALMAPLPV | 0.966 |
| 90 | FNSTTIQFDA | 0.865 |
| 198 | NVVYGLIVII | 0.861 |
| 233 | REAQAKAFGT | 0.840 |
| 129 | ICHPLRHATV | 0.772 |
| 43 | LGNLTIIYIV | 0.728 |
| 191 | ACDDIRVNVV | 0.702 |
| 11 | SATYFILIGL | 0.682 |
| 85 | LAIFWFNSTT | 0.669 |
| 188 | MKLACDDIRV | 0.608 |
| 282 | YLLVPPVLNP | 0.583 |
| 272 | SPLPVILANI | 0.580 |
| 36 | SLYLIAVLGN | 0.548 |
| 112 | GMESTVLLAM | 0.528 |
| 149 | VAAVVRGAAL | 0.504 |
| 163 | PVFIKQLPFC | 0.448 |
| 117 | VLLAMAFDRY | 0.436 |
| 151 | AVVRGAALMA | 0.435 |
| 66 | LCMLSGIDIL | 0.405 |
| 213 | DSLLISFSYL | 0.404 |
| 113 | MESTVLLAMA | 0.378 |
| 211 | GLDSLLISFS | 0.377 |
| 1 | MMVDPNGNES | 0.375 |
| 29 | WLAFPLCSLY | 0.343 |
| 32 | FPLCSLYLIA | 0.339 |
| 60 | EPMYIFLCML | 0.338 |
| 93 | TTIQFDACLL | 0.297 |
| 80 | SMPKMLAIFW | 0.296 |
| 307 | RLFHVATHAS | 0.276 |

TABLE VIII

101P3A11-V2-A2-10 mers

| Start | Subsequence | Score | |
|---|---|---|---|
| 4 | YLIAVLASGV | 319.939 | Portion of SEQ ID NO: 30; each start position is specified - the length of each peptide is 10 amino acids, the end position for each peptide is the start position plus nine |
| 28 | FLLCSTQLSM | 84.555 | |
| 8 | VLASGVTLRC | 8.446 | |
| 21 | WPISICWFLL | 6.325 | |
| 14 | TLRCPSSWPI | 5.947 | |
| 24 | SICWFLLCST | 2.357 | |
| 2 | SLYLIAVLAS | 0.548 | |
| 6 | IAVLASGVTL | 0.504 | |
| 20 | SWPISICWFL | 0.122 | |
| 1 | CSLYLIAVLA | 0.120 | |
| 5 | LIAVLASGVT | 0.093 | |
| 16 | RCPSSWPISI | 0.068 | |
| 29 | LLCSTQLSME | 0.058 | |
| 19 | SSWPISICWF | 0.051 | |
| 17 | CPSSWPISIC | 0.031 | |
| 22 | PISICWFLLC | 0.029 | |
| 7 | AVLASGVTLR | 0.011 | |
| 26 | CWFLLCSTQL | 0.011 | |
| 23 | ISICWFLLCS | 0.007 | |
| 13 | VTLRCPSSWP | 0.007 | |
| 12 | GVTLRCPSSW | 0.007 | |
| 25 | ICWFLLCSTQ | 0.001 | |
| 27 | WFLLCSTQLS | 0.001 | |
| 11 | SGVTLRCPSS | 0.000 | |
| 10 | ASGVTLRCPS | 0.000 | |
| 9 | LASGVTLRCP | 0.000 | |
| 3 | LYLIAVLASG | 0.000 | |

TABLE VIII-continued

101P3A11-V2-A2-10 mers

| Start | Subsequence | Score |
|---|---|---|
| 15 | LRCPSSWPIS | 0.000 |
| 18 | PSSWPISICW | 0.000 |

TABLE VIII

101P3A11-V3-A2-10 mers

| Start | Subsequence | Score | |
|---|---|---|---|
| 7 | LLQMFAIHSL | 83.257 | Portion of SEQ ID NO: 32; each start position is specified - the length of each peptide is 10 amino acids, the end position for each peptide is the start position plus nine |
| 1 | IQFDACLLQM | 29.877 | |
| 6 | CLLQMFAIHS | 1.048 | |
| 9 | QMFAIHSLSG | 0.199 | |
| 3 | FDACLLQMFA | 0.175 | |
| 4 | DACLLQMFAI | 0.145 | |
| 8 | LQMFAIHSLS | 0.048 | |
| 10 | MFAIHSLSGM | 0.013 | |
| 5 | ACLLQMFAIH | 0.001 | |
| 2 | QFDACLLQMF | 0.000 | |

TABLE IX

101P3A11-V1-A3-9 mers

| Start | Subsequence | Score | |
|---|---|---|---|
| 230 | GLTREAQAK | 60.000 | Portion of SEQ ID NO: 28; each start position is specified - the length of each peptide is 9 amino acids, the end position for each peptide is the start position plus eight |
| 138 | VLTLPRVTK | 30.000 | |
| 57 | SLHEPMYIF | 20.250 | |
| 211 | GLDSLLISF | 18.000 | |
| 261 | SMVHRFSKR | 18.000 | |
| 117 | VLLAMAFDR | 18.000 | |
| 45 | NLTIIYIVR | 12.000 | |
| 118 | LLAMAFDRY | 12.000 | |
| 215 | LLISFSYLL | 8.100 | |
| 22 | GLEEAQFWL | 8.100 | |
| 42 | VLGNLTIIY | 8.000 | |
| 157 | ALMAPLPVF | 6.750 | |
| 202 | GLIVIISAI | 6.075 | |
| 288 | VLNPIVYGV | 4.050 | |
| 75 | LISTSSMPK | 4.000 | |
| 112 | GMESTVLLA | 3.600 | |
| 246 | HVCAVFIFY | 3.600 | |
| 182 | CLHQDVMKL | 3.600 | |
| 249 | AVFIFYVPF | 3.000 | |
| 80 | SMPKMLAIF | 3.000 | |
| 68 | MLSGIDILI | 2.700 | |
| 214 | SLLISFSYL | 2.700 | |
| 159 | MAPLPVFIK | 2.700 | |
| 307 | RLFHVATHA | 1.500 | |
| 29 | WLAFPLCSL | 1.350 | |
| 61 | PMYIFLCML | 1.350 | |
| 100 | CLLQIFAIH | 1.350 | |
| 67 | CMLSGIDIL | 1.350 | |
| 83 | KMLAIFWFM | 1.215 | |
| 146 | KIGVAAVVR | 1.200 | |
| 165 | FIKQLPFCR | 1.200 | |
| 189 | KLACDDIRV | 1.200 | |
| 221 | YLLILKTVL | 0.900 | |
| 158 | LMAPLPVFI | 0.900 | |
| 199 | VVYGLIVII | 0.675 | |
| 12 | ATYFILIGL | 0.675 | |
| 38 | YLIAVLGNL | 0.608 | |
| 120 | AMAFDRYVA | 0.600 | |
| 257 | FIGLSMVHR | 0.600 | |
| 277 | ILANIYLLV | 0.600 | |
| 168 | QLPFCRSNI | 0.600 | |
| 187 | VMKLACDDI | 0.600 | |
| 262 | MVHRFSKRR | 0.600 | |
| 223 | LILKTVLGL | 0.540 | |

TABLE IX-continued

101P3A11-V1-A3-9 mers

| Start | Subsequence | Score |
|---|---|---|
| 291 | PIVYGVKTK | 0.450 |
| 260 | LSMVHRFSK | 0.450 |
| 283 | LLVPPVLNP | 0.405 |
| 276 | VILANIYLL | 0.405 |
| 126 | YVAICHPLR | 0.400 |
| 84 | MLAIFWFNS | 0.360 |
| 115 | STVLLAMAF | 0.300 |
| 305 | ILRLFHVAT | 0.300 |
| 280 | NIYLLVPPV | 0.300 |
| 109 | SLSGMESTV | 0.300 |
| 181 | YCLHQDVMK | 0.300 |
| 243 | CVSHVCAVF | 0.300 |
| 30 | LAFPLCSLY | 0.300 |
| 26 | AQFWLAFPL | 0.270 |
| 198 | NVVYGLIVI | 0.270 |
| 175 | NILSHSYCL | 0.270 |
| 101 | LLQIFAIHS | 0.240 |
| 139 | LTLPRVTKI | 0.203 |
| 297 | KTKEIRQRI | 0.203 |
| 41 | AVLGNLTII | 0.203 |
| 284 | LVPPVLNPI | 0.203 |
| 176 | ILSHSYCLH | 0.200 |
| 163 | PVFIKQLPF | 0.200 |
| 204 | IVIISAIGL | 0.180 |
| 36 | SLYLIAVLG | 0.150 |
| 86 | AIFWFNSTT | 0.150 |
| 48 | IIYIVRTEH | 0.150 |
| 93 | TTIQFDACL | 0.135 |
| 273 | PLPVILANI | 0.135 |
| 217 | ISFSYLLIL | 0.135 |
| 161 | PLPVFIKQL | 0.135 |
| 15 | FILIGLPGL | 0.135 |
| 209 | AIGLDSLLI | 0.120 |
| 216 | LISFSYLLI | 0.120 |
| 299 | KEIRQRILR | 0.108 |
| 50 | YIVRTEHSL | 0.090 |
| 304 | RILRLFHVA | 0.090 |
| 19 | GLPGLEEAQ | 0.090 |
| 135 | HATVLTLPR | 0.080 |
| 224 | ILKTVLGLT | 0.068 |
| 218 | SFSYLLILK | 0.060 |
| 94 | TIQFDACLL | 0.060 |
| 274 | LPVILANIY | 0.060 |
| 254 | YVPFIGLSM | 0.060 |
| 152 | VVRGAALMA | 0.060 |
| 300 | EIRQRILRL | 0.054 |
| 10 | SSATYFILI | 0.054 |
| 251 | FIFYVPFIG | 0.045 |
| 282 | YLLVPPVLN | 0.045 |
| 238 | KAFGTCVSH | 0.045 |
| 32 | FPLCSLYLI | 0.041 |
| 99 | ACLLQIFAI | 0.041 |
| 102 | LQIFAIHSL | 0.041 |
| 213 | DSLLISFSY | 0.041 |
| 33 | PLCSLYLIA | 0.040 |
| 46 | LTIIYIVRT | 0.034 |

TABLE IX

101P3A11-V2-A3-9 mers

| Start | Subsequence | Score | |
|---|---|---|---|
| 7 | VLASGVTLR | 12.000 | Portion of SEQ ID NO: 30; each start position is specified - the length of each peptide is 9 amino acids, the end position for each peptide is the start position plus eight |
| 1 | SLYLIAVLA | 1.500 | |
| 28 | LLCSTQLSM | 0.400 | |
| 6 | AVLASGVTL | 0.090 | |
| 3 | YLIAVLASG | 0.068 | |
| 27 | FLLCSTQLS | 0.060 | |
| 20 | WPISICWFL | 0.041 | |
| 23 | SICWFLLCS | 0.036 | |
| 16 | CPSSWPISI | 0.036 | |

TABLE IX-continued

101P3A11-V2-A3-9 mers

| Start | Subsequence | Score |
|---|---|---|
| 13 | TLRCPSSWP | 0.030 |
| 22 | ISICWFLLC | 0.027 |
| 18 | SSWPISICW | 0.022 |
| 4 | LIAVLASGV | 0.020 |
| 21 | PISICWFLL | 0.018 |
| 12 | VTLRCPSSW | 0.015 |
| 11 | GVTLRCPSS | 0.012 |
| 8 | LASGVTLRC | 0.009 |
| 24 | ICWFLLCST | 0.007 |
| 19 | SWPISICWF | 0.003 |
| 14 | LRCPSSWPI | 0.003 |
| 26 | WFLLCSTQL | 0.001 |
| 5 | IAVLASGVT | 0.000 |
| 15 | RCPSSWPIS | 0.000 |
| 2 | LYLIAVLAS | 0.000 |
| 29 | LCSTQLSME | 0.000 |
| 17 | PSSWPISIC | 0.000 |
| 25 | CWFLLCSTQ | 0.000 |
| 10 | SGVTLRCPS | 0.000 |
| 9 | ASGVTLRCP | 0.000 |

TABLE IX

101P3A11-V3-A3-9 mers

| Start | Subsequence | Score | |
|---|---|---|---|
| 5 | CLLQMFAIH | 0.900 | Portion of SEQ ID NO: 32; each start position is specified - the length of each peptide is 9 amino acids, the end position for each peptide is the start position plus eight |
| 8 | QMFAIHSLS | 0.300 | |
| 6 | LLQMFAIHS | 0.240 | |
| 7 | LQMFAIHSL | 0.041 | |
| 4 | ACLLQMFAI | 0.041 | |
| 2 | FDACLLQMF | 0.003 | |
| 3 | DACLLQMFA | 0.001 | |
| 1 | QFDACLLQM | 0.001 | |
| 9 | MFAIHSLSG | 0.000 | |

TABLE X

101P3A11-V1-AC-10 mers

| Start | Subsequence | Score | |
|---|---|---|---|
| 158 | LMAPLPVFIK | 405.000 | Portion of SEQ ID NO: 28; each start postion is specified - the length of each peptide is 10 amino acids, the end position for each peptide is the start position plus nine |
| 259 | GLSMVHRFSK | 180.000 | |
| 74 | ILISTSSMPK | 60.000 | |
| 117 | VLLAMAFDRY | 18.000 | |
| 288 | VLNPIVYGVK | 13.500 | |
| 19 | GLPGLEEAQF | 9.000 | |
| 261 | SMVHRFSKRR | 9.000 | |
| 214 | SLLISFSYLL | 8.100 | |
| 22 | GLEEAQFWLA | 8.100 | |
| 224 | ILKTVLGLTR | 8.000 | |
| 222 | LLILKTVLGL | 5.400 | |
| 137 | TVLTLPRVTK | 4.500 | |
| 187 | VMKLACDDIR | 4.000 | |
| 29 | WLAFPLCSLY | 4.000 | |
| 283 | LLVPPVLNPI | 3.038 | |
| 249 | AVFIFYVPFI | 2.700 | |
| 112 | GMESTVLLAM | 2.700 | |
| 251 | FIFYVPFIGL | 2.700 | |
| 67 | CMLSGIDILI | 2.700 | |
| 116 | TVLLAMAFDR | 1.800 | |
| 42 | VLGNLTIITI | 1.800 | |
| 57 | SLHEPMYIFL | 1.800 | |
| 138 | VLTLPRVTKI | 1.800 | |
| 41 | AVLGNLTIIY | 1.800 | |
| 215 | LLISFSYLLI | 1.800 | |
| 83 | KMLAIFWFNS | 1.620 | |
| 217 | ISFSYLLILK | 1.500 | |

TABLE X-continued

101P3A11-V1-AC-10 mers

| Start | Subsequence | Score |
|---|---|---|
| 65 | FLCMLSGIDI | 1.200 |
| 101 | LLQIFAIHSL | 0.900 |
| 157 | ALMAPLPVFI | 0.900 |
| 109 | SLSGMESTVL | 0.900 |
| 84 | MLAIFWFNST | 0.900 |
| 36 | SLYLIAVLGN | 0.600 |
| 305 | ILRLFHVATH | 0.600 |
| 168 | QLPFCRSNIL | 0.600 |
| 230 | GLTREAQAKA | 0.600 |
| 120 | AMAFDRYVAI | 0.600 |
| 257 | FIGLSMVHRF | 0.600 |
| 216 | LISFSYLLIL | 0.540 |
| 63 | YIFLCMLSGI | 0.450 |
| 280 | NIYLLVPPVL | 0.450 |
| 290 | NPIVYGVKTK | 0.450 |
| 45 | NLTIIYIVRT | 0.450 |
| 140 | TLPRVTKIGV | 0.400 |
| 273 | PLPVILANIY | 0.400 |
| 80 | SMPKMLAIFW | 0.400 |
| 100 | CLLQIFAIHS | 0.360 |
| 132 | PLRHATVLTL | 0.360 |
| 86 | AIFWFNSTTI | 0.300 |
| 246 | HVCAVFIFYV | 0.270 |
| 95 | IQFDACLLQI | 0.270 |
| 282 | YLLVPPVLNP | 0.270 |
| 199 | VVYGLIVIIS | 0.270 |
| 194 | DIRVNVVYGL | 0.243 |
| 292 | IVYGVKTKEI | 0.225 |
| 182 | CLHQDVMKLA | 0.225 |
| 228 | VLGLTREAQA | 0.200 |
| 307 | RLFHVATHAS | 0.200 |
| 203 | LIVIISAIGL | 0.180 |
| 68 | MLSGIDILIS | 0.180 |
| 277 | ILANIYLLVP | 0.180 |
| 33 | PLCSLYLIAV | 0.180 |
| 211 | GLDSLLISFS | 0.180 |
| 295 | GVKTKEIRQR | 0.180 |
| 38 | YLIAVLGNLT | 0.150 |
| 198 | NVVYGLIVII | 0.135 |
| 16 | ILIGLPGLEE | 0.135 |
| 202 | GLIVIISAIG | 0.135 |
| 238 | KAFGTCVSHV | 0.135 |
| 167 | KQLPFCRSNI | 0.121 |
| 196 | RVNVVYGLIV | 0.120 |
| 176 | ILSHSYCLHQ | 0.120 |
| 39 | LIAVLGNLTI | 0.120 |
| 44 | GNLTIIYIVR | 0.108 |
| 56 | HSLHEPMYIF | 0.101 |
| 92 | STTIQFDACL | 0.090 |
| 244 | VSHVCAVFIF | 0.090 |
| 121 | MAFDRYVAIC | 0.090 |
| 206 | IISAIGLDSL | 0.090 |
| 81 | MPKMLAIFWF | 0.090 |
| 276 | VILANIYLLV | 0.090 |
| 241 | GTCVSHVCAV | 0.090 |
| 30 | LAFPLCSLYL | 0.090 |
| 260 | LSMVHRFSKR | 0.090 |
| 248 | CAVFIFYVPF | 0.090 |
| 26 | AQFWLAFPLC | 0.090 |
| 285 | VPPVLNPIVY | 0.080 |
| 231 | LTREAQAKAF | 0.075 |
| 156 | AALMAPLPVF | 0.068 |
| 151 | AVVRGAALMA | 0.060 |
| 243 | CVSHVCAVFI | 0.060 |
| 162 | LPVFIKQLPF | 0.060 |
| 143 | RVTKIGVAAV | 0.060 |
| 1 | MMVDPNGNES | 0.060 |
| 118 | LLAMAFDRYV | 0.060 |
| 245 | SHVCAVFIFY | 0.054 |
| 181 | YCLHQDVMKL | 0.054 |
| 93 | TTIQFDACLL | 0.045 |
| 304 | RILRLFHVAT | 0.045 |
| 47 | TIIYIVRTEH | 0.045 |

TABLE X

101P3A11-V2-A3-10 mers

| Start | Subsequence | Score | |
|---|---|---|---|
| 14 | TLRCPSSWPI | 1.800 | Portion of SEQ ID NO: 30; each start position is specified - the length of each peptide is 10 amino acids, the end position for each peptide is the start position plus nine |
| 7 | AVLASGVTLR | 1.800 | |
| 2 | SLYLIAVLAS | 1.200 | |
| 28 | FLLCSTQLSM | 0.600 | |
| 8 | VLASGVTLRC | 0.600 | |
| 4 | YLIAVLASGV | 0.300 | |
| 19 | SSWPISICWF | 0.113 | |
| 12 | GVTLRCPSSW | 0.060 | |
| 22 | PISICWFLLC | 0.036 | |
| 16 | RCPSSWPISI | 0.036 | |
| 29 | LLCSTQLSME | 0.030 | |
| 21 | WPISICWFLL | 0.027 | |
| 24 | SICWFLLCST | 0.015 | |
| 6 | IAVLASGVTL | 0.009 | |
| 17 | CPSSWPISIC | 0.005 | |
| 26 | CWFLLCSTQL | 0.003 | |
| 5 | LIAVLASGVT | 0.003 | |
| 20 | SWPISICWFL | 0.003 | |
| 23 | ISICWFLLCS | 0.003 | |
| 13 | VTLRCPSSWP | 0.002 | |
| 1 | CSLYLIAVLA | 0.002 | |
| 25 | ICWFLLCSTQ | 0.001 | |
| 18 | PSSWPISICW | 0.000 | |
| 10 | ASGVTLRCPS | 0.000 | |
| 3 | LYLIAVLASG | 0.000 | |
| 27 | WFLLCSTQLS | 0.000 | |
| 11 | SGVTLRCPSS | 0.000 | |
| 15 | LRCPSSWPIS | 0.000 | |
| 9 | LASGVTLRCP | 0.000 | |

TABLE X

101P3A11-V3-A3-10 mers

| Start | Subsequence | Score | |
|---|---|---|---|
| 7 | LLQMFAIHSL | 0.900 | Portion of SEQ ID NO: 32; each start position is specified - the length of each peptide is 10 amino acids, the end position for each peptide is the start position plus nine |
| 6 | CLLQMFAIHS | 0.360 | |
| 9 | QMFAIHSLSG | 0.200 | |
| 1 | IQFDACLLQM | 0.090 | |
| 5 | ACLLQMFAIH | 0.009 | |
| 4 | DACLLQMFAI | 0.008 | |
| 2 | QFDACLLQMF | 0.003 | |
| 8 | LQMFAIHSLS | 0.003 | |
| 3 | FDACLLQMFA | 0.000 | |
| 10 | MFAIHSLSGM | 0.000 | |

TABLE XI

101P3A11-V1-A3-9mers

| Start | Subsequence | Score | |
|---|---|---|---|
| 230 | GLTREAQAK | 1.200 | Portion of SEQ ID NO: 28 each start position is specified-the length of each peptide is 9 amino acids, the end position for each peptide is the start position plus eight |
| 75 | LISTSSMPK | 0.800 | |
| 159 | MAPLPVFIK | 0.600 | |
| 126 | YVAICHPLR | 0.400 | |
| 218 | SFSYLLILK | 0.400 | |
| 138 | VLTLPRVTK | 0.400 | |
| 117 | VLLAMAFDR | 0.360 | |
| 181 | YCLHQDVMK | 0.300 | |
| 146 | KIGVAAVVR | 0.240 | |
| 165 | FIKQLPFCR | 0.240 | |
| 262 | MVHRFSKRR | 0.200 | |
| 45 | NLTIIYIVR | 0.160 | |
| 260 | LSMVHRFSK | 0.120 | |
| 261 | SMVHRFSKR | 0.120 | |
| 299 | KEIRQRILR | 0.108 | |
| 135 | HATVLTLPR | 0.080 | |
| 257 | FIGLSMVHR | 0.080 | |

TABLE XI-continued

101P3A11-V1-A3-9mers

| Start | Subsequence | Score |
|---|---|---|
| 196 | RVNVVYGLI | 0.060 |
| 143 | RVTKIGVAA | 0.060 |
| 198 | NVVYSLIVI | 0.060 |
| 204 | IVIISAIGL | 0.060 |
| 289 | LNPIVYSVK | 0.040 |
| 254 | YVPFISLSM | 0.040 |
| 12 | ATYFILIGL | 0.040 |
| 199 | VVYSLIVII | 0.040 |
| 152 | VVRSAALMA | 0.040 |
| 249 | AVFIFYVPF | 0.040 |
| 246 | HVCAVFIFY | 0.040 |
| 22 | GLEEAQFWL | 0.036 |
| 26 | AQFWLAFPL | 0.036 |
| 302 | RQRILRLFH | 0.036 |
| 291 | PIVYSVKTK | 0.030 |
| 297 | KTKEIRQRI | 0.030 |
| 115 | STVLLAMAF | 0.030 |
| 151 | AVVRSAALM | 0.030 |
| 41 | AVLSNLTII | 0.030 |
| 241 | GTCVSHVCA | 0.030 |
| 189 | KLACDDIRV | 0.024 |
| 211 | SLDSLLISF | 0.024 |
| 307 | RLFHVATHA | 0.024 |
| 243 | CVSHVCAVF | 0.020 |
| 51 | IVRTEHSLH | 0.020 |
| 284 | LVPPVLNPI | 0.020 |
| 202 | GLIVIISAI | 0.018 |
| 125 | RYVAICHPL | 0.018 |
| 304 | RILRLFHVA | 0.018 |
| 136 | ATVLTLPRV | 0.015 |
| 139 | LTLPRVTKI | 0.015 |
| 93 | TTIQFDACL | 0.015 |
| 276 | VILANIYLL | 0.012 |
| 223 | LILKTVLSL | 0.012 |
| 215 | LLISFSYLL | 0.012 |
| 175 | NILSHSYCL | 0.012 |
| 295 | GVKTKEIRQ | 0.012 |
| 238 | KAFGTCVSH | 0.012 |
| 231 | LTREAQAKA | 0.010 |
| 144 | VTKISVAAV | 0.010 |
| 99 | ACLLQIFAI | 0.009 |
| 102 | LQIFAIHSL | 0.009 |
| 163 | PVFIKQLPF | 0.008 |
| 252 | IFYVPFISL | 0.008 |
| 182 | CLHQDVMKL | 0.008 |
| 216 | LISFSYLLI | 0.008 |
| 42 | VLSNLTIIY | 0.008 |
| 288 | VLNPIVYSV | 0.008 |
| 66 | LCMLSGIDI | 0.008 |
| 225 | LKTVLSLTR | 0.008 |
| 68 | MLSGIDILI | 0.008 |
| 277 | ILANIYLLV | 0.008 |
| 209 | AISLDSLLI | 0.008 |
| 120 | AMAFDRYVA | 0.008 |
| 280 | NIYLLVPPV | 0.008 |
| 57 | SLHEPMYIF | 0.008 |
| 48 | IIYIVRTEH | 0.008 |
| 157 | ALMAPLPVF | 0.008 |
| 188 | MKLACDDIR | 0.006 |
| 294 | YSVKTKEIR | 0.006 |
| 275 | PVILANIYL | 0.006 |
| 67 | CMLSGIDIL | 0.006 |
| 148 | SVAAVVRSA | 0.006 |
| 281 | IYLLVPPVL | 0.006 |
| 221 | YLLILKTVL | 0.006 |
| 15 | FILIGLPGL | 0.006 |
| 214 | SLLISFSYL | 0.006 |
| 100 | CLLQIFAIH | 0.006 |
| 127 | VAICHPLRH | 0.006 |
| 32 | FPLCSLYLI | 0.006 |
| 247 | VCAVFIFYV | 0.006 |
| 40 | IAVLSNLTI | 0.006 |
| 156 | AALMAPLPV | 0.006 |
| 50 | YIVRTEHSL | 0.006 |
| 38 | YLIAVLSNL | 0.006 |

TABLE XI-continued

101P3A11-V1-A3-9mers

| Start | Subsequence | Score |
|---|---|---|
| 77 | STSSMPKML | 0.005 |
| 226 | KTVLSLTRE | 0.005 |
| 80 | SMPKMLAIF | 0.004 |
| 29 | WLAFPLCSL | 0.004 |
| 109 | SLSGMESTV | 0.004 |
| 30 | LAFPLCSLY | 0.004 |
| 187 | VMKLACDDI | 0.004 |

TABLE XI

101P3A11-V2-A11-9mers

| Start | Subsequence | Score | |
|---|---|---|---|
| 7 | VLASGVTLR | 0.080 | Portion of SEQ ID NO: 30 |
| 6 | AVLASGVTL | 0.030 | each start position is |
| 12 | VTLRCPSSW | 0.015 | specified-the length of |
| 28 | LLCSTQLSM | 0.008 | each peptide is 9 amino |
| 1 | SLYLIAVLA | 0.008 | acids, the end position |
| 11 | GVTLRCPSS | 0.006 | for each peptide is the |
| 20 | WPISICWFL | 0.006 | start position plus |
| 16 | CPSSWPISI | 0.004 | eight |
| 4 | LIAVLASGV | 0.004 | |
| 26 | WFLLCSTQL | 0.003 | |
| 21 | PISICWFLL | 0.001 | |
| 2 | LYLIAVLAS | 0.001 | |
| 23 | SICWFLLCS | 0.001 | |
| 18 | SSWPISICW | 0.001 | |
| 27 | FLLCSTQLS | 0.001 | |
| 15 | RCPSSWPIS | 0.001 | |
| 3 | YLIAVLASG | 0.001 | |
| 13 | TLRCPSSWP | 0.000 | |
| 14 | LRCPSSWPI | 0.000 | |
| 8 | LASGVTLRC | 0.000 | |
| 24 | ICWFLLCST | 0.000 | |
| 5 | IAVLASGVT | 0.000 | |
| 29 | LCSTQLSME | 0.000 | |
| 19 | SWPISICWF | 0.000 | |
| 22 | ISICWFLLC | 0.000 | |
| 25 | CWFLLCSTQ | 0.000 | |
| 10 | SGVTLRCPS | 0.000 | |
| 9 | ASGVTLRCP | 0.000 | |
| 17 | PSSWPISIC | 0.000 | |

TABLE XI

101P3A11-V2-A11-9 mers

| Start | Subsequence | Score | |
|---|---|---|---|
| 7 | LQMFAIHSL | 0.012 | Portion of SEQ ID NO: 32; |
| 4 | ACLLQMFAI | 0.009 | each start position is |
| 5 | CLLQMFAIH | 0.006 | specified - the length of |
| 1 | QFDACLLQM | 0.004 | each peptide is 9 amino |
| 3 | DACLLQMFA | 0.001 | acids, the end position |
| 8 | QMFAIHSLS | 0.001 | for each peptide is the |
| 6 | LLQMFAIHS | 0.001 | start position plus eight |
| 9 | MFAIHSLSG | 0.000 | |
| 2 | FDACLLQMF | 0.000 | |

TABLE XII

101P3A11-V1-A11-10mers

| Start | Subsequence | Score | |
|---|---|---|---|
| 259 | GLSMVHRFSK | 3.600 | Portion of SEQ ID NO: 28 |
| 137 | TVLTLPRVTK | 3.000 | each start position is |

TABLE XII-continued

101P3A11-V1-A11-10mers

| Start | Subsequence | Score | |
|---|---|---|---|
| 116 | TVLLAMAFDR | 1.800 | specified-the length of |
| 158 | LMAPLPVFIK | 1.200 | each peptide is 10 amino |
| 74 | ILISTSSMPK | 1.200 | acids, the end position |
| 288 | VLNPIVYGVK | 0.400 | for each peptide is the |
| 180 | SYCLHQDVMK | 0.400 | start position plus |
| 125 | RYVAICHPLR | 0.360 | nine |
| 164 | VFIKQLPFCR | 0.180 | |
| 224 | ILKTVLSLTR | 0.160 | |
| 290 | NPIVYSVKTK | 0.150 | |
| 295 | GVKTKEIRQR | 0.120 | |
| 196 | RVNVVYSLIV | 0.120 | |
| 217 | ISFSYLLILK | 0.080 | |
| 187 | VMKLACDDIR | 0.080 | |
| 293 | VYGVKTKEIR | 0.080 | |
| 44 | GNLTIIYIVR | 0.072 | |
| 246 | HVCAVFIFYV | 0.060 | |
| 151 | AVVRGAALMA | 0.060 | |
| 148 | GVAAVVRGAA | 0.060 | |
| 143 | RVTKIGVAAV | 0.060 | |
| 261 | SMVHRFSKRR | 0.060 | |
| 41 | AVLSNLTIIY | 0.060 | |
| 302 | RQRILRLFHV | 0.054 | |
| 126 | YVAICHPLRH | 0.040 | |
| 249 | AVFIFYVPFI | 0.040 | |
| 229 | LGLTREAQAK | 0.030 | |
| 241 | GTCVSHVCAV | 0.030 | |
| 53 | RTEHSLHEPM | 0.030 | |
| 198 | NVVYSLIVII | 0.030 | |
| 167 | KQLPFCRSNI | 0.027 | |
| 134 | RHATVLTLPR | 0.024 | |
| 112 | GMESIVLLAM | 0.024 | |
| 95 | IQFDACLLQI | 0.024 | |
| 22 | GLEEAQFWLA | 0.024 | |
| 77 | STSSMPKMLA | 0.020 | |
| 254 | YVPFIGLSMV | 0.020 | |
| 292 | IVYGVKTKEI | 0.020 | |
| 284 | LVPPVLNPIV | 0.020 | |
| 243 | CVSHVCAVFI | 0.020 | |
| 251 | FIFYVPFIGL | 0.016 | |
| 93 | TTIQFDACLL | 0.015 | |
| 186 | DVMKLACDDI | 0.012 | |
| 222 | LLILKTVLGL | 0.012 | |
| 230 | GLTREAQAKA | 0.012 | |
| 155 | GAALMAPLPV | 0.012 | |
| 214 | SLLISFSYLL | 0.012 | |
| 253 | FYVPFISLSM | 0.012 | |
| 238 | KAFSTCVSHV | 0.012 | |
| 276 | VILANIYLLV | 0.012 | |
| 215 | LLISFSYLLI | 0.012 | |
| 19 | SLPGLEEAQF | 0.012 | |
| 203 | LIVIISAIGL | 0.012 | |
| 67 | CMLSGIDILI | 0.012 | |
| 92 | STTIQFDACL | 0.010 | |
| 144 | VTKISVAAVV | 0.010 | |
| 30 | LAFPLCSLYL | 0.008 | |
| 80 | SMPKMLAIFW | 0.008 | |
| 280 | NIYLLVPPVL | 0.008 | |
| 63 | YIFLCMLSGI | 0.008 | |
| 57 | SLHEPMYIFL | 0.008 | |
| 119 | LAMAFDRYVA | 0.008 | |
| 199 | VVYSLIVIIS | 0.008 | |
| 216 | LISFSYLLIL | 0.008 | |
| 42 | VLSNLTIIYI | 0.008 | |
| 255 | VPFISLSMVH | 0.008 | |
| 157 | ALMAPLPVFI | 0.008 | |
| 200 | VYSLIVIISA | 0.008 | |
| 39 | LIAVLSNLTI | 0.008 | |
| 140 | TLPRVTKISV | 0.008 | |
| 298 | TKEIRQRILR | 0.008 | |
| 65 | FLCMLSGIDI | 0.008 | |
| 86 | AIFWFNSTTI | 0.008 | |
| 260 | LSMVHRFSKR | 0.008 | |
| 256 | PFISLSMVHR | 0.006 | |
| 145 | TKISVAAVVR | 0.006 | |
| 50 | YIVRTEHSLH | 0.006 | |

TABLE XII-continued

101P3A11-V1-A11-10mers

| Start | Subsequence | Score |
|---|---|---|
| 162 | LPVFIKQLPF | 0.006 |
| 47 | TIIYIVRTEH | 0.006 |
| 265 | RFSKRRDSPL | 0.006 |
| 81 | MPKMLAIFWF | 0.006 |
| 37 | LYLIAVLSNL | 0.006 |
| 220 | SYLLILKTVL | 0.006 |
| 275 | PVILANIYLL | 0.006 |
| 175 | NILSHSYCLH | 0.006 |
| 181 | YCLHQDVMKL | 0.006 |
| 283 | LLVPPVLNPI | 0.006 |
| 32 | FPLCSLYLIA | 0.006 |
| 287 | PVLNPIVYSV | 0.006 |
| 235 | AQAKAFSTCV | 0.006 |
| 274 | LPVILANIYL | 0.006 |
| 49 | IYIVRTEHSL | 0.006 |
| 117 | VLLAMAFDRY | 0.006 |
| 208 | SAISLDSLLI | 0.006 |
| 83 | KMLAIFWFNS | 0.005 |
| 299 | KEIRQRILRL | 0.005 |
| 231 | LIREAQAKAF | 0.005 |
| 226 | KTVLSLTREA | 0.005 |
| 305 | ILRLFHVATH | 0.004 |
| 101 | LLQIFAIHSL | 0.004 |

TABLE XII

101P3A11-V2-A11-10mers

| Start | Subsequence | Score | |
|---|---|---|---|
| 7 | AVLASGVTLR | 0.600 | Portion of SEQ ID NO: 30 |
| 12 | SVTLRCPSSW | 0.060 | each start position is |
| 16 | RCPSSWPISI | 0.012 | specified-the length of |
| 28 | FLLCSTQLSM | 0.012 | each peptide is 10 amino |
| 21 | WPISICWFLI | 0.009 | acids, the end position |
| 14 | TLRCPSSWPI | 0.008 | for each peptide is the |
| 4 | YLIAVLASGV | 0.006 | start position plus nine |
| 6 | IAVLASGVTL | 0.003 | |
| 2 | SLYLIAVLAS | 0.002 | |
| 13 | VTIRCPSSWP | 0.002 | |
| 8 | VLASGVTLRC | 0.001 | |
| 3 | LYLIAVLASG | 0.001 | |
| 26 | CWFLLCSTQL | 0.000 | |
| 19 | SSWPISICWF | 0.000 | |
| 25 | ICWFLLCSTQ | 0.000 | |
| 5 | LIAVLASGVT | 0.000 | |
| 24 | SICWFLLCST | 0.000 | |
| 29 | LLCSTQLSME | 0.000 | |
| 20 | SWPISICWFL | 0.000 | |
| 1 | CSLYLIAVLA | 0.000 | |
| 27 | WFLLCSTQLS | 0.000 | |
| 17 | CPSSWPISIC | 0.000 | |
| 22 | PISICWFLLC | 0.000 | |
| 23 | ISICWFLLCS | 0.000 | |
| 18 | PSSWPISICW | 0.000 | |
| 11 | SSVTLRCPSS | 0.000 | |
| 15 | LRCPSSWPIS | 0.000 | |
| 10 | ASGVTLRCPS | 0.000 | |
| 9 | LASGVTLRCP | 0.000 | |

TABLE XII

101P3A11-V3-A11-10mers

| Start | Subsequence | Score | |
|---|---|---|---|
| 1 | IQFDACLLQM | 0.024 | Portion of SEQ ID NO: 32 |
| 7 | LLQMFAIHSL | 0.004 | each start position is |
| 5 | ACLLQMFAIH | 0.003 | specified-the length of |
| 2 | QFDACLLQMF | 0.002 | each peptide is 10 amino |

TABLE XII-continued

101P3A11-V3-A11-10mers

| Start | Subsequence | Score | |
|---|---|---|---|
| 10 | MFAIHSLSGM | 0.002 | acids, the end position for each peptide is the start position plus nine |
| 4 | DACLLQMFAI | 0.002 | |
| 9 | QMFAIHSLSG | 0.002 | |
| 6 | CLLQMFAIHS | 0.001 | |
| 8 | LQMFAIHSLS | 0.001 | |
| 3 | FDACLLQMFA | 0.000 | |

TABLE XIII

101P3A11-V1-A24-9mers

| Start | Subsequence | Score | |
|---|---|---|---|
| 125 | RYVAICHPL | 840.000 | Portion of SEQ ID NO: 28 each start position is specified-the length of each peptide is 9 amino acids, the end position for each peptide is the start position plus eight |
| 281 | IYLLVPPVL | 420.000 | |
| 293 | VYGVKTKEI | 55.000 | |
| 31 | AFPLCSLYL | 30.000 | |
| 180 | SYCLHQDVM | 25.000 | |
| 252 | IFYVPFIGL | 24.000 | |
| 89 | WFNSTTIQF | 15.000 | |
| 220 | SYLLILKTV | 10.500 | |
| 154 | RSAALMAPL | 9.600 | |
| 62 | MYIFLCMLS | 9.000 | |
| 253 | FYVPFISLS | 9.000 | |
| 38 | YLIAVLGNL | 8.400 | |
| 250 | VFIFYVPFI | 7.500 | |
| 64 | IFLCMLSGI | 7.500 | |
| 49 | IYIVRTEHS | 7.500 | |
| 37 | LYLIAVLGN | 7.500 | |
| 22 | GLEEAQFWL | 7.200 | |
| 214 | SLLISFSYL | 7.200 | |
| 111 | SGMESTVLL | 7.200 | |
| 208 | SAIGLDSLL | 7.200 | |
| 35 | CSLYLIAVL | 7.200 | |
| 221 | YLLILKTVL | 7.200 | |
| 200 | VYSLIVIIS | 7.000 | |
| 150 | AAVVRSAAL | 6.000 | |
| 67 | CMLSGIDIL | 6.000 | |
| 131 | HPLRHATVL | 6.000 | |
| 15 | FILIGLPGL | 6.000 | |
| 175 | NILSHSYCL | 6.000 | |
| 93 | TTIQFDACL | 6.000 | |
| 215 | LLISFSYLL | 6.000 | |
| 102 | LQIFAIHSL | 6.000 | |
| 50 | YIVRTEHSL | 6.000 | |
| 94 | TIQFDACLL | 6.000 | |
| 276 | VILANIYLL | 6.000 | |
| 204 | IVIISAIGL | 6.000 | |
| 223 | LILKTVLGL | 6.000 | |
| 12 | ATYFILIGL | 5.600 | |
| 87 | IFWFNSTTI | 5.000 | |
| 96 | QFDACLLQI | 5.000 | |
| 169 | LPFCRSNIL | 4.800 | |
| 26 | AQFWLAFPL | 4.800 | |
| 182 | CLHQDVMKL | 4.400 | |
| 196 | RVNVVYSLI | 4.200 | |
| 297 | KTKEIRQRI | 4.032 | |
| 9 | ESSATYFIL | 4.000 | |
| 300 | EIRQRILRL | 4.000 | |
| 266 | FSKRRDSPL | 4.000 | |
| 29 | WLAFPLCSL | 4.000 | |
| 110 | LSGMESTVL | 4.000 | |
| 217 | ISFSYLLIL | 4.000 | |
| 207 | ISAISLDSL | 4.000 | |
| 77 | STSSMPKML | 4.000 | |
| 115 | STVLLAMAF | 3.600 | |
| 284 | LVPPVLNPI | 3.024 | |
| 7 | GNESSATYF | 3.000 | |
| 157 | ALMAPLPVF | 3.000 | |
| 258 | ISLSMVHRF | 3.000 | |
| 80 | SMKMLAIF | 3.000 | |
| 243 | CVSHVCAVF | 2.800 | |

TABLE XIII-continued

101P3A11-V1-A24-9mers

| Start | Subsequence | Score |
|---|---|---|
| 57 | SLHEPMYIF | 2.400 |
| 211 | GLDSLLISF | 2.400 |
| 202 | GLIVIISAI | 2.100 |
| 249 | AVFIFYVPF | 2.000 |
| 20 | LPGLEEAQF | 2.000 |
| 139 | LTLPRVTKI | 1.980 |
| 79 | SSMPKMLAI | 1.800 |
| 41 | AVLSNLTII | 1.500 |
| 32 | FPLCSLYLI | 1.500 |
| 66 | LCMLSGIDI | 1.500 |
| 99 | ACLLQIFAI | 1.500 |
| 40 | IAVLSNLTI | 1.500 |
| 198 | NVVYSLIVI | 1.500 |
| 56 | HSLHEPMYI | 1.500 |
| 168 | QLPFCRSNI | 1.500 |
| 43 | LGNLTIIYI | 1.500 |
| 158 | LMAPLPVFI | 1.440 |
| 68 | MLSGIDILI | 1.400 |
| 60 | EPMYIFLCM | 1.260 |
| 10 | SSATYFILI | 1.200 |
| 121 | MAFDRYVAI | 1.200 |
| 199 | VVYSLIVII | 1.200 |
| 270 | RDSPLPVIL | 1.152 |
| 254 | YVPFISLSM | 1.050 |
| 216 | LISFSYLLI | 1.000 |
| 244 | VSHVCAVFI | 1.000 |
| 187 | VMKLACDDI | 1.000 |
| 209 | AISLDSLLI | 1.000 |
| 195 | IRVNVVYSL | 0.840 |
| 164 | VFIKQLPFC | 0.750 |
| 151 | AVVRSAALM | 0.750 |
| 73 | DILISTSSM | 0.750 |
| 105 | FAIHSLSGM | 0.750 |
| 58 | LHEPMYIFL | 0.720 |
| 13 | TYFILISLP | 0.600 |
| 298 | TKEIRQRIL | 0.600 |
| 275 | PVILANIYL | 0.600 |
| 161 | PLPVFIKQL | 0.600 |
| 27 | QFWLAFPLC | 0.600 |
| 76 | ISTSSMPKM | 0.550 |
| 83 | KMLAIFWFN | 0.504 |

TABLE XIII

101P3A11-V2-A24-9mers

| Start | Subsequence | Score | |
|---|---|---|---|
| 26 | WFLLCSTQL | 30.000 | Portion of SEQ ID NO: 30 each start position is specified-the length of each peptide is 9 amino acids, the end position for each peptide is the start position plus eight |
| 20 | WPISICWFL | 8.400 | |
| 2 | LYLIAVLAS | 7.500 | |
| 6 | AVLASGVTL | 6.000 | |
| 19 | SWPISICWF | 3.000 | |
| 16 | CPSSWPISI | 1.000 | |
| 28 | LLCSTQLSM | 0.500 | |
| 21 | PISICWFLL | 0.400 | |
| 15 | RCPSSWPIS | 0.300 | |
| 10 | SSVTLRCPS | 0.180 | |
| 22 | ISICWFLLC | 0.180 | |
| 27 | FLLCSTQLS | 0.180 | |
| 18 | SSWPISICW | 0.168 | |
| 5 | IAVLASGVT | 0.150 | |
| 12 | VTLRCPSSW | 0.150 | |
| 8 | LASGVTLRC | 0.140 | |
| 1 | SLYLIAVLA | 0.140 | |
| 4 | LIAVLASGV | 0.120 | |
| 14 | LRCPSSWPI | 0.120 | |
| 24 | ICWFLLCST | 0.120 | |
| 23 | SICWFLLCS | 0.100 | |
| 11 | SVTLRCPSS | 0.100 | |
| 3 | YLIAVLASG | 0.021 | |
| 25 | CWFLLCSTQ | 0.012 | |

TABLE XIII-continued

101P3A11-V2-A24-9mers

| Start | Subsequence | Score |
|---|---|---|
| 9 | ASGVTLRCP | 0.010 |
| 29 | LCSTQLSME | 0.010 |
| 13 | TLRCPSSWP | 0.010 |
| 7 | VLASGVTLR | 0.010 |
| 17 | PSSWPISIC | 0.010 |

TABLE XIII

101P3A11-V3-A24-9mers

| Start | Subsequence | Score | |
|---|---|---|---|
| 7 | LQMFAIHSL | 6.000 | Portion of SEQ ID NO: 30 each start position is specified-the length of each peptide is 9 amino acids, the end position for each peptide is the start position plus eight |
| 1 | QFDACLLQM | 2.500 | |
| 4 | ACLLQMFAI | 1.500 | |
| 2 | FDACLLQMF | 0.288 | |
| 6 | LLQMFAIHS | 0.150 | |
| 8 | QMFAIHSLS | 0.140 | |
| 3 | DACLLQMFA | 0.120 | |
| 9 | MFAIHSLSG | 0.050 | |
| 5 | CLLQMFAIH | 0.018 | |

TABLE XIV

101P3A11-V1-A24-10mers

| Start | Subsequence | Score | |
|---|---|---|---|
| 37 | LYLIAVLGNL | 420.000 | Portion of SEQ ID NO: 28 each start position is specified-the length of each peptide is 10 amino acids, the end position for each peptide is the start position plus nine |
| 220 | SYLLILKTVL | 360.000 | |
| 49 | IYIVRTEHSL | 300.000 | |
| 253 | FYVPFISLSM | 63.000 | |
| 265 | RFSKRRDSPL | 40.000 | |
| 14 | YFILIGLPGL | 30.000 | |
| 96 | QFDACLLQIF | 14.400 | |
| 297 | KTKEIRQRIL | 9.600 | |
| 31 | AFPLCSLYLI | 7.500 | |
| 281 | IYLLVPPVLN | 7.500 | |
| 168 | QLPFCRSNIL | 7.200 | |
| 213 | DSLLISFSYL | 7.200 | |
| 160 | APLPVFIKQL | 7.200 | |
| 25 | EAQFWLAFPL | 7.200 | |
| 200 | VYGLIVIISA | 7.000 | |
| 181 | YCLHQDVMKL | 6.600 | |
| 274 | LPVILANIYL | 6.000 | |
| 60 | EPMYIFLCML | 6.000 | |
| 203 | LIVIISAIGL | 6.000 | |
| 93 | TTIQFDACLL | 6.000 | |
| 101 | LLQIFAIHSL | 6.000 | |
| 28 | FWLAFPLCSL | 6.000 | |
| 66 | LCMLSGIDIL | 6.000 | |
| 214 | SLLISFSYLL | 6.000 | |
| 174 | SNILSHSYCL | 6.000 | |
| 222 | LLILKTVLSL | 6.000 | |
| 194 | DIRVNVVYSL | 5.600 | |
| 11 | SATYFILIGL | 5.600 | |
| 280 | NIYLLVPPVL | 5.600 | |
| 251 | FIFYVPFISL | 4.800 | |
| 34 | LCSLYLIAVL | 4.800 | |
| 57 | SLHEPMYIFL | 4.800 | |
| 30 | LAFPLCSLYL | 4.800 | |
| 207 | ISAISLDSLL | 4.800 | |
| 210 | ISLDSLLISF | 4.320 | |
| 242 | TCVSHVCAVF | 4.200 | |
| 206 | IISAISLDSL | 4.000 | |
| 149 | VAAVVRSAAL | 4.000 | |
| 109 | SLSGMESTVL | 4.000 | |
| 216 | LISFSYLLIL | 4.000 | |
| 92 | STTIQFDACL | 4.000 | |
| 76 | ISTSSMPKML | 4.000 | |

TABLE XIV-continued

101P3A11-V1-A24-10mers

| Start | Subsequence | Score |
|---|---|---|
| 110 | LSGMESTVLL | 4.000 |
| 79 | SSMPKMLAIF | 3.600 |
| 6 | NGNESSATYF | 3.600 |
| 167 | KQLPFCRSNI | 3.600 |
| 283 | LLVPPVLNPI | 3.024 |
| 248 | CAVFIFYVPF | 3.000 |
| 162 | LPVFIKQLPF | 3.000 |
| 56 | HSLHEPMYIF | 3.000 |
| 19 | SLPGLEEAQF | 3.000 |
| 156 | AALMAPLPVF | 3.000 |
| 300 | EIRQRILRLF | 2.800 |
| 272 | SPLPVILANI | 2.520 |
| 104 | IFAIHSLSGM | 2.500 |
| 114 | ESTVLLAMAF | 2.400 |
| 231 | LTREAQAKAF | 2.400 |
| 67 | CMLSGIDILI | 2.100 |
| 201 | YSLIVIISAI | 2.100 |
| 257 | FISLSMVHRF | 2.000 |
| 81 | MPKMLAIFWF | 2.000 |
| 88 | FWFNSTTIQF | 2.000 |
| 244 | VSHVCAVFIF | 2.000 |
| 198 | NVVYSLIVII | 1.800 |
| 53 | RTEHSLHEPM | 1.800 |
| 157 | ALMAPLPVFI | 1.800 |
| 197 | VNVVYSLIVI | 1.500 |
| 40 | IAVLSNLTII | 1.500 |
| 186 | DVMKLACDDI | 1.500 |
| 125 | RYVAICHPLR | 1.500 |
| 7 | SNESSATYFI | 1.500 |
| 215 | LLISFSYLLI | 1.500 |
| 208 | SAISLDSLLI | 1.500 |
| 299 | KEIRQRILRL | 1.200 |
| 9 | ESSATYFILI | 1.200 |
| 95 | IQFDACLLQI | 1.200 |
| 138 | VLTLPRVTKI | 1.100 |
| 292 | IVYSVKTKEI | 1.100 |
| 112 | SMESTVLLAM | 1.050 |
| 65 | FLCMLSGIDI | 1.000 |
| 42 | VLSNLTIIYI | 1.000 |
| 98 | DACLLQIFAI | 1.000 |
| 249 | AVFIFYVPFI | 1.000 |
| 78 | TSSMPKMLAI | 1.000 |
| 243 | CVSHVCAVFI | 1.000 |
| 39 | LIAVLSNLTI | 1.000 |
| 86 | AIFWFNSTTI | 1.000 |
| 63 | YIFLCMLSGI | 1.000 |
| 120 | AMAFDRYVAI | 1.000 |
| 269 | RRDSPLPVIL | 0.960 |
| 150 | AAVVRSAALM | 0.750 |
| 62 | MYIFLCMLSG | 0.750 |
| 21 | PGLEEAQFWL | 0.720 |
| 239 | AFSTCVSHVC | 0.700 |
| 13 | TYFILIGLPG | 0.700 |
| 218 | SFSYLLILKT | 0.660 |
| 130 | CHPLRHATVL | 0.600 |
| 275 | PVILANIYLL | 0.600 |
| 124 | DRYVAICHPL | 0.560 |
| 75 | LISTSSMPKM | 0.550 |

TABLE XIV

101P3A11-V2-A24-10mers

| Start | Subsequence | Score | |
|---|---|---|---|
| 20 | SWPISICWFL | 8.400 | Portion of SEQ ID NO: 30 each start position is specified-the length of each peptide is 10 amino acids, the end position for each peptide is the start position plus nine |
| 21 | WPISICWFLL | 6.000 | |
| 6 | IAVLASGVTL | 6.000 | |
| 26 | CWFLLCSTQL | 4.000 | |
| 16 | RCPSSWPISI | 3.000 | |
| 19 | SSWPISICWF | 2.400 | |
| 3 | LYLIAVLASG | 1.050 | |

TABLE XIV-continued

101P3A11-V2-A24-10mers

| Start | Subsequence | Score |
|---|---|---|
| 14 | TLRCPSSWPI | 1.000 |
| 27 | WFLLCSTQLS | 0.900 |
| 28 | FLLCSTQLSM | 0.750 |
| 1 | CSLYLIAVLA | 0.210 |
| 4 | YLIAVLASGV | 0.180 |
| 23 | ISICWFLLCS | 0.150 |
| 11 | SGVTLRCPSS | 0.150 |
| 8 | VLASGVTLRC | 0.140 |
| 10 | ASGVTLRCPS | 0.120 |
| 24 | SICWFLLCST | 0.120 |
| 2 | SLYLIAVLAS | 0.100 |
| 17 | CPSSWPISIC | 0.100 |
| 12 | GVTLRCPSSW | 0.100 |
| 5 | LIAVLASGVT | 0.100 |
| 13 | VTLRCPSSWP | 0.015 |
| 7 | AVLASGVTLR | 0.015 |
| 18 | PSSWPISICW | 0.014 |
| 15 | LRCPSSWPIS | 0.012 |
| 25 | ICWFLLCSTQ | 0.012 |
| 22 | PISICWFLLC | 0.012 |
| 29 | LLCSTQLSME | 0.010 |
| 9 | LASGVTLRCP | 0.010 |

TABLE XIV

101P3A11-V3-A24-10mers

| Start | Subsequence | Score | |
|---|---|---|---|
| 2 | QFDACLLQMF | 14.400 | Portion of SEQ ID NO: 32 each start position is specified-the length of each peptide is 10 amino acids, the end position for each peptide is the start position plus nine |
| 7 | LLQMFAIHSL | 6.000 | |
| 10 | MFAIHSLSGM | 2.500 | |
| 4 | DACLLQMFAI | 1.000 | |
| 1 | IQFDACLLQM | 0.600 | |
| 8 | LQMFAIHSLS | 0.210 | |
| 6 | CLLQMFAIHS | 0.150 | |
| 5 | ACLLQMFAIH | 0.018 | |
| 3 | FDACLLQMFA | 0.012 | |
| 9 | QMFAIHSLSG | 0.010 | |

TABLE XV

101P3A11-V1-B7-9mers

| Start | Subsequence | Score | |
|---|---|---|---|
| 169 | LPFCRSNIL | 80.000 | Portion of SEQ ID NO: 28 each start position is specified-the length of each peptide is 9 amino acids, the end position for each peptide is the start position plus eight |
| 131 | HPLRHATVL | 80.000 | |
| 60 | EPMYIFLCM | 60.000 | |
| 141 | LPRVTKISV | 40.000 | |
| 300 | EIRQRILRL | 40.000 | |
| 150 | AAVVRGAAL | 36.000 | |
| 204 | IVIISAIGL | 20.000 | |
| 151 | AVVRSAALM | 15.000 | |
| 26 | AQFWLAFPL | 12.000 | |
| 208 | SAISLDSLL | 12.000 | |
| 111 | SGMESTVLL | 12.000 | |
| 12 | ATYFILIGL | 12.000 | |
| 32 | FPLCSLYLI | 8.000 | |
| 41 | AVLSNLTII | 6.000 | |
| 29 | WLAFPLCSL | 6.000 | |
| 254 | YVPFISLSM | 5.000 | |
| 152 | VVRSAALMA | 5.000 | |
| 15 | FILIGLPGL | 4.000 | |
| 50 | YIVRTEHSL | 4.000 | |
| 102 | LQIFAIHSL | 4.000 | |
| 276 | VILANIYLL | 4.000 | |
| 110 | LSGMESTVL | 4.000 | |
| 94 | TIQFDACLL | 4.000 | |
| 93 | TTIQFDACL | 4.000 | |

TABLE XV-continued

101P3A11-V1-B7-9mers

| Start | Subsequence | Score |
|---|---|---|
| 255 | VPFISLSMV | 4.000 |
| 221 | YLLILKTVL | 4.000 |
| 77 | STSSMPKML | 4.000 |
| 35 | CSLYLIAVL | 4.000 |
| 182 | CLHQDVMKL | 4.000 |
| 215 | LLISFSYLL | 4.000 |
| 285 | VPPVLNPIV | 4.000 |
| 217 | ISFSYLLIL | 4.000 |
| 207 | ISAISLDSL | 4.000 |
| 67 | CMLSGIDIL | 4.000 |
| 38 | YLIAVLSNL | 4.000 |
| 266 | FSKRRDSPL | 4.000 |
| 223 | LILKTVLSL | 4.000 |
| 175 | NILSHSYCL | 4.000 |
| 154 | RSAALMAPL | 4.000 |
| 214 | SLLISFSYL | 4.000 |
| 9 | ESSATYFIL | 4.000 |
| 105 | FAIHSLSGM | 3.000 |
| 275 | PVILANIYL | 2.000 |
| 4 | DPNSNESSA | 2.000 |
| 198 | NVVYSLIVI | 2.000 |
| 290 | NPIVYSVKT | 2.000 |
| 196 | RVNVVYGLI | 2.000 |
| 199 | VVYSLIVII | 2.000 |
| 284 | LVPPVLNPI | 2.000 |
| 156 | AALMAPLPV | 1.800 |
| 119 | LAMAFDRYV | 1.800 |
| 209 | AISLDSLLI | 1.200 |
| 99 | ACLLQIFAI | 1.200 |
| 66 | LCMLSGIDI | 1.200 |
| 79 | SSMPKMLAI | 1.200 |
| 22 | GLEEAQFWL | 1.200 |
| 121 | MAFDRYVAI | 1.200 |
| 40 | IAVLSNLTI | 1.200 |
| 31 | AFPLCSLYL | 1.200 |
| 76 | ISTSSMPKM | 1.000 |
| 73 | DILISTSSM | 1.000 |
| 305 | ILRLFHVAT | 1.000 |
| 231 | LIREAQAKA | 1.000 |
| 252 | IFYVPFISL | 0.600 |
| 236 | QAKAFGTCV | 0.600 |
| 297 | KTKEIRQRI | 0.600 |
| 168 | QLPFCRSNI | 0.600 |
| 136 | ATVLTLPRV | 0.600 |
| 160 | APLPVFIKQ | 0.600 |
| 143 | RVTKISVAA | 0.500 |
| 148 | SVAAVVRSA | 0.500 |
| 227 | TVLSLTREA | 0.500 |
| 137 | TVLTLPRVT | 0.500 |
| 51 | IVRTEHSLH | 0.500 |
| 149 | VAAVVRSAA | 0.450 |
| 128 | AICHPLRHA | 0.450 |
| 120 | AMAFDRYVA | 0.450 |
| 272 | SPLPVILAN | 0.400 |
| 216 | LISFSYLLI | 0.400 |
| 274 | LPVILANIY | 0.400 |
| 56 | HSLHEPMYI | 0.400 |
| 125 | RYVAICHPL | 0.400 |
| 195 | IRVNVVYSL | 0.400 |
| 270 | RDSPLPVIL | 0.400 |
| 43 | LGNLTIIYI | 0.400 |
| 158 | LMAPLPVFI | 0.400 |
| 81 | MPKMLAIFW | 0.400 |
| 187 | VMKLACDDI | 0.400 |
| 202 | SLIVIISAI | 0.400 |
| 281 | IYLLVPPVL | 0.400 |
| 161 | PLPVFIKQL | 0.400 |
| 68 | MLSGIDILI | 0.400 |
| 133 | LRHATVLTL | 0.400 |
| 139 | LTLPRVTKI | 0.400 |
| 61 | PMYIFLCML | 0.400 |
| 20 | LPGLEEAQF | 0.400 |
| 244 | VSHVCAVFI | 0.400 |
| 10 | SSATYFILI | 0.400 |
| 98 | DACLIQIFA | 0.300 |

TABLE XV-continued

101P3A11-V1-B7-9mers

| Start | Subsequence | Score |
|---|---|---|
| 235 | AQAKAFGTC | 0.300 |

TABLE XV

101P3A11-V2-B7-9mers

| Start | Subsequence | Score | |
|---|---|---|---|
| 20 | WPISICWFL | 80.000 | Portion of SEQ ID NO: 30 each start position is specified-the length of each peptide is 9 amino acids, the end position for each peptide is the start position plus eight |
| 6 | AVLASGVTL | 60.000 | |
| 16 | CPSSWPISI | 8.000 | |
| 28 | LLCSTQLSM | 1.000 | |
| 21 | PISICWFLL | 0.400 | |
| 26 | WFLLCSTQL | 0.400 | |
| 8 | LASGVTLRC | 0.300 | |
| 5 | IAVLASGVT | 0.300 | |
| 4 | LIAVLASGV | 0.200 | |
| 13 | TLRCPSSWP | 0.150 | |
| 22 | ISICWFLLC | 0.100 | |
| 1 | SLYLIAVLA | 0.100 | |
| 11 | SVTLRCPSS | 0.100 | |
| 24 | ICWFLLCST | 0.100 | |
| 14 | LRCPSSWPI | 0.040 | |
| 9 | ASGVTLRCP | 0.030 | |
| 10 | SGVTLRCPS | 0.030 | |
| 27 | FLLCSTQLS | 0.020 | |
| 18 | SSWPISICW | 0.020 | |
| 12 | VTLRCPSSW | 0.020 | |
| 23 | SICWFLLCS | 0.020 | |
| 15 | RCPSSWPIS | 0.020 | |
| 17 | PSSWPISIC | 0.015 | |
| 7 | VLASGVTLR | 0.010 | |
| 29 | LCSTQLSME | 0.010 | |
| 3 | YLIAVLASG | 0.010 | |
| 19 | SWPISICWF | 0.002 | |
| 2 | LYLIAVLAS | 0.002 | |
| 25 | CWFLLCSTQ | 0.001 | |

TABLE XV

101P3A11-V3-B7-9mers

| Start | Subsequence | Score | |
|---|---|---|---|
| 7 | LQMFAIHSL | 12.000 | Portion of SEQ ID NO: 32 each start position is specified-the length of each peptide is 9 amino acids, the end position for each peptide is the start position plus eight |
| 4 | ACLLQMFAI | 1.200 | |
| 3 | DACLLQMFA | 0.300 | |
| 1 | QFDACLLQM | 0.030 | |
| 8 | QMFAIHSLS | 0.020 | |
| 6 | LLQMFAIHS | 0.020 | |
| 5 | CLLQMFAIH | 0.010 | |
| 2 | FDACLLQMF | 0.002 | |
| 9 | MFAIHSLSG | 0.001 | |

TABLE XVI

101P3A11-V1-B7-10mers

| Start | Subsequence | Score | |
|---|---|---|---|
| 60 | EPMYIFLCML | 240.000 | Portion of SEQ ID NO: 28 each start position is specified-the length of each peptide is 10 amino acids, the end position for each peptide is the start position plus nine |
| 160 | APLPVFIKQL | 240.000 | |
| 274 | LPVILANIYL | 80.000 | |
| 194 | DIRVNVVYGL | 40.000 | |
| 141 | LPRVTKISVA | 20.000 | |
| 149 | VAAVVRGAAL | 20.000 | |
| 30 | LAFPLCSLYL | 12.000 | |
| 11 | SATYFILIGL | 12.000 | |

TABLE XVI-continued

101P3A11-V1-B7-10mers

| Start | Subsequence | Score |
|---|---|---|
| 66 | LCMLSGIDIL | 12.000 |
| 25 | EAQFWLAFPL | 12.000 |
| 150 | AAVVRSAALM | 9.000 |
| 272 | SPLPVILANI | 8.000 |
| 249 | AVFIFYVPFI | 6.000 |
| 251 | FIFYVPFISL | 6.000 |
| 186 | DVMKLACDDI | 6.000 |
| 216 | LISFSYLLIL | 4.000 |
| 110 | LSGMESTVLL | 4.000 |
| 181 | YCLHQDVMKL | 4.000 |
| 93 | TTIQFDACLL | 4.000 |
| 297 | KTKEIRQRIL | 4.000 |
| 213 | DSLLISFSYL | 4.000 |
| 57 | SLHEPMYIFL | 4.000 |
| 168 | QLPFCRSNIL | 4.000 |
| 92 | STTIQFDACL | 4.000 |
| 206 | IISAIGLDSL | 4.000 |
| 203 | LIVIISAIGL | 4.000 |
| 222 | LLILKTVLSL | 4.000 |
| 280 | NIYLLVPPVL | 4.000 |
| 76 | ISTSSMPKMI | 4.000 |
| 101 | LLQIFAIHSL | 4.000 |
| 132 | PLRHATVLTL | 4.000 |
| 174 | SNILSHSYCL | 4.000 |
| 214 | SLLISFSYLL | 4.000 |
| 207 | ISAISLDSLL | 4.000 |
| 109 | SLSGMESTVL | 4.000 |
| 34 | LCSLYLIAVL | 4.000 |
| 157 | ALMAPLPVFI | 3.600 |
| 131 | HPLRHATVLT | 2.000 |
| 243 | CVSHVCAVFI | 2.000 |
| 32 | FPLCSLYLIA | 2.000 |
| 198 | NVVYSLIVII | 2.000 |
| 292 | IVYSVKTKEI | 2.000 |
| 4 | DPNSNESSAT | 2.000 |
| 275 | PVILANIYLL | 2.000 |
| 302 | RQRILRLFHV | 2.000 |
| 151 | AVVRSAALMA | 1.500 |
| 119 | LAMAFDRYVA | 1.350 |
| 120 | AMAFDRYVAI | 1.200 |
| 40 | IAVLSNLTII | 1.200 |
| 86 | AIFWFNSTTI | 1.200 |
| 98 | DACLLQIFAI | 1.200 |
| 208 | SAISLDSLLI | 1.200 |
| 75 | LISTSSMPKM | 1.000 |
| 246 | HVCAVFIFYV | 1.000 |
| 284 | LVPPVLNPIV | 1.000 |
| 196 | RVNVVYSLIV | 1.000 |
| 143 | RVTKISVAAV | 1.000 |
| 179 | HSYCLHQDVM | 1.000 |
| 254 | YVPFISLSMV | 1.000 |
| 190 | LACDDIRVNV | 0.900 |
| 148 | SVAAVVRSAA | 0.750 |
| 135 | HATVLTLPRV | 0.600 |
| 28 | FWLAFPLCSL | 0.600 |
| 155 | SAALMAPLPV | 0.600 |
| 167 | KQLPFCRSNI | 0.600 |
| 235 | AQAKAFSTCV | 0.600 |
| 238 | KAFSTCVSHV | 0.600 |
| 268 | KRRDSPLPVI | 0.600 |
| 279 | ANIYLLVPPV | 0.600 |
| 152 | VVRSAALMAP | 0.500 |
| 51 | IVRTEHSLHE | 0.500 |
| 127 | VAICHPLRHA | 0.450 |
| 128 | AICHPLRHAT | 0.450 |
| 67 | CMLSGIDILI | 0.400 |
| 20 | LPGLEEAQFW | 0.400 |
| 124 | DRYVAICHPL | 0.400 |
| 299 | KEIRQRILRL | 0.400 |
| 81 | MPKMLAIFWF | 0.400 |
| 78 | TSSMPKMLAI | 0.400 |
| 138 | VLTLPRVTKI | 0.400 |
| 9 | ESSATYFILI | 0.400 |
| 265 | RFSKRRDSPL | 0.400 |
| 201 | YSLIVIISAI | 0.400 |

TABLE XVI-continued

101P3A11-V1-B7-10mers

| Start | Subsequence | Score |
|---|---|---|
| 42 | VLSNLTIIYI | 0.400 |
| 37 | LYLIAVLSNL | 0.400 |
| 65 | FLCMLSGIDI | 0.400 |
| 283 | LLVPPVLNPI | 0.400 |
| 162 | LPVFIKQLPF | 0.400 |
| 215 | LLISFSYLLI | 0.400 |
| 130 | CHPLRHATVL | 0.400 |
| 285 | VPPVLNPIVY | 0.400 |
| 153 | VRSAALMAPL | 0.400 |
| 95 | IQFDACLLQI | 0.400 |
| 63 | YIFLCMLSGI | 0.400 |
| 14 | YFILISLPSL | 0.400 |
| 21 | PGLEEAQFWL | 0.400 |
| 220 | SYLLILKTVL | 0.400 |
| 49 | IYIVRTEHSL | 0.400 |
| 197 | VNVVYSLIVI | 0.400 |
| 39 | LIAVLSNLTI | 0.400 |

TABLE XVI

101P3A11-V2-B7-10mers

| Start | Subsequence | Score | |
|---|---|---|---|
| 21 | WPISICWFLL | 80.000 | Portion of |
| 6 | IAVLASGVTL | 12.000 | SEQ ID NO: 30; |
| 14 | TLRCPSSWPI | 4.000 | each start position |
| 17 | CPSSWPISIC | 3.000 | is specified - the |
| 28 | FLLCSTQLSM | 1.000 | length of each |
| 16 | RCPSSWPISI | 0.400 | peptide is 10 |
| 20 | SWPISICWFL | 0.400 | amino acids, the |
| 26 | CWFLLCSTQL | 0.400 | end position for |
| 4 | YLIAVLASGV | 0.200 | each peptide is |
| 7 | AVLASGVTLR | 0.150 | the start position |
| 8 | VLASGVTLRC | 0.100 | plus nine |
| 1 | CSLYLIAVLA | 0.100 | |
| 5 | LIAVLASGVT | 0.100 | |
| 24 | SICWFLLCST | 0.100 | |
| 12 | GVTLRCPSSW | 0.100 | |
| 10 | ASGVTLRCPS | 0.090 | |
| 9 | LASGVTLRCP | 0.030 | |
| 11 | SGVTLRCPSS | 0.020 | |
| 19 | SSWPISICWF | 0.020 | |
| 2 | SLYLIAVLAS | 0.020 | |
| 23 | ISICWFLLCS | 0.020 | |
| 13 | VTLRCPSSWP | 0.015 | |
| 29 | LLCSTQLSME | 0.010 | |
| 25 | ICWFLLCSTQ | 0.010 | |
| 22 | PISICWFLLC | 0.010 | |
| 18 | PSSWPISICW | 0.002 | |
| 27 | WFLLCSTQLS | 0.002 | |
| 15 | LRCPSSWPIS | 0.002 | |
| 3 | LYLIAVLASG | 0.001 | |

TABLE XVI

101P3A11-V3-B7-10mers

| Start | Subsequence | Score | |
|---|---|---|---|
| 7 | LLQMFAIHSL | 4.000 | Portion of SEQ ID NO: 32 |
| 4 | DACLLQMFAI | 1.200 | each start position is |
| 1 | IQFDACLLQM | 1.000 | specified-the length of |
| 10 | MFAIHSLSGM | 0.100 | each peptide is 10 amino |
| 8 | LQMFAIHSLS | 0.060 | acids, the end position |
| 5 | ACLLQMFAIH | 0.030 | for each peptide is the |
| 6 | CLLQMFAIHS | 0.020 | start position plus nine |
| 3 | FDACLLQMFA | 0.010 | |
| 9 | QMFAIHSLSG | 0.010 | |
| 2 | QFDACLLQMF | 0.001 | |

TABLE XVI-continued

101P3A11-V3-B7-10mers

| Start | Subsequence | Score |
|---|---|---|

TABLE XVII

101P3A11-V1-B35-9mers

| Start | Subsequence | Score | |
|---|---|---|---|
| 60 | EPMYIFLCM | 40.000 | Portion of SEQ ID NO: 28 |
| 274 | LPVILANIY | 40.000 | each start position is |
| 20 | LPGLEEAQF | 30.000 | specified-the length of |
| 81 | MPKMLAIFW | 30.000 | each peptide is 9 amino |
| 131 | HPLRHATVL | 20.000 | acids, the end position |
| 169 | LPFCRSNIL | 20.000 | for each peptide is the |
| 173 | RSNILSHSY | 20.000 | start position plus |
| 266 | FSKRRDSPL | 15.000 | eight |
| 141 | LPRVTKISV | 12.000 | |
| 213 | DSLLISFSY | 10.000 | |
| 76 | ISTSSMPKM | 10.000 | |
| 32 | FPLCSLYLI | 8.000 | |
| 110 | LSGMESTVL | 7.500 | |
| 30 | LAFPLCSLY | 6.000 | |
| 105 | FAIHSLSGM | 6.000 | |
| 217 | ISFSYLLIL | 5.000 | |
| 207 | ISAISLDSL | 5.000 | |
| 9 | ESSATYFIL | 5.000 | |
| 35 | NCSLYLIAVL | 5.000 | |
| 297 | KTKEIRQRI | 4.800 | |
| 285 | VPPVLNPIV | 4.000 | |
| 255 | VPFISLSMV | 4.000 | |
| 286 | PPVLNPIVY | 4.000 | |
| 6 | NGNESSATY | 4.000 | |
| 208 | SAIGLDSLL | 3.000 | |
| 300 | EIRQRILRL | 3.000 | |
| 150 | AAVVRSAAL | 3.000 | |
| 56 | HSLHEPMYI | 3.000 | |
| 121 | MAFDRYVAI | 2.400 | |
| 254 | YVPFISLSM | 2.000 | |
| 4 | DPNSNESSA | 2.000 | |
| 111 | SSMESTVLL | 2.000 | |
| 290 | NPIVYSVKT | 2.000 | |
| 272 | SPLPVILAN | 2.000 | |
| 244 | VSHVCAVFI | 2.000 | |
| 10 | SSATYFILI | 2.000 | |
| 79 | SSMPKMLAI | 2.000 | |
| 57 | SLHEPMYIF | 2.000 | |
| 118 | LLAMAFDRY | 2.000 | |
| 246 | HVCAVFIFY | 2.000 | |
| 151 | AVVRSAALM | 2.000 | |
| 73 | DILISTSSM | 2.000 | |
| 42 | VLSNLTIIY | 2.000 | |
| 154 | RSAALMAPL | 2.000 | |
| 236 | QAKAFSTCV | 1.800 | |
| 94 | TIQFDACLL | 1.500 | |
| 182 | CLHQDVMKL | 1.500 | |
| 40 | IAVLSNLTI | 1.200 | |
| 187 | VMKLACDDI | 1.200 | |
| 221 | YLLILKTVL | 1.000 | |
| 215 | LLISFSYLL | 1.000 | |
| 214 | SLLISFSYL | 1.000 | |
| 115 | STVLLAMAF | 1.000 | |
| 175 | NILSHSYCL | 1.000 | |
| 67 | CMLSGIDIL | 1.000 | |
| 38 | YLIAVLSNL | 1.000 | |
| 93 | TTIQFDACL | 1.000 | |
| 77 | STSSMPKML | 1.000 | |
| 15 | FILIGLPGL | 1.000 | |
| 26 | AQFWLAFPL | 1.000 | |
| 243 | CVSHVCAVF | 1.000 | |
| 276 | VILANIYLL | 1.000 | |
| 204 | IVIISAIGL | 1.000 | |
| 29 | WLAFPLCSL | 1.000 | |
| 80 | SMPKMLAIF | 1.000 | |

TABLE XVII-continued

101P3A11-V1-B35-9mers

| Start | Subsequence | Score |
|---|---|---|
| 157 | ALMAPLPVF | 1.000 |
| 223 | LILKTVLSL | 1.000 |
| 249 | AVFIFYVPF | 1.000 |
| 102 | LQIFAIHSL | 1.000 |
| 258 | ISLSMVHRF | 1.000 |
| 179 | HSYCLHQDV | 1.000 |
| 12 | ATYFILIGL | 1.000 |
| 50 | YIVRTEHSL | 1.000 |
| 190 | LACDDIRVN | 0.900 |
| 196 | RVNVVYSLI | 0.800 |
| 69 | LSGIDILIS | 0.750 |
| 144 | VTKISVAAV | 0.600 |
| 156 | AALMAPLPV | 0.600 |
| 189 | KLACDDIRV | 0.600 |
| 119 | LAMAFDRYV | 0.600 |
| 231 | LIREAQAKA | 0.600 |
| 209 | AISLDSLLI | 0.600 |
| 22 | GLEEAQFWL | 0.600 |
| 271 | DSPLPVILA | 0.500 |
| 219 | FSYLLILKT | 0.500 |
| 78 | TSSMPKMLA | 0.500 |
| 114 | ESTVLLAMA | 0.500 |
| 108 | HSLSGMEST | 0.500 |
| 91 | NSTTIQFDA | 0.500 |
| 43 | LGNLTIIYI | 0.400 |
| 198 | NVVYSLIVI | 0.400 |
| 199 | VVYSLIVII | 0.400 |
| 216 | LISFSYLLI | 0.400 |
| 202 | SLIVIISAI | 0.400 |
| 284 | LVPPVLNPI | 0.400 |
| 158 | LMAPLPVFI | 0.400 |
| 68 | MLSGIDILI | 0.400 |
| 168 | QLPFCRSNI | 0.400 |
| 66 | LCMLSGIDI | 0.400 |
| 41 | AVLSNLTII | 0.400 |

TABLE XVII

101P3A11-V2-B35-9mers

| Start | Subsequence | Score | |
|---|---|---|---|
| 20 | WPISICWFL | 20.000 | Portion of SEQ ID NO: 30 |
| 16 | CPSSWPISI | 8.000 | each start position is |
| 18 | SSWPISICW | 2.500 | specified-the length of |
| 28 | LLCSTQLSM | 2.000 | each peptide is 9 amino |
| 6 | AVLASGVTL | 1.000 | acids, the end position |
| 12 | VTLRCPSSW | 0.500 | for each peptide is the |
| 22 | ISICWFLLC | 0.500 | start position plus |
| 8 | LASGVTLRC | 0.300 | eight |
| 5 | IAVLASGVT | 0.300 | |
| 4 | LIAVLASGV | 0.200 | |
| 15 | RCPSSWPIS | 0.200 | |
| 19 | SWPISICWF | 0.100 | |
| 26 | WFLLCSTQL | 0.100 | |
| 27 | FLLCSTQLS | 0.100 | |
| 11 | SVTLRCPSS | 0.100 | |
| 23 | SICWFLLCS | 0.100 | |
| 10 | SSVTLRCPS | 0.100 | |
| 21 | PISICWFLL | 0.100 | |
| 1 | SLYLIAVLA | 0.100 | |
| 24 | ICWFLLCST | 0.100 | |
| 9 | ASGVTLRCP | 0.050 | |
| 17 | PSSWPISIC | 0.050 | |
| 14 | LRCPSSWPI | 0.040 | |
| 13 | TLRCPSSWP | 0.030 | |
| 29 | LCSTQLSME | 0.010 | |
| 3 | YLIAVLASG | 0.010 | |
| 7 | VLASGVTLR | 0.010 | |
| 2 | LYLIAVLAS | 0.010 | |
| 25 | CWFLLCSTQ | 0.001 | |

TABLE XVII

101P3A11-V3-B35-9mers

| Start | Subsequence | Score | |
|---|---|---|---|
| 7 | LQMFAIHSL | 1.000 | Portion of SEQ ID NO: 32 |
| 4 | ACLLQMFAI | 0.400 | each start position is |
| 3 | DACLLQMFA | 0.300 | specified-the length of |
| 8 | QMFAIHSLS | 0.100 | each peptide is 9 amino |
| 2 | FDACLLQMF | 0.100 | acids, the end position |
| 6 | LLQMFAIHS | 0.100 | for each peptide is the |
| 1 | QFDACLLQM | 0.060 | start position plus |
| 5 | CLLQMFAIH | 0.010 | eight |
| 9 | MFAIHSLSG | 0.001 | |

TABLE XVIII

101P3A11-V1-B35-10mers

| Start | Subsequence | Score | |
|---|---|---|---|
| 81 | MPKMLAIFWF | 60.000 | Portion of SEQ ID NO: 28 |
| 285 | VPPVLNPIVY | 40.000 | each start position is |
| 60 | EPMYIFLCML | 20.000 | specified-the length of |
| 160 | APLPVFIKQL | 20.000 | each peptide is 10 amino |
| 162 | LPVFIKQLPF | 20.000 | acids, the end position |
| 274 | LPVILANIYL | 20.000 | for each peptide is the |
| 20 | LPGLEEAQFW | 15.000 | start position plus nine |
| 297 | KTKEIRQRIL | 12.000 | |
| 179 | HSYCLHQDVM | 10.000 | |
| 272 | SPLPVILANI | 8.000 | |
| 141 | LPRVTKISVA | 6.000 | |
| 150 | AAVVRGAALM | 6.000 | |
| 231 | LIREAQAKAF | 6.000 | |
| 110 | LSGMESTVLL | 5.000 | |
| 114 | ESTVLLAMAF | 5.000 | |
| 213 | DSLLISFSYL | 5.000 | |
| 207 | ISAISLDSLL | 5.000 | |
| 76 | ISTSSMPKML | 5.000 | |
| 79 | SSMPKMLAIF | 5.000 | |
| 244 | VSHVCAVFIF | 5.000 | |
| 56 | HSLHEPMYIF | 5.000 | |
| 156 | AALMAPLPVF | 3.000 | |
| 30 | LAFPLCSLYL | 3.000 | |
| 4 | DPNSNESSAT | 3.000 | |
| 300 | EIRQRILRLF | 3.000 | |
| 149 | VAAVVRSAAL | 3.000 | |
| 194 | DIRVNVVYSL | 3.000 | |
| 248 | CAVFIFYVPF | 3.000 | |
| 11 | SATYFILIGL | 3.000 | |
| 25 | EAQFWLAFPL | 3.000 | |
| 57 | SLHEPMYIFL | 2.000 | |
| 169 | LPFCRSNILS | 2.000 | |
| 210 | ISLDSLLISF | 2.000 | |
| 6 | NGNESSATYF | 2.000 | |
| 29 | WLAFPLCSLY | 2.000 | |
| 75 | LISTSSMPKM | 2.000 | |
| 131 | HPLRHATVLT | 2.000 | |
| 41 | AVLGNLTIIY | 2.000 | |
| 9 | ESSATYFILI | 2.000 | |
| 32 | FPLCSLYLIA | 2.000 | |
| 78 | TSSMPKMLAI | 2.000 | |
| 117 | VLLAMAFDRY | 2.000 | |
| 208 | SAIGLDSLLI | 1.800 | |
| 109 | SLSGMESTVL | 1.500 | |
| 181 | YCLHQDVMKL | 1.500 | |
| 93 | TTIQFDACLL | 1.500 | |
| 19 | GLPGLEEAQF | 1.500 | |
| 190 | LACDDIRVNV | 1.200 | |
| 98 | DACLLQIFAI | 1.200 | |
| 302 | RQRILRLFHV | 1.200 | |
| 40 | IAVLSNLTII | 1.200 | |
| 238 | KAFSTCVSHV | 1.200 | |
| 53 | RTEHSLHEPM | 1.200 | |
| 92 | STTIQFDACL | 1.000 | |
| 173 | RSNILSHSYC | 1.000 | |
| 168 | QLPFCRSNIL | 1.000 | |

TABLE XVIII-continued

101P3A11-V1-B35-10mers

| Start | Subsequence | Score |
|---|---|---|
| 216 | LISFSYLLIL | 1.000 |
| 174 | SNILSHSYCL | 1.000 |
| 66 | LCMLSGIDIL | 1.000 |
| 214 | SLLISFSYLL | 1.000 |
| 206 | IISAISLDSL | 1.000 |
| 34 | LCSLYLIAVL | 1.000 |
| 242 | TCVSHVCAVF | 1.000 |
| 203 | LIVIISAIGL | 1.000 |
| 101 | LLQIFAIHGL | 1.000 |
| 222 | LLILKTVLGL | 1.000 |
| 280 | NIYLLVPPVL | 1.000 |
| 219 | FSYLLILKTV | 1.000 |
| 257 | FIGLSMVHRF | 1.000 |
| 251 | FIFYVPFIGL | 1.000 |
| 108 | HSLSGMESTV | 1.000 |
| 236 | QAKAFSTCVS | 0.900 |
| 95 | IQFDACLLQI | 0.800 |
| 167 | KQLPFCRSNI | 0.800 |
| 121 | MAFDRYVAIC | 0.600 |
| 144 | VTKISVAAVV | 0.600 |
| 155 | GAALMAPLPV | 0.600 |
| 112 | GMESTVLLAM | 0.600 |
| 135 | HATVLTLPRV | 0.600 |
| 69 | LSGIDILIST | 0.500 |
| 271 | DSPLPVILAN | 0.500 |
| 80 | SMPKMLAIFW | 0.500 |
| 91 | NSTTIQFDAC | 0.500 |
| 268 | KRRDSPLPVI | 0.480 |
| 119 | LAMAFDRYVA | 0.450 |
| 201 | YGLIVIISAI | 0.400 |
| 198 | NVVYSLIVII | 0.400 |
| 243 | CVSHVCAVFI | 0.400 |
| 283 | LLVPPVLNPI | 0.400 |
| 67 | CMLSGIDILI | 0.400 |
| 120 | AMAFDRYVAI | 0.400 |
| 65 | FLCMLSGIDI | 0.400 |
| 42 | VLSNLTIIYI | 0.400 |
| 186 | DVMKLACDDI | 0.400 |
| 39 | LIAVLSNLTI | 0.400 |
| 157 | ALMAPLPVFI | 0.400 |
| 292 | IVYSVKTKEI | 0.400 |
| 143 | RVTKIGVAAV | 0.400 |
| 86 | AIFWFNSTTI | 0.400 |
| 196 | RVNVVYSLIV | 0.400 |

TABLE XVIII

101P3A11-V2-B35-10mers

| Start | Subsequence | Score | |
|---|---|---|---|
| 21 | WPISICWFLL | 20.000 | Portion of SEQ ID NO: 30 |
| 19 | SSWPISICWF | 5.000 | each start position is |
| 6 | IAVLASGVTL | 3.000 | specified-the length of |
| 28 | FLLCSTQLSM | 2.000 | each peptide is 10 amino |
| 17 | CPSSWPISIC | 2.000 | acids, the end position |
| 14 | TLRCPSSWPI | 1.200 | for each peptide is the |
| 16 | RCPSSWPISI | 0.800 | start position plus nine |
| 23 | ISICWFLLCS | 0.500 | |
| 10 | ASGVTLRCPS | 0.500 | |
| 12 | SVTLRCPSSW | 0.500 | |
| 1 | CSLYLIAVLA | 0.500 | |
| 18 | PSSWPISICW | 0.250 | |
| 4 | YLIAVLASGV | 0.200 | |
| 26 | CWFLLCSTQL | 0.100 | |
| 2 | SLYLIAVLAS | 0.100 | |
| 8 | VLASGVTLRC | 0.100 | |
| 24 | SICWFLLCST | 0.100 | |
| 11 | SGVTLRCPSS | 0.100 | |
| 20 | SWPISICWFL | 0.100 | |
| 5 | LIAVLASGVT | 0.100 | |
| 9 | LASGVTLRCP | 0.030 | |

TABLE XVIII-continued

101P3A11-V2-B35-10mers

| Start | Subsequence | Score |
|---|---|---|
| 7 | AVLASGVTLR | 0.010 |
| 15 | LRCPSSWPIS | 0.010 |
| 27 | WFLLCSTQLS | 0.010 |
| 29 | LLCSTQLSME | 0.010 |
| 22 | PISICWFLLC | 0.010 |
| 25 | ICWFLLCSTQ | 0.010 |
| 13 | VTLRCPSSWP | 0.010 |
| 3 | LYLIAVLASG | 0.001 |

TABLE XVIII

101P3A11-V3-B35-10mers

| Start | Subsequence | Score | |
|---|---|---|---|
| 1 | IQFDACLLQM | 4.000 | Portion of SEQ ID NO: 32 |
| 4 | DACLLQMFAI | 1.200 | each start position is |
| 7 | LLQMFAIHSL | 1.000 | specified-the length of |
| 10 | MFAIHSLSGM | 0.200 | each peptide is 10 amino |
| 6 | CLLQMFAIHS | 0.100 | acids, the end position |
| 8 | LQMFAIHSLS | 0.100 | for each peptide is the |
| 2 | QFDACLLQMF | 0.030 | start position plus nine |
| 3 | FDACLLQMFA | 0.010 | |
| 9 | QMFAIHSLSG | 0.010 | |
| 5 | ACLLQMFAIH | 0.010 | |

TABLE XIX

Motifs and Post-translational Modifications of 101P3A11

N-glycosylation site
Number of matches: 3

| | | | |
|---|---|---|---|
| 1 | 7-10 | NESS | (SEQ ID NO: 133) |
| 2 | 44-47 | NLTI | (SEQ ID NO: 134) |
| 3 | 90-93 | NSTT | (SEQ ID NO: 135) |

cAMP- and cGMP-dependent protein kinase phosphorylation site

| | | | |
|---|---|---|---|
| | 268-271 | RRDS | (SEQ ID NO: 136) |

Protein kinase C phosphorylation site

| | | | |
|---|---|---|---|
| | 266-268 | SKR | |

Casein kinase II phosphorylation site
Number of matches: 3

| | | | |
|---|---|---|---|
| 1 | 56-59 | SLHE | (SEQ ID NO: 137) |
| 2 | 69-72 | SGID | (SEQ ID NO: 138) |
| 3 | 110-113 | SGME | (SEQ ID NO: 139) |

N-myristoylation site
Number of matches: 4

| | | | |
|---|---|---|---|
| 1 | 6-11 | GNESSA | (SEQ ID NO: 140) |
| 2 | 21-26 | GLEEAQ | (SEQ ID NO: 141) |
| 3 | 111-116 | GMESTV | (SEQ ID NO: 142) |
| 4 | 240-245 | GTCVSH | (SEQ ID NO: 143) |

G-protein coupled receptors family 1 signature

| | | | |
|---|---|---|---|
| | 112-128 | MESTVLLAMAFDRYVAI | (SEQ ID NO: 144) |

TABLE XX

| Motifs | | | |
|---|---|---|---|
| Name | avrg. % identity | Description | Potential Function |
| zf-C2H2 | 34% | Zinc finger, C2H2 type | Nucleic acid-binding protein functions as transcription factor, nuclear location probable |
| cytochrome b N | 68% | Cytochrome b(N-terminal)/b6/petB | membrane bound oxidase, generate superoxide |
| ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored_q1 | 32% | NADH Ubiquinone/plastoquinone (complex I), various chains | membrane associated. Involved in proton translocation across the membrane |
| efhand | 24% | EF hand | calcium-binding domain, consists of a 12 residue loop flanked on both sides by a 12 residue alpha-helical domain |
| rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE XXI

| Properties of 101P3A11 | | | |
|---|---|---|---|
| Variants 1 and 3 | Bioin-formatic Program | URL | Outcome |
| ORF | ORF Finder | | 133-1086 (includes stop) |
| Protein Length | n/a | n/a | 317 amino acids |
| Transmembrane region | TM Pred | | 7 TM at aa: 27-52, 63-88, 104-129, 146-165, 196-224, 239-262, 273-295 |
| | HMMTop | | 7 TM at aa: 27-50, 63-86, 99-121, 146-165, 201-224, 239-262, 275-294 |
| | Sosui | | 6 TM, at aa: 29-51, 63-85, 100-122, 203-225, 239-261, 273-295 |
| | TMHMM | | 7 TM, at aa: 29-51,63-85, 100-122, 143-165, 202-224, 236-258, 273-295 |

TABLE XXI-continued

| Properties of 101P3A11 | | | |
|---|---|---|---|
| Variants 1 and 3 | Bioin-formatic Program | URL | Outcome |
| Signal Peptide | Signal P | | indicates no signal |
| pI | pI/MW tool | | pI 8.7 |
| Molecular weight | pI/MW tool | | 35.2 kDa |
| Localization | PSORT | | Plasma membrane 64% |
| | PSORT II | | Plasma membrane 56.4% |
| Motifs | Pfam | | 7 transmembrane receptor (rhodopsin family) |
| | Prints | | Rhodopsin-like GPCR superfamily |
| | Blocks | | Rhodopsin-like GPCR superfamily |
| | Prosite | | G-protein coupled receptors family I |

TABLE XXI-continued

Properties of 101P3A11

| Variants 1 and 3 | Bioinformatic Program | URL | Outcome |
|---|---|---|---|
| 101P3A11 var.2 | | | |
| ORF | ORF finder | | 130-348 bp including stop |
| Protein length | | | 72aa |
| Transmembrane region | TM Pred | | 2 TM helices aa28-49, 55-72 N terminus extracellular |
| | HMMTop | | 2 TM helices N terminus extracellular |
| | Sosui | | 2 TM helices aa28-50, 52-72 |
| | TMHMM | | 1 TM helix, aa27-49 |
| Signal Peptide | Signal P | | no |
| pI | pI/MW tool | | pI 4.12 |
| Molecular weight | pI/MW tool | | 7.95 kB |
| Localization | PSORT | | 82% extracellular, 16% peroxisome |
| | PSORT II | | 39% cytoplasmic, 17% mito-chondrial, 17% nuclear |
| Motifs | Pfam | | no motifs found |
| | Prints | | no motifs found |
| | Blocks | | Zein seed storage protein |

TABLE XXII

101P3A11-V1-HLA-A1 9-mers

| Pos | 123456789 | score | |
|---|---|---|---|
| 246 | HVCAVFIFY | 24 | Portion of SEQ ID NO: 28; each start position is specified - the length of each peptide is 9 amino acids, the end position for each peptide is the start position plus 8. |
| 30 | LAFPLCSLY | 21 | |
| 42 | VLGNLTIIY | 21 | |
| 286 | PPVLNPIVY | 20 | |
| 112 | GMESTVLLA | 19 | |
| 118 | LLAMAFDRY | 19 | |
| 173 | RSNILSHSY | 19 | |
| 193 | DDIRVNVVY | 19 | |
| 213 | DSLLISFSY | 19 | |
| 58 | LHEPMYIFL | 18 | |
| 23 | LEEAQFWLA | 17 | |
| 10 | SSATYFILI | 16 | |
| 53 | RTEHSLHEP | 16 | |
| 55 | EHSLHEPMY | 16 | |
| 79 | SSMPKMLAI | 16 | |
| 96 | QFDACLLQI | 16 | |
| 160 | APLPVFIKQ | 16 | |
| 184 | HQDVMKLAC | 16 | |
| 2 | MVDPNGNES | 15 | |
| 6 | NGNESSATY | 15 | |
| 211 | GLDSLLISF | 15 | |

TABLE XXII-continued

101P3A11-V1-HLA-A1 9-mers

| Pos | 123456789 | score |
|---|---|---|
| 274 | LPVILANIY | 15 |
| 272 | SPLPVILAN | 14 |
| 92 | STTIQFDAC | 13 |
| 122 | AFDRYVAIC | 13 |
| 139 | LTLPRVTKI | 13 |
| 219 | FSYLLILKT | 13 |
| 283 | LLVPPVLNP | 13 |
| 191 | ACDDIRVNV | 12 |
| 192 | CDDIRVNVV | 12 |
| 232 | TREAQAKAF | 12 |
| 269 | RRDSPLPVI | 12 |
| 271 | DSPLPVILA | 12 |
| 12 | ATYFILIGL | 11 |
| 22 | GLEEAQFWL | 11 |
| 177 | LSHSYCLHQ | 11 |
| 217 | ISFSYLLIL | 11 |

TABLE XXII

101P3A11 v2 HLA A1 - 9-mers

| Pos | 123456789 | score | SEQ ID |
|---|---|---|---|
| 22 | ISICWFLLC | 15 | Portion of SEQ ID NO: 30; each start position is specified - the length of each peptide is 9 amino acids, the end position for each peptide is the start position plus 8. |
| 18 | SSWPISICW | 14 | |
| 8 | LASGVTLRC | 9 | |
| 23 | SICWFLLCS | 8 | |
| 2 | LYLIAVLAS | 7 | |
| 7 | VLASGVTLR | 7 | |
| 12 | VTLRCPSSW | 7 | |
| 28 | LLCSTQLSM | 7 | |

TABLE XXII

101P3A11 v2 HLA A1 - 9-mers

| Pos | 1 | 2 | 3 | 4 | 5 | 6 | 7 | 8 | 9 | score | SEQ ID |
|---|---|---|---|---|---|---|---|---|---|---|---|
| 22 | I | S | I | C | W | F | L | L | C | 15 | Portion of SEQ ID NO: 30; each start position is specified - the length of each peptide is 9 amino acids, the end position for each peptide is the start position plus 8. |
| 18 | S | S | W | P | I | S | I | C | W | 14 | |
| 8 | L | A | S | G | V | T | L | R | C | 9 | |
| 23 | S | I | C | W | F | L | L | C | S | 8 | |
| 2 | L | Y | L | I | A | V | L | A | S | 7 | |
| 7 | V | L | A | S | G | V | T | L | R | 7 | |
| 12 | V | T | L | R | C | P | S | S | W | 7 | |
| 28 | L | L | C | S | T | Q | L | S | M | 7 | |

TABLE XXII

101P3A11-V3- HLA A1 9-mers

| Pos | 1 | 2 | 3 | 4 | 5 | 6 | 7 | 8 | 9 | score | SEQ ID |
|---|---|---|---|---|---|---|---|---|---|---|---|
| 1 | Q | F | D | A | C | L | L | Q | M | 16 | Portion of SEQ ID NO: 32; each start position is specified - the length of each peptide is 9 amino acids,the end position for each peptide is the start position plus 8. |

TABLE XXIII

101P3A11-V1- HLA-A0201 9-mers

| Pos | 123456789 | score | SEQ ID |
|---|---|---|---|
| 288 | VLNPIVYGV | 30 | Portion of |
| 15 | FILIGLPGL | 29 | SEQ ID NO: 28; |
| 29 | WLAFPLCSL | 28 | each start position |
| 38 | YLIAVLGNL | 28 | is specified - the |
| 223 | LILKTVLGL | 28 | length of each |
| 67 | CMLSGIDIL | 26 | peptide is 9 amino |
| 109 | SLSGMESTV | 26 | acids, the end |
| 182 | CLHQDVMKL | 26 | position for each |
| 202 | GLIVIISAI | 26 | peptide is the |
| 215 | LLISFSYLL | 26 | start position |
| 276 | VILANIYLL | 26 | plus 8. |
| 158 | LMAPLPVFI | 25 | |
| 221 | YLLILKTVL | 25 | |
| 277 | ILANIYLLV | 25 | |
| 280 | NIYLLVPPV | 25 | |
| 139 | LTLPRVTKI | 24 | |
| 214 | SLLISFSYL | 24 | |
| 50 | YIVRTEHSL | 23 | |
| 144 | VTKIGVAAV | 23 | |
| 189 | KLACDDIRV | 23 | |
| 199 | VVYGLIVII | 23 | |
| 22 | GLEEAQFWL | 22 | |
| 41 | AVLGNLTII | 22 | |
| 207 | ISAIGLDSL | 22 | |
| 12 | ATYFILIGL | 21 | |
| 61 | PMYIFLCML | 21 | |
| 136 | ATVLTLPRV | 21 | |
| 161 | PLPVFIKQL | 21 | |
| 175 | NILSHSYCL | 21 | |
| 208 | SAIGLDSLL | 21 | |
| 273 | PLPVILANI | 21 | |
| 284 | LVPPVLNPI | 21 | |
| 68 | MLSGIDILI | 20 | |
| 102 | LQIFAIHSL | 20 | |
| 283 | LLVPPVLNP | 20 | |
| 300 | EIRQRILRL | 20 | |
| 305 | ILRLFHVAT | 20 | |
| 40 | IAVLGNLTI | 19 | |
| 46 | LTIIYIVRT | 19 | |
| 93 | TTIQFDACL | 19 | |
| 111 | SGMESTVLL | 19 | |
| 128 | AICHPLRHA | 19 | |
| 133 | LRHATVLTL | 19 | |
| 150 | AAVVRGAAL | 19 | |
| 156 | AALMAPLPV | 19 | |
| 157 | ALMAPLPVF | 19 | |
| 204 | IVIISAIGL | 19 | |
| 209 | AIGLDSLLI | 19 | |
| 217 | ISFSYLLIL | 19 | |
| 220 | SYLLILKTV | 19 | |
| 222 | LLILKTVLG | 19 | |
| 224 | ILKTVLGLT | 19 | |
| 18 | IGLPGLEEA | 18 | |
| 34 | LCSLYLIAV | 18 | |
| 35 | CSLYLIAVL | 18 | |
| 39 | LIAVLGNLT | 18 | |
| 44 | GNLTIIYIV | 18 | |
| 86 | AIFWFNSTT | 18 | |
| 119 | LAMAFDRYV | 18 | |
| 195 | IRVNVVYGL | 18 | |
| 211 | GLDSLLISF | 18 | |
| 216 | LISFSYLLI | 18 | |
| 247 | VCAVFIFYV | 18 | |
| 255 | VPFIGLSMV | 18 | |
| 16 | ILIGLPGLE | 17 | |
| 64 | IFLCMLSGI | 17 | |
| 73 | DILISTSSM | 17 | |
| 94 | TIQFDACLL | 17 | |
| 99 | ACLLQIFAI | 17 | |
| 112 | GMESTVLLA | 17 | |
| 121 | MAFDRYVAI | 17 | |
| 168 | QLPFCRSNI | 17 | |
| 198 | NVVYGLIVI | 17 | |
| 227 | TVLGLTREA | 17 | |
| 282 | YLLVPPVLN | 17 | |

TABLE XXIII-continued

101P3A11-V1- HLA-A0201 9-mers

| Pos | 123456789 | score | SEQ ID |
|---|---|---|---|
| 32 | FPLCSLYLI | 16 | |
| 57 | SLHEPMYIF | 16 | |
| 71 | GIDILISTS | 16 | |
| 79 | SSMPKMLAI | 16 | |
| 80 | SMPKMLAIF | 16 | |
| 105 | FAIHSLSGM | 16 | |
| 120 | AMAFDRYVA | 16 | |
| 145 | TKIGVAAVV | 16 | |
| 148 | GVAAVVRGA | 16 | |
| 187 | VMKLACDDI | 16 | |
| 231 | LTREAQAKA | 16 | |
| 239 | AFGTCVSHV | 16 | |
| 250 | VFIFYVPFI | 16 | |
| 303 | QRILRLFHV | 16 | |
| 304 | RILRLFHVA | 16 | |
| 19 | GLPGLEEAQ | 15 | |
| 36 | SLYLIAVLG | 15 | |
| 43 | LGNLTIIYI | 15 | |
| 47 | TIIYIVRTE | 15 | |
| 70 | SGIDILIST | 15 | |
| 77 | STSSMPKML | 15 | |
| 132 | PLRHATVLT | 15 | |
| 138 | VLTLPRVTK | 15 | |
| 154 | RGAALMAPL | 15 | |
| 191 | ACDDIRVNV | 15 | |
| 192 | CDDIRVNVV | 15 | |
| 205 | VIISAIGLD | 15 | |
| 242 | TCVSHVCAV | 15 | |
| 252 | IFYVPFIGL | 15 | |
| 270 | RDSPLPVIL | 15 | |
| 281 | IYLLVPPVL | 15 | |
| 307 | RLFHVATHA | 15 | |
| 17 | LIGLPGLEE | 14 | |
| 26 | AQFWLAFPL | 14 | |
| 42 | VLGNLTIIY | 14 | |
| 63 | YIFLCMLSG | 14 | |
| 74 | ILISTSSMP | 14 | |
| 85 | LAIFWFNST | 14 | |
| 100 | CLLQIFAIH | 14 | |
| 118 | LLAMAFDRY | 14 | |
| 130 | CHPLRHATV | 14 | |
| 151 | AVVRGAALM | 14 | |
| 169 | LPFCRSNIL | 14 | |
| 201 | YGLIVIISA | 14 | |
| 219 | FSYLLILKT | 14 | |
| 236 | QAKAFGTCV | 14 | |
| 269 | RRDSPLPVI | 14 | |
| 297 | KTKEIRQRI | 14 | |

TABLE XXIII

101P3A11-V2-HLA A0201 - 9-mers

| Pos | 123456789 | score | SEQ ID |
|---|---|---|---|
| 4 | LIAVLASGV | 24 | Portion of |
| 3 | YLIAVLASG | 22 | SEQ ID NO: 30; |
| 6 | AVLASGVTL | 22 | each start position |
| 1 | SLYLIAVLA | 19 | is specified - the |
| 7 | VLASGVTLR | 19 | length of each |
| 28 | LLCSTQLSM | 19 | peptide is 9 amino |
| 23 | SICWFLLCS | 16 | acids, the end |
| 21 | PISICWFLL | 15 | position for each |
| 27 | FLLCSTQLS | 15 | peptide is the |
| 24 | ICWFLLCST | 13 | start position |
| 14 | LRCPSSWPI | 12 | plus 8. |
| 20 | WPISICWFL | 12 | |
| 26 | WFLLCSTQL | 12 | |
| 8 | LASGVTLRC | 11 | |
| 13 | TLRCPSSWP | 11 | |

TABLE XXIII

| 101P3A11-V3- HLA A0201 9-mers | | | |
|---|---|---|---|
| Pos | 123456789 | score | |
| 7 | LQMFAIHSL | 19 | Portion of SEQ ID NO: 32; each start position is specified - the length of each peptide is nine amino acids, the end position for each peptide is the start position plus eight |
| 5 | CLLQMFAIH | 14 | |
| 4 | ACLLQMFAI | 13 | |
| 6 | LLQMFAIHS | 13 | |
| 1 | QFDACLLQM | 9 | |
| 8 | QMFAIHSLS | 9 | |

Table XXIV: 101P3A11-V1 HLA-A0203 9-mers-No Results.

Table XXIV: 101P3A11-V2 HLA-A0203 9-mers-No Results.

Table XXIV: 101P3A11-V3 HLA-A0203 9-mers-No Results.

TABLE XXV

| 101P3A11-V1- HLA-A3 9-mers | | | |
|---|---|---|---|
| Pos | 123456789 | score | |
| 138 | VLTLPRVTK | 30 | Portion of SEQ ID NO: 28; each start position is specified - the length of each peptide is nine amino acids, the end position for each peptide is the start position plus eight |
| 230 | GLTREAQAK | 27 | |
| 146 | KIGVAAVVR | 26 | |
| 151 | AVVRGAALM | 24 | |
| 291 | PIVYGVKTK | 24 | |
| 36 | SLYLIAVLG | 23 | |
| 157 | ALMAPLPVF | 23 | |
| 48 | IIYIVRTEH | 22 | |
| 51 | IVRTEHSLH | 22 | |
| 143 | RVTKIGVAA | 22 | |
| 152 | VVRGAALMA | 22 | |
| 243 | CVSHVCAVF | 22 | |
| 249 | AVFIFYVPF | 22 | |
| 117 | VLLAMAFDR | 21 | |
| 193 | DDIRVNVVY | 21 | |
| 304 | RILRLFHVA | 21 | |
| 305 | ILRLFHVAT | 21 | |
| 109 | SLSGMESTV | 20 | |
| 199 | VVYGLIVII | 20 | |
| 292 | IVYGVKTKE | 20 | |
| 16 | ILIGLPGLE | 19 | |
| 45 | NLTIIYIVR | 19 | |
| 74 | ILISTSSMP | 19 | |
| 75 | LISTSSMPK | 19 | |
| 100 | CLLQIFAIH | 19 | |
| 163 | PVFIKQLPF | 19 | |
| 204 | IVIISAIGL | 19 | |
| 222 | LLILKTVLG | 19 | |
| 246 | HVCAVFIFY | 19 | |
| 307 | RLFHVATHA | 19 | |
| 41 | AVLGNLTII | 18 | |
| 86 | AIFWFNSTT | 18 | |
| 206 | IISAIGLDS | 18 | |
| 221 | YLLILKTVL | 18 | |
| 254 | YVPFIGLSM | 18 | |
| 38 | YLIAVLGNL | 17 | |
| 42 | VLGNLTIIY | 17 | |
| 118 | LLAMAFDRY | 17 | |
| 132 | PLRHATVLT | 17 | |
| 137 | TVLTLPRVT | 17 | |
| 181 | YCLHQDVMK | 17 | |
| 202 | GLIVIISAI | 17 | |
| 214 | SLLISFSYL | 17 | |
| 257 | FIGLSMVHR | 17 | |
| 262 | MVHRFSKRR | 17 | |

TABLE XXV-continued

| 101P3A11-V1- HLA-A3 9-mers | | |
|---|---|---|
| Pos | 123456789 | score |
| 277 | ILANIYLLV | 17 |
| 282 | YLLVPPVLN | 17 |
| 287 | PVLNPIVYG | 17 |
| 289 | LNPIVYGVK | 17 |
| 310 | HVATHASEP | 17 |
| 2 | MVDPNGNES | 16 |
| 57 | SLHEPMYIF | 16 |
| 71 | GIDILISTS | 16 |
| 73 | DILISTSSM | 16 |
| 116 | TVLLAMAFD | 16 |
| 126 | YVAICHPLR | 16 |
| 145 | TKIGVAAVV | 16 |
| 168 | QLPFCRSNI | 16 |
| 176 | ILSHSYCLH | 16 |
| 196 | RVNVVYGLI | 16 |
| 198 | NVVYGLIVI | 16 |
| 211 | GLDSLLISF | 16 |
| 283 | LLVPPVLNP | 16 |
| 300 | EIRQRILRL | 16 |
| 302 | RQRILRLFH | 16 |
| 17 | LIGLPGLEE | 15 |
| 47 | TIIYIVRTE | 15 |
| 103 | QIFAIHSLS | 15 |
| 194 | DIRVNVVYG | 15 |
| 209 | AIGLDSLLI | 15 |
| 224 | ILKTVLGLT | 15 |
| 238 | KAFGTCVSH | 15 |
| 6 | NGNESSATY | 14 |
| 63 | YIFLCMLSG | 14 |
| 101 | LLQIFAIHS | 14 |
| 140 | TLPRVTKIG | 14 |
| 148 | GVAAVVRGA | 14 |
| 165 | FIKQLPFCR | 14 |
| 189 | KLACDDIRV | 14 |
| 225 | LKTVLGLTR | 14 |
| 227 | TVLGLTREA | 14 |
| 256 | PFIGLSMVH | 14 |
| 275 | PVILANIYL | 14 |
| 284 | LVPPVLNPI | 14 |
| 299 | KEIRQRILR | 14 |

TABLE XXV

| 101P3A11-V2-HLA A3 - 9-mers | | | |
|---|---|---|---|
| Pos | 123456789 | score | |
| 6 | AVLASGVTL | 28 | Portion of SEQ ID NO: 30; each start position is specified - the length of each peptide is nine amino acids, the end position for each peptide is the start position plus eight |
| 1 | SLYLIAVLA | 23 | |
| 3 | YLIAVLASG | 21 | |
| 7 | VLASGVTLR | 18 | |
| 13 | TLRCPSSWP | 17 | |
| 4 | LIAVLASGV | 15 | |
| 11 | GVTLRCPSS | 15 | |
| 28 | LLCSTQLSM | 15 | |

TABLE XXV

| 101P3A11-V3- HLA A3 9-mers | | | |
|---|---|---|---|
| Pos | 123456789 | score | |
| 5 | CLLQMFAIH | 19 | Portion of SEQ ID NO: 32; each start position is specified - the length of each |
| 6 | LLQMFAIHS | 13 | |
| 1 | QFDACLLQM | 10 | |

TABLE XXV-continued

| 101P3A11-V3- HLA A3 9-mers | | | |
|---|---|---|---|
| Pos | 123456789 | score | |
| | | | peptide is nine amino acids, the end position for each peptide is the start position plus eight |

TABLE XXVI

| 101P3A11-V1- HLA-A26 9-mers | | | |
|---|---|---|---|
| Pos | 123456789 | score | |
| 300 | EIRQRILRL | 30 | Portion of SEQ ID NO: 28; each start position is specified - the length of each peptide is nine amino acids, the end position for each peptide is the start position plus eight |
| 73 | DILISTSSM | 27 | |
| 249 | AVFIFYVPF | 27 | |
| 211 | GLDSLLISF | 26 | |
| 15 | FILIGLPGL | 24 | |
| 57 | SLHEPMYIF | 24 | |
| 118 | LLAMAFDRY | 24 | |
| 223 | LILKTVLGL | 24 | |
| 246 | HVCAVFIFY | 24 | |
| 12 | ATYFILIGL | 23 | |
| 38 | YLIAVLGNL | 23 | |
| 115 | STVLLAMAF | 23 | |
| 157 | ALMAPLPVF | 23 | |
| 163 | PVFIKQLPF | 23 | |
| 182 | CLHQDVMKL | 23 | |
| 29 | WLAFPLCSL | 22 | |
| 93 | TTIQFDACL | 22 | |
| 161 | PLPVFIKQL | 22 | |
| 204 | IVIISAIGL | 22 | |
| 214 | SLLISFSYL | 22 | |
| 276 | VILANIYLL | 22 | |
| 194 | DIRVNVVYG | 21 | |
| 243 | CVSHVCAVF | 21 | |
| 77 | STSSMPKML | 20 | |
| 254 | YVPFIGLSM | 20 | |
| 275 | PVILANIYL | 20 | |
| 24 | EEAQFWLAF | 19 | |
| 42 | VLGNLTIIY | 19 | |
| 50 | YIVRTEHSL | 19 | |
| 151 | AVVRGAALM | 19 | |
| 175 | NILSHSYCL | 19 | |
| 193 | DDIRVNVVY | 19 | |
| 215 | LLISFSYLL | 19 | |
| 252 | IFYVPFIGL | 19 | |
| 9 | ESSATYFIL | 18 | |
| 22 | GLEEAQFWL | 18 | |
| 46 | LTIIYIVRT | 18 | |
| 55 | EHSLHEPMY | 18 | |
| 60 | EPMYIFLCM | 18 | |
| 89 | WFNSTTIQF | 18 | |
| 94 | TIQFDACLL | 18 | |
| 186 | DVMKLACDD | 18 | |
| 199 | VVYGLIVII | 18 | |
| 63 | YIFLCMLSG | 17 | |
| 71 | GIDILISTS | 17 | |
| 80 | SMPKMLAIF | 17 | |
| 97 | FDACLLQIF | 17 | |
| 105 | FAIHSLSGM | 17 | |
| 139 | LTLPRVTKI | 17 | |
| 144 | VTKIGVAAV | 17 | |
| 205 | VIISAIGLD | 17 | |
| 213 | DSLLISFSY | 17 | |
| 221 | YLLILKTVL | 17 | |
| 257 | FIGLSMVHR | 17 | |
| 284 | LVPPVLNPI | 17 | |
| 30 | LAFPLCSLY | 16 | |
| 41 | AVLGNLTII | 16 | |
| 47 | TIIYIVRTE | 16 | |
| 53 | RTEHSLHEP | 16 | |

TABLE XXVI-continued

| 101P3A11-V1- HLA-A26 9-mers | | |
|---|---|---|
| Pos | 123456789 | score |
| 76 | ISTSSMPKM | 16 |
| 92 | STTIQFDAC | 16 |
| 136 | ATVLTLPRV | 16 |
| 148 | GVAAVVRGA | 16 |
| 202 | GLIVIISAI | 16 |
| 258 | IGLSMVHRF | 16 |
| 280 | NIYLLVPPV | 16 |
| 31 | AFPLCSLYL | 15 |
| 102 | LQIFAIHSL | 15 |
| 116 | TVLLAMAFD | 15 |
| 128 | AICHPLRHA | 15 |
| 154 | RGAALMAPL | 15 |
| 164 | VFIKQLPFC | 15 |
| 216 | LISFSYLLI | 15 |
| 217 | ISFSYLLIL | 15 |
| 226 | KTVLGLTRE | 15 |
| 273 | PLPVILANI | 15 |
| 283 | LLVPPVLNP | 15 |
| 287 | PVLNPIVYG | 15 |
| 288 | VLNPIVYGV | 15 |
| 297 | KTKEIRQRI | 15 |
| 304 | RILRLFHVA | 15 |
| 2 | MVDPNGNES | 14 |
| 6 | NGNESSATY | 14 |
| 33 | PLCSLYLIA | 14 |
| 35 | CSLYLIAVL | 14 |
| 58 | LHEPMYIFL | 14 |
| 82 | PKMLAIFWF | 14 |
| 100 | CLLQIFAIH | 14 |
| 196 | RVNVVYGLI | 14 |
| 198 | NVVYGLIVI | 14 |
| 207 | ISAIGLDSL | 14 |
| 208 | SAIGLDSLL | 14 |
| 227 | TVLGLTREA | 14 |
| 231 | LTREAQAKA | 14 |
| 245 | SHVCAVFIF | 14 |
| 291 | PIVYGVKTK | 14 |
| 301 | IRQRILRLF | 14 |

TABLE XXVI

| 101P3A11-V2-HLA A26 - 9-mers | | | |
|---|---|---|---|
| Pos | 123456789 | score | |
| 6 | AVLASGVTL | 20 | Portion of SEQ ID NO: 30; each start position is specified - the length of each peptide is nine amino acids, the end position for each peptide is the start position plus eight |
| 21 | PISICWFLL | 18 | |
| 28 | LLCSTQLSM | 18 | |
| 3 | YLIAVLASG | 16 | |
| 19 | SWPISICWF | 16 | |
| 26 | WFLLCSTQL | 15 | |
| 4 | LIAVLASGV | 14 | |
| 7 | VLASGVTLR | 14 | |
| 23 | SICWFLLCS | 14 | |
| 11 | GVTLRCPSS | 12 | |
| 12 | VTLRCPSSW | 12 | |
| 20 | WPISICWFL | 11 | |
| 27 | FLLCSTQLS | 10 | |
| 1 | SLYLIAVLA | 9 | |
| 13 | TLRCPSSWP | 9 | |

TABLE XXVI

| 101P3A11-V3- HLA A26 9-mers | | | |
|---|---|---|---|
| Pos | 123456789 | score | |
| 1 | QFDACLLQM | 20 | Portion of SEQ ID NO: 32; each start position |
| 2 | FDACLLQMF | 18 | |
| 5 | CLLQMFAIH | 14 | |

TABLE XXVI-continued

101P3A11-V3- HLA A26 9-mers

| Pos | 123456789 | score | |
|---|---|---|---|
| 7 | LQMFAIHSL | 13 | is specified - the length of each peptide is nine amino acids, the end position for each peptide is the start position plus eight |
| 6 | LLQMFAIHS | 9 | |

TABLE XXVII

101P3A11-V1- HLA-B0702 9-mers

| Pos | 123456789 | score | |
|---|---|---|---|
| 131 | HPLRHATVL | 22 | Portion of SEQ ID NO: 28; each start position is specified - the length of each peptide is nine amino acids, the end position for each peptide is the start position plus eight |
| 60 | EPMYIFLCM | 21 | |
| 169 | LPFCRSNIL | 20 | |
| 290 | NPIVYGVKT | 19 | |
| 4 | DPNGNESSA | 18 | |
| 20 | LPGLEEAQF | 18 | |
| 141 | LPRVTKIGV | 18 | |
| 285 | VPPVLNPIV | 17 | |
| 32 | FPLCSLYLI | 16 | |
| 255 | VPFIGLSMV | 16 | |
| 270 | RDSPLPVIL | 16 | |
| 150 | AAVVRGAAL | 15 | |
| 154 | RGAALMAPL | 15 | |
| 157 | ALMAPLPVF | 15 | |
| 252 | IFYVPFIGL | 15 | |
| 300 | EIRQRILRL | 15 | |
| 9 | ESSATYFIL | 14 | |
| 29 | WLAFPLCSL | 14 | |
| 31 | AFPLCSLYL | 14 | |
| 111 | SGMESTVLL | 14 | |
| 133 | LRHATVLTL | 14 | |
| 160 | APLPVFIKQ | 14 | |
| 223 | LILKTVLGL | 14 | |
| 272 | SPLPVILAN | 14 | |
| 26 | AQFWLAFPL | 13 | |
| 110 | LSGMESTVL | 13 | |
| 125 | RYVAICHPL | 13 | |
| 217 | ISFSYLLIL | 13 | |
| 269 | RRDSPLPVI | 13 | |
| 281 | IYLLVPPVL | 13 | |
| 12 | ATYFILIGL | 12 | |
| 35 | CSLYLIAVL | 12 | |
| 58 | LHEPMYIFL | 12 | |
| 77 | STSSMPKML | 12 | |
| 143 | RVTKIGVAA | 12 | |
| 152 | VVRGAALMA | 12 | |
| 191 | ACDDIRVNV | 12 | |
| 195 | IRVNVVYGL | 12 | |
| 207 | ISAIGLDSL | 12 | |
| 208 | SAIGLDSLL | 12 | |
| 221 | YLLILKTVL | 12 | |
| 268 | KRRDSPLPV | 12 | |
| 305 | ILRLFHVAT | 12 | |
| 15 | FILIGLPGL | 11 | |
| 24 | EEAQFWLAF | 11 | |
| 38 | YLIAVLGNL | 11 | |
| 41 | AVLGNLTII | 11 | |
| 78 | TSSMPKMLA | 11 | |
| 79 | SSMPKMLAI | 11 | |
| 81 | MPKMLAIFW | 11 | |
| 93 | TTIQFDACL | 11 | |
| 113 | MESTVLLAM | 11 | |
| 120 | AMAFDRYVA | 11 | |
| 128 | AICHPLRHA | 11 | |
| 132 | PLRHATVLT | 11 | |
| 156 | AALMAPLPV | 11 | |
| 158 | LMAPLPVFI | 11 | |

TABLE XXVII-continued

101P3A11-V1- HLA-B0702 9-mers

| Pos | 123456789 | score |
|---|---|---|
| 182 | CLHQDVMKL | 11 |
| 204 | IVIISAIGL | 11 |
| 209 | AIGLDSLLI | 11 |
| 214 | SLLISFSYL | 11 |
| 249 | AVFIFYVPF | 11 |
| 266 | FSKRRDSPL | 11 |
| 276 | VILANIYLL | 11 |
| 286 | PPVLNPIVY | 11 |
| 8 | NESSATYFI | 10 |
| 22 | GLEEAQFWL | 10 |
| 50 | YIVRTEHSL | 10 |
| 61 | PMYIFLCML | 10 |
| 67 | CMLSGIDIL | 10 |
| 68 | MLSGIDILI | 10 |
| 94 | TIQFDACLL | 10 |
| 96 | QFDACLLQI | 10 |
| 102 | LQIFAIHSL | 10 |
| 109 | SLSGMESTV | 10 |
| 129 | ICHPLRHAT | 10 |
| 145 | TKIGVAAVV | 10 |
| 161 | PLPVFIKQL | 10 |
| 162 | LPVFIKQLP | 10 |
| 175 | NILSHSYCL | 10 |
| 199 | VVYGLIVII | 10 |
| 215 | LLISFSYLL | 10 |
| 216 | LISFSYLLI | 10 |
| 239 | AFGTCVSHV | 10 |
| 243 | CVSHVCAVF | 10 |
| 271 | DSPLPVILA | 10 |
| 274 | LPVILANIY | 10 |
| 275 | PVILANIYL | 10 |
| 277 | ILANIYLLV | 10 |
| 298 | TKEIRQRIL | 10 |

TABLE XXVII

101P3A11-V2-HLA B0702 - 9-mers

| Pos | 123456789 | score | |
|---|---|---|---|
| 20 | WPISICWFL | 21 | Portion of SEQ ID NO: 30; each start position is specified - the length of each peptide is nine amino acids, the end position for each peptide is the start position plus eight |
| 16 | CPSSWPISI | 18 | |
| 6 | AVLASGVTL | 16 | |
| 21 | PISICWFLL | 12 | |
| 26 | WFLLCSTQL | 11 | |

TABLE XXVII

101P3A11-V3- HLA B0702 9-mers

| Pos | 123456789 | score | |
|---|---|---|---|
| 7 | LQMFAIHSL | 11 | Portion of SEQ ID NO: 32; each start position is specified - the length of each peptide is nine amino acids, the end position for each peptide is the start position plus eight |
| 1 | QFDACLLQM | 10 | |
| 4 | ACLLQMFAI | 9 | |
| 2 | FDACLLQMF | 7 | |
| 3 | DACLLQMFA | 7 | |

TABLE XXVIII

101P3A11-V1- HLA-B08 9-mers

| Pos | 123456789 | score | |
|---|---|---|---|
| 300 | EIRQRILRL | 31 | Portion of SEQ ID NO: 28; each start position is specified - the length of each peptide is nine amino acids, the end position for each peptide is the start position plus eight |
| 266 | FSKRRDSPL | 29 | |
| 150 | AAVVRGAAL | 24 | |
| 169 | LPFCRSNIL | 24 | |
| 295 | GVKTKEIRQ | 21 | |
| 121 | MAFDRYVAI | 20 | |
| 293 | VYGVKTKEI | 20 | |
| 22 | GLEEAQFWL | 19 | |
| 79 | SSMPKMLAI | 19 | |
| 161 | PLPVFIKQL | 19 | |
| 187 | VMKLACDDI | 18 | |
| 214 | SLLISFSYL | 18 | |
| 222 | LLILKTVLG | 18 | |
| 297 | KTKEIRQRI | 18 | |
| 298 | TKEIRQRIL | 18 | |
| 131 | HPLRHATVL | 17 | |
| 182 | CLHQDVMKL | 17 | |
| 224 | ILKTVLGLT | 17 | |
| 29 | WLAFPLCSL | 16 | |
| 38 | YLIAVLGNL | 16 | |
| 57 | SLHEPMYIF | 16 | |
| 81 | MPKMLAIFW | 16 | |
| 163 | PVFIKQLPF | 16 | |
| 202 | GLIVIISAI | 16 | |
| 208 | SAIGLDSLL | 16 | |
| 215 | LLISFSYLL | 16 | |
| 221 | YLLILKTVL | 16 | |
| 234 | EAQAKAFGT | 16 | |
| 276 | VILANIYLL | 16 | |
| 305 | ILRLFHVAT | 16 | |
| 15 | FILIGLPGL | 15 | |
| 111 | SGMESTVLL | 15 | |
| 139 | LTLPRVTKI | 15 | |
| 165 | FIKQLPFCR | 15 | |
| 223 | LILKTVLGL | 15 | |

TABLE XXVIII

101P3A11-V2-HLA B08 - 9-mers

| Pos | 123456789 | score | |
|---|---|---|---|
| 20 | WPISICWFL | 16 | Portion of SEQ ID NO: 30; each start position is specified - the length of each peptide is nine amino acids, the end position for each peptide is the start position plus eight |
| 21 | PISICWFLL | 14 | |
| 13 | TLRCPSSWP | 12 | |
| 16 | CPSSWPISI | 12 | |
| 6 | AVLASGVTL | 11 | |
| 26 | WFLLCSTQL | 11 | |
| 1 | SLYLIAVLA | 10 | |
| 11 | GVTLRCPSS | 10 | |
| 19 | SWPISICWF | 9 | |
| 7 | VLASGVTLR | 8 | |
| 27 | FLLCSTQLS | 7 | |

TABLE XXVIII

101P3A11-V3- HLA B08 9-mers

| Pos | 123456789 | score | |
|---|---|---|---|
| 7 | LQMFAIHSL | 11 | Portion of SEQ ID NO: 32; each start position is specified - the length of each peptide is nine amino acids, the end position for each peptide is |
| 4 | ACLLQMFAI | 8 | |
| 2 | FDACLLQMF | 7 | |
| 5 | CLLQMFAIH | 6 | |
| 6 | LLQMFAIHS | 6 | |
| 3 | DACLLQMFA | 5 | |

TABLE XXVIII-continued

101P3A11-V3- HLA B08 9-mers

| Pos | 123456789 | score | |
|---|---|---|---|
| | | | the start position plus eight |

TABLE XXIX

101P3A11-V1- HLA-B1510 9-mers

| Pos | 123456789 | score | |
|---|---|---|---|
| 58 | LHEPMYIFL | 23 | Portion of SEQ ID NO: 28; each start position is specified - the length of each peptide is nine amino acids, the end position for each peptide is the start position plus eight |
| 245 | SHVCAVFIF | 17 | |
| 270 | RDSPLPVIL | 16 | |
| 281 | IYLLVPPVL | 16 | |
| 263 | VHRFSKRRD | 15 | |
| 300 | EIRQRILRL | 15 | |
| 107 | IHSLSGMES | 14 | |
| 207 | ISAIGLDSL | 14 | |
| 221 | YLLILKTVL | 14 | |
| 252 | IFYVPFIGL | 14 | |
| 298 | TKEIRQRIL | 14 | |
| 22 | GLEEAQFWL | 13 | |
| 35 | CSLYLIAVL | 13 | |
| 55 | EHSLHEPMY | 13 | |
| 111 | SGMESTVLL | 13 | |
| 195 | IRVNVVYGL | 13 | |
| 9 | ESSATYFIL | 12 | |
| 15 | FILIGLPGL | 12 | |
| 29 | WLAFPLCSL | 12 | |
| 67 | CMLSGIDIL | 12 | |
| 77 | STSSMPKML | 12 | |
| 93 | TTIQFDACL | 12 | |
| 110 | LSGMESTVL | 12 | |
| 131 | HPLRHATVL | 12 | |
| 133 | LRHATVLTL | 12 | |
| 150 | AAVVRGAAL | 12 | |
| 154 | RGAALMAPL | 12 | |
| 161 | PLPVFIKQL | 12 | |
| 182 | CLHQDVMKL | 12 | |
| 183 | LHQDVMKLA | 12 | |
| 204 | IVIISAIGL | 12 | |
| 217 | ISFSYLLIL | 12 | |
| 223 | LILKTVLGL | 12 | |
| 276 | VILANIYLL | 12 | |
| 38 | YLIAVLGNL | 11 | |
| 50 | YIVRTEHSL | 11 | |
| 94 | TIQFDACLL | 11 | |
| 102 | LQIFAIHSL | 11 | |
| 130 | CHPLRHATV | 11 | |
| 134 | RHATVLTLP | 11 | |
| 178 | SHSYCLHQD | 11 | |
| 208 | SAIGLDSLL | 11 | |
| 258 | IGLSMVHRF | 11 | |

TABLE XXIX

101P3A11-V2-HLA B1510 - 9-mers

| Pos | 123456789 | score | |
|---|---|---|---|
| 6 | AVLASGVTL | 13 | Portion of SEQ ID NO: 30; each start position is specified - the length of each peptide is nine amino acids, the end position for each peptide is the start position plus eight |
| 21 | PISICWFLL | 11 | |
| 20 | WPISICWFL | 10 | |
| 26 | WFLLCSTQL | 10 | |
| 19 | SWPISICWF | 7 | |
| 28 | LLCSTQLSM | 6 | |

TABLE XXIX

| 101P3A11-V3-HLA B1510 9-mers | | | |
|---|---|---|---|
| Pos | 123456789 | score | |
| 7 | LQMFAIHSL | 11 | Portion of SEQ ID NO: 32; each start position is specified - the length of each peptide is nine amino acids, the end position for each peptide is the start position plus eight |
| 2 | FDACLLQMF | 7 | |
| 1 | QFDACLLQM | 6 | |

TABLE XXX

| 101P3A11-V1- HLA-B2705 9-mers | | | |
|---|---|---|---|
| Pos | 123456789 | score | |
| 195 | IRVNVVYGL | 25 | Portion of SEQ ID NO: 28; each start position is specified - the length of each peptide is nine amino acids, the end position for each peptide is the start position plus eight |
| 269 | RRDSPLPVI | 24 | |
| 133 | LRHATVLTL | 23 | |
| 301 | IRQRILRLF | 23 | |
| 306 | LRLFHVATH | 23 | |
| 232 | TREAQAKAF | 21 | |
| 35 | CSLYLIAVL | 18 | |
| 300 | EIRQRILRL | 18 | |
| 7 | GNESSATYF | 17 | |
| 67 | CMLSGIDIL | 17 | |
| 163 | PVFIKQLPF | 17 | |
| 208 | SAIGLDSLL | 17 | |
| 211 | GLDSLLISF | 17 | |
| 221 | YLLILKTVL | 17 | |
| 238 | KAFGTCVSH | 17 | |
| 270 | RDSPLPVIL | 17 | |
| 281 | IYLLVPPVL | 17 | |
| 296 | VKTKEIRQR | 17 | |
| 12 | ATYFILIGL | 16 | |
| 15 | FILIGLPGL | 16 | |
| 22 | GLEEAQFWL | 16 | |
| 26 | AQFWLAFPL | 16 | |
| 38 | YLIAVLGNL | 16 | |
| 93 | TTIQFDACL | 16 | |
| 102 | LQIFAIHSL | 16 | |
| 125 | RYVAICHPL | 16 | |
| 131 | HPLRHATVL | 16 | |
| 142 | PRVTKIGVA | 16 | |
| 154 | RGAALMAPL | 16 | |
| 182 | CLHQDVMKL | 16 | |
| 202 | GLIVIISAI | 16 | |
| 204 | IVIISAIGL | 16 | |
| 217 | ISFSYLLIL | 16 | |
| 223 | LILKTVLGL | 16 | |
| 256 | PFIGLSMVH | 16 | |
| 258 | IGLSMVHRF | 16 | |
| 276 | VILANIYLL | 16 | |
| 48 | IIYIVRTEH | 15 | |
| 110 | LSGMESTVL | 15 | |
| 115 | STVLLAMAF | 15 | |
| 124 | DRYVAICHP | 15 | |
| 146 | KIGVAAVVR | 15 | |
| 157 | ALMAPLPVF | 15 | |
| 169 | LPFCRSNIL | 15 | |
| 173 | RSNILSHSY | 15 | |
| 199 | VVYGLIVII | 15 | |
| 207 | ISAIGLDSL | 15 | |
| 230 | GLTREAQAK | 15 | |
| 249 | AVFIFYVPF | 15 | |
| 252 | IFYVPFIGL | 15 | |
| 275 | PVILANIYL | 15 | |
| 291 | PIVYGVKTK | 15 | |
| 299 | KEIRQRILR | 15 | |
| 20 | LPGLEEAQF | 14 | |

TABLE XXX-continued

| 101P3A11-V1- HLA-B2705 9-mers | | |
|---|---|---|
| Pos | 123456789 | score |
| 30 | IAFPLCSLY | 14 |
| 31 | AFPLCSLYL | 14 |
| 40 | IAVLGNLTI | 14 |
| 41 | AVLGNLTII | 14 |
| 80 | SMPKMLAIF | 14 |
| 82 | PKMLAIFWF | 14 |
| 100 | CLLQIFAIH | 14 |
| 138 | VLTLPRVTK | 14 |
| 139 | LTLPRVTKI | 14 |
| 151 | AVVRGAALM | 14 |
| 161 | PLPVFIKQL | 14 |
| 175 | NILSHSYCL | 14 |
| 181 | YCLHQDVMK | 14 |
| 193 | DDIRVNVVY | 14 |
| 213 | DSLLISFSY | 14 |
| 214 | SLLISFSYL | 14 |
| 215 | LLISFSYLL | 14 |
| 261 | SMVHRFSKR | 14 |
| 264 | HRFSKRRDS | 14 |
| 268 | KRRDSPLPV | 14 |
| 294 | YGVKTKEIR | 14 |
| 302 | RQRILRLFH | 14 |
| 303 | QRILRLFHV | 14 |
| 6 | NGNESSATY | 13 |
| 24 | EEAQFWLAF | 13 |
| 29 | WLAFPLCSL | 13 |
| 45 | NLTIIYIVR | 13 |
| 52 | VRTEHSLHE | 13 |
| 57 | SLHEPMYIF | 13 |
| 61 | PMYIFLCML | 13 |
| 73 | DILISTSSM | 13 |
| 75 | LISTSSMPK | 13 |
| 76 | ISTSSMPKM | 13 |
| 99 | ACLLQIFAI | 13 |
| 105 | FAIHSLSGM | 13 |
| 111 | SGMESTVLL | 13 |
| 117 | VLLAMAFDR | 13 |
| 127 | VAICHPLRH | 13 |
| 150 | AAVVRGAAL | 13 |
| 159 | MAPLPVFIK | 13 |
| 165 | FIKQLPFCR | 13 |
| 171 | FCRSNILSH | 13 |
| 172 | CRSNILSHS | 13 |
| 188 | MKLACDDIR | 13 |
| 218 | SFSYLLILK | 13 |
| 225 | LKTVLGLTR | 13 |
| 243 | CVSHVCAVF | 13 |
| 257 | FIGLSMVHR | 13 |
| 262 | MVHRFSKRR | 13 |
| 50 | YIVRTEHSL | 12 |
| 58 | LHEPMYIFL | 12 |
| 89 | WFNSTTIQF | 12 |
| 97 | FDACLLQIF | 12 |
| 135 | HATVLTLPR | 12 |
| 153 | VRGAALMAP | 12 |
| 180 | SYCLHQDVM | 12 |
| 198 | NVVYGLIVI | 12 |
| 245 | SHVCAVFIF | 12 |
| 266 | FSKRRDSPL | 12 |
| 274 | LPVILANIY | 12 |
| 286 | PPVLNPIVY | 12 |
| 289 | LNPIVYGVK | 12 |
| 297 | KTKEIRQRI | 12 |
| 298 | TKEIRQRIL | 12 |

TABLE XXX

| 101P3A11-V2-HLA B2705 - 9-mers | | | |
|---|---|---|---|
| Pos | 123456789 | score | |
| 14 | LRCPSSWPI | 20 | Portion of SEQ ID NO: 30; each start position |
| 26 | WFLLCSTQL | 17 | |
| 6 | AVLASGVTL | 16 | |

TABLE XXX-continued

| 101P3A11-V2-HLA B2705 - 9-mers | | | |
|---|---|---|---|
| Pos | 123456789 | score | |
| 7 | VLASGVTLR | 15 | is specified - the length of each peptide is nine amino acids, the end position for each peptide is the start position plus eight |
| 19 | SWPISICWF | 14 | |
| 20 | WPISICWFL | 14 | |
| 28 | LLCSTQLSM | 12 | |
| 21 | PISICWFLL | 10 | |

TABLE XXX

| 101P3A11-V3- HLA B2705 9-mers | | | |
|---|---|---|---|
| Pos | 123456789 | score | |
| 7 | LQMFAIHSL | 14 | Portion of SEQ ID NO: 32; each start position is specified - the length of each peptide is nine amino acids, the end position for each peptide is the start position plus eight |
| 5 | CLLQMFAIH | 13 | |
| 2 | FDACLLQMF | 12 | |
| 1 | QFDACLLQM | 11 | |
| 4 | ACLLQMFAI | 10 | |

TABLE XXXI

| 101P3A11-V1- HLA-B2709 9-mers | | | |
|---|---|---|---|
| Pos | 123456789 | score | |
| 195 | IRVNVVYGL | 24 | Portion of SEQ ID NO: 28; each start position is specified - the length of each peptide is nine amino acids, the end position for each peptide is the start position plus eight |
| 269 | RRDSPLPVI | 24 | |
| 133 | LRHATVLTL | 22 | |
| 268 | KRRDSPLPV | 21 | |
| 301 | IRQRILRLF | 20 | |
| 232 | TREAQAKAF | 19 | |
| 303 | QRILRLFHV | 19 | |
| 125 | RYVAICHPL | 16 | |
| 270 | RDSPLPVIL | 16 | |
| 44 | GNLTIIYIV | 15 | |
| 217 | ISFSYLLIL | 15 | |
| 12 | ATYFILIGL | 14 | |
| 26 | AQFWLAFPL | 14 | |
| 154 | RGAALMAPL | 14 | |
| 175 | NILSHSYCL | 14 | |
| 223 | LILKTVLGL | 14 | |
| 258 | IGLSMVHRF | 14 | |
| 281 | IYLLVPPVL | 14 | |
| 7 | GNESSATYF | 13 | |
| 15 | FILIGLPGL | 13 | |
| 22 | GLEEAQFWL | 13 | |
| 67 | CMLSGIDIL | 13 | |
| 131 | HPLRHATVL | 13 | |
| 202 | GLIVIISAI | 13 | |
| 204 | IVIISAIGL | 13 | |
| 215 | LLISFSYLL | 13 | |
| 252 | IFYVPFIGL | 13 | |
| 264 | HRFSKRRDS | 13 | |
| 276 | VILANIYLL | 13 | |
| 306 | LRLFHVATH | 13 | |
| 31 | AFPLCSLYL | 12 | |
| 35 | CSLYLIAVL | 12 | |
| 38 | YLIAVLGNL | 12 | |
| 52 | VRTEHSLHE | 12 | |
| 61 | PMYIFLCML | 12 | |
| 76 | ISTSSMPKM | 12 | |
| 94 | TIQFDACLL | 12 | |

TABLE XXXI-continued

| 101P3A11-V1- HLA-B2709 9-mers | | |
|---|---|---|
| Pos | 123456789 | score |
| 124 | DRYVAICHP | 12 |
| 136 | ATVLTLPRV | 12 |
| 139 | LTLPRVTKI | 12 |
| 150 | AAVVRGAAL | 12 |
| 156 | AALMAPLPV | 12 |
| 169 | LPFCRSNIL | 12 |
| 182 | CLHQDVMKL | 12 |
| 189 | KLACDDIRV | 12 |
| 191 | ACDDIRVNV | 12 |
| 196 | RVNVVYGLI | 12 |
| 211 | GLDSLLISF | 12 |
| 214 | SLLISFSYL | 12 |
| 221 | YLLILKTVL | 12 |
| 249 | AVFIFYVPF | 12 |
| 280 | NIYLLVPPV | 12 |
| 288 | VLNPIVYGV | 12 |
| 297 | KTKEIRQRI | 12 |
| 300 | EIRQRILRL | 12 |
| 32 | FPLCSLYLI | 11 |
| 40 | IAVLGNLTI | 11 |
| 41 | AVLGNLTII | 11 |
| 50 | YIVRTEHSL | 11 |
| 58 | LHEPMYIFL | 11 |
| 64 | IFLCMLSGI | 11 |
| 77 | STSSMPKML | 11 |
| 93 | TTIQFDACL | 11 |
| 99 | ACLLQIFAI | 11 |
| 102 | LQIFAIHSL | 11 |
| 111 | SGMESTVLL | 11 |
| 121 | MAFDRYVAI | 11 |
| 142 | PRVTKIGVA | 11 |
| 151 | AVVRGAALM | 11 |
| 161 | PLPVFIKQL | 11 |
| 163 | PVFIKQLPF | 11 |
| 172 | CRSNILSHS | 11 |
| 199 | VVYGLIVII | 11 |
| 207 | ISAIGLDSL | 11 |
| 208 | SAIGLDSLL | 11 |
| 209 | AIGLDSLLI | 11 |
| 220 | SYLLILKTV | 11 |
| 242 | TCVSHVCAV | 11 |
| 250 | VFIFYVPFI | 11 |
| 275 | PVILANIYL | 11 |
| 277 | ILANIYLLV | 11 |

TABLE XXXI

| 101P3A11-V2-HLA B2709 - 9-mers | | | |
|---|---|---|---|
| Pos | 123456789 | score | |
| 14 | LRCPSSWPI | 19 | Portion of SEQ ID NO: 30; each start position is specified - the length of each peptide is nine amino acids, the end position for each peptide is the start position plus eight |
| 6 | AVLASGVTL | 14 | |
| 20 | WPISICWFL | 13 | |
| 26 | WFLLCSTQL | 13 | |
| 21 | PISICWFLL | 10 | |
| 28 | LLCSTQLSM | 10 | |
| 4 | LIAVLASGV | 9 | |
| 16 | CPSSWPISI | 9 | |

TABLE XXXI

| 101P3A11-V3- HLA B2709 9-mers | | | |
|---|---|---|---|
| Pos | 123456789 | score | |
| 4 | ACLLQMFAI | 11 | Portion of SEQ ID NO: 32; each start position |
| 1 | QFDACLLQM | 10 | |
| 7 | LQMFAIHSL | 10 | |

TABLE XXXI-continued

| 101P3A11-V3- HLA B2709 9-mers | | | |
|---|---|---|---|
| Pos | 123456789 | score | |
| 2 | FDACLLQMF | 8 | is specified - the length of each peptide is nine amino acids, the end position for each peptide is the start position plus eight |

TABLE XXXII

| 101P3A11-V1- HLA-B4402 9-mers | | | |
|---|---|---|---|
| Pos | 123456789 | score | |
| 24 | EEAQFWLAF | 25 | Portion of SEQ ID NO: 28; each start position is specified - the length of each peptide is nine amino acids, the end position for each peptide is the start position plus eight |
| 8 | NESSATYFI | 21 | |
| 99 | ACLLQIFAI | 18 | |
| 299 | KEIRQRILR | 18 | |
| 102 | LQIFAIHSL | 17 | |
| 161 | PLPVFIKQL | 17 | |
| 202 | GLIVIISAI | 17 | |
| 300 | EIRQRILRL | 17 | |
| 12 | ATYFILIGL | 16 | |
| 26 | AQFWLAFPL | 16 | |
| 30 | LAFDLCSLY | 16 | |
| 31 | AFPLCSLYL | 16 | |
| 79 | SSMPKMLAI | 16 | |
| 113 | MESTVLLAM | 16 | |
| 150 | AAVVRGAAL | 16 | |
| 157 | ALMAPLPVF | 16 | |
| 193 | DDIRVNVVY | 16 | |
| 208 | SAIGLDSLL | 16 | |
| 249 | AVFIFYVPF | 16 | |
| 270 | RDSPLPVIL | 16 | |
| 276 | VILANIYLL | 16 | |
| 35 | CSLYLIAVL | 15 | |
| 41 | AVLGNLTII | 15 | |
| 59 | HEPMYIFLC | 15 | |
| 77 | STSSMPKML | 15 | |
| 82 | PKMLAIFWF | 15 | |
| 111 | SGMESTVLL | 15 | |
| 115 | STVLLAMAF | 15 | |
| 121 | MAFDRYVAI | 15 | |
| 139 | LTLPRVTKI | 15 | |
| 204 | IVIISAIGL | 15 | |
| 232 | TREAQAKAF | 15 | |
| 275 | PVILANIYL | 15 | |
| 286 | PPVLNPIVY | 15 | |
| 301 | IRQRILRLF | 15 | |
| 38 | YLIAVLGNL | 14 | |
| 55 | EHSLHEPMY | 14 | |
| 58 | LHEPMYIFL | 14 | |
| 67 | CMLSGIDIL | 14 | |
| 131 | HPLRHATVL | 14 | |
| 169 | LPFCRSNIL | 14 | |
| 209 | AIGLDSLLI | 14 | |
| 215 | LLISFSYLL | 14 | |
| 217 | ISFSYLLIL | 14 | |
| 281 | IYLLVPPVL | 14 | |
| 284 | LVPPVLNPI | 14 | |
| 9 | ESSATYFIL | 13 | |
| 10 | SSATYFILI | 13 | |
| 42 | VLGNLTIIY | 13 | |
| 43 | LGNLTIIYI | 13 | |
| 68 | MLSGIDILI | 13 | |
| 80 | SMPKMLAIF | 13 | |
| 89 | WFNSTTIQF | 13 | |
| 93 | TTIQFDACL | 13 | |
| 133 | LRHATVLTL | 13 | |
| 158 | LMAPLPVFI | 13 | |
| 163 | PVFIKQLPF | 13 | |

TABLE XXXII-continued

| 101P3A11-V1- HLA-B4402 9-mers | | |
|---|---|---|
| Pos | 123456789 | score |
| 199 | VVYGLIVII | 13 |
| 211 | GLDSLLISF | 13 |
| 213 | DSLLISFSY | 13 |
| 214 | SLLISFSYL | 13 |
| 223 | LILKTVLGL | 13 |
| 258 | IGLSMVHRF | 13 |
| 6 | NGNESSATY | 12 |
| 15 | FILIGLPGL | 12 |
| 20 | LPGLEEAQF | 12 |
| 21 | PGLEEAQFW | 12 |
| 23 | LEEAQFWLA | 12 |
| 50 | YIVRTEHSL | 12 |
| 81 | MPKMLAIFW | 12 |
| 94 | TIQFDACLL | 12 |
| 96 | QFDACLLQI | 12 |
| 125 | RYVAICHPL | 12 |
| 175 | NILSHSYCL | 12 |
| 182 | CLHQDVMKL | 12 |
| 195 | IRVNVVYGL | 12 |
| 198 | NVVYGLIVI | 12 |
| 221 | YLLILKTVL | 12 |
| 243 | CVSHVCAVF | 12 |
| 245 | SHVCAVFIF | 12 |
| 246 | HVCAVFIFY | 12 |
| 250 | VFIFYVPFI | 12 |
| 252 | IFYVPFIGL | 12 |
| 266 | FSKRRDSPL | 12 |
| 274 | LPVILANIY | 12 |
| 298 | TKEIRQRIL | 12 |

TABLE XXXII

| 101P3A11-V2-HLA B4402 - 9-mers | | | |
|---|---|---|---|
| Pos | 123456789 | score | |
| 6 | AVLASGVTL | 16 | Portion of SEQ ID NO: 30; each start position is specified - the length of each peptide is nine amino acids, the end position for each peptide is the start position plus eight |
| 18 | SSWPISICW | 16 | |
| 19 | SWPISICWF | 15 | |
| 20 | WPISICWFL | 14 | |
| 12 | VTLRCPSSW | 13 | |
| 26 | WFLLCSTQL | 13 | |
| 21 | PISICWFLL | 12 | |
| 14 | LRCPSSWPI | 11 | |
| 16 | CPSSWPISI | 11 | |

TABLE XXXII

| 101P3A11-V3- HLA B4402 9-mers | | | |
|---|---|---|---|
| Pos | 123456789 | score | |
| 4 | ACLLQMFAI | 15 | Portion of SEQ ID NO: 32; each start position is specified - the length of each peptide is nine amino acids, the end position for each peptide is the start position plus eight |
| 7 | LQMFAIHSL | 15 | |
| 2 | FDACLLQMF | 11 | |

TABLE XXXIII

101P3A11-V1- HLA-B5101 9-mers

| Pos | 123456789 | score | |
|---|---|---|---|
| 40 | IAVLGNLTI | 26 | Portion of SEQ ID NO: 28; each start position is specified - the length of each peptide is nine amino acids, the end position for each peptide is the start position plus eight |
| 32 | FPLCSLYLI | 25 | |
| 121 | MAFDRYVAI | 24 | |
| 131 | HPLRHATVL | 23 | |
| 119 | LAMAFDRYV | 22 | |
| 141 | LPRVTKIGV | 22 | |
| 156 | AALMAPLPV | 22 | |
| 43 | LGNLTIIYI | 21 | |
| 255 | VPFIGLSMV | 21 | |
| 285 | VPPVLNPIV | 21 | |
| 169 | LPFCRSNIL | 20 | |
| 236 | QAKAFGTCV | 20 | |
| 139 | LTLPRVTKI | 19 | |
| 160 | APLPVFIKQ | 18 | |
| 190 | LACDDIRVN | 18 | |
| 199 | VVYGLIVII | 18 | |
| 278 | LANIYLLVP | 18 | |
| 208 | SAIGLDSLL | 17 | |
| 284 | LVPPVLNPI | 17 | |
| 64 | IFLCMLSGI | 16 | |
| 87 | IFWFNSTTI | 16 | |
| 111 | SGMESTVLL | 16 | |
| 145 | TKIGVAAVV | 16 | |
| 150 | AAVVRGAAL | 16 | |
| 198 | NVVYGLIVI | 16 | |
| 272 | SPLPVILAN | 16 | |
| 281 | IYLLVPPVL | 16 | |
| 4 | DPNGNESSA | 15 | |
| 41 | AVLGNLTII | 15 | |
| 98 | DACLLQIFA | 15 | |
| 133 | LRHATVLTL | 15 | |
| 223 | LILKTVLGL | 15 | |
| 280 | NIYLLVPPV | 15 | |
| 286 | PPVLNPIVY | 15 | |
| 290 | NPIVYGVKT | 15 | |
| 10 | SSATYFILI | 14 | |
| 66 | LCMLSGIDI | 14 | |
| 85 | LAIFWFNST | 14 | |
| 127 | VAICHPLRH | 14 | |
| 158 | LMAPLPVFI | 14 | |
| 159 | MAPLPVFIK | 14 | |
| 192 | CDDIRVNVV | 14 | |
| 201 | YGLIVIISA | 14 | |
| 210 | IGLDSLLIS | 14 | |
| 216 | LISFSYLLI | 14 | |
| 220 | SYLLILKTV | 14 | |
| 221 | YLLILKTVL | 14 | |
| 238 | KAFGTCVSH | 14 | |
| 248 | CAVFIFYVP | 14 | |
| 250 | VFIFYVPFI | 14 | |
| 252 | IFYVPFIGL | 14 | |
| 258 | IGLSMVHRF | 14 | |
| 269 | RRDSPLPVI | 14 | |
| 274 | LPVILANIY | 14 | |
| 30 | LAFPLCSLY | 13 | |
| 34 | LCSLYLIAV | 13 | |
| 56 | HSLHEPMYI | 13 | |
| 68 | MLSGIDILI | 13 | |
| 81 | MPKMLAIFW | 13 | |
| 96 | QFDACLLQI | 13 | |
| 99 | ACLLQIFAI | 13 | |
| 105 | FAIHSLSGM | 13 | |
| 147 | IGVAAVVRG | 13 | |
| 149 | VAAVVRGAA | 13 | |
| 154 | RGAALMAPL | 13 | |
| 234 | EAQAKAFGT | 13 | |
| 244 | VSHVCAVFI | 13 | |
| 293 | VYGVKTKEI | 13 | |
| 297 | KTKEIRQRI | 13 | |
| 6 | NGNESSATY | 12 | |
| 11 | SATYFILIG | 12 | |
| 12 | ATYFILIGL | 12 | |
| 20 | LPGLEEAQF | 12 | |
| 35 | CSLYLIAVL | 12 | |
| 38 | YLIAVLGNL | 12 | |

TABLE XXXIII-continued

101P3A11-V1- HLA-B5101 9-mers

| Pos | 123456789 | score |
|---|---|---|
| 44 | GNLTIIYIV | 12 |
| 60 | EPMYIFLCM | 12 |
| 79 | SSMPKMLAI | 12 |
| 109 | SLSGMESTV | 12 |
| 110 | LSGMESTVL | 12 |
| 155 | GAALMAPLP | 12 |
| 162 | LPVFIKQLP | 12 |
| 179 | HSYCLHQDV | 12 |
| 195 | IRVNVVYGL | 12 |
| 196 | RVNVVYGLI | 12 |
| 217 | ISFSYLLIL | 12 |
| 239 | AFGTCVSHV | 12 |
| 240 | FGTCVSHVC | 12 |
| 268 | KRRDSPLPV | 12 |
| 273 | PLPVILANI | 12 |
| 292 | IVYGVKTKE | 12 |

TABLE XXXIII

101P3A11-V2-HLA B5101 - 9-mers

| Pos | 123456789 | score | |
|---|---|---|---|
| 16 | CPSSWPISI | 22 | Portion of SEQ ID NO: 30; each start position is specified - the length of each peptide is nine amino acids, the end position for each peptide is the start position plus eight |
| 8 | LASGVTLRC | 17 | |
| 20 | WPISICWFL | 16 | |
| 5 | IAVLASGVT | 15 | |
| 6 | AVLASGVTL | 13 | |
| 14 | LRCPSSWPI | 13 | |
| 4 | LIAVLASGV | 11 | |

TABLE XXXIII

101P3A11-V3- HLA B5101 9-mers

| Pos | 123456789 | score | |
|---|---|---|---|
| 3 | DACLLQMFA | 14 | Portion of SEQ ID NO: 32; each start position is specified - the length of each peptide is nine amino acids, the end position for each peptide is the start position plus eight |
| 4 | ACLLQMFAI | 12 | |
| 7 | LQMFAIHSL | 9 | |

TABLE XXXIV

101P3A11-V1- HLA-A1 10-mers

| Pos | 1234567890 | score | |
|---|---|---|---|
| 192 | CDDIRVNVVY | 27 | Portion of SEQ ID NO: 28; each start position is specified - the length of each peptide is nine amino acids, the end position for each peptide is |
| 245 | SHVCAVFIFY | 24 | |
| 41 | AVLGNLTIIY | 21 | |
| 285 | VPPVLNPIVY | 21 | |
| 117 | VLLAMAFDRY | 20 | |
| 29 | WLAFPLCSLY | 18 | |
| 298 | TKEIRQRILR | 17 | |
| 22 | GLEEAQFWLA | 16 | |
| 23 | LEEAQFWLAF | 16 | |

TABLE XXXIV-continued

101P3A11-V1- HLA-A1 10-mers

| Pos | 1234567890 | score | |
|---|---|---|---|
| 53 | RTEHSLHEPM | 16 | the start position |
| 54 | TEHSLHEPMY | 16 | plus nine |
| 58 | LHEPMYIFLC | 16 | |
| 112 | GMESTVLLAM | 16 | |
| 273 | PLPVILANIY | 16 | |
| 2 | MVDPNGNESS | 15 | |
| 5 | PNGNESSATY | 15 | |
| 122 | AFDRYVAICH | 15 | |
| 172 | CRSNILSHSY | 15 | |
| 212 | LDSLLISFSY | 15 | |
| 9 | ESSATYFILI | 13 | |
| 191 | ACDDIRVNVV | 13 | |

TABLE XXXIV

101P3A11-V2-- HLA A1 10-mers

| Pos | 1234567890 | score | |
|---|---|---|---|
| 22 | PISICWFLLC | 11 | Portion of |
| 2 | SLYLIAVLAS | 10 | SEQ ID NO: 30; |
| 19 | SSWPISICWF | 10 | each start position |
| 23 | ISICWFLLCS | 10 | is specified - the |
| 8 | VLASGVTLRC | 8 | length of each |
| 18 | PSSWPISICW | 8 | peptide is ten |
| 28 | FLLCSTQLSM | 8 | amino acids, the |
| 13 | VTLRCPSSWP | 7 | end position for |
| 1 | CSLYLIAVLA | 6 | each peptide is |
| 10 | ASGVTLRCPS | 6 | the start position |
| | | | plus nine |

TABLE XXXIV

101P3A11-V3- HLA A1 10-mers

| Pos | 1234567890 | score | |
|---|---|---|---|
| 2 | QFDACLLQMF | 11 | Portion of |
| 1 | IQFDACLLQM | 6 | SEQ ID NO: 32; |
| 9 | QMFAIHSLSG | 6 | each start position |
| 6 | CLLQMFAIHS | 5 | is specified - the |
| | | | length of each |
| | | | peptide is ten |
| | | | amino acids, the |
| | | | end position for |
| | | | each peptide is |
| | | | the start position |
| | | | plus nine |

TABLE XXXV

101P3A11-V1- HLA-A0201 10-mers

| Pos | 1234567890 | score | |
|---|---|---|---|
| 222 | LLILKTVLGL | 30 | Portion of |
| 101 | LLQIFAIHSL | 29 | SEQ ID NO: 28; |
| 283 | LLVPPVLNPI | 27 | each start position |
| 206 | IISAIGLDSL | 26 | is specified - the |
| 214 | SLLISFSYLL | 25 | length of each |
| 57 | SLHEPMYIFL | 24 | peptide is ten |
| 63 | YIFLCMLSGI | 24 | amino acids, the |
| 109 | SLSGMESTVL | 24 | end position for |
| 118 | LLAMAFDRYV | 24 | each peptide is |
| 132 | PLRHATVLTL | 24 | the start position |
| 138 | VLTLPRVTKI | 24 | plus nine |
| 216 | LISFSYLLIL | 24 | |
| 39 | LIAVLGNLTI | 23 | |

TABLE XXXV-continued

101P3A11-V1- HLA-A0201 10-mers

| Pos | 1234567890 | score |
|---|---|---|
| 42 | VLGNLTIIYI | 23 |
| 157 | ALMAPLPVFI | 23 |
| 194 | DIRVNVVYGL | 23 |
| 215 | LLISFSYLLI | 23 |
| 33 | PLCSLYLIAV | 22 |
| 120 | AMAFDRYVAI | 22 |
| 238 | KAFGTCVSHV | 22 |
| 276 | VILANIYLLV | 22 |
| 86 | AIFWFNSTTI | 21 |
| 140 | TLPRVTKIGV | 21 |
| 203 | LIVIISAIGL | 21 |
| 14 | YFILIGLPGL | 20 |
| 17 | LIGLPGLEEA | 20 |
| 30 | LAFPLCSLYL | 20 |
| 143 | RVTKIGVAAV | 20 |
| 149 | VAAVVRGAAL | 20 |
| 168 | QLPFCRSNIL | 20 |
| 181 | YCLHQDVMKL | 20 |
| 223 | LILKTVLGLT | 20 |
| 241 | GTCVSHVCAV | 20 |
| 249 | AVFIFYVPFI | 20 |
| 251 | FIFYVPFIGL | 20 |
| 272 | SPLPVILANI | 20 |
| 280 | NIYLLVPPVL | 20 |
| 305 | ILRLFHVATH | 20 |
| 11 | SATYFILIGL | 19 |
| 16 | ILIGLPGLEE | 19 |
| 28 | FWLAFPLCSL | 19 |
| 36 | SLYLIAVLGN | 19 |
| 38 | YLIAVLGNLT | 19 |
| 45 | NLTIIYIVRT | 19 |
| 65 | FLCMLSGIDI | 19 |
| 84 | MLAIFWFNST | 19 |
| 160 | APLPVFIKQL | 19 |
| 190 | LACDDIRVNV | 19 |
| 208 | SAIGLDSLLI | 19 |
| 254 | YVPFIGLSMV | 19 |
| 277 | ILANIYLLVP | 19 |
| 282 | YLLVPPVLNP | 19 |
| 284 | LVPPVLNPIV | 19 |
| 287 | PVLNPIVYGV | 19 |
| 34 | LCSLYLIAVL | 18 |
| 37 | LYLIAVLGNL | 18 |
| 40 | IAVLGNLTII | 18 |
| 43 | LGNLTIIYIV | 18 |
| 67 | CMLSGIDILI | 18 |
| 112 | GMESTVLLAM | 18 |
| 129 | ICHPLRHATV | 18 |
| 135 | HATVLTLPRV | 18 |
| 155 | GAALMAPLPV | 18 |
| 158 | LMAPLPVFIK | 18 |
| 191 | ACDDIRVNVV | 18 |
| 230 | GLTREAQAKA | 18 |
| 246 | HVCAVFIFYV | 18 |
| 275 | PVILANIYLL | 18 |
| 279 | ANIYLLVPPV | 18 |
| 292 | IVYGVKTKEI | 18 |
| 299 | KEIRQRILRL | 18 |
| 49 | IYIVRTEHSL | 17 |
| 66 | LCMLSGIDIL | 17 |
| 68 | MLSGIDILIS | 17 |
| 75 | LISTSSMPKM | 17 |
| 92 | STTIQFDACL | 17 |
| 95 | IQFDACLLQI | 17 |
| 189 | KLACDDIRVN | 17 |
| 198 | NVVYGLIVII | 17 |
| 201 | YGLIVIISAI | 17 |
| 219 | FSYLLILKTV | 17 |
| 228 | VLGLTREAQA | 17 |
| 304 | RILRLFHVAT | 17 |
| 22 | GLEEAQFWLA | 16 |
| 93 | TTIQFDACLL | 16 |
| 98 | DACLLQIFAI | 16 |
| 128 | AICHPLRHAT | 16 |
| 144 | VTKIGVAAVV | 16 |

TABLE XXXV-continued

101P3A11-V1- HLA-A0201 10-mers

| Pos | 1234567890 | score |
|---|---|---|
| 196 | RVNVVYGLIV | 16 |
| 221 | YLLILKTVLG | 16 |
| 297 | KTKEIRQRIL | 16 |
| 19 | GLPGLEEAQF | 15 |
| 31 | AFPLCSLYLI | 15 |
| 127 | VAICHPLRHA | 15 |
| 146 | KIGVAAVVRG | 15 |
| 174 | SNILSHSYCL | 15 |
| 202 | GLIVIISAIG | 15 |
| 209 | AIGLDSLLIS | 15 |
| 211 | GLDSLLISFS | 15 |
| 268 | KRRDSPLPVI | 15 |
| 46 | LTIIYIVRTE | 14 |
| 74 | ILISTSSMPK | 14 |
| 108 | HSLSGMESTV | 14 |
| 110 | LSGMESTVLL | 14 |
| 111 | SGMESTVLLA | 14 |
| 207 | ISAIGLDSLL | 14 |
| 220 | SYLLILKTVL | 14 |
| 224 | ILKTVLGLTR | 14 |
| 235 | AQAKAFGTCV | 14 |
| 243 | CVSHVCAVFI | 14 |
| 257 | FIGLSMVHRF | 14 |
| 288 | VLNPIVYGVK | 14 |
| 302 | RQRILRLFHV | 14 |

TABLE XXXV

101P3A11-V2-- HLA A0201 10-mers

| Pos | 1234567890 | score | |
|---|---|---|---|
| 4 | YLIAVLASGV | 25 | Portion of SEQ ID NO: 30; each start position is specified - the length of each peptide is ten amino acids, the end position for each peptide is the start position plus nine |
| 6 | IAVLASGVTL | 20 | |
| 24 | SICWFLLCST | 20 | |
| 28 | FLLCSTQLSM | 20 | |
| 2 | SLYLIAVLAS | 19 | |
| 14 | TLRCPSSWPI | 18 | |
| 5 | LIAVLASGVT | 16 | |
| 29 | LLCSTQLSME | 16 | |
| 8 | VLASGVTLRC | 14 | |
| 3 | LYLIAVLASG | 12 | |
| 7 | AVLASGVTLR | 12 | |
| 9 | LASGVTLRCP | 12 | |
| 20 | SWPISICWFL | 12 | |
| 21 | WPISICWFLL | 12 | |

TABLE XXXV

101P3A11-V3- HLA A0201 10-mers

| Pos | 1234567890 | score | |
|---|---|---|---|
| 7 | LLQMFAIHSL | 29 | Portion of SEQ ID NO: 32; each start position is specified - the length of each peptide is ten amino acids, the end position for each peptide is the start position plus nine |

TABLE XXXVI

101P3A11-V1- HLA-A0203 10-mers

| Pos | 1234567890 | score | |
|---|---|---|---|
| 142 | PRVTKIGVAA | 19 | Portion of SEQ ID NO: 28; each start position is specified - the length of each peptide is ten amino acids, the end position for each peptide is the start position plus nine |
| 148 | GVAAVVRGAA | 19 | |
| 113 | MESTVLLAMA | 18 | |
| 228 | VLGLTREAQA | 18 | |
| 230 | GLTREAQAKA | 18 | |
| 143 | RVTKIGVAAV | 17 | |
| 149 | VAAVVRGAAL | 17 | |
| 3 | VDPNGNESSA | 10 | |
| 17 | LIGLPGLEEA | 10 | |
| 22 | GLEEAQFWLA | 10 | |
| 32 | FPLCSLYLIA | 10 | |
| 77 | STSSMPKMLA | 10 | |
| 90 | FNSTTIQFDA | 10 | |
| 97 | FDACLLQIFA | 10 | |
| 111 | SGMESTVLLA | 10 | |
| 119 | LAMAFDRYVA | 10 | |
| 127 | VAICHPLRHA | 10 | |
| 141 | LPRVTKIGVA | 10 | |
| 147 | IGVAAVVRGA | 10 | |
| 151 | AVVRGAALMA | 10 | |
| 182 | CLHQDVMKLA | 10 | |
| 200 | VYGLIVIISA | 10 | |
| 226 | KTVLGLTREA | 10 | |
| 240 | FGTCVSHVCA | 10 | |
| 270 | RDSPLPVILA | 10 | |
| 303 | QRILRLFHVA | 10 | |
| 306 | LRLFHVATHA | 10 | |
| 4 | DPNGNESSAT | 9 | |
| 18 | IGLPGLEEAQ | 9 | |
| 23 | LEEAQFWLAF | 9 | |
| 33 | PLCSLYLIAV | 9 | |
| 78 | TSSMPKMLAI | 9 | |
| 91 | NSTTIQFDAC | 9 | |
| 98 | DACLLQIFAI | 9 | |
| 112 | GMESTVLLAM | 9 | |
| 114 | ESTVLLAMAF | 9 | |
| 120 | AMAFDRYVAI | 9 | |
| 128 | AICHPLRHAT | 9 | |
| 152 | VVRGAALMAP | 9 | |
| 183 | LHQDVMKLAC | 9 | |
| 201 | YGLIVIISAI | 9 | |
| 227 | TVLGLTREAQ | 9 | |
| 229 | LGLTREAQAK | 9 | |
| 231 | LTREAQAKAF | 9 | |
| 241 | GTCVSHVCAV | 9 | |
| 271 | DSPLPVILAN | 9 | |
| 304 | RILRLFHVAT | 9 | |
| 307 | RLFHVATHAS | 9 | |

TABLE XXXVI

101P3A11-V2-- HLA A0203 10-mers

| Pos | 1234567890 | score | |
|---|---|---|---|
| 1 | CSLYLIAVLA | 10 | Portion of SEQ ID NO: 30; each start position is specified - the length of each peptide is ten amino acids, the end position for each peptide is the start position plus nine |
| 2 | SLYLIAVLAS | 9 | |
| 3 | LYLIAVLASG | 8 | |

TABLE XXXVI

101P3A11-V3- HLA A0203 10-mers

| Pos | 1234567890 | score |
|---|---|---|
| 3 | FDACLLQMFA | 10 |
| 4 | DACLLQMFAI | 9 |
| 5 | ACLLQMFAIH | 8 |

Portion of SEQ ID NO: 32; each start position is specified - the length of each peptide is ten amino acids, the end position for each peptide is the start position plus nine

TABLE XXXVII

101P3A11-V1-HLA-A3 10-mers

| Pos | 1 2 3 4 5 6 7 8 9 0 | score |
|---|---|---|
| 137 | T V L T L P R V T K | 31 |
| 288 | V L N P I V Y G V K | 28 |
| 224 | I L K T V L G L T R | 27 |
| 305 | I L R L F H V A T H | 27 |
| 74 | I L I S T S S M P K | 26 |
| 16 | I L I G L P G L E E | 23 |
| 41 | A V L G N L T I I Y | 23 |
| 151 | A V V R G A A L M A | 23 |
| 259 | G L S M V H R F S K | 23 |
| 19 | G L P G L E E A Q F | 22 |
| 304 | R I L R L F H V A T | 22 |
| 277 | I L A N I Y L L V P | 21 |
| 29 | W L A F P L C S L Y | 20 |
| 116 | T V L L A M A F D R | 20 |
| 117 | V L L A M A F D R Y | 20 |
| 126 | Y V A I C H P L R H | 20 |
| 132 | P L R H A T V L T L | 20 |
| 145 | T K I G V A A V V R | 20 |
| 157 | A L M A P L P V F I | 20 |
| 196 | R V N V V Y G L I V | 20 |
| 36 | S L Y L I A V L G N | 19 |
| 273 | P L P V I L A N I Y | 19 |
| 38 | Y L I A V L G N L T | 18 |
| 50 | Y I V R T E H S L H | 18 |
| 51 | I V R T E H S L H E | 18 |
| 109 | S L S G M E S T V L | 18 |
| 143 | R V T K I G V A A V | 18 |
| 189 | K L A C D D I R V N | 18 |
| 280 | N I Y L L V P P V L | 18 |
| 292 | I V Y G V K T K E I | 18 |
| 295 | G V K T K E I R Q R | 18 |
| 47 | T I I Y I V R T E H | 17 |
| 103 | Q I F A I H S L S G | 17 |
| 152 | V V R G A A L M A P | 17 |
| 180 | S Y C L H Q D V M K | 17 |
| 204 | I V I I S A I G L D | 17 |
| 205 | V I I S A I G L D S | 17 |
| 221 | Y L L I L K T V L G | 17 |
| 222 | L L I L K T V L G L | 17 |
| 228 | V L G L T R E A Q A | 17 |
| 243 | C V S H V C A V F I | 17 |
| 290 | N P I V Y G V K T K | 17 |
| 39 | L I A V L G N L T I | 16 |
| 86 | A I F W F N S T T I | 16 |
| 148 | G V A A V V R G A A | 16 |
| 199 | V V Y G L I V I I S | 16 |
| 202 | G L I V I I S A I G | 16 |
| 215 | L L I S F S Y L L I | 16 |
| 227 | T V L G L T R E A Q | 16 |
| 229 | L G L T R E A Q A K | 16 |
| 230 | G L T R E A Q A K A | 16 |
| 2 | M V D P N G N E S S | 15 |
| 45 | N L T I I Y I V R T | 15 |
| 48 | I I Y I V R T E H S | 15 |

Portion of SEQ ID NO: 28; each start position is specified-the length of each peptide is ten amino acids, the end position for each peptide is the start position plus nine TABLE XXXVII-continued 101P3A11-V1-HLA-A3 10-mers

| Pos | 1 2 3 4 5 6 7 8 9 0 | score |
|---|---|---|
| 68 | M L S G I D I L I S | 15 |
| 73 | D I L I S T S S M P | 15 |
| 100 | C L L Q I F A I H S | 15 |
| 106 | A I H S L S G M E S | 15 |
| 146 | K I G V A A V V R G | 15 |
| 176 | I L S H S Y C L H Q | 15 |
| 192 | C D D I R V N V V Y | 15 |
| 209 | A I G L D S L L I S | 15 |
| 276 | V I L A N I Y L L V | 15 |
| 282 | Y L L V P P V L N P | 15 |
| 300 | E I R Q R I L R L F | 15 |
| 307 | R L F H V A T H A S | 15 |

TABLE XXXVII

101P3A11-V2--HLA A3 10-mers

| Pos | 1 2 3 4 5 6 7 8 9 0 | score |
|---|---|---|
| 7 | A V L A S G V T L R | 22 |
| 4 | Y L I A V L A S G V | 21 |
| 2 | S L Y L I A V L A S | 20 |
| 12 | G V T L R C P S S W | 17 |
| 28 | F L L C S T Q L S M | 17 |
| 5 | L I A V L A S G V T | 14 |
| 6 | I A V L A S G V T L | 14 |
| 8 | V L A S G V T L R C | 14 |
| 29 | L L C S T Q L S M E | 14 |
| 14 | T L R C P S S W P I | 13 |
| 22 | P I S I C W F L L C | 12 |
| 24 | S I C W F L L C S T | 11 |

Portion of SEQ ID NO: 30; each start position is specified-the length of each peptide is ten amino acids, the end position for each peptide is the start position plus nine

TABLE XXXVII

101P3A11-V3-HLA-A3 10-mers

| Pos | 1 2 3 4 5 6 7 8 9 0 | score |
|---|---|---|
| 6 | C L L Q M F A I H S | 15 |
| 5 | A C L L Q M F A I H | 13 |
| 7 | L L Q M F A I H S L | 12 |
| 1 | I Q F D A C L L Q M | 9 |
| 2 | Q F D A C L L Q M F | 9 |
| 9 | Q M F A I H S L S G | 9 |

Portion of SEQ ID NO: 28; each start position is specified-the length of each peptide is ten amino acids, the end position for each peptide is the start position plus nine

TABLE XXXVIII

101P3A11-V1-HLA-A26 10-mers

| Pos | 1 2 3 4 5 6 7 8 9 0 | score |
|---|---|---|
| 300 | E I R Q R I L R L F | 31 |
| 194 | D I R V N V V Y G L | 29 |
| 251 | F I F Y V P F I G L | 25 |
| 257 | F I G L S M V H R F | 25 |
| 75 | L I S T S S M P K M | 24 |
| 275 | P V I L A N I Y L L | 24 |
| 19 | G L P G L E E A Q F | 23 |
| 117 | V L L A M A F D R Y | 23 |
| 206 | I I G A I G L D S L | 23 |
| 222 | L L I L K T V L G L | 23 |
| 231 | L T R E A Q A K A F | 23 |
| 14 | Y F I L I G L P G L | 22 |
| 41 | A V L G N L T I I Y | 22 |
| 57 | S L H E P M Y I F L | 22 |

Portion of SEQ ID NO: 28; each start position is specified-the length of each peptide is ten amino acids, the end position for each peptide is the start position plus nine TABLE XXXVIII-continued 101P3A11-V1-HLA-A26 10-mers

| Pos | 1 | 2 | 3 | 4 | 5 | 6 | 7 | 8 | 9 | 0 | score |
|---|---|---|---|---|---|---|---|---|---|---|---|
| 96 | Q | F | D | A | C | L | L | Q | I | F | 22 |
| 216 | L | I | S | F | S | Y | L | L | I | L | 22 |
| 93 | T | T | I | Q | F | D | A | C | L | L | 21 |
| 101 | L | L | Q | I | F | A | I | H | S | L | 21 |
| 104 | I | F | A | I | H | S | L | S | G | M | 21 |
| 297 | K | T | K | E | I | R | Q | R | I | L | 21 |
| 29 | W | L | A | F | P | L | C | S | L | Y | 20 |
| 132 | P | L | R | H | A | T | V | L | T | L | 20 |
| 60 | E | P | M | Y | I | F | L | C | M | L | 19 |
| 92 | S | T | T | I | Q | F | D | A | C | L | 19 |
| 203 | L | I | V | I | I | S | A | I | G | L | 19 |
| 213 | D | S | L | L | I | S | F | S | Y | L | 19 |
| 273 | P | L | P | V | I | L | A | N | I | Y | 19 |
| 280 | N | I | Y | L | L | V | P | P | V | L | 19 |
| 53 | R | T | E | H | S | L | H | E | P | M | 18 |
| 63 | Y | I | F | L | C | M | L | S | G | I | 18 |
| 73 | D | I | L | I | S | T | S | S | M | P | 18 |
| 109 | S | L | S | G | M | E | S | T | V | L | 18 |
| 114 | E | S | T | V | L | L | A | M | A | F | 18 |
| 152 | V | V | R | G | A | A | L | M | A | P | 18 |
| 79 | S | S | M | P | K | M | L | A | I | F | 17 |
| 143 | R | V | T | K | I | G | V | A | A | V | 17 |
| 163 | P | V | F | I | K | Q | L | P | F | C | 17 |
| 165 | F | I | K | Q | L | P | F | C | R | S | 17 |
| 168 | Q | L | P | F | C | R | S | N | I | L | 17 |
| 186 | D | V | M | K | L | A | C | D | D | I | 17 |
| 249 | A | V | F | I | F | Y | V | P | F | I | 17 |
| 254 | Y | V | P | F | I | S | L | S | M | V | 17 |
| 46 | L | T | I | I | Y | I | V | R | T | E | 16 |
| 146 | K | I | G | V | A | A | V | V | R | G | 16 |
| 199 | V | V | Y | G | L | I | V | I | I | S | 16 |
| 204 | I | V | I | I | S | A | I | G | L | D | 16 |
| 210 | I | G | L | D | S | L | L | I | S | F | 16 |
| 214 | S | L | L | I | S | F | S | Y | L | L | 16 |
| 256 | P | F | I | G | L | S | M | V | H | R | 16 |
| 265 | R | F | S | K | R | R | D | S | P | L | 16 |
| 295 | G | V | K | T | K | E | I | R | Q | R | 16 |
| 17 | L | I | G | L | P | G | L | E | E | A | 15 |
| 81 | M | P | K | M | L | A | I | F | W | F | 15 |
| 115 | S | T | V | L | L | A | M | A | F | D | 15 |
| 156 | A | A | L | M | A | P | L | P | V | F | 15 |
| 160 | A | P | L | P | V | F | I | K | Q | L | 15 |
| 175 | N | I | L | S | H | S | Y | C | L | H | 15 |
| 198 | N | V | V | Y | G | L | I | V | I | I | 15 |
| 211 | G | L | D | S | L | L | I | S | F | S | 15 |
| 215 | L | L | I | S | F | S | Y | L | L | I | 15 |
| 223 | L | I | L | K | T | V | L | G | L | T | 15 |
| 241 | G | T | C | V | S | H | V | C | A | V | 15 |
| 248 | C | A | V | F | I | F | Y | V | P | F | 15 |
| 287 | P | V | L | N | P | I | V | Y | G | V | 15 |
| 299 | K | E | I | R | Q | R | I | L | R | L | 15 |

TABLE XXXVIII

101P3A11-V2--HLA-A26 10-mers

| Pos | 1 | 2 | 3 | 4 | 5 | 6 | 7 | 8 | 9 | 0 | score | |
|---|---|---|---|---|---|---|---|---|---|---|---|---|
| 28 | F | L | I | C | S | T | Q | L | S | M | 17 | Portion of SEQ ID |
| 19 | S | S | W | P | I | S | I | C | W | F | 16 | NO: 30; each start |
| 24 | S | I | C | W | F | L | L | C | S | T | 15 | position is |
| 29 | L | L | C | S | T | Q | L | S | M | E | 15 | specified-the length |
| 7 | A | V | L | A | S | G | V | T | L | R | 14 | of each peptide is |
| 22 | P | I | S | I | C | W | F | L | L | C | 14 | ten amino acids, the |
| 2 | S | L | Y | L | I | A | V | L | A | S | 13 | end position for each |
| 4 | Y | L | I | A | V | L | A | S | G | V | 12 | peptide is the start |
| 12 | G | V | T | L | R | C | P | S | S | W | 12 | position plus nine |
| 5 | L | I | A | V | L | A | S | G | V | T | 11 | |
| 8 | V | L | A | S | G | V | T | L | R | C | 11 | |
| 13 | V | T | L | R | C | P | S | S | W | P | 11 | |
| 21 | W | P | I | S | I | C | W | F | L | L | 11 | |
| 26 | C | W | F | L | L | C | S | T | Q | L | 11 | |

TABLE XXXVIII-continued

101P3A11-V2--HLA-A26 10-mers

| Pos | 1 | 2 | 3 | 4 | 5 | 6 | 7 | 8 | 9 | 0 | score |
|---|---|---|---|---|---|---|---|---|---|---|---|
| 6 | I | A | V | L | A | S | G | V | T | L | 9 |
| 20 | S | W | P | I | S | I | C | W | F | L | 9 |
| 14 | T | L | R | C | P | S | S | W | P | I | 8 |

TABLE XXXVIII

101P3A11-V3-HLA-A26 10-mers

| Pos | 1 | 2 | 3 | 4 | 5 | 6 | 7 | 8 | 9 | 0 | score | |
|---|---|---|---|---|---|---|---|---|---|---|---|---|
| 2 | Q | F | D | A | C | L | L | Q | M | F | 23 | Portion of SEQ ID |
| 7 | L | L | Q | M | F | A | I | H | S | L | 21 | NO: 32; each start |
| 10 | M | F | A | I | H | S | L | S | G | M | 21 | position is |
| 1 | I | Q | F | D | A | C | L | L | Q | M | 16 | specified-the length |
| 4 | D | A | C | L | L | Q | M | F | A | I | 11 | of each peptide is |
| | | | | | | | | | | | | ten amino acids, the |
| | | | | | | | | | | | | end position for each |
| | | | | | | | | | | | | peptide is the start |
| | | | | | | | | | | | | position plus nine |

TABLE XXXIX

101P3A11-V1-HLA-B0702 10-mers

| Pos | 1 | 2 | 3 | 4 | 5 | 6 | 7 | 8 | 9 | 0 | score | |
|---|---|---|---|---|---|---|---|---|---|---|---|---|
| 160 | A | P | L | P | V | F | I | K | Q | L | 23 | Portion of SEQ ID |
| 60 | E | P | M | Y | I | F | L | C | M | L | 22 | NO: 28; each start |
| 274 | L | P | V | I | L | A | N | I | Y | L | 20 | position is |
| 4 | D | P | N | G | N | E | S | S | A | T | 19 | specified-the length |
| 131 | H | P | L | R | H | A | T | V | L | T | 19 | of each peptide is |
| 141 | L | P | R | V | T | K | I | G | V | A | 19 | ten amino acids, the |
| 162 | L | P | V | F | I | K | Q | L | P | F | 19 | end position for each |
| 32 | F | P | L | C | S | L | Y | L | I | A | 18 | peptide is the start |
| 272 | S | P | L | P | V | I | L | A | N | I | 18 | position plus nine |
| 81 | M | P | K | M | L | A | I | F | W | F | 16 | |
| 109 | S | L | S | G | M | E | S | T | V | L | 16 | |
| 132 | P | L | R | H | A | T | V | L | T | L | 15 | |
| 265 | R | F | S | K | R | R | D | S | P | L | 15 | |
| 34 | L | C | S | L | Y | L | I | A | V | L | 14 | |
| 110 | L | S | G | M | E | S | T | V | L | L | 14 | |
| 153 | V | R | G | A | A | L | M | A | P | L | 14 | |
| 206 | I | I | S | A | I | G | L | D | S | L | 14 | |
| 216 | L | I | S | F | S | Y | L | L | I | L | 14 | |
| 269 | R | R | D | S | P | L | P | V | I | L | 14 | |
| 30 | L | A | F | P | L | C | S | L | Y | L | 13 | |
| 149 | V | A | A | V | V | R | G | A | A | L | 13 | |
| 157 | A | L | M | A | P | L | P | V | F | I | 13 | |
| 194 | D | I | R | V | N | V | V | Y | G | L | 13 | |
| 222 | L | L | I | L | K | T | V | L | G | L | 13 | |
| 299 | K | E | I | R | Q | R | I | L | R | L | 13 | |
| 8 | N | E | S | S | A | T | Y | F | I | L | 12 | |
| 20 | L | P | G | L | E | E | A | Q | F | W | 12 | |
| 25 | E | A | Q | F | W | L | A | F | P | L | 12 | |
| 120 | A | M | A | F | D | R | Y | V | A | I | 12 | |
| 130 | C | H | P | L | R | H | A | T | V | L | 12 | |
| 207 | I | S | A | I | G | L | D | S | L | L | 12 | |
| 220 | S | Y | L | L | I | L | K | T | V | L | 12 | |
| 280 | N | I | Y | L | L | V | P | P | V | L | 12 | |
| 286 | P | P | V | L | N | P | I | V | Y | G | 12 | |
| 9 | E | S | S | A | T | Y | F | I | L | I | 11 | |
| 14 | Y | F | I | L | I | G | L | P | G | L | 11 | |
| 28 | F | W | L | A | F | P | L | C | S | L | 11 | |
| 49 | I | Y | I | V | R | T | E | H | S | L | 11 | |
| 57 | S | L | H | E | P | M | Y | I | F | L | 11 | |
| 66 | L | C | M | L | S | G | I | D | I | L | 11 | |
| 76 | I | S | T | S | S | M | P | K | M | L | 11 | |
| 78 | T | S | S | M | P | K | M | L | A | I | 11 | |
| 92 | S | T | T | I | Q | F | D | A | C | L | 11 | |
| 124 | D | R | Y | V | A | I | C | H | P | L | 11 | |

TABLE XXXIX-continued

101P3A11-V1-HLA-B0702 10-mers

| Pos | 1 2 3 4 5 6 7 8 9 0 | score |
|---|---|---|
| 143 | R V I K I G V A A V | 11 |
| 181 | Y C L H Q D V M K L | 11 |
| 191 | A C D D I R V N V V | 11 |
| 213 | D S L L I S F S Y L | 11 |
| 235 | A Q A K A F G T C V | 11 |
| 243 | C V S H V C A V F I | 11 |
| 249 | A V F I F Y V P F I | 11 |
| 251 | F I F Y V P F I G L | 11 |
| 255 | V P F I G L S M V H | 11 |
| 267 | S K R R D S P L P V | 11 |
| 268 | K R R D S P L P V I | 11 |
| 270 | R D S P L P V I L A | 11 |
| 279 | A N I Y L L V P P V | 11 |
| 285 | V P P V L N P I V Y | 11 |
| 290 | N P I V Y G V K T K | 11 |
| 297 | K T K E I R Q R I L | 11 |

TABLE XXXIX

101P3A11-V2--HLA B0702 10-mers

| Pos | 1 2 3 4 5 6 7 8 9 0 | score | |
|---|---|---|---|
| 21 | W P I S I C W F L L | 20 | Portion of SEQ ID NO: 30; each start position is specified-the length of each peptide is ten amino acids, the end position for each peptide is the start position plus nine |
| 6 | I A V L A S S V T L | 13 | |
| 17 | C P S S W P I S I C | 12 | |
| 20 | S W P I S I C W F L | 11 | |
| 26 | C W F L L C S T Q L | 11 | |
| 14 | T L R C P S S W P I | 9 | |

TABLE XXXIX

101P3A11-V3-HLA B0702 10-mers

| Pos | 1 2 3 4 5 6 7 8 9 0 | score | |
|---|---|---|---|
| 7 | L L Q M F A I H S L | 10 | Portion of SEQ ID NO: 32; each start position is specified-the length of each peptide is ten amino acids, the end position for each peptide is the start position plus nine |
| 1 | I Q F D A C L L Q M | 9 | |
| 2 | Q F D A C L L Q M F | 8 | |
| 3 | F D A C L L Q M F A | 8 | |
| 4 | D A C L L Q M F A I | 7 | |
| 10 | M F A I H S L S G M | 7 | |
| 5 | A C L L Q M F A I H | 4 | |

TABLE XLIV

101P3A11-V1-HLA-B4402 10-mers

| Pos | 1 2 3 4 5 6 7 8 9 0 | score | |
|---|---|---|---|
| 299 | K E I R Q R I L R L | 29 | Portion of SEQ ID NO: 28; each start position is specified-the length of each peptide is ten amino acids, the end position for each peptide is the start position plus nine |
| 23 | L E E A Q F W L A F | 23 | |
| 160 | A P L P V F I K Q L | 23 | |
| 8 | N E S S A T Y F I L | 22 | |
| 54 | T E H S L H E P M Y | 20 | |
| 275 | P V I L A N I Y L L | 18 | |
| 41 | A V L G N L T I I Y | 17 | |
| 30 | L A F P L C S L Y L | 16 | |
| 34 | L C S L Y L I A V L | 16 | |
| 79 | S S M P K M L A I F | 16 | |
| 88 | F W F N S T T I Q F | 16 | |
| 156 | A A L M A P L P V F | 16 | |
| 222 | L L I L K T V L G L | 16 | |

TABLE XLIV-continued

101P3A11-V1-HLA-B4402 10-mers

| Pos | 1 2 3 4 5 6 7 8 9 0 | score |
|---|---|---|
| 14 | Y F I L I G L P G L | 15 |
| 31 | A F P L C S L Y L I | 15 |
| 66 | L C M L S G I D I L | 15 |
| 93 | T T I Q F D A C L L | 15 |
| 114 | E S T V L L A M A F | 15 |
| 174 | S N I L S H S Y C L | 15 |
| 208 | S A I G L D S L L I | 15 |
| 231 | L T R E A Q A K A F | 15 |
| 300 | E I R Q R I L R L F | 15 |
| 9 | E S S A T Y F I L I | 14 |
| 49 | I Y I V R T E H S L | 14 |
| 60 | E P M Y I F L C M L | 14 |
| 80 | S M P K M L A I F W | 14 |
| 86 | A I F W F N S T T I | 14 |
| 95 | I Q F D A C L L Q I | 14 |
| 98 | D A C L L Q I F A I | 14 |
| 101 | L L Q I F A I H S L | 14 |
| 109 | S L S G M E S T V L | 14 |
| 120 | A M A F D R Y V A I | 14 |
| 130 | C H P L R H A T V L | 14 |
| 157 | A L M A P L P V F I | 14 |
| 167 | K Q L P F C R S N I | 14 |
| 201 | Y G L I V I I S A I | 14 |
| 210 | I G L D S L L I S F | 14 |
| 220 | S Y L L I L K T V L | 14 |
| 249 | A V F I F Y V P F I | 14 |
| 251 | F I F Y V P F I G L | 14 |
| 272 | S P L P V I L A N I | 14 |
| 280 | N I Y L L V P P V L | 14 |
| 285 | V P P V L N P I V Y | 14 |

TABLE XLIV

101P3A11-V2--HLA B4402 10-mers

| Pos | 1 2 3 4 5 6 7 8 9 0 | score | |
|---|---|---|---|
| 19 | S S W P I S I C W F | 17 | Portion of SEQ ID NO: 30; each start position is specified-the length of each peptide is ten amino acids, the end position for each peptide is the start position plus nine |
| 21 | W P I S I C W F L L | 14 | |
| 26 | C W F L L C S T Q L | 14 | |
| 6 | I A V L A S G V T L | 13 | |
| 12 | G V T L R C P S S W | 12 | |
| 18 | P S S W P I S I C W | 12 | |
| 20 | S W P I S I C W F L | 12 | |
| 16 | R C P S S W P I S I | 11 | |
| 14 | T L R C P S S W P I | 8 | |

TABLE XLIV

101P3A11-V3-HLA B4402 10-mers

| Pos | 1 2 3 4 5 6 7 8 9 0 | score | |
|---|---|---|---|
| 7 | L L Q M F A I H S L | 14 | Portion of SEQ ID NO: 32; each start position is specified-the length of each peptide is ten amino acids, the end position for each peptide is the start position plus nine |
| 2 | Q F D A C L L Q M F | 12 | |
| 4 | D A C L L Q M F A I | 11 | |
| 1 | I Q F D A C L L Q M | 6 | |
| 5 | A C L L Q M F A I H | 6 | |

Table XLV-101P3A11 v1-HLA B5101 10-mers No Results

Table XLV-101P3A11 v2-HLA B5101 10-mers No Results

Table XLV-101P3A11 v3 HLA B5101 10-mers No results.

TABLE XLVI

101P3A11-V1-DRB-0101 15-mers

| Pos | 1 | 2 | 3 | 4 | 5 | 6 | 7 | 8 | 9 | 0 | 1 | 2 | 3 | 4 | 5 | score |
|---|---|---|---|---|---|---|---|---|---|---|---|---|---|---|---|---|
| 201 | Y | G | L | I | V | I | I | S | A | I | G | L | D | S | L | 36 |
| 69 | L | S | G | I | D | I | L | I | S | T | S | S | M | P | K | 34 |
| 63 | Y | I | F | L | C | M | L | S | G | I | D | I | L | I | S | 33 |
| 104 | I | F | A | I | H | S | L | S | G | M | E | S | T | V | L | 32 |
| 46 | L | T | I | I | Y | I | V | R | T | E | H | S | L | H | E | 31 |
| 194 | D | I | R | V | N | V | V | Y | G | L | I | V | I | I | S | 31 |
| 278 | L | A | N | I | Y | L | L | V | P | P | V | L | N | P | I | 31 |
| 98 | D | A | C | L | L | Q | I | F | A | I | H | S | L | S | G | 30 |
| 107 | I | H | S | L | S | G | M | E | S | T | V | L | L | A | M | 30 |
| 241 | G | T | C | V | S | H | V | C | A | V | F | I | F | Y | V | 30 |
| 11 | S | A | T | Y | F | I | L | I | G | L | P | G | L | E | E | 29 |
| 290 | N | P | I | V | Y | G | V | K | T | K | E | I | R | Q | R | 29 |
| 12 | A | T | Y | F | I | L | I | G | L | P | G | L | E | E | A | 28 |
| 251 | F | I | F | Y | V | P | F | I | G | L | S | M | V | H | R | 27 |
| 141 | L | P | R | V | T | K | I | G | V | A | A | V | V | R | G | 26 |
| 184 | H | Q | D | V | M | K | L | A | C | D | D | I | R | V | N | 26 |
| 218 | S | F | S | Y | L | L | I | L | K | T | V | L | G | L | T | 26 |
| 17 | L | I | G | L | P | G | L | E | E | A | Q | F | W | L | A | 25 |
| 25 | F | A | Q | F | W | L | A | F | P | L | C | S | L | Y | L | 25 |
| 37 | L | Y | L | I | A | V | L | G | N | L | T | I | I | Y | I | 25 |
| 71 | G | I | D | I | L | I | S | T | S | S | M | P | K | M | L | 25 |
| 112 | S | M | E | S | T | V | L | L | A | M | A | F | D | R | Y | 25 |
| 149 | V | A | A | V | V | R | G | A | A | L | M | A | P | L | P | 25 |
| 163 | P | V | F | I | K | Q | L | P | F | C | R | S | N | I | L | 25 |
| 198 | N | V | V | Y | G | L | I | V | I | I | S | A | I | G | L | 25 |
| 212 | L | D | S | L | L | I | S | F | S | Y | L | L | I | L | K | 25 |
| 219 | F | S | Y | L | L | I | L | K | T | V | L | G | L | T | R | 25 |
| 14 | Y | F | I | L | I | G | L | P | G | L | E | E | A | Q | F | 24 |
| 31 | A | F | P | L | C | S | L | Y | L | I | A | V | L | G | N | 24 |
| 40 | I | A | V | L | G | N | L | T | I | I | Y | I | V | R | T | 24 |
| 78 | T | S | S | M | P | K | M | L | A | I | F | W | F | N | S | 24 |
| 86 | A | I | F | W | F | N | S | T | T | I | Q | F | D | A | C | 24 |
| 138 | V | L | T | L | P | R | V | T | K | I | G | V | A | A | V | 24 |
| 152 | V | V | R | G | A | A | L | M | A | P | L | P | V | F | I | 24 |
| 162 | L | P | V | F | I | K | Q | L | P | F | C | R | S | N | I | 24 |
| 197 | V | N | V | V | Y | G | L | I | V | I | I | S | A | I | G | 24 |
| 203 | L | I | V | I | I | S | A | I | G | L | D | S | L | L | I | 24 |
| 209 | A | I | G | L | D | S | L | L | I | S | F | S | Y | L | L | 24 |
| 249 | A | V | F | I | F | Y | V | P | F | I | G | L | S | M | V | 24 |
| 252 | I | F | Y | V | P | F | I | G | L | S | M | V | H | R | F | 24 |
| 84 | M | L | A | I | F | W | F | N | S | T | T | I | Q | F | D | 23 |
| 102 | L | Q | I | F | A | I | H | S | L | S | G | M | E | S | T | 23 |
| 166 | I | K | Q | L | P | F | C | R | S | N | I | L | S | H | S | 23 |
| 204 | I | V | I | I | S | A | I | G | L | D | S | L | L | I | S | 23 |
| 222 | L | L | I | L | K | L | V | L | G | L | T | R | E | A | Q | 23 |
| 279 | A | N | I | Y | L | L | V | P | P | V | L | N | P | I | V | 23 |
| 28 | F | W | L | A | F | P | L | C | S | L | Y | L | I | A | V | 22 |
| 36 | S | L | Y | L | I | A | V | L | G | N | L | T | I | I | Y | 22 |
| 62 | M | Y | I | F | L | C | M | L | S | G | I | D | I | L | I | 22 |
| 66 | L | C | M | L | S | G | I | D | I | L | I | S | T | S | S | 22 |
| 81 | M | P | K | M | L | A | I | F | W | F | N | S | T | T | I | 22 |
| 146 | K | I | G | V | A | A | V | V | R | G | A | A | L | M | A | 22 |
| 147 | I | G | V | A | A | V | V | R | G | A | A | L | M | A | P | 22 |
| 155 | G | A | A | L | M | A | P | L | P | V | F | I | K | Q | L | 22 |
| 206 | I | I | S | A | I | G | L | D | S | L | L | I | S | F | S | 22 |
| 244 | V | S | H | V | C | A | V | F | I | F | Y | V | P | F | I | 22 |
| 271 | D | S | P | L | P | V | I | L | A | N | I | Y | L | L | V | 22 |
| 275 | P | V | I | L | A | N | I | Y | L | L | V | P | P | V | L | 22 |
| 282 | Y | L | L | V | P | P | V | L | N | P | I | V | Y | G | V | 22 |
| 35 | C | S | L | Y | L | I | A | V | L | G | N | L | T | I | I | 21 |
| 70 | S | G | I | D | I | L | I | S | T | S | S | M | P | K | M | 21 |
| 153 | V | R | G | A | A | L | M | A | P | L | P | V | F | I | K | 21 |
| 300 | E | I | R | Q | R | I | L | R | L | F | H | V | A | T | H | 21 |
| 101 | L | L | Q | I | F | A | I | H | S | L | S | G | M | E | S | 20 |
| 136 | A | T | V | L | T | L | P | R | V | T | K | I | G | V | A | 20 |
| 142 | P | R | V | T | K | I | G | V | A | A | V | V | R | G | A | 20 |
| 192 | C | D | D | I | R | V | N | V | V | Y | G | L | I | V | I | 20 |
| 200 | V | Y | G | L | I | V | I | I | S | A | I | G | L | D | S | 20 |
| 263 | V | H | R | F | S | K | R | R | D | S | P | L | P | V | I | 20 |
| 272 | S | P | L | P | V | I | L | A | N | I | Y | L | L | V | P | 20 |
| 29 | W | L | A | F | P | L | C | S | L | Y | L | I | A | V | L | 19 |
| 59 | H | E | P | M | Y | I | F | L | C | M | L | S | G | I | D | 19 |
| 60 | E | P | M | Y | I | F | L | C | M | L | S | G | I | D | I | 19 |
| 61 | P | M | Y | I | F | L | C | M | L | S | G | I | D | I | L | 19 |
| 99 | A | C | L | L | Q | I | F | A | I | H | S | L | S | G | M | 19 |

Portion of SEQ ID NO: 28; each start position is specified-the length of each peptide is 15 amino acids, the end position for each peptide is the start position plus fourteen TABLE XLVI-continued 101P3A11-V1-DRB-0101 15-mers

| Pos | 1 | 2 | 3 | 4 | 5 | 6 | 7 | 8 | 9 | 0 | 1 | 2 | 3 | 4 | 5 | score |
|---|---|---|---|---|---|---|---|---|---|---|---|---|---|---|---|---|
| 216 | L | I | S | F | S | Y | L | L | I | L | K | T | V | L | G | 19 |
| 220 | S | Y | L | L | I | L | K | T | V | L | G | L | T | R | E | 19 |
| 229 | L | G | L | T | R | E | A | Q | A | K | A | F | G | T | C | 19 |
| 233 | R | E | A | Q | A | K | A | F | G | T | C | V | S | H | V | 19 |
| 247 | V | C | A | V | F | I | F | Y | V | P | F | I | G | L | S | 19 |
| 298 | T | K | E | I | R | Q | R | I | L | R | L | F | H | V | A | 19 |
| 4 | D | P | N | G | N | E | S | S | A | T | Y | F | I | L | I | 18 |
| 15 | F | I | L | I | G | L | P | G | L | E | E | A | Q | F | W | 18 |
| 26 | A | Q | F | W | L | A | F | P | L | C | S | L | Y | L | I | 18 |
| 43 | L | G | N | L | T | I | I | Y | I | V | R | T | E | H | S | 18 |
| 47 | T | I | I | Y | I | V | R | T | E | H | S | L | H | E | P | 18 |
| 79 | S | S | M | P | K | M | L | A | I | F | W | F | N | S | T | 18 |
| 85 | L | A | I | F | W | F | N | S | T | T | I | Q | F | D | A | 18 |
| 90 | F | N | S | T | T | I | Q | F | D | A | C | L | L | Q | I | 18 |
| 94 | T | I | Q | F | D | A | C | L | L | Q | I | F | A | I | H | 18 |
| 116 | T | V | L | L | A | M | A | F | D | R | Y | V | A | I | C | 18 |
| 120 | A | M | A | F | D | R | Y | V | A | I | C | H | P | L | R | 18 |
| 128 | A | I | C | H | P | L | R | H | A | T | V | L | T | L | P | 18 |
| 130 | C | H | P | L | R | H | A | T | V | L | T | L | P | R | V | 18 |
| 148 | G | V | A | A | V | V | R | G | A | A | L | M | A | P | L | 18 |
| 150 | A | A | V | V | R | G | A | A | L | M | A | P | L | P | V | 18 |
| 217 | I | S | F | S | Y | L | L | I | L | K | T | V | L | G | L | 18 |
| 228 | V | L | G | L | T | R | E | A | Q | A | K | A | F | G | T | 18 |
| 250 | V | F | I | F | Y | V | P | F | I | G | L | S | M | V | H | 18 |
| 254 | Y | V | P | F | I | G | L | S | M | V | H | R | F | S | K | 18 |
| 285 | V | P | P | V | L | N | P | I | V | Y | G | V | K | T | K | 18 |
| 287 | P | V | L | N | P | I | V | Y | G | V | K | T | K | E | I | 18 |
| 304 | R | I | L | R | L | F | H | V | A | T | H | A | S | E | P | 18 |
| 13 | T | Y | F | I | L | I | G | L | P | G | L | E | E | A | Q | 17 |
| 23 | L | E | E | A | Q | F | W | L | A | F | P | L | C | S | L | 17 |
| 34 | L | C | S | L | Y | L | I | A | V | L | G | N | L | T | I | 17 |
| 73 | D | I | L | I | S | T | S | S | M | P | K | M | L | A | I | 17 |
| 96 | Q | F | D | A | C | L | L | Q | I | F | A | I | H | S | L | 17 |
| 114 | E | S | T | V | L | L | A | M | A | F | D | R | Y | V | A | 17 |
| 118 | L | L | A | M | A | F | D | R | Y | V | A | I | C | H | P | 17 |
| 123 | F | D | R | Y | V | A | I | C | H | P | L | R | H | A | T | 17 |
| 124 | D | R | Y | V | A | I | C | H | P | L | R | H | A | T | V | 17 |
| 133 | L | R | H | A | T | V | L | T | L | P | R | V | T | K | I | 17 |
| 140 | T | L | P | R | V | T | K | I | G | V | A | A | V | V | R | 17 |
| 180 | S | Y | C | L | H | Q | D | V | M | K | L | A | C | D | D | 17 |
| 196 | R | V | N | V | V | Y | G | L | I | V | I | I | S | A | I | 17 |
| 199 | V | V | Y | G | L | I | V | I | I | S | A | I | G | L | D | 17 |
| 207 | I | S | A | I | G | L | D | S | L | L | I | S | F | S | Y | 17 |
| 214 | S | L | L | I | S | F | S | Y | L | L | I | L | K | T | V | 17 |
| 224 | I | L | K | T | V | L | G | L | T | R | E | A | Q | A | K | 17 |
| 226 | K | T | V | L | G | L | T | R | E | A | Q | A | K | A | F | 17 |
| 248 | C | A | V | F | I | F | Y | V | P | F | I | G | L | S | M | 17 |
| 255 | V | P | F | I | G | L | S | M | V | H | R | F | S | K | R | 17 |
| 273 | P | L | P | V | I | L | A | N | I | Y | L | L | V | P | P | 17 |
| 281 | I | Y | L | L | V | P | P | V | L | N | P | I | V | Y | G | 17 |

TABLE XLVI

101P3A11-V2-DRB 0101 15-mers

| Pos | 1 | 2 | 3 | 4 | 5 | 6 | 7 | 8 | 9 | 0 | 1 | 2 | 3 | 4 | 5 | score | |
|---|---|---|---|---|---|---|---|---|---|---|---|---|---|---|---|---|---|
| 29 | S | I | C | W | F | L | L | C | S | T | Q | L | S | M | E | 34 | Portion of SEQ ID NO: 30; each start position is specified-the length of each peptide is 15 amino acids, the end position for each peptide is the start position plus fourteen |
| 7 | S | L | Y | L | I | A | V | L | A | S | G | V | T | L | R | 32 | |
| 2 | A | F | P | L | C | S | L | Y | L | I | A | V | L | A | S | 24 | |
| 4 | P | L | C | S | L | Y | L | I | A | V | L | A | S | G | V | 24 | |
| 17 | G | V | T | L | R | C | P | S | S | W | P | I | S | I | C | 24 | |
| 5 | L | C | S | L | Y | L | I | A | V | L | A | S | G | V | T | 23 | |
| 8 | L | Y | L | I | A | V | L | A | S | G | V | T | L | R | C | 22 | |
| 23 | P | S | S | W | P | I | S | I | C | W | F | L | L | C | S | 21 | |
| 9 | Y | L | I | A | V | L | A | S | G | V | T | L | R | C | P | 18 | |
| 14 | L | A | S | G | V | T | L | R | C | P | S | S | W | P | I | 17 | |
| 15 | A | S | G | V | T | L | R | C | P | S | S | W | P | I | S | 16 | |

TABLE XLVI

101P3A11-V3-DRB 0101 15-mers

| Pos | 1 2 3 4 5 6 7 8 9 0 1 2 3 4 5 | score | |
|---|---|---|---|
| 15 | M F A I H S L S G M E S T V L | 32 | Portion of SEQ ID |
| 9 | D A C L L Q M F A I H S L S G | 30 | NO: 32; each start |
| 13 | L Q M F A I H S L S G M E S T | 23 | position is |
| 12 | L L Q M F A I H S L S G M E S | 20 | specified-the length |
| 1 | F N S T T I Q F D A C L L Q M | 18 | of each peptide is |
| 5 | T I Q F D A C L L Q M F A I H | 18 | 15 amino acids, the |
| 7 | Q F D A C L L Q M F A I H S L | 17 | end position for each |
| 10 | A C L L Q M F A I H S L S G M | 17 | peptide is the start |
| 2 | N S T T I Q F D A C L L Q M F | 16 | position plus |
| 6 | I Q F D A C L L Q M F A I H S | 16 | fourteen |

TABLE XLVII

101P3A11-V1-DRB 0301 15-mers

| Pos | 1 2 3 4 5 6 7 8 9 0 1 2 3 4 5 | score | |
|---|---|---|---|
| 17 | L I G L P G L E E A Q F W L A | 26 | Portion of SEQ ID |
| 207 | I S A I G L D S L L I S F S Y | 23 | NO: 28; each start |
| 92 | S T T I Q F D A C L L Q I F A | 22 | position is |
| 118 | L L A M A F D R Y V A I C H P | 22 | specified-the length |
| 39 | L I A V L G N L T I I Y I V R | 21 | of each peptide is |
| 180 | S Y C L H Q D V M K L A C D D | 21 | 15 amino acids, the |
| 212 | L D S L L I S F S Y L L I L K | 21 | end position for each |
| 220 | S Y L L I L K T V L G L T R E | 21 | peptide is the start |
| 273 | P L P V I L A N I Y L L V P P | 21 | position plus |
| 27 | Q F W L A F P L C S L Y L I A | 20 | fourteen |
| 115 | S T V L L A M A F D R Y V A I | 20 | |
| 130 | C H P L R H A T V L T L P R V | 20 | |
| 135 | H A T V L T L P R V T K I G V | 20 | |
| 187 | V M K L A C D D I R V N V V Y | 20 | |
| 201 | Y G L I V I I S A I G L D S L | 20 | |
| 271 | D S P L P V I L A N I Y L L V | 20 | |
| 298 | T K E I R Q R I L R L F H V A | 20 | |
| 12 | A T Y F I L I G L P G L E E A | 19 | |
| 55 | E H S L H E P M Y I F L C M L | 19 | |
| 107 | I H S L S G M E S T V L L A M | 19 | |
| 166 | I K Q L P F C R S N I L S H S | 19 | |
| 192 | C D D I R V N V V Y G L I V I | 19 | |
| 204 | I V I I S A I G L D S L L I S | 19 | |
| 214 | S L L I S F S Y L L I L K T V | 19 | |
| 225 | L K T V L G L T R E A Q A K A | 19 | |
| 228 | V L G L T R E A Q A K A F G T | 19 | |
| 249 | A V F I F Y V P F I G L S M V | 19 | |
| 255 | V P F I G L S M V H R F S K R | 19 | |
| 278 | L A N I Y L L V P P V L N P I | 19 | |
| 37 | L Y L I A V L G N L T I I Y I | 18 | |
| 94 | T I Q F D A C L L Q I F A I H | 18 | |
| 99 | A C L L Q I F A I H S L S G M | 18 | |
| 126 | Y V A I C H P L R H A T V L T | 18 | |
| 159 | M A P L P V F I K Q L P F C R | 18 | |
| 188 | M K L A C D D I R V N V V Y G | 18 | |
| 218 | S F S Y L L I L K T V L G L T | 18 | |
| 226 | K T V L G L T R E A Q A K A F | 18 | |
| 282 | Y L L V P P V L N P I V Y G V | 18 | |
| 289 | L N P I V Y G V K T K E I R Q | 18 | |
| 19 | G L P G L E E A Q F W L A F P | 17 | |
| 45 | N L T I I Y I V R T E H S L H | 17 | |
| 146 | K I G V A A V V R G A A L M A | 17 | |
| 160 | A P L P V F I K Q L P F C R S | 17 | |
| 257 | F I G L S M V H R F S K R R D | 17 | |
| 260 | L S M V H R F S K R R D S P L | 17 | |
| 138 | V L T L P R V T K I G V A A V | 16 | |
| 263 | V H R F S K R R D S P L P V I | 16 | |
| 295 | G V K T K E I R Q R I L R L F | 16 | |
| 47 | T I I Y I V R T E H S L H E P | 15 | |
| 52 | V R T E H S L H E P M Y I F L | 15 | |
| 173 | R S N I L S H S Y C L H Q D V | 15 | |
| 190 | L A C D D I R V N V V Y G L I | 15 | |
| 213 | D S L L I S F S Y L L I L K T | 15 | |
| 219 | F S Y L L I L K T V L G L T R | 15 | |
| 272 | S P L P V I L A N I Y L L V P | 15 | |

TABLE XLVII-continued

101P3A11-V1-DRB 0301 15-mers

| Pos | 1 | 2 | 3 | 4 | 5 | 6 | 7 | 8 | 9 | 0 | 1 | 2 | 3 | 4 | 5 | score |
|---|---|---|---|---|---|---|---|---|---|---|---|---|---|---|---|---|
| 280 | N | I | Y | L | L | V | P | P | V | L | N | P | I | V | Y | 15 |
| 13 | T | Y | F | I | L | I | G | L | P | G | L | E | E | A | Q | 14 |
| 36 | S | L | Y | L | I | A | V | L | G | N | L | T | I | I | Y | 14 |
| 65 | F | L | C | M | L | S | G | I | D | I | L | I | S | T | S | 14 |
| 141 | L | P | R | V | T | K | I | G | V | A | A | V | V | R | G | 14 |
| 274 | L | P | V | I | L | A | N | I | Y | L | L | V | P | P | V | 14 |
| 302 | R | Q | R | I | L | R | L | F | H | V | A | T | H | A | S | 14 |
| 14 | Y | F | I | L | I | G | L | P | G | L | E | E | A | Q | F | 13 |
| 48 | I | I | Y | I | V | R | T | E | H | S | L | H | E | P | M | 13 |
| 72 | I | D | I | L | I | S | T | S | S | M | P | K | M | L | A | 13 |
| 81 | M | P | K | M | L | A | I | F | W | F | N | S | T | T | I | 13 |
| 110 | L | S | G | M | E | S | T | V | L | L | A | M | A | F | D | 13 |
| 114 | E | S | T | V | L | L | A | M | A | F | D | R | Y | V | A | 13 |
| 136 | A | T | V | L | T | L | P | R | V | T | K | I | G | V | A | 13 |
| 196 | R | V | N | V | V | Y | G | L | I | V | I | I | S | A | I | 13 |
| 203 | L | I | V | I | I | S | A | I | G | L | D | S | L | L | I | 13 |
| 221 | Y | L | L | I | L | K | T | V | L | G | L | T | R | E | A | 13 |
| 222 | L | L | I | L | K | T | V | L | G | L | T | R | E | A | Q | 13 |
| 265 | R | F | S | K | R | R | D | S | P | L | P | V | I | L | A | 13 |
| 281 | I | Y | L | L | V | P | P | V | L | N | P | I | V | Y | G | 13 |
| 303 | Q | R | I | L | R | L | F | H | V | A | T | H | A | S | E | 13 |
| 15 | F | I | L | I | G | L | P | G | L | E | E | A | Q | F | W | 12 |
| 20 | L | P | G | L | E | E | A | Q | F | W | L | A | F | P | L | 12 |
| 31 | A | F | P | L | C | S | L | Y | L | I | A | V | L | G | N | 12 |
| 34 | L | C | S | L | Y | L | I | A | V | L | G | N | L | T | I | 12 |
| 43 | L | G | N | L | T | I | I | Y | I | V | R | T | E | H | S | 12 |
| 49 | I | Y | I | V | R | T | E | H | S | L | H | E | P | M | Y | 12 |
| 59 | H | E | P | M | Y | I | F | L | C | M | L | S | G | I | D | 12 |
| 63 | Y | I | F | L | C | M | L | S | G | I | D | I | L | I | S | 12 |
| 71 | G | I | D | I | L | I | S | T | S | S | M | P | K | M | L | 12 |
| 73 | D | I | L | I | S | T | S | S | M | P | K | M | L | A | I | 12 |
| 98 | D | A | C | L | L | Q | I | F | A | I | H | S | L | S | G | 12 |
| 104 | I | F | A | I | H | S | L | S | G | M | E | S | T | V | L | 12 |
| 108 | H | S | L | S | G | M | E | S | T | V | L | L | A | M | A | 12 |
| 149 | V | A | A | V | V | R | G | A | A | L | M | A | P | L | P | 12 |
| 150 | A | A | V | V | R | G | A | A | L | M | A | P | L | P | V | 12 |
| 154 | R | G | A | A | L | M | A | P | L | P | V | F | I | K | Q | 12 |
| 155 | G | A | A | L | M | A | P | L | P | V | F | I | K | Q | L | 12 |
| 156 | A | A | L | M | A | P | L | P | V | F | I | K | Q | L | P | 12 |
| 163 | P | V | F | I | K | Q | L | P | F | C | R | S | N | I | L | 12 |
| 185 | Q | D | V | M | K | L | A | C | D | D | I | R | V | N | V | 12 |
| 200 | V | Y | G | L | I | V | I | I | S | A | I | G | L | D | S | 12 |
| 202 | G | L | I | V | I | I | S | A | I | G | L | D | S | L | L | 12 |
| 209 | A | I | G | L | D | S | L | L | I | S | F | S | Y | L | L | 12 |
| 211 | G | L | D | S | L | L | I | S | F | S | Y | L | L | I | L | 12 |
| 285 | V | P | P | V | L | N | P | I | V | Y | G | V | K | T | K | 12 |
| 293 | V | Y | G | V | K | T | K | E | I | R | Q | R | I | L | R | 12 |

TABLE XLVII

101P3A11-V2-DRB 0301 15-mers

| Pos | 1 | 2 | 3 | 4 | 5 | 6 | 7 | 8 | 9 | 0 | 1 | 2 | 3 | 4 | 5 | score |
|---|---|---|---|---|---|---|---|---|---|---|---|---|---|---|---|---|
| 10 | L | I | A | V | L | A | S | G | V | T | L | R | C | P | S | 14 |
| 5 | L | C | S | L | Y | L | I | A | V | L | A | S | G | V | T | 13 |
| 2 | A | F | P | L | C | S | L | Y | L | I | A | V | L | A | S | 12 |
| 7 | S | L | Y | L | I | A | V | L | A | S | G | V | T | L | R | 12 |
| 9 | Y | L | I | A | V | L | A | S | G | V | T | L | R | C | P | 12 |
| 11 | I | A | V | L | A | S | G | V | T | L | R | C | P | S | S | 12 |
| 15 | A | S | G | V | T | L | R | C | P | S | S | W | P | I | S | 12 |
| 17 | G | V | T | L | R | C | P | S | S | W | P | I | S | I | C | 12 |
| 25 | S | W | P | I | S | I | C | W | F | L | L | C | S | T | Q | 12 |
| 3 | F | P | L | C | S | L | Y | L | I | A | V | L | A | S | G | 11 |
| 24 | S | S | W | P | I | S | I | C | W | F | L | L | C | S | T | 11 |
| 27 | P | I | S | I | C | W | F | L | L | C | S | T | Q | L | S | 11 |
| 8 | L | Y | L | I | A | V | L | A | S | G | V | T | L | R | C | 10 |
| 22 | C | P | S | S | W | P | I | S | I | C | W | F | L | L | C | 10 |
| 29 | S | I | C | W | F | L | L | C | S | T | Q | L | S | M | E | 9 |
| 23 | P | S | S | W | P | I | S | I | C | W | F | L | L | C | S | 8 |
| 13 | V | L | A | S | S | V | T | L | R | C | P | S | S | W | P | 7 |

Portion of SEQ ID NO: 30; each start position is specified-the length of each peptide is 15 amino acids, the end position for each peptide is the start position plus fourteen

TABLE XLVII

101P3A11-V3-DRB 0301 15-mers

| Pos | 1 2 3 4 5 6 7 8 9 0 1 2 3 4 5 | score | |
|---|---|---|---|
| 3 | S T T I Q F D A C L L Q M F A | 22 | Portion of SEQ ID NO: 32; each start position is specified-the length of each peptide is 15 amino acids, the end position for each peptide is the start position plus fourteen |
| 10 | A C L L Q M F A I H S L S G M | 19 | |
| 5 | T I Q F D A C L L Q M F A I H | 18 | |
| 9 | D A C L L Q M F A I H S L S G | 12 | |
| 15 | M F A I H S L S G M E S T V L | 12 | |
| 12 | L L Q M F A I H S L S G M E S | 11 | |
| 1 | F N S T T I Q F D A C L L Q M | 10 | |
| 2 | N S T T I Q F D A C L L Q M F | 10 | |

TABLE XLVIII

101P3A11-V1-DR1-0401 15-mers

| Pos | 1 2 3 4 5 6 7 8 9 0 1 2 3 4 5 | score | |
|---|---|---|---|
| 37 | L Y L I A V L G N L T I I Y I | 26 | Portion of SEQ ID NO: 28; each start position is specified-the length of each peptide is 15 amino acids, the end position for each peptide is the start position plus fourteen |
| 46 | L T I I Y I V R T E H S L H E | 26 | |
| 69 | L S G I D I l I S T S S M P K | 26 | |
| 84 | M L A I F W F N S T T I Q F D | 26 | |
| 135 | H A G V L T L P R V T K I G V | 26 | |
| 146 | K I G V A A V V R G A A L M A | 26 | |
| 225 | L K T V L G L T R E A Q A K A | 26 | |
| 228 | V L G L T R E A Q A K A F G T | 26 | |
| 257 | F I G L S M V H R F S K R R D | 26 | |
| 282 | Y L L V P P V L N P I V Y G V | 26 | |
| 290 | N P I V Y G V K T K E I R Q R | 26 | |
| 302 | R Q R I L R L F H V A T H A S | 26 | |
| 12 | A T Y F I L I G L P G L E E A | 22 | |
| 25 | E A Q F W L A F P L C S L Y L | 22 | |
| 26 | A Q F W L A F P L C S L Y L I | 22 | |
| 35 | C S L Y L I A V L G N L T I I | 22 | |
| 85 | L A I F W F N S T T I Q F D A | 22 | |
| 123 | F D R Y V A I C H P L R H A T | 22 | |
| 198 | N V V Y G L I V I I S A I G L | 22 | |
| 216 | L I S F S Y L L I L K T V L G | 22 | |
| 218 | S F S Y L L I L K T V L G L T | 22 | |
| 251 | F I F Y V P F I G L S M V H R | 22 | |
| 279 | A N I Y L L V P P V L N P I V | 22 | |
| 20 | L P G L E E A Q F W L A F P L | 20 | |
| 31 | A F P L C S L Y L I A V L G N | 20 | |
| 34 | L C S L Y L I A V L G N L T I | 20 | |
| 36 | S L Y L I A V L G N L T I I Y | 20 | |
| 40 | I A V L G N L T I I Y I V R T | 20 | |
| 43 | L G N L T I I Y I V R T E H S | 20 | |
| 45 | N L T I I Y I V R T E H S L H | 20 | |
| 49 | I Y I V R T E H S L H E P M Y | 20 | |
| 59 | H E P M Y I F L C M L S G I D | 20 | |
| 63 | Y I F L C M L S G I D I L I S | 20 | |
| 66 | L C M L S G I D I L I S T S S | 20 | |
| 72 | I D I L I S T S S M P K M L A | 20 | |
| 81 | M P K M L A I F W F N S T T I | 20 | |
| 82 | P K M L A I F W F N S T T I Q | 20 | |
| 92 | S T T I Q F D A C L L Q I F A | 20 | |
| 98 | D A C L L Q I F A I H S L S G | 20 | |
| 99 | A C L L Q I F A I H S L S G M | 20 | |
| 101 | L L Q I F A I H S L S G M E S | 20 | |
| 104 | I F A I H S L S G M E S T V L | 20 | |
| 107 | I H S L S G M E S T V L L A M | 20 | |
| 116 | T V L L A M A F D R Y V A I C | 20 | |
| 118 | L L A M A F D R Y V A I C H P | 20 | |
| 126 | Y V A I C H P L R H A T V L T | 20 | |
| 130 | C H P L R H A T V L T L P R V | 20 | |
| 138 | V L T L P R V T K I G V A A V | 20 | |
| 141 | L P R V T K I G V A A V V R G | 20 | |
| 156 | A A L M A P L P V F I K Q L P | 20 | |
| 163 | P V F I K Q L P F C R S N I L | 20 | |
| 166 | I K Q L P F C R S N I L S H S | 20 | |
| 180 | S Y C L H Q D V M K L A C D D | 20 | |
| 184 | H Q D V M K L A C D D I R V N | 20 | |
| 187 | V M K L A C D D I R V N V V Y | 20 | |

TABLE XLVIII-continued

| 101P3A11-V1-DR1-0401 15-mers | | | | | | | | | | | | | | | | |
|---|---|---|---|---|---|---|---|---|---|---|---|---|---|---|---|---|
| Pos | 1 | 2 | 3 | 4 | 5 | 6 | 7 | 8 | 9 | 0 | 1 | 2 | 3 | 4 | 5 | score |
| 194 | D | I | R | V | N | V | V | Y | G | L | I | V | I | I | S | 20 |
| 197 | V | N | V | V | Y | G | L | I | V | I | I | S | A | I | G | 20 |
| 200 | V | Y | G | L | I | V | I | I | S | A | I | G | L | D | S | 20 |
| 201 | Y | S | L | I | V | I | I | S | A | I | G | L | D | S | L | 20 |
| 203 | L | I | V | I | I | S | A | I | G | L | D | S | L | L | I | 20 |
| 204 | I | V | I | I | S | A | I | G | L | D | S | L | L | I | S | 20 |
| 207 | I | S | A | I | G | L | D | S | L | L | I | S | F | S | Y | 20 |
| 209 | A | I | G | L | D | S | L | L | I | S | F | S | Y | L | L | 20 |
| 212 | L | D | S | L | L | I | S | F | S | Y | L | L | I | L | K | 20 |
| 213 | D | S | L | L | I | S | F | S | Y | L | L | I | L | K | T | 20 |
| 219 | F | S | Y | L | L | I | L | K | T | V | L | G | L | T | R | 20 |
| 241 | G | t | C | V | S | H | V | C | A | V | F | I | F | Y | V | 20 |
| 244 | V | S | H | V | C | A | V | F | I | F | Y | V | P | F | I | 20 |
| 247 | V | C | A | V | F | I | F | Y | V | P | F | I | G | L | S | 20 |
| 249 | A | V | F | I | F | Y | V | P | F | I | G | L | S | M | V | 20 |
| 252 | I | F | Y | V | P | F | I | G | L | S | M | V | H | R | F | 20 |
| 273 | P | L | P | V | I | L | A | N | I | Y | L | L | V | P | P | 20 |
| 278 | L | A | N | I | Y | L | L | V | P | P | V | L | N | P | I | 20 |
| 286 | P | P | V | L | N | P | I | V | Y | G | V | K | T | K | E | 20 |
| 19 | G | L | P | G | L | E | E | A | Q | F | W | L | A | F | P | 18 |
| 28 | F | W | L | A | F | P | L | C | S | L | Y | L | I | A | V | 18 |
| 70 | S | G | I | D | I | L | I | S | T | S | S | M | P | K | M | 18 |
| 95 | I | Q | F | D | A | C | L | L | Q | I | F | A | I | H | S | 18 |
| 100 | C | L | L | Q | I | F | A | I | H | S | L | S | G | M | E | 18 |
| 108 | H | S | L | S | G | M | E | S | T | V | L | L | A | M | A | 18 |
| 117 | V | L | L | A | M | A | F | D | R | Y | V | A | I | C | H | 18 |
| 127 | V | A | I | C | H | P | L | R | H | A | T | V | L | T | L | 18 |
| 165 | F | I | K | Q | L | P | F | C | R | S | N | I | L | S | H | 18 |
| 177 | L | S | H | S | Y | C | L | H | Q | D | V | M | K | L | A | 18 |
| 188 | M | K | L | A | C | D | D | I | R | V | N | V | V | Y | G | 18 |
| 206 | I | I | S | A | I | G | L | D | S | L | L | I | S | F | S | 18 |
| 234 | E | A | Q | A | K | A | F | G | T | C | V | S | H | V | C | 18 |
| 238 | K | A | F | G | T | C | V | S | H | V | C | A | V | F | I | 18 |
| 272 | S | P | L | P | V | I | L | A | N | I | Y | L | L | V | P | 18 |
| 294 | Y | G | V | K | T | K | E | I | R | Q | R | I | L | R | L | 18 |
| 295 | G | V | K | T | K | E | I | R | Q | R | I | L | R | L | F | 18 |
| 11 | S | A | T | Y | F | I | L | I | G | L | P | G | L | E | E | 16 |
| 29 | W | L | A | F | P | L | C | S | L | Y | L | I | A | V | L | 16 |
| 60 | E | P | M | Y | I | F | L | C | M | L | S | G | I | D | I | 16 |
| 62 | M | Y | I | F | L | C | M | L | S | G | I | D | I | L | I | 16 |
| 86 | A | I | F | W | F | N | S | T | T | I | Q | F | D | A | C | 16 |
| 102 | L | Q | I | F | A | I | H | S | L | S | G | M | E | S | T | 16 |
| 178 | S | H | S | Y | C | L | H | Q | D | V | M | K | L | A | C | 16 |
| 237 | A | K | A | F | G | T | C | V | S | H | V | C | A | V | F | 16 |
| 250 | V | F | I | F | Y | V | P | F | I | G | L | S | M | V | H | 16 |
| 254 | Y | V | P | F | I | G | L | S | M | V | H | R | F | S | K | 16 |
| 14 | Y | F | I | L | I | G | L | P | G | L | E | E | A | Q | F | 14 |
| 15 | F | I | L | I | G | L | P | G | L | E | E | A | Q | F | W | 14 |
| 17 | L | I | G | L | P | G | L | E | E | A | Q | F | W | L | A | 14 |
| 39 | L | I | A | V | L | S | N | L | T | I | I | Y | I | V | R | 14 |
| 48 | I | I | Y | I | V | R | T | E | H | S | L | H | E | P | M | 14 |
| 55 | E | H | S | L | H | E | P | M | Y | I | F | L | C | M | L | 14 |
| 61 | P | M | Y | I | F | L | C | M | L | S | G | I | D | I | L | 14 |
| 65 | F | L | C | M | L | S | G | I | D | I | L | I | S | T | S | 14 |
| 71 | G | I | D | I | L | I | S | T | S | S | M | P | K | M | L | 14 |
| 73 | D | I | L | I | S | T | S | S | M | P | K | M | L | A | I | 14 |
| 110 | L | S | S | M | E | S | T | V | L | L | A | M | A | F | D | 14 |
| 114 | E | S | T | V | L | L | A | M | A | F | D | R | Y | V | A | 14 |
| 136 | A | T | V | L | T | L | P | R | V | T | K | I | G | V | A | 14 |
| 144 | V | T | K | I | G | V | A | A | V | V | R | G | A | A | L | 14 |
| 149 | V | A | A | V | V | R | G | A | A | L | M | A | P | L | P | 14 |
| 150 | A | A | V | V | R | G | A | A | L | M | A | P | L | P | V | 14 |
| 155 | G | A | A | L | M | A | P | L | P | V | F | I | K | Q | L | 14 |
| 159 | M | A | P | L | P | V | F | I | K | Q | L | P | F | C | R | 14 |
| 174 | S | N | I | L | S | H | S | Y | C | L | H | Q | D | V | M | 14 |
| 185 | Q | D | V | M | K | L | A | C | D | D | I | R | V | N | V | 14 |
| 192 | C | D | D | I | R | V | N | V | V | Y | G | L | I | V | I | 14 |
| 196 | R | V | N | V | V | Y | G | L | I | V | I | I | S | A | I | 14 |
| 214 | S | L | L | I | S | F | S | Y | L | L | I | L | K | T | V | 14 |
| 221 | Y | L | L | I | L | K | I | V | L | G | L | T | R | E | A | 14 |
| 222 | L | L | I | L | K | I | V | L | G | L | T | R | E | A | Q | 14 |
| 226 | K | T | V | L | G | L | T | R | E | A | Q | A | K | A | F | 14 |
| 260 | L | S | M | V | H | R | F | S | K | R | R | D | S | P | L | 14 |
| 271 | D | S | P | L | P | V | I | L | A | N | I | Y | L | L | V | 14 |
| 274 | L | P | V | I | L | A | N | I | Y | L | L | V | P | P | V | 14 |

TABLE XLVIII-continued

101P3A11-V1-DR1-0401 15-mers

| Pos | 1 | 2 | 3 | 4 | 5 | 6 | 7 | 8 | 9 | 0 | 1 | 2 | 3 | 4 | 5 | score |
|---|---|---|---|---|---|---|---|---|---|---|---|---|---|---|---|---|
| 275 | P | V | I | L | A | N | I | Y | L | L | V | P | P | V | L | 14 |
| 281 | I | Y | L | L | V | P | P | V | L | N | P | I | V | Y | G | 14 |
| 285 | V | P | P | V | L | N | P | I | V | Y | G | V | K | T | K | 14 |
| 303 | Q | R | I | L | R | L | F | H | V | A | T | H | A | S | E | 14 |
| 2 | M | V | D | P | N | G | N | E | S | S | A | T | Y | F | I | 12 |
| 3 | V | D | P | N | G | N | E | S | S | A | T | Y | F | I | L | 12 |
| 5 | P | N | G | N | E | S | S | A | T | Y | F | I | L | I | G | 12 |
| 6 | N | G | N | E | S | S | A | T | Y | F | I | L | I | G | L | 12 |
| 9 | E | S | S | A | T | Y | F | I | L | I | G | L | P | G | L | 12 |
| 51 | I | V | R | T | E | H | S | L | H | E | P | M | Y | I | F | 12 |
| 58 | L | H | E | P | M | Y | I | F | L | C | M | L | S | G | I | 12 |
| 67 | C | M | L | S | G | I | D | I | L | I | S | T | S | S | M | 12 |
| 68 | M | L | S | G | I | D | I | L | I | S | T | S | S | M | P | 12 |
| 80 | S | M | P | K | M | L | A | I | F | W | F | N | S | T | T | 12 |
| 83 | K | M | L | A | I | F | W | F | N | S | T | T | I | Q | F | 12 |
| 88 | F | W | F | N | S | T | T | I | Q | F | D | A | C | L | L | 12 |
| 91 | N | S | T | T | I | Q | F | D | A | C | L | L | Q | I | F | 12 |
| 93 | T | T | I | Q | F | D | A | C | L | L | Q | I | F | A | I | 12 |
| 96 | Q | F | D | A | C | L | L | Q | I | F | A | I | H | S | L | 12 |
| 111 | S | G | M | E | S | T | V | L | L | A | M | A | F | D | R | 12 |
| 122 | A | F | D | R | Y | V | A | I | C | H | P | L | R | H | A | 12 |
| 129 | I | C | H | P | L | R | H | A | T | V | L | T | L | P | R | 12 |
| 132 | P | L | R | H | A | T | V | L | T | L | P | R | V | T | K | 12 |
| 133 | L | R | H | A | T | V | L | T | L | P | R | V | T | K | I | 12 |
| 145 | T | K | I | G | V | A | A | V | V | R | G | A | A | L | M | 12 |
| 147 | I | G | V | A | A | V | V | R | G | A | A | L | M | A | P | 12 |
| 151 | A | V | V | R | G | A | A | L | M | A | P | L | P | V | F | 12 |
| 158 | L | M | A | P | L | P | V | F | I | K | Q | L | P | F | C | 12 |
| 160 | A | P | L | P | V | F | I | K | Q | L | P | F | C | R | S | 12 |
| 170 | P | F | C | R | S | N | I | L | S | H | S | Y | C | L | H | 12 |
| 171 | F | C | R | S | N | I | L | S | H | S | Y | C | L | H | Q | 12 |
| 172 | C | R | S | N | I | L | S | H | S | Y | C | L | H | Q | D | 12 |
| 176 | I | L | S | H | S | Y | C | L | H | Q | D | V | M | K | L | 12 |
| 189 | K | L | A | C | D | D | I | R | V | N | V | V | Y | G | L | 12 |
| 193 | D | D | I | R | V | N | V | V | Y | G | L | I | V | I | I | 12 |
| 199 | V | V | Y | G | L | I | V | I | I | S | A | I | G | L | D | 12 |
| 210 | I | G | L | D | S | L | L | I | S | F | S | Y | L | L | I | 12 |
| 211 | G | L | D | S | L | L | I | S | F | S | Y | L | L | I | L | 12 |
| 217 | I | S | F | S | Y | L | L | I | L | K | T | V | L | G | L | 12 |
| 224 | I | L | K | T | V | L | G | L | T | R | E | A | Q | A | K | 12 |
| 231 | L | T | R | E | A | Q | A | K | A | F | G | T | C | V | S | 12 |
| 233 | R | E | A | Q | A | K | A | F | G | T | C | V | S | H | V | 12 |
| 256 | P | F | I | G | L | S | M | V | H | R | F | S | K | R | R | 12 |
| 261 | S | M | V | H | R | F | S | K | R | R | D | S | P | L | P | 12 |
| 265 | R | F | S | K | R | R | D | S | P | L | P | V | I | L | A | 12 |
| 268 | K | R | R | D | S | P | L | P | V | I | L | A | N | I | Y | 12 |
| 270 | R | D | S | P | L | P | V | I | L | A | N | I | Y | L | L | 12 |
| 277 | I | L | A | N | I | Y | L | L | V | P | P | V | L | N | P | 12 |
| 287 | P | V | L | N | P | I | V | Y | G | V | K | T | K | E | I | 12 |
| 299 | K | E | I | R | Q | R | I | L | R | L | F | H | V | A | T | 12 |
| 300 | E | I | R | Q | R | I | L | R | L | F | H | V | A | T | H | 12 |

TABLE XLVIII

101P3A11-V2-DRB 0401 15-mers

| Pos | 1 | 2 | 3 | 4 | 5 | 6 | 7 | 8 | 9 | 0 | 1 | 2 | 3 | 4 | 5 | score | |
|---|---|---|---|---|---|---|---|---|---|---|---|---|---|---|---|---|---|
| 29 | S | I | C | W | F | L | L | C | S | T | Q | L | S | M | E | 28 | Portion of SEQ ID NO: 30; each start position is specified-the length of each peptide is 15 amino acids, the end position for each peptide is the start position plus fourteen |
| 8 | L | Y | L | I | A | V | L | A | S | G | V | T | L | R | C | 26 | |
| 2 | A | F | P | L | C | S | L | Y | L | I | A | V | L | A | S | 20 | |
| 5 | L | C | S | L | Y | L | I | A | V | L | A | S | G | V | T | 20 | |
| 7 | S | L | Y | L | I | A | V | L | A | S | G | V | T | L | R | 20 | |
| 17 | G | V | T | L | R | C | P | S | S | W | P | I | S | I | C | 20 | |
| 27 | P | I | S | I | C | W | F | L | L | C | S | T | Q | L | S | 20 | |
| 6 | C | S | L | Y | L | I | A | V | L | A | S | G | V | T | L | 16 | |
| 23 | P | S | S | W | P | I | S | I | C | W | F | L | L | C | S | 16 | |
| 11 | I | A | V | L | A | S | G | V | T | L | R | C | P | S | S | 14 | |

TABLE XLVIII

101P3A11-V3-DRB 0401 15-mers

| Pos | 1 2 3 4 5 6 7 8 9 0 1 2 3 4 5 | score | |
|---|---|---|---|
| 3 | S T T I Q F D A C L L Q M F A | 20 | Portion of SEQ ID NO: 32; each start position is specified-the length of each peptide is 15 amino acids, the end position for each peptide is the start position plus fourteen |
| 10 | A C L L Q M F A I H S L S G M | 20 | |
| 12 | L L Q M F A I H S L S G M E S | 20 | |
| 15 | M F A I H S L S G M E S T V L | 20 | |
| 6 | I Q F D A C L L Q M F A I H S | 18 | |
| 11 | C L L Q M F A I H S L S G M E | 18 | |
| 13 | L Q M F A I H S L S G M E S T | 16 | |
| 9 | D A C L L Q M F A I H S L S G | 14 | |
| 2 | N S T T I Q F D A C L L Q M F | 12 | |
| 4 | T T I Q F D A C L L Q M F A I | 12 | |
| 7 | Q F D A C L L Q M F A I H S L | 12 | |
| 5 | T I Q F D A C L L Q M F A I H | 10 | |

TABLE XLIX

101P3A11-V1-DRB1-1101 15-mers

| Pos | 1 2 3 4 5 6 7 8 9 0 1 2 3 4 5 | score | SEQ ID |
|---|---|---|---|
| 146 | K I G V A A V V R G A A L M A | 28 | Portion of SEQ ID NO: 28; each start position is specified-the length of each peptide is 15 amino acids, the end position for each peptide is the start position plus fourteen |
| 123 | F D R Y V A I C H P L R H A T | 25 | |
| 218 | S F S Y L L I L K T V L G L T | 25 | |
| 198 | N V V Y G L I V I I S A I G L | 24 | |
| 11 | S A T Y F I L I G L P G L E E | 23 | |
| 256 | P F I G L S M V H R F S K R R | 23 | |
| 45 | N L T I I Y I V R T E H S L H | 22 | |
| 60 | E P M Y I F L C M L S G I D I | 22 | |
| 159 | M A P L P V F I K Q L P F C R | 22 | |
| 238 | K A F G T C V S H V C A V F I | 22 | |
| 75 | L I S T S S M P K M L A I F W | 21 | |
| 135 | H A T V L T L P R V T K I G V | 20 | |
| 138 | V L T L P R V T K I G V A A V | 20 | |
| 163 | P V F I K Q L P F C R S N I L | 20 | |
| 200 | V Y G L I V I I S A I G L D S | 20 | |
| 225 | L K T V L G L T R E A Q A K A | 20 | |
| 257 | F I G L S M V H R F S K R R D | 20 | |
| 291 | P I V Y G V K T K E I R Q R I | 20 | |
| 302 | R Q R I L R L F H V A T H A S | 20 | |
| 66 | L C M L S G I D I L I S T S S | 19 | |
| 101 | L L Q I F A I H S L S G M E S | 19 | |
| 197 | V N V V Y G L I V I I S A I G | 19 | |
| 219 | F S Y L L I L K T V L G L T R | 19 | |
| 248 | C A V F I F Y V P F I G L S M | 19 | |
| 275 | P V I L A N I Y L L V P P V L | 19 | |
| 46 | L T I I Y I V R T E H S L H E | 18 | |
| 69 | L S G I D I L I S T S S M P K | 18 | |
| 81 | M P K M L A I F W F N S T T I | 18 | |
| 98 | D A C L L Q I F A I H S L S G | 18 | |
| 104 | I F A I H S L S G M E S T V L | 18 | |
| 209 | A I G L D S L L I S F S Y L L | 18 | |
| 250 | V F I F Y V P F I G L S M V H | 18 | |
| 62 | M Y I F L C M L S G I D I L I | 17 | |
| 216 | L I S F S Y L L I L K T V L G | 17 | |
| 260 | L S M V H R F S K R R D S P L | 17 | |
| 279 | A N I Y L L V P P V L N P I V | 17 | |
| 289 | L N P I V Y G V K T K E I R Q | 17 | |
| 12 | A T Y F I L I G L P G L E E A | 16 | |
| 25 | E A Q F W L A F P L C S L Y L | 16 | |
| 43 | L G N L T I I Y I V R T E H S | 16 | |
| 254 | Y V P F I G L S M V H R F S K | 16 | |
| 48 | I I Y I V R T E H S L H E P M | 15 | |
| 100 | C L L Q I F A I H S L S G M E | 15 | |
| 117 | V L L A M A F D R Y V A I C H | 15 | |
| 144 | V T K I G V A A V V R G A A L | 15 | |
| 180 | S Y C L H Q D V M K L A C D D | 15 | |
| 228 | V L G L T R E A Q A K A F G T | 15 | |
| 261 | S M V H R F S K R R D S P L P | 15 | |
| 262 | M V H R F S K R R D S P L P V | 15 | |
| 278 | L A N I Y L L V P P V L N P I | 15 | |
| 286 | P P V L N P I V Y G V K T K E | 15 | |
| 115 | S T V L L A M A F D R Y V A I | 14 | |
| 126 | Y V A I C H P L R H A T V L T | 14 | |

TABLE XLIX-continued

101P3A11-V1-DRB1-1101 15-mers

| Pos | 1 | 2 | 3 | 4 | 5 | 6 | 7 | 8 | 9 | 0 | 1 | 2 | 3 | 4 | 5 | score | SEQ ID |
|---|---|---|---|---|---|---|---|---|---|---|---|---|---|---|---|---|---|
| 127 | V | A | I | C | H | P | L | R | H | A | T | V | L | T | L | 14 | |
| 141 | L | P | R | V | T | K | I | G | V | A | A | V | V | R | G | 14 | |
| 171 | F | C | R | S | N | I | L | S | H | S | Y | C | L | H | Q | 14 | |
| 181 | Y | C | L | H | Q | D | V | M | K | L | A | C | D | D | I | 14 | |
| 194 | D | I | R | V | N | V | V | Y | G | L | I | V | I | I | S | 14 | |
| 230 | G | L | T | R | E | A | Q | A | K | A | F | G | T | C | V | 14 | |
| 271 | D | S | P | L | P | V | I | L | A | N | I | Y | L | L | V | 14 | |
| 299 | K | E | I | R | Q | R | I | L | R | L | F | H | V | A | T | 14 | |
| 10 | S | S | A | T | Y | F | I | L | I | G | L | P | G | L | E | 13 | |
| 20 | L | P | G | L | E | E | A | Q | F | W | L | A | F | P | L | 13 | |
| 33 | P | L | C | S | L | Y | L | I | A | V | L | G | N | L | T | 13 | |
| 36 | S | L | Y | L | I | A | V | L | G | N | L | T | I | I | Y | 13 | |
| 37 | L | Y | L | I | A | V | L | G | N | L | I | I | I | Y | I | 13 | |
| 59 | H | E | P | M | Y | I | F | L | C | M | L | S | G | I | D | 13 | |
| 107 | I | H | S | L | S | G | M | E | S | T | V | L | L | A | M | 13 | |
| 152 | V | V | R | G | A | A | L | M | A | P | L | P | V | F | I | 13 | |
| 156 | A | A | L | M | A | P | L | P | V | F | I | K | Q | L | P | 13 | |
| 207 | I | S | A | I | G | L | D | S | L | L | I | S | F | S | Y | 13 | |
| 237 | A | K | A | F | G | T | C | V | S | H | V | C | A | V | F | 13 | |
| 249 | A | V | F | I | F | Y | V | P | F | I | G | L | S | M | V | 13 | |
| 268 | K | R | R | D | S | P | L | P | V | I | L | A | N | I | Y | 13 | |
| 280 | N | I | Y | L | L | V | P | P | V | L | N | P | I | V | Y | 13 | |
| 282 | Y | L | L | V | P | P | V | L | N | P | I | V | Y | G | V | 13 | |

TABLE XLIX

101P3A11-V2-DRB 1101 15-mers

| Pos | 1 | 2 | 3 | 4 | 5 | 6 | 7 | 8 | 9 | 0 | 1 | 2 | 3 | 4 | 5 | score | SEQ ID |
|---|---|---|---|---|---|---|---|---|---|---|---|---|---|---|---|---|---|
| 5 | L | C | S | L | Y | L | I | A | V | L | A | S | G | V | T | 18 | Portion of SEQ ID NO: |
| 6 | C | S | L | Y | L | I | A | V | L | A | S | G | V | T | L | 18 | 30; each start |
| 29 | S | I | C | W | F | L | L | C | S | T | Q | L | S | M | E | 17 | position is |
| 13 | V | L | A | S | G | V | T | L | R | C | P | S | S | W | P | 15 | specified-the length |
| 8 | L | Y | L | I | A | V | L | A | S | G | V | T | L | R | C | 14 | of each peptide is 15 |
| 4 | P | L | C | S | L | Y | L | I | A | V | L | A | S | G | V | 13 | amino acids, the end |
| 12 | A | V | L | A | S | G | V | T | L | R | C | P | S | S | W | 13 | position for each |
| 2 | A | F | P | L | C | S | L | Y | L | I | A | V | L | A | S | 12 | peptide is the start |
| 7 | S | L | Y | L | I | A | V | L | A | S | G | V | T | L | R | 12 | position plus |
| 14 | L | A | S | G | V | T | L | R | C | P | S | S | W | P | I | 12 | fourteen |
| 11 | I | A | V | L | A | S | G | V | T | L | R | C | P | S | S | 10 | |
| 23 | P | S | S | W | P | I | S | I | C | W | F | L | L | C | S | 10 | |
| 15 | A | S | G | V | T | L | R | C | P | S | S | W | P | I | S | 8 | |

TABLE XLIX

101P3A11-V3-DRB 1101 15-mers

| Pos | 1 | 2 | 3 | 4 | 5 | 6 | 7 | 8 | 9 | 0 | 1 | 2 | 3 | 4 | 5 | score | SEQ ID |
|---|---|---|---|---|---|---|---|---|---|---|---|---|---|---|---|---|---|
| 12 | L | L | Q | M | F | A | I | H | S | L | S | G | M | E | S | 19 | Portion of SEQ ID NO: |
| 9 | D | A | C | L | L | Q | M | F | A | I | H | S | L | S | G | 18 | 30; each start |
| 15 | M | F | A | I | H | S | L | S | G | M | E | S | T | V | L | 18 | position is |
| 11 | C | L | L | Q | M | F | A | I | H | S | L | S | G | M | E | 15 | specified-the length |

TABLE XLIX-continued

| 101P3A11-V3-DRB 1101 15-mers | | | |
|---|---|---|---|
| Pos | 1 2 3 4 5 6 7 8 9 0 1 2 3 4 5 | score | SEQ ID |
| 6 | I Q F D A C L L Q M F A I H S | 12 | of each peptide is 15 |
| 5 | T I Q F D A C L L Q M F A I H | 10 | amino acids, the end |
| 13 | L Q M F A I H S L S G M E S T | 10 | position for each peptide is the start position plus fourteen |

TABLE LIV

Nucleotide sequence in the 5' region close to 101P3A11 gene (SEQ ID NO: 1)

| | |
|---|---|
| 1 | TGCGCTCCAC CAAGCCTGGC TAACTTTTGC ATTTTTAATA GAGGCAGGGT TTCACCATGT |
| 61 | TGGCCTGGCT GGTCTCGAAC CCCTGACCTT GCGATCTGCC CACCTCGGCC TCCCAAAGTG |
| 121 | CTGGGATTAC AGGCGTGAGC CACTGTACCT GGCGGGGCTT ATTGTTTTTT AAAAAGATTT |
| 181 | CCAAAACCTT GCCCTGGCAA TTCTGATTTT CTGGGCCTGG AGCAGGACCT GGAGGGATGG |
| 241 | TGTTGTCAAT TACTTTAGAT GTTTCTATCA GGAAAGTTTG AGAAATGGTA TTCAGGCCTA |
| 301 | AACACAAACC TCTCTTGAAA TCTCATCCCA GACTGAGCCC CTGCTCCCTA TCTTAAATTA |
| 361 | GATTATAGTA GGTCTTAAAG TCAGCTGTAG ACTGAGCCTC TAAATCTGAA CCCAGACCCA |
| 421 | CCCTAACCCC AGGATACATC AGAAGAGCTG GTCAATGTGG ACCATTCTGA GCAATCCTGC |
| 481 | AAGTCTACTC TGATGGGAAA AGGCTAAGAG CAGTGCCCTG GGCAGCAACA TCAGCTCTGA |
| 541 | AGATGCAGGA CTGTGTTACA TGTTTTATGA GTGGGTCTTC ACACACTGAG ATTCATGGGA |
| 601 | CAGTAATAGA ATCTGCTTGT GCAGCACTGG GGCCTTGGAG GGTCAGGGTA AGGCTCAAGA |
| 661 | TGTCCAGGAA GTTGTATATA AGGAGAATCA GAGCAGAGAG AGACTAGGGT TCAGAATTAC |
| 721 | CAGGATGACT TAGTCCTGTT TGTTACTGTC ACCACTCCAA TGCCTTTTCC TCATTAGTCC |
| 781 | TTTCTCTCCT CTGAGCCACA ACTAAATGAT GTTTCTACTT TTCCCTTTCT ACTTTCCTAG |
| 841 | ACCCTGGATT TTGTATGCAG AAGCCCCAGC TCTTGGTCCC TATCATAGCC ACTTCAAATG |
| 901 | GAAATCTGGT CCACGCAGCA TACTTCCTTT TGGTGGGTAT CCCTGGCCTG GGGCCTACCA |
| 961 | TACACTTTTG GCTGGCTTTC CCACTGTGTT TTATGTATGC CTTGGCCACC CTGGGTAACC |
| 1021 | TGACCATTGT CCTCATCATT CGTGTGGAGA GGCGACTGCA TGAGCCCATG TACCTCTTCC |
| 1081 | TGGCCATGCT TTCCACTATT GACCTAGTCC TCTCCTCTAT CACCATGCCC AAGATGGCCA |

TABLE LIV-continued

Nucleotide sequence in the 5' region close to 101P3A11 gene (SEQ ID NO: 1)

| | |
|---|---|
| 1141 | GTCTTTTCCT GATGGGCATC CAGGAGATCG AGTTCAACAT TTGCCTGGCC CAGATGTTCC |
| 1201 | TTATCCATGC TCTGTCAGCC GTGGAGTCAG CTGTCCTGCT GGCCATGGCT TTTGACCGCT |
| 1261 | TTGTGGCCAT TTGCCACCCA TTGCGCCATG CTTCTGTGCT GACAGGGTGT ACTGTGGCCA |
| 1321 | AGATTGGACT ATCTGCCCTG ACCAGGGGGT TTGTATTCTT CTTCCCACTG CCCTTCATCC |
| 1381 | TCAAGTGGTT GTCCTACTGC CAAACACATA CTGTCACACA CTCCTTCTGT CTGCACCAAG |
| 1441 | ATATTATGAA GCTGTCCTGT ACTGACACCA GGGTCAATGT GGTTTATGGA CTCTTCATCA |
| 1501 | TCCTCTCAGT CATGGGTGTG GACTCTCTCT TCATTGGCTT CTCATATATC CTCATCCTGT |
| 1561 | GGGCTGTTTT GGAGCTGTCC TCTCGGAGGG CAGCACTCAA GGCTTTCAAC ACCTGCATCT |
| 1621 | CCCACCTCTG TGCTGTTCTG GTCTTCTATG TACCCCTCAT TGGGCTCTCG GTGGTGCATA |
| 1681 | GGCTGGGTGG TCCCACCTCC CTCCTCCATG TGGTTATGGC TAATACCTAC TTGCTGCTAC |
| 1741 | CACCTGTAGT CAACCCCCTT GTCTATGGAG CCAAGACCAA AGAGATCTGT TCAAGGGTCC |
| 1801 | TCTGTATGTT CTCACAAGGT GGCAAGTGAG ACACCTTAGT GTCTCGCTTC TACTACTACT |
| 1861 | ACAGAAGATG GGAATATTAG GATCCTATTG AATGCCTTGG TGATTAAAGT ATCAAACCTA |
| 1921 | TTGTGCTGTC TTCTTCCAGC AATTTAAGTA GATCATGTAT TCTGTCTCCA GGAATGTGTC |
| 1981 | AGTACTGAAC TTATGACCCT GTCTGGACAT CCTGGAGAAT GACTGCACTA GTCCCTCTGC |
| 2041 | TATGGTGGTC TTGCCTTCTC CTTCTCTCTC AGCTAGAAAA TACATCTAGT TTTGACATGG |
| 2101 | GGAGGCTGTA AAGATCACAC CTCATGGTTC ATTCCAGTTT TGAAGTATGA TTTTAATGTT |
| 2161 | CTTGCCCCCA TGTGCCCATG TTGGTGAATT TGCATGGACT ATAAACGTTA TTGCAAATAC |
| 2221 | CCTAAAGTGG TTACCCAGCC ATAATCAGGG GTTAATGAAG GTATTTGGGG AATAGTAACT |

TABLE LIV-continued

| Nucleotide sequence in the 5' region close to 101P3A11 gene (SEQ ID NO: 1) |
|---|
| 2281 GGAGAGACAG CAACAAGACA AGAGGCAGCT CACATGCAAT GTTGAAGTTT CTGTATGCAA |
| 2341 GAGGGTGTGT TGGCAGATTT GTGAAATCTG CCCATTTGCA TCTGTATGGC TCTATATGAC |
| 2401 TATTTGTCCA TAAGGGTGCC ATGTATTCTG GTTGTGGGTG TGAATGTGTG GGTGTGTTTA |
| 2461 TGTGGACACT TGCTTTTCAG TGTGCGTATA TGTGAGAGAG AGGGTGCACA CATGGAATAC |
| 2521 GTACTGGTTG TGTCCTGGTG AGTGTGGTAG CTATGTCCTG GCACATGTAT GTTTCATGAG |
| 2581 ACGTGTCTCT GATTGCGCAT TTGTATTTCT GTGGTATCTG TTAGTTGGTA TATGATATGT |
| 2641 GTCTACGTGA GAATGCTGGT GTCTGTATCT GCATGGTGGG CAGTACCTTT ATGTGTATCT |
| 2701 GGTAAGAATG CTGCCTCTAC CTTTTCTTCC TATTTGTACT ATGTGAATGT GGTGCATGAA |
| 2761 TGTGTGGAAT GTGTGGAATG TGTAGTATTG GGATGCCTGT ATCTTTCAGC GTGTTTGGGT |
| 2821 GTATGTCCAC TGTGCATAAT ATTTGAGATG TAAAACCATT TTGTGCGGTA TATGTGTTAT |
| 2881 TAGTTGTAAG TCGGTGAAAT GTACATCTGA ATTCTGTGTG CATATTGTTG GTACTGATGC |
| 2941 TATTTTCGTG CATATGTCTA GTGTATATGT TTTAAGGCAA ACTTTCTTTG TGTGTTGGGT |
| 3001 GTGTATGTGA CACGAATGGG GACAGCATCT GTATTTCTGA GCATGGATTG ATGTGTGGTG |
| 3061 TCTGTATGTA TCTTGGAATG GAGGAGGGAG ATTGAAGAAG TCTGGCTGTG AGCAGCAGAA |
| 3121 ATAATTTCCA AAGTTGAGTG ACATGACTCT AAGATGCCCA GTTTCTCGGC CTGGGGTCAG |
| 3181 CCTGGGTGAT AGCTCAGTCT GTCAGAATGA AAGGAAACAC GGTGCTTCCT TGCTCCACCT |
| 3241 TTTCACAGGC CAGACCACAC CTTCTTCATC CTGAACACAA GGATTTCAAG GGCTTTTGTT |
| 3301 ACCTCTTCCT ACGTTTCCTG CCTCTGCTAT CCGAGGCACT GGCCTCCCTA AACCCTGCCC |
| 3361 TCCTGCCTCA ATAGCAAGTC ATGGTATCCT CACCTCTCCC TTCCCTTTTT GGCTTATCT**G** |
| 3421 **CCAAACATGT ATAAAAGTCC TTGGTTCCCC ATCTCTACTA AAAATACAA**C AATTAGCCGG |
| 3481 GTGTGATGGC GCGTGCCTGT AGTCCCAGCT AGTTGGGAGG CTGAGGCAGG AGAAACGCTT |
| 3541 GAGCCCGCAA GGTGGAGGTT GCAGTGAGCC GAGATCATGC CACTGCACTC CAGCCTGGTG |
| 3601 ACAGAGCAAG ACTCTGTGTC AAAAAAAAAA AAAAAAAAAA AGCCTTGGTT GTAGGGAGTT |
| 3661 TCTCCTAATC CCTCTGGGAA AGCAAGGGTG GAGGGGAAGC CAGTCAATCT CCCTTCTGTT |
| 3721 GCCGCATGGA AACTCCCTTA AGGCAGGAAG CTGAAAAAAC TGTAGCATTC ACCTCATTAT |
| 3781 TCACCTTGTC TCATGTCTCA CTGTCCTTCC ACATGTCTCA TTGTTACTCC ATATTGGATG |
| 3841 GAAGTAGAAG TCCCTTTGGT ATTTTTTAAA GTCTTTGCCA TGTCTAAGTT AATGAGGTTA |
| 3901 ATGGAGGCAG CAGAGATGGC TCCAGGGTTC TGATAGCAAG TGTCAGGCTG CGTGCTCTGT |
| 3961 AGGCACCAGA AACTGTTGTC ACCAGTAATT TTGATGTGGT CTGAGTTAGA ATGGTCTGAT |
| 4021 TTGCCATGAT CTATTTAACA TAGCTTGATT TAGCGTGTCC TGTGTTCTGA ATTTAAAACT |
| 4081 CACAGTTGTG AA**ACTGATCA GTAAAAAATA AGGGGAGACC AACTAAAAAC CATGTTGTTC** |
| 4141 **TA**TTTATAGA TGTAGTTTTT ACTTATTTCA AAATACGAGG TATTTAGTTT TACATTCAAA |
| 4201 TTGTTCTCTA ACTCTCTAAA ATGTTCTCTG ACTATTTTTG CCCTTAAGGG AGAAACCAGA |
| 4261 TGTCATTGGT CTTACGTGGC TGGTGTTGGG GGTGGGGAGG GTTAAAGAAA CCACGTTCTC |
| 4321 TGTCCTCAGC CAGAAGTTCA GTAATCCAAG GCCAGAGAGT GGACGGCAGA GGCACTGTCC |
| 4381 CTGGGGACCT TGGTTATAAG TTATCCAGAC ACAGGGACCA GAGCCTGGGA GACAAAAAAA |
| 4441 GATGTAGCCC TAGGGCTTTG GGAAAAGGAG GATGGACCCA GTGAATTCCA CGCTTAGCAA |
| 4501 GGACCTAAAC AGTGTCCCCC AAATGAGAGA AGGGAGGACA GAAAGAACAC TTCAGGATGG |
| 4561 AAATGGGCTG ACACTTAACC GTGGAGTGTC TCTGCAAACT TCCTTTGCCA TTCTCCTGTT |
| 4621 TGAGTTTGAT AAACCTGAGA AGAGACTTGG ATAAAGACCG TCACGAAGAC TACACTAATG |
| 4681 AGTTTCTTCT AGCTTTTTTC TACTCACTTT CCCTATCTAT CCTTCACATT GGGAGTTGGC |
| 4741 ATGAGGATCC CAGCAGCCCA TCAGGGGAGG ACTCTAGAGA TCCCTTTCCC CATTGCCTCT |
| 4801 CCTCCCCATA CCCCCAGGCA TATCCTCCCA GGGCACGGAA GCTGAGAAGC AGTCCAGAAC |
| 4861 CACAGTGGGC TAGTGAGGGG TACCTGCTGA TGTACCCTTT GGACAGCATT CTGCCCCACC |
| 4921 CTGCAGGAAG AAGCAGAAGG AGGGAGAGGG TG**AGGCAGAG AATAAATAAC CCTGACCAGG** |
| 4981 **GAGGTCCAAG GGAGTAGGCG GAG**Acagaga ggctgtattt cagtgcagcc tgccagacct |

Note:
The three high score predictions of promoters were bold and underlined. The lower case sequence indicates the beginning part of the transcript of 101P3A11 gene.

TABLE LV

| Start | End | Score | SEQ ID NO: | Promoter Sequence |
|---|---|---|---|---|
| 25 | 75 | 0.91 | 2 | TTTTGCATTTTTAATAGAGGCAGGGTTTC ACCATGTTGGCCTGGCTGGTC |
| 665 | 715 | 0.95 | 3 | CAGGAAGTTGTATATAAGGAGAATCAGAG CAGAGAGAGACTAGGGTTCAG |
| 2477 | 2527 | 0.91 | 4 | TCAGTGTGCGTATATGTGAGAGAGAGGGT GCACACATGGAATACGTACTG |
| 3139 | 3189 | 0.82 | 5 | TGACATGACTCTAAGATGCCCAGTTTCTC GGCCTGGGGTCAGCCTGGGTG |

Promoters and their positions predicted by Neural Network Promoter Prediction computer program.

TABLE LV-continued

Promoters and their positions predicted by Neural Network Promoter Prediction computer program.

| Start | End | Score | SEQ ID NO: | Promoter Sequence |
|---|---|---|---|---|
| 3420 | 3470 | 0.96 | 6 | GCCAAACATGTATAAAAGTCCTTGGTTCC CCATCTCTACTAAAAATACAA |
| 4092 | 4142 | 0.99 | 7 | AACTGATCAGTAAAAAATAAGGGGAGACC AACTAAAAACCATGTTGTTCT |
| 4953 | 5003 | 0.97 | 8 | AGGCAGAGAATAAATAACCCTGACCAGGG AGGTCCAAGGGAGTAGGCGGA |

TABLE LVI

Alignment of five homologous 5' upstream genomic regulatory regions of the human 101P3A11 and PSA genes.

Query: 5' upstream regulatory region of the PSA gene)

Subject: Putative 5' upstream regulatory region of the 101P3A11 gene SEQ ID NO: 10)

Nucleic acid sequences predicted to be binding sites for the indicated transcription factors are bolded, <u>underlined</u>, or *italicized*.

1. (SEQ ID NO: 9 and SEQ ID NO: 10)

NF-1 SP-1 NF-1

Query: 3864 ccaggctggagtgcagtggcgcagtctcggctcactgcaacctctgcctcccaggttcaa 3923

||||||||||||||||||      ||||||||||||||||||  |||   |  ||  ||||

Sbjct: 3598 ccaggctggagtgcagtggcatgatctcggctcactgcaacctccaccttgcgggctcaa 3539

Query: 3924 gtgattctcctgcctcagcctcctgagttgctgggattacaggcatgcagcaccatgccc 3983

| |  ||||||||||||||||   |  |  ||||||  |||||||  ||   ||  ||   |||

Sbjct: 3538 gcgtttctcctgcctcagcctcccaactagctgggactacaggcacgcgccatcacaccc 3479

Query: 3984 agctaatttttgtatttttagtagagatgggg 4015

||||||| |||||||||||||||||||||

Sbjct: 3478 ggctaattgttgtatttttagtagagatgggg 3447

2. (SEQ ID NO: 11 and SEQ ID NO: 12)

Query: 4670 cctgtaatcccagctactgaggaggctgaggcaggagaatcacttgaacccagaaggcag 4729

|||||| ||||||||  |   |||||||||||||||||  |  |||||  |||    ||||    |

Sbjct: 3496 cctgtagtcccagctagttgggaggctgaggcaggagaaacgcttgagcccgcaaggtgg 3555

*SP1* NF-E

NF-1 NF-1 GR GR

Query: 4730 aggttgcaatgagccgagattgcgcca*ctgcac*tccagcctgggt<u>gacag</u>agtgagactc 4789

||||||| ||||||||||     ||||||||||||||||  |||||||||     |||||

Sbjct: 3556 aggttgcagtgagccgagatcatgcca*ctgcac*tccagcct-ggt<u>gacag</u>agcaagactc 3614

Query: 4790 tgtctcaaaaaaaaaaaa 4807

||| |||||||||||||

Sbjct: 3615 tgtgtcaaaaaaaaaaaa 3632

3. (SEQ ID NO: 13 and SEQ ID NO: 14)

GR NF-1 SP1

Query: 142 tgagactgagtctcgctctgtgcccaggctggagtgcagtggtgcaaccttggctcactg 201

||| ||  ||||||  |||||||   |||||||||||||||||      |  ||  |||||||||

Sbjct: 3621 tgacacagagtcttgctctgtcaccaggctggagtgcagtggcatgatctcggctcactg 3562

Query: 202 caagctccgcctcctgggttcacgccattctcctgcctcagcctcctgagtagctgggac 261

||| |||| |||      ||| |||  ||    ||||||||||||||||     |  |||||||||

Sbjct: 3561 caacctccaccttgcgggctcaagcgtttctcctgcctcagcctcccaactagctgggac 3502

NF-1

Query: 262 tacaggcacccgccaccacgcctggctaannnnnnngtatttttagtagagatgggg 318

|||||||| ||||| |||  ||  |||||          ||||||||||||||||||

Sbjct: 3501 tacaggcacgcgccatcacacccggctaa--ttgttgtatttttagtagagatgggg 3447

TABLE LVI-continued

Alignment of five homologous 5' upstream genomic regulatory regions of the human 101P3A11 and PSA genes.

```
4. (SEQ ID NO: 15 and SEQ ID NO: 16)
Query:   300 atttttagtagagatggggtttcactgtgttagccaggatggtctcagtctcctgacctc   359
             ||||||| |||||   |||||||||  |||| ||| || |||||||   | ||||||||
Sbjct:    31 atttttaatagaggcagggtttcaccatgttggcctggctggtctcgaacccctgacctt    90

                     SP1                                        NF-1
                   LF-A1                                    CP2
Query:   360 gtgatctgcccaccttggcctcccaaagtgctgggattacaggcgtgagccactgcgcct   419
             | ||||||||||| ||||||||||||||||||||||||||||||||||||   |||
Sbjct:    91 gcgatctgcccacctcggcctcccaaagtgctgggattacaggcgtgagccactgtacct   150

             NF-1
Query:   420 ggc                                                            422
             |||
Sbjct:   151 ggc                                                            153

5. (SEQ ID NO: 17 and SEQ ID NO: 18)
                         NF-1
              NF-1      CP2
Query:  4506 gccaggcacagtggctcacgcctgtaatcccaacaccatgggaggctgagatgggtggat  4565
             |||||| |||||||||||||||||||||| |||   |||||||| ||| ||||   |||
Sbjct:   153 gccaggtacagtggctcacgcctgtaatcccagcactttgggaggccgaggtgggcagat    94

Query:  4566 cacgaggtcaggagtttgagaccagcctgaccaacatggtgaaactctgtctcta       4620
             | | ||||||| ||| ||||||||| | |||||||||||||| ||| |||||
Sbjct:    93 cgcaaggtcaggggttcgagaccagccaggccaacatggtgaaaccctgcctcta         39
```

TABLE LVII (SEQ ID NO: 19)
>101P3A11 v.1 aa 1-318: for 9-mers, 10-mers, 15-mers
MMVDPNGNES SATYFILIGL PGLEEAQFWL APPLCSLYLI
AVLGNLTIIY IVRTEHSLHE PMYIFLCMLS GIDILISTSS
MPKMLAIFWF NSTTIQFDAC LLQIFAIHSL SGMESTVLLA
MAFDRYVAIC HPLRHATVLT LPRVTKIGVA AVVRGAALMA
PLPVFIKQLP FCRSNILSHS YCLHQDVMKL ACDDIRVNVV
YGLIVIISAI GLDSLLISFS YLLILKTVLG LTREAQAKAF
GTCVSHVCAV FIFYVPFIGL SMVHRFSKRR DSPLPVILAN
IYLLVPPVLN PIVYGVKTKE IRQRILRLFH VATHASEP >101P3A11 v.2
9-mers, aa 36-72 (SEQ ID NO: 20)
SLYLIAVLASGVTLRCPSSWPISICWFLLCSTQLSME TABLE LVII-continued 10-mers, aa 35-72 (SEQ ID NO: 21)
CSLYLIAVLASGVTLRCPSSWPISICWFLLCSTQLSME 15-mers, aa 30-72 (SEQ ID NO: 22)
LAFPLCSLYLIAVLASGVTLRCPSSWPISICWFLLCSTQLSME >101P3A11 v.3
9-mers: aa 96-112 (SEQ ID NO: 23)
QFDACLLQMFAIHSLSG 10-mers: aa 95-113 (SEQ ID NO: 24)
IQFDACLLQMFAIHSLSGM 15-mers, aa 90-118 (SEQ ID NO: 25)
FNSTTIQFDACLLQMFAIHSLSGMESTVL

The invention claimed is:

1. An isolated 101P3A11 (PHOR 1) v.1 protein that comprises the amino acid sequence of SEQ ID NO: 28.

2. The protein of claim 1, which further comprises a label.

3. An isolated 101P3A11 (PHOR 1) v.1 protein that consists of the amino acid sequence of SEQ ID NO: 28.

4. The protein of claim 3, which further comprises a label.

5. An isolated 101P3A11 (PHOR 1) v.1 protein, which is encoded by the cDNA contained in plasmid 101P3A11 deposited with the American Type Culture Collection (ATCC) as Accession No. PTA312.

6. The protein of claim 5, which further comprises a label.

* * * * *

SEQUENCE LISTING

<160> NUMBER OF SEQ ID NOS: 146

<210> SEQ ID NO 1
<211> LENGTH: 5040
<212> TYPE: DNA
<213> ORGANISM: Homo Sapiens

<400> SEQUENCE: 1

```
tgcgctccac caagcctggc taacttttgc atttttaata gaggcagggt ttcaccatgt     60

tggcctggct ggtctcgaac ccctgacctt gcgatctgcc cacctcggcc tcccaaagtg    120

ctgggattac aggcgtgagc cactgtacct ggcggggctt attgtttttt aaaaagattt    180

ccaaaacctt gccctggcaa ttctgatttt ctgggcctgg agcaggacct ggagggatgg    240

tgttgtcaat tactttagat gtttctatca ggaaagtttg agaaatggta ttcaggccta    300
```

-continued

```
aacacaaacc tctcttgaaa tctcatccca gactgagccc ctgctcccta tcttaaatta    360
gattatagta ggtcttaaag tcagctgtag actgagcctc taaatctgaa cccagaccca    420
ccctaacccc aggatacatc agaagagctg gtcaatgtgg accattctga gcaatcctgc    480
aagtctactc tgatgggaaa aggctaagag cagtgccctg ggcagcaaca tcagctctga    540
agatgcagga ctgtgttaca tgttttatga gtgggtcttc acacactgag attcatggga    600
cagtaataga atctgcttgt gcagcactgg ggccttggag ggtcagggta aggctcaaga    660
tgtccaggaa gttgtatata aggagaatca gagcagagag agactagggt tcagaattac    720
caggatgact tagtcctgtt tgttactgtc accactccaa tgccttttcc tcattagtcc    780
tttctctcct ctgagccaca actaaatgat gtttctactt ttccctttct actttcctag    840
accctggatt ttgtatgcag aagccccagc tcttggtccc tatcatagcc acttcaaatg    900
gaaatctggt ccacgcagca tacttccttt tggtgggtat ccctggcctg gggcctacca    960
tacacttttg gctggctttc ccactgtgtt ttatgtatgc cttggccacc ctgggtaacc   1020
tgaccattgt cctcatcatt cgtgtggaga ggcgactgca tgagcccatg tacctcttcc   1080
tggccatgct ttccactatt gacctagtcc tctcctctat caccatgccc aagatggcca   1140
gtcttttcct gatgggcatc caggagatcg agttcaacat ttgcctggcc cagatgttcc   1200
ttatccatgc tctgtcagcc gtggagtcag ctgtcctgct ggccatggct tttgaccgct   1260
ttgtggccat ttgccaccca ttgcgccatg cttctgtgct gacagggtgt actgtggcca   1320
agattggact atctgccctg accagggggt ttgtattctt cttcccactg cccttcatcc   1380
tcaagtggtt gtcctactgc caaacacata ctgtcacaca ctccttctgt ctgcaccaag   1440
atattatgaa gctgtcctgt actgacacca gggtcaatgt ggtttatgga ctcttcatca   1500
tcctctcagt catgggtgtg gactctctct tcattggctt ctcatatatc ctcatcctgt   1560
gggctgtttt ggagctgtcc tctcggaggg cagcactcaa ggctttcaac acctgcatct   1620
cccacctctg tgctgttctg gtcttctatg taccccctcat tgggctctcg gtggtgcata   1680
ggctgggtgg tcccacctcc ctcctccatg tggttatggc taatacctac ttgctgctac   1740
cacctgtagt caaccccctt gtctatggag ccaagaccaa agagatctgt tcaagggtcc   1800
tctgtatgtt ctcacaaggt ggcaagtgag acaccttagt gtctcgcttc tactactact   1860
acagaagatg ggaatattag gatcctattg aatgccttgg tgattaaagt atcaaaccta   1920
ttgtgctgtc ttcttccagc aatttaagta gatcatgtat tctgtctcca ggaatgtgtc   1980
agtactgaac ttatgaccct gtctggacat cctggagaat gactgcacta gtccctctgc   2040
tatggtggtc ttgccttctc cttctctctc agctagaaaa tacatctagt tttgacatgg   2100
ggaggctgta aagatcacac ctcatggttc attccagttt tgaagtatga ttttaatgtt   2160
cttgcccccca tgtgcccatg ttggtgaatt tgcatggact ataaacgtta ttgcaaatac   2220
cctaaagtgg ttacccagcc ataatcaggg gttaatgaag gtatttgggg aatagtaact   2280
ggagagacag caacaagaca agaggcagct cacatgcaat gttgaagttt ctgtatgcaa   2340
gagggtgtgt tggcagattt gtgaaatctg cccatttgca tctgtatggc tctatatgac   2400
tatttgtcca taagggtgcc atgtattctg gttgtgggtg tgaatgtgtg ggtgtgttta   2460
tgtggacact tgcttttcag tgtgcgtata tgtgagagag agggtgcaca catggaatac   2520
gtactggttg tgtcctggtg agtgtggtag ctatgtcctg gcacatgtat gtttcatgag   2580
acgtgtctct gattgcgcat ttgtatttct gtggtatctg ttagttggta tatgatatgt   2640
```

-continued

```
gtctacgtga gaatgctggt gtctgtatct gcatggtggg cagtaccttt atgtgtatct   2700
ggtaagaatg ctgcctctac cttttcttcc tatttgtact atgtgaatgt ggtgcatgaa   2760
tgtgtggaat gtgtggaatg tgtagtattg ggatgcctgt atctttcagc gtgtttgggt   2820
gtatgtccac tgtgcataat atttgagatg taaaaccatt ttgtgcggta tatgtgttat   2880
tagttgtaag tcggtgaaat gtacatctga attctgtgtg catattgttg gtactgatgc   2940
tattttcgtg catatgtcta gtgtatatgt tttaaggcaa actttctttg tgtgttgggt   3000
gtgtatgtga cacgaatggg gacagcatct gtatttctga gcatggattg atgtgtggtg   3060
tctgtatgta tcttggaatg gaggagggag attgaagaag tctggctgtg agcagcagaa   3120
ataatttcca aagttgagtg acatgactct aagatgccca gtttctcggc ctggggtcag   3180
cctgggtgat agctcagtct gtcagaatga aaggaaacac ggtgcttcct tgctccacct   3240
tttcacaggc cagaccacac cttcttcatc ctgaacacaa ggatttcaag ggcttttgtt   3300
acctcttcct acgtttcctg cctctgctat ccgaggcact ggcctcccta aaccctgccc   3360
tcctgcctca atagcaagtc atggtatcct cacctctccc ttccctttt ggcttatctg   3420
ccaaacatgt ataaaagtcc ttggttcccc atctctacta aaaatacaac aattagccgg   3480
gtgtgatggc gcgtgcctgt agtcccagct agttgggagg ctgaggcagg agaaacgctt   3540
gagcccgcaa ggtggaggtt gcagtgagcc gagatcatgc cactgcactc cagcctggtg   3600
acagagcaag actctgtgtc aaaaaaaaaa aaaaaaaaaa agccttggtt gtagggagtt   3660
tctcctaatc cctctgggaa agcaagggtg gaggggaagc cagtcaatct cccttctgtt   3720
gccgcatgga aactccctta aggcaggaag ctgaaaaaac tgtagcattc acctcattat   3780
tcaccttgtc tcatgtctca ctgtccttcc acatgtctca ttgttactcc atattggatg   3840
gaagtagaag tccctttggt atttttaaa gtctttgcca tgtctaagtt aatgaggtta   3900
atggaggcag cagagatggc tccagggttc tgatagcaag tgtcaggctg cgtgctctgt   3960
aggcaccaga aactgttgtc accagtaatt ttgatgtggt ctgagttaga atggtctgat   4020
ttgccatgat ctatttaaca tagcttgatt tagcgtgtcc tgtgttctga atttaaaact   4080
cacagttgtg aaactgatca gtaaaaaata aggggagacc aactaaaaac catgttgttc   4140
tatttataga tgtagttttt acttatttca aaatacgagg tatttagttt tacattcaaa   4200
ttgttctcta actctctaaa atgttctctg actatttttg cccttaaggg agaaaccaga   4260
tgtcattggt cttacgtggc tggtgttggg ggtggggagg gttaaagaaa ccacgttctc   4320
tgtcctcagc cagaagttca gtaatccaag gccagagagt ggacggcaga ggcactgtcc   4380
ctggggacct tggttataag ttatccagac acagggacca gagcctggga gacaaaaaaa   4440
gatgtagccc tagggctttg ggaaaaggag gatggaccca gtgaattcca cgcttagcaa   4500
ggacctaaac agtgtccccc aaatgagaga agggaggaca gaaagaacac ttcaggatgg   4560
aaatgggctg acacttaacc gtggagtgtc tctgcaaact tcctttgcca ttctcctgtt   4620
tgagtttgat aaacctgaga agagacttgg ataaagaccg tcacgaagac tacactaatg   4680
agtttcttct agctttttc tactcacttt ccctatctat ccttcacatt gggagttggc   4740
atgaggatcc cagcagccca tcaggggagg actctagaga tccctttccc cattgcctct   4800
cctccccata cccccaggca tatcctccca gggcacggaa gctgagaagc agtccagaac   4860
cacagtgggc tagtgagggg tacctgctga tgtacccttt ggacagcatt ctgccccacc   4920
ctgcaggaag aagcagaagg agggagaggg tgaggcagag aataaataac cctgaccagg   4980
gaggtccaag ggagtaggcg gagacagaga ggctgtattt cagtgcagcc tgccagacct   5040
```

<210> SEQ ID NO 2
<211> LENGTH: 50
<212> TYPE: DNA
<213> ORGANISM: Homo Sapiens

<400> SEQUENCE: 2
ttttgcattt ttaatagagg cagggtttca ccatgttggc ctggctggtc 50

<210> SEQ ID NO 3
<211> LENGTH: 50
<212> TYPE: DNA
<213> ORGANISM: Homo Sapiens

<400> SEQUENCE: 3
caggaagttg tatataagga gaatcagagc agagagagac tagggttcag 50

<210> SEQ ID NO 4
<211> LENGTH: 50
<212> TYPE: DNA
<213> ORGANISM: Homo Sapiens

<400> SEQUENCE: 4
tcagtgtgcg tatatgtgag agagagggtg cacacatgga atacgtactg 50

<210> SEQ ID NO 5
<211> LENGTH: 50
<212> TYPE: DNA
<213> ORGANISM: Homo Sapiens

<400> SEQUENCE: 5
tgacatgact ctaagatgcc cagtttctcg gcctggggtc agcctgggtg 50

<210> SEQ ID NO 6
<211> LENGTH: 50
<212> TYPE: DNA
<213> ORGANISM: Homo Sapiens

<400> SEQUENCE: 6
gccaaacatg tataaaagtc cttggttccc catctctact aaaaatacaa 50

<210> SEQ ID NO 7
<211> LENGTH: 50
<212> TYPE: DNA
<213> ORGANISM: Homo Sapiens

<400> SEQUENCE: 7
aactgatcag taaaaaataa ggggagacca actaaaaacc atgttgttct 50

<210> SEQ ID NO 8
<211> LENGTH: 50
<212> TYPE: DNA
<213> ORGANISM: Homo Sapiens

<400> SEQUENCE: 8
aggcagagaa taaataaccc tgaccaggga ggtccaaggg agtaggcgga 50

<210> SEQ ID NO 9
<211> LENGTH: 152
<212> TYPE: DNA
<213> ORGANISM: Homo Sapiens

<400> SEQUENCE: 9

-continued

```
ccaggctgga gtgcagtggc gcagtctcgg ctcactgcaa cctctgcctc ccaggttcaa     60

gtgattctcc tgcctcagcc tcctgagttg ctgggattac aggcatgcag caccatgccc    120

agctaatttt tgtattttta gtagagatgg gg                                  152


<210> SEQ ID NO 10
<211> LENGTH: 152
<212> TYPE: DNA
<213> ORGANISM: Homo Sapiens

<400> SEQUENCE: 10

ccaggctgga gtgcagtggc atgatctcgg ctcactgcaa cctccacctt gcgggctcaa     60

gcgtttctcc tgcctcagcc tcccaactag ctgggactac aggcacgcgc catcacaccc    120

ggctaattgt tgtattttta gtagagatgg gg                                  152


<210> SEQ ID NO 11
<211> LENGTH: 138
<212> TYPE: DNA
<213> ORGANISM: Homo Sapiens

<400> SEQUENCE: 11

cctgtaatcc cagctactga ggaggctgag gcaggagaat cacttgaacc cagaaggcag     60

aggttgcaat gagccgagat tgcgccactg cactccagcc tgggtgacag agtgagactc    120

tgtctcaaaa aaaaaaaa                                                  138


<210> SEQ ID NO 12
<211> LENGTH: 137
<212> TYPE: DNA
<213> ORGANISM: Homo Sapiens

<400> SEQUENCE: 12

cctgtagtcc cagctagttg ggaggctgag gcaggagaaa cgcttgagcc cgcaaggtgg     60

aggttgcagt gagccgagat catgccactg cactccagcc tggtgacaga gcaagactct    120

gtgtcaaaaa aaaaaaa                                                   137


<210> SEQ ID NO 13
<211> LENGTH: 177
<212> TYPE: DNA
<213> ORGANISM: Homo Sapiens
<220> FEATURE:
<221> NAME/KEY: misc_feature
<222> LOCATION: 150, 151, 152, 153, 154, 155, 156
<223> OTHER INFORMATION: n = A,T,C or G

<400> SEQUENCE: 13

tgagactgag tctcgctctg tgcccaggct ggagtgcagt ggtgcaacct tggctcactg     60

caagctccgc ctcctgggtt cacgccattc tcctgcctca gcctcctgag tagctgggac    120

tacaggcacc cgccaccacg cctggctaan nnnnnngtat ttttagtaga gatgggg       177


<210> SEQ ID NO 14
<211> LENGTH: 175
<212> TYPE: DNA
<213> ORGANISM: Homo Sapiens

<400> SEQUENCE: 14

tgacacagag tcttgctctg tcaccaggct ggagtgcagt ggcatgatct cggctcactg     60

caacctccac cttgcgggct caagcgtttc tcctgcctca gcctcccaac tagctgggac    120

tacaggcacg cgccatcaca cccggctaat tgttgtattt ttagtagaga tgggg         175
```

-continued

<210> SEQ ID NO 15
<211> LENGTH: 123
<212> TYPE: DNA
<213> ORGANISM: Homo Sapiens

<400> SEQUENCE: 15 attttagta gagatggggt ttcactgtgt tagccaggat ggtctcagtc tcctgacctc 60
gtgatctgcc caccttggcc tcccaaagtg ctgggattac aggcgtgagc cactgcgcct 120
ggc 123

<210> SEQ ID NO 16
<211> LENGTH: 123
<212> TYPE: DNA
<213> ORGANISM: Homo Sapiens

<400> SEQUENCE: 16
atttttaata gaggcagggt ttcaccatgt tggcctggct ggtctcgaac ccctgacctt 60
gcgatctgcc cacctcggcc tcccaaagtg ctgggattac aggcgtgagc cactgtacct 120
ggc 123

<210> SEQ ID NO 17
<211> LENGTH: 115
<212> TYPE: DNA
<213> ORGANISM: Homo Sapiens

<400> SEQUENCE: 17
gccaggcaca gtggctcacg cctgtaatcc caacaccatg ggaggctgag atgggtggat 60
cacgaggtca ggagtttgag accagcctga ccaacatggt gaaactctgt ctcta 115

<210> SEQ ID NO 18
<211> LENGTH: 115
<212> TYPE: DNA
<213> ORGANISM: Homo Sapiens

<400> SEQUENCE: 18
gccaggtaca gtggctcacg cctgtaatcc cagcactttg ggaggccgag gtgggcagat 60
cgcaaggtca ggggttcgag accagccagg ccaacatggt gaaaccctgc ctcta 115

<210> SEQ ID NO 19
<211> LENGTH: 318
<212> TYPE: PRT
<213> ORGANISM: Homo Sapiens

<400> SEQUENCE: 19

Met Met Val Asp Pro Asn Gly Asn Glu Ser Ser Ala Thr Tyr Phe Ile
1 5 10 15

Leu Ile Gly Leu Pro Gly Leu Glu Glu Ala Gln Phe Trp Leu Ala Phe
20 25 30

Pro Leu Cys Ser Leu Tyr Leu Ile Ala Val Leu Gly Asn Leu Thr Ile
35 40 45

Ile Tyr Ile Val Arg Thr Glu His Ser Leu His Glu Pro Met Tyr Ile
50 55 60

Phe Leu Cys Met Leu Ser Gly Ile Asp Ile Leu Ile Ser Thr Ser Ser
65 70 75 80

Met Pro Lys Met Leu Ala Ile Phe Trp Phe Asn Ser Thr Thr Ile Gln
85 90 95

-continued

```
Phe Asp Ala Cys Leu Leu Gln Ile Phe Ala Ile His Ser Leu Ser Gly
            100                 105                 110

Met Glu Ser Thr Val Leu Leu Ala Met Ala Phe Asp Arg Tyr Val Ala
        115                 120                 125

Ile Cys His Pro Leu Arg His Ala Thr Val Leu Thr Leu Pro Arg Val
    130                 135                 140

Thr Lys Ile Gly Val Ala Ala Val Val Arg Gly Ala Ala Leu Met Ala
145                 150                 155                 160

Pro Leu Pro Val Phe Ile Lys Gln Leu Pro Phe Cys Arg Ser Asn Ile
                165                 170                 175

Leu Ser His Ser Tyr Cys Leu His Gln Asp Val Met Lys Leu Ala Cys
            180                 185                 190

Asp Asp Ile Arg Val Asn Val Val Tyr Gly Leu Ile Val Ile Ile Ser
        195                 200                 205

Ala Ile Gly Leu Asp Ser Leu Leu Ile Ser Phe Ser Tyr Leu Leu Ile
    210                 215                 220

Leu Lys Thr Val Leu Gly Leu Thr Arg Glu Ala Gln Ala Lys Ala Phe
225                 230                 235                 240

Gly Thr Cys Val Ser His Val Cys Ala Val Phe Ile Phe Tyr Val Pro
                245                 250                 255

Phe Ile Gly Leu Ser Met Val His Arg Phe Ser Lys Arg Arg Asp Ser
            260                 265                 270

Pro Leu Pro Val Ile Leu Ala Asn Ile Tyr Leu Leu Val Pro Pro Val
        275                 280                 285

Leu Asn Pro Ile Val Tyr Gly Val Lys Thr Lys Glu Ile Arg Gln Arg
    290                 295                 300

Ile Leu Arg Leu Phe His Val Ala Thr His Ala Ser Glu Pro
305                 310                 315


<210> SEQ ID NO 20
<211> LENGTH: 37
<212> TYPE: PRT
<213> ORGANISM: Homo Sapiens

<400> SEQUENCE: 20

Ser Leu Tyr Leu Ile Ala Val Leu Ala Ser Gly Val Thr Leu Arg Cys
 1               5                  10                  15

Pro Ser Ser Trp Pro Ile Ser Ile Cys Trp Phe Leu Leu Cys Ser Thr
            20                  25                  30

Gln Leu Ser Met Glu
        35


<210> SEQ ID NO 21
<211> LENGTH: 38
<212> TYPE: PRT
<213> ORGANISM: Homo Sapiens

<400> SEQUENCE: 21

Cys Ser Leu Tyr Leu Ile Ala Val Leu Ala Ser Gly Val Thr Leu Arg
 1               5                  10                  15

Cys Pro Ser Ser Trp Pro Ile Ser Ile Cys Trp Phe Leu Leu Cys Ser
            20                  25                  30

Thr Gln Leu Ser Met Glu
        35


<210> SEQ ID NO 22
<211> LENGTH: 43
```

-continued

<212> TYPE: PRT
<213> ORGANISM: Homo Sapiens

<400> SEQUENCE: 22

Leu Ala Phe Pro Leu Cys Ser Leu Tyr Leu Ile Ala Val Leu Ala Ser
1 5 10 15

Gly Val Thr Leu Arg Cys Pro Ser Ser Trp Pro Ile Ser Ile Cys Trp
20 25 30

Phe Leu Leu Cys Ser Thr Gln Leu Ser Met Glu
35 40

<210> SEQ ID NO 23
<211> LENGTH: 17
<212> TYPE: PRT
<213> ORGANISM: Homo Sapiens

<400> SEQUENCE: 23

Gln Phe Asp Ala Cys Leu Leu Gln Met Phe Ala Ile His Ser Leu Ser
1 5 10 15

Gly

<210> SEQ ID NO 24
<211> LENGTH: 19
<212> TYPE: PRT
<213> ORGANISM: Homo Sapiens

<400> SEQUENCE: 24

Ile Gln Phe Asp Ala Cys Leu Leu Gln Met Phe Ala Ile His Ser Leu
1 5 10 15

Ser Gly Met

<210> SEQ ID NO 25
<211> LENGTH: 29
<212> TYPE: PRT
<213> ORGANISM: Homo Sapiens

<400> SEQUENCE: 25

Phe Asn Ser Thr Thr Ile Gln Phe Asp Ala Cys Leu Leu Gln Met Phe
1 5 10 15

Ala Ile His Ser Leu Ser Gly Met Glu Ser Thr Val Leu
20 25

<210> SEQ ID NO 26
<211> LENGTH: 427
<212> TYPE: DNA
<213> ORGANISM: Homo Sapiens

<400> SEQUENCE: 26
gatcaaactt cttttccatt cagagtcctc tgattcagat tttaatgtta acattttgga 60
agacagtatt cagaaaaaaa atttccttaa taaaaataca actcagatcc ttcaaatatg 120
aaactggttg gggaatctcc attttttcaa tattattttc ttctttgttt tcttgctacg 180
tataattatt aatatcctga ctaggttgtg gttggagggt tattactttt cattttacca 240
tgcagtccaa atctaaactg cttctactga tggtttacag cattctgaga taagaatggt 300
acatctagag aacatttgcc aaaggcctaa gcacagcaaa ggaaaataaa cacagaatat 360
aataaaatga gataatctag cttaaaacta taacttcctc tttagaactc ccaaccacat 420
ttggatc 427

-continued

```
<210> SEQ ID NO 27
<211> LENGTH: 3136
<212> TYPE: DNA
<213> ORGANISM: Homo Sapiens
<220> FEATURE:
<221> NAME/KEY: CDS
<222> LOCATION: (130)...(1083)

<400> SEQUENCE: 27

cagagaggct gtatttcagt gcagcctgcc agacctcttc tggaggaaga ctggacaaag     60

ggggtcacac attccttcca tacggttgag cctctacctg cctggtgctg gtcacagttc    120

agcttcttc atg atg gtg gat ccc aat ggc aat gaa tcc agt gct aca tac    171
          Met Met Val Asp Pro Asn Gly Asn Glu Ser Ser Ala Thr Tyr
           1               5                  10

ttc atc cta ata ggc ctc cct ggt tta gaa gag gct cag ttc tgg ttg      219
Phe Ile Leu Ile Gly Leu Pro Gly Leu Glu Glu Ala Gln Phe Trp Leu
15                  20                  25                  30

gcc ttc cca ttg tgc tcc ctc tac ctt att gct gtg cta ggt aac ttg      267
Ala Phe Pro Leu Cys Ser Leu Tyr Leu Ile Ala Val Leu Gly Asn Leu
                35                  40                  45

aca atc atc tac att gtg cgg act gag cac agc ctg cat gag ccc atg      315
Thr Ile Ile Tyr Ile Val Arg Thr Glu His Ser Leu His Glu Pro Met
            50                  55                  60

tat ata ttt ctt tgc atg ctt tca ggc att gac atc ctc atc tcc acc      363
Tyr Ile Phe Leu Cys Met Leu Ser Gly Ile Asp Ile Leu Ile Ser Thr
        65                  70                  75

tca tcc atg ccc aaa atg ctg gcc atc ttc tgg ttc aat tcc act acc      411
Ser Ser Met Pro Lys Met Leu Ala Ile Phe Trp Phe Asn Ser Thr Thr
    80                  85                  90

atc cag ttt gat gct tgt ctg cta cag att ttt gcc atc cac tcc tta      459
Ile Gln Phe Asp Ala Cys Leu Leu Gln Ile Phe Ala Ile His Ser Leu
95                  100                 105                 110

tct ggc atg gaa tcc aca gtg ctg ctg gcc atg gct ttt gac cgc tat      507
Ser Gly Met Glu Ser Thr Val Leu Leu Ala Met Ala Phe Asp Arg Tyr
                115                 120                 125

gtg gcc atc tgt cac cca ctg cgc cat gcc aca gta ctt acg ttg cct      555
Val Ala Ile Cys His Pro Leu Arg His Ala Thr Val Leu Thr Leu Pro
            130                 135                 140

cgt gtc acc aaa att ggt gtg gct gct gtg gtg cgg ggg gct gca ctg      603
Arg Val Thr Lys Ile Gly Val Ala Ala Val Val Arg Gly Ala Ala Leu
        145                 150                 155

atg gca ccc ctt cct gtc ttc atc aag cag ctg ccc ttc tgc cgc tcc      651
Met Ala Pro Leu Pro Val Phe Ile Lys Gln Leu Pro Phe Cys Arg Ser
    160                 165                 170

aat atc ctt tcc cat tcc tac tgc cta cac caa gat gtc atg aag ctg      699
Asn Ile Leu Ser His Ser Tyr Cys Leu His Gln Asp Val Met Lys Leu
175                 180                 185                 190

gcc tgt gat gat atc cgg gtc aat gtc gtc tat ggc ctt atc gtc atc      747
Ala Cys Asp Asp Ile Arg Val Asn Val Val Tyr Gly Leu Ile Val Ile
                195                 200                 205

atc tcc gcc att ggc ctg gac tca ctt ctc atc tcc ttc tca tat ctg      795
Ile Ser Ala Ile Gly Leu Asp Ser Leu Leu Ile Ser Phe Ser Tyr Leu
            210                 215                 220

ctt att ctt aag act gtg ttg ggc ttg aca cgt gaa gcc cag gcc aag      843
Leu Ile Leu Lys Thr Val Leu Gly Leu Thr Arg Glu Ala Gln Ala Lys
        225                 230                 235

gca ttt ggc act tgc gtc tct cat gtg tgt gct gtg ttc ata ttc tat      891
Ala Phe Gly Thr Cys Val Ser His Val Cys Ala Val Phe Ile Phe Tyr
    240                 245                 250

gta cct ttc att gga ttg tcc atg gtg cat cgc ttt agc aag cgg cgt      939
```

-continued

```
Val Pro Phe Ile Gly Leu Ser Met Val His Arg Phe Ser Lys Arg Arg
255                 260                 265                 270

gac tct ccg ctg ccc gtc atc ttg gcc aat atc tat ctg ctg gtt cct      987
Asp Ser Pro Leu Pro Val Ile Leu Ala Asn Ile Tyr Leu Leu Val Pro
                275                 280                 285

cct gtg ctc aac cca att gtc tat gga gtg aag aca aag gag att cga     1035
Pro Val Leu Asn Pro Ile Val Tyr Gly Val Lys Thr Lys Glu Ile Arg
            290                 295                 300

cag cgc atc ctt cga ctt ttc cat gtg gcc aca cac gct tca gag ccc     1083
Gln Arg Ile Leu Arg Leu Phe His Val Ala Thr His Ala Ser Glu Pro
        305                 310                 315

taggtgtcag tgatcaaact tcttttccat tcagagtcct ctgattcaga ttttaatgtt   1143

aacattttgg aagacagtat tcagaaaaaa aatttcctta ataaaaaata caactcagat   1203

ccttcaaata tgaaactggt tggggaatct ccatttttc aatattattt tcttctttgt    1263

tttcttgcta catataatta ttaataccct gactaggttg tggttggagg gttattactt   1323

ttcattttac catgcagtcc aaatctaaac tgcttctact gatggtttac agcattctga   1383

gataagaatg gtacatctag agaacatttg ccaaaggcct aagcacggca aaggaaaata   1443

aacacagaat ataataaaat gagataatct agcttaaaac tataacttcc tcttcagaac   1503

tcccaaccac attggatctc agaaaaatgc tgtcttcaaa atgacttcta cagagaagaa   1563

ataatttttc ctctggacac tagcacttaa ggggaagatt ggaagtaaag ccttgaaaag   1623

agtacattta cctacgttaa tgaaagttga cacactgttc tgagagtttt cacagcatat   1683

ggaccctgtt tttcctattt aattttctta tcaacccttt aattaggcaa agatattatt   1743

agtaccctca ttgtagccat gggaaaattg atgttcagtg gggatcagtg aattaaatgg   1803

ggtcatacaa gtataaaaat taaaaaaaaa aaagacttca tgcccaatct catatgatgt   1863

ggaagaactg ttagagagac caacagggta gtgggttaga gatttccaga gtcttacatt   1923

ttctagagga ggtatttaat ttcttctcac tcatccagtg ttgtatttag gaatttcctg   1983

gcaacagaac tcatggcttt aatcccacta gctattgctt attgtcctgg tccaattgcc   2043

aattacctgt gtcttggaag aagtgatttc taggttcacc attatggaag attcttattc   2103

agaaagtctg catagggctt atagcaagtt atttattttt aaaagttcca taggtgattc   2163

tgataggcag tgaggttagg gagccaccag ttatgatggg aagtatggaa tggcaggtct   2223

tgaagataac attggccttt tgagtgtgac tcgtagctgg aaagtgaggg aatcttcagg   2283

accatgcttt atttggggct ttgtgcagta tggaacaggg actttgagac caggaaagca   2343

atctgactta ggcatgggaa tcaggcattt ttgcttctga ggggctatta ccaagggtta   2403

ataggtttca tcttcaacag gatatgacaa cagtgttaac caagaaactc aaattacaaa   2463

tactaaaaca tgtgatcata tatgtggtaa gtttcatttt ctttttcaat cctcaggttc   2523

cctgatatgg attcctataa catgctttca tccccttttg taatggatat catatttgga   2583

aatgcctatt taatacttgt atttgctgct ggactgtaag cccatgaggg cactgtttat   2643

tattgaatgt catctctgtt catcattgac tgctctttgc tcatcattga atccccccagc  2703

aaagtgccta gaacataata gtgcttatgc ttgacaccgg ttatttttca tcaaacctga   2763

ttccttctgt cctgaacaca tagccaggca attttccagc cttctttgag ttgggtatta   2823

ttaaattctg gccattactt ccaatgtgag tggaagtgac atgtgcaatt tctatacctg   2883

gctcataaaa ccctcccatg tgcagccttt catgttgaca ttaaatgtga cttgggaagc   2943

tatgtgttac acagagtaaa tcaccagaag cctggatttc tgaaaaaact gtgcagagcc   3003
```

-continued

```
aaacctctgt catttgcaac tcccacttgt atttgtacga ggcagttgga taagtgaaaa   3063

ataaagtact attgtgtcaa gaaaaaaaaa aaaaaaaaaa aaaaaaaaaa aaaaaaaaaa   3123

aaaaaaaaaa aaa                                                      3136


<210> SEQ ID NO 28
<211> LENGTH: 317
<212> TYPE: PRT
<213> ORGANISM: Homo Sapiens

<400> SEQUENCE: 28

Met Val Asp Pro Asn Gly Asn Glu Ser Ser Ala Thr Tyr Phe Ile
 1               5                  10                  15

Leu Ile Gly Leu Pro Gly Leu Glu Glu Ala Gln Phe Trp Leu Ala Phe
                20                  25                  30

Pro Leu Cys Ser Leu Tyr Leu Ile Ala Val Leu Gly Asn Leu Thr Ile
            35                  40                  45

Ile Tyr Ile Val Arg Thr Glu His Ser Leu His Glu Pro Met Tyr Ile
        50                  55                  60

Phe Leu Cys Met Leu Ser Gly Ile Asp Ile Leu Ile Ser Thr Ser Ser
    65                  70                  75

Met Pro Lys Met Leu Ala Ile Phe Trp Phe Asn Ser Thr Thr Ile Gln
80                  85                  90                  95

Phe Asp Ala Cys Leu Leu Gln Ile Phe Ala Ile His Ser Leu Ser Gly
                100                 105                 110

Met Glu Ser Thr Val Leu Leu Ala Met Ala Phe Asp Arg Tyr Val Ala
            115                 120                 125

Ile Cys His Pro Leu Arg His Ala Thr Val Leu Thr Leu Pro Arg Val
        130                 135                 140

Thr Lys Ile Gly Val Ala Ala Val Val Arg Gly Ala Ala Leu Met Ala
    145                 150                 155

Pro Leu Pro Val Phe Ile Lys Gln Leu Pro Phe Cys Arg Ser Asn Ile
160                 165                 170                 175

Leu Ser His Ser Tyr Cys Leu His Gln Asp Val Met Lys Leu Ala Cys
                180                 185                 190

Asp Asp Ile Arg Val Asn Val Val Tyr Gly Leu Ile Val Ile Ile Ser
            195                 200                 205

Ala Ile Gly Leu Asp Ser Leu Leu Ile Ser Phe Ser Tyr Leu Leu Ile
        210                 215                 220

Leu Lys Thr Val Leu Gly Leu Thr Arg Glu Ala Gln Ala Lys Ala Phe
    225                 230                 235

Gly Thr Cys Val Ser His Val Cys Ala Val Phe Ile Phe Tyr Val Pro
240                 245                 250                 255

Phe Ile Gly Leu Ser Met Val His Arg Phe Ser Lys Arg Arg Asp Ser
                260                 265                 270

Pro Leu Pro Val Ile Leu Ala Asn Ile Tyr Leu Leu Val Pro Pro Val
            275                 280                 285

Leu Asn Pro Ile Val Tyr Gly Val Lys Thr Lys Glu Ile Arg Gln Arg
        290                 295                 300

Ile Leu Arg Leu Phe His Val Ala Thr His Ala Ser Glu Pro
    305                 310                 315


<210> SEQ ID NO 29
<211> LENGTH: 2466
<212> TYPE: DNA
<213> ORGANISM: Homo Sapiens
```

-continued

```
<220> FEATURE:
<221> NAME/KEY: CDS
<222> LOCATION: (130)...(345)

<400> SEQUENCE: 29

cagagaggct gtatttcagt gcagcctgcc agacctcttc tggaggaaga ctggacaaag     60

ggggtcacac attccttcca tacggttgag cctctacctg cctggtgctg gtcacagttc    120

agcttcttc atg atg gtg gat ccc aat ggc aat gaa tcc agt gct aca tac    171
          Met Met Val Asp Pro Asn Gly Asn Glu Ser Ser Ala Thr Tyr
           1               5                  10

ttc atc cta ata ggc ctc cct ggt tta gaa gag gct cag ttc tgg ttg      219
Phe Ile Leu Ile Gly Leu Pro Gly Leu Glu Glu Ala Gln Phe Trp Leu
15                  20                  25                  30

gcc ttc cca ttg tgc tcc ctc tac ctt att gct gtg cta gca agc ggc      267
Ala Phe Pro Leu Cys Ser Leu Tyr Leu Ile Ala Val Leu Ala Ser Gly
                35                  40                  45

gtg act ctc cgc tgc ccg tca tct tgg cca ata tct atc tgc tgg ttc      315
Val Thr Leu Arg Cys Pro Ser Ser Trp Pro Ile Ser Ile Cys Trp Phe
            50                  55                  60

ctc ctg tgc tca acc caa ttg tct atg gag tgaagacaaa ggagattcga        365
Leu Leu Cys Ser Thr Gln Leu Ser Met Glu
        65                  70

cagcgcatcc ttcgactttt ccatgtggcc acacacgctt cagagcccta ggtgtcagtg    425

atcaaacttc ttttccattc agagtcctct gattcagatt ttaatgttaa catttttggaa   485

gacagtattc agaaaaaaaa tttccttaat aaaaaataca actcagatcc ttcaaatatg    545

aaactggttg gggaatctcc atttttttcaa tattattttc ttctttgttt tcttgctaca   605

tataattatt aataccctga ctaggttgtg gttggagggt tattactttt cattttacca    665

tgcagtccaa atctaaactg cttctactga tggtttacag cattctgaga taagaatggt    725

acatctagag aacatttgcc aaaggcctaa gcacggcaaa ggaaaataaa cacagaatat    785

aataaaatga gataatctag cttaaaacta taacttcctc ttcagaactc ccaaccacat    845

tggatctcag aaaaatgctg tcttcaaaat gacttctaca gagaagaaat aatttttcct    905

ctggacacta gcacttaagg ggaagattgg aagtaaagcc ttgaaaagag tacatttacc    965

tacgttaatg aaagttgaca cactgttctg agagttttca cagcatatgg accctgtttt   1025

tcctatttaa ttttcttatc aaccctttaa ttaggcaaag atattattag taccctcatt   1085

gtagccatgg gaaaattgat gttcagtggg gatcagtgaa ttaaatgggg tcatacaagt   1145

ataaaaatta aaaaaaaaaa agacttcatg cccaatctca tatgatgtgg aagaactgtt   1205

agagagacca acagggtagt gggttagaga tttccagagt cttacatttt ctagaggagg   1265

tatttaattt cttctcactc atccagtgtt gtatttagga atttcctggc aacagaactc   1325

atggctttaa tcccactagc tattgcttat tgtcctggtc caattgccaa ttacctgtgt   1385

cttggaagaa gtgatttcta ggttcaccat tatggaagat tcttattcag aaagtctgca   1445

tagggcttat agcaagttat ttatttttaa aagttccata ggtgattctg ataggcagtg   1505

aggttaggga gccaccagtt atgatgggaa gtatggaatg gcaggtcttg aagataacat   1565

tggccttttg agtgtgactc gtagctggaa agtgagggaa tcttcaggac catgctttat   1625

ttggggcttt gtgcagtatg gaacagggac tttgagacca ggaaagcaat ctgacttagg   1685

catgggaatc aggcattttt gcttctgagg ggctattacc aagggttaat aggtttcatc   1745

ttcaacagga tatgacaaca gtgttaacca agaaactcaa attacaaata ctaaaacatg   1805

tgatcatata tgtggtaagt ttcattttct ttttcaatcc tcaggttccc tgatatggat   1865
```

-continued

```
tcctataaca tgctttcatc cccttttgta atggatatca tatttggaaa tgcctattta   1925

atacttgtat ttgctgctgg actgtaagcc catgagggca ctgtttatta ttgaatgtca   1985

tctctgttca tcattgactg ctctttgctc atcattgaat cccccagcaa agtgcctaga   2045

acataatagt gcttatgctt gacaccggtt atttttcatc aaacctgatt ccttctgtcc   2105

tgaacacata gccaggcaat tttccagcct tctttgagtt gggtattatt aaattctggc   2165

cattacttcc aatgtgagtg gaagtgacat gtgcaatttc tatacctggc tcataaaacc   2225

ctcccatgtg cagcctttca tgttgacatt aaatgtgact tgggaagcta tgtgttacac   2285

agagtaaatc accagaagcc tggatttctg aaaaaactgt gcagagccaa acctctgtca   2345

tttgcaactc ccacttgtat ttgtacgagg cagttggata agtgaaaaat aaagtactat   2405

tgtgtcaaga aaaaaaaaaa aaaaaaaaaa aaaaaaaaaa aaaaaaaaaa aaaaaaaaaa   2465

a                                                                   2466


<210> SEQ ID NO 30
<211> LENGTH: 72
<212> TYPE: PRT
<213> ORGANISM: Homo Sapiens

<400> SEQUENCE: 30

Met Met Val Asp Pro Asn Gly Asn Glu Ser Ser Ala Thr Tyr Phe Ile
 1               5                  10                  15

Leu Ile Gly Leu Pro Gly Leu Glu Glu Ala Gln Phe Trp Leu Ala Phe
            20                  25                  30

Pro Leu Cys Ser Leu Tyr Leu Ile Ala Val Leu Ala Ser Gly Val Thr
        35                  40                  45

Leu Arg Cys Pro Ser Ser Trp Pro Ile Ser Ile Cys Trp Phe Leu Leu
    50                  55                  60

Cys Ser Thr Gln Leu Ser Met Glu
65                  70


<210> SEQ ID NO 31
<211> LENGTH: 3136
<212> TYPE: DNA
<213> ORGANISM: Homo Sapiens
<220> FEATURE:
<221> NAME/KEY: CDS
<222> LOCATION: (130)...(1083)

<400> SEQUENCE: 31

cagagaggct gtatttcagt gcagcctgcc agacctcttc tggaggaaga ctggacaaag     60

ggggtcacac attccttcca tacggttgag cctctacctg cctggtgctg gtcacagttc    120

agcttcttc atg atg gtg gat ccc aat ggc aat gaa tcc agt gct aca tac    171
          Met Met Val Asp Pro Asn Gly Asn Glu Ser Ser Ala Thr Tyr
           1               5                  10

ttc atc cta ata ggc ctc cct ggt tta gaa gag gct cag ttc tgg ttg      219
Phe Ile Leu Ile Gly Leu Pro Gly Leu Glu Glu Ala Gln Phe Trp Leu
15                  20                  25                  30

gcc ttc cca ttg tgc tcc ctc tac ctt att gct gtg cta ggt aac ttg      267
Ala Phe Pro Leu Cys Ser Leu Tyr Leu Ile Ala Val Leu Gly Asn Leu
                35                  40                  45

aca atc atc tac att gtg cgg act gag cac agc ctg cat gag ccc atg      315
Thr Ile Ile Tyr Ile Val Arg Thr Glu His Ser Leu His Glu Pro Met
            50                  55                  60

tat ata ttt ctt tgc atg ctt tca ggc att gac atc ctc atc tcc acc      363
Tyr Ile Phe Leu Cys Met Leu Ser Gly Ile Asp Ile Leu Ile Ser Thr
```

```
                65                   70                  75
tca tcc atg ccc aaa atg ctg gcc atc ttc tgg ttc aat tcc act acc    411
Ser Ser Met Pro Lys Met Leu Ala Ile Phe Trp Phe Asn Ser Thr Thr
        80                  85                  90

atc cag ttt gat gct tgt ctg cta cag atg ttt gcc atc cac tcc tta    459
Ile Gln Phe Asp Ala Cys Leu Leu Gln Met Phe Ala Ile His Ser Leu
 95                 100                 105                 110

tct ggc atg gaa tcc aca gtg ctg ctg gcc atg gct ttt gac cgc tat    507
Ser Gly Met Glu Ser Thr Val Leu Leu Ala Met Ala Phe Asp Arg Tyr
                115                 120                 125

gtg gcc atc tgt cac cca ctg cgc cat gcc aca gta ctt acg ttg cct    555
Val Ala Ile Cys His Pro Leu Arg His Ala Thr Val Leu Thr Leu Pro
            130                 135                 140

cgt gtc acc aaa att ggt gtg gct gct gtg gtg cgg ggg gct gca ctg    603
Arg Val Thr Lys Ile Gly Val Ala Ala Val Val Arg Gly Ala Ala Leu
        145                 150                 155

atg gca ccc ctt cct gtc ttc atc aag cag ctg ccc ttc tgc cgc tcc    651
Met Ala Pro Leu Pro Val Phe Ile Lys Gln Leu Pro Phe Cys Arg Ser
    160                 165                 170

aat atc ctt tcc cat tcc tac tgc cta cac caa gat gtc atg aag ctg    699
Asn Ile Leu Ser His Ser Tyr Cys Leu His Gln Asp Val Met Lys Leu
175                 180                 185                 190

gcc tgt gat gat atc cgg gtc aat gtc gtc tat ggc ctt atc gtc atc    747
Ala Cys Asp Asp Ile Arg Val Asn Val Val Tyr Gly Leu Ile Val Ile
                195                 200                 205

atc tcc gcc att ggc ctg gac tca ctt ctc atc tcc ttc tca tat ctg    795
Ile Ser Ala Ile Gly Leu Asp Ser Leu Leu Ile Ser Phe Ser Tyr Leu
            210                 215                 220

ctt att ctt aag act gtg ttg ggc ttg aca cgt gaa gcc cag gcc aag    843
Leu Ile Leu Lys Thr Val Leu Gly Leu Thr Arg Glu Ala Gln Ala Lys
        225                 230                 235

gca ttt ggc act tgc gtc tct cat gtg tgt gct gtg ttc ata ttc tat    891
Ala Phe Gly Thr Cys Val Ser His Val Cys Ala Val Phe Ile Phe Tyr
    240                 245                 250

gta cct ttc att gga ttg tcc atg gtg cat cgc ttt agc aag cgg cgt    939
Val Pro Phe Ile Gly Leu Ser Met Val His Arg Phe Ser Lys Arg Arg
255                 260                 265                 270

gac tct ccg ctg ccc gtc atc ttg gcc aat atc tat ctg ctg gtt cct    987
Asp Ser Pro Leu Pro Val Ile Leu Ala Asn Ile Tyr Leu Leu Val Pro
                275                 280                 285

cct gtg ctc aac cca att gtc tat gga gtg aag aca aag gag att cga    1035
Pro Val Leu Asn Pro Ile Val Tyr Gly Val Lys Thr Lys Glu Ile Arg
            290                 295                 300

cag cgc atc ctt cga ctt ttc cat gtg gcc aca cac gct tca gag ccc    1083
Gln Arg Ile Leu Arg Leu Phe His Val Ala Thr His Ala Ser Glu Pro
        305                 310                 315

taggtgtcag tgatcaaact tcttttccat tcagagtcct ctgattcaga ttttaatgtt    1143

aacattttgg aagacagtat tcagaaaaaa aatttcctta ataaaaaata caactcagat    1203

ccttcaaata tgaaactggt tggggaatct ccattttttc aatattattt tcttctttgt    1263

tttcttgcta catataatta ttaataccct gactaggttg tggttggagg ttattactt     1323

ttcattttac catgcagtcc aaatctaaac tgcttctact gatggtttac agcattctga    1383

gataagaatg gtacatctag agaacatttg ccaaaggcct aagcacggca aaggaaaata    1443

aacacagaat ataataaaat gagataatct agcttaaaac tataacttcc tcttcagaac    1503

tcccaaccac attggatctc agaaaaatgc tgtcttcaaa atgacttcta cagagaagaa    1563

ataatttttc ctctggacac tagcacttaa ggggaagatt ggaagtaaag ccttgaaaag    1623
```

-continued

```
agtacattta cctacgttaa tgaaagttga cacactgttc tgagagtttt cacagcatat   1683

ggaccctgtt tttcctattt aattttctta tcaacccttt aattaggcaa agatattatt   1743

agtaccctca ttgtagccat gggaaaattg atgttcagtg gggatcagtg aattaaatgg   1803

ggtcatacaa gtataaaaat taaaaaaaaa aaagacttca tgcccaatct catatgatgt   1863

ggaagaactg ttagagagac caacagggta gtgggttaga gatttccaga gtcttacatt   1923

ttctagagga ggtatttaat ttcttctcac tcatccagtg ttgtatttag gaatttcctg   1983

gcaacagaac tcatggcttt aatcccacta gctattgctt attgtcctgg tccaattgcc   2043

aattacctgt gtcttggaag aagtgatttc taggttcacc attatggaag attcttattc   2103

agaaagtctg catagggctt atagcaagtt atttattttt aaaagttcca taggtgattc   2163

tgataggcag tgaggttagg gagccaccag ttatgatggg aagtatggaa tggcaggtct   2223

tgaagataac attggccttt tgagtgtgac tcgtagctgg aaagtgaggg aatcttcagg   2283

accatgcttt atttggggct ttgtgcagta tggaacaggg actttgagac caggaaagca   2343

atctgactta ggcatgggaa tcaggcattt ttgcttctga ggggctatta ccaagggtta   2403

ataggtttca tcttcaacag gatatgacaa cagtgttaac caagaaactc aaattacaaa   2463

tactaaaaca tgtgatcata tatgtggtaa gtttcatttt ctttttcaat cctcaggttc   2523

cctgatatgg attcctataa catgctttca tccccttttg taatggatat catatttgga   2583

aatgcctatt taatacttgt atttgctgct ggactgtaag cccatgaggg cactgtttat   2643

tattgaatgt catctctgtt catcattgac tgctctttgc tcatcattga atcccccagc   2703

aaagtgccta gaacataata gtgcttatgc ttgacaccgg ttatttttca tcaaacctga   2763

ttccttctgt cctgaacaca tagccaggca attttccagc cttctttgag ttgggtatta   2823

ttaaattctg gccattactt ccaatgtgag tggaagtgac atgtgcaatt tctatacctg   2883

gctcataaaa ccctcccatg tgcagccttt catgttgaca ttaaatgtga cttgggaagc   2943

tatgtgttac acagagtaaa tcaccagaag cctggatttc tgaaaaaact gtgcagagcc   3003

aaacctctgt catttgcaac tcccacttgt atttgtacga ggcagttgga taagtgaaaa   3063

ataaagtact attgtgtcaa gaaaaaaaaa aaaaaaaaaa aaaaaaaaaa aaaaaaaaaa   3123

aaaaaaaaaa aaa                                                       3136
```

<210> SEQ ID NO 32
<211> LENGTH: 318
<212> TYPE: PRT
<213> ORGANISM: Homo Sapiens

<400> SEQUENCE: 32

```
Met Met Val Asp Pro Asn Gly Asn Glu Ser Ser Ala Thr Tyr Phe Ile
 1               5                  10                  15

Leu Ile Gly Leu Pro Gly Leu Glu Glu Ala Gln Phe Trp Leu Ala Phe
            20                  25                  30

Pro Leu Cys Ser Leu Tyr Leu Ile Ala Val Leu Gly Asn Leu Thr Ile
        35                  40                  45

Ile Tyr Ile Val Arg Thr Glu His Ser Leu His Glu Pro Met Tyr Ile
    50                  55                  60

Phe Leu Cys Met Leu Ser Gly Ile Asp Ile Leu Ile Ser Thr Ser Ser
65                  70                  75                  80

Met Pro Lys Met Leu Ala Ile Phe Trp Phe Asn Ser Thr Thr Ile Gln
                85                  90                  95
```

-continued

```
Phe Asp Ala Cys Leu Leu Gln Met Phe Ala Ile His Ser Leu Ser Gly
            100                 105                 110

Met Glu Ser Thr Val Leu Leu Ala Met Ala Phe Asp Arg Tyr Val Ala
        115                 120                 125

Ile Cys His Pro Leu Arg His Ala Thr Val Leu Thr Leu Pro Arg Val
    130                 135                 140

Thr Lys Ile Gly Val Ala Ala Val Val Arg Gly Ala Ala Leu Met Ala
145                 150                 155                 160

Pro Leu Pro Val Phe Ile Lys Gln Leu Pro Phe Cys Arg Ser Asn Ile
                165                 170                 175

Leu Ser His Ser Tyr Cys Leu His Gln Asp Val Met Lys Leu Ala Cys
            180                 185                 190

Asp Asp Ile Arg Val Asn Val Val Tyr Gly Leu Ile Val Ile Ile Ser
        195                 200                 205

Ala Ile Gly Leu Asp Ser Leu Leu Ile Ser Phe Ser Tyr Leu Leu Ile
    210                 215                 220

Leu Lys Thr Val Leu Gly Leu Thr Arg Glu Ala Gln Ala Lys Ala Phe
225                 230                 235                 240

Gly Thr Cys Val Ser His Val Cys Ala Val Phe Ile Phe Tyr Val Pro
                245                 250                 255

Phe Ile Gly Leu Ser Met Val His Arg Phe Ser Lys Arg Arg Asp Ser
            260                 265                 270

Pro Leu Pro Val Ile Leu Ala Asn Ile Tyr Leu Leu Val Pro Pro Val
        275                 280                 285

Leu Asn Pro Ile Val Tyr Gly Val Lys Thr Lys Glu Ile Arg Gln Arg
    290                 295                 300

Ile Leu Arg Leu Phe His Val Ala Thr His Ala Ser Glu Pro
305                 310                 315


<210> SEQ ID NO 33
<211> LENGTH: 316
<212> TYPE: PRT
<213> ORGANISM: Homo Sapiens

<400> SEQUENCE: 33

Met Val Asp Pro Asn Gly Asn Glu Ser Ser Ala Thr Tyr Phe Ile Leu
 1               5                  10                  15

Ile Gly Leu Pro Gly Leu Glu Glu Ala Gln Phe Trp Leu Ala Phe Pro
            20                  25                  30

Leu Cys Ser Leu Tyr Leu Ile Ala Val Leu Gly Asn Leu Thr Ile Ile
        35                  40                  45

Tyr Ile Val Arg Thr Glu His Ser Leu His Glu Pro Met Tyr Ile Phe
    50                  55                  60

Leu Cys Met Leu Ser Gly Ile Asp Ile Leu Ile Ser Thr Ser Ser Met
65                  70                  75                  80

Pro Lys Met Leu Ala Ile Phe Trp Phe Asn Ser Thr Thr Ile Gln Phe
                85                  90                  95

Asp Ala Cys Leu Leu Gln Ile Phe Ala Ile His Ser Leu Ser Gly Met
            100                 105                 110

Glu Ser Thr Val Leu Leu Ala Met Ala Phe Asp Arg Tyr Val Ala Ile
        115                 120                 125

Cys His Pro Leu Arg His Ala Thr Val Leu Thr Leu Pro Arg Val Thr
    130                 135                 140

Lys Ile Gly Val Ala Ala Val Val Arg Gly Ala Ala Leu Met Ala Pro
145                 150                 155                 160
```

```
Leu Pro Val Phe Ile Lys Gln Leu Pro Phe Cys Arg Ser Asn Ile Leu
                165                 170                 175

Ser His Ser Tyr Cys Leu His Gln Asp Val Met Lys Leu Ala Cys Asp
            180                 185                 190

Asp Ile Arg Val Asn Val Val Tyr Gly Leu Ile Val Ile Ile Ser Ala
        195                 200                 205

Ile Gly Leu Asp Ser Leu Leu Ile Ser Phe Ser Tyr Leu Leu Ile Leu
    210                 215                 220

Lys Thr Val Leu Gly Leu Thr Arg Glu Ala Gln Ala Lys Ala Phe Gly
225                 230                 235                 240

Thr Cys Val Ser His Val Cys Ala Val Phe Ile Phe Tyr Val Pro Phe
                245                 250                 255

Ile Gly Leu Ser Met Val His Arg Phe Ser Lys Arg Arg Asp Ser Pro
            260                 265                 270

Leu Pro Val Ile Leu Ala Asn Ile Tyr Leu Leu Val Pro Pro Val Leu
        275                 280                 285

Asn Pro Ile Val Tyr Gly Val Lys Thr Lys Glu Ile Arg Gln Arg Ile
    290                 295                 300

Leu Arg Leu Phe His Val Ala Thr His Ala Ser Glu
305                 310                 315


<210> SEQ ID NO 34
<211> LENGTH: 316
<212> TYPE: PRT
<213> ORGANISM: Homo Sapiens

<400> SEQUENCE: 34

Met Val Gly Phe Asn Ser Asn Glu Ser Ser Ala Thr Tyr Phe Ile Leu
 1               5                  10                  15

Ile Gly Leu Pro Gly Leu Glu Glu Val Gln Phe Trp Leu Ala Phe Pro
            20                  25                  30

Leu Cys Ser Leu Tyr Leu Ile Ala Val Leu Gly Asn Leu Thr Ile Ile
        35                  40                  45

Tyr Ile Val Arg Thr Glu His Ser Leu His Glu Pro Met Tyr Ile Phe
    50                  55                  60

Leu Cys Met Leu Ser Gly Leu Asp Ile Leu Ile Ser Thr Ser Ser Met
65                  70                  75                  80

Pro Lys Met Met Ala Ile Phe Trp Phe Asn Ser Thr Thr Ile Gln Phe
                85                  90                  95

Asp Ala Cys Leu Val Gln Met Phe Ala Ile His Ser Leu Ser Gly Met
            100                 105                 110

Glu Ser Thr Val Leu Leu Ala Met Ala Phe Asp Arg Tyr Val Ala Ile
        115                 120                 125

Cys His Pro Leu Arg His Ala Thr Val Leu Thr Leu Pro Arg Val Ala
    130                 135                 140

Lys Ile Gly Met Ala Ala Val Val Arg Gly Ala Val Leu Met Ala Pro
145                 150                 155                 160

Leu Pro Val Phe Ile Lys Arg Leu Pro Phe Cys Arg Ser Asn Ile Leu
                165                 170                 175

Ser His Ser Tyr Cys Leu His Gln Asp Val Met Lys Leu Ala Cys Ala
            180                 185                 190

Asp Ile Arg Val Asn Ile Ile Tyr Gly Leu Ile Val Ile Ile Ser Ala
        195                 200                 205

Ile Gly Leu Asp Ser Leu Leu Ile Ser Phe Ser Tyr Leu Leu Ile Leu
```

-continued

```
    210                 215                 220

Lys Thr Val Leu Gly Leu Thr Arg Glu Ala Gln Ala Lys Ala Phe Gly
225                 230                 235                 240

Thr Cys Val Ser His Val Cys Ala Val Phe Ile Phe Tyr Val Pro Phe
                245                 250                 255

Ile Gly Leu Ser Met Val His Arg Phe Ser Lys Arg Arg Asp Ser Leu
            260                 265                 270

Leu Pro Val Ile Met Ala Asn Ile Tyr Leu Leu Val Pro Pro Val Leu
        275                 280                 285

Asn Pro Ile Val Tyr Gly Val Lys Thr Lys Glu Ile Arg Gln Arg Ile
    290                 295                 300

Leu Arg Leu Phe Leu Val Thr Thr His Thr Ser Asp
305                 310                 315


<210> SEQ ID NO 35
<211> LENGTH: 298
<212> TYPE: PRT
<213> ORGANISM: Homo Sapiens

<400> SEQUENCE: 35

Phe Ile Leu Ile Gly Leu Pro Gly Leu Glu Glu Ala Gln Phe Trp Leu
 1               5                  10                  15

Ala Phe Pro Leu Cys Ser Leu Tyr Leu Ile Ala Val Leu Gly Asn Leu
            20                  25                  30

Thr Ile Ile Tyr Ile Val Arg Thr Glu His Ser Leu His Glu Pro Met
        35                  40                  45

Tyr Ile Phe Leu Cys Met Leu Ser Gly Ile Asp Ile Leu Ile Ser Thr
    50                  55                  60

Ser Ser Met Pro Lys Met Leu Ala Ile Phe Trp Phe Asn Ser Thr Thr
65                  70                  75                  80

Ile Gln Phe Asp Ala Cys Leu Leu Gln Ile Phe Ala Ile His Ser Leu
                85                  90                  95

Ser Gly Met Glu Ser Thr Val Leu Leu Ala Met Ala Phe Asp Arg Tyr
            100                 105                 110

Val Ala Ile Cys His Pro Leu Arg His Ala Thr Val Leu Thr Leu Pro
        115                 120                 125

Arg Val Thr Lys Ile Gly Val Ala Ala Val Val Arg Gly Ala Ala Leu
    130                 135                 140

Met Ala Pro Leu Pro Val Phe Ile Lys Gln Leu Pro Phe Cys Arg Ser
145                 150                 155                 160

Asn Ile Leu Ser His Ser Tyr Cys Leu His Gln Asp Val Met Lys Leu
                165                 170                 175

Ala Cys Asp Asp Ile Arg Val Asn Val Val Tyr Gly Leu Ile Val Ile
            180                 185                 190

Ile Ser Ala Ile Gly Leu Asp Ser Leu Leu Ile Ser Phe Ser Tyr Leu
        195                 200                 205

Leu Ile Leu Lys Thr Val Leu Gly Leu Thr Arg Glu Ala Gln Ala Lys
    210                 215                 220

Ala Phe Gly Thr Cys Val Ser His Val Cys Ala Val Phe Ile Phe Tyr
225                 230                 235                 240

Val Pro Phe Ile Gly Leu Ser Met Val His Arg Phe Ser Lys Arg Arg
                245                 250                 255

Asp Ser Pro Leu Pro Val Ile Leu Ala Asn Ile Tyr Leu Leu Val Pro
            260                 265                 270
```

-continued

```
Pro Val Leu Asn Pro Ile Val Tyr Gly Val Lys Thr Lys Glu Ile Arg
        275                 280                 285

Gln Arg Ile Leu Arg Leu Phe His Val Ala
    290                 295


<210> SEQ ID NO 36
<211> LENGTH: 299
<212> TYPE: PRT
<213> ORGANISM: Rattus ratticus

<400> SEQUENCE: 36

Phe Met Leu Ile Gly Ile Pro Gly Leu Glu Glu Ala His Phe Trp Phe
 1               5                  10                  15

Gly Phe Pro Leu Leu Ser Met Tyr Ala Val Ala Leu Phe Gly Asn Cys
            20                  25                  30

Ile Val Val Phe Ile Val Arg Thr Glu Arg Ser Leu His Ala Pro Met
        35                  40                  45

Tyr Leu Phe Leu Cys Met Leu Ala Ala Ile Asp Leu Ala Leu Ser Thr
    50                  55                  60

Ser Thr Met Pro Lys Ile Leu Ala Leu Phe Trp Phe Asp Ser Arg Glu
65                  70                  75                  80

Ile Thr Phe Asp Ala Cys Leu Ala Gln Met Phe Phe Ile His Ala Leu
                85                  90                  95

Ser Ala Ile Glu Ser Thr Ile Leu Leu Ala Met Ala Phe Asp Arg Tyr
            100                 105                 110

Val Ala Ile Cys His Pro Leu Arg His Ala Ala Val Leu Asn Asn Thr
        115                 120                 125

Val Thr Val Gln Ile Gly Met Val Ala Leu Val Arg Gly Ser Leu Phe
    130                 135                 140

Phe Phe Pro Leu Pro Leu Leu Ile Lys Arg Leu Ala Phe Cys His Ser
145                 150                 155                 160

Asn Val Leu Ser His Ser Tyr Cys Val His Gln Asp Val Met Lys Leu
                165                 170                 175

Ala Tyr Thr Asp Thr Leu Pro Asn Val Val Tyr Gly Leu Thr Ala Ile
            180                 185                 190

Leu Leu Val Met Gly Val Asp Val Met Phe Ile Ser Leu Ser Tyr Phe
        195                 200                 205

Leu Ile Ile Arg Ala Val Leu Gln Leu Pro Ser Lys Ser Glu Arg Ala
    210                 215                 220

Lys Ala Phe Gly Thr Cys Val Ser His Ile Gly Val Val Leu Ala Phe
225                 230                 235                 240

Tyr Val Pro Leu Ile Gly Leu Ser Val Val His Arg Phe Gly Asn Ser
                245                 250                 255

Leu Asp Pro Ile Val His Val Leu Met Gly Asp Val Tyr Leu Leu Leu
            260                 265                 270

Pro Pro Val Ile Asn Pro Ile Ile Tyr Gly Ala Lys Thr Lys Gln Ile
        275                 280                 285

Arg Thr Arg Val Leu Ala Met Phe Lys Ile Ser
    290                 295


<210> SEQ ID NO 37
<211> LENGTH: 298
<212> TYPE: PRT
<213> ORGANISM: Homo Sapiens

<400> SEQUENCE: 37
```

-continued

```
Phe Ile Leu Ile Gly Leu Pro Gly Leu Glu Glu Ala Gln Phe Trp Leu
 1               5                  10                  15

Ala Phe Pro Leu Cys Ser Leu Tyr Leu Ile Ala Val Leu Gly Asn Leu
            20                  25                  30

Thr Ile Ile Tyr Ile Val Arg Thr Glu His Ser Leu His Glu Pro Met
        35                  40                  45

Tyr Ile Phe Leu Cys Met Leu Ser Gly Ile Asp Ile Leu Ile Ser Thr
    50                  55                  60

Ser Ser Met Pro Lys Met Leu Ala Ile Phe Trp Phe Asn Ser Thr Thr
65                  70                  75                  80

Ile Gln Phe Asp Ala Cys Leu Leu Gln Ile Phe Ala Ile His Ser Leu
                85                  90                  95

Ser Gly Met Glu Ser Thr Val Leu Leu Ala Met Ala Phe Asp Arg Tyr
            100                 105                 110

Val Ala Ile Cys His Pro Leu Arg His Ala Thr Val Leu Thr Leu Pro
        115                 120                 125

Arg Val Thr Lys Ile Gly Val Ala Ala Val Val Arg Gly Ala Ala Leu
    130                 135                 140

Met Ala Pro Leu Pro Val Phe Ile Lys Gln Leu Pro Phe Cys Arg Ser
145                 150                 155                 160

Asn Ile Leu Ser His Ser Tyr Cys Leu His Gln Asp Val Met Lys Leu
                165                 170                 175

Ala Cys Asp Asp Ile Arg Val Asn Val Val Tyr Gly Leu Ile Val Ile
            180                 185                 190

Ile Ser Ala Ile Gly Leu Asp Ser Leu Leu Ile Ser Phe Ser Tyr Leu
        195                 200                 205

Leu Ile Leu Lys Thr Val Leu Gly Leu Thr Arg Glu Ala Gln Ala Lys
    210                 215                 220

Ala Phe Gly Thr Cys Val Ser His Val Cys Ala Val Phe Ile Phe Tyr
225                 230                 235                 240

Val Pro Phe Ile Gly Leu Ser Met Val His Arg Phe Ser Lys Arg Arg
                245                 250                 255

Asp Ser Pro Leu Pro Val Ile Leu Ala Asn Ile Tyr Leu Leu Val Pro
            260                 265                 270

Pro Val Leu Asn Pro Ile Val Tyr Gly Val Lys Thr Lys Glu Ile Arg
        275                 280                 285

Gln Arg Ile Leu Arg Leu Phe His Val Ala
    290                 295


<210> SEQ ID NO 38
<211> LENGTH: 299
<212> TYPE: PRT
<213> ORGANISM: Homo Sapiens

<400> SEQUENCE: 38

Phe Val Leu Ile Gly Ile Pro Gly Leu Glu Lys Ala His Phe Trp Val
 1               5                  10                  15

Gly Phe Pro Leu Leu Ser Met Tyr Val Val Ala Met Phe Gly Asn Cys
            20                  25                  30

Ile Val Val Phe Ile Val Arg Thr Glu Arg Ser Leu His Ala Pro Met
        35                  40                  45

Tyr Leu Phe Leu Cys Met Leu Ala Ala Ile Asp Leu Ala Leu Ser Thr
    50                  55                  60

Ser Thr Met Pro Lys Ile Leu Ala Leu Phe Trp Phe Asp Ser Arg Glu
65                  70                  75                  80
```

-continued

```
Ile Ser Phe Glu Ala Cys Leu Thr Gln Met Phe Phe Ile His Ala Leu
                85                  90                  95

Ser Ala Ile Glu Ser Thr Ile Leu Leu Ala Met Ala Phe Asp Arg Tyr
            100                 105                 110

Val Ala Ile Cys His Pro Leu Arg His Ala Ala Val Leu Asn Asn Thr
        115                 120                 125

Val Thr Ala Gln Ile Gly Ile Val Ala Val Val Arg Gly Ser Leu Phe
    130                 135                 140

Phe Phe Pro Leu Pro Leu Leu Ile Lys Arg Leu Ala Phe Cys His Ser
145                 150                 155                 160

Asn Val Leu Ser His Ser Tyr Cys Val His Gln Asp Val Met Lys Leu
                165                 170                 175

Ala Tyr Ala Asp Thr Leu Pro Asn Val Val Tyr Gly Leu Thr Ala Ile
            180                 185                 190

Leu Leu Val Met Gly Val Asp Val Met Phe Ile Ser Leu Ser Tyr Phe
        195                 200                 205

Leu Ile Ile Arg Thr Val Leu Gln Leu Pro Ser Lys Ser Glu Arg Ala
    210                 215                 220

Lys Ala Phe Gly Thr Cys Val Ser His Ile Gly Val Val Leu Ala Phe
225                 230                 235                 240

Tyr Val Pro Leu Ile Gly Leu Ser Val Val His Arg Phe Gly Asn Ser
                245                 250                 255

Leu His Pro Ile Val Arg Val Val Met Gly Asp Ile Tyr Leu Leu Leu
            260                 265                 270

Pro Pro Val Ile Asn Pro Ile Ile Tyr Gly Ala Lys Thr Lys Gln Ile
        275                 280                 285

Arg Thr Arg Val Leu Ala Met Phe Lys Ile Ser
    290                 295


<210> SEQ ID NO 39
<211> LENGTH: 14
<212> TYPE: PRT
<213> ORGANISM: Clostridiumn toxi

<400> SEQUENCE: 39

Gln Tyr Ile Lys Ala Asn Ser Lys Phe Ile Gly Ile Thr Glu
 1               5                  10


<210> SEQ ID NO 40
<211> LENGTH: 21
<212> TYPE: PRT
<213> ORGANISM: Plasmodium falciparum

<400> SEQUENCE: 40

Asp Ile Glu Lys Lys Ile Ala Lys Met Glu Lys Ala Ser Ser Val Phe
 1               5                  10                  15

Asn Val Val Asn Ser
            20


<210> SEQ ID NO 41
<211> LENGTH: 16
<212> TYPE: PRT
<213> ORGANISM: Streptococcus aureus

<400> SEQUENCE: 41

Gly Ala Val Asp Ser Ile Leu Gly Gly Val Ala Thr Tyr Gly Ala Ala
 1               5                  10                  15
```

```
<210> SEQ ID NO 42
<211> LENGTH: 13
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = cyclohexylalanine, phenylalanine or
      tyrosine
<220> FEATURE:
<221> NAME/KEY: VARIANT
<222> LOCATION: 1, 13
<223> OTHER INFORMATION: Xaa = D-alanine or L-alanine
<220> FEATURE:
<223> OTHER INFORMATION: Pan-DR-binding Epitope

<400> SEQUENCE: 42

Xaa Lys Xaa Val Ala Ala Trp Thr Leu Lys Ala Ala Xaa
 1               5                  10


<210> SEQ ID NO 43
<211> LENGTH: 4
<212> TYPE: PRT
<213> ORGANISM: Homo Sapiens

<400> SEQUENCE: 43

Lys Asp Glu Leu
 1


<210> SEQ ID NO 44
<211> LENGTH: 24
<212> TYPE: DNA
<213> ORGANISM: Homo Sapiens

<400> SEQUENCE: 44

gattacaagg atgacgacga taag                                            24


<210> SEQ ID NO 45
<211> LENGTH: 24
<212> TYPE: DNA
<213> ORGANISM: Homo Sapiens

<400> SEQUENCE: 45

gattacaagg atgacgacga taag                                            24


<210> SEQ ID NO 46
<211> LENGTH: 14
<212> TYPE: PRT
<213> ORGANISM: Homo Sapiens

<400> SEQUENCE: 46

Met Val Asp Pro Asn Gly Asn Glu Ser Ser Ala Thr Tyr Phe
 1               5                  10


<210> SEQ ID NO 47
<211> LENGTH: 23
<212> TYPE: PRT
<213> ORGANISM: Homo Sapiens

<400> SEQUENCE: 47

Met Val Asp Pro Asn Gly Asn Glu Ser Ser Ala Thr Tyr Phe Ile Leu
 1               5                  10                  15

Ile Gly Leu Pro Gly Leu Glu
            20
```

-continued

<210> SEQ ID NO 48
<211> LENGTH: 6
<212> TYPE: PRT
<213> ORGANISM: Homo Sapiens

<400> SEQUENCE: 48

Thr Ile Leu Val Met Ser
1 5

<210> SEQ ID NO 49
<211> LENGTH: 7
<212> TYPE: PRT
<213> ORGANISM: Homo Sapiens

<400> SEQUENCE: 49

Leu Ile Val Met Ala Thr Gln
1 5

<210> SEQ ID NO 50
<211> LENGTH: 6
<212> TYPE: PRT
<213> ORGANISM: Homo Sapiens

<400> SEQUENCE: 50

Ile Val Met Ala Thr Leu
1 5

<210> SEQ ID NO 51
<211> LENGTH: 7
<212> TYPE: PRT
<213> ORGANISM: Homo Sapiens

<400> SEQUENCE: 51

Val Ser Met Ala Thr Leu Ile
1 5

<210> SEQ ID NO 52
<211> LENGTH: 8
<212> TYPE: PRT
<213> ORGANISM: Homo Sapiens

<400> SEQUENCE: 52

Tyr Phe Trp Ile Val Leu Met Thr
1 5

<210> SEQ ID NO 53
<211> LENGTH: 6
<212> TYPE: PRT
<213> ORGANISM: Homo Sapiens

<400> SEQUENCE: 53

Phe Ile Tyr Trp Leu Met
1 5

<210> SEQ ID NO 54
<211> LENGTH: 8
<212> TYPE: PRT
<213> ORGANISM: Homo Sapiens

<400> SEQUENCE: 54

Val Ile Leu Phe Met Trp Tyr Ala
1 5

<210> SEQ ID NO 55
<211> LENGTH: 8

-continued

<212> TYPE: PRT
<213> ORGANISM: Homo Sapiens

<400> SEQUENCE: 55

Phe Tyr Leu Trp Met Ile Val Ala
1 5

<210> SEQ ID NO 56
<211> LENGTH: 8
<212> TYPE: PRT
<213> ORGANISM: Homo Sapiens

<400> SEQUENCE: 56

Phe Trp Tyr Leu Ile Met Val Ala
1 5

<210> SEQ ID NO 57
<211> LENGTH: 8
<212> TYPE: PRT
<213> ORGANISM: Homo Sapiens

<400> SEQUENCE: 57

Phe Trp Tyr Leu Ile Val Met Ala
1 5

<210> SEQ ID NO 58
<211> LENGTH: 6
<212> TYPE: PRT
<213> ORGANISM: Homo Sapiens

<400> SEQUENCE: 58

Gln Leu Ile Val Met Pro
1 5

<210> SEQ ID NO 59
<211> LENGTH: 8
<212> TYPE: PRT
<213> ORGANISM: Homo Sapiens

<400> SEQUENCE: 59

Phe Trp Tyr Met Ile Val Leu Ala
1 5

<210> SEQ ID NO 60
<211> LENGTH: 4
<212> TYPE: PRT
<213> ORGANISM: Homo Sapiens

<400> SEQUENCE: 60

Asp Glu Ala Ser
1

<210> SEQ ID NO 61
<211> LENGTH: 7
<212> TYPE: PRT
<213> ORGANISM: Homo Sapiens

<400> SEQUENCE: 61

Leu Met Val Gln Ile Ala Thr
1 5

<210> SEQ ID NO 62
<211> LENGTH: 6
<212> TYPE: PRT
<213> ORGANISM: Homo Sapiens

-continued

<400> SEQUENCE: 62

Val Leu Ile Met Ala Thr
 1               5

<210> SEQ ID NO 63
<211> LENGTH: 11
<212> TYPE: PRT
<213> ORGANISM: Homo Sapiens

<400> SEQUENCE: 63

Leu Met Val Ile Ser Ala Thr Phe Cys Gly Asp
 1               5                   10

<210> SEQ ID NO 64
<211> LENGTH: 6
<212> TYPE: PRT
<213> ORGANISM: Homo Sapiens

<400> SEQUENCE: 64

Lys Tyr Arg His Phe Ala
 1               5

<210> SEQ ID NO 65
<211> LENGTH: 12
<212> TYPE: PRT
<213> ORGANISM: Homo Sapiens

<400> SEQUENCE: 65

Val Thr Met Leu Ile Ser Ala Gly Asn Cys Asp Phe
 1               5                   10

<210> SEQ ID NO 66
<211> LENGTH: 4
<212> TYPE: PRT
<213> ORGANISM: Homo Sapiens

<400> SEQUENCE: 66

Lys Arg Tyr His
 1

<210> SEQ ID NO 67
<211> LENGTH: 4
<212> TYPE: PRT
<213> ORGANISM: Homo Sapiens

<400> SEQUENCE: 67

Tyr Phe Trp Met
 1

<210> SEQ ID NO 68
<211> LENGTH: 4
<212> TYPE: PRT
<213> ORGANISM: Homo Sapiens

<400> SEQUENCE: 68

Phe Leu Ile Trp
 1

<210> SEQ ID NO 69
<211> LENGTH: 7
<212> TYPE: PRT
<213> ORGANISM: Homo Sapiens

<400> SEQUENCE: 69

-continued

Met Val Thr Ala Leu Ile Ser
1 5

<210> SEQ ID NO 70
<211> LENGTH: 7
<212> TYPE: PRT
<213> ORGANISM: Homo Sapiens

<400> SEQUENCE: 70

Met Val Ala Leu Phe Ile Ser
1 5

<210> SEQ ID NO 71
<211> LENGTH: 7
<212> TYPE: PRT
<213> ORGANISM: Homo Sapiens

<400> SEQUENCE: 71

Ala Val Thr Met Ser Leu Ile
1 5

<210> SEQ ID NO 72
<211> LENGTH: 8
<212> TYPE: PRT
<213> ORGANISM: Homo Sapiens

<400> SEQUENCE: 72

Leu Met Phe Trp Tyr Ala Ile Val
1 5

<210> SEQ ID NO 73
<211> LENGTH: 8
<212> TYPE: PRT
<213> ORGANISM: Homo Sapiens

<400> SEQUENCE: 73

Leu Met Phe Trp Tyr Ile Val Ala
1 5

<210> SEQ ID NO 74
<211> LENGTH: 8
<212> TYPE: PRT
<213> ORGANISM: Homo Sapiens

<400> SEQUENCE: 74

Leu Ile Val Phe Trp Tyr Ala Met
1 5

<210> SEQ ID NO 75
<211> LENGTH: 8
<212> TYPE: PRT
<213> ORGANISM: Homo Sapiens

<400> SEQUENCE: 75

Ile Met Phe Trp Tyr Ala Leu Val
1 5

<210> SEQ ID NO 76
<211> LENGTH: 9
<212> TYPE: PRT
<213> ORGANISM: Homo Sapiens

<400> SEQUENCE: 76

Ala Thr Ile Val Leu Met Phe Trp Tyr

-continued 1 5

<210> SEQ ID NO 77
<211> LENGTH: 7
<212> TYPE: PRT
<213> ORGANISM: Homo Sapiens

<400> SEQUENCE: 77

Phe Met Tyr Leu Ile Val Trp
1 5

<210> SEQ ID NO 78
<211> LENGTH: 9
<212> TYPE: PRT
<213> ORGANISM: Homo Sapiens

<400> SEQUENCE: 78

Val Ser Thr Cys Pro Ala Leu Ile Met
1 5

<210> SEQ ID NO 79
<211> LENGTH: 7
<212> TYPE: PRT
<213> ORGANISM: Homo Sapiens

<400> SEQUENCE: 79

Met Phe Leu Ile Val Trp Tyr
1 5

<210> SEQ ID NO 80
<211> LENGTH: 4
<212> TYPE: PRT
<213> ORGANISM: Homo Sapiens

<400> SEQUENCE: 80

Pro Ala Met Gln
1

<210> SEQ ID NO 81
<211> LENGTH: 9
<212> TYPE: PRT
<213> ORGANISM: Homo Sapiens

<400> SEQUENCE: 81

Val Met Ala Thr Ser Pro Leu Ile Cys
1 5

<210> SEQ ID NO 82
<211> LENGTH: 9
<212> TYPE: PRT
<213> ORGANISM: Homo Sapiens

<400> SEQUENCE: 82

Ile Val Met Ser Ala Cys Thr Pro Leu
1 5

<210> SEQ ID NO 83
<211> LENGTH: 6
<212> TYPE: PRT
<213> ORGANISM: Homo Sapiens

<400> SEQUENCE: 83

Leu Ile Val Met Phe Tyr
1 5

<210> SEQ ID NO 84
<211> LENGTH: 7
<212> TYPE: PRT
<213> ORGANISM: Homo Sapiens

<400> SEQUENCE: 84

Leu Ile Val Met Phe Ala Tyr
1               5

<210> SEQ ID NO 85
<211> LENGTH: 6
<212> TYPE: PRT
<213> ORGANISM: Homo Sapiens

<400> SEQUENCE: 85

Asp Asn Gln Glu Ser Thr
1               5

<210> SEQ ID NO 86
<211> LENGTH: 9
<212> TYPE: PRT
<213> ORGANISM: Homo Sapiens

<400> SEQUENCE: 86

Val Met Ser Thr Ala Cys Pro Leu Ile
1               5

<210> SEQ ID NO 87
<211> LENGTH: 6
<212> TYPE: PRT
<213> ORGANISM: Homo Sapiens

<400> SEQUENCE: 87

Leu Ile Val Met Ala Thr
1               5

<210> SEQ ID NO 88
<211> LENGTH: 6
<212> TYPE: PRT
<213> ORGANISM: Homo Sapiens

<400> SEQUENCE: 88

Phe Ile Tyr Trp Leu Met
1               5

<210> SEQ ID NO 89
<211> LENGTH: 4
<212> TYPE: PRT
<213> ORGANISM: Homo Sapiens

<400> SEQUENCE: 89

Leu Ile Val Met
1

<210> SEQ ID NO 90
<211> LENGTH: 4
<212> TYPE: PRT
<213> ORGANISM: Homo Sapiens

<400> SEQUENCE: 90

Gly Phe Tyr Trp
1

<210> SEQ ID NO 91

-continued

<211> LENGTH: 4
<212> TYPE: PRT
<213> ORGANISM: Homo Sapiens

<400> SEQUENCE: 91

Asp Glu Gln Asn
1

<210> SEQ ID NO 92
<211> LENGTH: 4
<212> TYPE: PRT
<213> ORGANISM: Homo Sapiens

<400> SEQUENCE: 92

Gly Arg His Lys
1

<210> SEQ ID NO 93
<211> LENGTH: 8
<212> TYPE: PRT
<213> ORGANISM: Homo Sapiens

<400> SEQUENCE: 93

Ala Ser Thr Cys Leu Ile Val Met
1 5

<210> SEQ ID NO 94
<211> LENGTH: 4
<212> TYPE: PRT
<213> ORGANISM: Homo Sapiens

<400> SEQUENCE: 94

Gly Ser Thr Cys
1

<210> SEQ ID NO 95
<211> LENGTH: 4
<212> TYPE: PRT
<213> ORGANISM: Homo Sapiens

<400> SEQUENCE: 95

Ala Ser Thr Cys
1

<210> SEQ ID NO 96
<211> LENGTH: 5
<212> TYPE: PRT
<213> ORGANISM: Homo Sapiens

<400> SEQUENCE: 96

Asp Glu Ala Gln Asn
1 5

<210> SEQ ID NO 97
<211> LENGTH: 5
<212> TYPE: PRT
<213> ORGANISM: Homo Sapiens

<400> SEQUENCE: 97

Tyr Phe Trp Gln Asn
1 5

<210> SEQ ID NO 98
<211> LENGTH: 5
<212> TYPE: PRT

<213> ORGANISM: Homo Sapiens

<400> SEQUENCE: 98

Pro Ala Ser Thr Cys
1 5

<210> SEQ ID NO 99
<211> LENGTH: 8
<212> TYPE: PRT
<213> ORGANISM: Homo Sapiens

<400> SEQUENCE: 99

Arg His Lys Gly Leu Ile Val Met
1 5

<210> SEQ ID NO 100
<211> LENGTH: 6
<212> TYPE: PRT
<213> ORGANISM: Homo Sapiens

<400> SEQUENCE: 100

Arg His Lys Tyr Phe Trp
1 5

<210> SEQ ID NO 101
<211> LENGTH: 7
<212> TYPE: PRT
<213> ORGANISM: Homo Sapiens

<400> SEQUENCE: 101

Ser Thr Cys Leu Ile Val Met
1 5

<210> SEQ ID NO 102
<211> LENGTH: 7
<212> TYPE: PRT
<213> ORGANISM: Homo Sapiens

<400> SEQUENCE: 102

Arg His Lys Asp Glu Pro Tyr
1 5

<210> SEQ ID NO 103
<211> LENGTH: 4
<212> TYPE: PRT
<213> ORGANISM: Homo Sapiens

<400> SEQUENCE: 103

Pro Arg His Lys
1

<210> SEQ ID NO 104
<211> LENGTH: 7
<212> TYPE: PRT
<213> ORGANISM: Homo Sapiens

<400> SEQUENCE: 104

Leu Met Ile Val Gln Ala Thr
1 5

<210> SEQ ID NO 105
<211> LENGTH: 5
<212> TYPE: PRT
<213> ORGANISM: Homo Sapiens

<400> SEQUENCE: 105

Asp Glu Arg Lys His
 1               5

<210> SEQ ID NO 106
<211> LENGTH: 7
<212> TYPE: PRT
<213> ORGANISM: Homo Sapiens

<400> SEQUENCE: 106

Phe Tyr Trp Leu Val Ile Met
 1               5

<210> SEQ ID NO 107
<211> LENGTH: 4
<212> TYPE: PRT
<213> ORGANISM: Homo Sapiens

<400> SEQUENCE: 107

Arg Lys His Ala
 1

<210> SEQ ID NO 108
<211> LENGTH: 11
<212> TYPE: PRT
<213> ORGANISM: Homo Sapiens

<400> SEQUENCE: 108

Leu Met Val Ile Ser Ala Thr Phe Cys Gly Asp
 1               5                   10

<210> SEQ ID NO 109
<211> LENGTH: 7
<212> TYPE: PRT
<213> ORGANISM: Homo Sapiens

<400> SEQUENCE: 109

Pro Arg His Lys Tyr Phe Trp
 1               5

<210> SEQ ID NO 110
<211> LENGTH: 12
<212> TYPE: PRT
<213> ORGANISM: Homo Sapiens

<400> SEQUENCE: 110

Val Thr Leu Met Ile Ser Ala Gly Asn Cys Asp Phe
 1               5                   10

<210> SEQ ID NO 111
<211> LENGTH: 6
<212> TYPE: PRT
<213> ORGANISM: Homo Sapiens

<400> SEQUENCE: 111

Tyr Phe Trp Arg His Lys
 1               5

<210> SEQ ID NO 112
<211> LENGTH: 5
<212> TYPE: PRT
<213> ORGANISM: Homo Sapiens

<400> SEQUENCE: 112

-continued

Asp Glu Arg His Lys
1 5

<210> SEQ ID NO 113
<211> LENGTH: 4
<212> TYPE: PRT
<213> ORGANISM: Homo Sapiens

<400> SEQUENCE: 113

Tyr Phe Trp Pro
1

<210> SEQ ID NO 114
<211> LENGTH: 4
<212> TYPE: PRT
<213> ORGANISM: Homo Sapiens

<400> SEQUENCE: 114

Ala Tyr Phe Trp
1

<210> SEQ ID NO 115
<211> LENGTH: 6
<212> TYPE: PRT
<213> ORGANISM: Homo Sapiens

<400> SEQUENCE: 115

Tyr Phe Trp Ser Thr Cys
1 5

<210> SEQ ID NO 116
<211> LENGTH: 7
<212> TYPE: PRT
<213> ORGANISM: Homo Sapiens

<400> SEQUENCE: 116

Tyr Phe Trp Leu Ile Val Met
1 5

<210> SEQ ID NO 117
<211> LENGTH: 6
<212> TYPE: PRT
<213> ORGANISM: Homo Sapiens

<400> SEQUENCE: 117

Arg His Lys Phe Trp Tyr
1 5

<210> SEQ ID NO 118
<211> LENGTH: 5
<212> TYPE: PRT
<213> ORGANISM: Homo Sapiens

<400> SEQUENCE: 118

Asp Glu Gln Asn Pro
1 5

<210> SEQ ID NO 119
<211> LENGTH: 7
<212> TYPE: PRT
<213> ORGANISM: Homo Sapiens

<400> SEQUENCE: 119

Phe Trp Tyr Leu Ile Val Met
1 5

-continued

<210> SEQ ID NO 120
<211> LENGTH: 7
<212> TYPE: PRT
<213> ORGANISM: Homo Sapiens

<400> SEQUENCE: 120

Leu Ile Val Met Phe Trp Tyr
 1               5

<210> SEQ ID NO 121
<211> LENGTH: 11
<212> TYPE: PRT
<213> ORGANISM: Homo Sapiens

<400> SEQUENCE: 121

Ala Gly Pro Asp Glu Arg His Lys Ser Thr Cys
 1               5                  10

<210> SEQ ID NO 122
<211> LENGTH: 5
<212> TYPE: PRT
<213> ORGANISM: Homo Sapiens

<400> SEQUENCE: 122

Ala Gly Pro Gln Asn
 1               5

<210> SEQ ID NO 123
<211> LENGTH: 5
<212> TYPE: PRT
<213> ORGANISM: Homo Sapiens

<400> SEQUENCE: 123

Arg His Lys Gln Asn
 1               5

<210> SEQ ID NO 124
<211> LENGTH: 5
<212> TYPE: PRT
<213> ORGANISM: Homo Sapiens

<400> SEQUENCE: 124

Ala Leu Ile Val Met
 1               5

<210> SEQ ID NO 125
<211> LENGTH: 5
<212> TYPE: PRT
<213> ORGANISM: Homo Sapiens

<400> SEQUENCE: 125

Phe Trp Tyr Ala Pro
 1               5

<210> SEQ ID NO 126
<211> LENGTH: 6
<212> TYPE: PRT
<213> ORGANISM: Homo Sapiens

<400> SEQUENCE: 126

Gly Pro Gln Asn Asp Glu
 1               5

-continued

<210> SEQ ID NO 127
<211> LENGTH: 6
<212> TYPE: PRT
<213> ORGANISM: Homo Sapiens

<400> SEQUENCE: 127

Gly Asp Glu Ser Thr Cys
 1               5

<210> SEQ ID NO 128
<211> LENGTH: 5
<212> TYPE: PRT
<213> ORGANISM: Homo Sapiens

<400> SEQUENCE: 128

Arg His Lys Asp Glu
 1               5

<210> SEQ ID NO 129
<211> LENGTH: 5
<212> TYPE: PRT
<213> ORGANISM: Homo Sapiens

<400> SEQUENCE: 129

Gln Asn Asp Gly Glu
 1               5

<210> SEQ ID NO 130
<211> LENGTH: 8
<212> TYPE: PRT
<213> ORGANISM: Homo Sapiens

<400> SEQUENCE: 130

Arg His Lys Leu Ile Val Met Pro
 1               5

<210> SEQ ID NO 131
<211> LENGTH: 4
<212> TYPE: PRT
<213> ORGANISM: Homo Sapiens

<400> SEQUENCE: 131

Asn Glu Ser Ser
 1

<210> SEQ ID NO 132
<211> LENGTH: 4
<212> TYPE: PRT
<213> ORGANISM: Homo Sapiens

<400> SEQUENCE: 132

Asn Leu Thr Ile
 1

<210> SEQ ID NO 133
<211> LENGTH: 4
<212> TYPE: PRT
<213> ORGANISM: Homo Sapiens

<400> SEQUENCE: 133

Asn Ser Thr Thr
 1

<210> SEQ ID NO 134
<211> LENGTH: 4

-continued

<212> TYPE: PRT
<213> ORGANISM: Homo Sapiens

<400> SEQUENCE: 134

Arg Arg Asp Ser
1

<210> SEQ ID NO 135
<211> LENGTH: 4
<212> TYPE: PRT
<213> ORGANISM: Homo Sapiens

<400> SEQUENCE: 135

Ser Leu His Glu
1

<210> SEQ ID NO 136
<211> LENGTH: 4
<212> TYPE: PRT
<213> ORGANISM: Homo Sapiens

<400> SEQUENCE: 136

Ser Gly Ile Asp
1

<210> SEQ ID NO 137
<211> LENGTH: 4
<212> TYPE: PRT
<213> ORGANISM: Homo Sapiens

<400> SEQUENCE: 137

Ser Gly Met Glu
1

<210> SEQ ID NO 138
<211> LENGTH: 6
<212> TYPE: PRT
<213> ORGANISM: Homo Sapiens

<400> SEQUENCE: 138

Gly Asn Glu Ser Ser Ala
1 5

<210> SEQ ID NO 139
<211> LENGTH: 6
<212> TYPE: PRT
<213> ORGANISM: Homo Sapiens

<400> SEQUENCE: 139

Gly Leu Glu Glu Ala Gln
1 5

<210> SEQ ID NO 140
<211> LENGTH: 6
<212> TYPE: PRT
<213> ORGANISM: Homo Sapiens

<400> SEQUENCE: 140

Gly Met Glu Ser Thr Val
1 5

<210> SEQ ID NO 141
<211> LENGTH: 6
<212> TYPE: PRT
<213> ORGANISM: Homo Sapiens

<400> SEQUENCE: 141

Gly Thr Cys Val Ser His
1 5

<210> SEQ ID NO 142
<211> LENGTH: 17
<212> TYPE: PRT
<213> ORGANISM: Homo Sapiens

<400> SEQUENCE: 142

Met Glu Ser Thr Val Leu Leu Ala Met Ala Phe Asp Arg Tyr Val Ala
1 5 10 15

Ile

<210> SEQ ID NO 143
<211> LENGTH: 300
<212> TYPE: PRT
<213> ORGANISM: Homo sapiens

<400> SEQUENCE: 143

Gly Asn Tyr Thr Val Val Thr Glu Phe Ile Leu Leu Gly Leu Thr Asp
1 5 10 15

Asp Ile Thr Val Ser Val Ile Leu Phe Val Met Phe Leu Ile Val Tyr
20 25 30

Ser Val Thr Leu Met Gly Asn Leu Asn Ile Ile Val Leu Ile Arg Thr
35 40 45

Ser Pro Gln Leu His Thr Pro Met Tyr Leu Phe Leu Ser His Leu Ala
50 55 60

Phe Leu Asp Ile Gly Tyr Ser Ser Ser Val Thr Pro Ile Met Leu Arg
65 70 75 80

Gly Phe Leu Arg Lys Gly Thr Phe Ile Pro Val Ala Gly Cys Val Ala
85 90 95

Gln Leu Cys Ile Val Val Ala Phe Gly Thr Ser Glu Ser Phe Leu Leu
100 105 110

Ala Ser Met Ala Tyr Asp Arg Tyr Val Ala Ile Cys Ser Pro Leu Leu
115 120 125

Tyr Ser Thr Gln Met Ser Ser Thr Val Cys Ile Leu Leu Val Gly Thr
130 135 140

Ser Tyr Leu Gly Gly Trp Val Asn Ala Trp Ile Phe Thr Gly Cys Ser
145 150 155 160

Leu Asn Leu Ser Phe Cys Gly Pro Asn Lys Ile Asn His Phe Phe Cys
165 170 175

Asp Tyr Ser Pro Leu Leu Lys Leu Ser Cys Ser His Asp Phe Ser Phe
180 185 190

Glu Val Ile Pro Ala Ile Ser Ser Gly Ser Ile Ile Val Val Thr Val
195 200 205

Phe Ile Ile Ala Leu Ser Tyr Val Tyr Ile Leu Val Ser Ile Leu Lys
210 215 220

Met Arg Ser Thr Glu Gly Arg Gln Lys Ala Phe Ser Thr Cys Thr Ser
225 230 235 240

His Leu Thr Ala Val Thr Leu Phe Phe Gly Thr Ile Thr Phe Ile Tyr
245 250 255

Val Met Pro Gln Ser Ser Tyr Ser Thr Asp Gln Asn Val Val Ser Val
260 265 270

Phe Tyr Thr Val Val Ile Pro Met Leu Asn Pro Leu Ile Tyr Ser Phe

-continued

```
        275                 280                 285

Arg Asn Lys Glu Val Lys Glu Ala Met Lys Lys Leu
    290                 295                 300


<210> SEQ ID NO 144
<211> LENGTH: 302
<212> TYPE: PRT
<213> ORGANISM: Mus musculus

<400> SEQUENCE: 144

Gly Asn Glu Ser Ser Ala Thr Tyr Phe Ile Leu Ile Gly Leu Pro Gly
 1               5                  10                  15

Leu Glu Glu Ala Gln Phe Trp Leu Ala Phe Pro Leu Cys Ser Leu Tyr
            20                  25                  30

Leu Ile Ala Val Leu Gly Asn Leu Thr Ile Ile Tyr Ile Val Arg Thr
        35                  40                  45

Glu His Ser Leu His Glu Pro Met Tyr Ile Phe Leu Cys Met Leu Ser
    50                  55                  60

Gly Ile Asp Ile Leu Ile Ser Thr Ser Ser Met Pro Lys Met Leu Ala
65                  70                  75                  80

Ile Phe Trp Phe Asn Ser Thr Thr Ile Gln Phe Asp Ala Cys Leu Leu
                85                  90                  95

Gln Ile Phe Ala Ile His Ser Leu Ser Gly Met Glu Ser Thr Val Leu
            100                 105                 110

Leu Ala Met Ala Phe Asp Arg Tyr Val Ala Ile Cys His Pro Leu Arg
        115                 120                 125

His Ala Thr Val Leu Thr Leu Pro Arg Val Thr Lys Ile Gly Val Ala
    130                 135                 140

Ala Val Val Arg Gly Ala Ala Leu Met Ala Pro Leu Pro Val Phe Ile
145                 150                 155                 160

Lys Gln Leu Pro Phe Cys Arg Ser Asn Ile Leu Ser His Ser Tyr Cys
                165                 170                 175

Leu His Gln Asp Val Met Lys Leu Ala Cys Asp Asp Ile Arg Val Asn
            180                 185                 190

Val Val Tyr Gly Leu Ile Val Ile Ile Ser Ala Ile Gly Leu Asp Ser
        195                 200                 205

Leu Leu Ile Ser Phe Ser Tyr Leu Leu Ile Leu Lys Thr Val Leu Gly
    210                 215                 220

Leu Thr Arg Glu Ala Gln Ala Lys Ala Phe Gly Thr Cys Val Ser His
225                 230                 235                 240

Val Cys Ala Val Phe Ile Phe Tyr Val Pro Phe Ile Gly Leu Ser Met
                245                 250                 255

Val His Arg Phe Ser Lys Arg Arg Asp Ser Pro Leu Pro Val Ile Leu
            260                 265                 270

Ala Asn Ile Tyr Leu Leu Val Pro Pro Val Leu Asn Pro Ile Val Tyr
        275                 280                 285

Gly Val Lys Thr Lys Glu Ile Arg Gln Arg Ile Leu Arg Leu
    290                 295                 300


<210> SEQ ID NO 145
<211> LENGTH: 303
<212> TYPE: PRT
<213> ORGANISM: Homo sapiens

<400> SEQUENCE: 145

Asn Glu Ser Ser Ala Thr Tyr Phe Ile Leu Ile Gly Leu Pro Gly Leu
```

-continued

```
1               5                   10                  15

Glu Glu Ala Gln Phe Trp Leu Ala Phe Pro Leu Cys Ser Leu Tyr Leu
            20                  25                  30

Ile Ala Val Leu Gly Asn Leu Thr Ile Ile Tyr Ile Val Arg Thr Glu
        35                  40                  45

His Ser Leu His Glu Pro Met Tyr Ile Phe Leu Cys Met Leu Ser Gly
    50                  55                  60

Ile Asp Ile Leu Ile Ser Thr Ser Ser Met Pro Lys Met Leu Ala Ile
65                  70                  75                  80

Phe Trp Phe Asn Ser Thr Thr Ile Gln Phe Asp Ala Cys Leu Leu Gln
                85                  90                  95

Ile Phe Ala Ile His Ser Leu Ser Gly Met Glu Ser Thr Val Leu Leu
            100                 105                 110

Ala Met Ala Phe Asp Arg Tyr Val Ala Ile Cys His Pro Leu Arg His
        115                 120                 125

Ala Thr Val Leu Thr Leu Pro Arg Val Thr Lys Ile Gly Val Ala Ala
    130                 135                 140

Val Val Arg Gly Ala Ala Leu Met Ala Pro Leu Pro Val Phe Ile Lys
145                 150                 155                 160

Gln Leu Pro Phe Cys Arg Ser Asn Ile Leu Ser His Ser Tyr Cys Leu
                165                 170                 175

His Gln Asp Val Met Lys Leu Ala Cys Asp Asp Ile Arg Val Asn Val
            180                 185                 190

Val Tyr Gly Leu Ile Val Ile Ile Ser Ala Ile Gly Leu Asp Ser Leu
        195                 200                 205

Leu Ile Ser Phe Ser Tyr Leu Leu Ile Leu Lys Thr Val Leu Gly Leu
    210                 215                 220

Thr Arg Glu Ala Gln Ala Lys Ala Phe Gly Thr Cys Val Ser His Val
225                 230                 235                 240

Cys Ala Val Phe Ile Phe Tyr Val Pro Phe Ile Gly Leu Ser Met Val
                245                 250                 255

His Arg Phe Ser Lys Arg Arg Asp Ser Pro Leu Pro Val Ile Leu Ala
            260                 265                 270

Asn Ile Tyr Leu Leu Val Pro Pro Val Leu Asn Pro Ile Val Tyr Gly
        275                 280                 285

Val Lys Thr Lys Glu Ile Arg Gln Arg Ile Leu Arg Leu Phe His
    290                 295                 300


<210> SEQ ID NO 146
<211> LENGTH: 304
<212> TYPE: PRT
<213> ORGANISM: Homo sapiens

<400> SEQUENCE: 146

Asn Val Thr His Pro Ala Phe Phe Leu Leu Thr Gly Ile Pro Gly Leu
1               5                   10                  15

Glu Ser Ser His Ser Trp Leu Ser Gly Pro Leu Cys Val Met Tyr Ala
            20                  25                  30

Val Ala Leu Gly Gly Asn Thr Val Ile Leu Gln Ala Val Arg Val Glu
        35                  40                  45

Pro Ser Leu His Glu Pro Met Tyr Tyr Phe Leu Ser Met Leu Ser Phe
    50                  55                  60

Ser Asp Val Ala Ile Ser Met Ala Thr Leu Pro Thr Val Leu Arg Thr
65                  70                  75                  80
```

-continued

```
Phe Cys Leu Asn Ala Arg Asn Ile Thr Phe Asp Ala Cys Leu Ile Gln
                85                  90                  95

Met Phe Leu Ile His Phe Phe Ser Met Met Glu Ser Gly Ile Leu Leu
            100                 105                 110

Ala Met Ser Phe Asp Arg Tyr Val Ala Ile Cys Asp Pro Leu Arg Tyr
        115                 120                 125

Ala Thr Val Leu Thr Thr Glu Val Ile Ala Ala Met Gly Leu Gly Ala
    130                 135                 140

Ala Ala Arg Ser Phe Ile Thr Leu Phe Pro Leu Pro Phe Leu Ile Lys
145                 150                 155                 160

Arg Leu Pro Ile Cys Arg Ser Asn Val Leu Ser His Ser Tyr Cys Leu
                165                 170                 175

His Pro Asp Met Met Arg Leu Ala Cys Ala Asp Ile Ser Ile Asn Ser
            180                 185                 190

Ile Tyr Gly Leu Phe Val Leu Val Ser Thr Phe Gly Met Asp Leu Phe
        195                 200                 205

Phe Ile Phe Leu Ser Tyr Val Leu Ile Leu Arg Ser Val Met Ala Thr
    210                 215                 220

Ala Ser Arg Glu Glu Arg Leu Lys Ala Leu Asn Thr Cys Val Ser His
225                 230                 235                 240

Ile Leu Ala Val Leu Ala Phe Tyr Val Pro Met Ile Gly Val Ser Thr
                245                 250                 255

Val His Arg Phe Gly Lys His Val Pro Cys Tyr Ile His Val Leu Met
            260                 265                 270

Ser Asn Val Tyr Leu Phe Val Pro Pro Val Leu Asn Pro Leu Ile Tyr
        275                 280                 285

Ser Ala Lys Thr Lys Glu Ile Arg Arg Ala Ile Phe Arg Met Phe His
    290                 295                 300
```